(12) United States Patent
Taniguchi et al.

(10) Patent No.: US 8,563,575 B2
(45) Date of Patent: Oct. 22, 2013

(54) FUSED HETEROCYCLIC COMPOUNDS

(75) Inventors: Takahiko Taniguchi, Cambridge (GB); Masato Yoshikawa, Osaka (JP); Kasei Miura, Kanagawa (JP); Tomoaki Hasui, Kanagawa (JP); Eiji Honda, Kanagawa (JP); Keisuke Imamura, Kanagawa (JP); Makoto Kamata, Kanagawa (JP); Haruhi Kamisaki, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/166,212

(22) Filed: Jun. 22, 2011

(65) Prior Publication Data

US 2011/0319394 A1  Dec. 29, 2011

Related U.S. Application Data

(60) Provisional application No. 61/358,121, filed on Jun. 24, 2010, provisional application No. 61/422,845, filed on Dec. 14, 2010.

(51) Int. Cl.
*A01N 43/42* (2006.01)
*A61K 31/44* (2006.01)

(52) U.S. Cl.
USPC ........................ 514/301; 514/302; 514/303

(58) Field of Classification Search
USPC ............ 544/350; 514/258.1, 301, 302, 303
See application file for complete search history.

(56) References Cited

U.S. PATENT DOCUMENTS

| | | | |
|---|---|---|---|
| 4,144,341 A | 3/1979 | Clark et al. | |
| 5,597,826 A | 1/1997 | Howard et al. | |
| 6,552,192 B1 | 4/2003 | Hanus et al. | |
| 7,429,665 B2 | 9/2008 | Verhoest et al. | |
| 8,217,069 B2 * | 7/2012 | Yonekubo et al. | 514/392 |
| 2003/0187261 A1 | 10/2003 | Havlicek et al. | |
| 2003/0191086 A1 | 10/2003 | Hanus et al. | |
| 2004/0166137 A1 | 8/2004 | Lackey | |
| 2006/0154931 A1 | 7/2006 | Verhoest et al. | |
| 2008/0090834 A1 | 4/2008 | Hoover et al. | |
| 2009/0042890 A1 * | 2/2009 | Mortensen et al. | 514/249 |
| 2009/0264403 A1 | 10/2009 | Schwink et al. | |
| 2010/0016353 A1 | 1/2010 | Henne et al. | |
| 2010/0112090 A1 | 5/2010 | Yonekubo et al. | |
| 2010/0125062 A1 | 5/2010 | Allen et al. | |
| 2010/0137278 A1 | 6/2010 | Allen et al. | |
| 2010/0197651 A1 | 8/2010 | Taniguchi et al. | |
| 2010/0267714 A1 | 10/2010 | Jorgensen et al. | |
| 2011/0160182 A1 | 6/2011 | Allen et al. | |
| 2011/0160202 A1 | 6/2011 | Allen et al. | |
| 2012/0004261 A1 | 1/2012 | Jorgensen et al. | |
| 2012/0040974 A1 | 2/2012 | Jorgensen et al. | |

FOREIGN PATENT DOCUMENTS

| | | |
|---|---|---|
| AU | 2011/299894 | 3/2013 |
| EP | 0 701 819 | 3/1996 |
| WO | 94/21619 | 9/1994 |
| WO | 9421619 | * 9/1994 |
| WO | 00/43394 | 7/2000 |
| WO | 01/49688 | 7/2001 |
| WO | 2004/043913 | 5/2004 |
| WO | 2006/038111 | 4/2006 |
| WO | 2006/072828 | 7/2006 |
| WO | 2007/093364 | 8/2007 |
| WO | 2008/001182 | 1/2008 |
| WO | 2008/004117 | 1/2008 |
| WO | 2008/129994 | 10/2008 |
| WO | 2010/021693 | 2/2010 |
| WO | 2010/057121 | 5/2010 |
| WO | 2010/057126 | 5/2010 |
| WO | 2010/090737 | 8/2010 |
| WO | 2012/033149 | 3/2012 |

OTHER PUBLICATIONS

Kehler et. al., "The potential therapeutic use of phosphodiesterase 10 inhibitors", Expert Opinion Ther. Patents (2007) 17 (2), pp. 147-158.*
Leszek et. al., "Alzheimer's disease—immunological aspects", Acta Neurobiol. Exp. 1993, 53:351-355.*
F. S. Menniti et al., "Phosphodiesterases in the CNS: Targets for Drug Development", Nat. Rev. Drug Discov., vol. 5, pp. 660-670, Aug. 2006.
M. D. Houslay et al., "cAMP-Specific Phosphodiesterase-4 Enzymes in the Cardiovascular System: A Molecular Toolbox for Generating Compartmentalized cAMP Signaling", Circulation Research, vol. 100, No. 7, pp. 950-966, 2007.
Nakayama et al., "Expression Cloning of a Human α1,4-N-Acetylglucosaminyltransferase that forms GlcNAcα1 →4Galβ→R, A Glycan Specifically Expressed in the Gastric Gland Mucous Cell-Type Mucin", Proc. Natl. Acad. Sci., vol. 96, pp. 8991-8996, Aug. 1999.
K. Fujishige et al., "Cloning and Characterization of a Novel Human Phosphodiesterase that Hydrolyzes both cAMP and cGMP (PDE10A)", The Journal of Biological Chemistry, vol. 274, No. 26, pp. 18438-18445, Jun. 25, 1999.

(Continued)

*Primary Examiner* — Niloofar Rahmani
(74) *Attorney, Agent, or Firm* — Wenderoth, Lind & Ponack, L.L.P.

(57) ABSTRACT

The present invention provides a compound which has the effect of PDE inhibition, and which is useful as an agent for preventing or treating schizophrenia. The compound is represented by the formula (I):

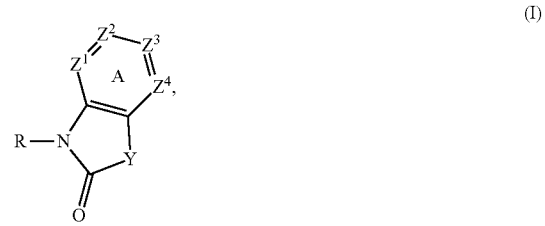

wherein the symbols are defined in the specification.

15 Claims, 2 Drawing Sheets

(56) References Cited

OTHER PUBLICATIONS

K. Loughney et al., "Isolation and Characterization of PDE10A, A Novel Human 3',5'-Cyclic Nucleotide Phosphodiesterase", Gene, vol. 234, pp. 109-117, 1999.

K. Fujishige et al., "Striatum- and Testis-Specific Phosphodiesterase PDE10A Isolation and Characterization of a Rat PDE10A", Eur. J. Biochem., vol. 266, pp. 1118-1127, 1999.

T. F. Seeger et al., "Immunohistochemical Localization of PDE10A in the Rat Brain", Brain Research, vol. 985, pp. 113-126, 2003.

Y. M. Yutilov et al., "Synthesis of 1- and 3-Substituted Imidazo[4,5-b]pyridine-2-ones", Russian Journal of Organic Chemistry, vol. 42, No. 6, pp. 897-900, 2006.

J. T. Kuethe et al., "Synthesis of Disubstituted Imidazo[4,5-b]pyridine-2-ones", Journal of Organic Chemistry, vol. 69, No. 22, pp. 7752-7754, 2004.

R. L. Clark et al., "Synthesis and Analgesic Activity of 1,3-Dihydro-3-(substituted phenyl)imidazo[4,5-b]pyridine-2-ones and 3-(Substituted phenyl)-1,2,3-triazolo[4,5-b]pyridines", Journal of Medicinal Chemistry, vol. 21, No. 9, pp. 965-978, 1978.

Chemical Library (RN 392735-33-0), Registry, Feb. 15, 2002.

International Search Report issued Oct. 12, 2011 in International (PCT) Application No. PCT/US2011/041443 along with the Written Opinion.

\* cited by examiner

FUSED HETEROCYCLIC COMPOUNDS

This application claims the benefit of U.S. provisional application Ser. No. 61/358,121, filed Jun. 24, 2010 and claims the benefit of U.S. provisional application Ser. No. 61/422,845, filed Dec. 14, 2010.

TECHNICAL FIELD

The present invention relates to fused heterocyclic compounds.

BACKGROUND OF THE INVENTION

Phosphodiesterases (PDEs) are a superfamily of enzymes encoded by 21 genes and subdivided into 11 distinct families according to structural and functional properties. These enzymes metabolically inactivate the ubiquitous intracellular second messengers, cyclic adenosine monophosphate (cAMP) and cyclic guanosine monophosphate (cGMP); PDEs selectively catalyze the hydrolysis of the 3'-ester bond, forming the inactive 5'-monophosphate. On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11).

The cAMP and cGMP are involved in the regulation of virtually every physiological process such as pro-inflammatory mediator production and action, ion channel function, muscle relaxation, learning and memory formation, differentiation, apoptosis, lipogenesis, glycogenolysis and gluconeogenesis. Especially, in neurons, these second messengers have important role in the regulation of synaptic transmission as well as in neuronal differentiation and survival (Nat. Rev. Drug Discov. 2006, vol. 5: 660-670). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, spatially, and functionally compartmentalized by regulation of adenyl and guanyl cyclases in response to extracellular signaling and their degradation by PDEs (Circ. Res. 2007, vol. 100(7): 950-966). PDEs provide the only means of degrading the cyclic nucleotides cAMP and cGMP in cells, thus PDEs play an essential role in cyclic nucleotide signaling. Thereby, PDEs could be promising targets for various therapeutic drugs.

Phosphodiesterase 10A (PDE10A) was discovered in 1999 by three independent groups (Proc. Natl. Acad. Sci. USA 1999, vol. 96: 8991-8996, J. Biol. Chem. 1999, vol. 274: 18438-18445, Gene 1999, vol. 234: 109-117). Expression studies have shown that PDE10A has the most restricted distribution within the all known PDE families; the PDE10A mRNA is highly expressed only in brain and testes (Eur. J. Biochem. 1999, vol. 266: 1118-1127, J. Biol. Chem. 1999, vol. 274: 18438-18445). In the brain, mRNA and protein of PDE10A are highly enriched in medium spiny neurons (MSNs) of the striatum (Eur. J. Biochem. 1999, vol. 266: 1118-1127, Brain Res. 2003, vol. 985: 113-126). MSNs are classified into two groups: the MSN that express $D_1$ dopamine receptors responsible for a direct (striatonigral) pathway and the MSN that express $D_2$ dopamine receptors responsible for an indirect (striatopallidal) pathway. The function of direct pathway is to plan and execution, while indirect pathway is to act as a brake on behavioral activation. As PDE10A expresses in both MSNs, PDE10A inhibitors could activate both of these pathways. The antipsychotic efficacy of current medications, $D_2$ or $D_2$/5-$HT_{2A}$ antagonists, mainly derives from their activation of the indirect pathway in the striatum. As PDE10A inhibitors are able to activate this pathway, this suggests that PDE10A inhibitors are promising as antipsychotic drugs. The excessive $D_2$ receptor antagonism in the brain by $D_2$ antagonists causes problems of extrapyramidal side effects and hyperprolactinaemia. However the expression of PDE10A is limited to these striatal pathways in the brain, thus side effects by PDE10A inhibitors were expected to be weaker compared with current $D_2$ antagonists. Regarding hyperprolactinaemia, PDE10A inhibitors would produce no prolactin elevation due to lack of $D_2$ receptor antagonism in the pituitary. Moreover, the presence of PDE10A in a direct pathway makes it likely that PDE10A inhibition will have some advantage over current $D_2$ antagonists; the direct pathway is thought to promote desired action, and activation of this pathway by PDE10A inhibitors may counteract extrapyramidal symptoms induced by excessive $D_2$ receptor antagonism. In addition, activation of this pathway could facilitate striatal-thalamic outflow, promoting the execution of procedural strategies. Furthermore, enhancement of second messenger levels without blockade of dopamine and/or other neurotransmitter receptors may also provide therapeutic advantages with fewer adverse side-effects compared with current antipsychotics (e.g., hyperprolactinaemia and weight gain). This unique distribution and function in the brain indicates that PDE10A represents an important new target for the treatment of neurological and psychiatric disorders, in particular psychotic disorders like schizophrenia.

As a phosphodiesterase (PDE) 10 inhibitor, compounds represented by the formulae:

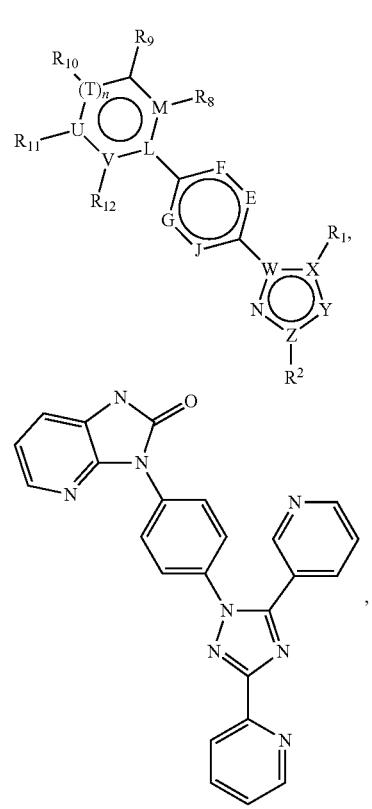

I

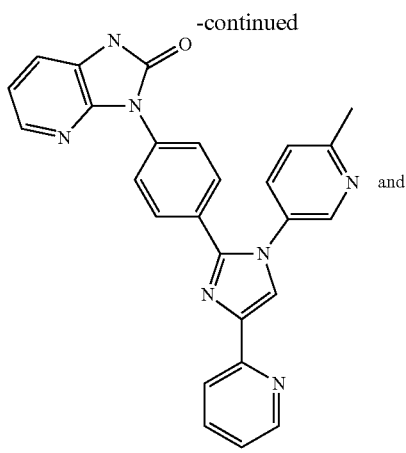

and

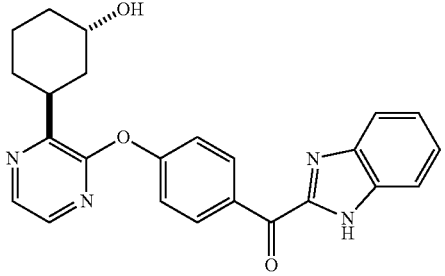

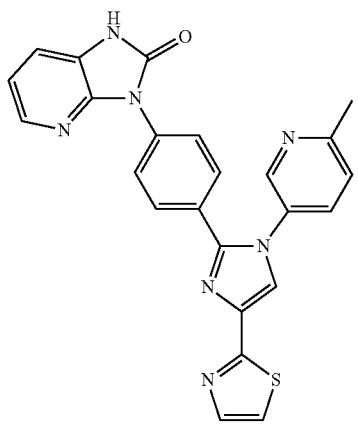

were disclosed in WO2010/0057121 Pamphlet.

Further, as a phosphodiesterase (PDE) 10 inhibitor, compounds represented by the formulae:

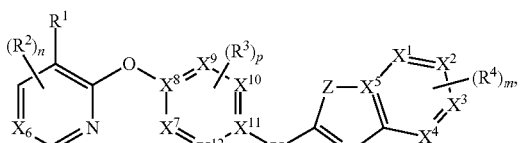

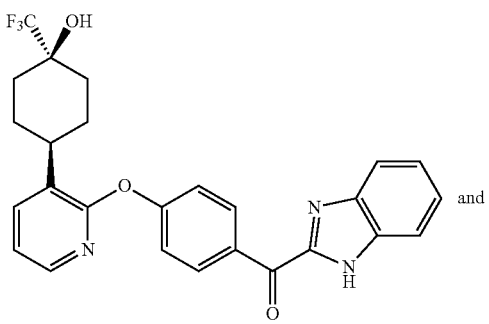

were disclosed in WO2008/004117 Pamphlet.

Further, as a phosphodiesterase (PDE) 10 inhibitor, compounds represented by the formulae:

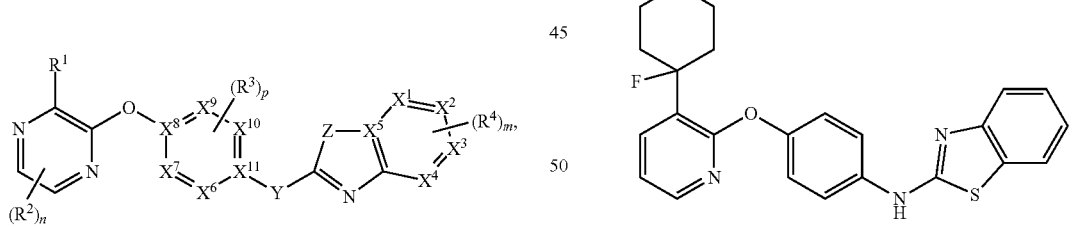

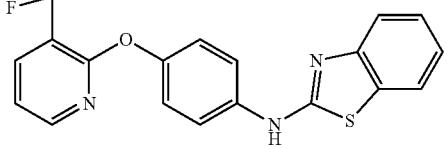

and

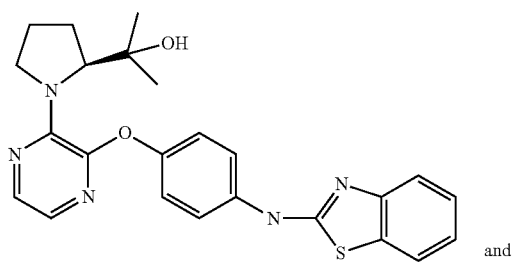

were also disclosed in WO2010/57126 Pamphlet.

Further as a phosphodiesterase (PDE) 10 inhibitor, a compound represented by the formula:

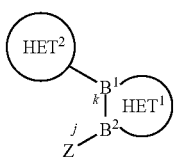

I and wherein Z is

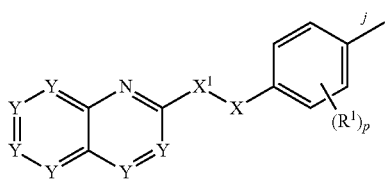

was disclosed in WO2006/072828 Pamphlet.

Further, as a phosphodiesterase (PDE) 10 inhibitor, a compound represented by the general formula

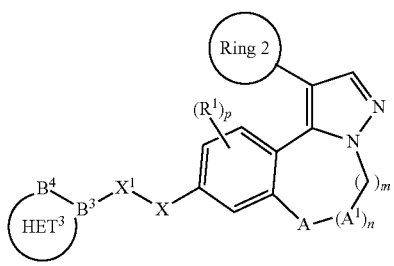

was also disclosed in WO2008/001182 Pamphlet.

Further, as a phosphodiesterase (PDE) 10 inhibitor, a compound represented by the general formula

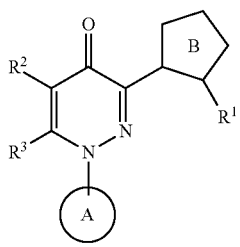

was also disclosed in WO2010/090737 Pamphlet.

SUMMARY OF INVENTION

Technical Problem

However, development of new phosphodiesterase (PDE) 10A inhibitors is further requested.

Solution to Problem

The present inventors discovered that a compound expressed by the formula (I) or a salt thereof (referred to as compound (I) in this specification) has a PDE 10A inhibitory action and after extensive investigation, completed the present invention.

In this specification, the compound (I) or a prodrug thereof is also referred to as the compound of the present invention.

That is, the present invention provides the following.
[1] A compound represented by the formula (I):

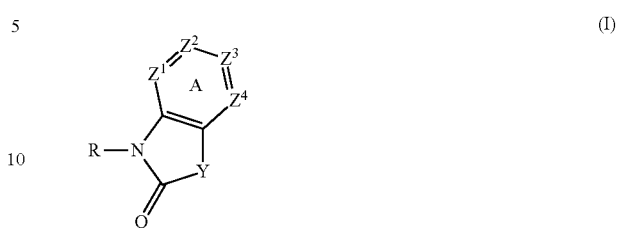

wherein
ring A represents an optionally substituted 6-membered ring, any one or two of $Z^1$ to $Z^4$ represent —N=, and the others m represent —CH=,
Y represents an oxygen atom, a sulfur atom, an optionally substituted methylene group or —$NR^c$— wherein $R^c$ represents a hydrogen atom or a substituent, and
R represents
(1) a group represented by the formula:

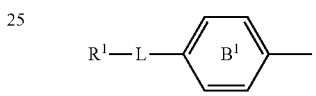

wherein
$R^1$ is a phenyl group or a 5- to 10-membered heterocyclic group, each of which is optionally substituted,
L is a sulfur atom, an oxygen atom, an optionally substituted methylene group, —CO—, —$NR^a$—, —$CH_2O$—, —$OCH_2$—, —$NR^aCOO$—, —$OCONR^a$—, —$NR^a$-$CONR^b$—, —$NR^aCOCH_2$—, —$CH_2CONR^a$—, —$NR^aCO$—, —$CONR^a$—,

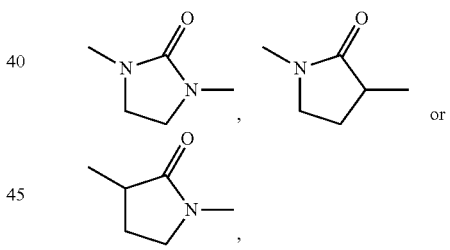

wherein
$R^a$ and $R^b$ are the same or different and each is a hydrogen atom or an optionally substituted $C_{1-6}$ alkyl group, or
L and $R^1$ in combination optionally form an optionally substituted bi- or tri-cyclic fused heterocyclic group, and
ring $B^1$ is a benzene ring, a pyridine ring, a pyrimidine ring, a pyrazine ring or a pyridazine ring, each of which is optionally substituted, or
(2) a group represented by the formula:

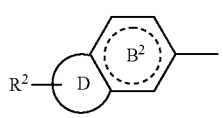

wherein
$R^2$ is a phenyl group or a 5- to 10-membered heterocyclic group, each of which is optionally substituted, ring $B^2$ is a benzene ring, a pyridine ring, a pyrimidine ring, a pyrazine ring or a pyridazine ring, each of which is optionally substituted, and ring D is an optionally further substituted 5- or 6-membered ring, provided that 3,3'-benzene-1,4-diylbis(1,3-dihydro-2H-imidazo[4,5-b]pyridin-2-one), 1-cyclohexyl-3-(4-{[4-(methylsulfonyl)piperazin-1-yl]methyl}phenyl)-1,3-dihydro-2H-imidazo[4,5-b]pyridin-2-one, 3-(4-phenoxyphenyl)-1,3-dihydro-2H-imidazo[4,5-b]pyridin-2-one, 3,3'-benzene-1,4-diylbis(1,3-dihydro-2H-imidazo[4,5-c]pyridin-2-one), and 3-[8-(4-methylpiperazin-1-yl)naphthalen-2-yl]-1,3-dihydro-2H-imidazo[4,5-b]pyridin-2-one are excluded, or a salt thereof.

[1'] The compound of the aforementioned [1], wherein R is
(1) a group represented by the formula:

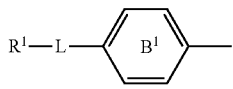

wherein each symbol is as defined in the aforementioned [1], or
(2) a group represented by the formula:

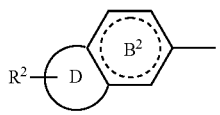

wherein ring $B^2$ is a benzene ring, a pyridine ring, a pyrimidine ring, a pyrazine ring or a pyridazine ring, each of which is optionally substituted, and ring D is an optionally further substituted 5- or 6-membered ring, $R^2$ is as defined in the aforementioned [1], provided that when ring $B^2$ is a benzene ring, ring D is not a benzene ring, or a salt thereof.

[1"] The compound of the aforementioned [1], wherein R is
(1) a group represented by the formula:

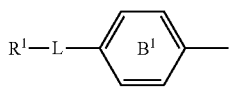

wherein $R^1$ is a phenyl group or a 5- to 10-membered heterocyclic group, each of which is optionally substituted, L is a sulfur atom, an oxygen atom, an optionally substituted methylene group, —CO—, —NR$^a$—, —CH$_2$O—, —OCH$_2$—, —NR$^a$COO—, —OCONR$^a$—, —NR$^a$CONR$^b$—, —NR$^a$COCH$_2$—, —CH$_2$CONR$^a$—, —NR$^a$CO—, —CONR$^a$—,

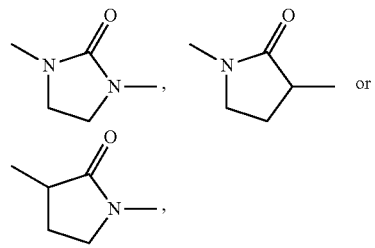

wherein $R^a$ and $R^b$ are as defined in the aforementioned [1], or L and $R^1$ in combination optionally form an optionally substituted bi- or tri-cyclic fused heterocyclic group, and ring $B^1$ is a benzene ring, a pyridine ring, a pyrimidine ring, a pyrazine ring or a pyridazine ring, each of which is optionally substituted, provided that when L is an oxygen atom, $R^1$ is not an optionally substituted phenyl, or (2) a group represented by the formula:

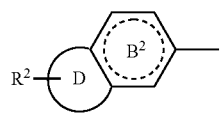

wherein each symbol is as defined in the aforementioned [1], or a salt thereof.

[2] The compound of the aforementioned [1], wherein any one of $Z^1$ to $Z^4$ is —N═, and the others are —CH═, or a salt thereof.

[3] The compound of the aforementioned [1], wherein the partial structure of the formula (I):

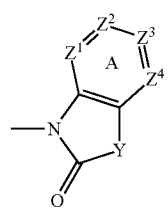

is a group represented by the formula:

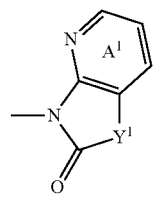

wherein $Y^1$ is an optionally substituted methylene group or —NR$^c$— wherein $R^c$ is a hydrogen atom or a substituent, and ring A[1] is an optionally substituted pyridine ring, or a group represented by the formula:

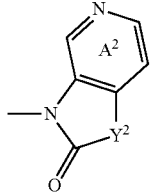

wherein
Y[2] is —NR[d]— wherein R[d] is a substituent, and
ring A[2] is an optionally substituted pyridine ring,
or a salt thereof.

[4] The compound of the aforementioned [1], wherein L is an oxygen atom, or —NR[a]— wherein R[a] is a hydrogen atom or an optionally substituted $C_{1-6}$ alkyl group, or
L and R[1] in combination optionally form an optionally substituted bi- or tri-cyclic fused heterocyclic group,
or a salt thereof.

[5] The compound of the aforementioned [3], wherein the partial structure of formula (I):

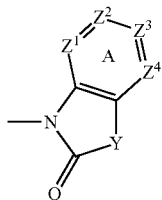

is a group represented by the formula:

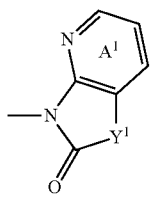

wherein ring A[1] and Y[1] are as defined in the aforementioned [3],
or a salt thereof.

[6] The compound of the aforementioned [3], wherein the partial structure of formula of formula (I):

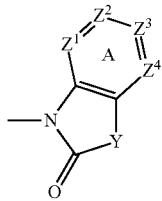

is a group represented by the formula:

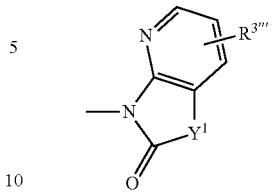

wherein
the R[3‴] represents a hydrogen atom, a halogen atom, an optionally substituted $C_{1-4}$ alkyl group, or an optionally substituted $C_{1-4}$ alkoxy group, and
Y[1] is as defined in the aforementioned [3],
or a salt thereof.

[7] The compound of the aforementioned [3], wherein the partial structure of formula (I):

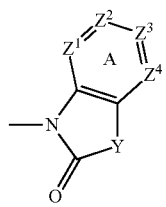

is a group represented by the formula:

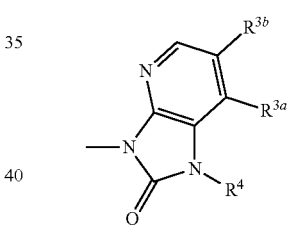

wherein
R[3a] and R[3b] represent the same or different a hydrogen atom, a halogen atom, cyano, an optionally substituted $C_{1-4}$ alkyl group or an optionally substituted $C_{1-4}$ alkoxy group, and
R[4] represents an optionally substituted $C_{1-4}$ alkyl group, provided that when one of R[3a] and R[3b] is a hydrogen atom, the other is not a hydrogen atom,
or a salt thereof.

[8] The compound of the aforementioned [1], wherein ring B[1] is an optionally substituted benzene ring, or a salt thereof.

[9] The compound of the aforementioned [1], wherein R[1] is a 5- to 10-membered heterocyclic group which is optionally substituted, or a salt thereof.

[10] The compound of the aforementioned [9], wherein the 5- to 10-membered heterocyclic group which is optionally substituted is a group represented by the formula:

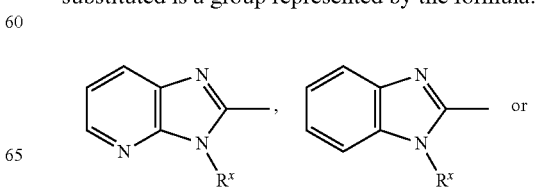

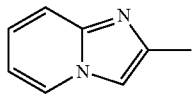

wherein R<sup>x</sup> represents a hydrogen atom or an optionally substituted C$_{1-6}$ alkyl group,
or a salt thereof.

[11] 1-Ethyl-6-methyl-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[12] 1-Ethyl-6-methoxy-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[13] 1-Ethyl-7-methyl-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[14] 6-Methyl-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[15] 1-Ethyl-6-fluoro-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[16] 1,7-Dimethyl-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[17] 1-Ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one, or a salt thereof.

[18] A medicament comprising the compound of the aforementioned [1], or a salt thereof.

[19] The medicament of the aforementioned [18], which is a phosphodiesterase 10A inhibitor.

[20] The medicament of the aforementioned [18], which is an agent for the prophylaxis or treatment of schizophrenia.

[21] A method for preventing or treating schizophrenia in a mammal, which comprises administering an effective amount of a compound represented by the formula (I):

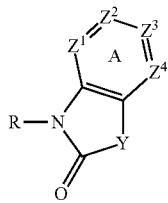
(I)

wherein
ring A represents an optionally substituted 6-membered ring, any one or two of Z$^1$ to Z$^4$ represent —N═, and the others represent —CH═,
Y represents an oxygen atom, a sulfur atom, an optionally substituted methylene group, or —NR$^c$— wherein R$^c$ represents a hydrogen atom or a substituent, and
R represents
(1) a group represented by the formula:

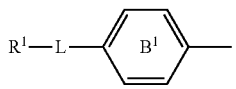

wherein
R$^1$ is a phenyl group or a 5- to 10-membered heterocyclic group, each of which is optionally substituted,
L is a sulfur atom, an oxygen atom, an optionally substituted methylene group, —CO—, —NR$^a$—, —CH$_2$O—, —OCH$_2$—, —NR$^a$COO—, —OCONR$^a$—, —NR$^a$CONR$^b$—, —NR$^a$COCH$_2$—, —CH$_2$CONR$^a$—, —NR$^a$CO—, —CONR$^a$—,

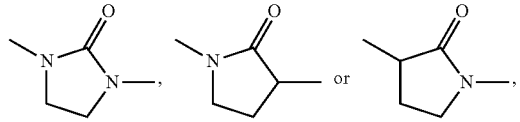

wherein
R$^a$ and R$^b$ are the same or different and each is a hydrogen atom or an optionally substituted C$_{1-6}$ alkyl group, or
L and R$^1$ in combination optionally form an optionally substituted bi- or tri-cyclic fused heterocyclic group, and ring B$^1$ is a benzene ring, a pyridine ring, a pyrimidine ring, a pyrazine ring or a pyridazine ring, each of which is optionally substituted, or (2) a group represented by the formula:

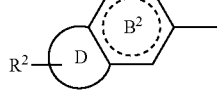

wherein
R$^2$ is a phenyl group or a 5- to 10-membered heterocyclic group, each of which is optionally substituted, ring B$^2$ is a benzene ring, a pyridine ring, a pyrimidine ring, a pyrazine ring or a pyridazine ring, each of which is optionally substituted, and
ring D is an optionally further substituted 5- or 6-membered ring,
to the mammal.

[22] Use of a compound represented by the formula (I):

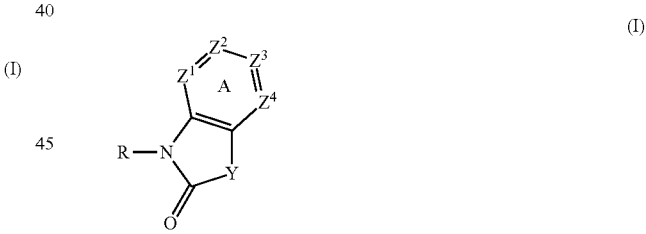
(I)

wherein each symbol is as defined above,
or salt thereof for the production of an agent for the prophylaxis or treatment of schizophrenia.

[23] A compound represented by the formula (I):

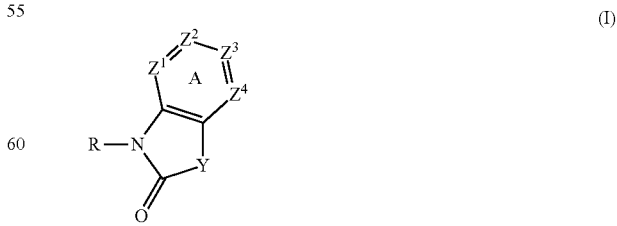
(I)

wherein each symbol is as defined above,
or salt thereof for use in the prophylaxis or treatment of schizophrenia.

[24] Use of a compound represented by the formula (I):

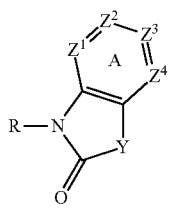

wherein each symbol is as defined above,
or a salt thereof for use in the prophylaxis or treatment of schizophrenia.

[25] A compound represented by the formula (I'):

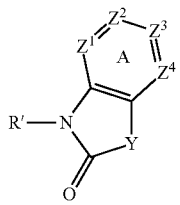

wherein
ring A represents an optionally substituted 6-membered ring, any one or two of $Z^1$ to $Z^4$ represent —N=, and the others represent —CH=,
Y represents an oxygen atom, a sulfur atom, an optionally substituted methylene group, or —$NR^c$— wherein $R^c$ represents a hydrogen atom or a substituent, and
R' represents
(1) a group represented by the formula:

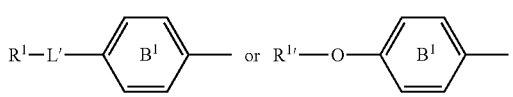

wherein
$R^1$ is a phenyl group or a 5- to 10-membered heterocyclic group, each of which is optionally substituted,
L' is a sulfur atom, —CO—, —$NR^a$—, —$CH_2O$—, —$OCH_2$—, —$NR^aCOO$—, —$OCONR^a$—, —$NR^a$-$CONR^b$—, —$NR^aCOCH_2$—, —$CH_2CONR^a$—, —$NR^aCO$—, —$CONR^a$—,

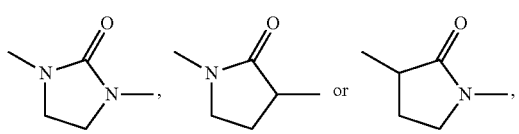

wherein
$R^a$ and $R^b$ are the same or different and each is a hydrogen atom or an optionally substituted $C_{1-6}$ alkyl group,
$R^{1'}$ is an optionally substituted 5- to 10-membered heterocyclic group, or
L and $R^1$ in combination optionally form a bi- or tri-cyclic fused heterocyclic group which is optionally substituted by 1 to 3 substitutents selected from (a) a halogen atom, (b) an optionally esterified carboxy group, and
(c) an optionally substituted alkyl group, and
ring $B^1$ is a benzene ring, a pyridine ring, a pyrimidine ring, a pyrazine ring or a pyridazine ring, each of which is optionally substituted, or
(2) a group represented by the formula:

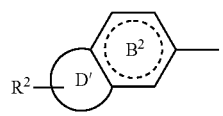

wherein
$R^2$ is a phenyl group or a 5- to 10-membered heterocyclic group, each of which is optionally substituted,
ring $B^2$ is a benzene ring, a pyridine ring, a pyrimidine ring, a pyrazine ring or a pyridazine ring, each of which is optionally substituted, and
ring D' is optionally further substituted 5- or 6-membered heterocycle,
or a salt thereof.

DETAILED DESCRIPTION OF THE INVENTION

Figure 1A:
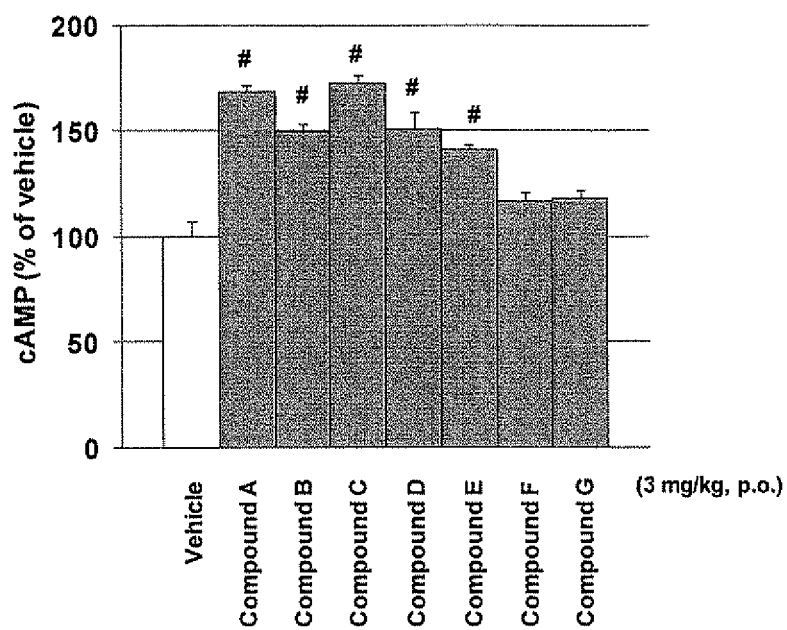
FIG. 1 shows increase of cAMP (FIG. 1A) and cGMP (FIG. 1B) contents in the mouse striatum by oral administration of compounds. Sixty min after oral administration of the compounds, striatum was isolated from mice and then cAMP and cGMP contents were measured using EIA kits.

In the present specification, unless otherwise specified, examples of the "halogen atom" include fluorine, chlorine, bromine and iodine.

In the present specification, unless otherwise specified, the term "optionally halogenated" or "halogeno" means the optionally presence of one or more (e.g., 1 to 3) halogen atoms as substituents.

In the present specification, unless otherwise specified, examples of the "alkyl (group)" include a $C_{1-6}$ alkyl (group).

In the present specification, unless otherwise specified, examples of the "$C_{1-6}$ alkyl (group)" include methyl, ethyl, propyl, isopropyl, butyl, isobutyl, sec-butyl, tert-butyl, pentyl, isopentyl, neopentyl, hexyl and the like.

In the present specification, unless otherwise specified, the "optionally halogenated $C_{1-6}$ alkyl (group)" means a $C_{1-6}$ alkyl (group) optionally substituted by halogen atom(s), and examples thereof include trifluoromethyl and the like.

In the present specification, unless otherwise specified, examples of the "alkenyl (group)" include a $C_{2-6}$ alkenyl (group).

In the present specification, unless otherwise specified, examples of the "$C_{2-6}$ alkenyl (group)" include vinyl, 1-propen-1-yl, 2-propen-1-yl, isopropenyl, 2-buten-1-yl, 4-penten-1-yl, 5-hexen-1-yl and the like.

In the present specification, unless otherwise specified, examples of the "alkynyl (group)" include a $C_{2-6}$ alkynyl group. Examples of the "$C_{2-6}$ alkynyl (group)" include ethynyl, 1-propyn-1-yl, 2-propyn-1-yl, 4-pentyn-1-yl, 5-hexyn-1-yl and the like.

In the present specification, unless otherwise specified, examples of the "$C_{3-7}$ cycloalkyl-$C_{2-6}$ alkynyl (group)" include cyclopropylethynyl and the like.

In the present specification, unless otherwise specified, examples of the "$C_{3-7}$ cycloalkyl (group)" include cyclopropyl, cyclobutyl, cyclopentyl, cyclohexyl and the like.

In the present specification, unless otherwise specified, examples of the "$C_{6-14}$ aryl (group)" include phenyl, 1-naphthyl, 2-naphthyl, 2-biphenylyl, 3-biphenylyl, 4-biphenylyl, 2-anthryl and the like.

In the present specification, unless otherwise specified, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

In the present specification, unless otherwise specified, examples of the "$C_{6-14}$ aryl-$C_{2-6}$ alkenyl (group)" include styryl and the like.

In the present specification, unless otherwise specified, examples of the "carbocycle having 5 or 6 carbon atoms" include a $C_{5-6}$ cycloalkane (e.g., cyclopentane, cyclohexane), a $C_{5-6}$ cycloalkene (e.g., cyclopentene, cyclohexene), a $C_{5-6}$ cycloalkadiene (e.g., cyclopentadiene, cyclohexadiene) and a benzene ring.

In the present specification, unless otherwise specified, examples of the "$C_{3-6}$ cycloalkane" include cyclopropane, cyclobutane, cyclohexane and cyclopentane.

In the present specification, unless otherwise specified, examples of the "5- or 6-membered heterocycle" include a 5- or 6-membered heterocycle containing, besides carbon atoms, 1 to 4 hetero atoms selected from a nitrogen atom, a sulfur atom and an oxygen atom.

In the present specification, unless otherwise specified, examples of the "5- or 6-membered heterocycle containing, besides carbon atoms, 1 to 4 hetero atoms selected from a nitrogen atom, a sulfur atom and an oxygen atom" include a pyrrolidine ring, a tetrahydrofuran ring, a tetrahydrothiophene ring, a piperidine ring, a tetrahydropyran ring, a morpholine ring, a thiomorpholine ring, a piperazine ring, a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring and the like.

In the present specification, unless otherwise specified, "heterocyclic group" (and the heterocyclic moiety of the substituent) is a non-aromatic heterocyclic group or a heteroaryl group (i.e., an aromatic heterocyclic group), and examples thereof include a 3- to 14-membered heterocyclic group containing 1 to 5 hetero atoms selected from a nitrogen atom, a sulfur atom and an oxygen atom. The "heterocyclic group" can be monocyclic, bicyclic or tricyclic.

In the present specification, unless otherwise specified, examples of the "3- to 14-membered heterocyclic group" include 3- to 14-membered aromatic heterocyclic groups containing 1 to 5 hetero atoms selected from a nitrogen atom, a sulfur atom and an oxygen atom, such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 5-phthalazinyl, 6-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 5-quinoxalinyl, 6-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridine-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like; and 3- to 14-membered saturated or unsaturated non-aromatic heterocyclic groups containing 1 to 5 hetero atoms selected from a nitrogen atom, a sulfur atom and an oxygen atom, such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidyl (e.g., 1-piperidyl, 2-piperidyl, 3-piperidyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), azonanyl (e.g., 1-azonanyl, 2-azonanyl, 3-azonanyl, 4-azonanyl, 5-azonanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4- diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, dihydroisoquinolyl (e.g., 3,4-dihydroisoquinolin-2-yl) and the like.

In the present specification, unless otherwise specified, examples of the "aromatic heterocyclic group" (and the aromatic heterocyclic moiety of the substituent) include those similar to the "3- to 14-membered aromatic heterocyclic group containing 1 to 5 hetero atoms selected from a nitrogen atom, a sulfur atom and an oxygen atom" exemplified above as the aforementioned "heterocyclic group".

In the present specification, unless otherwise specified, examples of the "non-aromatic heterocyclic group" (and the non-aromatic heterocyclic moiety of the substituent) include those similar to the "3- to 14-membered saturated or unsaturated non-aromatic heterocyclic group containing 1 to 5 hetero atoms selected from a nitrogen atom, a sulfur atom and an oxygen atom" exemplified above as the aforementioned "heterocyclic group".

In the present specification, unless otherwise specified, examples of the "saturated heterocyclic group" (and the saturated heterocyclic moiety of the substituent) include a saturated heterocyclic group, from among the aforementioned "non-aromatic heterocyclic groups", and specific examples thereof include tetrahydrofuryl, morpholinyl, thiomorpholinyl, piperidyl, pyrrolidinyl, piperazinyl and the like.

In the present specification, unless otherwise specified, examples of the "5- or 6-membered saturated heterocyclic group" (and the 5- or 6-membered saturated heterocyclic moiety of the substituent) include a 5- or 6-membered saturated heterocyclic group, from among the aforementioned "saturated heterocyclic groups".

In the present specification, unless otherwise specified, examples of the "alkoxy (group)" include a $C_{1-6}$ alkoxy (group).

In the present specification, unless otherwise specified, examples of the "$C_{1-6}$ alkoxy (group)" include methoxy, ethoxy, propoxy, isopropoxy, butoxy, isobutoxy, sec-butoxy, pentyloxy, hexyloxy and the like.

In the present specification, unless otherwise specified, examples of the "$C_{3-7}$ cycloalkyloxy (group)" include cyclopropyloxy, cyclobutyloxy, cyclopentyloxy, cyclohexyloxy and the like.

In the present specification, unless otherwise specified, examples of the "$C_{6-14}$ aryloxy (group)" include phenyloxy, 1-naphthyloxy, 2-naphthyloxy and the like.

In the present specification, unless otherwise specified, examples of the "$C_{7-16}$ aralkyloxy (group)" include benzyloxy, phenethyloxy and the like.

In the present specification, unless otherwise specified, examples of the "alkyl-carbonyloxy (group)" include a $C_{1-6}$ alkyl-carbonyloxy (group).

In the present specification, unless otherwise specified, examples of the "$C_{1-6}$ alkyl-carbonyloxy (group)" include acetoxy, propionyloxy and the like.

In the present specification, unless otherwise specified, examples of the "alkoxy-carbonyloxy (group)" include a $C_{1-6}$ alkoxy-carbonyloxy (group).

In the present specification, unless otherwise specified, examples of the "$C_{1-6}$ alkoxy-carbonyloxy (group)" include methoxycarbonyloxy, ethoxycarbonyloxy, propoxycarbonyloxy, butoxycarbonyloxy and the like.

In the present specification, unless otherwise specified, examples of the "mono-alkyl-carbamoyloxy (group)" include a mono-$C_{1-6}$ alkyl-carbamoyloxy (group).

In the present specification, unless otherwise specified, examples of the "mono-$C_{1-6}$ alkyl-carbamoyloxy (group)" include methylcarbamoyloxy, ethylcarbamoyloxy and the like.

In the present specification, unless otherwise specified, examples of the "di-alkyl-carbamoyloxy (group)" include a di-$C_{1-6}$ alkyl-carbamoyloxy (group).

In the present specification, unless otherwise specified, examples of the "di-$C_{1-6}$ alkyl-carbamoyloxy (group)" include dimethylcarbamoyloxy, diethylcarbamoyloxy and the like.

In the present specification, unless otherwise specified, examples of the "$C_{6-14}$ aryl-carbonyloxy (group)" include benzoyloxy, naphthylcarbonyloxy and the like.

In the present specification, unless otherwise specified, examples of the "mono- or di-$C_{6-14}$ aryl-carbamoyl (group)" include phenylcarbamoyl, naphthylcarbamoyl and the like.

In the present specification, unless otherwise specified, examples of the "mono- or di-$C_{6-14}$ aryl-carbamoyloxy (group)" include phenylcarbamoyloxy, naphthylcarbamoyloxy and the like.

In the present specification, unless otherwise specified, examples of the heterocyclic moiety of the "heterocyclyl-oxy (group)" include those similar to the aforementioned "heterocyclic group". Specific examples of the "heterocyclyl-oxy (group)" include a 5- to 14-membered heterocyclyl-oxy (group) containing 1 to 5 hetero atoms selected from a nitrogen atom, a sulfur atom and an oxygen atom.

In the present specification, unless otherwise specified, examples of the aromatic heterocyclic moiety of the "aromatic heterocyclyl-oxy (group)" include those similar to the "aromatic heterocyclic group" exemplified as the aforementioned "heterocyclic group". Specific examples of the "aromatic heterocyclyl-oxy (group)" include a 3- to 14-membered aromatic heterocyclyl-oxy containing 1 to 5 hetero atoms selected from a nitrogen atom, a sulfur atom and an oxygen atom.

In the present specification, unless otherwise specified, examples of the "$C_{1-6}$ alkylsulfonyloxy group" include methylsulfonyloxy, ethylsulfonyloxy and the like.

In the present specification, unless otherwise specified, examples of the "halogeno $C_{1-6}$ alkylsulfonyloxy group" include halogenomethylsulfonyloxy, halogenoethylsulfonyloxy and the like.

In the present specification, unless otherwise specified, examples of the "alkylsulfanyl (group)" include a $C_{1-6}$ alkylsulfanyl (group).

In the present specification, unless otherwise specified, examples of the "$C_{1-6}$ alkylsulfanyl (group)" include methylsulfanyl, ethylsulfanyl, propylsulfanyl, isopropylsulfanyl, butylsulfanyl, sec-butylsulfanyl, tert-butylsulfanyl and the like.

In the present specification, unless otherwise specified, examples of the "$C_{3-7}$ cycloalkylsulfanyl (group)" include cyclopropylsulfanyl, cyclobutylsulfanyl, cyclopentylsulfanyl, cyclohexylsulfanyl and the like.

In the present specification, unless otherwise specified, examples of the "$C_{6-14}$ arylsulfanyl (group)" include phenylsulfanyl, 1-naphthylsulfanyl, 2-naphthylsulfanyl and the like.

In the present specification, unless otherwise specified, examples of the "$C_{7-16}$ aralkylsulfanyl (group)" include benzylsulfanyl, phenethylsulfanyl and the like.

In the present specification, unless otherwise specified, examples of the heterocyclic moiety of the "heterocyclyl-sulfanyl (group)" include those similar to the aforementioned "heterocyclic group". Specific examples of the "heterocyclyl-sulfanyl (group)" include a 3- to 14-membered heterocyclyl-sulfanyl (group) containing 1 to 5 hetero atoms selected from a nitrogen atom, a sulfur atom and an oxygen atom.

In the present specification, unless otherwise specified, examples of the "alkyl-carbonyl (group)" include a $C_{1-6}$ alkyl-carbonyl.

In the present specification, unless otherwise specified, examples of the "$C_{1-6}$ alkyl-carbonyl (group)" include acetyl, propionyl, pivaloyl and the like.

In the present specification, unless otherwise specified, examples of the "$C_{3-7}$ cycloalkyl-carbonyl (group)" include cyclopropylcarbonyl, cyclopentylcarbonyl, cyclohexylcarbonyl and the like.

In the present specification, unless otherwise specified, examples of the "$C_{6-14}$ aryl-carbonyl (group)" include benzoyl, 1-naphthoyl, 2-naphthoyl and the like.

In the present specification, unless otherwise specified, examples of the "$C_{7-16}$ aralkyl-carbonyl (group)" include phenylacetyl, 3-phenylpropionyl and the like.

In the present specification, unless otherwise specified, examples of the heterocyclic moiety of the "heterocyclyl-carbonyl (group)" include those similar to the above-mentioned "heterocyclic group". Specific examples thereof include a 3- to 14-membered heterocyclyl-carbonyl (group) containing 1 to 5 hetero atoms selected from a nitrogen atom, a sulfur atom and an oxygen atom. More specific examples thereof include picolinoyl, nicotinoyl, isonicotinoyl, 2-thenoyl, 3-thenoyl, 2-furoyl, 3-furoyl, 4-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl, 1,5-diazocan-3-ylcarbonyl and the like.

In the present specification, unless otherwise specified, examples of the "optionally esterified carboxy (group)" include carboxy, optionally substituted alkoxy-carbonyl, optionally substituted $C_{6-14}$ aryloxy-carbonyl, optionally substituted $C_{7-16}$ aralkyloxy-carbonyl, optionally substituted silyloxy-carbonyl (e.g., trimethylsilyloxycarbonyl (TMS-O—CO—), triethylsilyloxycarbonyl (TES-O—CO—), tert-butyldimethylsilyloxycarbonyl (TBS-O—CO—), triisopropylsilyloxycarbonyl (TIPS-O—CO—), tert-butyldiphenylsilyloxycarbonyl (TBDPS-O—CO—)) and the like.

In the present specification, unless otherwise specified, examples of the "alkoxy-carbonyl (group)" include a $C_{1-6}$ alkoxy-carbonyl (group).

In the present specification, unless otherwise specified, examples of the "$C_{1-6}$ alkoxy-carbonyl (group)" include methoxycarbonyl, ethoxycarbonyl, propoxycarbonyl, tert-butoxycarbonyl and the like.

In the present specification, unless otherwise specified, examples of the "$C_{6-14}$ aryloxy-carbonyl (group)" include phenoxycarbonyl and the like.

In the present specification, unless otherwise specified, examples of the "$C_{7-16}$ aralkyloxy-carbonyl (group)" include benzyloxycarbonyl, phenethyloxycarbonyl and the like.

In the present specification, unless otherwise specified, examples of the "alkylsulfonyl (group)" include a $C_{1-6}$ alkylsulfonyl (group).

In the present specification, unless otherwise specified, examples of the "$C_{1-6}$ alkylsulfonyl (group)" include methylsulfonyl, ethylsulfonyl and the like.

In the present specification, unless otherwise specified, examples of the "$C_{3-7}$ cycloalkylsulfonyl (group)" include cyclopropylsulfonyl, cyclobutylsulfonyl, cyclopentylsulfonyl, cyclohexylsulfonyl and the like.

In the present specification, unless otherwise specified, examples of the "$C_{6-14}$ arylsulfonyl (group)" include phenylsulfonyl, 1-naphthylsulfonyl, 2-naphthylsulfonyl and the like.

In the present specification, unless otherwise specified, examples of the heterocyclic moiety of the "heterocyclyl-sulfonyl (group)" include those similar to the aforementioned "heterocyclic group". Specific examples of the "heterocyclyl-sulfonyl (group)" include a 3- to 14-membered heterocyclyl-sulfonyl (group) containing 1 to 5 hetero atoms selected from a nitrogen atom, a sulfur atom and an oxygen atom.

In the present specification, unless otherwise specified, examples of the "alkylsulfinyl (group)" include a $C_{1-6}$ alkylsulfinyl (group).

In the present specification, unless otherwise specified, examples of the "$C_{1-6}$ alkylsulfinyl (group)" include methylsulfinyl, ethylsulfinyl and the like.

In the present specification, unless otherwise specified, examples of the "$C_{3-7}$ cycloalkylsulfinyl (group)" include cyclopropylsulfinyl, cyclobutylsulfinyl, cyclopentylsulfinyl, cyclohexylsulfinyl and the like.

In the present specification, unless otherwise specified, examples of the "$C_{6-14}$ arylsulfinyl (group)" include phenylsulfinyl, 1-naphthylsulfinyl, 2-naphthylsulfinyl and the like.

In the present specification, unless otherwise specified, examples of the heterocyclic moiety of the "heterocyclyl-sulfinyl (group)" include those similar to the aforementioned "heterocyclic group". Specific examples of the "heterocyclyl-sulfinyl (group)" include a 3- to 14-membered heterocyclyl-sulfinyl (group) containing 1 to 5 hetero atoms selected from a nitrogen atom, a sulfur atom and an oxygen atom.

In the present specification, unless otherwise specified, examples of the "alkyl-carbamoyl (group)" include a mono- or di-$C_{1-6}$ alkyl-carbamoyl.

In the present specification, unless otherwise specified, examples of the "mono- or di-$C_{1-6}$ alkyl-carbamoyl (group)" include methylcarbamoyl, ethylcarbamoyl, propylcarbamoyl and the like.

In the present specification, unless otherwise specified, examples of the "mono- or di-alkylamino (group)" include a mono- or di-$C_{1-6}$ alkylamino (group).

In the present specification, unless otherwise specified, examples of the "mono- or di-$C_{1-6}$ alkylamino (group)" include methylamino, ethylamino, propylamino, dimethylamino, diethylamino and the like.

In the present specification, unless otherwise specified, examples of the "alkyl-carbonylamino (group)" include a mono- or di-$C_{1-6}$ alkyl-carbonylamino.

In the present specification, unless otherwise specified, examples of the "mono- or di-$C_{1-6}$ alkyl-carbonylamino (group)" include acetylamino, propionylamino, pivaloylamino and the like.

In the present specification, unless otherwise specified, examples of the "heterocyclyl (group)" of the "heterocyclyl-amino (group)" include those similar to the above-mentioned "heterocyclic group". Examples of the "heterocyclyl-amino (group)" include 2-pyridyl-amino and the like.

In the present specification, unless otherwise specified, examples of the "heterocyclyl-carbonyl" of the "heterocyclyl-carbonylamino (group)" include those similar to the above-mentioned "heterocyclyl-carbonyl". Examples of the "heterocyclyl-carbonylamino (group)" include pyridyl-carbonylamino.

In the present specification, unless otherwise specified, examples of the "heterocyclyl (group)" of the "heterocyclyl-oxycarbonylamino (group)" include those similar to the above-mentioned "heterocyclic group". Examples of the "heterocyclyl-oxycarbonylamino (group)" include 2-pyridyl-oxycarbonylamino.

In the present specification, unless otherwise specified, examples of the "heterocyclyl (group)" of the "heterocyclyl-sulfonylamino (group)" include those similar to the above-mentioned "heterocyclic group". Examples of the "heterocyclyl-sulfonylamino (group)" include 2-pyridyl-sulfonylamino and the like.

In the present specification, unless otherwise specified, examples of the "alkoxy-carbonylamino (group)" include a $C_{1-6}$ alkoxy-carbonylamino (group).

In the present specification, unless otherwise specified, examples of the "$C_{1-6}$ alkoxy-carbonylamino (group)" include methoxycarbonylamino, ethoxycarbonylamino, propoxycarbonylamino, butoxycarbonylamino and the like.

In the present specification, unless otherwise specified, examples of the "alkylsulfonylamino (group)" include a $C_{1-6}$ alkylsulfonylamino (group).

In the present specification, unless otherwise specified, examples of the "$C_{1-6}$ alkylsulfonylamino (group)" include methylsulfonylamino, ethylsulfonylamino and the like.

In the present specification, unless otherwise specified, examples of the "mono- or di-$C_{3-7}$ cycloalkylamino (group)" include cyclopropylamino, cyclopentylamino, cyclohexylamino and the like.

In the present specification, unless otherwise specified, examples of the "$C_{3-7}$ cycloalkyl-carbonylamino (group)" include cyclopropylcarbonylamino, cyclopentylcarbonylamino, cyclohexylcarbonylamino and the like.

In the present specification, unless otherwise specified, examples of the "$C_{3-8}$ cycloalkoxy-carbonylamino (group)" include cyclopropoxycarbonylamino, cyclopentyloxycarbonylamino, cyclohexyloxycarbonylamino and the like.

In the present specification, unless otherwise specified, examples of the "$C_{3-8}$ cycloalkylsulfonylamino (group)" include cyclopropylsulfonylamino, cyclopentylsulfonylamino, cyclohexylsulfonylamino and the like.

In the present specification, unless otherwise specified, examples of the "mono- or di-$C_{6-14}$ arylamino (group)" include phenylamino, diphenylamino and the like.

In the present specification, unless otherwise specified, examples of the "mono- or di-$C_{7-16}$ aralkylamino (group)" include benzylamino and the like.

In the present specification, unless otherwise specified, examples of the "$C_{6-14}$ aryl-carbonylamino (group)" include benzoylamino, naphthoylamino and the like.

In the present specification, unless otherwise specified, examples of the "$C_{6-14}$ arylsulfonylamino (group)" include phenylsulfonylamino, 2-naphthylsulfonylamino, 1-naphthylsulfonylamino and the like.

[Substituent Group A]
(1) a halogen atom;
(2) nitro;
(3) cyano;
(4) an optionally esterified carboxy group;
(5) an optionally substituted alkyl group;
(6) an optionally substituted alkenyl group;
(7) an optionally substituted alkynyl group (e.g., an optionally substituted $C_{3-7}$ cycloalkyl-$C_{2-6}$ alkynyl group);
(8) an optionally substituted $C_{3-7}$ cycloalkyl group;
(9) an optionally substituted $C_{6-14}$ aryl group;
(10) an optionally substituted $C_{7-16}$ aralkyl group;
(11) an optionally substituted $C_{6-14}$ aryl-$C_{2-6}$ alkenyl group;
(12) an optionally substituted heterocyclic group;
(13) a hydroxy group;
(14) an optionally substituted alkoxy group;
(15) an optionally substituted $C_{3-7}$ cycloalkyloxy group;
(16) an optionally substituted $C_{6-14}$ aryloxy group;
(17) an optionally substituted $C_{7-16}$ aralkyloxy group;
(18) an optionally substituted alkyl-carbonyloxy group;
(19) an optionally substituted alkoxy-carbonyloxy group;
(20) an optionally substituted mono-alkyl-carbamoyloxy group;
(21) an optionally substituted di-alkyl-carbamoyloxy group;
(22) an optionally substituted $C_{6-14}$ aryl-carbonyloxy group;
(23) an optionally substituted mono- or di-$C_{6-14}$ aryl-carbamoyloxy group;
(24) an optionally substituted heterocyclyl-oxy group (e.g., an optionally substituted aromatic heterocyclyl-oxy group);
(25) an optionally substituted $C_{1-6}$ alkylsulfonyloxy group (e.g., an optionally substituted halogeno $C_{1-6}$ alkylsulfonyloxy group);
(26) a mercapto group;
(27) an optionally substituted alkylsulfanyl group;
(28) an optionally substituted $C_{3-7}$ cycloalkylsulfanyl group;
(29) an optionally substituted $C_{6-14}$ arylsulfanyl group;
(30) an optionally, substituted $C_{7-16}$ aralkylsulfanyl group;
(31) an optionally substituted heterocyclyl-sulfanyl group;
(32) a formyl group;
(33) an optionally substituted alkyl-carbonyl group;
(34) an optionally substituted $C_{3-7}$ cycloalkyl-carbonyl group;
(35) an optionally substituted $C_{6-14}$ aryl-carbonyl group;
(36) an optionally substituted $C_{7-16}$ aralkyl-carbonyl group;
(37) an optionally substituted heterocyclyl-carbonyl group;
(38) an optionally substituted alkylsulfonyl group;
(39) an optionally substituted $C_{3-7}$ cycloalkylsulfonyl group;
(40) an optionally substituted $C_{6-14}$ arylsulfonyl group;
(41) an optionally substituted heterocyclyl-sulfonyl group;
(42) an optionally substituted alkylsulfinyl group;
(43) an optionally substituted $C_{3-7}$ cycloalkylsulfinyl group;
(44) an optionally substituted $C_{6-14}$ arylsulfinyl group;
(45) an optionally substituted heterocyclyl-sulfinyl group;
(46) a sulfo group;
(47) a sulfamoyl group;
(48) a sulfinamoyl group;
(49) a sulfenamoyl group;
(50) a thiocarbamoyl group;
(51) an optionally substituted carbamoyl group [e.g., an optionally substituted alkyl-carbamoyl and the like];
(52) an optionally substituted amino group
[e.g.,
amino,
an optionally substituted mono- or di-alkylamino group,
an optionally substituted mono- or di-$C_{3-7}$ cycloalkylamino group,
an optionally substituted mono- or di-$C_{6-14}$ arylamino group,
an optionally substituted mono- or di-$C_{7-16}$ aralkylamino group,
an optionally substituted heterocyclyl-amino group, an optionally substituted C$_{6-14}$ aryl-carbonylamino group,
a formylamino group,
an optionally substituted alkyl-carbonylamino group (e.g., a mono-(C$_{1-6}$ alkyl-carbonyl)-amino group),
an optionally substituted C$_{3-7}$ cycloalkyl-carbonylamino group,
an optionally substituted heterocyclyl-carbonylamino group,
an optionally substituted alkoxy-carbonylamino group,
an optionally substituted C$_{3-8}$ cycloalkoxy-carbonylamino group,
an optionally substituted heterocyclyl-oxycarbonylamino group,
an optionally substituted carbamoylamino group,
an optionally substituted alkylsulfonylamino group,
an optionally substituted C$_{3-8}$ cycloalkylsulfonylamino group,
an optionally substituted heterocyclyl-sulfonylamino group,
an optionally substituted C$_{6-14}$ arylsulfonylamino group];
(53) an optionally substituted alkoxy-carbonyl group;
(54) an optionally substituted C$_{6-14}$ aryloxy-carbonyl group;
(55) an optionally substituted C$_{7-16}$ aralkyloxy-carbonyl group.

The number of the substituents is preferably 0 (i.e., unsubstituted), or 1 or 2.

The number of the substituents is more preferably 0 (i.e., unsubstituted).

Among Substituent Group A, examples of the substituent of the "optionally substituted alkoxy-carbonyl group",
"optionally substituted alkyl group",
"optionally substituted alkenyl group",
"optionally substituted alkynyl group",
"optionally substituted alkoxy group",
"optionally substituted alkyl-carbonyloxy group",
"optionally substituted alkoxy-carbonyloxy group",
"optionally substituted mono-alkyl-carbamoyloxy group",
"optionally substituted di-alkyl-carbamoyloxy group",
"optionally substituted C$_{1-6}$ alkylsulfonyloxy group"
"optionally substituted halogeno C$_{1-6}$ alkylsulfonyloxy group",
"optionally substituted alkylsulfanyl group",
"optionally substituted alkyl-carbonyl group",
"optionally substituted alkylsulfonyl group",
"optionally substituted alkylsulfinyl group",
"optionally substituted alkyl-carbamoyl group",
"optionally substituted mono- or di-alkylamino group",
"optionally substituted alkyl-carbonylamino group",
"optionally substituted mono-(C$_{1-6}$ alkyl-carbonyl)-amino group",
"optionally substituted alkoxy-carbonylamino group" and
"optionally substituted alkylsulfonylamino group" include substituents selected from the following Substituent Group B. The number of the substituents is 1 to the maximum substitutable number, more preferably 1 to 3.

Among Substituent Group A, examples of the substituent of the "optionally substituted C$_{6-14}$ aryloxy-carbonyl group",
"optionally substituted C$_{7-16}$ aralkyloxy-carbonyl group",
"optionally substituted C$_{3-7}$ cycloalkyl-C$_{2-6}$ alkynyl group",
"optionally substituted C$_{3-7}$ cycloalkyl group",
"optionally substituted C$_{6-14}$ aryl group",
"optionally substituted C$_{7-16}$ aralkyl group",
"optionally substituted C$_{6-14}$ aryl-C$_{2-6}$ alkenyl group",
"optionally substituted heterocyclic group",
"optionally substituted C$_{3-7}$ cycloalkyloxy group",
"optionally substituted C$_{6-14}$ aryloxy group",
"optionally substituted C$_{7-16}$ aralkyloxy group",
"optionally substituted C$_{6-14}$ aryl-carbonyloxy group",
"optionally substituted mono- or di-C$_{6-14}$ aryl-carbamoyloxy group",
"optionally substituted heterocyclyl-oxy group",
"optionally substituted aromatic heterocyclyl-oxy group",
"optionally substituted C$_{3-7}$ cycloalkylsulfanyl group",
"optionally substituted C$_{6-14}$ arylsulfanyl group",
"optionally substituted C$_{7-16}$ aralkylsulfanyl group",
"optionally substituted heterocyclyl-sulfanyl group",
"optionally substituted C$_{3-7}$ cycloalkyl-carbonyl group",
"optionally substituted C$_{6-14}$ aryl-carbonyl group",
"optionally substituted C$_{7-16}$ aralkyl-carbonyl group",
"optionally substituted heterocyclyl-carbonyl group",
"optionally substituted C$_{3-7}$ cycloalkylsulfonyl group",
"optionally substituted C$_{6-14}$ arylsulfonyl group",
"optionally substituted heterocyclyl-sulfonyl group",
"optionally substituted C$_{3-7}$ cycloalkylsulfinyl group",
"optionally substituted C$_{6-14}$ arylsulfinyl group",
"optionally substituted heterocyclyl-sulfinyl group",
"optionally substituted carbamoyl group",
"optionally substituted amino group",
"optionally substituted mono- or di-C$_{3-7}$ cycloalkylamino group",
"optionally substituted mono- or di-C$_{6-14}$ arylamino group",
"optionally substituted mono- or di-C$_{7-16}$ aralkylamino group",
"optionally substituted heterocyclyl-amino group",
"optionally substituted C$_{6-14}$ aryl-carbonylamino group",
"optionally substituted C$_{3-8}$ cycloalkyl-carbonylamino group",
"optionally substituted heterocyclyl-carbonylamino group",
"optionally substituted C$_{3-6}$ cycloalkoxy-carbonylamino group",
"optionally substituted heterocyclyl-oxycarbonylamino group",
"optionally substituted carbamoylamino group",
"optionally substituted C$_{3-6}$ cycloalkylsulfonylamino group",
"optionally substituted heterocyclyl-sulfonylamino group" and
"optionally substituted C$_{6-14}$ arylsulfonylamino group" include substituents selected from the following Substituent Group B and the following Substituent Group B'. The number of the substituents is 1 to the maximum substitutable number, more preferably 1 to 3, further more preferably 1.

In the present specification, Substituent Group B consists of (a) a halogen atom;
(b) a hydroxy group;
(c) a nitro group;
(d) a cyano group;
(e) an optionally substituted C$_{6-14}$ aryl group (the C$_{6-14}$ aryl group is optionally substituted by 1 to 5 (preferably 1 to 3, more preferably 1) substituents selected from a halogen atom, hydroxy, cyano, amino, optionally halogenated C$_{1-6}$ alkyl by 1 to 3 halogen atoms, mono- or di-C$_{1-6}$ alkylamino, mono- or di-C$_{6-14}$ arylamino, mono- or di-C$_{7-16}$ aralkylamino, C$_{3-7}$ cycloalkyl, C$_{1-6}$ alkoxy, formyl, C$_{1-6}$ alkyl-carbonyl, C$_{3-7}$ cycloalkyl-carbonyl, C$_{6-14}$ aryl-carbonyl, C$_{7-16}$ aralkyl-carbonyl, C$_{1-6}$ alkoxy-carbonyl, C$_{6-14}$ aryloxy-carbonyl, C$_{7-16}$ aralkyloxy-carbonyl, C$_{1-6}$ alkylsulfanyl, C$_{1-6}$ alkylsulfinyl, C$_{1-6}$ alkylsulfonyl, carbamoyl, thiocarbamoyl, mono- or di-C$_{1-6}$ alkyl-carbamoyl, mono- or di-C$_{6-14}$ aryl-carbamoyl and the like);
(f) an optionally substituted C$_{6-14}$ aryloxy group (the C$_{6-14}$ aryloxy group is optionally substituted by 1 to 5 (preferably 1 to 3, more preferably 1) substituents selected from a halogen atom, hydroxy, cyano, amino, optionally halogenated $C_{1-6}$ alkyl by 1 to 3 halogen atoms, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);

(g) an optionally substituted $C_{7-16}$ aralkyloxy group (the $C_{7-16}$ aralkyloxy group is optionally substituted by 1 to 5 (preferably 1 to 3, more preferably 1) substituents selected from a halogen atom, hydroxy, cyano, amino, optionally halogenated $C_{1-6}$ alkyl by 1 to 3 halogen atoms, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);

(h) an optionally substituted 5- to 10-membered heterocyclic group containing 1 to 4 hetero atoms selected from a nitrogen atom, a sulfur atom and an oxygen atom (e.g., furyl, pyridyl, thienyl, 1-pyrrolidinyl, 1-piperidyl, 4-piperidyl, piperazinyl, 1-morpholinyl, 4-thiomorpholinyl, 1-azepanyl, 1-azocanyl, 1-azonanyl, 3,4-dihydroisoquinolin-2-yl and the like) (the heterocyclic group is optionally substituted by 1 to 5 (preferably 1 to 3, more preferably 1) substituents selected from a halogen atom, hydroxy, cyano, amino, optionally halogenated $C_{1-6}$ alkyl by 1 to 3 halogen atoms, mono- or di-$C_{1-6}$ alkylamino, mono- or di-$C_{6-14}$ arylamino, mono- or di-$C_{7-16}$ aralkylamino, $C_{3-7}$ cycloalkyl, alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);

(i) an optionally substituted amino group [e.g., an amino group optionally substituted by 1 or 2 substituent(s) selected from the group consisting of $C_{1-6}$ alkyl, $C_{2-6}$ alkenyl, $C_{6-14}$ aryl, $C_{7-16}$ aralkyl, a heterocyclic group and heterocyclyl-alkyl (the $C_{1-6}$ alkyl, $C_{2-6}$ alkenyl, $C_{6-14}$ aryl, $C_{7-16}$ aralkyl, heterocyclic group and heterocyclyl-alkyl are each optionally substituted by 1 to 5 (preferably 1 to 3, more preferably 1) substituents selected from a halogen atom, hydroxy, cyano, amino, $C_{1-6}$ alkyl optionally halogenated by 1 to 3 halogen atoms (which is not a substituent for alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, mono- or di-$C_{6-14}$ aryl-carbamoyl and the like). Examples of the "heterocyclic group" and the "heterocyclyl-" of the "heterocyclyl-alkyl" include those similar to the above-mentioned "heterocyclic group"];

(j) $C_{3-7}$ cycloalkyl;

(k) an optionally substituted $C_{1-6}$ alkoxy group (the $C_{1-6}$ alkoxy group is optionally substituted by 1 to 5 (preferably 1 to 3, more preferably 1) substituents selected from a halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, trimethylsilyl (TMS) and the like);

(l) a formyl group;
(m) a $C_{1-6}$ alkyl-carbonyl group (e.g., acetyl);
(n) a $C_{3-7}$ cycloalkyl-carbonyl group;
(o) a $C_{6-14}$ aryl-carbonyl group;
(p) a $C_{7-16}$ aralkyl-carbonyl group;
(q) a $C_{1-6}$ alkoxy-carbonyl group;
(r) a $C_{6-14}$ aryloxy-carbonyl group;
(s) a $C_{7-16}$ aralkyloxy-carbonyl group;
(t) a $C_{1-6}$ alkylsulfanyl group;
(u) a $C_{1-6}$ alkylsulfinyl group;
(v) a $C_{1-6}$ alkylsulfonyl group;
(w) a carbamoyl group;
(x) a thiocarbamoyl group;
(y) a mono-$C_{1-6}$ alkyl-carbamoyl group (e.g., methylcarbamoyl, ethylcarbamoyl and the like);
(z) a di-$C_{1-6}$ alkyl-carbamoyl group (e.g., dimethylcarbamoyl, diethylcarbamoyl, ethylmethylcarbamoyl and the like);
(aa) a mono- or di-$C_{6-14}$ aryl-carbamoyl group (e.g., phenylcarbamoyl, 1-naphthylcarbamoyl, 2-naphthylcarbamoyl and the like);
(bb) a mono- or di-(5- to 7-membered heterocyclyl containing 1 to 4 hetero atoms selected from a nitrogen atom, a sulfur atom and an oxygen atom)-carbamoyl group (e.g., 2-pyridylcarbamoyl, 3-pyridylcarbamoyl, 4-pyridylcarbamoyl, 2-thienylcarbamoyl, 3-thienylcarbamoyl and the like); and
(cc) a $C_{1-6}$ alkyl-carbonyloxy group (e.g., acetoxy and the like).

In the present specification, Substituent Group B' consists of (a) an optionally substituted $C_{1-6}$ alkyl group (the $C_{1-6}$ alkyl group is optionally substituted by 1 to 5 (preferably 1 to 3, more preferably 1) substituents selected from a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like);

(b) an optionally substituted $C_{2-6}$ alkenyl group (the $C_{2-6}$ alkenyl group is optionally substituted by 1 to 5 (preferably 1 to 3, more preferably 1) substituents selected from a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like); and (c) an optionally substituted $C_{2-6}$ alkynyl group (the $C_{2-6}$ alkynyl group is optionally substituted by 1 to 5 (preferably 1 to 3, more preferably 1) substituents selected from a halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like).

Each symbol in formula (I) is explained in the following.

Ring A is an optionally substituted 6-membered ring.

Any one or two of $Z^1$ to $Z^4$, which are ring A-constituting atoms, is(are) —N=, and the others are —CH=. That is, the "6-membered ring" of the "optionally substituted 6-membered ring" for ring A is a pyridine ring, a pyridazine ring, a pyrimidine ring or a pyrazine ring, preferably a pyridine ring or a pyrimidine ring.

Preferably, $Z^1$ or $Z^2$ is —N= and the others are —CH=; or $Z^1$ and $Z^3$ are —N= and the others are —CH=.

More preferably, $Z^1$ is —N= and the others (i.e., $Z^2$, $Z^3$ and $Z^4$) are —CH=; or $Z^1$ and $Z^3$ are —N= and the others (i.e., $Z^2$ and $Z^4$) are —CH=.

Particularly preferably, $Z^1$ is —N= and the others (i.e., $Z^2$, $Z^3$ and $Z^4$) are —CH=.

The nitrogen atom of —N= for $Z^1$ to $Z^4$ may be oxidized. For example, when $Z^1$ is —N= and the others (i.e., $Z^2$, $Z^3$ and $Z^4$) are each —CH=, a compound represented by the formula:

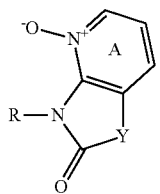

(I″)

wherein each symbol is as defined above, is also encompassed in the compound represented by the formula (I). Particularly, when $Z^1$ is —N=, the nitrogen atom of —N= for $Z^1$ is preferably oxidized.

Examples of the substituent of the "optionally substituted 6-membered ring" for ring A include substituents selected from the above-mentioned Substituent Group A.

Among them, a halogen atom, cyano, an optionally substituted alkyl group, an optionally substituted alkoxy group and the like are preferable, a halogen atom, cyano, an optionally substituted $C_{1-6}$ alkyl group and an optionally substituted $C_{1-6}$ alkoxy group are more preferable, a halogen atom (preferably a chlorine atom, a fluorine atom), cyano, a $C_{1-6}$ alkyl group (preferably methyl) optionally substituted by 1 to 3 substituents selected from the group consisting of (1) a halogen atom (preferably a fluorine atom), (2) hydroxy and (3) a $C_{1-6}$ alkyl-carbonyloxy group (preferably acetoxy), and a $C_{1-6}$ alkoxy group (preferably methoxy, ethoxy) optionally substituted by 1 to 3 halogen atoms (preferably a fluorine atom) are further more preferable, and a halogen atom (preferably a chlorine atom, a fluorine atom), cyano, methyl, hydroxymethyl, acetoxymethyl, trifluoromethyl, methoxy, difluoromethoxy, 2,2-difluoroethoxy and 2,2,2-trifluoroethoxy are particularly preferable.

The number of the substituents of the "optionally substituted 6-membered ring" for ring A is 0 (i.e., unsubstituted), or 1 to 3, preferably 0, or 1 to 2, more preferably 0 or 1. When the number of the substituents is not less than 2, the respective substituents may be the same or different.

Ring A is preferably a pyridine ring or a pyrimidine ring, each of which is optionally substituted by 1 to 3 substituents selected from a halogen atom, cyano, an optionally substituted alkyl group and an optionally substituted alkoxy group [preferably a halogen atom, cyano, an optionally substituted $C_{1-6}$ alkyl group and an optionally substituted $C_{1-6}$ alkoxy group, more preferably a halogen atom (preferably a chlorine atom, a fluorine atom), cyano, a $C_{1-6}$ alkyl group (preferably methyl) optionally substituted by 1 to 3 substituents selected from the group consisting of (1) a halogen atom (preferably a fluorine atom), (2) hydroxy, and (3) a $C_{1-6}$ alkyl-carbonyloxy group (preferably acetoxy), and a $C_{1-6}$ alkoxy group (preferably methoxy, ethoxy) optionally substituted by 1 to 3 halogen atoms (preferably a fluorine atom), further more preferably a halogen atom (preferably a chlorine atom, a fluorine atom), cyano, methyl, trifluoromethyl, hydroxymethyl, acetoxymethyl, methoxy, difluoromethoxy, 2,2-difluoroethoxy and 2,2,2-trifluoroethoxy, further more preferably a fluorine atom, methyl, hydroxymethyl and methoxy].

In another embodiment, ring A is preferably (1) a pyridine ring which is optionally substituted by one substituent selected from (i) a $C_{1-6}$ alkyl group optionally substituted by 1 to 3 substituents selected from a halogen atom, hydroxy and a $C_{1-6}$ alkyl-carbonyloxy group (preferably methyl, trifluoromethyl, acetoxymethyl, hydroroxymethyl), (ii) a halogen atom (preferably chlorine, fluorine), (iii) cyano, and (iv) a $C_{1-4}$ alkoxy group optionally substituted by 1 to 3 halogen atoms (preferably methoxy, difluoromethoxy, difluoroethoxy, trifluoroethoxy)

[preferably a pyridine ring which is optionally substituted by (1) a pyridine ring which is optionally substituted by one substituent selected from (i) a $C_{1-6}$ alkyl group optionally substituted by 1 to 3 substituents selected from a halogen atom and hydroxy (preferably methyl, trifluoromethyl, hydroxymethyl), (ii) a halogen atom (preferably chlorine, fluorine), (iii) cyano, and (iv) a $C_{1-4}$ alkoxy optionally substituted by 1 to 3 halogen atoms (preferably methoxy, difluoromethoxy, difluoroethoxy, trifluoroethoxy)], or (2) a pyrimidine ring.

Y is an oxygen atom, a sulfur atom, an optionally substituted methylene group or —$NR^c$—.

Examples of the substituent of the "optionally substituted methylene group" for Y include substituents selected from the above-mentioned Substituent Group A.

Among them, an optionally substituted alkyl group and the like are preferable.

The number of the substituents of the "optionally substituted methylene group" for Y is 0 (i.e., unsubstituted), 1 or 2. When the number of the substituents is 2, the respective substituents may be the same or different.

The "alkyl group" of the "optionally substituted alkyl group" exemplified as the substituent of the "optionally substituted methylene group" for Y is preferably a $C_{1-6}$ alkyl group (preferably methyl) or the like.

As the substituent of the "optionally substituted alkyl group" exemplified as the substituent of the "optionally substituted methylene group" for Y, a halogen atom, a hydroxy group, a cycloalkyl group, an optionally substituted $C_{1-6}$ alkoxy group (e.g., a trimethylsilyl-$C_{1-6}$ alkoxy group), a $C_{1-6}$ alkoxy-carbonyl group and the like are preferable.

The number of the substituents of the "optionally substituted alkyl group" exemplified as the substituent of the "optionally substituted methylene group" for Y is preferably 0 (i.e., unsubstituted), or 1 to 5, particularly preferably 0 (i.e., unsubstituted). When the number of the substituents is not less than 2, the respective substituents may be the same or different.

When the number of the substituents of the "optionally substituted methylene group" for Y is 2, these two substituents optionally form, together with the adjacent carbon atom, an optionally substituted $C_{3-6}$ cycloalkane (preferably cyclobutane).

As the substituent of the "optionally substituted $C_{3-6}$ cycloalkane", a halogen atom, a hydroxy group, a $C_{3-7}$ cycloalkyl group, an optionally substituted $C_{1-6}$ alkoxy group (e.g., a trimethylsilyl-$C_{1-6}$ alkoxy group), a $C_{1-6}$ alkoxy-carbonyl group and the like are preferable.

The number of the substituents of the "optionally substituted $C_{3-6}$ cycloalkane" is preferably 0 (i.e., unsubstituted), or 1 to 5, particularly preferably 0 (i.e., unsubstituted). When the number of the substituents is not less than 2, the respective substituents may be the same or different.

$R^c$ is a hydrogen atom or a substituent.

Examples of the substituent for $R^c$ include substituents selected from the above-mentioned Substituent Group A.

Among them, an optionally substituted alkyl group, an optionally substituted $C_{3-7}$ cycloalkyl group and the like are preferable.

The "alkyl group" of the "optionally substituted alkyl group" exemplified as the substituent for $R^c$ is preferably a $C_{1-6}$ alkyl group (preferably methyl, ethyl, propyl, isopropyl, isobutyl) or the like.

As the substituent of the "optionally substituted alkyl group" exemplified as the substituent for $R^c$, a halogen atom (preferably a fluorine atom), a hydroxy group, a $C_{3-7}$ cycloalkyl group (preferably cyclopropyl), an optionally substituted $C_{1-6}$ alkoxy group (e.g., methoxy, ethoxy, a trimethylsilyl-$C_{1-6}$ alkoxy group (preferably trimethylsilyl-ethoxy)), a $C_{1-6}$ alkoxy-carbonyl group (preferably ethoxycarbonyl) and the like are preferable.

The number of the substituents of the "optionally substituted alkyl group" exemplified as the substituent for $R^c$ is preferably 0 (i.e., unsubstituted), or 1 to 5, more preferably 0 (i.e., unsubstituted), or 1 to 3. When the number of the substituents is not less than 2, the respective substituents may be the same or different.

The "optionally substituted $C_{3-7}$ cycloalkyl group" exemplified as the substituent for $R^c$ is preferably cyclopropyl or the like.

As the substituent of the "optionally substituted $C_{3-7}$ cycloalkyl group" exemplified as the substituent for $R^c$, a halogen atom, a hydroxy group, a $C_{3-7}$ cycloalkyl group, an optionally substituted $C_{1-6}$ alkoxy group (e.g., methoxy, ethoxy, a trimethylsilyl-$C_{1-6}$ alkoxy group), a $C_{1-6}$ alkoxy-carbonyl group and the like are preferable.

The number of the substituents of the "optionally substituted $C_{3-7}$ cycloalkyl group" is preferably 0 (i.e., unsubstituted), or 1 to 5, particularly preferably 0 (i.e., unsubstituted). When the number of the substituents is not less than 2, the respective substituents may be the same or different.

Y is preferably an oxygen atom, an optionally substituted methylene group, or —$NR^c$— wherein $R^c$ is preferably a hydrogen atom, an optionally substituted alkyl group or an optionally substituted $C_{3-7}$ cycloalkyl group, more preferably an oxygen atom, a methylene group optionally substituted by 1 or 2 $C_{1-6}$ alkyl group(s) (preferably methyl) (the two substituents for the methylene group optionally form, together with the adjacent carbon atom, a $C_{3-6}$ cycloalkane (preferably cyclobutane)), or —$NR^c$— wherein $R^c$ is (i) a hydrogen atom, (ii) a $C_{1-6}$ alkyl group (preferably methyl, ethyl, propyl, isopropyl, isobutyl) optionally substituted by 1 to 3 (preferably 1 or 2) substituents selected from the group consisting of a halogen atom (preferably a fluorine atom), a hydroxy group, a $C_{3-7}$ cycloalkyl group (preferably cyclopropyl), an optionally substituted $C_{1-6}$ alkoxy group (e.g., methoxy, ethoxy, a trimethylsilyl-$C_{1-6}$ alkoxy group (preferably trimethylsilyl-ethoxy)) and a $C_{1-6}$ alkoxy-carbonyl group (preferably ethoxycarbonyl), or (iii) a $C_{3-7}$ cycloalkyl group (preferably cyclopropyl), particularly preferably —$NR^c$— wherein $R^c$ is preferably a $C_{1-6}$ alkyl group (preferably methyl, ethyl, propyl, isopropyl, isobutyl), a di$C_{1-6}$ alkylmethylene group (preferably dimethylmethylene group) or the like, more preferably —$NR^c$— wherein $R^c$ is preferably a $C_{1-6}$ alkyl group (preferably methyl, ethyl, isopropyl).

In another embodiment, Y is preferably —$NR^c$— wherein $R^c$ is preferably an optionally substituted $C_{1-6}$ alkyl group, more preferably a $C_{1-6}$ alkyl group (preferably methyl, ethyl, propyl, isopropyl, isobutyl) optionally substituted by 1 to 3 substituents selected from the group consisting of a halogen atom (preferably a fluorine atom), a hydroxy group, a $C_{3-7}$ cycloalkyl group (preferably cyclopropyl), an optionally substituted $C_{1-6}$ alkoxy group (e.g., a trimethylsilyl-$C_{1-6}$ alkoxy group (preferably trimethylsilyl-ethoxy)) and a $C_{1-6}$ alkoxy-carbonyl group (preferably ethoxycarbonyl).

In another embodiment, Y is preferably —$NR^c$— wherein $R^c$ is preferably an optionally substituted $C_{1-6}$ alkyl group, more preferably an optionally substituted $C_{1-4}$ alkyl group (preferably methyl, ethyl, propyl, isopropyl, isobutyl).

In another embodiment, Y is preferably a methylene group which is optionally substituted by 1 to 2 $C_{1-6}$ alkyl group(s) (preferably methyl), or —$NR^c$— wherein $R^c$ is (1) a hydrogen atom, (2) a $C_{1-6}$ alkyl which is optionally substituted by 1 to 3 substituents selected from the group consisting of hydroxy and a halogen atom (preferably methyl, ethyl, propyl, isopropyl, hydroxymethyl, difluoromethyl), or (3) a $C_{3-7}$ cycloalkyl (preferably cyclopropyl).

The partial structure of the formula (I):

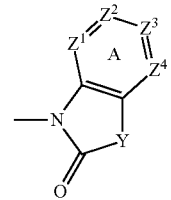

is preferably, for example, a group represented by the formula:

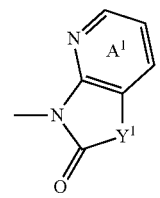

wherein
Y¹ is an optionally substituted methylene group, or —NR$^c$— wherein R$^c$ is a hydrogen atom or a substituent, and ring A¹ is an optionally substituted pyridine ring, or a group represented by the formula:

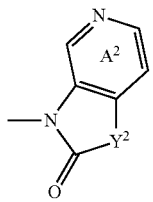

wherein
Y² is —NR$^d$— wherein R$^d$ is a substituent, and
ring A² is an optionally substituted pyridine ring.

Examples of the "optionally substituted methylene group" for Y¹ include those similar to the "optionally substituted methylene group" for Y.

Examples of the "substituent" of the "optionally substituted pyridine ring" for ring A¹ include those similar to the "substituent" of the "optionally substituted 6-membered ring" for ring A.

Examples of the "substituent" for R$^d$ include those similar to the "substituent" for R$^c$.

Among them, an optionally substituted alkyl group and the like are preferably.

The "alkyl group" of the "optionally substituted alkyl group" exemplified as the substituent for R$^d$ is preferably a $C_{1-6}$ alkyl group (preferably a $C_{1-4}$ alkyl group, more preferably methyl, ethyl, propyl, isopropyl, isobutyl) or the like.

As the substituent of the "optionally substituted alkyl group" exemplified as the substituent for R$^d$, a halogen atom (preferably a fluorine atom), a hydroxy group, a $C_{3-7}$ cycloalkyl group (preferably cyclopropyl), an optionally substituted $C_{1-6}$ alkoxy group (e.g., a trimethylsilyl-$C_{1-6}$ alkoxy group (preferably trimethylsilyl-ethoxy)), a $C_{1-6}$ alkoxy-carbonyl group (preferably ethoxycarbonyl) and the like are preferable, and a halogen atom (preferably a fluorine atom), a hydroxy group, an optionally substituted $C_{1-6}$ alkoxy group (e.g., methoxy, ethoxy, a trimethylsilyl-$C_{1-6}$ alkoxy group (preferably trimethylsilyl-ethoxy)), a $C_{1-6}$ alkoxy-carbonyl group (preferably ethoxycarbonyl) and the like are more preferable.

The number of the substituents of the "optionally substituted alkyl group" exemplified as the substituent for R$^d$ is preferably 0 (i.e., unsubstituted), or 1 to 5, more preferably 0 (i.e., unsubstituted), or 1 to 3. When the number of the substituents is not less than 2, the respective substituents may be the same or different.

Examples of the "substituent" of the "optionally substituted pyridine ring" for ring A² include those similar to the "substituent" of the "optionally substituted 6-membered ring" for ring A.

The partial structure of the formula (I):

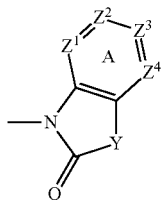

is more preferably a group represented by the formula:

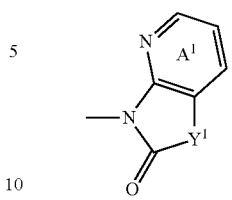

wherein each symbol is as defined above, further more preferably a group represented by the formula:

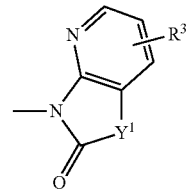

wherein
R³ is a hydrogen atom, a halogen atom, cyano, an optionally substituted $C_{1-6}$ alkyl group or an optionally substituted $C_{1-6}$ alkoxy group, and
Y¹ is as defined above.

The "optionally substituted $C_{1-6}$ alkyl group" for R³ is preferably an optionally substituted $C_{1-4}$ alkyl group, more preferably a $C_{1-4}$ alkyl group (preferably methyl) optionally substituted by 1 to 3 halogen atoms (preferably a fluorine atom).

The "optionally substituted $C_{1-6}$ alkoxy group" for R³ is preferably an optionally substituted $C_{1-4}$ alkoxy group, more preferably a $C_{1-4}$ alkoxy group (preferably methoxy, ethoxy) optionally substituted by 1 to 3 halogen atoms (preferably a fluorine atom).

R³ is preferably a halogen atom (preferably a chlorine atom, a fluorine atom), cyano, $C_{1-6}$ alkyl (preferably $C_{1-4}$ alkyl, more preferably methyl) optionally substituted by 1 to 3 halogen atoms (preferably a fluorine atom), or $C_{1-6}$ alkoxy (preferably $C_{1-4}$ alkoxy, more preferably methoxy, ethoxy) optionally substituted by 1 to 3 halogen atoms (preferably a fluorine atom), particularly preferably a halogen atom (preferably a chlorine atom, a fluorine atom), cyano, trifluoromethyl, difluoromethoxy, 2,2-difluoroethoxy or 2,2,2-trifluoroethoxy.

In another embodiment, R³ is preferably a hydrogen atom, a halogen atom (preferably a chlorine atom, a fluorine atom), cyano, an optionally substituted $C_{1-4}$ alkyl group or an optionally substituted $C_{1-4}$ alkoxy group, more preferably a hydrogen atom, a halogen atom (preferably a chlorine atom, a fluorine atom), an optionally substituted $C_{1-4}$ alkyl group or an optionally substituted $C_{1-4}$ alkoxy group.

The partial structure of the formula (I):

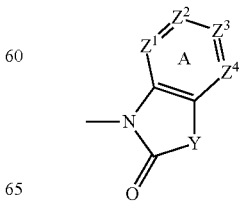

is particularly preferably a group represented by the formula:

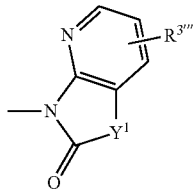

wherein

R$^{3'''}$ is a hydrogen atom, a halogen atom, an optionally substituted C$_{1-6}$ alkyl group (preferably an optionally substituted C$_{1-4}$ alkyl group) or an optionally substituted C$_{1-6}$ alkoxy group (preferably an optionally substituted C$_{1-4}$ alkoxy group), and Y$^1$ is as defined above.

In another embodiment, the group represented by the formula:

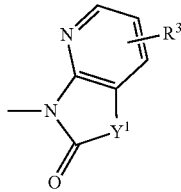

is preferably

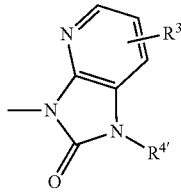

wherein

R$^{4'}$ is an optionally substituted C$_{1-6}$ alkyl group, and

R$^3$ is as defined above.

The "optionally substituted C$_{1-6}$ alkyl group" for R$^{4'}$ is preferably an optionally substituted C$_{1-4}$ alkyl group, more preferably a C$_{1-4}$ alkyl group (preferably methyl, ethyl, propyl, isopropyl, isobutyl) optionally substituted by 1 to 3 substituents selected from the group consisting of a halogen atom (preferably a fluorine atom), a hydroxy group, a C$_{3-7}$ cycloalkyl group (preferably cyclopropyl), an optionally substituted C$_{1-6}$ alkoxy group (preferably C$_{1-4}$ alkoxy) (e.g., methoxy, ethoxy, a trimethylsilyl-C$_{1-6}$ alkoxy group (preferably trimethylsilyl-ethoxy)), and a C$_{1-6}$ alkoxy-carbonyl group (preferably ethoxycarbonyl).

R$^{4'}$ is preferably an optionally substituted C$_{1-6}$ alkyl group, more preferably an optionally substituted C$_{1-4}$ alkyl group.

In another embodiment, the partial structure of the formula (I):

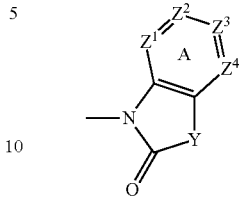

is preferably a group represented by the formula:

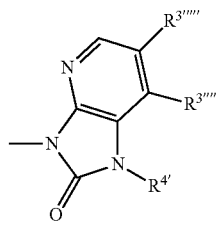

wherein

R$^{3''''}$ and R$^{3'''''}$ represent the same or different a hydrogen atom, a halogen atom, cyano, an optionally substituted C$_{1-6}$ alkyl group or an optionally substituted C$_{1-6}$ alkoxy group, and R$^{4'}$ is as defined above.

The "optionally substituted C$_{1-6}$ alkyl group" for R$^{3''''}$ or R$^{3'''''}$ is preferably an optionally substituted C$_{1-4}$ alkyl group, more preferably a C$_{1-4}$ alkyl group (preferably methyl) optionally substituted by 1 to 3 halogen atoms (preferably a fluorine atom).

The "optionally substituted C$_{1-6}$ alkoxy group" for R$^{3''''}$ or R$^{3'''''}$ is preferably an optionally substituted C$_{1-4}$ alkoxy group, more preferably a C$_{1-4}$ alkoxy group (preferably methoxy, ethoxy) optionally substituted by 1 to 3 halogen atoms (preferably a fluorine atom).

R$^{3''''}$ is preferably a hydrogen atom, a halogen atom, an optionally substituted C$_{1-6}$ alkyl group or an optionally substituted C$_{1-6}$ alkoxy group, more preferably a hydrogen atom or an optionally substituted C$_{1-6}$ alkyl group, further more preferably a hydrogen atom or an optionally substituted C$_{1-4}$ alkyl group (preferably methyl, hydroxymethyl).

R$^{3'''''}$ is preferably a hydrogen atom, a halogen atom, cyano, an optionally substituted C$_{1-6}$ alkyl group or an optionally substituted C$_{1-6}$ alkoxy group, more preferably a hydrogen atom, a halogen atom, cyano, an optionally substituted C$_{1-4}$ alkyl group or an optionally substituted C$_{1-4}$ alkoxy group.

The group represented by the formula:

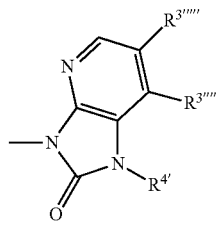

is preferably a group represented by the formula:

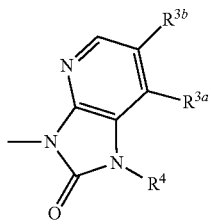

wherein
R$^{3a}$ and R$^{3b}$ represent the same or different a hydrogen atom, a halogen atom, cyano, an optionally substituted C$_{1-4}$ alkyl group or an optionally substituted C$_{1-4}$ alkoxy group, and
R$^4$ represents an optionally substituted C$_{1-4}$ alkyl group, provided that when one of R$^{3a}$ and R$^{3b}$ is a hydrogen atom, the other is not a hydrogen atom, and
more preferably a group represented by the formula:

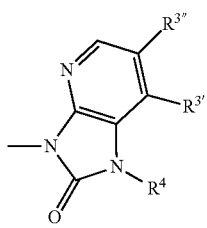

wherein
R$^{3'}$ represents a hydrogen atom, or an optionally substituted C$_{1-4}$ alkyl group (preferably, methyl, hydroxymethyl),
R$^{3''}$ represents a hydrogen atom, a halogen atom, cyano, an optionally substituted C$_{1-4}$ alkyl group or an optionally substituted C$_{1-4}$ alkoxy group, and
R$^4$ represents an optionally substituted C$_{1-4}$ alkyl group, provided that when one of R$^{3'}$ and R$^{3''}$ is a hydrogen atom, the other is not a hydrogen atom.
R$^{3''}$ is preferably a hydrogen atom, a halogen atom, an optionally substituted C$_{1-4}$ alkyl group (preferably, methyl) or an optionally substituted C$_{1-4}$ alkoxy group (preferably, methoxy).
R is
(1) a group represented by the formula:

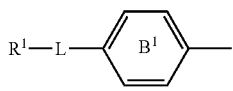

or
(2) a group represented by the formula:

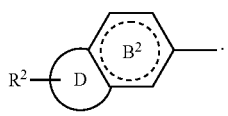

That is, the compound represented by the formula (I) or a salt thereof encompasses a compound represented by the formula (I-1) or the formula (I-2):

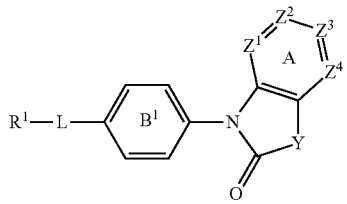

(I-1)

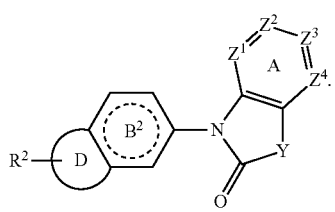

(I-2)

Each symbol for R is explained in the following.

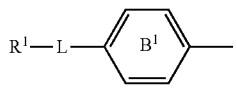

wherein
R$^1$ is a phenyl group or a 5- to 10-membered heterocyclic group, each of which is optionally substituted,
L is a sulfur atom (—S—), an oxygen atom (—O—), an optionally substituted methylene group, —CO—, —NR$^a$—, —CH$_2$O—, —OCH$_2$—, —NR$^a$COO—, —OCONR$^a$—, —NR$^a$CONR$^b$—, —NR$^a$COCH$_2$—, —CH$_2$CONR$^a$—, —NR$^a$CO—, —CONR$^a$—,

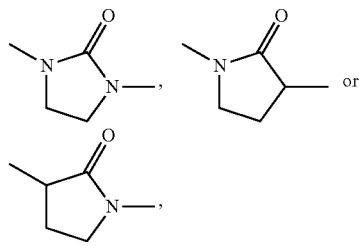

wherein
R$^a$ and R$^b$ are the same or different and each is a hydrogen atom or an optionally substituted C$_{1-6}$ alkyl group, or
L and R$^1$ in combination optionally form an optionally substituted bi- or tri-cyclic fused heterocyclic group, and ring B$^1$ is a benzene ring, a pyridine ring, a pyrimidine ring, a pyrazine ring or a pyridazine ring, each of which is optionally substituted.
Examples of the "5- to 10-membered heterocyclic group" of the "optionally substituted 5- to 10-membered heterocyclic group" for R$^1$ include a 5- to 10-membered heterocyclic group from among the "3- to 14-membered heterocyclic groups" exemplified above.
Among them, a 5- or 6-membered monocyclic heterocyclic group, a bicyclic fused heterocyclic group (preferably a 9- to 10-membered bicyclic fused heterocyclic group) and the like are preferable.
The nitrogen atom(s) contained in the "5- to 10-membered heterocyclic group" of the "optionally substituted 5- to 10-membered heterocyclic group" for R$^1$ may be oxidized.

The "5- or 6-membered monocyclic heterocyclic group" is preferably, for example, a 5- or 6-membered monocyclic nitrogen-containing aromatic heterocyclic group such as imidazolyl, pyridyl, pyridazinyl, pyrazinyl, pyrimidinyl, thiadiazolyl and the like. Among them, imidazolyl, pyridyl and thiadiazolyl are preferable, and the following groups:

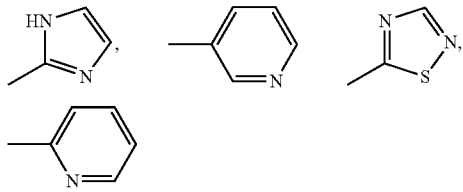

and the like are more preferable, and the following groups:

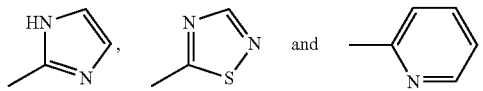

are particularly preferable.

Examples of the aforementioned "bicyclic fused heterocyclic group" include (1) a fused heterocyclic group formed by condensation of a phenyl group with a 5- or 6-membered heterocycle, (2) a fused heterocyclic group formed by condensation of a 5- or 6-membered heterocyclic group with a carbocycle having 5 or 6 carbon atoms, and (3) a fused heterocyclic group formed by condensation of a 5- or 6-membered heterocyclic group with a 5- or 6-membered heterocycle. Among them, the following groups:

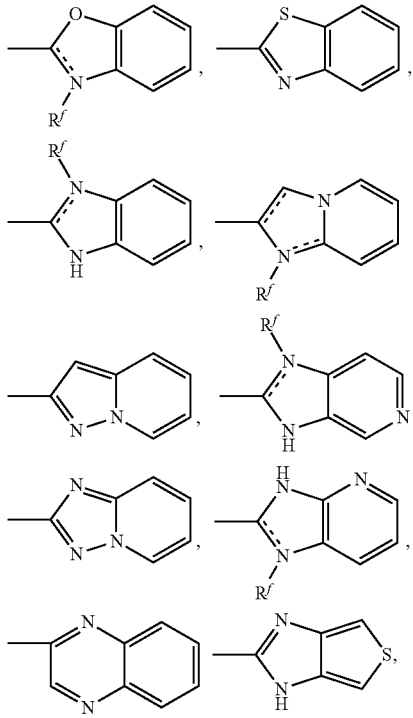

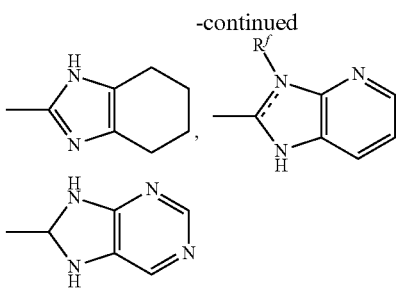

wherein $R^f$ is absent or a hydrogen atom (when $R^f$ is absent, —N($R^f$)— is =N—; $R^f$ is preferably absent), and the like are preferable, and the following groups:

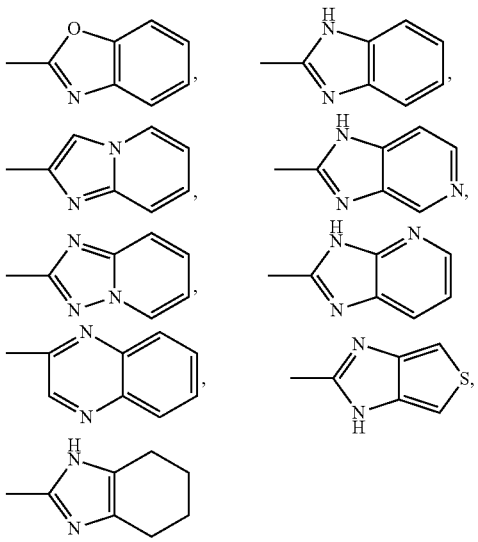

and the like are more preferable.

Examples of the substituent of the "phenyl group or 5- to 10-membered heterocyclic group, each of which is optionally substituted" for $R^1$ include substituents selected from the above-mentioned Substituent Group A.

Among them,
(a) a halogen atom,
(b) an optionally esterified carboxy group,
(c) an optionally substituted alkyl group,
(d) an optionally substituted $C_{6-14}$ aryl group,
(e) an optionally substituted alkyl-carbonyl group, and the like are preferable,
(a) a halogen atom (preferably fluorine, bromine, chlorine),
(b) a $C_{1-6}$ alkoxy-carbonyl group (preferably ethoxycarbonyl),
(c) a $C_{1-6}$ alkyl group (preferably methyl, ethyl, butyl, isobutyl) optionally substituted by one or more (preferably 1 to 3) substituents selected from the group consisting of
  (i) a halogen atom (preferably a fluorine atom),
  (ii) a hydroxy group, and
  (iii) an optionally substituted $C_{1-6}$ alkoxy group (e.g., a $C_{1-6}$ alkoxy group (preferably ethoxy) optionally substituted by trimethylsilyl),
(d) a $C_{6-44}$ aryl group (preferably phenyl),
(e) a $C_{1-6}$ alkyl-carbonyl group (preferably acetyl), and the like are more preferable.

The number of the substituents of the "phenyl group or 5- to 10-membered heterocyclic group, each of which is optionally substituted" for $R^1$ is preferably 0 (i.e., unsubstituted), or 1 to 3. When the number of the substituents is not less than 2, the respective substituents may be the same or different.

$R^1$ is preferably a phenyl group, imidazolyl, pyridyl, thiadiazolyl (preferably the following group:

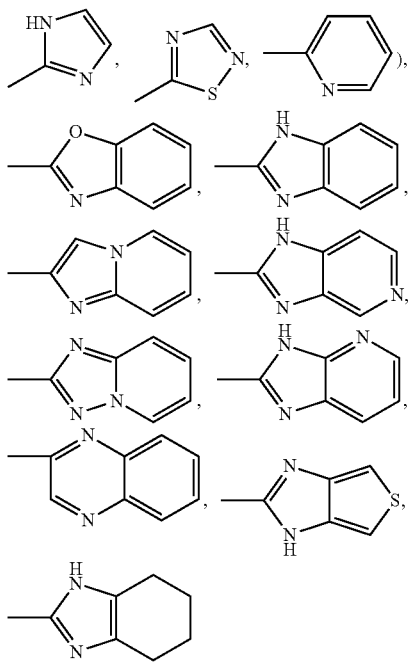

or the like, each of which is optionally substituted by 1 to 3 substituents selected from the group consisting of
(a) a halogen atom,
(b) an optionally esterified carboxy group,
(c) an optionally substituted alkyl group,
(d) an optionally substituted $C_{6-14}$ aryl group, and
(e) an optionally substituted alkyl-carbonyl group [preferably
(a) a halogen atom (preferably fluorine, bromine, chlorine),
(b) a $C_{2-6}$ alkoxy-carbonyl group (preferably ethoxycarbonyl),
(c) a $C_{2-6}$ alkyl group (preferably methyl, ethyl, butyl, isobutyl) optionally substituted by one or more (preferably 1 to 3) substituents selected from the group consisting of
(i) a halogen atom (preferably fluorine),
(ii) a hydroxy group, and
(iii) an optionally substituted $C_{2-6}$ alkoxy group (e.g., a $C_{2-6}$ alkoxy group (preferably ethoxy) optionally substituted by trimethylsilyl),
(d) a $C_{6-24}$ aryl group (preferably phenyl), and
(e) a $C_{1-6}$ alkyl-carbonyl group (preferably acetyl)].

In another embodiment, $R^1$ is preferably

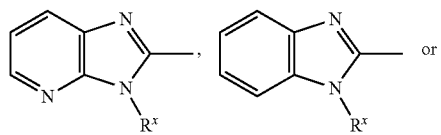 or

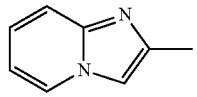

wherein
$R^x$ is a hydrogen atom or an optionally substituted $C_{1-6}$ alkyl group (preferably a $C_{1-6}$ alkyl group),
or the like.

Examples of the substituent of the "optionally substituted methylene group" for L include substituents selected from the above-mentioned Substituent Group A.

The "optionally substituted methylene group" for L is preferably (unsubstituted) methylene.

Preferable examples of the substituent of the "optionally substituted $C_{1-6}$ alkyl group" for $R^a$ include substituents selected from the above-mentioned Substituent Group A.

$R^a$ is preferably a hydrogen atom, a $C_{1-6}$ alkyl group or the like, more preferably a hydrogen atom, methyl or the like.

Preferable examples of the substituent of the "optionally substituted $C_{1-6}$ alkyl group" for $R^b$ include substituents selected from the above-mentioned Substituent Group A.

$R^b$ is preferably a hydrogen atom, a $C_{1-6}$ alkyl group or the like, more preferably a hydrogen atom, methyl or the like.

L is preferably an oxygen atom (—O—), —CO—, —$NR^a$—COO— wherein $R^a$ is preferably a hydrogen atom or a $C_{1-6}$ alkyl group (preferably methyl), or

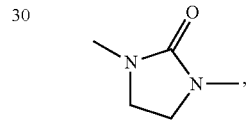

more preferably an oxygen atom or —$NR^a$— wherein $R^a$ is a hydrogen atom or a $C_{1-6}$ alkyl group (preferably methyl), or the like,
further more preferably an oxygen atom or the like.

The "optionally substituted bi- or tri-cyclic fused heterocyclic group formed by L and $R^1$ in combination" means that the moiety represented by the formula:

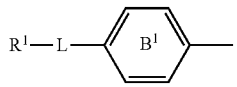

is a moiety represented by the formula:

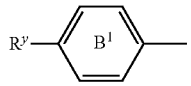

wherein
$R^y$ is an optionally substituted bi- or tri-cyclic fused heterocyclic group, and
$B^1$ is as defined above.

That is, the substituent on the ring-constituting atom of the "phenyl group" or the "5- to 10-membered heterocyclic group" for $R^1$ and the substituent on the main chain-constituting atom of L form a ring together with the ring-constituting atom and the main chain-constituting atom. In the present specification, this structure is sometimes represented by the following formula:

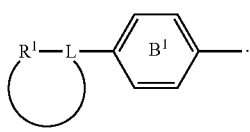

Examples of the "bi- or tri-cyclic fused heterocyclic group" of the "optionally substituted bi- or tri-cyclic fused heterocyclic group" formed by L and R¹ in combination include a bi- or tri-cyclic group, from among the aforementioned "3- to 14-membered heterocyclic groups containing 1 to 5 hetero atoms selected from a nitrogen atom, a sulfur atom and an oxygen atom".

The "bi- or tri-cyclic fused heterocyclic group" is preferably the following group:

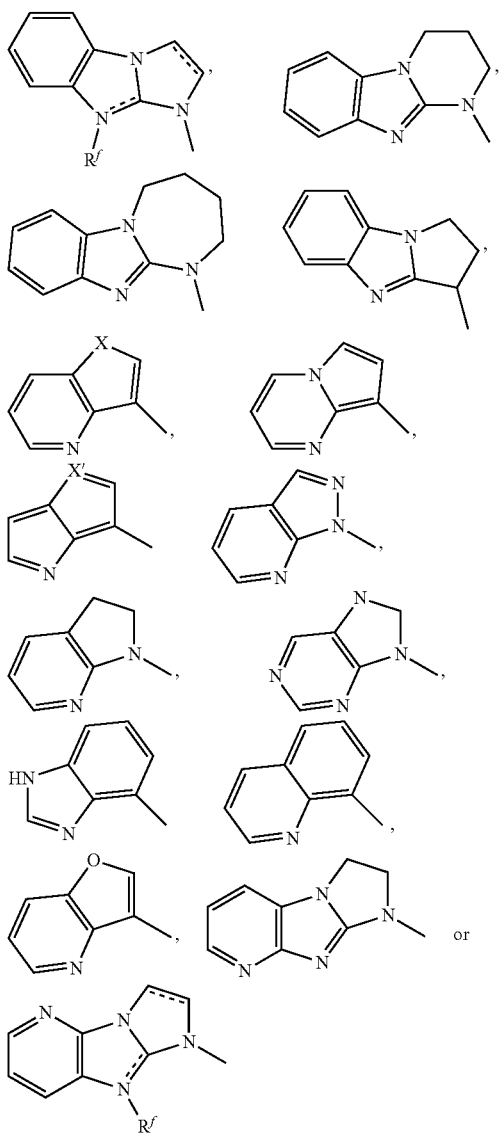

wherein
X is —CH$_2$—, —NH—, an oxygen atom or a sulfur atom,
X' is =CH— or =N—, and
R$^f$ is absent or a hydrogen atom (when R$^f$ is absent, —N(R$^f$)— is =N—; R$^f$ is preferably absent), or the like, more preferably the following group:

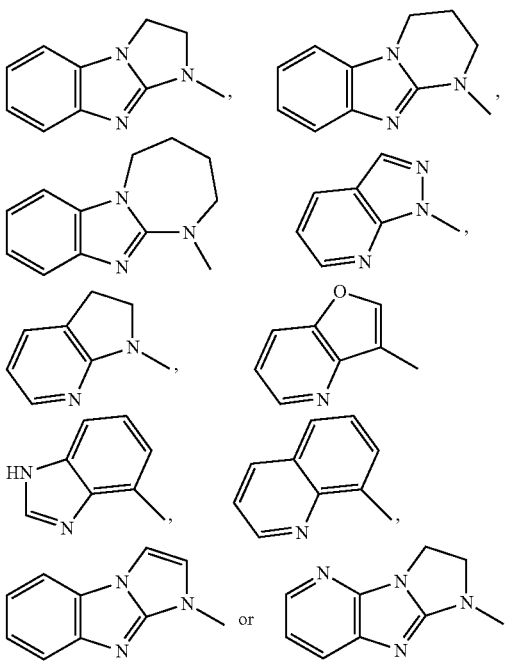

Examples of the substituent of the "optionally substituted bi- or tri-cyclic fused heterocyclic group" optionally formed by L and R¹ in combination include substituents selected from the aforementioned Substituent Group A and an oxo group.

Among them,
(a) a halogen atom,
to (b) an optionally esterified carboxy group,
(c) an optionally substituted alkyl group,
(d) an oxo group
and the like are preferable, and
(a) a halogen atom,
(b) a C$_{1-6}$ alkoxy-carbonyl group (preferably ethoxycarbonyl),
(c) a C$_{1-6}$ alkyl group (preferably methyl) optionally substituted by C$_{6-14}$ aryl group(s) (preferably phenyl),
(d) an oxo group
and the like are more preferable, and
(a) a C$_{1-6}$ alkoxy-carbonyl group (preferably ethoxycarbonyl),
(b) a C$_{1-6}$ alkyl group (preferably methyl) optionally substituted by C$_{6-14}$ aryl group(s) (preferably phenyl), and
(c) an oxo group
are further more preferable.

In another embodiment, as the substituents of the "optionally substituted bi- or tri-cyclic fused heterocyclic group" optionally formed by L and R¹ in combination,
(a) a halogen atom,
(b) an optionally esterified carboxy group,
(c) an optionally substituted alkyl group,
and the like are preferable, and
(a) a halogen atom,
(b) a C$_{1-6}$ alkoxy-carbonyl group (preferably ethoxycarbonyl),
(c) a C$_{1-6}$ alkyl group (preferably methyl) optionally substituted by C$_{6-14}$ aryl group(s) (preferably phenyl), and the like are more preferable, and (a) a $C_{1-6}$ alkoxy-carbonyl group (preferably ethoxycarbonyl), and (b) a $C_{1-6}$ alkyl group (preferably methyl) optionally substituted by $C_{6-14}$ aryl group(s) (preferably phenyl) are furthermore preferable.

The number of the substituents of the "optionally substituted bi- or tri-cyclic fused heterocyclic group" optionally formed by L and $R^1$ in combination is preferably 0 (i.e., unsubstituted), or 1 to 3. When the number of the substituents is not less than 2, the respective substituents may be the same or different.

The "optionally substituted bi- or tri-cyclic fused heterocyclic group" optionally formed by L and $R^1$ in combination is preferably

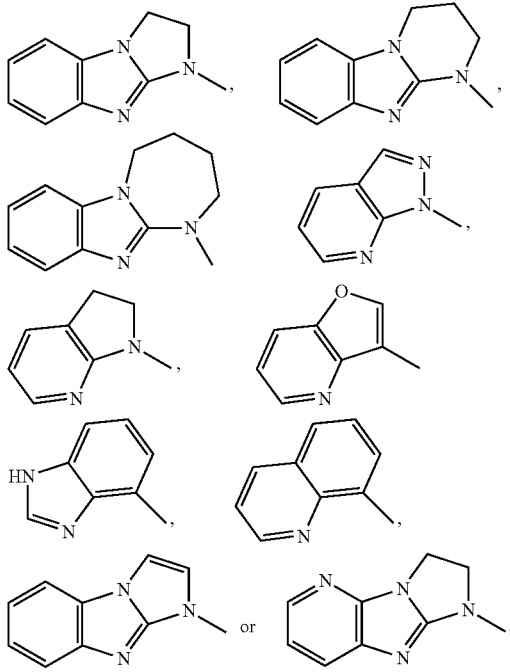

each of which is optionally substituted by 1 to 3 substituents selected from the group consisting of (a) a $C_{1-6}$ alkoxy-carbonyl group (preferably ethoxycarbonyl), (b) $C_{1-6}$ alkyl group (preferably methyl) optionally substituted by $C_{5-14}$ aryl group(s) (preferably phenyl), and (c) an oxo group.

The partial structure of the formula (I-1):

$R^1$-L- is preferably a group represented by the following formula:

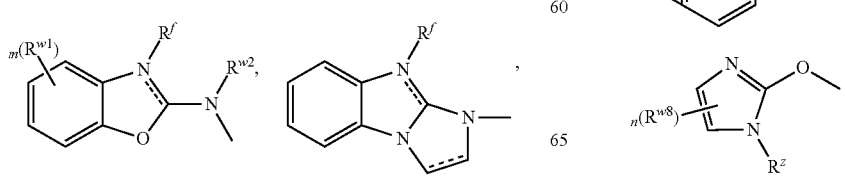

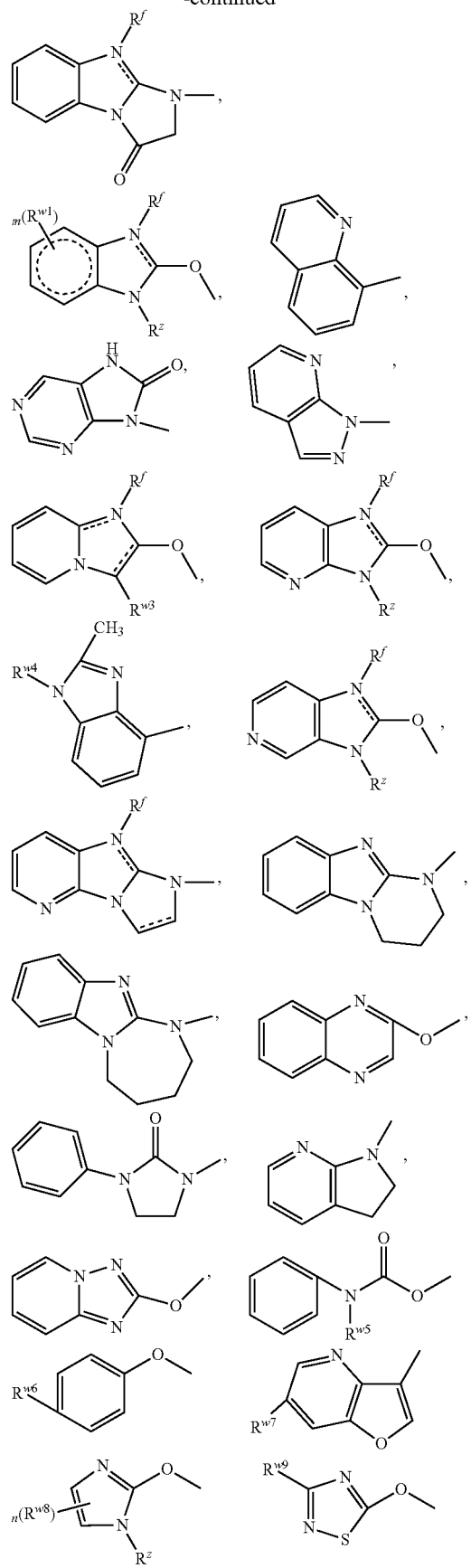

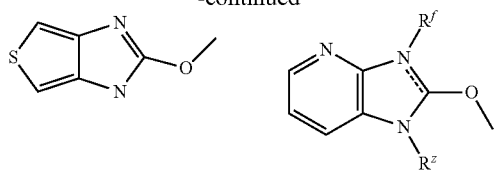

wherein
$R^f$ is absent or a hydrogen atom (when $R^f$ is absent, —N($R^f$)— is =N—; $R^f$ is preferably absent);
$R^z$ is (i) a hydrogen atom, (ii) a $C_{1-4}$ alkyl group optionally substituted by one substituent selected from (1) a hydroxy group (preferably, methyl, ethyl, hydroxyethyl, buthyl, hydroxyisobutyl) and (2) a $C_{1-4}$ alkoxy group optionally substituted by trimethylsilyl (preferably, trimethylsilylmethoxy), or (iii) a $C_{1-6}$ alkyl-carbonyl group (preferably, acetyl);
$R^{w1}$ is a halogen atom (preferably, fluorine);
m is 0 to 2;
$R^{w2}$ is a hydrogen atom or a methyl group;
$R^{w3}$ is a hydrogen atom or a $C_{1-2}$ alkoxy-carbonyl group (preferably, ethoxycarbonyl);
$R^{w4}$ is a hydrogen atom or benzyl;
$R^{w5}$ is a hydrogen atom or methyl;
$R^{w6}$ is a hydrogen atom, a halogen atom (preferably, fluorine, chlorine), or a $C_{1-6}$ alkyl group optionally substituted by 1 to 3 halogen atoms (preferably, trifluoromethyl);
$R^{w7}$ is a $C_{1-6}$ alkoxyl-carbonyl group (preferably, ethoxycarbonyl);
$R^{w8}$ is a halogen atom (preferably, chlorine, bromine), or a $C_{1-6}$ alkyl group optionally substituted by 1 to 3 halogen atoms (preferably, trifluoromethyl);
n is 0 to 2;
$R^{w9}$ is a hydrogen atom or a halogen atom (preferably, bromine);
more preferably a group represented by the following formula:

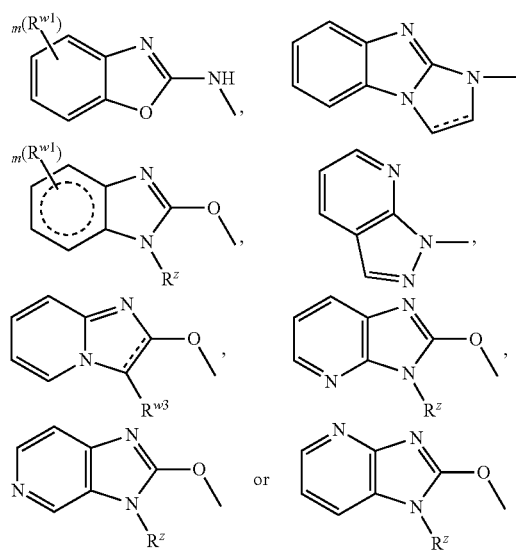

wherein
$R^{w1}$ is a halogen atom (preferably, fluorine);
m is 0 to 1;

$R^z$ is (i) a hydrogen atom, (ii) a $C_{1-4}$ alkyl group optionally substituted by one hydroxy group (preferably, methyl, hydroxyethyl, hydroxyisobutyl) and
$R^{w3}$ is a hydrogen atom or a $C_{1-2}$ alkoxy-carbonyl group (preferably, ethoxycarbonyl).

In another embodiment, the partial structure of the formula (I-1):

$R^1$-L- is preferably a group represented by the following formula:

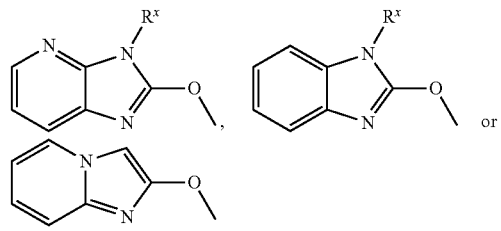

wherein
$R^x$ is an optionally substituted $C_{1-6}$ alkyl group, each of which is further optionally substituted.

The "optionally substituted $C_{1-6}$ alkyl group" for $R^x$ is preferably a $C_{1-6}$ alkyl group (preferably methyl, ethyl, butyl, isobutyl) optionally substituted by one or more (preferably 1 to 3) substituents selected from the group consisting of
(i) a halogen atom (preferably a fluorine atom),
(ii) a hydroxy group, and
(iii) an optionally substituted $C_{1-6}$ alkoxy group (e.g., a $C_{1-6}$ alkoxy group (preferably ethoxy) optionally substituted by trimethylsilyl), more preferably a $C_{1-6}$ alkyl group (preferably methyl, ethyl, butyl, isobutyl) optionally substituted by one or more (preferably 1 to 3) substituents selected from the group consisting of
(i) a hydroxy group, and
(ii) an optionally substituted $C_{1-6}$ alkoxy group (e.g., a $C_{1-6}$ alkoxy group (preferably ethoxy) optionally substituted by trimethylsilyl).

As the substituent that the group represented by the formula:

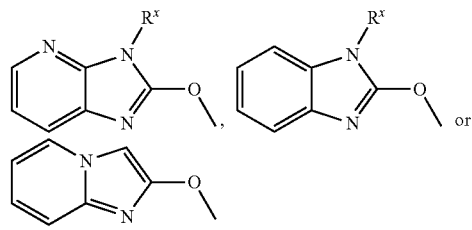

wherein
$R^x$ is an optionally substituted $C_{1-6}$ alkyl group, optionally further has,
(a) a halogen atom,
(b) an optionally esterified carboxy group,
(c) an optionally substituted alkyl group,
(d) an optionally substituted $C_{6-14}$ aryl group,
(e) an optionally substituted alkyl-carbonyl group,
and the like are preferable, and
(a) a halogen atom (preferably fluorine),
(b) a $C_{1-6}$ alkoxy-carbonyl group (preferably ethoxycarbonyl),
(c) a $C_{1-6}$ alkyl group (preferably methyl)
and the like are more preferable.

The number of the substituents is preferably 0 (i.e., unsubstituted), or 1 to 3, more preferably 0 (i.e., unsubstituted), or 1. When the number of the substituents is not less than 2, the respective substituents may be the same or different.

The cyclic moiety of the group represented by the formula:

(i.e., the moiety other than the substituent) is preferably

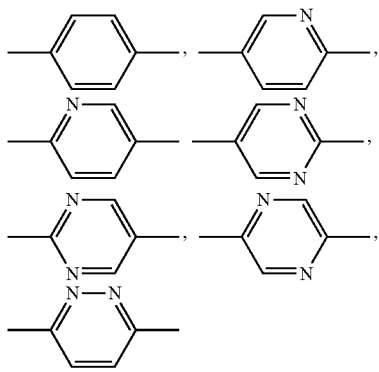

or the like, more preferably

Examples of the substituent of the "benzene ring, pyridine ring, pyrimidine ring, pyrazine ring or pyridazine ring, each of which is optionally substituted" for ring $B^1$ include substituents selected from the above-mentioned Substituent Group A.

Among them, a halogen atom, an optionally substituted alkyl group and the like are preferable, a halogen atom, an optionally substituted $C_{1-6}$ alkyl group and the like are more preferably, and a halogen atom (preferably a fluorine atom), a $C_{1-6}$ alkyl group (preferably methyl) and the like are further more preferable.

The number of the substituents of the "benzene ring, pyridine ring, pyrimidine ring, pyrazine ring or pyridazine ring, each of which is optionally substituted" for ring $B^1$ is preferably 0 (i.e., unsubstituted), or 1 to 3, more preferably 0 or 1. When the number of the substituents is not less than 2, the respective substituents may be the same or different.

Ring $B^1$ is preferably an optionally substituted benzene ring, more preferably a benzene ring optionally substituted by 1 to 3 substituents selected from the group consisting of a halogen atom and an optionally substituted alkyl group [more preferably a halogen atom and an optionally substituted $C_{1-6}$ alkyl group, further more preferably a halogen atom (preferably a fluorine atom) and a $C_{1-6}$ alkyl group (preferably methyl), particularly preferably a halogen atom (preferably a fluorine atom)].

The compound represented by the formula (I-1) or a salt thereof is preferably a compound wherein $Z^1$ is —N= and the others (i.e., $Z^2$, $Z^3$, and $Z^4$) are —CH=; or $Z^1$ and $Z^3$ are —N= and the others (i.e., $Z^2$ and $Z^4$) are —CH= [preferably $Z^1$ is —N= and the others (i.e., $Z^2$, $Z^3$, and $Z^4$) are —CH=];

ring A is a pyridine ring or a pyrimidine ring, each of which is optionally substituted by 1 to 3 substituents selected from the group consisting of a halogen atom, cyano, an optionally substituted alkyl group and an optionally substituted alkoxy group [preferably a halogen atom, cyano, an optionally substituted $C_{1-6}$ alkyl group and an optionally substituted $C_{1-6}$ alkoxy group, further more preferably a halogen atom (preferably a chlorine atom, a fluorine atom), cyano, a $C_{1-6}$ alkyl group (preferably methyl) optionally substituted by 1 to 3 substituents selected from the group consisting of (1) a halogen atom (preferably a fluorine atom), (2) hydroxyl, and (3) $C_{1-6}$ alkyl-carbonyl group (preferably acetoxy), and a $C_{1-6}$ alkoxy group (preferably methoxy, ethoxy) optionally substituted by 1 to 3 halogen atoms (preferably a fluorine atom)];

Y is an oxygen atom, an optionally substituted methylene group, or —NR$^c$— wherein R$^c$ is preferably a hydrogen atom, an optionally substituted alkyl group or an optionally substituted $C_{3-7}$ cycloalkyl group {preferably an oxygen atom, a methylene group optionally substituted by 1 or 2 $C_{1-6}$ alkyl groups (preferably methyl) (the two substituents for the methylene group optionally form, together with the adjacent carbon atom, a $C_{3-6}$ cycloalkane (preferably cyclobutane)), or —NR$^c$— wherein R$^c$ is preferably (i) a hydrogen atom, (ii) a $C_{1-6}$ alkyl group (e.g., methyl, ethyl, propyl, isopropyl, isobutyl) optionally substituted by 1 to 3 substituents selected from the group consisting of a halogen atom (preferably a fluorine atom), a hydroxy group, a $C_{3-7}$ cycloalkyl group (preferably cyclopropyl), an optionally substituted $C_{1-6}$ alkoxy group (e.g., methoxy, ethoxy, a trimethylsilyl-$C_{1-6}$ alkoxy group (preferably trimethylsilyl-ethoxy)), and an $C_{1-6}$ alkoxy-carbonyl group (preferably ethoxycarbonyl), or (iii) a $C_{3-7}$ cycloalkyl group (preferably cyclopropyl)};

$R^1$ is a phenyl group or a 5- to 10-membered heterocyclic group [preferably imidazolyl, pyridyl, thiadiazolyl (preferably the following group:

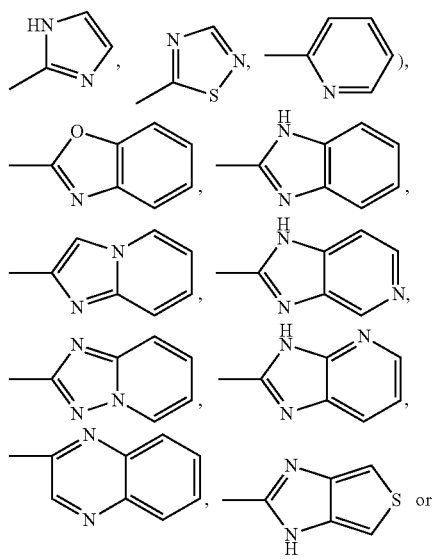

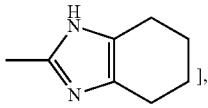

each of which is optionally substituted by 1 to 3 substituents selected from the group consisting of
(a) a halogen atom,
(b) an optionally esterified carboxy group,
(c) an optionally substituted alkyl group,
(d) an optionally substituted $C_{6-14}$ aryl group, and
(e) an optionally substituted alkyl-carbonyl group [preferably
(a) a halogen atom (preferably fluorine, bromine, chlorine),
(b) a $C_{1-6}$ alkoxy-carbonyl group (preferably ethoxycarbonyl),
(c) a $C_{1-6}$ alkyl group (preferably methyl, ethyl, butyl, isobutyl) optionally substituted by one or more (preferably 1 to 3) substituents selected from the group consisting of
(i) a halogen atom (preferably fluorine),
(ii) a hydroxy group, and
(iii) an optionally substituted $C_{1-6}$ alkoxy group (e.g., a $C_{1-6}$ alkoxy group (preferably ethoxy) optionally substituted by trimethylsilyl),
(d) a $C_{6-14}$ aryl group (preferably phenyl), and
(e) a $C_{1-6}$ alkyl-carbonyl group (preferably acetyl)];

L is an oxygen atom (—O—), —CO—, —NR$^a$—, —NR$^a$-COO— wherein R$^a$ is preferably a hydrogen atom or a $C_{1-6}$ alkyl group (preferably methyl), or

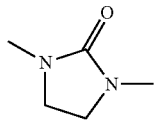

[preferably an oxygen atom, or —NR$^a$— wherein R$^a$ is a hydrogen atom or a $C_{1-6}$ alkyl group (preferably methyl)]; or L and R$^1$ in combination optionally form a bi- or tri-cyclic fused heterocyclic group optionally substituted by 1 to 3 substituents selected from the group consisting of
(a) a $C_{1-6}$ alkoxy-carbonyl group (preferably ethoxycarbonyl),
(b) a $C_{1-6}$ alkyl group (preferably methyl) optionally substituted by $C_{6-14}$ aryl group(s) (preferably phenyl), and
(c) an oxo group
(preferably

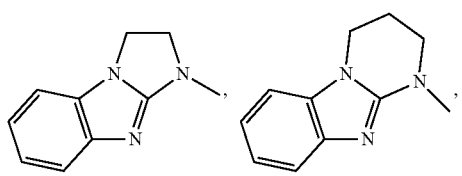

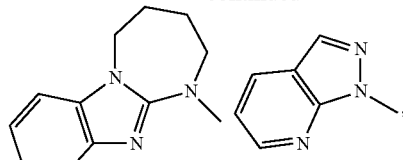

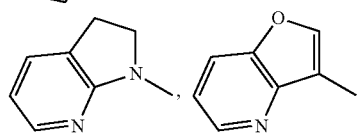

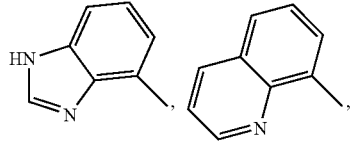

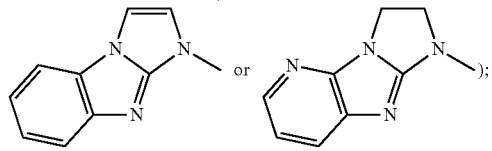

and
ring B$^1$ is preferably an optionally substituted benzene ring, more preferably a benzene ring optionally substituted by 1 to 3 substituents selected from the group consisting of a halogen atom and an optionally substituted alkyl group [preferably a halogen atom and an optionally substituted $C_{1-6}$ alkyl group, more preferably a halogen atom (preferably a fluorine atom) and a $C_{1-6}$ alkyl group (preferably methyl)],
or a salt thereof.

In another embodiment, the compound represented by the formula (I-1) or a salt thereof is preferably a compound wherein
$Z^1$ is —N=,
$Z^2$, $Z^3$ and $Z^4$ are —CH=,
Y is —NR$^c$— or a di-$C_{1-6}$ alkylmethylene group,
R$^c$ is a $C_{1-6}$ alkyl group optionally substituted by 1 to 3 substituents selected from the group consisting of a halogen atom, a hydroxy group, a $C_{3-7}$ cycloalkyl group, a trimethylsilyl-$C_{1-6}$ alkoxy group and a $C_{1-6}$ alkoxy-carbonyl group, R$^1$ is a 5- to 10-membered heterocyclic group optionally substituted by 1 to 3 substituents selected from
(a) a halogen atom,
(b) a $C_{1-6}$ alkoxy-carbonyl group,
(c) a $C_{1-6}$ alkyl group optionally substituted by one or more (preferably 1 to 3) substituents selected from the group consisting of
(i) a hydroxy group, and
(ii) an optionally substituted $C_{1-6}$ alkoxy group (e.g., a $C_{1-6}$ alkoxy group optionally substituted by trimethylsilyl), and
(d) a $C_{1-6}$ alkyl-carbonyl group;
L is an oxygen atom, or —NR$^a$— wherein R$^a$ is a hydrogen atom or a $C_{1-6}$ alkyl group, or
L and R$^1$ in combination optionally form a bi- or tri-cyclic fused heterocyclic group optionally substituted by 1 to 3 substituents selected from the group consisting of
(a) a halogen atom,
(b) a $C_{1-6}$ alkyl group optionally substituted by $C_{6-14}$ aryl group(s), and
(c) an oxo group, and
ring B$^1$ is a benzene ring,
or a salt thereof.

The compound represented by the formula (I-1) or a salt thereof is more preferably a compound wherein $Z^1$ is —N=, $Z^2$, $Z^3$ and $Z^4$ are —CH=, Y is —NR$^c$— wherein R$^c$ is a $C_{1-6}$ alkyl group, or a di-$C_{1-6}$ alkylmethylene group, $R^1$ is

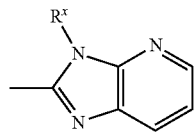

wherein $R^x$ is a hydrogen atom or a $C_{1-6}$ alkyl group,

L is an oxygen atom, and ring $B^1$ is a benzene ring, or a salt thereof.

In the partial structure of the formula (I-2):

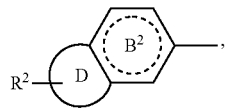

$R^2$ is a phenyl group or a 5- to 10-membered heterocyclic group, each of which is optionally substituted, ring $B^2$ is a benzene ring, a pyridine ring, a pyrimidine ring, a pyrazine ring or a pyridazine ring, each of which is optionally substituted, and ring D is an optionally further substituted 5- or 6-membered ring.

Examples of the "5- to 10-membered heterocyclic group" of the "phenyl group or 5- to 10-membered heterocyclic group, each of which is optionally substituted" for $R^2$ include those similar to the "5- to 10-membered heterocyclic group" of the "optionally substituted 5- to 10-membered heterocyclic group" for $R^1$.

Among them, a 5- or 6-membered monocyclic heterocyclic group, a bicyclic fused heterocyclic group (preferably a 9- or 10-membered bicyclic fused heterocyclic group) and the like are preferable.

The "5- or 6-membered monocyclic heterocyclic group" is preferably, for example, a 5- or 6-membered monocyclic nitrogen-containing aromatic heterocyclic group such as imidazolyl, pyridyl, pyridazinyl, pyrazinyl, pyrimidinyl, thiazolyl and the like, (preferably pyridyl, pyrimidinyl, thiazolyl etc.). Among them, the following group:

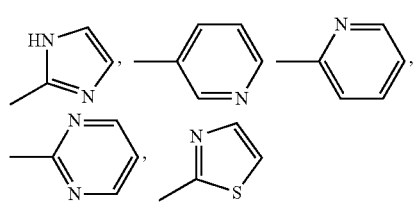

and the like are preferable, and the following group:

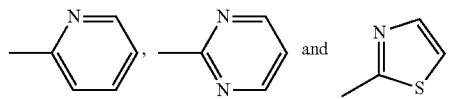

are more preferable.

Examples of the aforementioned "bicyclic fused heterocyclic group" include (1) a fused heterocyclic group formed by condensation of a phenyl group with a 5- or 6-membered heterocycle, (2) a fused heterocyclic group formed by condensation of a 5- or 6-membered heterocyclic group with a benzene ring, and (3) a fused heterocyclic group formed by condensation of a 5- or 6-membered heterocyclic group with a 5- or 6-membered heterocycle. Among them, the following group:

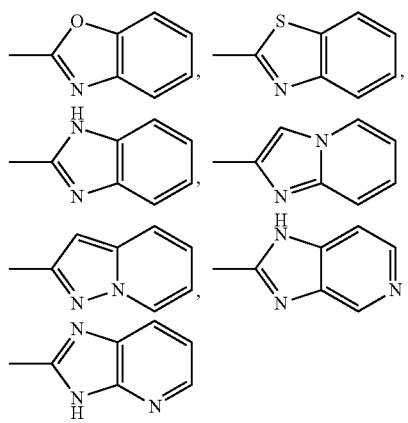

and the like are preferable, and the following group:

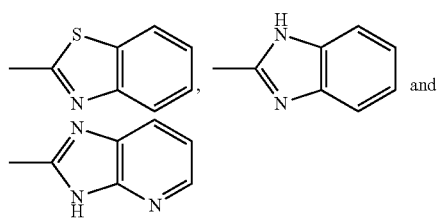

are more preferable.

Examples of the substituent of the "phenyl group or 5- to 10-membered heterocyclic group, each of which is optionally substituted" for $R^2$ include substituents selected from the above-mentioned Substituent Group A.

Among them, an optionally substituted alkyl group and the like are preferable, a $C_{1-6}$ alkyl group and the like are more preferable, and methyl is further more preferable.

The number of the substituents of the "phenyl group or 5- to 10-membered heterocyclic group, each of which is optionally substituted" for $R^2$ is preferably 0 (i.e., unsubstituted), or 1 to 3, more preferably 0 or 1. When the number of the substituents is not less than 2, the respective substituents may be the same or different.

R² is preferably a 5- to 10-membered heterocyclic group (preferably the following group:

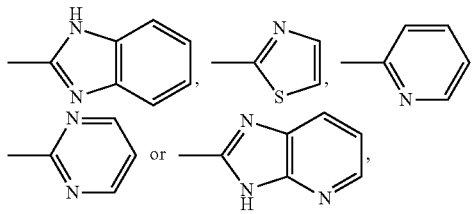

more preferably the following group:

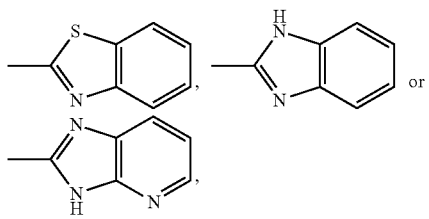

further more preferably the following group:

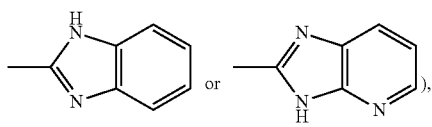

optionally substituted by 1 to 3 (preferably 1) substituents selected from an optionally substituted alkyl group (preferably a $C_{1-6}$ alkyl group, more preferably methyl).

Examples of the substituent of the "benzene ring, pyridine ring, pyrimidine ring, pyrazine ring or pyridazine ring, each of which is optionally substituted" for ring $B^2$ include substituents selected from the above-mentioned Substituent Group A.

The number of the substituents is preferably 0 (i.e., unsubstituted), or 1 to 3, more preferably 0. When the number of the substituents is not less than 2, the respective substituents may be the same or different.

Ring $B^2$ is preferably an optionally substituted benzene ring, more preferably a benzene ring.

The "5- or 6-membered ring" of the "optionally further substituted 5- or 6-membered ring" for ring D is a carbocycle having 5 or 6 carbon atoms (e.g., benzene) or a 5- or 6-membered heterocycle (e.g., pyrrolidine, dihydropyrrole, dihydropyrazole).

Among them, a pyrrolidine ring, a dihydropyrrole ring and a dihydropyrazole ring are preferable, and a pyrrolidine ring is more preferable.

Examples of the substituent of the "optionally further substituted 5- or 6-membered ring" for ring D include substituents selected from the above-mentioned Substituent Group A.

Among them, an optionally substituted alkyl group and the like are preferable, a $C_{1-6}$ alkyl group and the like are more preferable, and methyl is further more preferable.

The number of the substituents of the "optionally further substituted 5- or 6-membered ring" for ring D is preferably 0 (i.e., unsubstituted), or 1 to 3, more preferably 0 or 1, more preferably 0. When the number of the substituents is not less than 2, the respective substituents may be the same or different.

Ring D is preferably a pyrrolidine ring, a dihydropyrrole ring or a dihydropyrazole ring, each of which is optionally substituted, more preferably a pyrrolidine ring, a dihydropyrrole ring or a dihydropyrazole ring.

The partial structure of the formula (I-2):

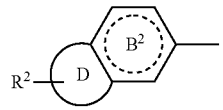

is preferably a structure represented by the formula:

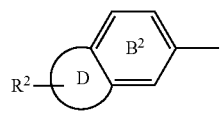

wherein each symbol is as defined above.

The partial structure of the formula (I-2):

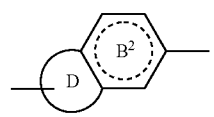

is preferably

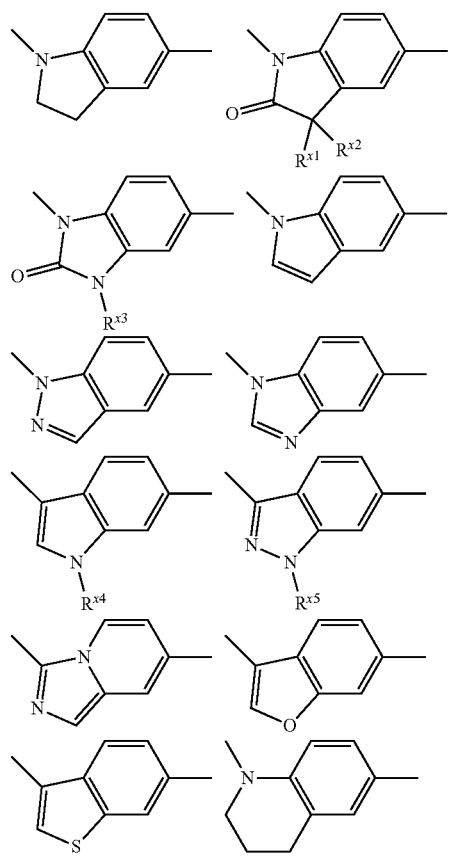

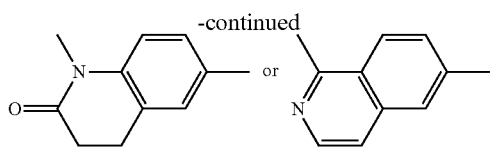 or wherein
$R^{x1}$ and $R^{x2}$ are the same or different and each is a hydrogen atom or an optionally substituted $C_{1-6}$ alkyl group,
$R^{x3}$-$R^{x5}$ are each a hydrogen atom or an optionally substituted $C_{1-6}$ alkyl group, and
the ring-constituting atom(s) optionally further have substituent(s),
and the like, more preferably

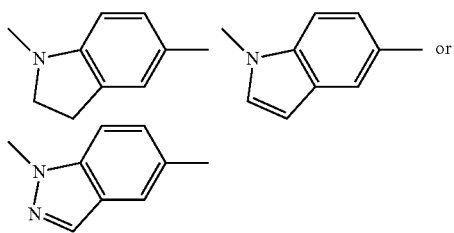 or wherein the ring-constituting atom(s) optionally further have substituent(s),
further more preferably

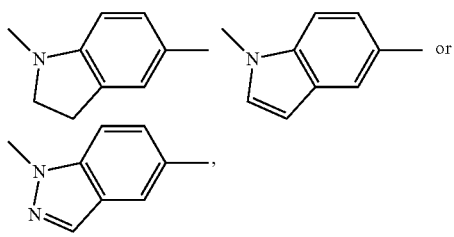 or particularly preferably

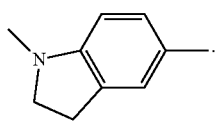.

Examples of the "optionally substituted $C_{1-6}$ alkyl group" for $R^{x1}$ or $R^{x2}$ include those similar to the "optionally substituted $C_{1-6}$ alkyl group" exemplified as the substituent for ring D.

Examples of the "optionally substituted $C_{1-6}$ alkyl group" for $R^{x3}$-$R^{x5}$ include those similar to the "optionally substituted $C_{1-6}$ alkyl group" exemplified as the substituent for ring D.

Examples of the substituent that the aforementioned ring-constituting atom(s) optionally further have include those similar to exemplified as the substituent for ring $B^2$ or ring D.

The compound represented by the formula (I-2) or a salt thereof is preferably a compound wherein
$Z^1$ is —N= and the others (i.e., $Z^2$, $Z^3$ and $Z^4$) are —CH=; or $Z^1$ and $Z^3$ are —N= and the others (i.e., $Z^2$ and $Z^4$) are —CH= [preferably $Z^1$ is —N= and the others (i.e., $Z^2$, $Z^3$ and $Z^4$) are —CH=];

ring A is a pyridine ring or a pyrimidine ring, each of which is optionally substituted by 1 to 3 substituents selected from the group consisting of a halogen atom, cyano, an optionally substituted alkyl group and an optionally substituted alkoxy group [preferably a halogen atom, cyano, optionally substituted $C_{1-6}$ alkyl and optionally substituted $C_{1-6}$ alkoxy, more preferably a halogen atom (preferably a chlorine atom, a fluorine atom), cyano, $C_{1-6}$ alkyl (preferably methyl) optionally substituted by 1 to 3 halogen atoms (preferably a fluorine atom), and $C_{1-6}$ alkoxy (preferably methoxy, ethoxy) optionally substituted by 1 to 3 halogen atoms (preferably a fluorine atom)];

Y is an oxygen atom, an optionally substituted methylene group, or —$NR^c$— wherein $R^c$ is preferably a hydrogen atom, an optionally substituted alkyl group or an optionally substituted $C_{3-7}$ cycloalkyl group
{preferably an oxygen atom, a methylene group optionally substituted by 1 or 2 $C_{1-6}$ alkyl group(s) (preferably methyl) (the two substituents for the methylene group optionally form, together with the adjacent carbon atom, a $C_{3-6}$ cycloalkane (preferably cyclobutane)), or —$NR^c$— wherein $R^c$ is preferably (i) a hydrogen atom, (ii) a $C_{1-6}$ alkyl group (preferably methyl, ethyl, propyl, isopropyl, isobutyl) optionally substituted by 1 to 3 substituents selected from the group consisting of a halogen atom (preferably a fluorine atom), a hydroxy group, a $C_{3-7}$ cycloalkyl group (preferably cyclopropyl), an optionally substituted $C_{1-6}$ alkoxy group (e.g., a trimethylsilyl-$C_{1-6}$ alkoxy group (preferably trimethylsilyl-ethoxy)), and a $C_{1-6}$ alkoxy-carbonyl group (preferably ethoxycarbonyl), or (iii) a $C_{3-7}$ cycloalkyl group (preferably cyclopropyl)};

$R^2$ is a 5- to 10-membered heterocyclic group (preferably the following group:

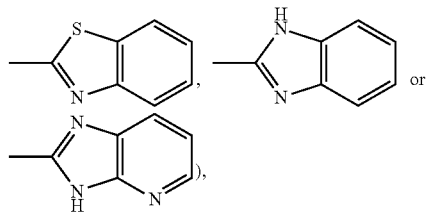

optionally substituted by 1 to 3 (preferably 1) substituents selected from an optionally substituted alkyl group (preferably a $C_{1-6}$ alkyl group, more preferably methyl);
ring $B^2$ is an optionally substituted benzene ring (preferably a benzene ring); and
ring D is a pyrrolidine ring, a dihydropyrrole ring or a dihydropyrazole ring, each of which is optionally substituted (preferably a pyrrolidine ring, a dihydropyrrole ring or a dihydropyrazole ring),
or a salt thereof.

The compound represented by the formula (I) or a salt thereof is preferably a compound (W-1) wherein
$Z^1$ is —N= and the others (i.e., $Z^2$, $Z^3$ and $Z^4$) are —CH=; or $Z^1$ and $Z^3$ are —N= and the other (i.e., $Z^2$ and $Z^4$) are —CH=; wherein the nitrogen atom of —N= for $Z^1$ may be oxidized; ring A is
(1) a pyridine ring which is optionally substituted by one substituent selected from (i) a $C_{1-6}$ alkyl group optionally substituted by 1 to 3 substituents selected from a halogen atom, hydroxy and a $C_{1-6}$ alkyl-carbonyloxy (preferably methyl, trifluoromethyl, acetoxymethyl, hydroroxymethyl), (ii) a halogen atom (preferably chlorine, fluorine), (iii) cyano, and (iv) a $C_{1-4}$ alkoxy optionally substituted by 1 to 3 halogen atoms (preferably methoxy, difluoromethoxy, difluoroethoxy, trifluoroethoxy), or (2) a pyrimidine ring, Y is a oxygen atom, a methylene group which is optionally substituted by 1 to 2 $C_{1-6}$ alkyl group(s) (preferably methyl) (the two substituents for the methylene group optionally form, together with the adjacent carbon atom, a $C_{3-6}$ cycloalkane (preferably cyclobutane)), or —NR$^e$— wherein R$^e$ is (1) a hydrogen atom, (2) a $C_{1-6}$ alkyl group which is optionally substituted by 1 to 3 (preferably 1 or 2) substituents selected from the group consisting of (i) a $C_{1-6}$ alkoxy group optionally substituted by trimethylsilyl, and (ii) a halogen atom (preferably methyl, ethyl, propyl, isopropyl, trimethylsilyl-ethoxy-methyl, difluoromethyl), or (3) a $C_{3-7}$ cycloalkyl (preferably cyclopropyl), R is (1) a group represented by the formula:

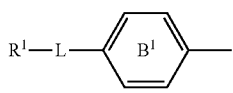

wherein
the partial structure:

R$^1$-L- is a group represented by the following formula:

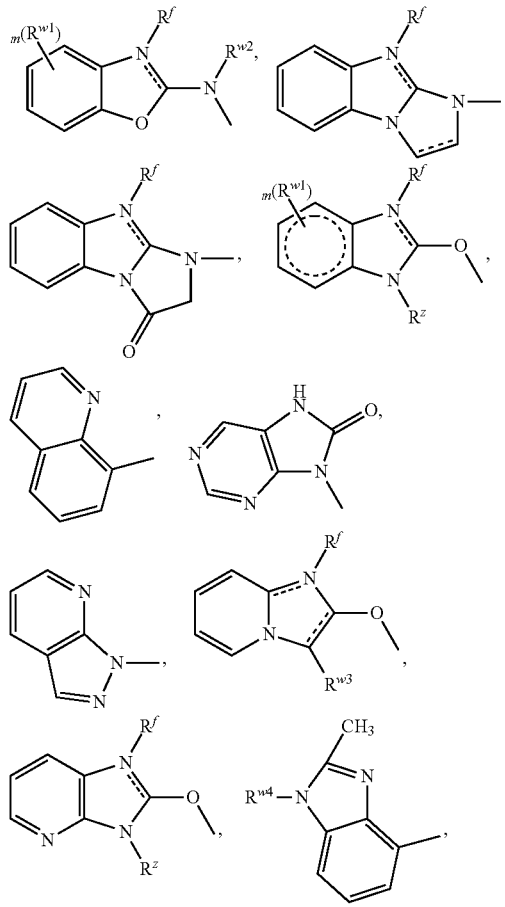

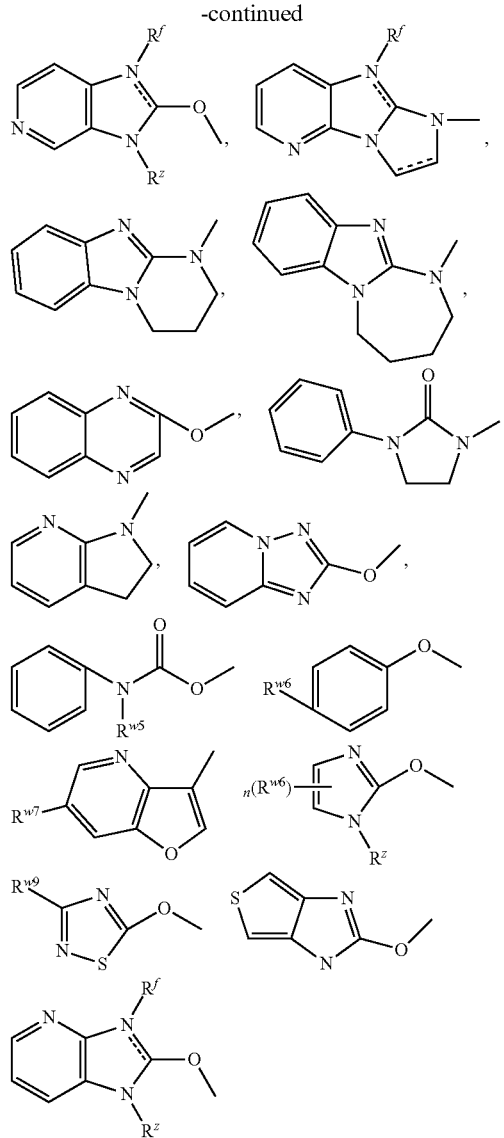

wherein
R$^f$ is absent or a hydrogen atom (when R$^f$ is absent, —N(R$^f$)— is =N—; R$^f$ is preferably absent);

R$^z$ is (i) a hydrogen atom, (ii) a $C_{1-4}$ alkyl group optionally substituted by one substituent selected from (1) a hydroxy group (preferably methyl, ethyl, hydroxyethyl, buthyl, hydroxyisobutyl) and (2) a $C_{1-4}$ alkoxy group optionally substituted by trimethylsilyl (preferably trimethylsilylmethoxy), or (iii) a $C_{1-6}$ alkyl-carbonyl group (preferably acetyl);

R$^{w1}$ is a halogen atom (preferably fluorine);

m is 0 to 2;

R$^{w2}$ is a hydrogen atom or a methyl group;

R$^{w3}$ is a hydrogen atom or a $C_{1-2}$ alkoxy-carbonyl group (preferably ethoxycarbonyl);

R$^{w4}$ is a hydrogen atom or benzyl;

R$^{w5}$ is a hydrogen atom or methyl;

R$^{w6}$ is a hydrogen atom, a halogen atom (preferably fluorine, chlorine), or a $C_{1-6}$ alkyl group optionally substituted by 1 to 3 halogen atoms (preferably trifluoromethyl);

R$^{w7}$ is a $C_{1-6}$ alkoxyl-carbonyl group (preferably ethoxycarbonyl);

$R^{w8}$ is a halogen atom (preferably chlorine, bromine), or a $C_{1-6}$ alkyl optionally substituted by 1 to 3 halogen atoms (preferably trifluoromethyl);

n is 0 to 2; and $R^{w9}$ is a hydrogen atom or a halogen atom (preferably bromine); and ring $B^1$ is a benzene ring optionally substituted by one halogen atom (preferably fluorine); or (2) a group represented by the formula:

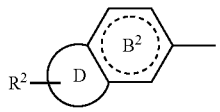

wherein $R^2$ is a 5- to 10-membered heterocyclic group (preferably the following group:

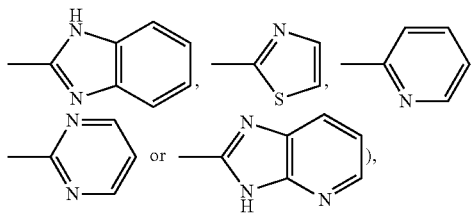

optionally substituted by one $C_{1-6}$ alkyl group (preferably methyl);

ring $B^2$ is a benzene ring; and ring D is a pyrrolidine ring, a dihydropyrrole ring, a dihydropirazole ring, (i.e., the partial structure of the formula:

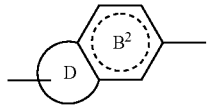

is

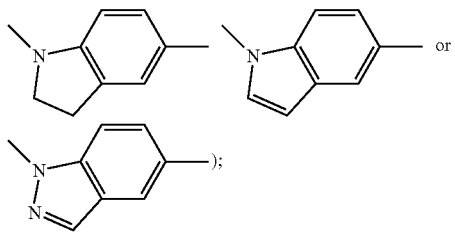

or a salt thereof.

In another embodiment, the compound represented by the formula (I) or a salt thereof is preferably a compound (W-2) wherein $Z^1$ is —N= and the others (i.e., $Z^2$, $Z^3$ and $Z^4$) are —CH=; or $Z^1$ and $Z^3$ are —N= and the other (i.e., $Z^2$ and $Z^4$) are —CH=; ring A is (1) a pyridine ring which is optionally substituted by one substituent selected from (i) a $C_{1-6}$ alkyl group optionally substituted by 1 to 3 substituents selected from a halogen atom or hydroxy (preferably methyl, trifluoromethyl, hydroxymethyl), (ii) a halogen atom (preferably chlorine, fluorine), (iii) cyano, and (iv) a $C_{1-4}$ alkoxy optionally substituted by 1 to 3 halogen atoms (preferably methoxy, difluoromethoxy, difluoroethoxy, trifluoroethoxy), or (2) a pyrimidine ring, Y is a methylene group which is optionally substituted by 1 to 2 $C_{1-6}$ alkyl group(s) (preferably methyl), or —$NR^c$— wherein $R^c$ is (1) a hydrogen atom, (2) a $C_{1-6}$ alkyl which is optionally substituted by 1 to 3 substituents selected from the group consisting of hydroxy and a halogen atom (preferably methyl, ethyl, propyl, isopropyl, hydroxymethyl, difluoromethyl), or (3) a $C_{3-7}$ cycloalkyl (preferably cyclopropyl), R is (1) a group represented by the formula:

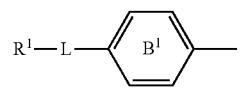

wherein the partial structure:

is a group represented by the following formula:

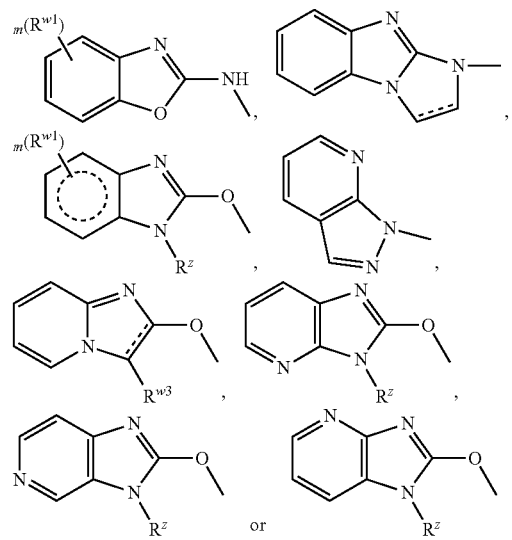

wherein $R^{w1}$ is a halogen atom (preferably fluorine);

m is 0 to 1;

$R^z$ is (i) a hydrogen atom, (ii) a $C_{1-4}$ alkyl group optionally substituted by one hydroxy (preferably methyl, hydroxyethyl, hydroxyisobutyl); and $R^{w3}$ is a hydrogen atom or a $C_{1-2}$ alkoxy-carbonyl group (preferably, ethoxycarbonyl), and ring $B^1$ is a benzene ring; or (2) a group represented by the formula:

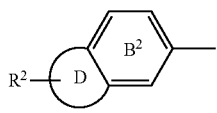

wherein
$R^2$ is a 5- to 10-membered heterocyclic group (preferably the following group:

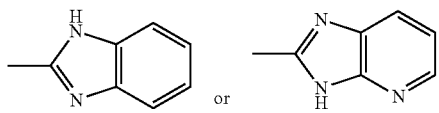

optionally substituted by one $C_{1-6}$ alkyl group (preferably methyl); and
the partial structure of the formula:

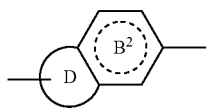

is

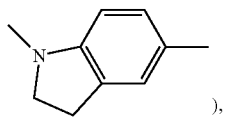

), or a salt thereof.

In another embodiment, the compound represented by the formula (I) or a salt thereof is preferably a compound represented by the formula:

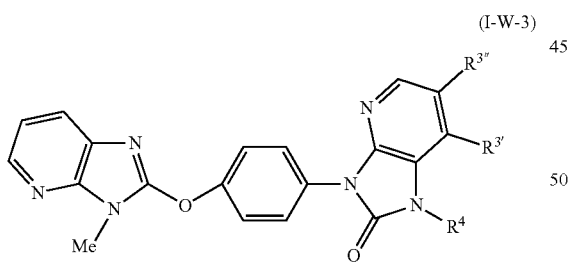

(I-W-3)

wherein
$R^{3'}$ is a hydrogen atom, or a $C_{1-6}$ alkyl which may optionally be substituted by one hydroxy (i.e., methyl, hydroxymethyl);
$R^{3''}$ is a hydrogen atom, a halogen atom (preferably fluorine), a $C_{1-6}$ alkyl group (preferably methyl) or a $C_{1-6}$ alkoxy group (preferably methoxy);
$R^4$ is a $C_{1-6}$ alkyl group (preferably methyl, ethyl, isopropyl);
or a salt thereof.

In another embodiment, the compound represented by the formula (I) or a salt thereof is preferably a compound wherein $Z^1$ is —N= and the others (i.e., $Z^2$, $Z^3$ and $Z^4$) are —CH=;

ring A is a pyridine ring optionally substituted by a halogen atom, cyano, an optionally substituted alkyl group or an optionally substituted alkoxy group [preferably a halogen atom, cyano, optionally substituted $C_{1-6}$ alkyl or optionally substituted $C_{1-6}$ alkoxy, more preferably a halogen atom (preferably a chlorine atom, a fluorine atom), cyano, $C_{1-6}$ alkyl (preferably methyl) optionally substituted by 1 to 3 halogen atoms (preferably a fluorine atom), or $C_{1-6}$ alkoxy (preferably methoxy, ethoxy) optionally substituted by 1 to 3 halogen atoms (preferably a fluorine atom)];

Y is —$NR^c$— wherein $R^c$ is preferably an optionally substituted alkyl group, more preferably a $C_{1-6}$ alkyl group (preferably methyl, ethyl, propyl, isopropyl, isobutyl) optionally substituted by 1 to 3 substituents selected from the group consisting of a halogen atom (preferably a fluorine atom), a hydroxy group, a $C_{3-7}$ cycloalkyl group (preferably cyclopropyl), an optionally substituted $C_{1-6}$ alkoxy group (e.g., a trimethylsilyl-$C_{1-6}$ alkoxy group (preferably trimethylsilyl-ethoxy)) and a $C_{1-6}$ alkoxy-carbonyl group (preferably ethoxycarbonyl)]; and R is
(1) a group represented by the formula:

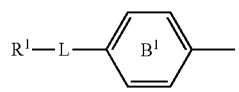

wherein
the partial structure:

$R^1$-L- is a group represented by the following formula:

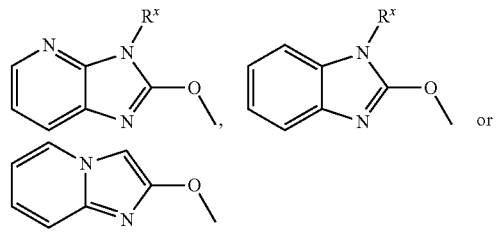

wherein
$R^x$ is an optionally substituted $C_{1-6}$ alkyl group [preferably a $C_{1-6}$ alkyl group (preferably methyl, ethyl, butyl, isobutyl) optionally substituted by 1 to 3 substituents selected from the group consisting of (i) a hydroxy group and (ii) an optionally substituted $C_{1-6}$ alkoxy group (e.g., a $C_{1-6}$ alkoxy group (preferably ethoxy) optionally substituted by trimethylsilyl)]; and ring $B^1$ is an optionally substituted benzene ring [preferably a benzene ring optionally substituted by 1 to 3 substituents selected from the group consisting of a halogen atom and an optionally substituted alkyl group (preferably a halogen atom and an optionally substituted $C_{1-6}$ alkyl group, more preferably a halogen atom (preferably a fluorine atom) and a $C_{1-6}$ alkyl group (preferably methyl))], or (2) a group represented by the formula:

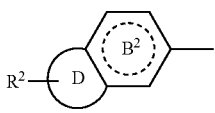

wherein,
R² is a 5- to 10-membered heterocyclic group (preferably the following group:

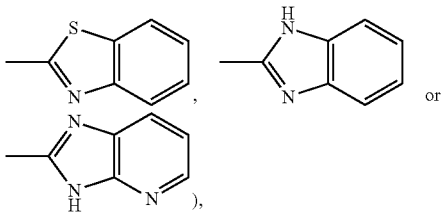

optionally substituted by 1 to 3 (preferably 1) substituents selected from an optionally substituted alkyl group (preferably a $C_{1-6}$ alkyl group, more preferably methyl);
ring B² is an optionally substituted benzene ring (preferably a benzene ring); and
ring D is a pyrrolidine ring, a pyrrole ring or a pyrazole ring, each of which is optionally substituted (preferably a pyrrolidine ring, a pyrrole ring or a pyrazole ring),
or a salt thereof.

In another embodiment, the compound represented by the formula (I) or a salt thereof is preferably a compound wherein $Z^1$ is —N= and the others (i.e., $Z^2$, $Z^3$ and $Z^4$) are —CH=; or $Z^1$ and $Z^3$ are —N= and the others (i.e., $Z^2$ and $Z^4$) are —CH=; or $Z^1$ and $Z^4$ are —N= and the others (i.e., $Z^2$ and $Z^3$) are —CH=; ring A is a pyridine ring, a pyrimidine ring or a pyrazine ring, each of which is optionally substituted by 1 or 2 (preferably 1) substituents selected from a halogen atom, an optionally substituted $C_{1-6}$ alkyl group (preferably a $C_{1-2}$ alkyl group such as methyl, ethyl and the like) and an optionally substituted $C_{1-6}$ alkoxy (e.g., methoxy) [preferably a halogen atom (preferably a fluorine atom) and a methyl group];
Y is —NR$^c$— wherein R$^c$ is preferably a $C_{1-3}$ alkyl group (e.g., methyl, ethyl, isopropyl), preferably —N(—CH$_2$CH$_3$)—; and
R is a group represented by the formula:

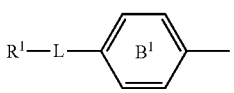

wherein
the partial structure:
R¹-L-
is a group represented by the following formula:

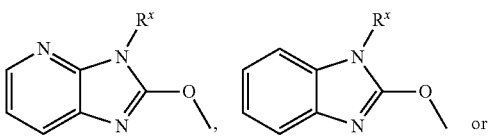

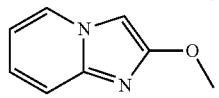

wherein
R$^x$ is an optionally substituted $C_{1-6}$ alkyl group [preferably a $C_{1-6}$ alkyl group (preferably methyl, ethyl, butyl, isobutyl) optionally substituted by 1 to 3 substituents selected from the group consisting of (i) a hydroxy group and (ii) an optionally substituted $C_{1-6}$ alkoxy group (e.g., methoxy)]; and
ring B¹ is an optionally substituted benzene ring [preferably a benzene ring optionally substituted by one substituent selected from the group consisting of a halogen atom and an optionally substituted $C_{1-6}$ alkyl group, more preferably a halogen atom (preferably a fluorine atom) and a $C_{1-6}$ alkyl group (preferably methyl)] or a pyridine ring [more preferably a benzene ring],
or a salt thereof.

Among the embodiments of the above-mentioned formula (I), a compound wherein ring A is a pyridine ring wherein $Z^1$ is —N= and the others (i.e., $Z^2$, $Z^3$ and $Z^4$) are —CH=, and each of —CH= for $Z^3$ and $Z^4$ has one substituent instead of a hydrogen atom, or the one of —CH= for $Z^3$ and $Z^4$ has one substituent instead of a hydrogen atom, is preferable, and a compound wherein ring A is a pyridine ring wherein $Z^1$ is —N= and the others (i.e., $Z^2$, $Z^3$ and $Z^4$) are —CH=, and —CH= for $Z^4$ has one substituent instead of a hydrogen atom, is more preferable. Examples of the substituent include a halogen atom, an optionally substituted $C_{1-6}$ alkyl group (preferably a $C_{1-2}$ alkyl group such as methyl, ethyl and the like) and an optionally substituted $C_{1-6}$ alkoxy (e.g., methoxy) [preferable examples thereof include a halogen atom (preferably a fluorine atom) and a methyl group].

In another embodiment, the compound represented by the formula (I) or a salt thereof is preferably a compound represented by the formula (I') or a salt thereof.

As the compound represented by the formula (I) or a salt thereof,
1-ethyl-6-methyl-3-{4-[(3-methyl-3H-imidazo[4,5-b]pyridin-2-yl)oxy]phenyl}-1,3-dihydro-2H-imidazo[4,5-b]pyridin-2-one, or a salt thereof;
1-ethyl-6-methoxy-3-{4-[(3-methyl-3H-imidazo[4,5-b]pyridin-2-yl)oxy]phenyl}-1,3-dihydro-2H-imidazo[4,5-b]pyridin-2-one, or a salt thereof;
1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one, or a salt thereof;
6-methyl-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one, or a salt thereof;
1-ethyl-6-fluoro-3-{4-[(3-methyl-3H-imidazo[4,5-b]pyridin-2-yl)oxy]phenyl}-1,3-dihydro-2H-imidazo[4,5-b]pyridin-2-one, or a salt thereof;
1,7-dimethyl-3-{4-[(3-methyl-3H-imidazo[4,5-b]pyridin-2-yl)oxy]phenyl}-1,3-dihydro-2H-imidazo[4,5-b]pyridin-2-one, or a salt thereof; and
1-ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one, or a salt thereof are preferable.

When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; aluminum salts and the like. Preferable examples of salts with organic bases include salts with trimethylamine, triethylamine, pyridine, picoline, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmacologically acceptable are preferable. For example, in the case when acidic functional group are present in the compound, for example, inorganic salts including alkali metal salts (e.g., sodium salts, potassium salts etc.), alkali earth metal salts (e.g., calcium salts, magnesium salts, barium salts etc.) and the like, ammonium salts and the like are preferable. In contrast, in the case when basic functional group are present in the compound, for example, salts with inorganic acids such as hydrochloric acid, hydrobromic acid, nitric acid, sulfuric acid, phosphoric acid etc. or salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid etc. are preferable.

In the following, compound (I) and a salt thereof are generally also referred to as the compound of the present invention.

The compound (I) can be obtained in the crystal form. Either single crystalline form or crystalline mixture can be included in the compound (I).

The compound of the formula (I) can be a pharmaceutically acceptable co-crystal or a co-crystal salt. The term "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be obtained according to a per se known co-crystallization method.

The compound (I) can be provided as a solvate (e.g., hydrate) or as a non-solvate and both are included in the compound (I).

The compounds labeled with isotopes (e.g., $^2$H, $^3$H, $^{11}$C, $^{18}$F, $^{35}$S, $^{125}$I etc.) are also included in the compound (I).

Compound (I) labeled or substituted with an isotope can be utilized as, for example, a tracer (PET tracer) used for Positron Emission Tomography (PET) and is useful in the fields of medical diagnosis and the like.

[Manufacturing Method]

The methods for manufacturing compound (I), and compound (Ia), compound (Ia') and compound (Ib) encompassed in compound (I) are explained in the following.

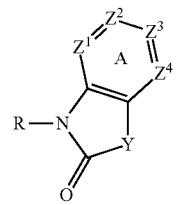

I

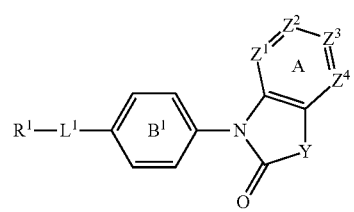

Ia

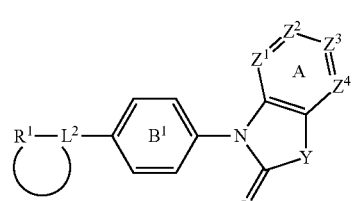

Ia'

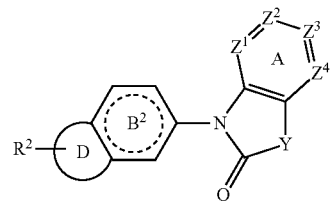

Ib wherein $L^1$ in compound (Ia) is a sulfur atom, an oxygen atom, an optionally substituted methylene group, —CO—, —NR$^a$—, —CH$_2$O—, —OCH$_2$—, —NR$^a$COO—, —OCONR$^a$—, —NR$^a$CONR$^b$—, —NR$^a$COCH$_2$—, —CH$_2$CONR$^a$—, —NR$^a$CO—, —CONR$^a$—,

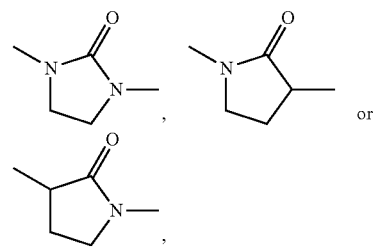

the "optionally substituted methylene group" for $L^1$ means the same as the "optionally substituted methylene group" for L, $L^2$ in compound (Ia') forms, together with $R^1$, an optionally substituted bi- or tri-cyclic fused heterocyclic group, the "optionally substituted bi- or tri-cyclic fused heterocyclic group" formed by $L^2$ and $R^1$ in combination means the same as the "optionally substituted bi- or tri-cyclic fused heterocyclic group" optionally formed by L and $R^1$, and other symbols are each as defined above.

Compound (I) comprises compounds (Ia), (Ia') and (Ib).

The compound of the present invention and starting compounds therefor can be produced by a means known per se, for example, according to the methods shown by the following schemes and the like. In the following, the "room temperature" generally means 0-30° C., and each symbol in the chemical structural formulas described in the schemes is, unless otherwise specified, as defined above. The compounds in the formulas also include the salts formed, and examples of such salts include those similar to the salts of compound (I) and the like. The compounds obtained in respective steps can be used for the next reaction in the form of a reaction mixture or as a crude product. They can also be isolated from a reaction mixture according to a conventional method, and can be easily purified by a separation means such as recrystallization, distillation, chromatography and the like. When the compounds in the formulas are commercially available, the commercially available products can be directly used. In addition, when each ring in the formula (I) has a substituent, the corresponding precursor has the same substituent.

When the starting compound contains an amino group, a carboxy group, a hydroxy group or a heterocyclic group, these groups may be protected with a protective group generally used in the peptide chemistry and the like. In this case, after the reaction, the target compound can be obtained by removing the protective group as necessary. The protective group can be introduced or removed by a method known per se, for example, the method described in "Protective Groups in Organic Synthesis, $3^{rd}$ Ed." by Theodora W. Greene, Peter G. M. Wuts, Wiley-Interscience Corporation (1999) and the like. In the formula, $P^1$-$P^3$ are each a nitrogen-protective group of an amino group or an amide group, a hydroxy-protective group, a carboxy-protective group, or a hydrogen atom, and those known per se can be used.

Examples of the nitrogen-protective group of an amino group or an amide group include a formyl group, and a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl (Boc) etc.), an allyloxycarbonyl(Alloc) group, a phenyloxycarbonyl group, a fluorenylmethoxycarbonyl(Fmoc) group, a $C_{7-10}$ aralkyl-carbonyl group (e.g., benzylcarbonyl etc.), a $C_{7-10}$ aralkyl-oxycarbonyl group (e.g., benzyloxycarbonyl (Z) etc.), a $C_{7-10}$ aralkyl group (e.g., benzyl etc.), a 2-(trimethylsilyl)ethoxymethyl(SEM) group, a trityl group, a phthaloyl group, an N,N-dimethylaminomethylene group, a tert-butylcarbamate group, a benzylcarbamate group and the like, each of which may have substituent(s). Examples of the substituent these may have include a phenyl group, a halogen atom (e.g., fluorine, chlorine, bromine, iodine etc.), a $C_{1-6}$ alkyl-carbonyl group (e.g., methylcarbonyl, ethylcarbonyl, butylcarbonyl etc.), a nitro group and the like. The number of the substituents is about 1 to 3.

Examples of the carboxy-protective group include a $C_{1-6}$ alkyl group (e.g., methyl, ethyl, n-propyl, isopropyl, n-butyl, tert-butyl etc.), an allyl group, a benzyl group, a phenyl group, a trityl group, a tri $C_{1-6}$ alkylsilyl group and the like, each of which may have substituent(s). Examples of the substituents these may have include a halogen atom (e.g., fluorine, chlorine, bromine, iodine etc.), a formyl group, a $C_{1-6}$ alkyl-carbonyl group (e.g., acetyl, ethylcarbonyl, butylcarbonyl etc.), a nitro group and the like. The number of the substituents is about 1 to 3.

Examples of the hydroxy-protective group include a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furyl group, a silyl group and the like, each of which may have substituent(s). Examples of the substituent these may have include a halogen atom (e.g., fluorine, chlorine, bromine, iodine etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like. The number of the substituents is about 1 to 4.

Preferable examples of $P^1$-$P^3$ include a tert-butylcarbamate group, a benzylcarbamate group, a benzyl group, a $C_{1-6}$ alkyl group (e.g., a methyl group, an ethyl group) and the like. In addition, $P^1$-$P^3$ themselves can sometimes be the substituent of the compound of the present invention and, for example, a tert-butylcarbamate group, a benzylcarbamate group, a benzyl group, a $C_{1-6}$ alkyl group (e.g., a methyl group, an ethyl group) and the like can be mentioned.

As the "leaving group" for $X^1$-$X^{12}$, a halogen atom (e.g., a chlorine atom, a bromine atom, an iodine atom etc.), optionally halogenated $C_{1-6}$ alkylsulfonyloxy (e.g., methanesulfonyloxy, ethanesulfonyloxy, trifluoromethanesulfonyloxy, trifluoroethanesulfonyloxy etc.), $C_{6-10}$ arylsulfonyloxy optionally substituted by 1 to 3 $C_{1-6}$ alkyl groups (e.g., benzenesulfonyloxy, p-toluenesulfonyloxy etc.), optionally halogenated $C_{1-6}$ alkylsulfonyl (e.g., methanesulfonyl, ethanesulfonyl, trifluoroethanesulfonyl etc.) and the like are used. In addition, $X^1$-$X^{12}$ also include a substituent convertible to a leaving group, and the substituent can be converted to a leaving group by a reaction known per se in a desired step. For example, $X^1$-$X^{12}$ may be a methylthio group convertible to a methanesulfonyl group by an oxidation reaction.

When compound (I) contains optical isomer, stereoisomer, regioisomer, rotamer or tautomer, they are also encompassed in compound (I), and each can be obtained as a single isomer by a synthetic method and separation method known per se. For example, when compound (I) is an optically active form, the racemate can be separated into (+) form and (−) form by a conventional optical resolution method.

The method of optical resolution may be a method known per se, such as a fractional recrystallization method, a chiral column method, a diastereomer method etc. described in detail below.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemate is prepared into a diastereomeric mixture by chemical reaction with an optically active reagent, which is made into a single substance by a typical separation means (e.g., a fractional recrystallization method, a chromatography method etc.) and the like, and is is subjected to a chemical treatment such as hydrolysis and the like to separate an optically active reagent moiety, whereby an optical isomer is obtained. For example, when compound (I) contains hydroxy, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxy group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Each step described below can be performed without solvent, or by dissolving or suspending in an appropriate solvent, where two or more kinds of solvents may be used by mixing them at an appropriate ratio. Of those recited as examples of the solvent to be used in the manufacturing method of the compound of the present invention, the following solvents are specifically used.
Alcohols:
methanol, ethanol, 1-propanol, 2-propanol, tert-butyl alcohol, 2-methoxyethanol, 1-pentanol, etc.
Ethers:
diethyl ether, diisopropyl ether, diphenylether, tetrahydrofuran, 1,4-dioxane, 1,2-dimethoxyethane, etc. aromatic hydrocarbons:
benzene, chlorobenzene, toluene, xylene, etc.
Saturated Hydrocarbons:
cyclohexane, hexane, etc.
Amides:
N,N-dimethylformamide, N,N-dimethylacetamide, hexamethylphosphoric triamide, N-methylpyrrolidone, etc. halogenated hydrocarbons:
dichloromethane, chloroform, carbon tetrachloride, 1,2-dichloroethane, etc.
Nitriles:
acetonitrile, propionitrile, etc.
Sulfoxides:
dimethylsulfoxide, etc.
Aromatic Organic Bases:
pyridine, lutidine, etc.
Esters:
methyl acetate, ethyl acetate, butyl acetate, etc.

Of those recited as examples of the base or deoxidizer to be used in the manufacturing method of the compound of the present invention, the following bases and deoxidizers are specifically used.

Inorganic Bases:
sodium hydroxide, potassium hydroxide, magnesium hydroxide, etc.
Basic Salts:
sodium carbonate, potassium carbonate, cesium carbonate, calcium carbonate, sodium hydrogen carbonate, etc.
Organic Bases:
triethylamine, diisopropylethylamine, tributylamine, cyclohexyldimethylamine, $N^1,N^2$-dimethylethane-1,2-diamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole, etc.
Metal Alkoxides:
sodium methoxide, sodium ethoxide, potassium tert-butoxide, etc.
Alkali Metal Hydrides:
sodium hydride, potassium hydride, etc.
Metal Amides:
sodium amide, lithiumdiisopropylamide, lithiumhexamethyl disilazide, etc.

Compound (Ia) can be produced by scheme 1. In addition, of compounds (Ia), the following compound (Ia-I) and compound (Ia-II) can also be produced by scheme 2.

Compound (Ia') can be produced by scheme 3. In addition, of compounds (Ia'), the following compound (Ia'-I) and compound (Ia'-II) can also be produced by scheme 4, and the following compound (Ia'-III) can also be produced by scheme 5.

Compound (Ib) can be produced by scheme 6. In addition, of compounds (Ib), the following compound (Ib-I) can also be produced by scheme 7.

Compound (Ia-III) can be produced by scheme 8.

In the formulas shown in these schemes 1-8, when the starting compound in each reaction has a hydroxy group, an amino group and the like, these groups may be appropriately subjected to a general protection and deprotection reactions (e.g., the reaction described in step 2). The protective groups may be selected, introduced or removed according to a method known per se, for example, the method described in "Protective Groups in Organic Synthesis, $3^{rd}$ Ed." by Theodora W. Greene, Peter G. M. Wuts, Wiley-Interscience Corporation (1999), or a method analogous thereto and the like. In addition, when the starting compound in each reaction has an amino group, a compound introduced with a nitro group instead of an amino group may be used as a starting compound, and after the reaction, the nitro group may be reduced to give a desired amino group (e.g., the reaction described in step 7).

In addition, compound (I) can also be produced by an appropriate combination of the reaction of each step shown by these schemes 1-8.

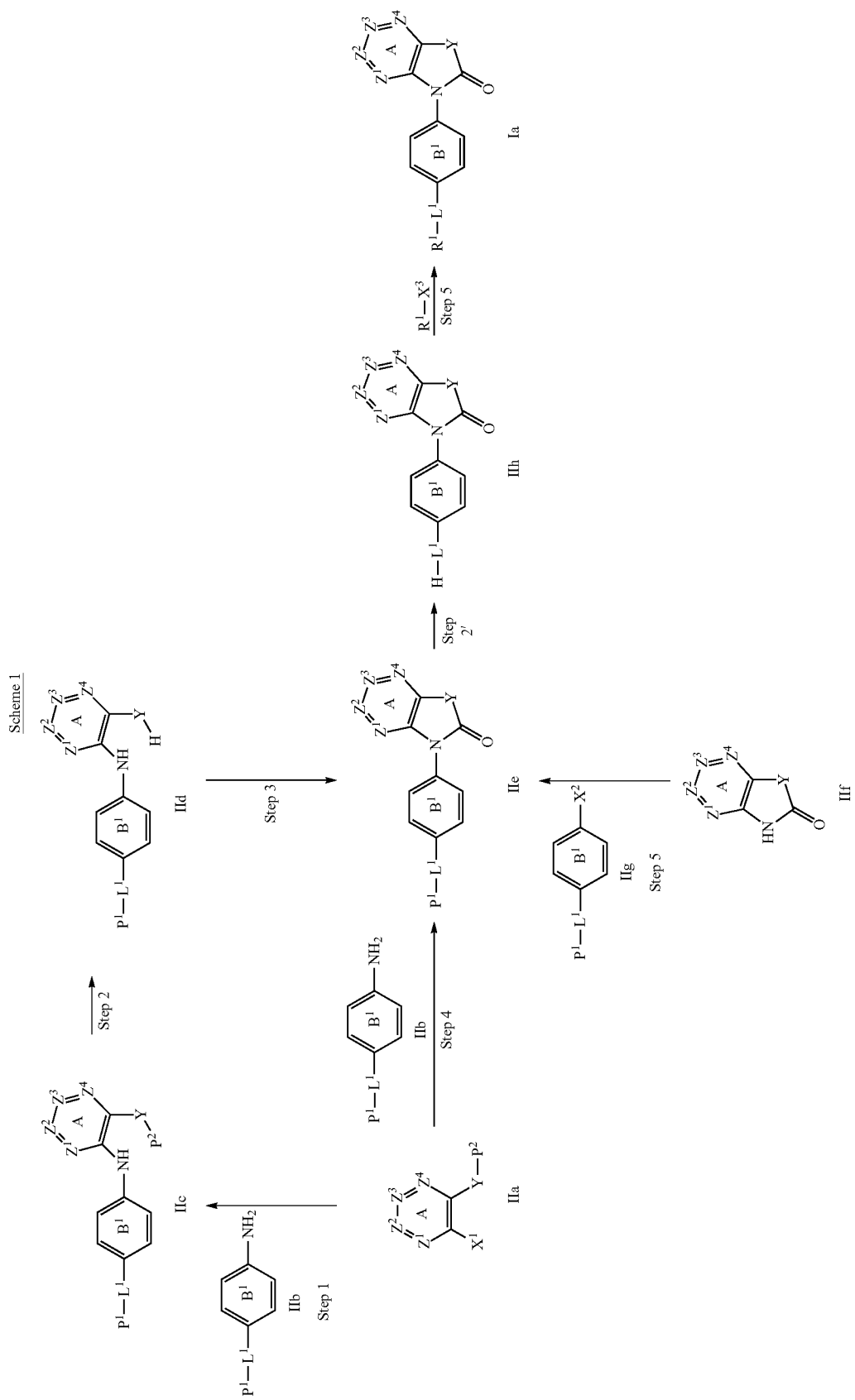

wherein $X^1$-$X^3$ are each a leaving group, and the other symbols are as defined above.

The compound of the present invention can be produced by subjecting compound (IIa) to a series of reaction steps of Steps 1, 2, 3, 2' and 6.

In addition, the compound can also be produced by subjecting compound (IIa) to a series of reaction steps in Steps 4, 2' and 6.

Furthermore, the compound can also be produced by subjecting compound (IIf) to a series of reaction steps in Steps 5, 2' and 6.

(Step 1)

Compound (IIc) can be produced by subjecting compound (IIa) and compound (IIb) to a substitution reaction. Compound (IIa) is generally used in about 0.2-5.0 mol, preferably about 0.5-2.0 mol, per 1 mol of compound (IIb). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. In addition, when an acidic substance is released by the reaction, the reaction can be performed in the presence of a deoxidizer to remove the acidic substance from the reaction system. As such deoxidizer, for example, inorganic bases, basic salts, organic bases, metal alkoxides, alkali metal hydrides, metal amides and the like are used. The deoxidizer is generally used in about 0.05-20 mol, preferably about 1-10 mol, per 1 mol of compound (IIb). While the reaction time varies depending on the reagent and solvent to be used, it is generally 10 min-72 hr, preferably 30 min-24 hr. The reaction temperature is generally 0-200° C., preferably 50-150° C. In addition, microwave irradiation may be performed to promote the reaction.

(Step 2)

Compound (IId) can be produced by removing the protective group ($P^2$) of compound (IIc). When $P^2$ is a hydrogen atom, this step can be omitted. The protective group can be removed according to a method known per se, for example, the method described in "Protective Groups in Organic Synthesis, 3$^{rd}$ Ed." by Theodora W. Greene, Peter G. M. Wuts, Wiley-Interscience Corporation (1999), and the like. This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, halogenated hydrocarbons, nitriles, sulfoxides, aromatic organic bases and the like or a mixed solvent thereof and the like are preferable. While the reaction time varies depending on the reagent and solvent to be used, it is generally 10 min-72 hr, preferably 30 min-24 hr. The reaction temperature is generally 0-200° C., preferably 0-50° C. In addition, microwave irradiation may be performed to promote the reaction.

(Step 3)

Compound (IIe) can be produced by subjecting compound (IId) to a cyclization reaction. The reaction can be performed according to a manufacturing method known per se or a method analogous thereto and, for example, a method using a carbonating agent can be mentioned. Examples of the carbonating agent include 1,1'-carbonylbis(1H-imidazole), phosgene, triphosgene, diethyl carbonate, dimethyl carbonate, di-tert-butyl dicarbonate and the like. When these carbonating agents are used, the reaction is considered to proceed via a reactive derivative of amine. The synthesis from compound (IId) to compound (IIe) sometimes proceeds via compound (IIc). The carbonating agent is generally used in about 0.2-5.0 mol, preferably about 0.5-2.0 mol, per 1 mol of compound (IId). In addition, a base can be used to promote the reaction. Examples of the base include inorganic bases, organic bases, metal alkoxides, alkali metal hydrides, metal amides and the like. The base is used in about 1.0-20 mol, preferably about 1.0-5.0 mol, per 1 mol of compound (IId). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. While the reaction time varies depending on the reagent and solvent to be used, it is generally 10 min-72 hr, preferably 30 min-24 hr. The reaction temperature is generally 0-200° C., preferably 0-100° C. In addition, microwave irradiation may be performed to promote the reaction.

(Step 4)

Compound (IIe) can also be produced by subjecting compound (IIa) and compound (IIb) to a condensation reaction. This reaction can also be performed according to a manufacturing method known per se, for example, the method described in Synlett, vol. 13, page 2083 (2006) and the like, or a method analogous thereto. Compound (IIa) is generally used in about 0.2-5.0 mol, preferably about 0.5-2.0 mol, per 1 mol of compound (IIb). This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, halogenated hydrocarbons, nitriles, sulfoxides, aromatic organic bases and the like or a mixed solvent thereof and the like are preferable. In addition, when an acidic substance is released from the reaction, the reaction can be performed in the presence of a deoxidizer to remove the substance from the reaction system. As such deoxidizer, inorganic bases, basic salts, organic bases, metal alkoxides, alkali metal hydrides, metal amides and the like are used. The deoxidizer is generally used in about 0.05-20 mol, preferably about 1-10 mol, per 1 mol of compound (IIb). In addition, for example, basic salts, organic bases and the like can also be used to promote the reaction. Such basic salts, organic bases and the like are generally used in about 0.05-20 mol, preferably about 1-10 mol, per 1 mol of compound (IIb). While the reaction time varies depending on the reagent and solvent to be used, it is generally 10 min-200 hr, preferably 30 min-48 hr. The reaction temperature is generally 0-200° C., preferably 50-150° C. In addition, microwave irradiation may be performed to promote the reaction.

(Step 5)

Compound (IIe) can be produced by subjecting compound (IIf) and compound (IIg) to a substitution reaction, or a coupling reaction in the presence of a metal catalyst. Compound (IIg) is used in about 0.5-20 mol, preferably about 0.8-10 mol, per 1 mol of compound (IIf). As the metal catalyst, a metal complex having a variety of ligands is used and, for example, palladium compounds [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium(0), complex of palladium(II) acetate and 1,1'-bis(diphenylphosphino)ferrocene, complex of [1,1'-bis(diphenylphosphino)ferrocene]dichloropalladium(II) and dichloromethane, complex of tris(dibenzylideneacetone)dipalladium(0) and 2-dicyclohexylphosphino-2'-(N,N-dimethylamino)biphenyl (DavePhos), 2-dicyclohexylphosphino-2',4',6'-triisopropyl-biphenyl(Xphos), (9,9-dimethyl-9H-xanthene-4,5-diyl)bis (diphenylphosphane) (Xantphos), or dicyclohexyl(2',6'-dimethoxybiphenyl-2-yl)phosphane (SPhos), etc.], nickel compounds [e.g., tetrakis(triphenylphosphine)nickel (0), bis(triethylphosphine)nickel (II) chloride, bis(triphenylphosphine)nickel (II) chloride, etc.], copper compounds [e.g., copper oxide, copper(I) iodide, copper sulfate, copper(II) chloride, etc.] and the like can be mentioned. The metal catalyst is used in about 0.0001-5 mol, preferably about 0.001-1 mol, per 1 mol of compound (IIf). This reaction is preferably performed in the presence of a base. Examples of the base include inorganic bases, organic bases, metal alkoxides, alkali metal hydrides, metal amides and the like. The base is used in about 1.0-20 mol, preferably about 1.0-5.0 mol, per 1 mol of compound (IIf). To promote the reaction, for example, sodium iodide, potassium iodide and the like may be added. Such sodium iodide, potassium iodide and the like are used in about 0.05-100 mol, preferably about 0.1-50 mol, per 1 mol of compound (IIf). In addition, when a metal catalyst unstable to oxygen is used in this reaction, for example, the reaction is preferably performed in an inert gas stream such as argon gas, nitrogen gas and the like. This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, nitriles, sulfoxides, esters, water and the like or a mixed solvent thereof and the like are preferable. While the reaction time varies depending on the reagent and solvent to be used, it is generally 10 min-100 hr, preferably 30 min-50 hr. The reaction temperature is −10 to 250° C., preferably 50 to 150° C. In addition, microwave irradiation may be performed to promote the reaction.

(Step 2')

Compound (IIh) can be produced by removing the protective group ($P^1$) of compound (IIe). When $P^1$ is a hydrogen atom, this step can be omitted. This reaction may be performed according to a method similar to that of the above-mentioned (Step 2).

(Step 6)

Compound (Ia), which is the compound of the present invention, can be produced by subjecting compound (IIh) and $R^1$—$X^3$ to a substitution reaction in the presence of a base. $R^1$—$X^3$ is used in about 0.05-100 mol, preferably about 0.1-10 mol, per 1 mol of compound (IIh). Examples of the base include inorganic bases, basic salts, organic bases, metal amides, alkali metal hydrides and the like. The base is used in about 0.5-10.0 mol, preferably about 1.0-5.0 mol, per 1 mol of compound (IIh). To promote the reaction, for example, sodium iodide, potassium iodide and the like may be added. Such sodium iodide, potassium iodide and the like are used in about 0.05-100 mol, preferably about 0.1-50 mol, per 1 mol of compound (IIh). This reaction is advantageously performed in a solvent inert to the reaction. The solvent is not particularly limited as long as the reaction proceeds and, for example, solvents such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-24 hr. The reaction temperature is generally −20-250° C., preferably 0-230° C. In addition, microwave irradiation may be performed to promote the reaction.

Compounds (IIa), (IIb), (IIc), (IId), (IIe), (IIf), (IIg) and (IIh) and $R^1$—$X^3$ may be commercially available products, or can be produced according to a method known per se or a method analogous thereto. In addition, compound (IIa) can be produced according to the method described in Synlett, vol. 13, page 2083 (2006) and the like, or a method analogous thereto. Compound (IIf) can also be produced according to the method described in Tetrahedron Letters, vol. 47, page 7567 (1993), Journal of Medicinal Chemistry, vol. 10, page 2697 (1990) and the like, or a method analogous thereto. Compound (IIh) and $R^1$—$X^3$ can also be produced by a known substituent conversion reaction, condensation reaction, oxidation reaction, reduction reaction and the like, which may be used alone or in a combination of two or more thereof. These reactions may be performed, for example, according to the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC., (1989); Comprehensive Organic Transformations, VCH Publishers Inc. (1989) and the like.

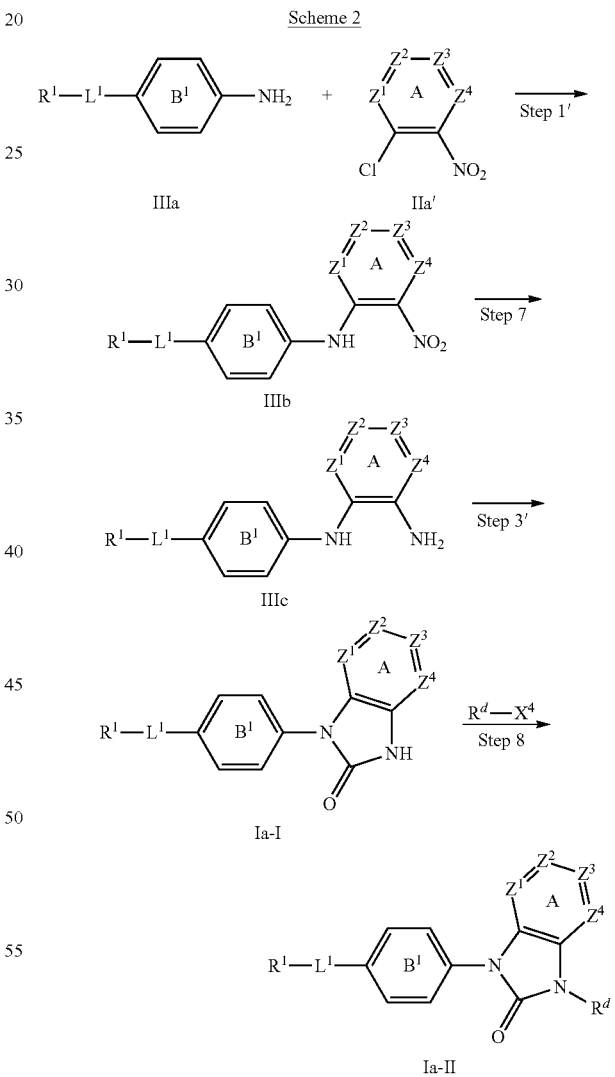

wherein $X^4$ is a leaving group, and other symbols are as defined above.

Compound (Ia-I) and compound (Ia-II), which are the compounds of the present invention, can be produced by subjecting compound (IIIa) to a series of reaction steps in Steps 1', 7 and 3', and Steps 1', 7, 3' and 8, respectively.

(Step 1')

Compound (IIIb) can be produced by reacting compound (IIIa) with compound (IIa'). Compound (IIIa) is generally used in about 0.2-5.0 mol, preferably about 0.5-2.0 mol, per 1 mol of compound (IIa'). This reaction is advantageously performed in a solvent inert to the reaction. The solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. In addition, when an acidic substance is released by the reaction, the reaction can be performed in the presence of a deoxidizer to remove the substance from the reaction system. As the deoxidizer, for example, inorganic bases, basic salts, organic bases, metal alkoxides, alkali metal hydrides, metal amides and the like are used. The deoxidizer is generally used in about 0.05-20 mol, preferably about 0.1-10 mol, per 1 mol of compound (IIa'). In addition, for example, basic salts, organic bases and the like can also be used to promote the reaction. Such basic salts, organic bases and the like are generally used in about 0.05-20 mol, preferably about 0.1-10 mol, per 1 mol of compound (IIa'). While the reaction time varies depending on the reagent and solvent to be used, it is generally 10 min-72 hr, preferably 30 min-24 hr. The reaction temperature is generally 0-200° C., preferably 50-150° C. In addition, microwave irradiation may be performed to promote the reaction.

(Step 7)

Compound (IIIc) can be produced by subjecting compound (IIIb) to a reduction reaction. This reaction can be performed according to a method known per se such as the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989) and the like, or a method analogous thereto. For example, a method using a reducing agent can be mentioned. Examples of the reducing agent include zinc, tin chloride, and complexes of hydrogen and, for example, palladium-carbon, palladium hydroxide-carbon, rhodium-carbon, platinum-carbon, Raney-nickel or the like. The reducing agent is generally used in about 0.0001-100 mol, preferably about 0.01-10 mol, per 1 mol of compound (IIIb). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable.

(Step 3')

Compound (Ia-I), which is the compound of the present invention, can be produced by subjecting compound (IIIc) to a cyclization reaction. This reaction can be performed according to a manufacturing method known per se, for example, the method described in Australian Journal of Chemistry, vol. 4, page 775 (1982), Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989) and the like, or a method analogous thereto. For example, a method using a carbonating agent can be mentioned. Examples of the carbonating agent include 1,1'-carbonylbis(1H-imidazole), phosgene, triphosgene, diethyl carbonate, dimethyl carbonate, di-tert-butyl dicarbonate, bis(2,5-dioxopyrrolidin-1-yl)carbonate and the like. The carbonating agent is generally used in about 0.2-5.0 mol, preferably about 0.5-2.0 mol, per 1 mol of compound (IIIc). In addition, a base can be used to promote the reaction.

Examples of the base include inorganic bases, organic bases, metal alkoxides, alkali metal hydrides, metal amides and the like. The base is used in about 1.0-20 mol, preferably about 1.0-5.0 mol, per 1 mol of compound (IIIc). This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, halogenated hydrocarbons, nitriles, sulfoxides, aromatic organic bases, water and the like or a mixed solvent thereof and the like are preferable. While the reaction time varies depending on the reagent and solvent to be used, it is generally 10 min-72 hr, preferably 30 min-24 hr. The reaction temperature is generally 0-200° C., preferably 0-100° C. In addition, microwave irradiation may be performed to promote the reaction.

(Step 8)

Compound (Ia-II), which is the compound of the present invention, can be produced by reacting compound (Ia-I) with $R^d$—$X^4$ in the presence of a base. The $R^d$—$X^4$ is used in about 0.05-100 mol, preferably about 0.1-10 mol, per 1 mol of compound (Ia-I). Examples of the base include inorganic bases, basic salts, organic bases, metal amides and the like. The base is used in about 0.5-10.0 mol, preferably about 1.0-5.0 mol, per 1 mol of compound (Ia-I). To promote the reaction, for example, sodium iodide, potassium iodide and the like may be added. Such sodium iodide, potassium iodide and the like are used in about 0.05-100 mol, preferably about 0.1-50 mol, per 1 mol of compound (Ia-I). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-24 hr. The reaction temperature is generally −20 to 250° C., preferably 0 to 230° C. In addition, microwave irradiation may be performed to promote the reaction.

Compounds (IIIc), (IIa'), (IIIb) and (IIIc) may be commercially available products, or can be produced according to a method known per se or a method analogous thereto. In addition, $R^d$—$X^4$ may be a commercially available product, or can also be produced by a known substituent conversion reaction, condensation reaction, oxidation reaction, reduction reaction and the like, which may be used alone or in a combination of two or more thereof. These reactions may be performed according to, for example, the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989) and the like.

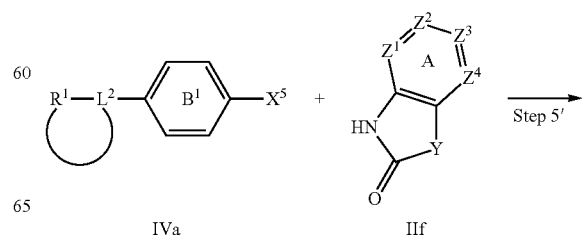

Scheme 3

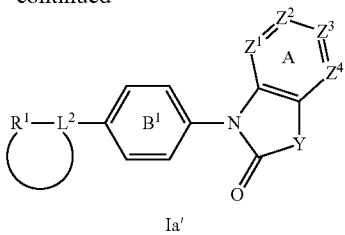

Ia' wherein X⁵ is a leaving group, and other symbols are as defined above.

Compound (Ia'), which is the compound of the present invention, can be produced by subjecting compound (IVa) to the reaction step of Step 5'.

(Step 5')

Compound (Ia'), which is the compound of the present invention, can be produced by subjecting compound (IIf) and compound (IVa) to a substitution reaction in the presence of a metal catalyst as necessary. Compound (IIf) is used in about 0.5-20 mol, preferably about 0.8-10 mol, per 1 mol of compound (IVa). As the metal catalyst, a metal complex having a variety of ligands is used and, for example, palladium compounds [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium(0), complex of palladium(II) acetate and 1,1'-bis(diphenylphosphino)ferrocene, complex of [1,1'-bis(diphenylphosphino)ferrocene]dichloropalladium(II) and dichloromethane, complex of tris(dibenzylideneacetone)dipalladium(0) and 2-dicyclohexylphosphino-2'-(N,N-dimethylamino)biphenyl(DavePhos), 2-dicyclohexylphosphino-2',4',6'-triisopropylbiphenyl (Xphos), (9,9-dimethyl-9H-xanthene-4,5-diyl)bis(diphenylphosphane) (xantphos), or dicyclohexyl(2',6'-dimethoxybiphenyl-2-yl)phosphane (SPhos), etc.], nickel compounds [e.g., tetrakis(triphenylphosphine)nickel (0), bis(triethylphosphine)nickel (II) chloride, bis(triphenylphosphine)nickel (II) chloride, etc.], rhodium compounds [e.g., tris(triphenylphosphine)rhodium (III) chloride, etc.], cobalt compound, copper compounds [e.g., copper oxide, copper(I) iodide, copper sulfate, copper(II) chloride, etc.], platinum compound and the like can be mentioned. Of these, a palladium compound and a copper compound are preferable. The metal catalyst is used in about 0.0001-5 mol, preferably about 0.001-1 mol, per 1 mol of compound (IIf). This reaction is preferably performed in the presence of a base. Examples of the base include inorganic bases, organic bases, metal alkoxides, alkali metal hydrides, metal amides and the like. The base is used in about 1.0-20 mol, preferably about 1.0-5.0 mol, per 1 mol of compound (IIf). In addition, when a metal catalyst unstable to oxygen is used in this reaction, for example, the reaction is preferably performed in an inert gas stream such as argon gas, nitrogen gas and the like. This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, nitriles, sulfoxides, esters, water and the like or a mixed solvent thereof and the like are preferable. While the reaction time varies depending on the reagent and solvent to be used, it is generally 10 min-100 hr, preferably 30 min-50 hr. The reaction temperature is −10 to 250° C., preferably 50 to 150° C. In addition, microwave irradiation may be performed to promote the reaction.

Compound (IIf) and compound (IVa) may be commercially available products, or can also be produced according to the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC., (1989); Comprehensive Organic Transformations, VCH Publishers Inc. (1989), Heterocycles, vol. 4, page 799 (1985) and the like, or a method analogous thereto.

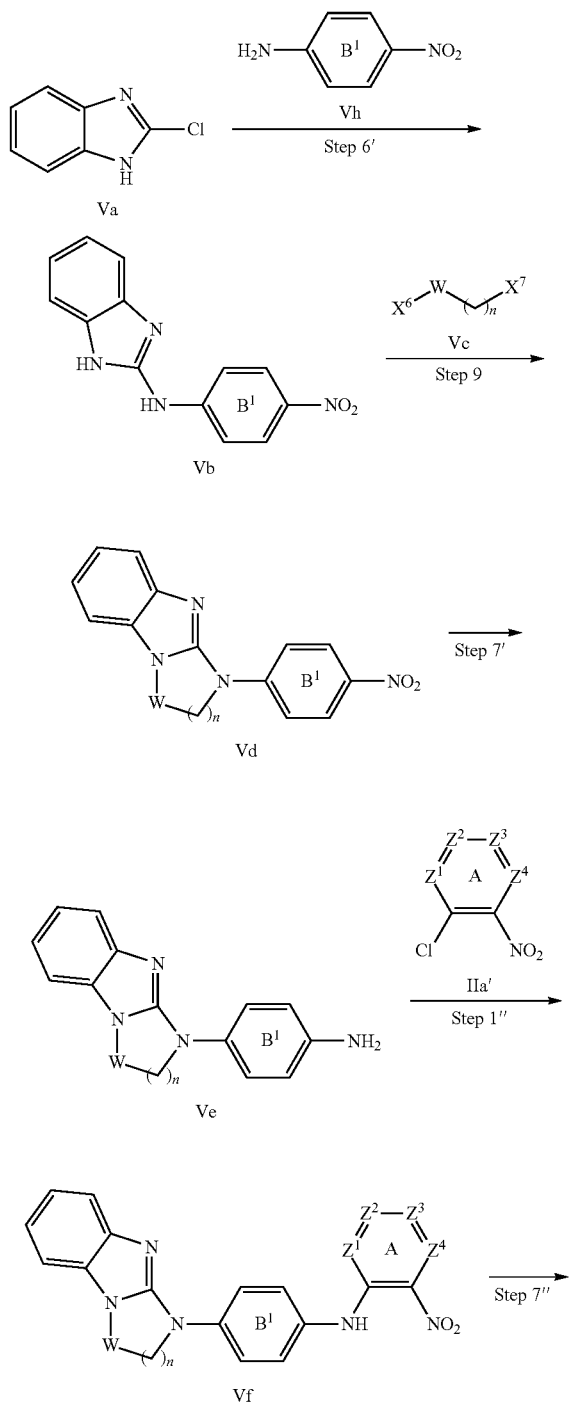

Scheme 4

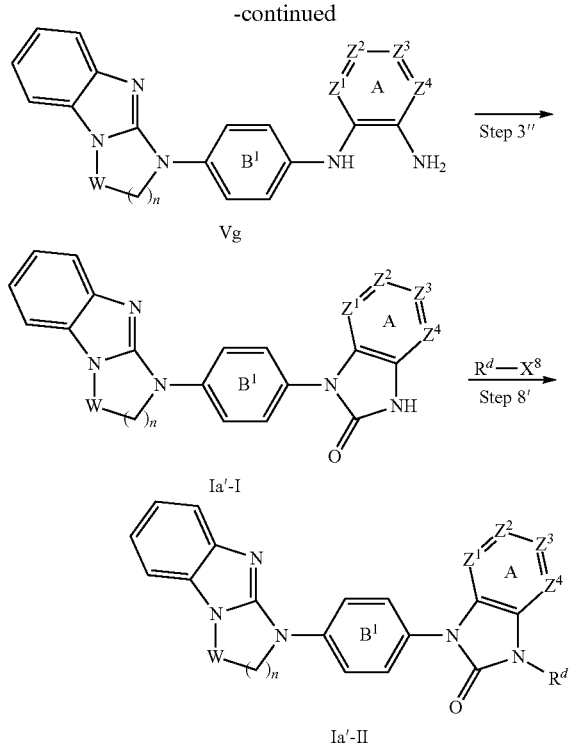

wherein W is an optionally substituted methylene group or a carbonyl group, $X^6$-$X^8$ are each a leaving group, n is an integer of 1 to 5, and other symbols are as defined above. Examples of the substituent that the "methylene group" of the "optionally substituted methylene group" for W may have include 1 or 2 substituent selected from substituent group A.

Compound (Ia'-I) and compound (Ia'-II), which are the compounds of the present invention, can be produced by subjecting compound (Va) to a series of reaction steps in Steps 6', 9, 7', 1", 7" and 3", and Steps 6', 9, 7', 1", 7", 3" and 8', respectively.

(Step 6')

Compound (Vb) can be produced by subjecting compound (Va) and compound (Vh) to a substitution reaction. This reaction may be performed according to a method similar to that in (Step 6) above.

(Step 9)

Compound (Vd) can be produced by subjecting compound (Vb) and compound (Vc) to a substitution reaction. Compound (Vc) is used in about 0.5-10.0 mol, preferably about 1.0-5.0 mol, per 1 mol of compound (Vb). This reaction can be performed in the presence of a base to promote the reaction. Examples of the base include inorganic bases, basic salts, organic bases, metal alkoxides, alkali metal hydrides, metal amides and the like. The base is used in about 0.5-10.0 mol, preferably 0.8-5.0 mol, per 1 mol of compound (Vb). In addition, to promote the reaction, for example, sodium iodide, potassium iodide and the like may be added. Such sodium iodide, potassium iodide and the like are used in about 0.05-100 mol, preferably about 0.1-50 mol, per 1 mol of compound (Vc). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-24 hr. The reaction temperature is generally −20 to 250° C., preferably 0 to 230° C. In addition, microwave irradiation may be performed to promote the reaction.

(Step 7')

Compound (Ve) can be produced by subjecting compound (Vd) to a reduction reaction. This reaction may be performed according to a method similar to that in the above-mentioned (Step 7).

(Step 1")

Compound (Vf) can be produced by reacting compound (Ve) with compound (IIa'). This reaction may be performed according to a method similar to that in the above-mentioned (Step 1').

(Step 7")

Compound (Vg) can be produced by subjecting compound (Vf) to a reduction reaction. This reaction may be performed according to a method similar to that in the above-mentioned (Step 7).

(Step 3")

Compound (Ia'-I), which is the compound of the present invention, can be produced by subjecting compound (Vg) to a cyclization reaction. This reaction can be performed according to a manufacturing method known per se, for example, the method described in Bioorganic and Medicinal Chemistry Letters, vol. 6, page 1702 (2009); Journal of Medicinal Chemistry, vol. 13, page 3881 (2009); ORGANIC FUNCTIONAL GROUP PREPARATIONS, 2nd edition, ACADEMIC PRESS, INC., (1989); Comprehensive Organic Transformations, VCH Publishers Inc. (1989) and the like, or a method analogous thereto and, for example, a method using a carbonating agent can be mentioned. Examples of the carbonating agent include 1,1'-carbonylbis(1H-imidazole), phosgene, triphosgene, diethyl carbonate, dimethyl carbonate, di-tert-butyl dicarbonate and the like. The carbonating agent is generally used in about 0.2-5.0 mol, preferably about 0.5-2.0 mol, per 1 mol of compound (Vg). When an acidic substance is released by the reaction, the reaction can be performed in the presence of a deoxidizer to remove the substance from the reaction system. As such deoxidizer, inorganic bases, basic salts, organic bases, metal alkoxides, alkali metal hydrides, metal amides and the like are used. The deoxidizer is generally used in about 0.2-10 mol, preferably about 0.5-6.0 mol, per 1 mol of compound (Vg). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. While the reaction time varies depending on the reagent and solvent to be used, it is generally 10 min-72 hr, preferably 30 min-24 hr. The reaction temperature is generally 0-200° C., preferably 0-100° C. In addition, microwave irradiation may be performed to promote the reaction.

(Step 8')

Compound (Ia'-II), which is the compound of the present invention, can be produced by reacting compound (Ia'-I) with $R^d$—$X^8$ in the presence of a base. This reaction may be performed according to a method similar to that in the above-mentioned (Step 8).

Compounds (Va), (Vb), (Vc), (Vd), (Ve), (Vf) and (Vg) and $R^d$—$X^8$ may be commercially available products, or they can be produced according to a method known per se or a method analogous thereto. In addition, compound (Vc) can also be produced according to a known substituent conversion reaction, condensation reaction, oxidation reaction, reduction reaction and the like, which may be used alone or in a combination of two or more thereof. These reactions can also be performed according to, for example, the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989), Synthesis, vol. 7, page 577 (1982), Journal of Organic Chemistry, vol. 1, page 284 (2007), Russian Journal of General Chemistry, vol. 9, page 1457 (2003) and the like. Compound (Vb) can also be produced according to the method described in Tetrahedron Letters, vol. 22, page 3747 (2006) and the like, or a method analogous thereto.

dride, N-phenylbis(trifluoromethanesulfonimide), N-(5-chloropyridin-2-yl)-1,1,1-trifluoro-N—[(trifluoromethyl)sulfonyl]methanesulfonamide and the like. The trifluoromethanesulfonylating agent is generally used in about 0.2-5.0 mol, preferably about 0.5-2.0 mol, per 1 mol of compound (IIh'). In addition, bases such as basic salts, organic bases and the like can be used to promote the reaction. The base is generally used in about 0.2-20.0 mol, preferably about 0.5-10.0 mol, per 1 mol of compound (IIh'). This reaction is advantageously performed in a solvent inert to the 1° reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the

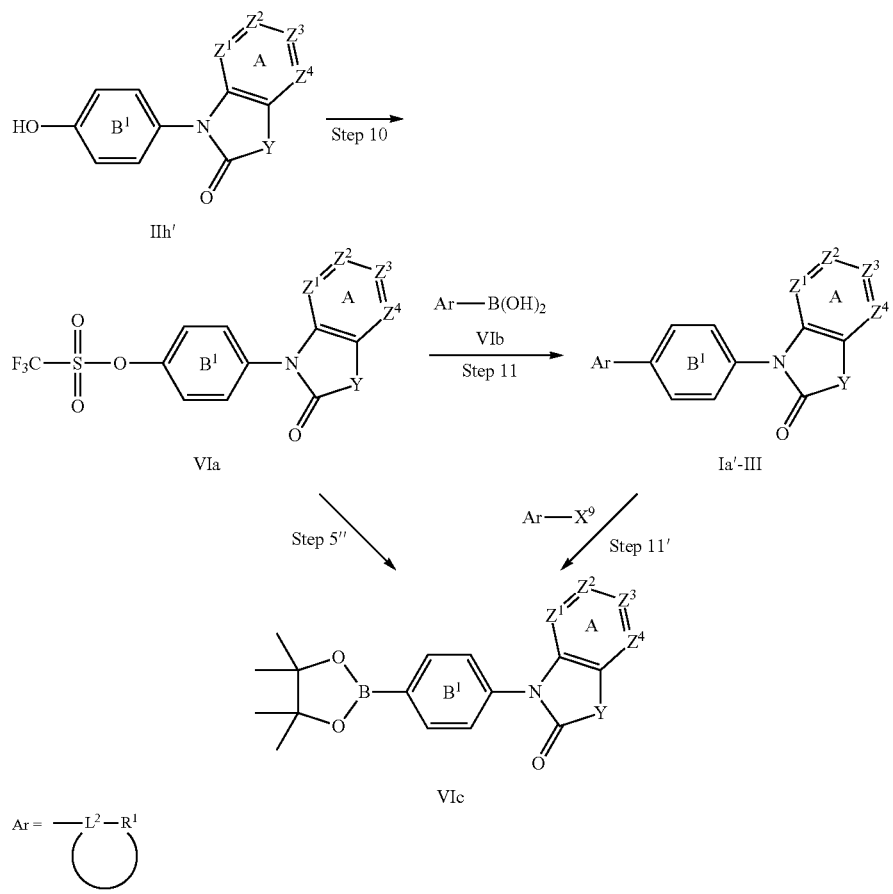

wherein $X^9$ is a leaving group, and other symbols are as defined above.

Compound (Ia'-III), which is the compound of the present invention, can be produced by subjecting compound (IIh') to a series of reaction steps in Steps 10 and 11.

Compound (Ia'-III) can also be produced by subjecting compound (IIh') to a series of reaction steps in Steps 10, 5" and 11'.

(Step 10)

Compound (VIa) can be produced by reacting compound (IIh') with a trifluoromethanesulfonylating agent. Examples of the trifluoromethanesulfonylating agent include trifluoromethanesulfonylchloride, trifluoromethanesulfonic anhylike are preferable. While the reaction time varies depending on the reagent and solvent to be used, it is generally 10 min-72 hr, preferably 30 min-24 hr. The reaction temperature is generally 0-100° C., preferably 0-70° C.

(Step 5")

Compound (VIc) can be produced by condensing compound (VIa) and 4,4,5,5-tetramethyl-1,3,2-dioxaborolane. The condensation reaction is performed by reacting compound (VIa) with 4,4,5,5-tetramethyl-1,3,2-dioxaborolane in the presence of a metal catalyst. The 4,4,5,5-tetramethyl-1,3,2-dioxaborolane is used in about 0.1-10 mol, preferably about 0.8-2.0 mol, per 1 mol of compound (VIa). As the metal catalyst, palladium compound [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium(0), complex of palladium(II) acetate and 1,1'-bis(diphenylphosphino)ferrocene, complex of [1,1'-bis(diphenylphosphino)ferrocene]dichloropalladium(II) and dichloromethane, complex of tris(dibenzylideneacetone)dipalladium(0) and 2-dicyclohexylphosphino-2'-(N,N-dimethylamino)biphenyl(DavePhos), 2-dicyclohexylphosphino-2',4',6'-triisopropylbiphenyl(Xphos), (9,9-dimethyl-9H-xanthene-4,5-diyl)bis(diphenylphosphane) (xantphos) or dicyclohexyl(2',6'-dimethoxybiphenyl-2-yl)phosphane (SPhos) etc.] are preferable. The metal catalyst is used in about 0.000001-5.0 mol, preferably about 0.0001-1.0 mol, per 1 mol of compound (VIa). This reaction is generally performed in the presence of a base. Examples of the base include inorganic bases, basic salts, organic bases, metal alkoxides, alkali metal hydrides, metal amides and the like. The base is used in about 1.0-20 mol, preferably about 1.0-5.0 mol, per 1 mol of compound (VIa). When a metal catalyst unstable to oxygen is used in these reactions, the reaction is preferably performed, for example, in an inert gas stream such as argon gas, nitrogen gas and the like. This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, esters, water and the like or a mixed solvent thereof and the like are preferable. While the reaction time varies depending on the reagent and solvent to be used, it is generally 1 min-200 hr, preferably 5 min-100 hr. The reaction temperature is −10 to 250° C., preferably 0 to 150° C. In addition, microwave irradiation may be performed to promote the reaction.

(Step 11)

Compound (Ia'-III), which is the compound of the present invention, can be produced by condensing compound (VIa) and compound (VIb). The condensation reaction is performed by reacting compound (VIa) with compound (VIb) in the presence of a metal catalyst. Compound (VIb) is used in about 0.1-10 mol, preferably about 0.8-2.0 mol, per 1 mol of compound (VIa). As the metal catalyst, palladium compound [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium(0), complex of palladium(II) acetate and 1,1'-bis(diphenylphosphino)ferrocene, complex of [1,1'-bis(diphenylphosphino)ferrocene]dichloropalladium(II) and dichloromethane, complex of tris(dibenzylideneacetone)dipalladium(0) and 2-dicyclohexylphosphino-2'-(N,N-dimethylamino)biphenyl(DavePhos), 2-dicyclohexylphosphino-2',4',6'-triisopropylbiphenyl (Xphos), (9,9-dimethyl-9H-xanthene-4,5-diyl)bis(diphenylphosphane) (xantphos) or dicyclohexyl(2',6'-dimethoxybiphenyl-2-yl)phosphane (SPhos), etc.] is preferable. The metal catalyst is used in about 0.000001-5.0 mol, preferably about 0.0001-1.0 mol, per 1 mol of compound (VIa). This reaction is generally performed in the presence of a base. Examples of the base include inorganic bases, basic salts and the like. The base is used in about 1.0-20 mol, preferably about 1.0-5.0 mol, per 1 mol of compound (VIa). When a metal catalyst unstable to oxygen is used in these reactions, the reaction is preferably performed, for example, in inert gas stream such as argon gas, nitrogen gas and the like. This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, halogenated hydrocarbons, nitriles, esters, water and the like or a mixed solvent thereof and the like are preferable. While the reaction time varies depending on the reagent and solvent to be used, it is generally 1 min-200 hr, preferably 5 min-100 hr. The reaction temperature is −10 to 250° C., preferably 0 to 150° C. In addition, microwave irradiation may be performed to promote the reaction.

(Step 11')

Compound (Ia'-III), which is the compound of the present invention, can be produced by reacting compound (VIc) with Ar—$X^9$ in the presence of a base and a metal catalyst. This reaction may be performed according to a method similar to that in the above-mentioned (Step 11).

Compounds (IIh'), (VIa), (VIb) and (VIc) and Ar—$X^9$ may be commercially available products, or can also be produced according to a method known per se or a method analogous thereto.

Scheme 6

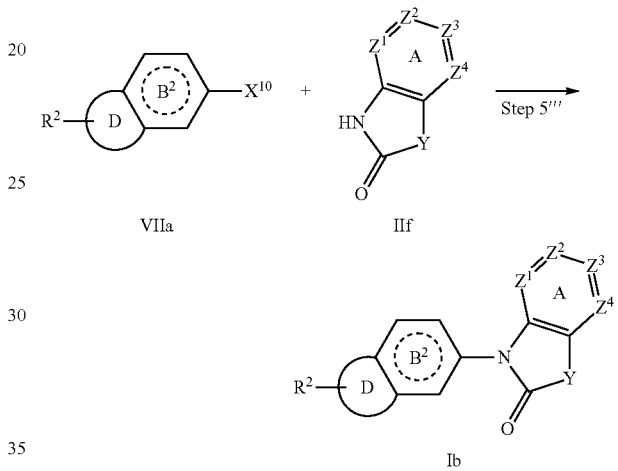

wherein $X^{10}$ is a leaving group, and other symbols are as defined above.

Compound (Ib), which is the compound of the present invention, can be produced by subjecting compound (VIIa) to the reaction step of Step 5'''.

(Step 5''')

Compound (Ib), which is the compound of the present invention, can be produced by reacting compound (VIIa) with compound (IIf) in the presence of a base and a metal catalyst. This reaction may be performed according to a method similar to that in the above-mentioned (Step 5).

Compound (VIIa) and compound (IIf) may be commercially available products, or can also be produced according to a method known per se or a method analogous thereto.

Scheme 7

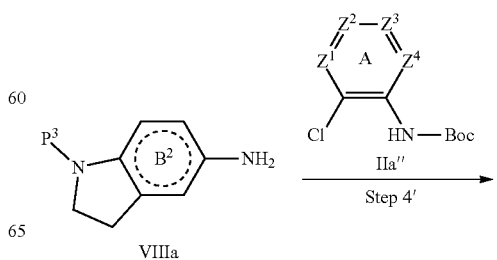

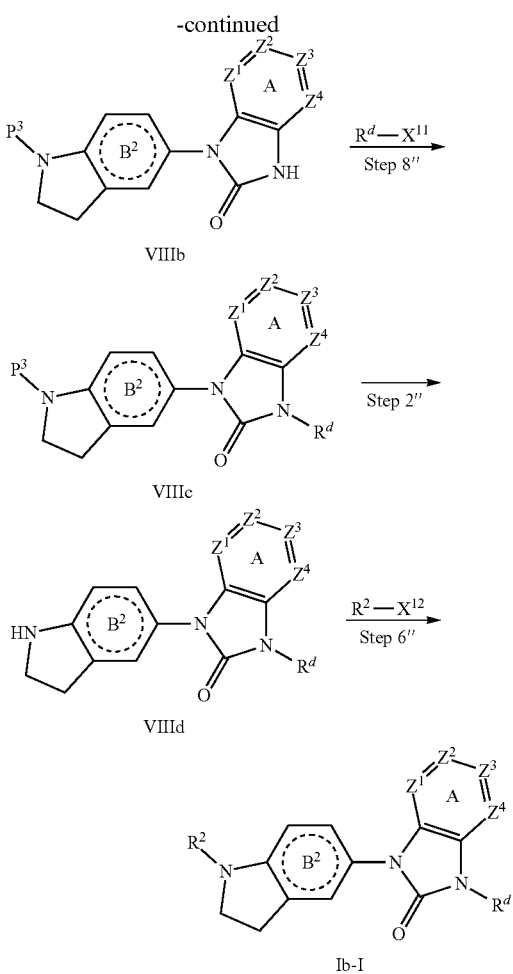

wherein $X^{11}$ and $X^{12}$ are each a leaving group, and other symbols are as defined above.

Compound (Ib-I), which is the compound of the present invention, can be produced by subjecting compound (VIIIa) to the reaction steps in Steps 4', 8", 2" and 6'".

(Step 4')

Compound (VIIIb) can be produced by subjecting compound (VIIIa) and compound (IIa") to a condensation reaction, or to a coupling reaction in the presence of a metal catalyst. This reaction can also be performed according to a manufacturing method known per se, the method described in Synlett, vol. 13, page 2083 (2006) and the like, or a method analogous thereto. Compound (IIa") is generally used in about 0.2-5.0 mol, preferably about 0.5-2.0 mol, per 1 mol of compound (VIIIa). As the metal catalyst, a metal complex having a variety of ligands is used and, for example, palladium compounds [e.g., palladium(II) acetate, tetrakis(triphenylphosphine)palladium(0), bis(triphenylphosphine)palladium(II) chloride, dichlorobis(triethylphosphine)palladium (0), tris(dibenzylideneacetone)dipalladium(0), complex of palladium(II) acetate and 1,1'-bis(diphenylphosphino)ferrocene, complex of [1,1'-bis(diphenylphosphino)ferrocene]dichloropalladium(II) and dichloromethane, complex of tris(dibenzylideneacetone)dipalladium(0) and 2-dicyclohexylphosphino-2'-(N,N-dimethylamino)biphenyl (DavePhos), 2-dicyclohexylphosphino-2',4',6'-triisopropyl-biphenyl(Xphos), (9,9-dimethyl-9H-xanthene-4,5-diyl)bis(diphenylphosphane) (Xantphos) or dicyclohexyl(2',6'-dimethoxybiphenyl-2-yl)phosphane (SPhos), etc.], nickel compounds [e.g., tetrakis(triphenylphosphine)nickel (0), bis(triethylphosphine)nickel (II) chloride, bis(triphenylphosphine)nickel (II) chloride, etc.], copper compounds [e.g., copper oxide, copper(I) iodide, copper sulfate, copper(II) chloride, etc.] and the like can be mentioned. The metal catalyst is used in about 0.0001-5 mol, preferably about 0.001-1 mol, per 1 mol of compound (IIf). This reaction is preferably performed in the presence of a base. Examples of the base include inorganic bases, organic bases, metal alkoxides, alkali metal hydrides, metal amides and the like. This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, halogenated hydrocarbons, nitriles, sulfoxides, aromatic organic bases and the like or a mixed solvent thereof and the like are preferable. In addition, when an acidic substance is released by the reaction, the reaction can be performed in the presence of a deoxidizer to remove the substance from the reaction system. As such deoxidizer, for example, inorganic bases, basic salts, organic bases, metal alkoxides, alkali metal hydrides, metal amides and the like are used. The deoxidizer is generally used in about 0.05-20 mol, preferably about 1-10 mol, per 1 mol of compound (VIIIa). In addition, for example, basic salts, organic bases and the like can be used to promote the reaction. Such basic salts, organic bases and the like are generally used in about 0.05-20 mol, preferably about 1-10 mol, per 1 mol of compound (VIIIa). While the reaction time varies depending on the reagent and solvent to be used, it is generally 10 min-200 hr, preferably 30 min-48 hr. The reaction temperature is generally 0-200° C., preferably 50-150° C. In addition, microwave irradiation may be performed to promote the reaction.

(Step 8")

Compound (VIIIc) can be produced by reacting compound (VIIIb) with $R^d$—$X^{11}$ in the presence of a base. This reaction can be performed according to a method similar to that in the above-mentioned (Step 8).

(Step 2")

Compound (VIIId) can be produced by removing the protective group ($P^3$) of compound (VIIIc). When $P^3$ is a hydrogen atom, this step can be omitted. This reaction can be performed according to a method similar to that in the above-mentioned (Step 2).

(Step 6")

Compound (Ib-I), which is the compound of the present invention, can be produced by reacting compound (VIIId) with $R^2$—$X^{12}$ in the presence of a base. This reaction may be performed according to a method similar to that in the above-mentioned (Step 6).

Compounds (VIIIa), (IIa"), (VIIIb), (VIIIc) and (VIIId), and $R^d$—$X^{11}$ and $R^2$—$X^{12}$ may be commercially available products, or can also be produced according to a method known per se or a method analogous thereto.

Scheme 8

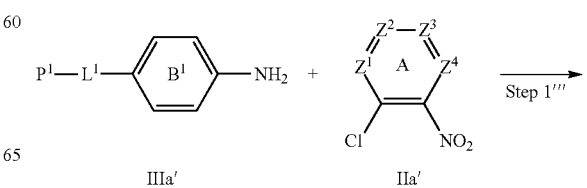

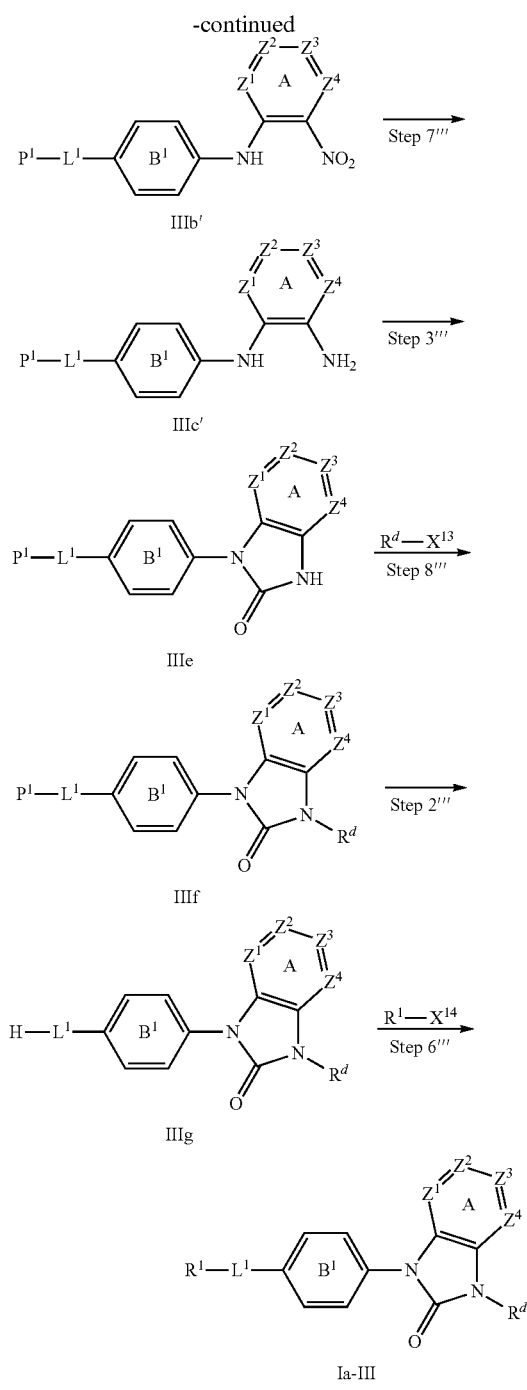

wherein $X^{13}$ and $X^{14}$ are each a leaving group, and the other symbols are as defined above.

Compound (Ia-III), which is the compounds of the present invention, can be produced by subjecting compound (IIIa') to a series of reaction steps in Steps 1''', 7''', 3''', 8''', 2''', and 6'''.

(Step 1''')

Compound (IIIb') can be produced by reacting compound (IIIa') with compound (IIa'). Compound (IIIa') is generally used in about 0.2-5.0 mol, preferably about 0.5-2.0 mol, per 1 mol of compound (IIa'). This reaction is advantageously performed in a solvent inert to the reaction. The solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. In addition, when an acidic substance is released by the reaction, the reaction can be performed in the presence of a deoxidizer to remove the substance from the reaction system. As the deoxidizer, for example, inorganic bases, basic salts, organic bases, metal alkoxides, alkali metal hydrides, metal amides and the like are used. The deoxidizer is generally used in about 0.05-20 mol, preferably about 0.1-10 mol, per 1 mol of compound (IIa'). In addition, for example, basic salts, organic bases and the like can also be used to promote the reaction. Such basic salts, organic bases and the like are generally used in about 0.05-20 mol, preferably about 0.1-10 mol, per 1 mol of compound (IIa'). While the reaction time varies depending on the reagent and solvent to be used, it is generally 10 min-72 hr, preferably 30 min-24 hr. The reaction temperature is generally 0-200° C., preferably 50-150° C. In addition, microwave irradiation may be performed to promote the reaction.

(Step 7''')

Compound (IIIc') can be produced by subjecting compound (IIIb') to a reduction reaction. This reaction can be performed according to a method known per se such as the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989) and the like, or a method analogous thereto. For example, a method using a reducing agent can be mentioned. Examples of the reducing agent include zinc, tin chloride, and complexes of hydrogen and, for example, palladium-carbon, palladium hydroxide-carbon, rhodium-carbon, platinum-carbon, Raney-nickel or the like. The reducing agent is generally used in about 0.0001-100 mol, preferably about 0.01-10 mol, per 1 mol of compound (IIIb'). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable.

(Step 3''')

Compound (IIIe) can be produced by subjecting compound (IIIc') to a cyclization reaction. This reaction can be produced according to a manufacturing method known per se, for example, the method described in Australian Journal of Chemistry, vol. 4, page 775 (1982), Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989) and the like, or a method analogous thereto. For example, a method using a carbonating agent can be mentioned. Examples of the carbonating agent include 1,1'-carbonylbis(1H-imidazole), phosgene, triphosgene, diethyl carbonate, dimethyl carbonate, di-tert-butyl dicarbonate, bis(2,5-dioxopyrrolidin-1-yl)carbonate and the like. The carbonating agent is generally used in about 0.2-5.0 mol, preferably about 0.5-2.0 mol, per 1 mol of compound (IIIc'). In addition, a base can be used to promote the reaction. Examples of the base include inorganic bases, organic bases, metal alkoxides, alkali metal hydrides, metal amides and the like. The base is used in about 1.0-20 mol, preferably about 1.0-5.0 mol, per 1 mol of compound (IIIc'). This reaction is advantageously performed in a solvent inert to the reaction. Such solvent is not particularly limited as long as the reaction proceeds and, for example, solvents such as alcohols, ethers, aromatic hydrocarbons, saturated hydrocarbons, amides, halogenated hydrocarbons, nitriles, sulfoxides, aromatic organic bases, water and the like or a mixed solvent thereof and the like are preferable. While the reaction time varies depending on the reagent and solvent to be used, it is generally 10 min-72 hr, preferably 30 min-24 hr. The reaction temperature is generally 0-200° C., preferably 0-100° C. In addition, microwave irradiation may be performed to promote the reaction.

(Step 8''')

Compound (IIIf) can be produced by reacting compound (IIIe) with $R^d$—$X^{13}$ in the presence of a base. $R^d$—$X^{13}$ is used in about 0.05-100 mol, preferably about 0.1-10 mol, per 1 mol of compound (IIIe). Examples of the base include inorganic bases, basic salts, organic bases, metal amides and the like. The base is used in about 0.5-10.0 mol, preferably about 1.0-5.0 mol, per 1 mol of compound (IIIe). To promote the reaction, for example, sodium iodide, potassium iodide and the like may be added. Such sodium iodide, potassium iodide and the like are used in about 0.05-100 mol, preferably about 0.1-50 mol, per 1 mol of compound (IIIe). This reaction is advantageously performed in a solvent inert to the reaction. Such solvent is not particularly limited as long as the reaction proceeds and, for example, solvents such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-24 hr. The reaction temperature is generally −20 to 250° C., preferably 0 to 230° C. In addition, microwave irradiation may be performed to promote the reaction.

(Step 2''')

Compound (IIIg) can be produced by removing the protective group ($P^1$) of compound (IIIf). When $P^1$ is a hydrogen atom, this step can be omitted. This reaction may be performed according to a method similar to that of the above-mentioned (Step 2).

(Step 6''')

Compound (Ia-III), which is the compound of the present invention, can be produced by subjecting compound (IIIg) and $R^1$—$X^{14}$ to a substitution reaction in the presence of a base. $R^1$—$X^{14}$ is used in about 0.05-100 mol, preferably about 0.1-10 mol, per 1 mol of compound (IIIg). Examples of the base include inorganic bases, basic salts, organic bases, metal amides, alkali metal hydrides and the like. The base is used in about 0.5-10.0 mol, preferably about 1.0-5.0 mol, per 1 mol of compound (IIIg). This reaction is advantageously performed in a solvent inert to the reaction. The solvent is not particularly limited as long as the reaction proceeds and, for example, solvents such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min-100 hr, preferably 30 min-24 hr. The reaction temperature is generally −20-250° C., preferably 0-230° C. In addition, microwave irradiation may be performed to promote the reaction.

Compounds (IIIc'), (IIa'), (IIIb''), (IIIc'), (IIIe), (IIIf) and (IIIg) may be commercially available products, or can be produced according to a method known per se or a method analogous thereto. In addition, $R^d$—$X^{13}$ and $R^1$—$X^{14}$ may be commercially available products, or can also be produced by a known substituent conversion reaction, condensation reaction, oxidation reaction, reduction reaction and the like, which may be used alone or in a combination of two or more thereof. These reactions may be performed according to, for example, the method described in Shinjikken Kagaku Koza (Courses in Experimental Chemistry), vols. 14 and 15 (The Chemical Society of Japan ed.), ORGANIC FUNCTIONAL GROUP PREPARATIONS, 2nd edition, ACADEMIC PRESS, INC. (1989); Comprehensive Organic Transformations, VCH Publishers Inc. (1989) and the like.

Compound (I) obtained by the above-mentioned methods can be isolated and purified by, for example, general separation means such as recrystallization, distillation, chromatography and the like. When the thus-obtained compound (I) of the present invention is in a free form, it can be converted to a salt thereof by a known method or a comparable method (e.g., neutralization etc.). Alternatively, when it is obtained as a salt, it can be converted to a free form or other salt by a known method or a comparable method.

In any of the above-mentioned manufacturing methods and steps, compound (I) can be synthesized by known protection and deprotection reactions, acylation reaction, alkylation reaction, hydrogenation reaction, oxidation reaction, reduction reaction, carbon chain extension reaction, substituent exchanging reactions and the like, which may be used alone or in a combination of two or more thereof.

Compound (I) may be used as a prodrug. A prodrug of compound (I) means a compound converted to compound (I) by a reaction due to an enzyme, a gastric acid, etc. under the physiological condition in the living body, that is, a compound converted to compound (I) by oxidation, reduction, hydrolysis, etc. due to an enzyme, a compound converted to compound (I) by hydrolysis etc. due to gastric acid, and the like.

A prodrug of compound (I) may be a compound obtained by subjecting an amino group in compound (I) to an acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to acylation, alkylation, phosphorylation or boration (e.g., a compound obtained by subjecting a hydroxy group in the compound (I) to acetylation, palmitoylation, propanoylation, pivaloylation, succinylation, fumarylation, alanylation or dimethylaminomethylcarbonylation, etc.); a compound obtained by subjecting a carboxy group in compound (I) to esterification or amidation (e.g., a compound obtained by subjecting a carboxy group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any one of these compounds can be produced from compound (I) by a method known per se. In addition, a prodrug of compound (I) may also be a compound converted into compound (I) under physiological conditions, such as those described in IYAKUHIN no KAIHATSU (Development of Pharmaceuticals), Vol. 7, Design of Molecules, p. 163-198, Published by HIROKAWA SHOTEN (1990).

The compound of the present invention has an excellent PDE10A inhibitory activity and is useful for the following diseases and symptoms in mammals (e.g., humans, cows, horses, dogs, cats, monkeys, mice, rats, etc. particularly in humans):

psychotic disorder (e.g., brief psychotic disorder, shared psychotic disorder);
psychosis induced by alcohol, amphetamine, cannabis, cocaine, hallucinogens, obesity, inhalants, opioids, or phencyclidine;
delusional disorder;
anxiety disorder;
movement disorder;
mood disorder;
major depressive disorder;
a major depressive disorder superimposed on a psychotic disorder comprising a delusional disorder or schizophrenia;
major depressive episode of the mild, moderate or severe type;
manic or mixed mood episode;
hypomanic mood episode;
depressive episode with atypical features;
depressive episode with melancholic features;
depressive episode with catatonic features;
mood episode with postpartum onset;
post-stroke depression;
dysthymic disorder;
minor depressive disorder;
autism;
drug addiction;
neurodegenerative disorder;
neurodegeneration associated with cerebral trauma;
neurodegeneration associated with stroke;
neurodegeneration associated with cerebral infarct;
hypoglycemia-induced neurodegeneration;
neurodegeneration associated with epileptic seizure;
neurodegeneration associated with neurotoxin poisoning;
multi-system atrophy;
Alzheimer's disease;
dementia;
multi-infarct dementia;
alcoholic dementia or other drug-related dementia;
dementia associated with intracranial tumors or cerebral trauma;
dementia associated with Huntington's disease or Parkinson's disease;
AIDS-related dementia;
frontotemporal dementia;
delirium;
amnestic disorder;
post-traumatic stress disorder;
mental retardation;
learning disorder (e.g., reading disorder, mathematics disorder, or a disorder of written expression);
attention-deficit/hyperactivity disorder;
age-related cognitive decline;
premenstrual dysphoric disorder;
post-psychotic depressive disorder of schizophrenia;
bipolar disorders comprising bipolar I disorder, and bipolar II disorder;
cyclothymic disorder;
Parkinson's disease;
Huntington's disease;
paranoid;
is schizophrenia (e.g., paranoid schizophrenia, disorganized schizophrenia, catatonic schizophrenia, undifferentiated schizophrenia, residual schizophrenia);
schizophreniform disorder;
schizoaffective disorder of the delusional type or the depressive type;
personality disorder of the paranoid type;
personality disorder of the schizoid type;
obesity;
metabolic syndrome;
non-insulin dependent diabetes mellitus (NIDDM);
glucose intolerance;

In particular, the compound of the present invention is useful for preventing or treating schizophrenia.

Since the compound of the present invention demonstrates excellent metabolic stability, superior therapeutic effects on the aforementioned diseases are expected even at a low dosage.

The compound of the present invention shows low toxicity and can be administered safely, as it is, or in a dosage form which is manufactured according to a per se known method for manufacturing pharmaceutical formulations (e.g., methods described in Japanese Pharmacopoeia) such as tablets (inclusive of sugar coated tablet, film coated tablet, sublingual tablet, orally disintegrable tablet, and buccal), pills, powders, granules, capsules (inclusive of soft capsule, and microcapsule), troches, syrups, liquid dosage forms, emulsions, controlled-release preparations (e.g., quick-release preparation, sustained-release preparation, sustained-release microcapsule), aerosols, films (e.g., orally disintegrable film, adhesive film for application to oral-cavity mucosa), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, directly to lesion).

The compound of the present invention can be administered orally or non-orally (e.g., including local, rectal and venous routes).

Here, as a pharmaceutical acceptable carrier, common organic or inorganic carrier substances are used as formulation raw materials. Carriers are added as vehicles, lubricants, binders and disintegrants in the solid formulations; and as solvents, solubilizing agents, suspending agents, isotonization agents, buffers and soothing agents in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light silicic anhydride, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, D-mannitol, trehalose, dextrin, pullulan, hydroxypropylcellulose, hydroxypropyl methyl cellulose and polyvinylpyrrolidone.

Favorable examples of the disintegrants are as follows: lactose, sucrose, starch, carboxymethylcellulose, calcium carboxymethylcellulose, croscarmellose sodium, sodium carboxymethyl starch, light silicic anhydride and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzylbenzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose; polysorbates, and polyoxyethylene-hardened castor oil.

Favorable examples of the isotonization agents include sodium chloride, glycerin, D-mannitol, D-sorbitol and glucose.

Favorable examples of the buffers include buffer solutions of phosphates, acetates, carbonates and citrates.

Favorable examples of the soothing agents include benzyl alcohol.

Favorable examples of the antiseptics include para-oxybenzoic acid esters, chlorobutanol, benzyl alcohol, phenethyl alcohol, dehydroacetic acid and sorbic acid.

Favorable examples of the antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, red iron oxide).

Favorable examples of the sweeteners include sodium saccharin, dipotassium glycyrrhizate, aspartame and stevia.

The medical compositions of the present invention can be manufactured by the common methods in the field of formulation technology, for example, methods listed in the Japanese pharmacopoeia. Specific manufacturing methods for formulations are described in detail below.

The content of the compound of the present invention in the medical compositions of the present invention varies based on the dosage forms, dosages of the compound of the present invention, etc. For example, the content approximately ranges from 0.01 to 100 wt % and preferably from 0.1 to 95 wt % relative to the entire amount of the composition.

The dosage of the compound of the present invention depends upon injection targets, administration routes, target diseases, symptoms, etc. For example, in the case of oral administration in patients with schizophrenia (adults, bodyweight of approximately 60 kg), generally a single dose ranges from approximately 0.1 to 20 mg/kg bodyweight, preferably from approximately 0.2 to 10 mg/kg bodyweight, further preferably from approximately 0.5 to 10 mg/kg bodyweight, and this dosage is preferably administered once daily or several times daily (e.g., 3 times).

The compounds can be administered as the sole active agent or in combination with other pharmaceutical agents such as other agents used in the treatment of psychosis, especially schizophrenia and bipolar disorder, obsessive-compulsive disorder, major depression, Parkinson's disease, Alzheimer's disease, cognitive impairment and/or memory loss, e.g., nicotinic α7 agonists, nicotinic α7 partial agonists, nicotinic α7 positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, and cholinesterase inhibitors (e.g., donepezil, rivastigimine, and galantamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Haloperidol, Clozapine, Olanzapine, Risperidone, Aripiprazole, Ziprasidone, Paliperidone, and Quetiapine fumarate; bipolar disorder drugs, including, but not limited to, Lithium, Olanzapine, Aripiprazole, and Valproic acid; Parkinson's disease drugs, including, but not limited to, Levodopa, Bromocriptine, Pergolide, Pramipexole, Tolcapone, Procyclidine, Trihexyphenidyl, and Benztropine; agents used in the treatment of major depression, including, but not limited to, Amitriptyline, Protriptyline, Desipramine, Nortriptyline, Paroxetine, Fluoxetine, Sertraline, Bupropion, Escitalopram, Mirtazapine, Venlafaxine, Duloxetine; agents used in the treatment of Alzheimer's disease, including, but not limited to, Galantamine, Tacrine, Donepezil, Rivastigmine, Memantine, Neotropin, Selegiline, Estrogen and Iodoquinol; agents used in the treatment of dementia, including, but not limited to, Thioridazine, Haloperidol, Risperidone, Tacrine, Donepezil, and Rivastigmine; agents used in the treatment of epilepsy, including, but not limited to, Phenyloin, Phenobarbital, Carbamazepine, Valproic acid, Ethosuximide, Gabapentin, Phenobarbital, Solfeton and Felbatol; agents used in the treatment of multiple sclerosis, including, but not limited to, Tolterodine, Oxybutynin, Oxycodone, Interferon beta-1b, Interferon beta-1a, Azathioprine, Methotrexate and Glatiramer; agents used in the treatment of Huntington's disease, including, but not limited to, Amitriptyline, Protripthline, Desipramine, Nortriptyline, Paroxetine, Fluoxetine, Setraline, Tetrabenazine, Haloperidol, Chlorpromazine, Thioridazine, Sulpiride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlopropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metformin, e.g., Glucophage and Glucophage XR), insulin and insulin derivatives (both long and short acting forms and formulations of insulin); and antiobesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

The form of administration of concomitant drugs with the compound of the present invention is not particularly limited and is acceptable as long as the compound of the present invention is combined with concomitant drugs at the time of administration. Examples of such forms of administration are as follows:

(1) administration of a single formula obtained by simultaneous formulation of the compound of the present invention with a concomitant drug, (2) simultaneous administration via the same administration route for two kinds of formulas obtained by independent formulations of the compound of the present invention and a concomitant drug, (3) administrations at different times via the same administration route for two kings of formulas obtained by independent formulations of the compound of the present invention and a concomitant drug, (4) simultaneous administration via different administration routes for two kinds of formulas obtained by independent formulations of the compound of the present invention and a concomitant drug, (5) administrations at different times via different administration routes for two kinds of formulas obtained by independent formulations of the compound of the present invention and a concomitant drug (For example, administration in the order of the composition of the present invention and then a concomitant drug, or administration in the reversed order). These forms of administration are summarized below and abbreviated as a concomitant agent of the present invention.

When administering the concomitant agent of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, drug forms and methods of administration. For example, when a concomitant drug is administered first, the compound of the present invention can be administered within 1 min to 3 days, preferably within 10 min to 1 day and more preferably within 15 min to 1 hour after the concomitant drug is administered. However, if the compound of the present invention is administered first, a concomitant drug can be administered within 1 min to 1 day, preferably within 10 min. to 6 hours and more preferably within 15 min to 1 hour after the compound of the present invention is administered.

If there are no problems with side effects of the concomitant drugs, any dosages can be set. A daily dosage as a concomitant drug depends upon dosages, administration subjects, administration routes, target diseases, symptoms, etc. For example, in the case of oral administration in patients with schizophrenia (adults, bodyweight of approximately 60 kg), a normal daily dosage ranges from about 0.1 to 20 mg/kg bodyweight, preferably from about 0.2 to 10 mg/kg bodyweight and more preferably from about 0.5 to 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The concomitant agent of the present invention exhibits low toxicity. For example, the compound of the present invention or(and) the aforementioned concomitant drug can be combined with a pharmaceutically acceptable carrier according to the known method to prepare a medical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal and venous routes).

The pharmaceutically acceptable carriers that can be used for manufacturing the concomitant agent of the present invention can be the same as those used in the medical composition of the present invention as mentioned above.

A mixing ratio between the compound of the present invention and a concomitant drug in the concomitant agent of the present invention can be selected appropriately based on the administration subjects, administration routes and diseases.

The aforementioned concomitant drugs can be combined at an appropriate proportion if two or more drugs are combined.

A dosage of the concomitant drug can be selected appropriately based on the dosages used clinically. In addition, a mixing ratio between the compound of the present invention and a concomitant drug can be selected appropriately based on the administration subjects, administration routes, target diseases, symptoms, combinations, etc. For example, if the administration subject is humans, a concomitant drug can be used in an amount ranging from 0.01 to 100 parts by weight relative to 1 part by weight of the compound of the present invention.

For example, the content of the compound of the present invention in the concomitant agent of the present invention varies with the drug form of formulations. Generally, it is present in a range from about 0.01 to 99.9 wt %, preferably from about 0.1 to 50 wt % and more preferably from about 0.5 to 20 wt % relative to the entire formula.

The content of a concomitant drug in the concomitant agent of the present invention varies with the drug form of formulations. Generally it is present in a range from about 0.01 to 99.9 wt %, preferably from about 0.1 to 50 wt % and more preferably from about 0.5 to 20 wt % relative to the entire formula.

The content of an additive such as carriers in the concomitant agent of the present invention varies with the drug form of formulations. Generally it is present in a range from about 1 to 99.99 wt % and preferably from about 10 to 90 wt % relative to the entire formula.

When the compound of the present invention and a concomitant drug are formulated independently, the same contents can be applied.

Since the dosages may fluctuate under various conditions as mentioned above, a dosage less than the aforementioned dosages may be sufficient or it may be necessary to administer at a dosage exceeding the range.

EXAMPLES

The present invention is explained in detail by referring to the following Reference Examples, Examples, Formulation Examples, and Experimental Examples. These examples are mere embodiments, which do not limit the present invention, and can be modified within the range not deviating from the scope of the present invention.

The "room temperature" in the following Reference Examples and Examples is generally about 10° C. to about 35° C. % in the yield means mol/mol %, % of solvent used for chromatography means % by volume, and % used for others means wt %. In proton NMR spectrum, OH and NH protons and the like that cannot be identified since they are broad bands are not recorded in the data. In silica gel chromatography, Kieselgel 60 manufactured by Merck & Co., Inc. was used, and Chromatorex NH manufactured by Fuji Silysia Chemical Ltd. was used in basic silica gel chromatography.

Other abbreviations used in the text mean the following.
s: singlet
d: doublet
dd: doublet of doublets
dt: doublet of triplets
t: triplet
tt: triplet of triplets
td: triplet of doublets
q: quartet
septet: septet
m: multiplet
br: broad
J: coupling constant
Hz: Hertz
$CDCl_3$: deuterated chloroform
$DMSO-d_6$: deuterated dimethyl sulfoxide
$^1H$ NMR: proton nuclear magnetic resonance
HPLC: high performance liquid chromatography
THF: tetrahydrofuran
DMF: N,N-dimethylformamide
DMSO: dimethyl sulfoxide
DMA: N,N-dimethylacetamide
DIEA: diisopropylethylamine
NMP: N-methylpyrrolidone
$Boc_2O$: di-tert-butyl dicarbonate
DMAP: 4-dimethylaminopyridine
TEA: triethylamine
NaHMDS: sodiumbis(trimethylsilyl)amide
mCPBA: meta-chloroperbenzoic acid
DMTMM: 4-(4,6-dimethoxy-1,3,5-triazin-2-yl)-4-methylmorpholinium chloride n-hydrate
CDI: 1,1'-carbonylbis(1H-imidazole)
DBU: 1,8-diazabicyclo[5.4.0]-7-undecene
$Pd(Ph_3P)_4$: tetrakis(triphenylphosphine)palladium(0)
$Pd_2(dba)_3$: tris(dibenzylideneacetone)dipalladium(0)
TBAF: tetra-n-butylammonium fluoride
TMEDA: tetramethylethylenediamine
IPE: diisopropyl ether
DME: 1,2-dimethoxyethane
DIPEA: N,N-diisopropylethylamine
LC-MS: liquid chromatography-mass spectrometry spectrum
ESI: electrospray-ionization method
aq.: aqueous solution
sat.: saturated
rt: room temperature All reagents and solvents were of commercial quality and used without further purification. Column chromatography was performed using Merck silica gel 60 (230-400 mesh). The compounds and/or intermediates were purified by preparative high performance liquid chromatography (prep. HPLC) using a Gilson High through Put purification system.

The columns were reversed phase YMC CombiPrep Pro C18, S-5 µm, 19×50 mm. A gradient elution was used (flow rate 20 mL/min), typically starting with 5% acetonitrile/95% water and progressing to 100% acetonitrile over a Period of 7 minutes. All solvents contained 0.1% trifluoroacetic acid (TFA).

Mass spectrometric analysis was performed according to liquid chromatography/mass spectroscopy (LCMS) methods. The method employed a Waters LC-MS System (Agilent HP1100 HPLC and a Micromass ZMD mass spectrometer for the LCMS instrument, a CAPCELL PAK C18, UG120, S-3 µm, 1.5×35 mm for the chromatography column), and a solvent system that was a 5-95% gradient of acetonitrile in water with 0.04% TFA over a 3.60 min period (flow rate 0.5 mL/min molecular weight range 200-800; cone Voltage 20 V; column temperature 40° C.). All masses were reported as those of the protonated parent ions.

EXAMPLE

Example 1

3-[4-(1,3-benzoxazol-2-ylamino)phenyl]-1,3-dihydro-2H-imidazo[4,5-b]pyridin-2-one

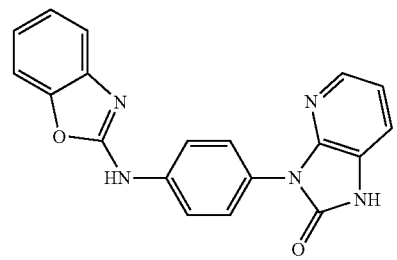 [SMILES: O=c1[nH]c2cccnc2n1-c1ccc(Nc2nc3ccccc3o2)cc1]

1a) N-(1,3-benzoxazol-2-yl)benzene-1,4-diamine

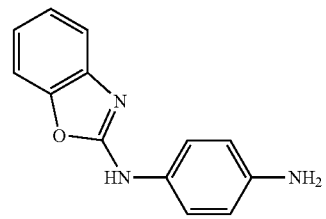 [SMILES: Nc1ccc(Nc2nc3ccccc3o2)cc1]

To a solution of benzene-1,4-diamine (5.0 g) in NMP (30 ml) was added dropwise, over 0.5 h, a solution of 2-chlorobenzo[d]oxazole (6.03 g) in NMP (50 mL). After the addition was complete, the mixture was stirred at ambient temperature for 1 h. After this time, the reaction mixture was diluted with water (200 mL) and extracted with ethyl acetate (3×200 mL). The combined organic extracts were washed with brine (150 ml), dried ($Na_2SO_4$) and filtered. The filtrate was concentrated under reduced pressure. The residue obtained was purified by chromatography (silica, methylene chloride to 1:19 methanol/methylene chloride) to afford N-(1,3-benzoxazol-2-yl)benzene-1,4-diamine (9.20 g) as an off-white solid.

MS (ESI+): [M+H]$^+$226.

1b) N-(1,3-benzoxazol-2-yl)-N'-(3-nitropyridin-2-yl)benzene-1,4-diamine

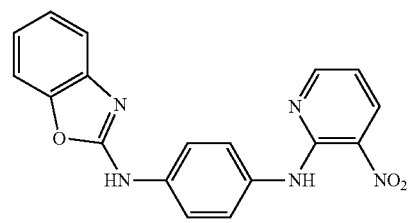 [SMILES: O=[N+]([O-])c1cccnc1Nc1ccc(Nc2nc3ccccc3o2)cc1]

A mixture of N-(1,3-benzoxazol-2-yl)benzene-1,4-diamine (0.50 g) and 2-chloro-3-nitropyridine (0.352 g) in NMP (3.0 mL) was stirred at 140° C. for 1.5 h. After this time, the reaction mixture was cooled to ambient temperature, diluted with water (50 mL), and extracted with ethyl acetate (3×100 ml). The combined organic extracts were washed with brine (100 mL), dried ($Na_2SO_4$), filtered and concentrated under reduced pressure. The residue obtained was purified by chromatography (silica, methylene chloride to 1:9 ethyl acetate/methylene chloride) to afford N-(1,3-benzoxazol-2-yl)-N'-(3-nitropyridin-2-yl)benzene-1,4-diamine (0.335 g) as a red solid.

MS (ESI+): [M+H]$^+$348.

1c) $N^2$-[4-(1,3-benzoxazol-2-ylamino)phenyl]pyridine-2,3-diamine

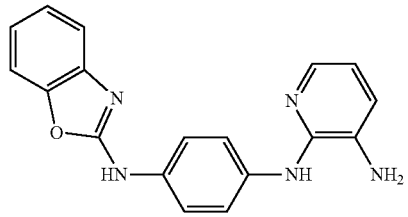 [SMILES: Nc1cccnc1Nc1ccc(Nc2nc3ccccc3o2)cc1]

A solution of N-(1,3-benzoxazol-2-yl)-N'-(3-nitropyridin-2-yl)benzene-1,4-diamine (0.330 g) in methanol (20 mL) was treated with palladium on carbon (0.060 g, 10% wt on activated carbon) and the mixture was hydrogenated (1 atm $H_2$) for 1 h. After this time, the reaction mixture was filtered through diatomaceous earth. The filtrate was concentrated under reduced pressure to afford $N^2$-[4-(1,3-benzoxazol-2-ylamino)phenyl]pyridine-2,3-diamine (0.294 g) as a yellow solid.

MS (ESI+): [M+H]$^+$318.

1d) 3-[4-(1,3-benzoxazol-2-ylamino)phenyl]-1,3-dihydro-2H-imidazo[4,5-b]pyridin-2-one

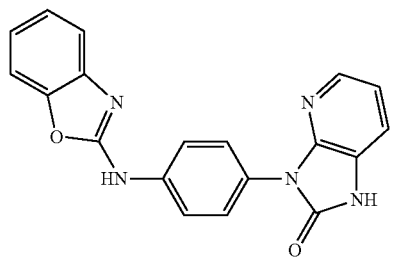 [SMILES: O=c1[nH]c2cccnc2n1-c1ccc(Nc2nc3ccccc3o2)cc1]

To a mixture of $N^2$-[4-(1,3-benzoxazol-2-ylamino)phenyl]pyridine-2,3-diamine (0.080 g) and triethylamine (0.0638 g) in THF (1.5 mL) at 0° C., was added dropwise a solution of triphosgene (0.030 g) in THF (0.6 ml). The reaction mixture was stirred at 0° C. for 0.5 h. The cold bath was removed and the stirring continued at ambient temperature for another 0.5 h. After this time, a saturated aqueous solution of sodium bicarbonate was added. The organic layer was extracted with ethyl acetate (3×100 mL). The combined organic extracts were washed with brine (50 mL), dried ($Na_2SO_4$), filtered, and concentrated under reduced pressure. The residue obtained was purified by chromatography (silica, methylene chloride to 0.3:5:95 ammonium hydroxide/methanol/methylene chloride) to afford 3-[4-(1,3-benzoxazol-2-ylamino)phenyl]-1,3-dihydro-2H-imidazo[4,5-b]pyridin-2-one (0.038 g) as a white solid.

MS (ESI+): [M+H]$^+$344.

$^1$H NMR (500 MHz, DMSO-$d_6$) δ 7.08 (1H, dd, J=8.0, 5.5 Hz), 7.15 (1H, dt, J=7.5, 1.0 Hz), 7.24 (1H, dt, J=7.5, 1.0 Hz), 7.39 (1H, dd, J=7.5, 1.5 Hz), 7.48 (1H, d, J=7.5 Hz), 7.52 (1H, d, J=8.0 Hz), 7.60-7.63 (2H, m), 7.88-7.91 (2H, m), 7.93 (1H, dd, J=5.0, 1.5 Hz), 10.79 (1H, s), 11.34 (1H, s)

Example 2

3-[4-(2,3-dihydro-1H-imidazo[1,2-a]benzimidazol-1-yl)phenyl]-1,3-dihydro-2H-imidazo[4,5-b]pyridin-2-one

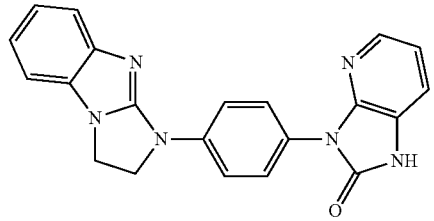 [SMILES: O=c1[nH]c2cccnc2n1-c1ccc(N2CCn3c2nc2ccccc23)cc1]

2a) N-(4-nitrophenyl)-1H-benzimidazol-2-amine

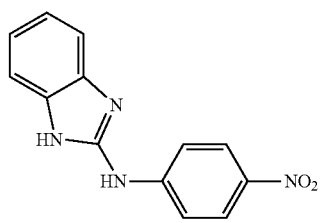 [SMILES: O=[N+]([O-])c1ccc(Nc2nc3ccccc3[nH]2)cc1]

A mixture of 2-chlorobenzimidazole (10.0 g) and 4-nitroaniline (9.05 g) in NMP (130 mL) was stirred at 120° C. for 3 days. After this time, the reaction mixture was cooled to ambient temperature, diluted with ethyl acetate (750 ml) and washed with water (750 mL). The aqueous layer was extracted with ethyl acetate (750 mL) and the combined organic extracts were washed with water (3×750 mL) then brine (750 mL), dried over sodium sulfate, and filtered and the filtrate was concentrated under reduced pressure. The residue obtained was triturated with 1:1 ethyl acetate/heptane (200 mL) and the solid that formed was collected by filtration to afford N-(4-nitrophenyl)-1H-benzimidazol-2-amine (4.00 g) as an orange solid.

$^1$H NMR (500 MHz, DMSO-$d_6$) δ 7.06-7.08 (2H, m), 7.36-7.37 (1H, m), 7.45-7.46 (1H, m), 8.00 (1H, d, J=9.0 Hz), 8.23-8.25 (2H, m), 10.43 (1H, brs), 11.31 (1H, brs).

2b) 1-(4-nitrophenyl)-2,3-dihydro-1H-imidazo[1,2-a]benzimidazole

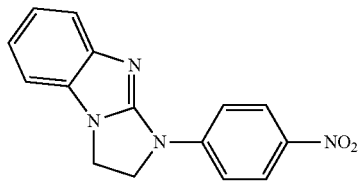 [SMILES: O=[N+]([O-])c1ccc(N2CCn3c2nc2ccccc23)cc1]

A mixture of N-(4-nitrophenyl)-1H-benzimidazol-2-amine (1.00 g) in DMF (20 mL) at ambient temperature was treated with a 60% dispersion of sodium hydride in mineral oil (393 mg) then stirred for 5 min. The mixture was treated with a solution of 1,2-dibromoethane (738 mg) in DMF (1 mL) then stirred at ambient temperature for 1 h. After this time, the reaction mixture was quenched with saturated aqueous ammonium chloride (10 mL), diluted with water (80 mL) and extracted with ethyl acetate (2×100 mL). The combined organic layers were washed with 5% aqueous lithium chloride (2×50 mL) then brine (50 mL), dried over sodium sulfate, and filtered and the filtrate was concentrated under reduced pressure. The residue obtained was purified by chromatography (silica, heptane to 1:1 ethyl acetate/heptane) to afford 1-(4-nitrophenyl)-2,3-dihydro-1H-imidazo[1,2-a]benzimidazole (63 mg) as a yellow solid.
MS (ESI+): [M+H]$^+$281.

2c) 4-(2,3-dihydro-1H-imidazo[1,2-a]benzimidazol-1-yl)aniline

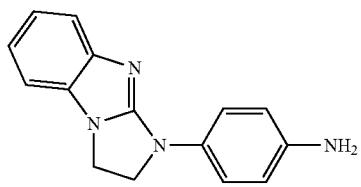 [SMILES: Nc1ccc(N2CCn3c2nc2ccccc23)cc1]

Same procedure of example 1c) with 1-(4-nitrophenyl)-2,3-dihydro-1H-imidazo[1,2-a]benzimidazole (61 mg) gave 4-(2,3-dihydro-1H-imidazo[1,2-a]benzimidazol-1-yl)aniline (55 mg) as an off-white solid.
MS (ESI+): [M+H]$^+$251.

2d) N-[4-(2,3-dihydro-1H-imidazo[1,2-a]benzimidazol-1-yl)phenyl]-3-nitropyridin-2-amine

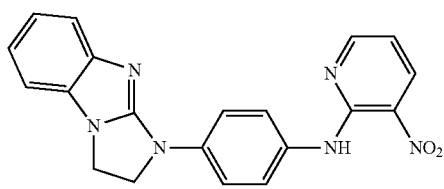 [SMILES: O=[N+]([O-])c1cccnc1Nc1ccc(N2CCn3c2nc2ccccc23)cc1]

A mixture of 4-(2,3-dihydro-1H-imidazo[1,2-a]benzimidazol-1-yl)aniline (55 mg) and 2-chloro-3-nitropyridine (35 mg) in NMP (3 mL) was stirred at 140° C. overnight. After this time, the reaction mixture was cooled to ambient temperature, diluted with water (50 mL) and extracted with ethyl acetate (2×75 mL). The combined organic layers were washed with water (50 mL) then brine (50 mL), dried over sodium sulfate, and filtered and the filtrate was concentrated under reduced pressure. The residue obtained was purified by chromatography (silica, methylene chloride to 1:9 ethyl acetate/methylene chloride) to afford N-[4-(2,3-dihydro-1H-imidazo[1,2-a]benzimidazol-1-yl)phenyl]-3-nitropyridin-2-amine (34 mg) as a dark brown solid.
MS (ESI+): [M+H]$^+$373.

2e) N$^2$-[4-(2,3-dihydro-1H-imidazo[1,2-a]benzimidazol-1-yl)phenyl]pyridine-2,3-diamine

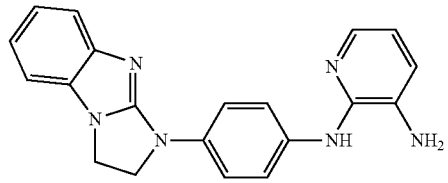

Same procedure of example 1c) with N-[4-(2,3-dihydro-1H-imidazo[1,2-a]benzimidazol-1-yl)phenyl]-3-nitropyridin-2-amine (34 mg) gave N$^2$-[4-(2,3-dihydro-1H-imidazo[1,2-a]benzimidazol-1-yl)phenyl]pyridine-2,3-diamine (20 mg) as a yellow solid.
MS (ESI+): [M+H]$^+$343.

2f) 3-[4-(2,3-dihydro-1H-imidazo[1,2-a]benzimidazol-1-yl)phenyl]-1,3-dihydro-2H-imidazo[4,5-b]pyridin-2-one

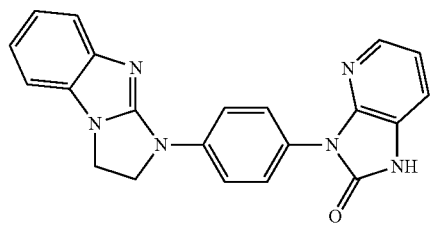 [SMILES: O=c1[nH]c2cccnc2n1-c1ccc(N2CCn3c2nc2ccccc23)cc1]

A mixture of N$^2$-[4-(2,3-dihydro-1H-imidazo[1,2-a]benzimidazol-1-yl)phenyl]pyridine-2,3-diamine (20 mg) and 1,1'-carbonyldiimidazole (19 mg) in THF (5 mL) was stirred at ambient temperature overnight. After this time, the solids that formed were collected by filtration to afford 3-[4-(2,3-dihydro-1H-imidazo[1,2-a]benzimidazol-1-yl)phenyl]-1,3-dihydro-2H-imidazo[4,5-b]pyridin-2-one (12 mg) as off-white crystals.
MS (ESI+): [M+H]$^+$369.
$^1$H NMR (500 MHz, DMSO-d$_6$) δ 4.38-4.41 (2H, m), 4.59-4.63 (2H, m), 7.06-7.10 (3H, m), 7.29-7.31 (1H, m), 7.39 (1H, dd, J=7.5, 1.0 Hz), 7.43-7.45 (1H, m), 7.65 (2H, d, J=9.0 Hz), 7.93-7.95 (3H, m), 11.34 (1H, brs).

Example 3

3-[4-(2,3-dihydro-1H-imidazo[1,2-a]benzimidazol-1-yl)phenyl]-1-methyl-1,3-dihydro-2H-imidazo[4,5-b]pyridin-2-one

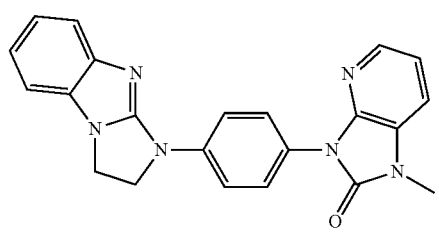 [SMILES: Cn1c(=O)n(-c2ccc(N3CCn4c3nc3ccccc34)cc2)c2ncccc21]

To a mixture of 3-[4-(2,3-dihydro-1H-imidazo[1,2-a]benzimidazol-1-yl)phenyl]-1,3-dihydro-2H-imidazo[4,5-b]pyridin-2-one (57 mg) and methyl iodide (0.012 mL) in DMF (2.0 mL) was added sodium hydride (62 mg) (60% in mineral oil) at 0° C. The mixture was stirred at 0° C. for 1 h, and then added H₂O. The precipitate was collected and washed with MeOH to give 3-[4-(2,3-dihydro-1H-imidazo[1,2-a]benzimidazol-1-yl)phenyl]-1-methyl-1,3-dihydro-2H-imidazo[4,5-b]pyridin-2-one (43 mg) as white powder.

MS (ESI+): [M+H]⁺383.0.

¹H NMR (300 MHz, DMSO-d₆) δ 3.44 (3H, s), 4.33-4.46 (2H, m), 4.53-4.71 (2H, m), 7.01-7.12 (2H, m), 7.13-7.22 (1H, m), 7.24-7.35 (1H, m), 7.39-7.50 (1H, m), 7.55-7.74 (3H, m), 7.82-8.15 (3H, m).

Example 4

1-[4-(2-oxo-1,2-dihydro-3H-imidazo[4,5-b]pyridin-3-yl)phenyl]-1,2-dihydro-3H-imidazo[1,2-a]benzimidazol-3-one

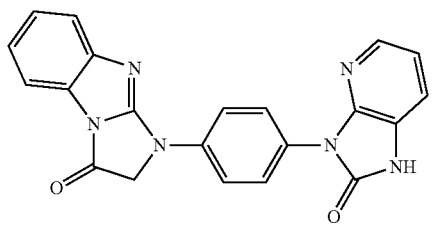 [SMILES: O=C1CN(c2ccc(-n3c(=O)[nH]c4cccnc43)cc2)c2nc3ccccc3n21]

4a) 1-(4-nitrophenyl)-1,2-dihydro-3H-imidazo[1,2-a]benzimidazol-3-one

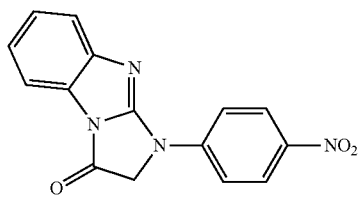 [SMILES: O=C1CN(c2ccc([N+](=O)[O-])cc2)c2nc3ccccc3n21]

A mixture of N-(4-nitrophenyl)-1H-benzimidazol-2-amine (947 mg) and N,N-diisopropylethylamine (1.45 g) in THF (10 mL) at −78° C. was treated dropwise with a solution of bromoacetyl bromide (826 mg) in THF (2.0 mL) then the resulting mixture was allowed to warm to ambient temperature overnight. After this time, the reaction mixture was diluted with water (50 mL) and extracted with ethyl acetate (2×100 mL). The organic layers were washed with brine (50 ml), dried over sodium sulfate, and filtered and the filtrate was concentrated under reduced pressure. The residue obtained was purified by chromatography (silica, heptane to 2:3 ethyl acetate/heptane) to afford 1-(4-nitrophenyl)-1,2-dihydro-3H-imidazo[1,2-a]benzimidazol-3-one (92 mg) as a yellow solid.

¹H NMR (300 MHz, CDCl₃) δ 4.84 (2H, s), 7.31 (1H, d, J=7.8 Hz), 7.40 (1H, td, J=7.8, 1.2 Hz), 7.63 (1H, d, J=9.6 Hz), 7.81 (1H, d, J=7.5 Hz), 7.91 (2H, d, J=9.3 Hz), 8.36 (2H, d, J=9.0 Hz).

4b) 1-(4-aminophenyl)-1,2-dihydro-3H-imidazo[1,2-a]benzimidazol-3-one

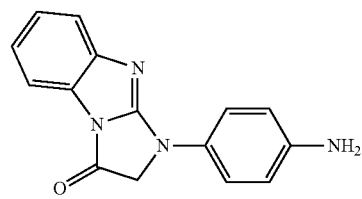 [SMILES: Nc1ccc(N2CC(=O)n3c2nc2ccccc23)cc1]

Same procedure of example 1c) with 1-(4-nitrophenyl)-1,2-dihydro-3H-imidazo[1,2-a]benzimidazol-3-one (92 mg) gave 1-(4-aminophenyl)-1,2-dihydro-3H-imidazo[1,2-a]benzimidazol-3-one (82 mg) as a yellow solid.

MS (ESI+): [M+H]⁺265.

4c) 1-{4-[(3-nitropyridin-2-yl)amino]phenyl}-1,2-dihydro-3H-imidazo[1,2-a]benzimidazol-3-one

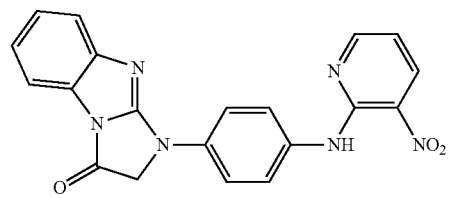 [SMILES: O=C1CN(c2ccc(Nc3ncccc3[N+](=O)[O-])cc2)c2nc3ccccc3n21]

Same procedure of example 2d) with 1-(4-aminophenyl)-1,2-dihydro-3H-imidazo[1,2-a]benzimidazol-3-one (82 mg) gave 1-{4-[(3-nitropyridin-2-yl)amino]phenyl}-1,2-dihydro-3H-imidazo[1,2-a]benzimidazol-3-one (7 mg) as a yellow solid.

MS (ESI+): [M+H]⁺387.

4d) 1-{4-[(3-aminopyridin-2-yl)amino]phenyl}-1,2-dihydro-3H-imidazo[1,2-a]benzimidazol-3-one

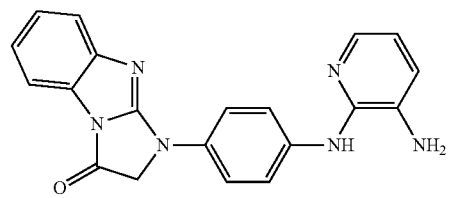 [SMILES: Nc1cccnc1Nc1ccc(N2CC(=O)n3c2nc2ccccc23)cc1]

Same procedure of example 1c) with 1-{4-[(3-nitropyridin-2-yl)amino]phenyl}-1,2-dihydro-3H-imidazo[1,2-a]benzimidazol-3-one (7 mg) gave 1-{4-[(3-aminopyridin-2-yl)amino]phenyl}-1,2-dihydro-3H-imidazo[1,2-a]benzimidazol-3-one (7 mg) as a yellow solid.

MS (ESI+): [M+H]⁺357.

4e) 1-[4-(2-oxo-1,2-dihydro-3H-imidazo[4,5-b]pyridin-3-yl)phenyl]-1,2-dihydro-3H-imidazo[1,2-a]benzimidazol-3-one

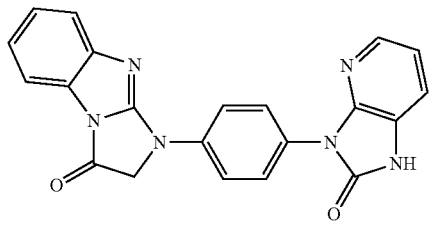 [SMILES: O=C1CN(c2ccc(-n3c(=O)[nH]c4cccnc43)cc2)c2nc3ccccc3n21]

Same procedure of example 2f) with 1-{4-[(3-aminopyridin-2-yl)amino]phenyl}-1,2-dihydro-3H-imidazo[1,2-a]benzimidazol-3-one (7 mg) gave 1-[4-(2-oxo-1,2-dihydro-3H-imidazo[4,5-b]pyridin-3-yl)phenyl]-1,2-dihydro-3H-imidazo[1,2-a]benzimidazol-3-one (4 mg) as yellow crystals.

MS (ESI+): [M+H]$^+$ 383.

$^1$H NMR (500 MHz, CDCl$_3$) δ 4.80 (2H, s), 7.08 (1H, dd, J=8.0, 5.5 Hz), 7.33-7.36 (3H, m), 7.59 (1H, d, J=8.0 Hz), 7.78 (1H, d, J=8.0 Hz), 7.81-7.83 (3H, m), 7.92 (2H, d, J=9.5 Hz), 8.09 (1H, dd, J=5.0, 1.0 Hz).

Example 5

1-[4-(1,3-benzoxazol-2-ylamino)phenyl]-1,3-dihydro-2H-pyrrolo[2,3-b]pyridin-2-one

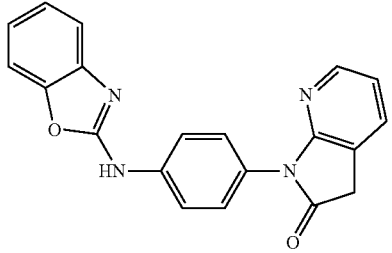 [SMILES: O=C1Cc2cccnc2N1c1ccc(Nc2nc3ccccc3o2)cc1]

5a) 1-(4-nitrophenyl)-1,3-dihydro-2H-pyrrolo[2,3-b]pyridin-2-one

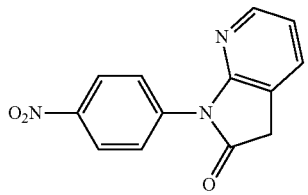 [SMILES: O=C1Cc2cccnc2N1c1ccc([N+](=O)[O-])cc1]

A mixture of 1H-pyrrolo[2,3-b]pyridin-2(3H)-one (431 mg), 1-bromo-4-nitrobenzene (778 mg), copper(I) iodide (122 mg), N$^1$,N$^2$-dimethylethane-1,2-diamine (113 mg) and potassium iodide (1.36 g) in 1,4-dioxane (10 mL) was sparged with argon for 5 min then heated overnight at 95° C. After this time, the reaction mixture was cooled to ambient temperature, diluted with ethyl acetate (100 mL), filtered through diatomaceous earth and the filtrate was concentrated under reduced pressure. The residue obtained was purified by chromatography (silica, heptane to 1:1 ethyl acetate/heptane) to afford 1-(4-nitrophenyl)-1,3-dihydro-2H-pyrrolo[2,3-b]pyridin-2-one (207 mg) as a white solid.

MS (ESI+): [M+H]$^+$256.

5b) 1-(4-aminophenyl)-1,3-dihydro-2H-pyrrolo[2,3-b]pyridin-2-one

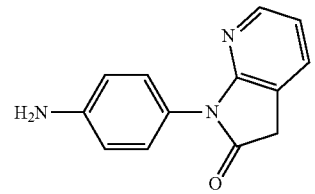

Same procedure of example 1c) with 1-(4-nitrophenyl)-1,3-dihydro-2H-pyrrolo[2,3-b]pyridin-2-one (145 mg) gave 1-(4-aminophenyl)-1,3-dihydro-2H-pyrrolo[2,3-b]pyridin-2-one (120 mg) as a yellow solid.

MS (ESI+): [M+H]$^+$226.

5c) 1-[4-(1,3-benzoxazol-2-ylamino)phenyl]-1,3-dihydro-2H-pyrrolo[2,3-b]pyridin-2-one

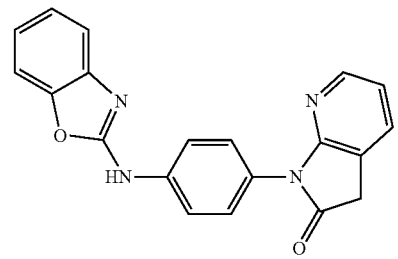 [SMILES: O=C1Cc2cccnc2N1c1ccc(Nc2nc3ccccc3o2)cc1]

Same procedure of example 1a) with 1-(4-aminophenyl)-1,3-dihydro-2H-pyrrolo[2,3-b]pyridin-2-one (120 mg) and 2-chlorobenzo[d]oxazole (98 mg) gave 1-[4-(1,3-benzoxazol-2-ylamino)phenyl]-1,3-dihydro-2H-pyrrolo[2,3-b]pyridin-2-one (126 mg) as yellow crystals.

MS (ESI+): [M+H]$^+$343.

$^1$H NMR (500 MHz, DMSO-d$_6$) δ 3.80 (2H, s), 7.08 (1H, dd, J=7.5, 5.5 Hz), 7.15 (1H, td, J=8.0, 1.5 Hz), 7.24 (1H, td, J=7.5, 1.0 Hz), 7.45-7.49 (3H, m), 7.52 (1H, d, J=8.0 Hz), 7.70 (1H, dd, J=7.0, 1.0 Hz), 7.87 (2H, d, J=9.0 Hz), 8.08-8.09 (1H, m), 10.79 (1H, brs).

Example 6

3-[4-(1,3-benzoxazol-2-ylamino)phenyl][1,3]oxazolo[4,5-b]pyridin-2(3H)-one

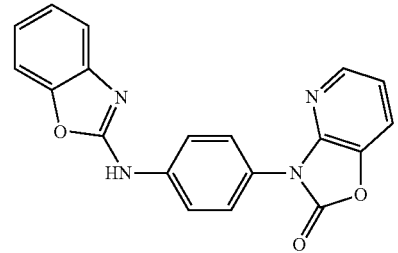 [SMILES: O=c1oc2cccnc2n1-c1ccc(Nc2nc3ccccc3o2)cc1]

6a) 3-(4-nitrophenyl)[1,3]oxazolo[4,5-b]pyridin-2(3H)-one

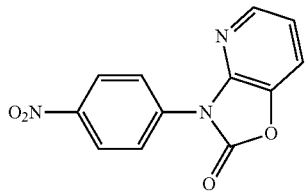 [SMILES: O=c1oc2cccnc2n1-c1ccc([N+](=O)[O-])cc1]

A solution of oxazolo[4,5-b]pyridin-2(3H)-one (200 mg) in DMF (3.5 mL) was treated with a 60% dispersion of sodium hydride in mineral oil (62 mg) and the resulting mixture stirred at ambient temperature for 5 min. The mixture was treated with 1-fluoro-4-nitrobenzene (248 mg) then stirred at 100° C. for 17 h. After this time, the reaction mixture was cooled to ambient temperature, diluted with ethyl acetate (100 ml), washed with water (2×50 ml), 5% aqueous lithium chloride (50 ml) then brine (50 mL), dried over sodium sulfate, and filtered and the filtrate was concentrated under reduced pressure. The residue obtained was purified by chromatography (silica, heptane to 1:1 ethyl acetate/heptane) to afford 3-(4-nitrophenyl)[1,3]oxazolo[4,5-b]pyridin-2(3H)-one (73 mg) as a yellow solid.

MS (ESI+): [M+H]$^+$ 258.

6b) 3-(4-aminophenyl)[1,3]oxazolo[4,5-b]pyridin-2(3H)-one

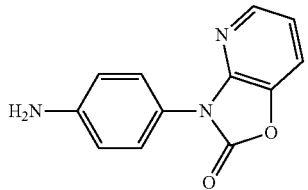

Same procedure of example 1c) with 3-(4-nitrophenyl)[1,3]oxazolo[4,5-b]pyridin-2(3H)-one (70 mg) gave 3-(4-aminophenyl)[1,3]oxazolo[4,5-b]pyridin-2(3H)-one (55 mg) as an off-white solid.

MS (ESI+): [M+H]$^+$228.

6c) 3-[4-(1,3-benzoxazol-2-ylamino)phenyl][1,3]oxazolo[4,5-s b]pyridin-2(3H)-one

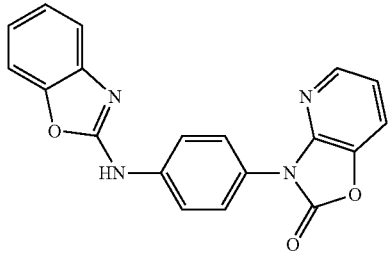 [SMILES: O=c1oc2cccnc2n1-c1ccc(Nc2nc3ccccc3o2)cc1]

Same procedure of example 1a) with 3-(4-aminophenyl)[1,3]oxazolo[4,5-b]pyridin-2(3H)-one (50 mg) and 2-chlorobenzo[d]oxazole (40 mg) gave 3-[4-(1,3-benzoxazol-2-ylamino)phenyl][1,3]oxazolo[4,5-b]pyridin-2(3H)-one (58 mg) as brown crystals.

MS (ESI+): [M+H]$^+$345.

$^1$H NMR (500 MHz, DMSO-d$_6$) δ 7.15-7.18 (1H, m), 7.23-7.27 (2H, m), 7.49 (1H, dd, J=7.5, 0.5 Hz), 7.52 (1H, d, J=8.0 Hz), 7.68-7.71 (2H, m), 7.81 (1H, dd, J=8.0, 1.5 Hz), 7.92-7.95 (2H, m), 8.11 (1H, dd, J=5.5, 1.5 Hz), 10.88 (1H, s).

Example 7

3-[4-(1H-benzimidazol-2-yloxy)phenyl]-1,3-dihydro-2H-imidazo[4,5-b]pyridin-2-one

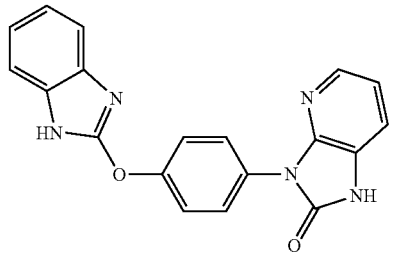 [SMILES: O=c1[nH]c2cccnc2n1-c1ccc(Oc2nc3ccccc3[nH]2)cc1]

7a) N-[4-(benzyloxy)phenyl]-3-nitropyridin-2-amine

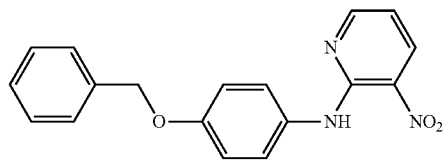 [SMILES: O=[N+]([O-])c1cccnc1Nc1ccc(OCc2ccccc2)cc1]

A mixture of 2-chloro-3-nitropyridine (2.0 g), 4-(benzyloxy)aniline hydrochloride (3.6 g), and cesium carbonate (12.3 g) in NMP (50 mL) was heated at 100° C. for 5 h. After cooling to rt, the mixture was partitioned between AcOEt and H$_2$O. The organic layer was washed with brine, dried over Na$_2$SO$_4$ and evaporated. The residue was purified by column chromatography (SiO$_2$, hexane/AcOEt=1/1) to give N-[4-(benzyloxy)phenyl]-3-nitropyridin-2-amine (3.04 g) as a brown solid.

MS (ESI+): [M+H]$^+$322.0.

7b) N$^2$-[4-(benzyloxy)phenyl]pyridine-2,3-diamine

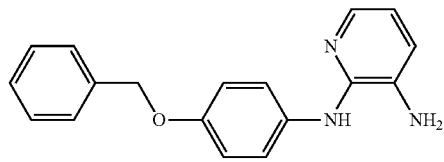 [SMILES: Nc1cccnc1Nc1ccc(OCc2ccccc2)cc1]

A mixture of N-[4-(benzyloxy)phenyl]-3-nitropyridin-2-amine (1.5 g), Fe (2.6 g), and CaCl$_2$ (260 mg) in EtOH (30 mL) and H$_2$O (6.0 mL) was heated at 100° C. for 6 h. After cooling to rt, the precipitate was removed by Celite, and the filtrate was concentrated. The residue was partitioned between AcOEt and sat.NaHCO$_3$aq. The organic layer was washed with brine, dried over Na$_2$SO$_4$ and evaporated. The residue was purified by column chromatography (SiO$_2$, hexane/AcOEt=3/2 to 1/1). The obtained solid was rinsed with $^i$Pr$_2$O-hexane to give N$^2$-[4-(benzyloxy)phenyl]pyridine-2,3-diamine (1.0 g) as a pale pink solid.

MS (ESI+): [M+H]$^+$292.1.

7c) 3-[4-(benzyloxy)phenyl]-1,3-dihydro-2H-imidazo[4,5-b]pyridin-2-one

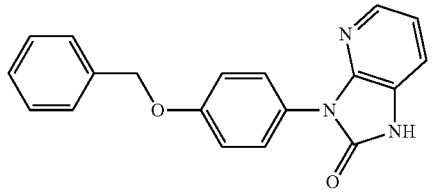

A mixture of N²-[4-(benzyloxy)phenyl]pyridine-2,3-diamine (1.0 g), CDI (668 mg), and DBU (1.2 mL) in THF (25 mL) was heated at 60° C. overnight. After cooling to rt, the mixture was partitioned between AcOEt and H₂O. The organic layer was washed with brine, dried over Na₂SO₄ and evaporated. The residue was purified by column chromatography (SiO₂, hexane/AcOEt=97/3 to 9/1) to give 3-[4-(benzyloxy)phenyl]-1,3-dihydro-2H-imidazo[4,5-b]pyridin-2-one (993 mg) as a pale brown solid.
MS (ESI+): [M+H]⁺318.0.

7d) 3-(4-hydroxyphenyl)-1,3-dihydro-2H-imidazo[4,5-b]pyridin-2-one

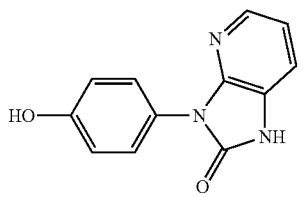 [SMILES: O=c1[nH]c2cccnc2n1-c1ccc(O)cc1]

A mixture of 3-[4-(benzyloxy)phenyl]-1,3-dihydro-2H-imidazo[4,5-b]pyridin-2-one (500 mg) and Pd—C (100 mg) in MeOH (30 mL) was stirred at room temperature for 5.5 h. The mixture was filtered by Celite, and the filtrate was concentrated. The resulting solid was rinsed with ⁱPr₂O to give 3-(4-hydroxyphenyl)-1,3-dihydro-2H-imidazo[4,5-b]pyridin-2-one (370% mg) as a pale brown solid.

7e) 3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one

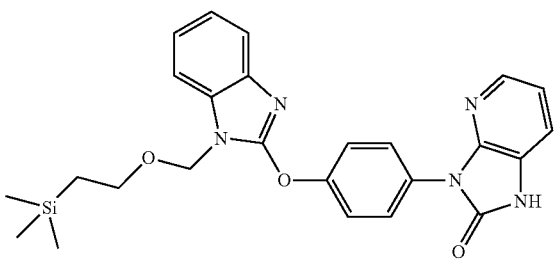 [SMILES: C[Si](C)(C)CCOCn1c(Oc2ccc(-n3c(=O)[nH]c4cccnc43)cc2)nc2ccccc21]

3-(4-hydroxyphenyl)-1,3-dihydro-2H-imidazo[4,5-b]pyridin-2-one (370 mg), 2-chloro-1-{[2-(trimethylsilyl)ethoxy]methyl}-1H-benzimidazole (507 mg) and cesium carbonate (1.17 g) in DMF (10 mL) was heated at 100° C. for 4 h. After cooling to rt, the mixture was partitioned between AcOEt and H₂O. The organic layer was washed with brine, dried over Na₂SO₄ and evaporated. The residue was purified by column chromatography (SiO₂, hexane/AcOEt=1/1 to 0/1) to give 3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (560 mg) as white crystals.
MS (ESI+): [M+H]⁺474.0.

7f) 3-[4-(1H-benzimidazol-2-yloxy)phenyl]-1,3-dihydro-2H-imidazo[4,5-b]pyridin-2-one

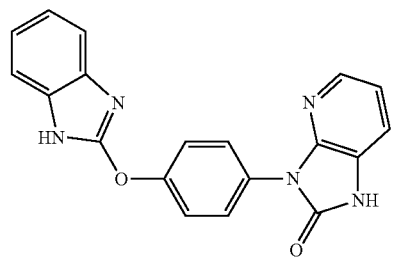 [SMILES: O=c1[nH]c2cccnc2n1-c1ccc(Oc2nc3ccccc3[nH]2)cc1]

A mixture of 3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (300 mg), 1 M TBAF in THF (6.3 mL), and TMEDA in THF (20 mL) was heated at 50° C. for 24 h. After cooling to rt, the mixture was partitioned between AcOEt and H₂O. The organic layer was washed with brine, dried over Na₂SO₄ and evaporated. The residue was purified by column chromatography (SiO₂, hexane/AcOEt=1/3 then AcOEt/MeOH=95/5). The obtained product was recrystallized from MeOH-iPr₂O to give 3-[4-(1H-benzimidazol-2-yloxy)phenyl]-1,3-dihydro-2H-imidazo[4,5-b]pyridin-2-one (75 mg) as white crystals.
MS (ESI+): [M+H]⁺343.9.
¹H NMR (300 MHz, DMSO-d₆) δ 7.11 (3 H, dd, J=5.7, 3.8 Hz), 7.32-7.47 (3 H, m), 7.54 (2 H, d, J=8.0 Hz), 7.74 (2 H, d, J=8.3 Hz), 7.95 (1 H, d, J=4.9 Hz), 12.04 (2 H, brs).

Example 8

3-[4-(1H-benzimidazol-2-yloxy)phenyl]-1-ethyl-1,3-dihydro-2H-imidazo[4,5-b]pyridin-2-one hydrochloride

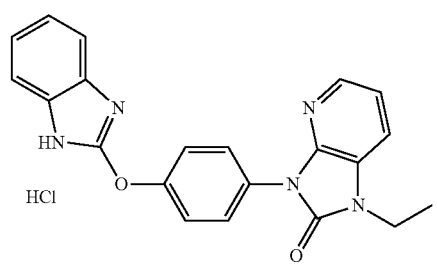 [SMILES: CCn1c(=O)n(-c2ccc(Oc3nc4ccccc4[nH]3)cc2)c2ncccc21 ; Cl]

2-Chloro-1-{[2-(trimethylsilyl)ethoxy]methyl}-1H-benzimidazole (1.861 g) was added to a solution of 1-ethyl-3-(4-hydroxyphenyl)-1,3-dihydro-2H-imidazo[4,5-b]pyridin-2-one (1.4 g) and sodium hydride (0.263 g) in DMF (dry) (10 mL) at room temperature. The mixture was heated at 200° C. for 1 h under microwave irradiation. The reaction mixture was concentrated under reduced pressure. The residue was purified by column chromatography (NH silica gel, eluted with 5%-50% EtOAc in hexane) to give 1-ethyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (2.60 g) as a colorless solid. A mixture of 1-ethyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (194 mg) and 2 M HCl in EtOH (6.0 mL) was stirred at 70° C. for 4 h. After cooling to room temperature, the solvent was removed in vacuo. The residue was recrystallized from EtOH-ether to give 3-[4-(1H-benzimidazol-2-yloxy)phenyl]-1-ethyl-1,3-dihydro-2H-imidazo[4,5-b]pyridin-2-one hydrochloride (154 mg).

MS (ESI+): [M+H]$^+$372.1.

$^1$H NMR (300 MHz, DMSO-d$_6$) δ 1.17-1.43 (3H, m), 3.78-4.15 (2H, m), 7.12-8.06 (10H, m), 8.62 (2H, brs).

Example 9

1-[4-(1H-benzimidazol-2-yloxy)phenyl]-3,3-dimethyl-1,3-dihydro-2H-pyrrolo[2,3-b]pyridin-2-one dihydrochloride

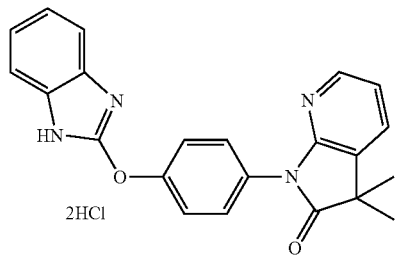 [SMILES: CC1(C)C(=O)N(c2ccc(Oc3nc4ccccc4[nH]3)cc2)c2ncccc21 ; "2HCl"]

9a) 1-[4-(benzyloxy)phenyl]-1,3-dihydro-2H-pyrrolo[2,3-b]pyridin-2-one

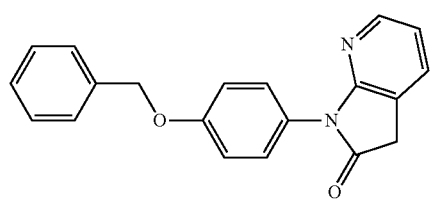 [SMILES: O=C1Cc2cccnc2N1c1ccc(OCc2ccccc2)cc1]

A mixture of 4-(benzyloxy)aniline hydrochloride (2.21 g), 4-methylbenzenesulfonic acid hydrate (0.178 g), and (2-chloropyridin-3-yl)acetic acid (Journal of Medicinal Chemistry, 1990, 33, 2697-2706.) (1.61 g) in 1-pentanol (15 mL) was stirred at 140° C. for 24 h. After cooling to room temperature, the mixture was added to SiO$_2$, and the mixture was concentrated and purified by column chromatography (silica gel, eluted with 0%-50% EtOAc in hexane) to give 1-[4-(benzyloxy)phenyl]-1,3-dihydro-2H-pyrrolo[2,3-b]pyridin-2-one (1.39 g) as a pale yellow solid.

MS (ESI+): [M+H]$^+$317.0.

9b) 1-[4-(benzyloxy)phenyl]-3,3-dimethyl-1,3-dihydro-2H-pyrrolo[2,3-b]pyridin-2-one

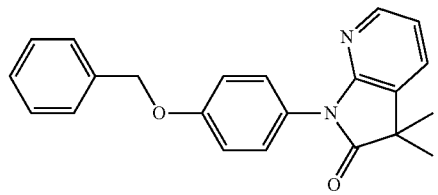 [SMILES: CC1(C)C(=O)N(c2ccc(OCc3ccccc3)cc2)c2ncccc21]

A mixture of 1-[4-(benzyloxy)phenyl]-1,3-dihydro-2H-pyrrolo[2,3-b]pyridin-2-one (350 mg), iodomethane (0.145 mL), and sodium hydride (49 mg) (60% in mineral oil) in DMF (5 mL) was stirred at 0° C. to room temperature overnight. The mixture was quenched with water at room temperature and extracted with EtOAc. The organic layer was separated, washed with brine, dried over MgSO$_4$ and concentrated in vacuo. The residue was purified by column chromatography (silica gel, eluted with 0%-50% EtOAc in hexane) to give 1-[4-(benzyloxy)phenyl]-3,3-dimethyl-1,3-dihydro-2H-pyrrolo[2,3-b]pyridin-2-one (198 mg) as an orange solid.

MS (ESI+): [M+H]$^+$345.4.

9c) 1-(4-hydroxyphenyl)-3,3-dimethyl-1,3-dihydro-2H-pyrrolo[2,3-b]pyridin-2-one

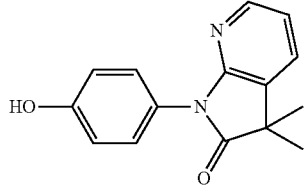 [SMILES: CC1(C)C(=O)N(c2ccc(O)cc2)c2ncccc21]

Same procedure of example 1c) with 1-[4-(benzyloxy)phenyl]-3,3-dimethyl-1,3-dihydro-2H-pyrrolo[2,3-b]pyridin-2-one (198 mg) gave 1-(4-hydroxyphenyl)-3,3-dimethyl-1,3-dihydro-2H-pyrrolo[2,3-b]pyridin-2-one (139 mg) as a white solid.

MS (ESI+): [M+H]$^+$255.4.

9d) 3,3-dimethyl-1-{4-[(1-{[2-(trimethylsilyl)ethoxy]methyl}-1H-benzimidazol-2-yl)oxy]phenyl}-1,3-dihydro-2H-pyrrolo[2,3-b]pyridin-2-one

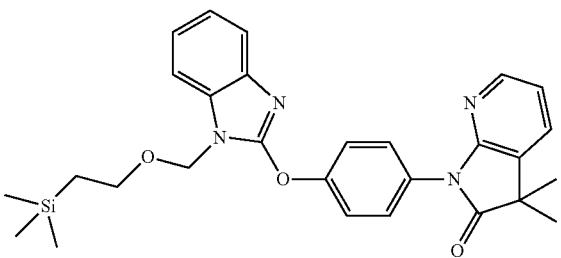

Same procedure of example 7e) with 1-(4-hydroxyphenyl)-3,3-dimethyl-1,3-dihydro-2H-pyrrolo[2,3-b]pyridin-2-one (139 mg) and 2-chloro-1-{[2-(trimethylsilyl)ethoxy]methyl}-1H-benzimidazole (155 mg) gave 3,3-dimethyl-1-{4-[(1-{[2-(trimethylsilyl)ethoxy]methyl}-1H-benzimidazol-2-yl)oxy]phenyl}-1,3-dihydro-2H-pyrrolo[2,3-b]pyridin-2-one (258 mg) as white crystals.

MS (ESI+): [M+H]⁺501.1.

9e) 1-[4-(1H-benzimidazol-2-yloxy)phenyl]-3,3-dimethyl-1,3-dihydro-2H-pyrrolo[2,3-b]pyridin-2-one dihydrochloride

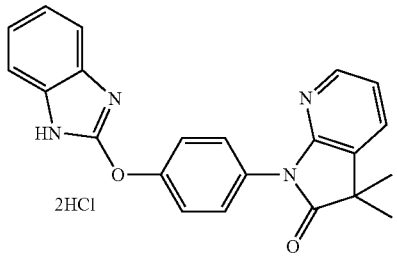 [SMILES: CC1(C)C(=O)N(c2ccc(Oc3nc4ccccc4[nH]3)cc2)c2ncccc21]

A mixture of 3,3-dimethyl-1-{4-[(1-{[2-(trimethylsilyl)ethoxy]methyl}-1H-benzimidazol-2-yl)oxy]phenyl}-1,3-dihydro-2H-pyrrolo[2,3-b]pyridin-2-one (258 mg) and 2N HCl in EtOH (5 mL) in EtOH (5 ml) was stirred at 60° C. for 10 h. After cooling to room temperature, the solvent was removed. The residue was recrystallized from EtOH—AcOEt to give 1-[4-(1H-benzimidazol-2-yloxy)phenyl]-3,3-dimethyl-1,3-dihydro-2H-pyrrolo[2,3-b]pyridin-2-one dihydrochloride (152 mg).

MS (ESI+): [M+H]⁺371.0.

¹H NMR (300 MHz, DMSO-d₆) δ 1.45 (6H, s), 7.12-7.23 (3H, m), 7.38-7.48 (2H, m), 7.49-7.72 (4H, m), 7.87 (1H, dd, J=7.4, 1.7 Hz), 8.13 (1H, dd, J=5.3, 1.9 Hz), 8.67 (3H, brs).

Example 10

3-[4-(1-benzyl-2-methyl-1H-benzimidazol-4-yl)phenyl]-1-{[2-(trimethylsilyl)ethoxy]methyl}-1,3-dihydro-2H-imidazo[4,5-b]pyridin-2-one

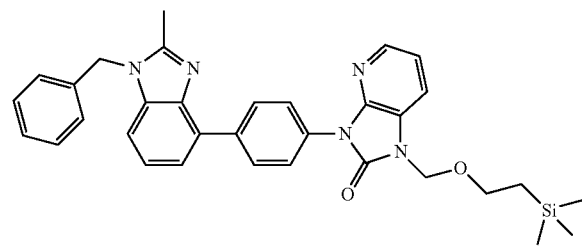 [SMILES: Cc1nc2c(-c3ccc(-n4c(=O)n(COCC[Si](C)(C)C)c5cccnc54)cc3)cccc2n1Cc1ccccc1]

10a) 3-[4-(benzyloxy)phenyl]-1-{[2-(trimethylsilyl)ethoxy]methyl}-1,3-dihydro-2H-imidazo[4,5-b]pyridin-2-one

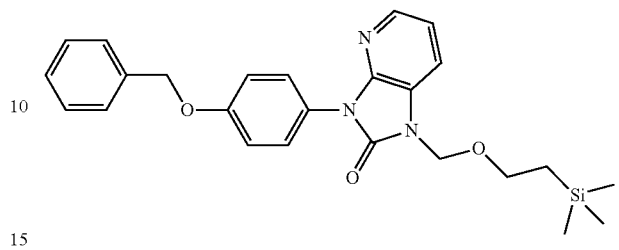

[2-(Chloromethoxy)ethyl](trimethyl)silane (1.673 mL) was added to a solution of 3-[4-(benzyloxy)phenyl]-1,3-dihydro-2H-imidazo[4,5-b]pyridin-2-one (2.0 g) and sodium hydride (0.504 g) (60% in mineral oil) in DMF (5.0 ml) at 0° C. The mixture was stirred at room temperature under a dry atmosphere (CaCl₂ tube) for 1 h. After the reaction, the reaction mixture was diluted with MeOH and concentrated in vacuo. The residue was purified by column chromatography (silica gel, eluted with 0%-100% EtOAc in hexane) to give 3-[4-(benzyloxy)phenyl]-1-{[2-(trimethylsilyl)ethoxy]methyl}-1,3-dihydro-2H-imidazo[4,5-b]pyridin-2-one (2.75 g) as a white solid.

MS (ESI+): [M+H] 448.1

10b) 3-(4-hydroxyphenyl)-1-{[2-(trimethylsilyl)ethoxy]methyl}-1,3-dihydro-2H-imidazo[4,5-b]pyridin-2-one

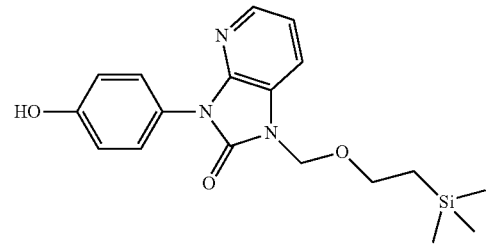 [SMILES: C[Si](C)(C)CCOCn1c(=O)n(-c2ccc(O)cc2)c2ncccc21]

Same procedure of example 7d) with 3-[4-(benzyloxy)phenyl]-1-{[2-(trimethylsilyl)ethoxy]methyl}-1,3-dihydro-2H-imidazo[4,5-b]pyridin-2-one (2.82 g) gave 3-(4-hydroxyphenyl)-1-{[2-(trimethylsilyl)ethoxy]methyl}-1,3-dihydro-2H-imidazo[4,5-b]pyridin-2-one (2.23 g) as a white solid.

MS (ESI+): [M+H]⁺358.4.

10c) 4-(2-oxo-1-{[2-(trimethylsilyl)ethoxy]methyl}-1,2-dihydro-3H-imidazo[4,5-b]pyridin-3-yl)phenyl trifluoromethanesulfonate

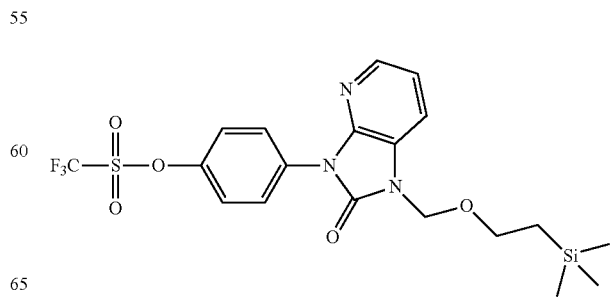

N-Phenylbis(trifluoromethanesulfonimide) (4.46 g) was added to a solution of 3-(4-hydroxyphenyl)-1-{[2-(trimethylsilyl)ethoxy]methyl}-1,3-dihydro-2H-imidazo[4,5-b]pyridin-2-one (2.23 g) and triethylamine (8.69 mL) in THF (20% mL) at room temperature. The mixture was stirred at 70° C. under a dry atmosphere (CaCl$_2$ tube) for 3 h. The mixture was neutralized with sat.NaHCO$_3$aq. at 0° C. and extracted with EtOAc. The organic layer was separated, washed with water and brine, dried over MgSO$_4$ and concentrated in vacuo. The residue was purified by column chromatography (silica gel, eluted with 0%-30% EtOAc in hexane) to give 4-(2-oxo-1-{[2-(trimethylsilyl)ethoxy]methyl}-1,2-dihydro-3H-imidazo[4,5-b]pyridin-3-yl)phenyl trifluoromethanesulfonate (2.90 g) as tan oil.

MS (ESI+): [M+H]$^+$490.3.

10d) 3-[4-(4,4,5,5-tetramethyl-1,3,2-dioxaborolan-2-yl)phenyl]-1-{[2-(trimethylsilyl)ethoxy]methyl}-1,3-dihydro-2H-imidazo[4,5-b]pyridin-2-one

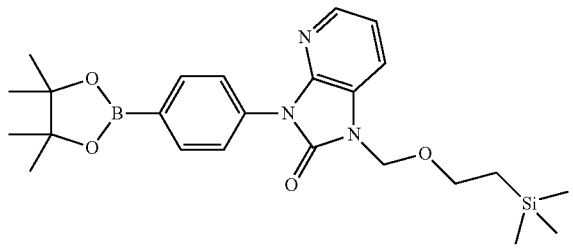

The mixture of 4-(2-oxo-1-{[2-(trimethylsilyl)ethoxy]methyl}-1,2-dihydro-3H-imidazo[4,5-b]pyridin-3-yl)phenyl trifluoromethanesulfonate (2.6 g), 4,4,5,5-tetramethyl-1,3,2-dioxaborolane (0.77 mL), triethylamine (2.23 mL), [1,1'-bis(diphenylphosphino)ferrocene]dichloropalladium(II) dichloromethane adduct (0.218 g) and THF (21.2 mL) was heated at 100° C. for 3 h under microwave irradiation. The mixture was concentrated in vacuo. The residue was purified by column chromatography (silica gel, eluted with 0%-30% EtOAc in hexane) to give 3-[4-(4,4,5,5-tetramethyl-1,3,2-dioxaborolan-2-yl)phenyl]-1-{[2-(trimethylsilyl)ethoxy]methyl}-1,3-dihydro-2H-imidazo[4,5-b]pyridin-2-one (1.5 g) as dark yellow oil.

MS (ESI+): [M+H]$^+$468.2.

10e) 3-[4-(1-benzyl-2-methyl-1H-benzimidazol-4-yl)phenyl]-1-{[2-(trimethylsilyl)ethoxy]methyl}-1,3-dihydro-2H-imidazo[4,5-b]pyridin-2-one

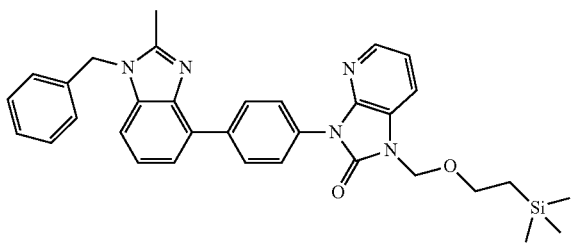 [SMILES: Cc1nc2c(-c3ccc(-n4c(=O)n(COCC[Si](C)(C)C)c5cccnc54)cc3)cccc2n1Cc1ccccc1]

Benzyl chloride (1.527 mL) was added to a solution of 4-bromo-2-methyl-1H-benzimidazole (1.40 g) and sodium hydride (0.531 g) in DMF (10 ml) at 0° C. The mixture was stirred at room temperature under a dry atmosphere for 1 h. The reaction mixture was diluted with MeOH and concentrated in vacuo. The residue was purified by column chromatography (NH silica gel, eluted with 5%-50% EtOAc in hexane) to give 1-benzyl-4-bromo-2-methyl-1H-benzo[d]imidazole (1.88 g) as tan oil. The mixture of 1-benzyl-4-bromo-2-methyl-1H-benzo[d]imidazole (496 mg), 3-[4-(4,4,5,5-tetramethyl-1,3,2-dioxaborolan-2-yl)phenyl]-1-{[2-(trimethylsilyl)ethoxy]methyl}-1,3-dihydro-2H-imidazo[4,5-b]pyridin-2-one (700 mg), Pd(Ph$_3$P)$_4$ (87 mg), sodium carbonate (476 mg) and THF (18 mL)-water (0.90 mL) was heated at 100° C. for 1 h under microwave irradiation. The mixture was poured into water at room temperature and extracted with EtOAc. The organic layer was separated, washed with brine, dried over MgSO$_4$ and concentrated in vacuo. The residue was purified by column chromatography (silica gel, eluted with 10%-50% EtOAc in hexane) to give 3-[4-(1-benzyl-2-methyl-1H-benzimidazol-4-yl)phenyl]-1-{[2-(trimethylsilyl)ethoxy]methyl}-1,3-dihydro-2H-imidazo[4,5-b]pyridin-2-one (450 mg) as white crystals.

MS (ESI+): [M+H]$^+$562.4.

Example 11

3-(4-quinolin-8-ylphenyl)-1-{[2-(trimethylsilyl)ethoxy]methyl}-1,3-dihydro-2H-imidazo[4,5-b]pyridin-2-one

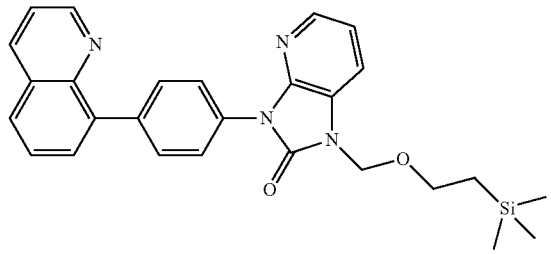 [SMILES: C[Si](C)(C)CCOCn1c(=O)n(-c2ccc(-c3cccc4cccnc34)cc2)c2ncccc21]

The mixture of 4-(2-oxo-1-{[2-(trimethylsilyl)ethoxy]methyl}-1,2-dihydro-3H-imidazo[4,5-b]pyridin-3-yl)phenyl trifluoromethanesulfonate (500 mg), 8-quinolineboronic acid (265 mg), Pd(Ph$_3$P)$_4$ (35.4 mg), 2 M Na$_2$CO$_3$ (1.02 mL) and CH$_3$CN (10 mL) was heated at 150° C. for 20 min under microwave irradiation. The mixture was diluted with sat.NaHCO$_3$aq. at 0° C. and extracted with EtOAc. The organic layer was separated, washed with water and brine, dried over MgSO$_4$ and concentrated in vacuo. The residue was purified by column chromatography (silica gel, eluted with 0%-50% EtOAc in hexane) to give 3-(4-quinolin-8-ylphenyl)-1-{[2-(trimethylsilyl)ethoxy]methyl}-1,3-dihydro-2H-imidazo[4,5-b]pyridin-2-one (410 mg) as white crystals.

MS (ESI+): [M+H]$^+$469.1.

Example 12

1-Ethyl-3-[4-(1H-pyrazolo[3,4-b]pyridin-1-yl)phenyl]-1,3-dihydro-2H-imidazo[4,5-b]pyridin-2-one

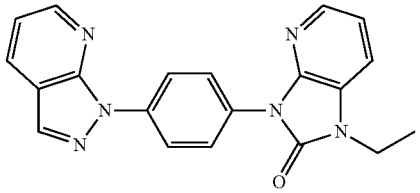 [SMILES: CCn1c(=O)n(-c2ccc(-n3ncc4cccnc43)cc2)c2ncccc21]

12a) 1-(4-nitrophenyl)-1H-pyrazolo[3,4-b]pyridine

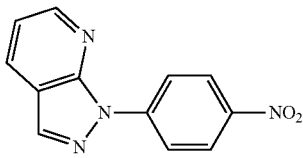 [SMILES: O=[N+]([O-])c1ccc(-n2ncc3cccnc32)cc1]

To a stirred solution of 1H-pyrazolo[3,4-b]pyridine (300 mg) in DMF (3.0 mL) was added sodium hydride (101 mg) (60% in mineral oil) with ice-cooling. The mixture was stirred at room temperature for 30 min, and then 1-fluoro-4-nitrobenzene (355 mg) was added. After stirring at room temperature for 2 h, the mixture was warmed up to 50° C. The mixture was stirred at 50° C. for 12 h. Cesium carbonate (821 mg) was added and the mixture was stirred at 100° C. for 12 h, and treated with water and AcOEt. The insoluble material was filtered off. The organic layer was separated and the aqueous layer was extracted with AcOEt. The organic layer was combined, dried over MgSO4 and concentrated in vacuo. The residue was used for the next reaction.

12b) 4-(1H-pyrazolo[3,4-b]pyridin-1-yl)aniline

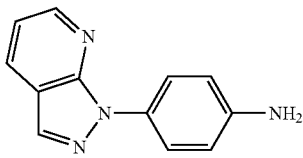 [SMILES: Nc1ccc(-n2ncc3cccnc32)cc1]

Same procedure of example 1c) with 1-(4-nitrophenyl)-1H-pyrazolo[3,4-b]pyridine obtained from example 12a) gave 4-(1H-pyrazolo[3,4-b]pyridin-1-yl)aniline (50 mg).
MS (ESI+): [M+H]$^+$211.1.

12c) 3-[4-(1H-pyrazolo[3,4-b]pyridin-1-yl)phenyl]-1,3-dihydro-2H-imidazo[4,5-b]pyridin-2-one

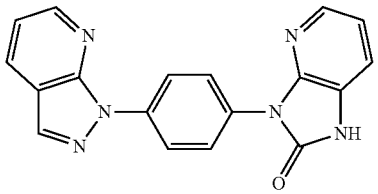 [SMILES: O=c1[nH]c2cccnc2n1-c1ccc(-n2ncc3cccnc32)cc1]

A mixture of tert-butyl 2-chloropyridin-3-ylcarbamate (120 mg), Pd$_2$(dba)$_3$ (21.8 mg), Xantphos (27.5 mg), and sodium tert-butoxide (34.3 mg) in 2-propanol (8.0 ml) and toluene (2.0 mL) was stirred at 90° C. for 16 h, treated with water and extracted with EtOAc. The organic layer was separated, dried over MgSO$_4$ and concentrated in vacuo. The residue was suspended in DMSO/CH$_3$CN and the insoluble material was collected by filtration to give 3-[4-(1H-pyrazolo[3,4-b]pyridin-1-yl)phenyl]-1,3-dihydro-2H-imidazo[4,5-b]pyridin-2-one (40 mg). The filtrate was concentrated and chromatographed on silica gel eluting with AcOEt/Hexane=2/1. Removal of solvent gave second crop (10 mg).
MS (ESI+): [M+H]$^+$329.0.

12d) 1-Ethyl-3-[4-(1H-pyrazolo[3,4-b]pyridin-1-yl)phenyl]-1,3-dihydro-2H-imidazo[4,5-b]pyridin-2-one

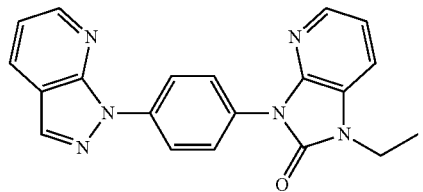 [SMILES: CCn1c(=O)n(-c2ccc(-n3ncc4cccnc43)cc2)c2ncccc21]

A mixture of 3-[4-(1H-pyrazolo[3,4-b]pyridin-1-yl)phenyl]-1,3-dihydro-2H-imidazo[4,5-b]pyridin-2-one (50 mg) and iodoethane (10.5 μl) was stirred at 50° C. for 30 min, treated with water and extracted with AcOEt. The organic layer was dried over MgSO$_4$ and concentrated in vacuo. The residue was chromatographed on silica gel eluting with Hexane/AcOEt=2/1-1/2. The product was crystallized from AcOEt/hexane to give 1-ethyl-3-[4-(1H-pyrazolo[3,4-b]pyridin-1-yl)phenyl]-1,3-dihydro-2H-imidazo[4,5-b]pyridin-2-one (13 mg).
MS (ESI+): [M+H]$^+$357.4.
$^1$H NMR (300 MHz, DMSO-d$_6$) δ 1.31 (3H, t, J=7.2 Hz), 4.00 (2H, q, J=7.2 Hz), 7.20 (1H, dd, J=7.7, 5.1 Hz), 7.35-7.48 (1H, m), 7.64-7.77 (1H, m), 7.83-7.97 (2H, m), 7.97-8.07 (1H, m), 8.39-8.50 (3H, m), 8.53 (1H, s), 8.73 (1H, dd, J=4.5, 1.5 Hz).

Example 13

3-[1-(1H-benzimidazol-2-yl)-2,3-dihydro-1H-indol-5-yl]-1-ethyl-1,3-dihydro-2H-imidazo[4,5-b]pyridin-2-one

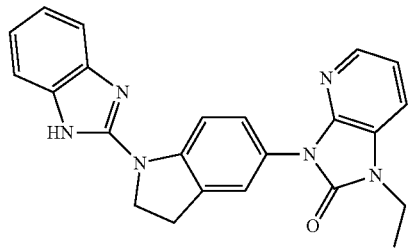 [SMILES: CCn1c(=O)n(-c2ccc3c(c2)CCN3c2nc3ccccc3[nH]2)c2ncccc21]

13a) tert-butyl 5-nitro-2,3-dihydro-1H-indole-1-carboxylate

To a stirred mixture of 5-nitroindoline (5.0 g) and Boc$_2$O (7.07 mL) in THF (100 mL) was added DMAP (0.5 g) at room temperature. The mixture was stirred at 60° C. for 3 h. The mixture was quenched with water, treated with sat. NaHCO$_3$aq. and extracted with EtOAc. The organic layer was dried over MgSO$_4$ and concentrated in vacuo. The residue was used for the next reaction without further purification.

13b) tert-butyl 5-amino-2,3-dihydro-1H-indole-1-carboxylate

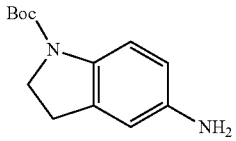

Under H$_2$ atmosphere, a mixture of tert-butyl 5-nitro-2,3-dihydro-1H-indole-1-carboxylate, obtained from example 13a), and 10% Pd—C (5 g) in EtOH (100 mL) was stirred at room temperature for 12 h, filtered and concentrated in vacuo to give tert-butyl 5-amino-2,3-dihydro-1H-indole-1-carboxylate (6.80 g).

$^1$H NMR (300 MHz, DMSO-d$_6$) δ 1.47 (9H, s), 2.91 (2H, t, J=8.5 Hz), 3.79 (2H, t, J=8.5 Hz), 4.73 (2H, brs), 6.33 (1H, dd, J=8.7, 2.3 Hz), 6.43 (1H, s), 6.95-7.53 (1H, m).

13c) tert-butyl 5-(2-oxo-1,2-dihydro-3H-imidazo[4,5-b]pyridin-3-yl)-2,3-dihydro-1H-indole-1-carboxylate

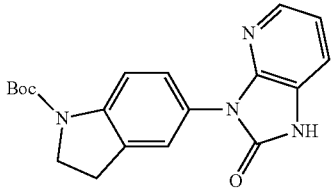 [SMILES: CC(C)(C)OC(=O)N1CCc2cc(-n3c(=O)[nH]c4cccnc43)ccc21]

A mixture of tert-butyl 5-amino-2,3-dihydro-1H-indole-1-carboxylate (4.10 g), tert-butyl 2-chloropyridin-3-ylcarbamate (4.20 g), Pd$_2$(dba)$_3$ (0.48 g), Xantphos (0.608 g), sodium tert-butoxide (2.52 g) in 2-propanol (64 ml) and toluene (12 mL) was stirred at 90° C. for 40 h, and treated with water and extracted with EtOAc. The organic layer was dried over MgSO$_4$ and concentrated in vacuo. The residue was suspended in CH$_3$CN and the precipitate was collected by filtration to give tert-butyl 5-(2-oxo-1,2-dihydro-3H-imidazo[4,5-b]pyridin-3-yl)-2,3-dihydro-1H-indole-1-carboxylate (1.64 g). The filtrate was evaporated and then the residue was chromatographed on silica gel eluting with AcOEt/Hexane=2/1 to afford second crop (1.4 g).

MS (ESI+): [M+H]$^+$353.3.

13d) tert-butyl 5-(1-ethyl-2-oxo-1,2-dihydro-3H-imidazo[4,5-b]pyridin-3-yl)-2,3-dihydro-1H-indole-1-carboxylate

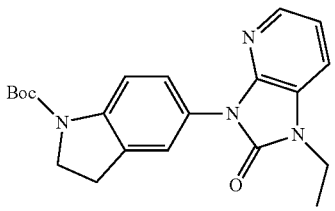 [SMILES: CCn1c(=O)n(-c2ccc3c(c2)CCN3C(=O)OC(C)(C)C)c2ncccc21]

A mixture of tert-butyl 5-(2-oxo-1,2-dihydro-3H-imidazo[4,5-b]pyridin-3-yl)-2,3-dihydro-1H-indole-1-carboxylate (900 mg), ethyl iodide (418 mg) and cesium carbonate (1.25 g) in DMF (10 mL) was stirred at 50° C. for 12 h, treated with water and extracted with EtOAc. The organic layer was dried over MgSO$_4$ and concentrated in vacuo. The residue was chromatographed on silica gel eluting with AcOEt/Hexane to give tert-butyl 5-(1-ethyl-2-oxo-1,2-dihydro-3H-imidazo[4,5-b]pyridin-3-yl)-2,3-dihydro-1H-indole-1-carboxylate (830 mg) as an amorphous solid.

MS (ESI+): [M+H]$^+$381.2.

13e) 3-(2,3-dihydro-1H-indol-5-yl)-1-ethyl-1,3-dihydro-2H-imidazo[4,5-b]pyridin-2-one

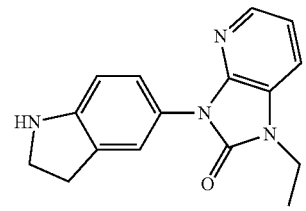 [SMILES: CCn1c(=O)n(-c2ccc3c(c2)CCN3)c2ncccc21]

To a stirred solution of tert-butyl 5-(1-ethyl-2-oxo-1,2-dihydro-3H-imidazo[4,5-b]pyridin-3-yl)-2,3-dihydro-1H-indole-1-carboxylate (100 mg) in EtOAc (2 mL) was added 4N HCl in AcOEt solution (2.0 mL). The mixture was stirred at 50° C. for 2 h and evaporated. The residue was treated with sat.NaHCO$_3$aq. and extracted with AcOEt. The organic layer was dried over MgSO$_4$ and concentrated in vacuo to give 3-(2,3-dihydro-1H-indol-5-yl)-1-ethyl-1,3-dihydro-2H-imidazo[4,5-b]pyridin-2-one. This residue was used for the next reaction.

MS (ESI+): [M+H]$^+$281.2.

13f) 3-[1-(1H-benzimidazol-2-yl)-2,3-dihydro-1H-indol-5-yl]-1-ethyl-1,3-dihydro-2H-imidazo[4,5-b]pyridin-2-one

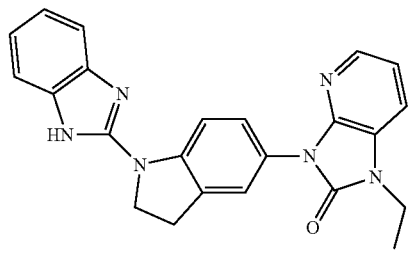 [SMILES: CCn1c(=O)n(-c2ccc3c(c2)CCN3c2nc3ccccc3[nH]2)c2ncccc21]

A mixture of 3-(2,3-dihydro-1H-indol-5-yl)-1-ethyl-1,3-dihydro-2H-imidazo[4,5-b]pyridin-2-one obtained from example 13e) and 2-chloro-1-{[2-(trimethylsilyl)ethoxy]methyl}-1H-benzimidazole (108 mg) in NMP (2.0 ml) was stirred at 120° C. for 12 h, treated with sat.NaHCO$_3$aq. and extracted with AcOEt. The organic layer was dried over MgSO$_4$ and concentrated in vacuo. The residue was purified by preparative HPLC and crystallized from AcOEt/Hexane to give 3-[1-(1H-benzimidazol-2-yl)-2,3-dihydro-1H-indol-5-yl]-1-ethyl-1,3-dihydro-2H-imidazo[4,5-b]pyridin-2-one (12 mg).

MS (ESI+): [M+H]$^+$397.4.

¹H NMR (300 MHz, DMSO-d₆) δ 1.29 (3H, t, J=7.2 Hz), 3.33-3.39 (2H, m), 3.92-4.03 (2H, m), 4.24 (2H, t, J=8.7 Hz), 6.96-7.20 (3H, m), 7.30-7.36 (1H, m), 7.38-7.48 (3H, m), 7.56-7.70 (1H, m), 7.91-8.03 (1H, m), 8.36 (1H, d, J=8.7 Hz), 11.72 (1H, s).

Example 14

9-[4-(1,3-benzoxazol-2-ylamino)phenyl]-7,9-dihydro-8H-purin-8-one

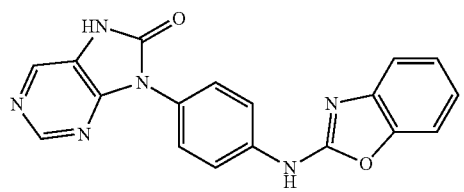 [SMILES: O=c1[nH]c2cncnc2n1-c1ccc(Nc2nc3ccccc3o2)cc1]

14a) 4-chloro-5-nitropyrimidine

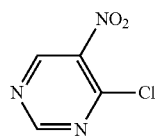

The mixture of 5-nitropyrimidin-4-ol (1.04 g) and phosphorus oxychloride (5.66 g) in acetonitrile (10 mL) was stirred at reflux for 2 h. After this time, the reaction mixture was cooled to ambient temperature, diluted with ethyl acetate (50 mL), and filtered and the filtrate was concentrated under reduced pressure. The residue obtained was diluted with ethyl acetate (100 mL), washed with saturated aqueous sodium bicarbonate (50 mL) then brine (50 mL), and filtered and the filtrate was concentrated under reduced pressure. The residue obtained was purified by chromatography (silica, heptane to 1:3 ethyl acetate/heptane) to afford 4-chloro-5-nitropyrimidine (383 mg, 33%) as a colorless oil.

¹H NMR (300 MHz, CDCl₃) δ 9.19 (s, 1H), 9.25 (s, 1H).

14b) N-(5-nitropyrimidin-4-yl)benzene-1,4-diamine

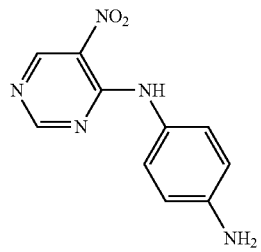 [SMILES: Nc1ccc(Nc2ncncc2[N+](=O)[O-])cc1]

A mixture of 4-chloro-5-nitropyrimidine (380 mg) and benzene-1,4-diamine (257 mg) in N-methylpyrrolidone (5 mL) was stirred overnight at ambient temperature. After this time, the reaction mixture was diluted with water (50 mL) and extracted with ethyl acetate (3×50 mL). The combined organic layers were washed with saturated sodium bicarbonate (50 ml) then brine (50 mL), dried over sodium sulfate, and filtered and the filtrate was concentrated under reduced pressure. The residue obtained was purified by chromatography (silica, methylene chloride to 3:97 methanol/methylene chloride) to afford N-(5-nitropyrimidin-4-yl)benzene-1,4-diamine (260 mg) as a brown oil.

MS (ESI+): [M+H]⁺232.

¹H NMR (300 MHz, CDCl₃) δ 3.79 (br s, 2H), 6.74 (d, J=8.7 Hz, 2H), 7.32 (d, J=8.4 Hz, 2H), 8.74 (s, 1H), 9.28 (s, 1H), 9.92 (br s, 1H).

14c) N-1,3-benzoxazol-2-yl-N'-(5-nitropyrimidin-4-yl)benzene-1,4-diamine

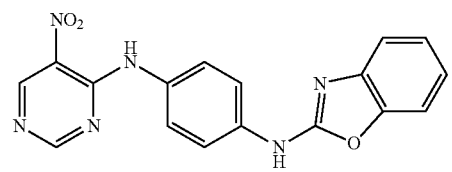 [SMILES: O=[N+]([O-])c1cncnc1Nc1ccc(Nc2nc3ccccc3o2)cc1]

A mixture of N-(5-nitropyrimidin-4-yl)benzene-1,4-diamine (256 mg), 2-chloro-1,3-benzoxazole (110 mg) in N-methylpyrrolidone (3 mL) was stirred at 120° C. for 45 min. After this time, the reaction mixture was cooled to ambient temperature, diluted with water (50 mL) and extracted with ethyl acetate (100 mL). The organic layer was washed with water (50 mL) then brine (50 mL), dried over sodium sulfate, and filtered and the filtrate was concentrated under reduced pressure. The residue obtained was purified by chromatography (silica, methylene chloride to 1:3 ethyl acetate/methylene chloride) to afford N-1,3-benzoxazol-2-yl-N'-(5-nitropyrimidin-4-yl)benzene-1,4-diamine (107 mg) as a red solid.

MS (ESI+): [M+H]⁺349.

14d) N⁴-[4-(1,3-benzoxazol-2-ylamino)phenyl]pyrimidine-4,5-diamine

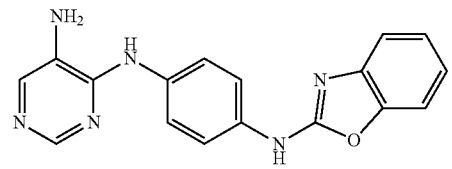

A mixture of N-1,3-benzoxazol-2-yl-N'-(5-nitropyrimidin-4-yl)benzene-1,4-diamine (54 mg) and 5% palladium on carbon (22 mg, 50% water by weight) in methanol (5 mL) was stirred under an atmosphere of hydrogen (balloon) for 1 h. After this time, the reaction mixture was filtered and the filtrate was concentrated under reduced pressure to afford N⁴-[4-(1,3-benzoxazol-2-ylamino)phenyl]pyrimidine-4,5-diamine (49 mg) as a brown solid.

MS (ESI+): [M+11]⁺319.

¹H NMR (300 MHz, DMSO-d₆) δ 5.14 (br s, 2H), 7.11 (td, J=7.5, 1.2 Hz, 1H), 7.21 (td, J=7.5, 0.9 Hz, 1H), 7.43 (dd,

14e) 9-[4-(1,3-benzoxazol-2-ylamino)phenyl]-7,9-dihydro-8H-purin-8-one

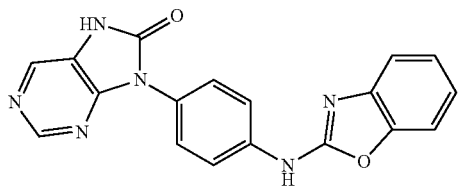 [SMILES: O=c1[nH]c2cncnc2n1-c1ccc(Nc2nc3ccccc3o2)cc1]

A mixture of $N^4$-[4-(1,3-benzoxazol-2-ylamino)phenyl]pyrimidine-4,5-diamine (55 mg) and bis(2,5-dioxopyrrolidin-1-yl) carbonate (53 mg) in DMF (5 mL) was stirred overnight at 80° C. then at 95° C. for 3 h. After this time, the reaction mixture was cooled to ambient temperature, diluted with water (50 mL) and extracted with ethyl acetate (100 ml). The organic layer was washed with water (50 ml), 5% aqueous lithium chloride (50 mL) then brine (50 ml), dried over sodium sulfate, and filtered and the filtrate was concentrated under reduced pressure. The residue obtained was purified by chromatography (silica, methylene chloride to 1:9 methanol/methylene chloride), solvent exchanged with acetonitrile and freeze dried from acetonitrile/water to afford 9-[4-(1,3-benzoxazol-2-ylamino)phenyl]-7,9-dihydro-8H-purin-8-one (19 mg) as off-white crystals.

MS (ESI+): [M+H]$^+$345.

$^1$H NMR (500 MHz, DMSO-d$_6$) δ 7.16 (td, J=7.5, 1.0 Hz, 1H), 7.25 (td, J=7.5, 1.0 Hz, 1H), 7.48 (d, J=7.0 Hz, 1H), 7.52 (d, J=7.5 Hz, 1H), 7.62 (d, J=9.0 Hz, 2H), 7.91 (d, J=9.0 Hz, 2H), 8.33 (s, 1H), 8.56 (s, 1H), 10.84 (br s, 1H), 11.62 (br s, 1H).

Example 19

1-ethyl-3-{4-[(1-methyl-1H-benzimidazol-2-yl)oxy]phenyl}-1,3-dihydro-2H-imidazo[4,5-b]pyridin-2-one

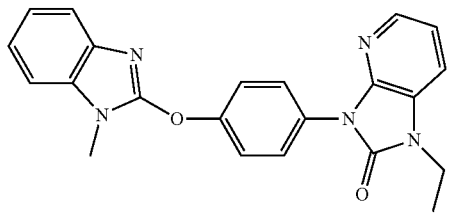 [SMILES: CCn1c(=O)n(-c2ccc(Oc3nc4ccccc4n3C)cc2)c2ncccc21]

2-Chloro-1-methyl-1H-benzimidazole (500 mg) was added to a solution of 1-ethyl-3-(4-hydroxyphenyl)-1,3-dihydro-2H-imidazo[4,5-b]pyridin-2-one (789 mg) and NaH (132 mg) in DMF (10 ml) at room temperature. The mixture was heated at 150° C. for 1 h under microwave irradiation. The reaction mixture was diluted with MeOH and concentrated in vacuo. The residue was purified by column chromatography (NH silica gel, eluted with 0%-50% EtOAc in hexane) to give 1-ethyl-3-{4-[(1-methyl-1H-benzimidazol-2-yl)oxy]phenyl}-1,3-dihydro-2H-imidazo[4,5-b]pyridin-2-one (950 mg) as white crystals.

MS (API+): [M+H]$^+$386.2.

$^1$H NMR (300 MHz, DMSO-d$_6$) δ 1.17-1.45 (3H, m), 3.76 (3H, s), 3.92-4.06 (2H, m), 7.08-7.27 (3H, m), 7.39-7.53 (2H, m), 7.56-7.64 (2H, m), 7.65-7.73 (1H, m), 7.73-7.84 (2H, m), 7.96-8.08 (1H, m).

Anal. Calcd for $C_{22}H_{19}N_5O_2$: C, 68.56; H, 4.97; N, 18.17. Found: C, 68.40; H, 5.00; N, 17.94.

Mp: 184-186° C.

Example 24

3-[4-(2,3-dihydro-1H-imidazo[1,2-a]benzimidazol-1-yl)phenyl]-1-ethyl-1,3-dihydro-2H-imidazo[4,5-b]pyridin-2-one

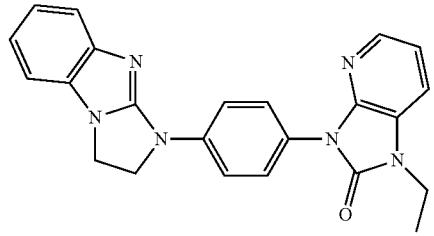 [SMILES: CCn1c(=O)n(-c2ccc(N3CCn4c3nc3ccccc34)cc2)c2ncccc21]

To a mixture of 3-[4-(2,3-dihydro-1H-imidazo[1,2-a]benzimidazol-1-yl)phenyl]-1,3-dihydro-2H-imidazo[4,5-b]pyridin-2-one (150 mg) and ethyl iodide (0.1 mL) in DMF (4.0 mL) was added sodium hydride (62 mg) (60% in mineral oil) at 0° C. The mixture was stirred at 0° C. for 1 h, and then H$_2$O was added. The precipitate was collected and washed with MeOH to give 3-[4-(2,3-dihydro-1H-imidazo[1,2-a]benzimidazol-1-yl)phenyl]-1-ethyl-1,3-dihydro-2H-imidazo[4,5-b]pyridin-2-one (23 mg) as white powder.

MS (API+): [M+H]$^+$397.1.

$^1$H NMR (300 MHz, DMSO-d$_6$) δ 1.30 (3H, t, J=7.2 Hz), 3.98 (2H, q, J=7.2 Hz), 4.34-4.46 (2H, m), 4.55-4.67 (2H, m), 7.03-7.11 (2H, m), 7.13-7.21 (1H, m), 7.27-7.35 (1H, m), 7.40-7.49 (1H, m), 7.62-7.71 (3H, m), 7.90-8.01 (3H, m).

Example 31

1-ethyl-3-[4-(imidazo[1,2-a]pyridin-2-yloxy)phenyl]-1,3-dihydro-2H-imidazo[4,5-b]pyridin-2-one

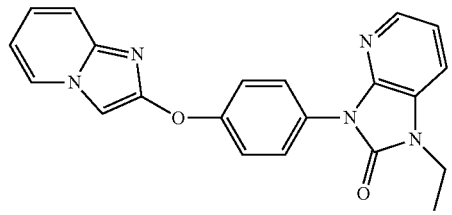 [SMILES: CCn1c(=O)n(-c2ccc(Oc3cn4ccccc4n3)cc2)c2ncccc21]

31a) 3-[4-(benzyloxy)phenyl]-1,3-dihydro-2H-imidazo[4,5-b]pyridin-2-one

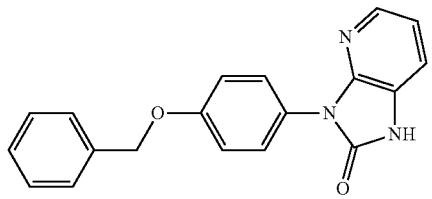 [SMILES: O=c1[nH]c2cccnc2n1-c1ccc(OCc2ccccc2)cc1]

The mixture of tert-butyl 2-chloropyridin-3-ylcarbamate (12.5 g), 4-benzyloxyaniline hydrochloride (19.3 g), 9,9-dimethyl-4,5-bis(diphenylphosphino)xanthene (2.53 g), Pd$_2$(dba)$_3$ (2.0 g) and sodium tert-butoxide (12.6 g) in toluene (160 ml)-2-propanol (40.0 mL) was stirred at 100° C. under Ar overnight. The reaction mixture was concentrated in vacuo. The residue was purified by column chromatography (silica gel, eluted with 0%-100% EtOAc in hexane) to give 3-[4-(benzyloxy)phenyl]-1,3-dihydro-2H-imidazo[4,5-b]pyridin-2-one (12 g) as a light brown solid.

MS (API+): [M+H]$^+$318.1.

$^1$H NMR (300 MHz, DMSO-d$_6$) δ 5.18 (2H, s), 7.02-7.22 (3H, m), 7.29-7.59 (8H, m), 7.86-7.94 (1H, m), 11.11-11.64 (1H, m).

31b) 3-[4-(benzyloxy)phenyl]-1-ethyl-1,3-dihydro-2H-imidazo[4,5-b]pyridin-2-one

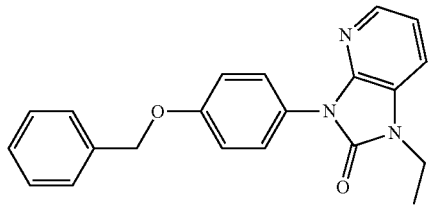 [SMILES: CCn1c(=O)n(-c2ccc(OCc3ccccc3)cc2)c2ncccc21]

The mixture of 3-[4-(benzyloxy)phenyl]-1,3-dihydro-2H-imidazo[4,5-b]pyridin-2-one (2.50 g), sodium hydride (380 mg) and iodoethane (1.60 mL) in DMF (40 mL) was stirred at 20° C. under a dry atmosphere (CaCl$_2$ tube) for 1 h. The mixture was concentrated under reduced pressure. The residue was purified by column chromatography (NH silica gel, eluted with 0%-30% EtOAc in hexane) to give 3-[4-(benzyloxy)phenyl]-1-ethyl-1,3-dihydro-2H-imidazo[4,5-b]pyridin-2-one (2.70 g) as a colorless solid.

MS (API+): [M+H]$^+$346.4.

$^1$H NMR (300 MHz, CDCl$_3$) δ 1.40 (3H, t, J=7.2 Hz), 4.02 (2H, q, J=7.2 Hz), 5.11 (2H, s), 7.01-7.17 (3H, m), 7.22-7.29 (1H, m), 7.29-7.49 (5H, m), 7.53-7.61 (2H, m), 8.00-8.09 (1H, m).

31c) 1-ethyl-3-(4-hydroxyphenyl)-1,3-dihydro-2H-imidazo[4,5-b]pyridin-2-one

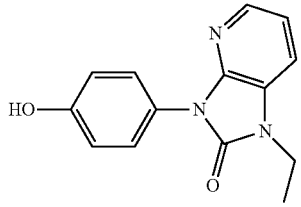 [SMILES: CCn1c(=O)n(-c2ccc(O)cc2)c2ncccc21]

A mixture of 3-[4-(benzyloxy)phenyl]-1-ethyl-1,3-dihydro-2H-imidazo[4,5-b]pyridin-2-one (2.70 g) and 10% palladium-carbon (0.83 g) in EtOH (250 ml) was hydrogenated under balloon pressure at room temperature for 3 h. The catalyst was removed by filtration and the filtrate was concentrated in vacuo to give 1-ethyl-3-(4-hydroxyphenyl)-1,3-dihydro-2H-imidazo[4,5-b]pyridin-2-one (1.42 g) as a white solid.

MS (API+): [M+H]$^+$256.1.

$^1$H NMR (300 MHz, DMSO-d$_6$) δ 1.27 (3H, t, J=7.2 Hz), 3.95 (2H, q, J=7.2 Hz), 6.84-6.95 (2H, m), 7.08-7.18 (1H, m), 7.32-7.40 (2H, m), 7.57-7.67 (1H, m), 7.89-7.99 (1H, m), 9.67-9.79 (1H, m).

31d) ethyl 2-chloroimidazo[1,2-a]pyridine-3-carboxylate

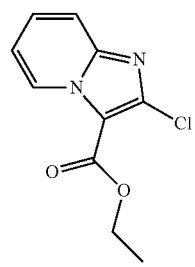

n-Butyllithium (1.6M in hexane, 45.1 mL) was added to a solution of 2-chloroimidazo[1,2-a]pyridine (10 g) in THF (120 mL) at −78° C. After stirring for 30 min, ethyl chlorocarbonate (7.82 g) in THF (10 ml) was added to the mixture at the same temperature and stirred for 1 h and then 10 h at room temperature. The mixture was quenched with water, and extracted with ethyl acetate, and the extract was washed with brine, and dried over magnesium sulfate. The residue was purified by column chromatography (silica gel, eluted with 10%-50% EtOAc in hexane) to give ethyl 2-chloroimidazo[1,2-a]pyridine-3-carboxylate (13.20 g) as an off-white solid.

MS (API+): [M+H]$^+$ 225.0.

$^1$H NMR (300 MHz, DMSO-d$_6$) δ 1.37 (3 H, m), 4.40 (2 H, m), 7.31 (1 H, s), 7.66 (1 H, s), 7.72-7.86 (1 H, m), 9.17-9.32 (1 H, m).

31e) 1-ethyl-3-[4-(imidazo[1,2-a]pyridin-2-yloxy)phenyl]-1,3-dihydro-2H-imidazo[4,5-b]pyridin-2-one

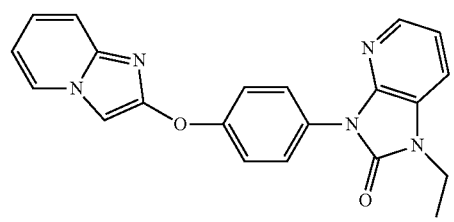 [SMILES: CCn1c(=O)n(-c2ccc(Oc3cn4ccccc4n3)cc2)c2ncccc21]

The mixture of ethyl 2-chloroimidazo[1,2-a]pyridine-3-carboxylate (220 mg), NaH (70 mg) and 1-ethyl-3-(4-hydroxyphenyl)-1,3-dihydro-2H-imidazo[4,5-b]pyridin-2-one (255 mg) in DMF (2 mL) was stirred at 100° C. under a dry atmosphere (CaCl$_2$ tube) for 1 h. The mixture was diluted with MeOH and concentrated under reduced pressure. The residue was purified by column chromatography (NH silica gel, eluted with 0%-30% EtOAc in hexane) to give 1-ethyl-3-[4-(imidazo[1,2-a]pyridin-2-yloxy)phenyl]-1,3-dihydro-2H-imidazo[4,5-b]pyridin-2-one (40 mg) as white crystals.

MS (API+): [M+H]$^+$372.4.

$^1$H NMR (300 MHz, DMSO-d$_6$) δ 1.23-1.36 (3H, m), 3.92-4.06 (2H, m), 6.90-7.00 (1H, m), 7.11-7.23 (1H, m), 7.23-7.41 (3H, m), 7.44-7.54 (1H, m), 7.60-7.75 (4H, m), 7.94-8.10 (1H, m), 8.47-8.60 (1H, m).

Example 39

1-ethyl-3-(4-{[1-(2-hydroxyethyl)-1H-benzimidazol-2-yl]oxy}phenyl)-1,3-dihydro-2H-imidazo[4,5-b]pyridin-2-one

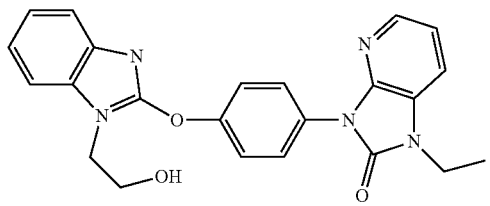

39a) ethyl [2-[4-(1-ethyl-2-oxo-1,2-dihydro-3H-imidazo[4,5-b]pyridin-3-yl)phenoxy]-1H-benzimidazol-1-yl]acetate

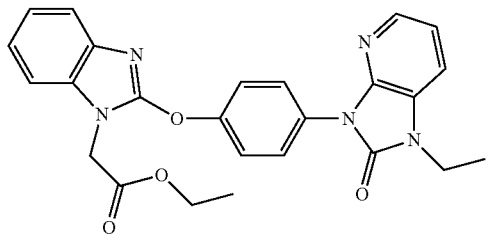 [SMILES: CCOC(=O)Cn1c(Oc2ccc(-n3c(=O)n(CC)c4cccnc43)cc2)nc2ccccc21]

Ethyl bromoacetate (0.240 mL) was added to a solution of 3-[4-(1H-benzimidazol-2-yloxy)phenyl]-1-ethyl-1,3-dihydro-2H-imidazo[4,5-b]pyridin-2-one (400 mg) and sodium hydride (86 mg) in DMF (2 mL) at room temperature. The mixture was stirred at room temperature under a dry atmosphere (CaCl$_2$ tube) for 2 h. The reaction mixture was diluted with MeOH (5 mL), and concentrated under reduced pressure. The residue was purified by column chromatography (silica gel, eluted with 0%-50% EtOAc in hexane) to give ethyl {2-[4-(1-ethyl-2-oxo-1,2-dihydro-3H-imidazo[4,5-b]pyridin-3-yl)phenoxy]-1H-benzimidazol-1-yl}acetate (480 mg) as off-white crystals.

MS (API+): [M+H]$^+$458.2.

$^1$H NMR (300 MHz, DMSO-d$_6$) δ 1.24 (3H, t, J=7.0 Hz), 1.30 (3H, t, J=7.2 Hz), 3.99 (2H, q, J=7.2 Hz), 4.22 (2H, q, J=7.0 Hz), 5.18-5.28 (2H, m), 7.11-7.25 (3H, m), 7.42-7.60 (4H, m), 7.65-7.72 (1H, m), 7.74-7.83 (2H, m), 7.96-8.05 (1H, m).

39b) 1-ethyl-3-(4-{[1-(2-hydroxyethyl)-1H-benzimidazol-2-yl]oxy}phenyl)-1,3-dihydro-2H-imidazo[4,5-b]pyridin-2-one

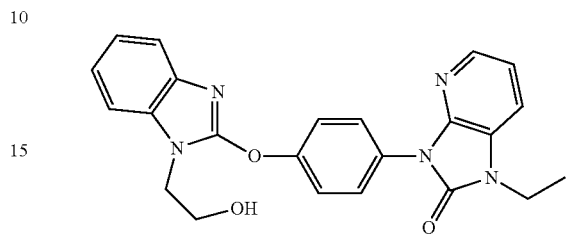

Lithium aluminum hydride (33.2 mg) was added to a solution of ethyl {2-[4-(1-ethyl-2-oxo-1,2-dihydro-3H-imidazo[4,5-b]pyridin-3-yl)phenoxy]-1H-benzimidazol-1-yl}acetate (200 mg) in THF (4 mL) at 0° C. The mixture was stirred at room temperature under a dry atmosphere (CaCl$_2$ tube) for 30 min. The mixture was quenched with EtOAc and concentrated in vacuo. The residue was purified by column chromatography (silica gel, eluted with 10%-50% EtOAc in hexane) to give 1-ethyl-3-(4-{[1-(2-hydroxyethyl)-1H-benzimidazol-2-yl]oxy}phenyl)-1,3-dihydro-2H-imidazo[4,5-b]pyridin-2-one (100 mg) as colorless crystals.

MS (API+): [M+H]$^+$416.5.

$^1$H NMR (300 MHz, DMSO-d$_6$) δ 1.31 (3H, t, J=7.0 Hz), 3.75-3.88 (2H, m), 3.99 (2H, q, J=7.0 Hz), 4.23-4.37 (2H, m), 4.98-5.07 (1H, m), 7.09-7.28 (3H, m), 7.39-7.65 (4H, m), 7.65-7.87 (3H, m), 7.95-8.08 (1H, m).

Example 40

1-ethyl-3-(4-{[1-(2-hydroxy-2-methylpropyl)-1H-benzimidazol-2-yl]oxy}phenyl)-1,3-dihydro-2H-imidazo[4,5-b]pyridin-2-one

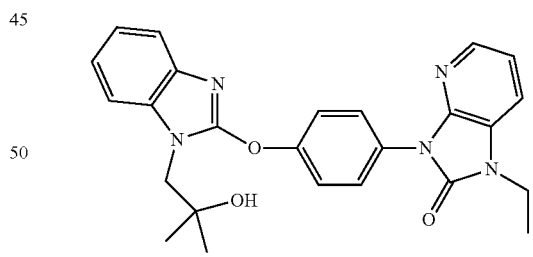

Bromomethylmagnesium (3M in ether, 1.924 mL) was added to a solution of ethyl {2-[4-(1-ethyl-2-oxo-1,2-dihydro-3H-imidazo[4,5-b]pyridin-3-yl)phenoxy]-1H-benzimidazol-1-yl}acetate (220 mg) in THF (40 mL) at 0° C. The mixture was stirred at room temperature under a dry atmosphere (CaCl$_2$ tube) for 3 h. The reaction mixture was concentrated under reduced pressure. The residue was purified by column chromatography (silica gel, eluted with 0%-50% EtOAc in hexane) to give 1-ethyl-3-(4-{[1-(2-hydroxy-2-methylpropyl)-1H-benzimidazol-2-yl]oxy}phenyl)-1,3-dihydro-2H-imidazo[4,5-b]pyridin-2-one (130 mg) as white crystals.

MS (API+): [M+H]+444.4.

$^1$H NMR (300 MHz, DMSO-d$_6$) δ 1.24 (6H, s), 1.31 (3H, t, J=7.2 Hz), 3.99 (2H, q, J=7.2 Hz), 4.11 (2H, s), 4.79 (1H, s), 7.07-7.26 (3H, m), 7.37-7.46 (1H, m), 7.50-7.64 (3H, m), 7.65-7.81 (3H, m), 7.96-8.05 (1H, m).

Example 48

1-ethyl-3-[1-(1-methyl-1H-benzimidazol-2-yl)-2,3-dihydro-1H-indol-5-yl]-1,3-dihydro-2H-imidazo[4,5-b]pyridin-2-one

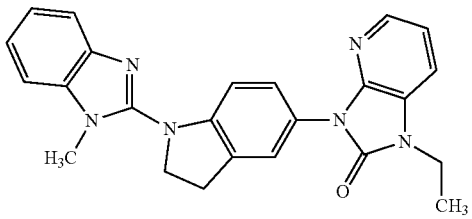 [SMILES: CCn1c(=O)n(-c2ccc3c(c2)CCN3c2nc3ccccc3n2C)c2ncccc21]

A mixture of 3-(2,3-dihydro-1H-indol-5-yl)-1-ethyl-1,3-dihydro-2H-imidazo[4,5-b]pyridin-2-one (100 mg) and 2-chloro-1-{[2-(trimethylsilyl)ethoxy]methyl}-1H-benzimidazole (101 mg) in NMP (2 mL) was stirred at 120° C. for 10 h, treated with saturated NaHCO$_3$ solution and extracted with AcOEt. The organic layer was dried over MgSO$_4$ and concentrated in vacuo. The residue was dissolved in DMF (2 mL), and then iodomethane (0.022 mL) and Cs$_2$CO$_3$ (0.176 g) were added. The mixture was stirred at room temperature for 3 h, treated with water and extracted with AcOEt. The organic layer was dried over MgSO$_4$ and concentrated in vacuo. The residue was suspended in CH$_3$CN and the precipitate was filtered off. The residue was purified by prep. HPLC, and then chromatographed on silica gel eluting with AcOEt/Hexane. Crystallization from AcOEt/Hexane gave the title compound (12 mg).

MS (API+): [M+H]+411.4.

$^1$H NMR (300 MHz, DMSO-d$_6$) δ 1.29 (3H, t, J=7.0 Hz), 3.26 (2H, t, J=8.1 Hz), 3.77 (3H, s), 3.96 (2H, q, J=6.8 Hz), 4.20 (2H, t, J=8.5 Hz), 7.06-7.25 (4H, m), 7.27-7.36 (1H, m), 7.43-7.54 (3H, m), 7.59-7.71 (1H, m), 7.87-8.05 (1H, m).

Example 62

3-[4-(1H-benzimidazol-2-yloxy)phenyl]-7-methyl-1,3-dihydro-2H-imidazo[4,5-b]pyridin-2-one dihydrochloride

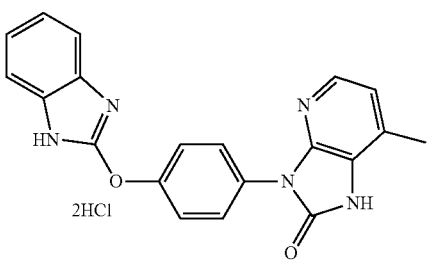 [SMILES: Cc1ccnc2c1[nH]c(=O)n2-c1ccc(Oc2nc3ccccc3[nH]2)cc1]

62a) tert-butyl {4-[(1-{[2-(trimethylsilyl)ethoxy]methyl}-1H-benzimidazol-2-yl)oxy]phenyl}carbamate

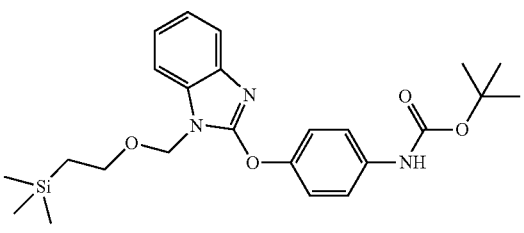 [SMILES: CC(C)(C)OC(=O)Nc1ccc(Oc2nc3ccccc3n2COCC[Si](C)(C)C)cc1]

A mixture of 2-chloro-1-{[2-(trimethylsilyl)ethoxy]methyl}-1H-benzimidazole (8.7 g), tert-butyl 4-hydroxyphenylcarbamate (6.4 g) and cesium carbonate (20 g) in DMF (60 mL) was stirred at 60° C. for 24 h. After cooling to room temperature, to the mixture was added SiO$_2$, the mixture was evaporated, and then the residue was purified by column chromatography (silica gel, eluted with 0%-50% EtOAc in hexane) to give tert-butyl {4-[(1-{[2-(trimethylsilyl)ethoxy]methyl}-1H-benzimidazol-2-yl)oxy]phenyl}carbamate (14 g) as brown oil.

MS (API+): [M+H]+456.2.

62b) 4-[(1-{[2-(trimethylsilyl)ethoxy]methyl}-1H-benzimidazol-2-yl)oxy]aniline

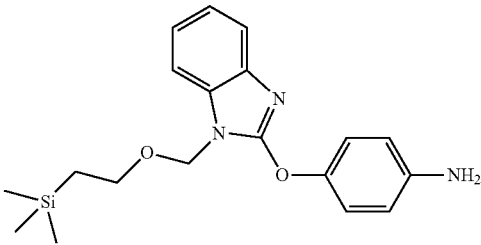 [SMILES: C[Si](C)(C)CCOCn1c(Oc2ccc(N)cc2)nc2ccccc21]

A mixture of tert-butyl {4-[(1-{[2-(trimethylsilyl)ethoxy]methyl}-1H-benzimidazol-2-yl)oxy]phenyl}carbamate (14 g) and 4N HCl/AcOEt (30 mL) in EtOAc (30 mL) was stirred at room temperature overnight. The mixture was neutralized with 1N NaOHaq., and extracted with AcOEt. The organic layer was dried over MgSO$_4$, and concentrated in vacuo. The residue was purified by column chromatography (silica gel, eluted with 0%-100% EtOAc in hexane) to give 4-[(1-{[2-(trimethylsilyl)ethoxy]methyl}-1H-benzimidazol-2-yl)oxy]aniline (5.4 g) as an orange solid.

MS (API+): [M+H]+356.2.

62c) 2-chloro-4-methylpyridin-3-amine

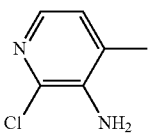

A mixture of 4-methylpyridin-3-amine (0.62 g), 12N hydrogen chloride (3.8 mL) and 30% hydrogen peroxide (0.75 mL) was stirred at 0° C. to room temperature for 1 h. The mixture was neutralized with K$_2$CO$_3$, and the mixture was extracted with AcOEt. The organic layer was dried over MgSO$_4$, and concentrated in vacuo to give 2-chloro-4-methylpyridin-3-amine (0.75 g) as an orange solid.

MS (API+): [M+H]$^+$ 143.1.

62d) tert-butyl (2-chloro-4-methylpyridin-3-yl)carbamate

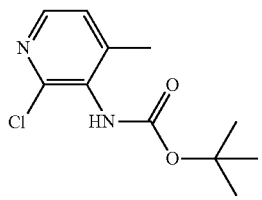 [SMILES: Cc1ccnc(Cl)c1NC(=O)OC(C)(C)C]

To a mixture of 2-chloro-4-methylpyridin-3-amine (0.75 g) and di-tert-butyl dicarbonate (1.3 mL) in THF (10 mL) was added dropwise hexamethyldisilazane sodium salt (2M in THF, 6.1 mL) at 0° C. The mixture was stirred at 0° C. to room temperature overnight. The mixture was neutralized with 1N HClaq., and the mixture was extracted with AcOEt. The organic layer was dried over MgSO$_4$, and concentrated in vacuo to give tert-butyl (2-chloro-4-methylpyridin-3-yl)carbamate (1.2 g) as an orange solid.

$^1$H NMR (300 MHz, DMSO-d$_6$) δ 1.34 (9H, brs), 2.15 (3H, s), 7.23 (1H, d, J=4.9 Hz), 8.05 (1H, d, J=4.9 Hz), 8.79 (1H, brs).

62e) 7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one

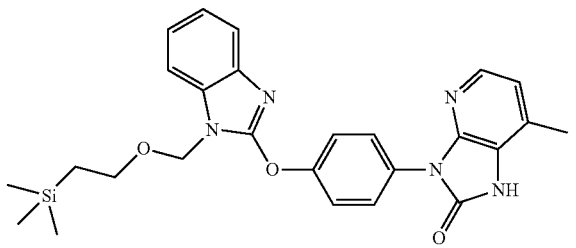

The mixture of sodium 2-methylpropan-2-olate (0.16 g), (9,9-dimethyl-9H-xanthene-4,5-diyl)bis(diphenylphosphine) (0.054 g), tert-butyl (2-chloro-4-methylpyridin-3-yl)carbamate (0.28 g), 4-[(1-{[2-(trimethylsilyl)ethoxy]methyl}-1H-benzimidazol-2-yl)oxy]aniline (0.41 g) and Pd$_2$(dba)$_3$ (0.043 g) in toluene (40 mL) and 2-propanol (10 mL) was stirred at 100° C. under N$_2$ overnight. After cooling to room temperature, the reaction mixture was concentrated in vacuo. The residue was purified by column chromatography (silica gel, eluted with 0%-100% EtOAc in hexane) to give 7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (0.21 g) as white crystals.

MS (API+): [M+H]$^+$ 488.3.

62f) 3-[4-(1H-benzimidazol-2-yloxy)phenyl]-7-methyl-1,3-dihydro-2H-imidazo[4,5-b]pyridin-2-one dihydrochloride

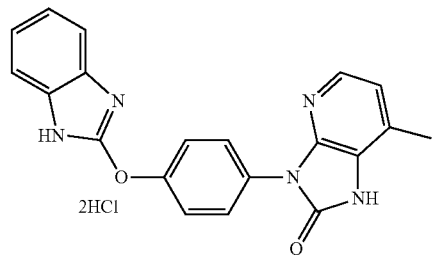 [SMILES: Cc1ccnc2c1[nH]c(=O)n2-c1ccc(Oc2nc3ccccc3[nH]2)cc1]

A mixture of 7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (0.053 g) and 2N HCl in EtOH (5.0 ml) was stirred at 60° C. for 10 h. After cooling to room temperature, the solvent was removed. The residue was recrystallized from EtOH—AcOEt to give 3-[4-(1H-benzimidazol-2-yloxy)phenyl]-7-methyl-1,3-dihydro-2H-imidazo[4,5-b]pyridin-2-one dihydrochloride (0.030 g).

MS (API+): [M+H]$^+$ 358.1.

$^1$H NMR (300 MHz, DMSO-d$_6$) δ 2.37 (3H, s), 4.57 (3H, brs), 6.97 (1H, d, J=5.3 Hz), 7.15 (2H, dd, J=6.1, 3.4 Hz), 7.40 (2H, dd, J=5.9, 3.2 Hz), 7.52-7.62 (2H, m), 7.71-7.80 (2H, m), 7.85 (1H, d, J=5.3 Hz), 11.54 (1H, s).

Example 64

3-[4-(1H-benzimidazol-2-yloxy)phenyl]-1-ethyl-7-methyl-1,3-dihydro-2H-imidazo[4,5-b]pyridin-2-one dihydrochloride

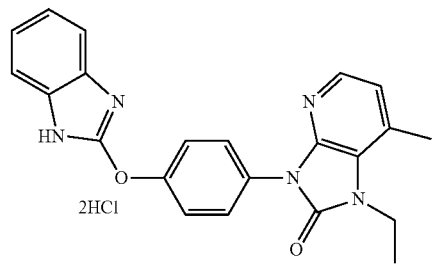 [SMILES: CCn1c(=O)n(-c2ccc(Oc3nc4ccccc4[nH]3)cc2)c2nccc(C)c21]

64a) 1-ethyl-7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one

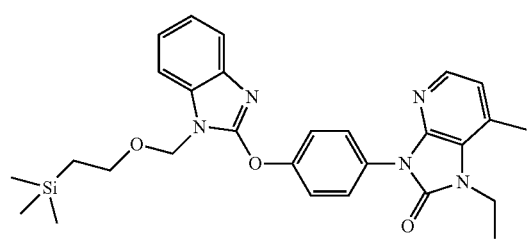

A mixture of 7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (0.15 g), iodoethane (0.027 mL) and sodium hydride (0.015 g) (60% in oil) in DMF (4.0 mL) was stirred at room temperature for 4 h. To the mixture was added H₂O, and the mixture was extracted with AcOEt. The organic layer was dried (MgSO₄) and concentrated in vacuo. The residue was purified by column chromatography (silica gel, eluted with 0%-50% EtOAc in hexane) to give 1-ethyl-7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (90 mg) as pale yellow crystals.

MS (API+): [M+H]⁺516.3.

64b) 3-[4-(1H-benzimidazol-2-yloxy)phenyl]-1-ethyl-7-methyl-1,3-dihydro-2H-imidazo[4,5-b]pyridin-2-one dihydrochloride

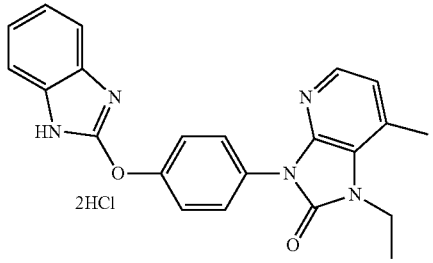 [SMILES: CCn1c(=O)n(-c2ccc(Oc3nc4ccccc4[nH]3)cc2)c2nccc(C)c21]

A mixture of 1-ethyl-7-methyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one (0.090 g) and 2N HCl in EtOH (5.0 ml) was stirred at 60° C. for 10 h. After cooling to room temperature, the solvent was removed. The residue was recrystallized from EtOH—AcOEt to give 3-[4-(1H-benzimidazol-2-yloxy)phenyl]-1-ethyl-7-methyl-1,3-dihydro-2H-imidazo[4,5-b]pyridin-2-one dihydrochloride (0.040 g).

MS (API+): [M+H]⁺386.2.
¹H NMR (300 MHz, DMSO-d₆) δ 1.32 (3H, t, J=7.2 Hz), 2.61 (3H, s), 4.12 (2H, q, J=7.2 Hz), 7.01 (1H, d, J=5.3 Hz), 7.20 (2H, dd, J=5.9, 3.2 Hz), 7.40-7.49 (2H, m), 7.58-7.66 (2H, m), 7.72-7.81 (2H, m), 7.87 (1H, d, J=4.9 Hz), 8.12 (3H, brs).

Example 65

1-Ethyl-3-[4-(1H-imidazo[1,2-a]benzimidazol-1-yl)phenyl]-1,3-dihydro-2H-imidazo[4,5-b]pyridin-2-one

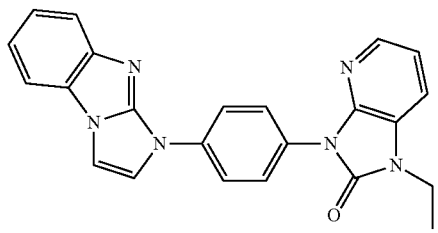 [SMILES: CCn1c(=O)n(-c2ccc(-n3ccn4c5ccccc5nc34)cc2)c2ncccc21]

65a) 3-(4-aminophenyl)-1-ethyl-1,3-dihydro-2H-imidazo[4,5-b]pyridin-2-one

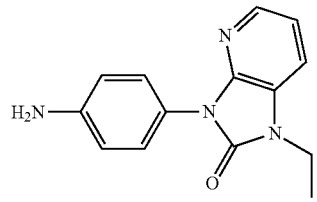 [SMILES: CCn1c(=O)n(-c2ccc(N)cc2)c2ncccc21]

The mixture of tert-butyl 2-chloropyridin-3-ylcarbamate (10.0 g), 4-nitroaniline (8.0 g), 9,9-dimethyl-4,5-bis(diphenylphosphino)xanthene (2.53 g), Pd₂(dba)₃ (2 g) and sodium tert-butoxide (12.5 g) in toluene (160 mL)-2-propanol (40.0 mL) was stirred at 100° C. under Ar overnight. The reaction mixture was concentrated in vacuo. The residue was purified by column chromatography (silica gel, eluted with 0%-100% EtOAc in hexane) to give 3-(4-nitrophenyl)-1,3-dihydro-2H-imidazo[4,5-b]pyridin-2-one (4.0 g) as a light brown solid. A mixture of 3-(4-nitrophenyl)-1,3-dihydro-2H-imidazo[4,5-b]pyridin-2-one (3.50 g), sodium hydride (0.400 g) and iodoethane (2.0 mL) in DMF (40 mL) was stirred at 20° C. under a dry atmosphere (CaCl₂ tube) for 1 h. The mixture was concentrated under reduced pressure. The residue was purified by column chromatography (NH silica gel, eluted with 0%-30% EtOAc in hexane) to give 1-ethyl-3-(4-nitrophenyl)-1,3-dihydro-2H-imidazo[4,5-b]pyridin-2-one (2.70 g) as a brown solid. A mixture of 1-ethyl-3-(4-nitrophenyl)-1,3-dihydro-2H-imidazo[4,5-b]pyridin-2-one (2.70 g) and 10% palladium-carbon (0.832 g) in EtOH (250 mL) was hydrogenated under balloon pressure at room temperature for 3 h. The catalyst was removed by filtration and the filtrate was concentrated in vacuo to give 3-(4-aminophenyl)-1-ethyl-1,3-dihydro-2H-imidazo[4,5-b]pyridin-2-one (1.00 g) as a brown solid.

MS (API+): [M+H]⁺255.1.

65b)
2-chloro-1-(2,2-diethoxyethyl)-1H-benzimidazole

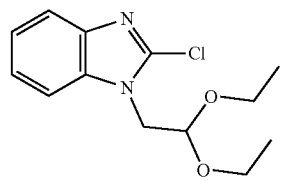 [SMILES: CCOC(Cn1c(Cl)nc2ccccc21)OCC]

A mixture of 2-chloro-1H-benzimidazole (6.10 g), bromoacetaldehyde diethyl acetal (7.22 mL), EtOH (70 mL), and 8 M NaOH aqueous solution (10 mL) was refluxed for 3 d. The reaction mixture was poured into water and the mixture was extracted with AcOEt. The extract was washed with brine, dried over MgSO₄, and concentrated under reduced pressure. The residue was purified by basic silica gel column chromatography eluting with hexane/AcOEt (10/1) to give 2-chloro-1-(2,2-diethoxyethyl)-1H-benzimidazole (5.50 g).

MS (API+): [M+H]⁺269.1.
¹H NMR (300 MHz, CDCl₃) δ 1.10 (6H, t, J=7.2 Hz), 3.39 (2H, dq, J=9.1, 7.2 Hz), 3.72 (2H, dq, J=9.1, 7.2 Hz), 4.29

(2H, d, J=5.7 Hz), 4.72 (1H, t, J=5.7 Hz), 7.23-7.32 (2H, m), 7.39-7.47 (1H, m), 7.64-7.72 (1H, m).

mp 29-31° C.

Anal. Calcd for $C_{13}H_{17}ClN_2O_2$: C, 58.10; H, 6.38; N, 10.42. Found: C, 57.80; H, 6.31; N, 10.47.

65c) 1-ethyl-3-[4-(1H-imidazo[1,2-a]benzimidazol-1-yl)phenyl]-1,3-dihydro-2H-imidazo[4,5-b]pyridin-2-one

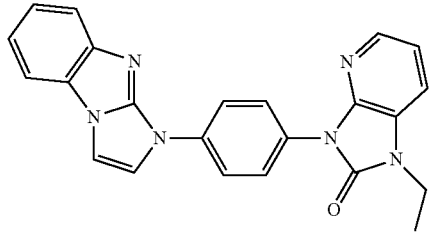 [SMILES: CCn1c(=O)n(-c2ccc(-n3ccn4c5ccccc5nc34)cc2)c2ncccc21]

A mixture of 2-chloro-1-(2,2-diethoxyethyl)-1H-benzimidazole (860 mg) and 3-(4-aminophenyl)-1-ethyl-1,3-dihydro-2H-imidazo[4,5-b]pyridin-2-one (636 mg) was heated at 150° C. for 50 min. The reaction mixture was partitioned between AcOEt/THF (1/1) and 1 M NaOH aqueous solution. The organic layer was separated, washed with brine, dried over MgSO₄, and concentrated under reduced pressure. The residue was purified by basic silica gel column chromatography eluting with THF and recrystallized from THF to give 1-ethyl-3-[4-(1H-imidazo[1,2-a]benzimidazol-1-yl)phenyl]-1,3-dihydro-2H-imidazo[4,5-b]pyridin-2-one (311 mg).

MS (API+): [M+H]⁺395.3.

¹H NMR (300 MHz, CDCl₃) δ 1.43 (3H, t, J=7.2 Hz), 4.05 (2H, q, J=7.2 Hz), 7.10 (1H, dd, J=7.9, 5.3 Hz), 7.17-7.22 (1H, m), 7.29 (1H, dd, J=7.9, 1.5 Hz), 7.32-7.37 (2H, m), 7.44 (1H, d, J=2.6 Hz), 7.62 (1H, d, J=7.6 Hz), 7.80 (1H, d, J=8.3 Hz), 7.91-7.96 (2H, m), 8.08 (1H, dd, J=5.3, 1.5 Hz), 8.15-8.20 (2H, m).

mp 220-221° C.

Anal. Calcd for $C_{23}H_{18}N_6O$: C, 70.04; H, 4.60; N, 21.31. Found: C, 70.12; H, 4.63; N, 21.39.

Example 66

1-ethyl-3-[1-(1,3-thiazol-2-yl)-1H-indol-5-yl]-1,3-dihydro-2H-imidazo[4,5-b]pyridin-2-one

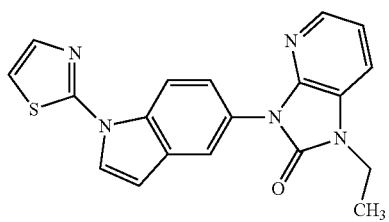 [SMILES: CCn1c(=O)n(-c2ccc3c(ccn3-c3nccs3)c2)c2ncccc21]

A mixture of 3-(2,3-dihydro-1H-indol-5-yl)-1-ethyl-1,3-dihydro-2H-imidazo[4,5-b]pyridin-2-one (75 mg), 2-chlorothiazole (48.0 mg) and Cs₂CO₃ (174 mg) in DMF (3 mL) was stirred at 100° C. for 3 days, treated with saturated NaHCO₃ solution, and extracted with AcOEt. The organic layer was separated, dried over MgSO₄ and concentrated in vacuo. The residue was purified by prep. HPLC and crystallized from AcOEt/Hexane to give the title compound as white crystals (27.0 mg).

MS (API+): [M+H]⁺362.0.

¹H NMR (300 MHz, DMSO-d₆) δ 1.31 (3H, t, J=7.2 Hz), 4.00 (2H, q, J=7.2 Hz), 6.93 (1H, d, J=3.4 Hz), 7.08-7.22 (1H, m), 7.54-7.64 (2H, m), 7.65-7.78 (2H, m), 7.88-8.08 (3H, m), 8.41-8.52 (1H, m).

Example 69

3-[1-(1H-benzimidazol-2-yl)-1H-indol-5-yl]-1-ethyl-1,3-dihydro-2H-imidazo[4,5-b]pyridin-2-one

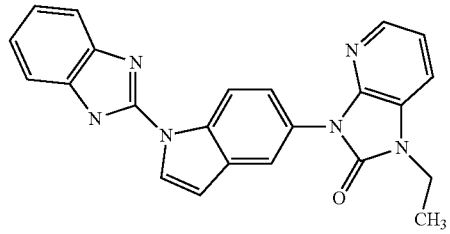 [SMILES: CCn1c(=O)n(-c2ccc3c(ccn3-c3nc4ccccc4[nH]3)c2)c2ncccc21]

A mixture of 3-[1-(1H-benzimidazol-2-yl)-2,3-dihydro-1H-indol-5-yl]-1-ethyl-1,3-dihydro-2H-imidazo[4,5-b]pyridin-2-one (100 mg) and manganese dioxide (439 mg) in toluene (8 mL) was stirred at 100° C. for 5 h, filtered, treated with water and extracted with AcOEt. The organic layer was dried over MgSO₄ and concentrated in vacuo. The residue was chromatographed on silica gel eluting with AcOEt/Hexane. Crystallization from AcOEt/Hexane gave the title compound (28.0 mg).

MS (API+): [M+H]⁺395.2.

Example 70

1-ethyl-3-[1-(5-methylpyridin-2-yl)-1H-indazol-5-yl]-1,3-dihydro-2H-imidazo[4,5-b]pyridin-2-one

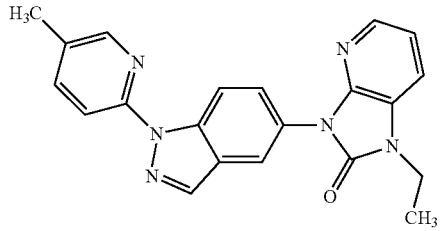 [SMILES: CCn1c(=O)n(-c2ccc3c(cnn3-c3ccc(C)cn3)c2)c2ncccc21]

70a) 1-(5-methylpyridin-2-yl)-1H-indazol-5-amine

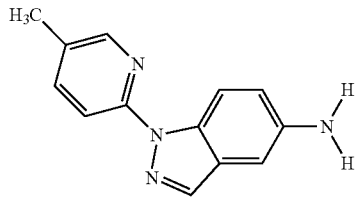 [SMILES: Cc1ccc(-n2ncc3cc(N)ccc32)nc1]

To a stirred solution of 5-nitro-1H-indazole (500 mg) in DMF (10 mL) was added 60% sodium hydride (129 mg) at room temperature. The mixture was stirred for 30 min, and 5-bromo-2-chloropyridine (649 mg) was added. The mixture was exposed to microwave irradiation at 230° C. for 1 h, treated with sat. ammonium chloride solution, and extracted with AcOEt. The organic layer was dried over MgSO$_4$ and concentrated in vacuo. The residue was chromatographed on silica gel eluting with AcOEt/Hexane to give a mixture of 1-(5-bromopyridin-2-yl)-5-nitro-1H-indazole and 2-(5-bromopyridin-2-yl)-5-nitro-2H-indazole.

To the mixture of 1-(5-bromopyridin-2-yl)-5-nitro-1H-indazole and 2-(5-bromopyridin-2-yl)-5-nitro-2H-indazole were added methylboronic acid (141 mg), Pd(Ph$_3$P)$_4$ (91 mg), DME (3 mL) and a solution of Cs$_2$CO$_3$ (766 mg) in H$_2$O (1 mL), successively. The mixture was exposed to microwave irradiation at 140° C. for 1 h, treated with water, and extracted with AcOEt. The organic layer was dried over MgSO$_4$ and concentrated in vacuo to give a mixture of 1-(5-methylpyridin-2-yl)-5-nitro-1H-indazole and 2-(5-methylpyridin-2-yl)-5-nitro-2H-indazole.

The mixture of 1-(5-methylpyridin-2-yl)-5-nitro-1H-indazole and 2-(5-methylpyridin-2-yl)-5-nitro-2H-indazole was dissolved in EtOH (20 mL), and 10% Pd/C (250 mg) was added. Under H$_2$ atmosphere, the mixture was stirred at room temperature for 12 h, filtered and concentrated in vacuo. The residue was chromatographed on silica gel eluting with AcOEt/Hexane to give the title compound as white crystals (76 mg).

$^1$H NMR (300 MHz, DMSO-d$_6$) δ 2.33 (3H, s), 5.06 (2H, s), 6.84 (1H, d, J=1.5 Hz), 6.91 (1H, dd, J=8.9, 2.1 Hz), 7.71-7.87 (2H, m), 8.09 (1H, s), 8.33 (1H, d, J=2.3 Hz), 8.38-8.46 (1H, m).

70b) 3-[1-(5-methylpyridin-2-yl)-1H-indazol-5-yl]-1,3-dihydro-2H-imidazo[4,5-b]pyridin-2-one

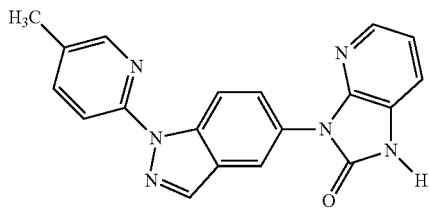 [SMILES: Cc1ccc(-n2ncc3cc(-n4c(=O)[nH]c5cccnc54)ccc32)nc1]

Under argon atmosphere, a mixture of 1-(5-methylpyridin-2-yl)-1H-indazol-5-amine (71 mg), tert-butyl 2-chloropyridin-3-ylcarbamate (80 mg), Pd$_2$(dba)$_3$ (29.0 mg), Xantphos (36.6 mg) and sodium tert-butoxide (33.5 mg) in 2-propanol (2 mL) and toluene (0.5 mL) was stirred at 90° C. for 24 h, treated with water and extracted with EtOAc. The organic layer was separated, dried over MgSO$_4$ and concentrated in vacuo. The residue was chromatographed on silica gel eluting with AcOEt/Hexane to give the title compound as white crystals (70.0 mg).

MS (API+): [M+H]$^+$343.3.

70c) 1-ethyl-3-[1-(5-methylpyridin-2-yl)-1H-indazol-5-yl]-1,3-dihydro-2H-imidazo[4,5-b]pyridin-2-one

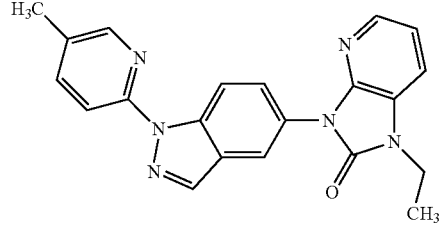 [SMILES: CCn1c(=O)n(-c2ccc3c(cnn3-c3ccc(C)cn3)c2)c2ncccc21]

A mixture of 3-[1-(5-methylpyridin-2-yl)-1H-indazol-5-yl]-1,3-dihydro-2H-imidazo[4,5-b]pyridin-2-one (70 mg) and iodoethane (35.1 mg) in DMF (2 mL) was stirred at 50° C. for 3 h, treated with water, and extracted with AcOEt. The organic layer was dried over MgSO$_4$ and concentrated in vacuo. The residue was chromatographed on silica gel eluting with AcOEt/Hexane. The product was crystallized from AcOEt/Hexane to give the title compound as white crystals (25.0 mg).

MS (API+): [M+H]$^+$371.0.

Example 71

1-ethyl-3-[1-(3H-imidazo[4,5-b]pyridin-2-yl)-2,3-dihydro-1H-indol-5-yl]-1,3-dihydro-2H-imidazo[4,5-b]pyridin-2-one

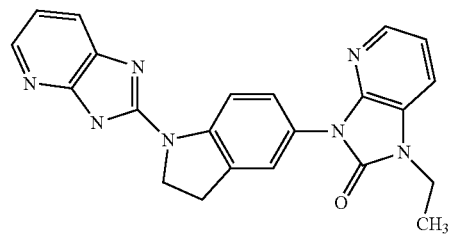

71a) 2-Chloro-3H-imidazo[4,5-b]pyridine

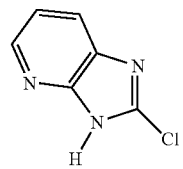

2-(Methylthio)-3H-imidazo[4,5-b]pyridine (3.5 g) was dissolved in conc. HCl (10 mL), and then the mixture was cooled to 0° C. Chlorine gas was bubbled through the mixture for 2 h in iced bath. The mixture was poured onto ice, and neutralized to pH 7 with aqueous ammonium solution. The precipitate was collected by filtration to give the title compound as white crystals (1.0 g).

MS (API+): [M+H]$^+$ 154.0.

71b) 1-ethyl-3-[1-(3H-imidazo[4,5-b]pyridin-2-yl)-2,3-dihydro-1H-indol-5-yl]-1,3-dihydro-2H-imidazo[4,5-b]pyridin-2-one

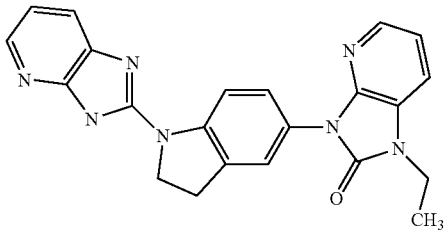 [SMILES: CCn1c(=O)n(-c2ccc3c(c2)CCN3c2nc3cccnc3[nH]2)c2ncccc21]

Under nitrogen atmosphere, a mixture of 3-(2,3-dihydro-1H-indol-5-yl)-1-ethyl-1,3-dihydro-2H-imidazo[4,5-b]pyridin-2-one (100 mg) and 2-chloro-3H-imidazo[4,5-b]pyridine (60.3 mg) in NMP (4 mL) was stirred at 150° C. for 2 h, treated with water, and extracted with AcOEt. The organic layer was dried over MgSO$_4$ and concentrated in vacuo. The residue was purified by prep. HPLC. Crystallization from EtOH/H$_2$O to give the title compound (18.0 mg).

MS (API+): [M+H]$^+$398.2.

$^1$H NMR (300 MHz, DMSO-d$_6$) δ 1.29 (3H, t, J=7.0 Hz), 3.36-3.41 (2H, m), 3.97 (2H, q, J=7.1 Hz), 4.19-4.34 (2H, m), 6.98-7.10 (1H, m), 7.12-7.20 (1H, m), 7.39-7.49 (2H, m), 7.62-7.72 (2H, m), 7.93-8.01 (1H, m), 8.02-8.17 (1H, m), 8.41 (1H, d, J=9.1 Hz).

Example 72

3-[1-(3H-imidazo[4,5-b]pyridin-2-yl)-2,3-dihydro-1H-indol-5-yl]-1-(1-methylethyl)-1,3-dihydro-2H-imidazo[4,5-b]pyridin-2-one

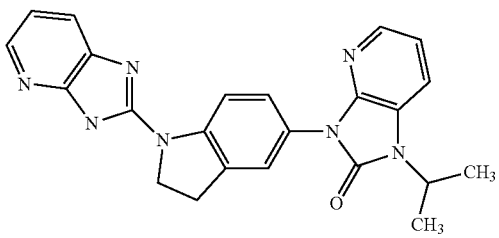 [SMILES: CC(C)n1c(=O)n(-c2ccc3c(c2)CCN3c2nc3cccnc3[nH]2)c2ncccc21]

72a) tert-Butyl 5-[1-(1-methylethyl)-2-oxo-1,2-dihydro-3H-imidazo[4,5-b]pyridin-3-yl]-2,3-dihydro-1H-indole-1-carboxylate

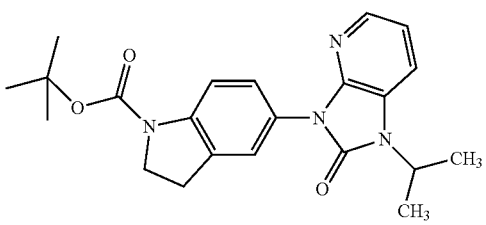 [SMILES: CC(C)n1c(=O)n(-c2ccc3c(c2)CCN3C(=O)OC(C)(C)C)c2ncccc21]

A mixture of tert-butyl 5-(2-oxo-1,2-dihydro-3H-imidazo[4,5-b]pyridin-3-yl)-2,3-dihydro-1H-indole-1-carboxylate (1480 mg) and 2-iodopropane (714 mg) in DMF (5 mL) was stirred at 60° C. for 4 h, treated with water, and extracted with AcOEt. The organic layer was dried over MgSO$_4$ and concentrated in vacuo. The residue was chromatographed on silica gel eluting with AcOEt/Hexane to give the title compound as white crystals (570 mg).

$^1$H NMR (300 MHz, DMSO-d$_6$) δ 1.44-1.60 (15H, m), 3.12 (2H, t, =8.7 Hz), 3.92-4.01 (2H, m), 4.65-4.74 (1H, m), 7.07-7.15 (1H, m), 7.31-7.45 (2H, m), 7.72-7.79 (2H, m), 7.90-7.99 (1H, m).

72b) 3-(2,3-dihydro-1H-indol-5-yl)-1-(1-methylethyl)-1,3-dihydro-2H-imidazo[4,5-b]pyridin-2-one

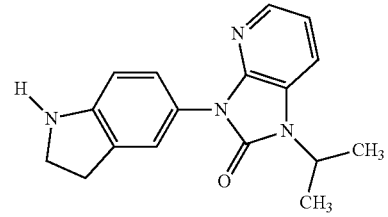 [SMILES: CC(C)n1c(=O)n(-c2ccc3c(c2)CCN3)c2ncccc21]

To a stirred mixture of tert-butyl 5-[1-(1-methylethyl)-2-oxo-1,2-dihydro-3H-imidazo[4,5-b]pyridin-3-yl]-2,3-dihydro-1H-indole-1-carboxylate in AcOEt/EtOH (1/1, 10 mL) was added 4N HCl in AcOEt (4 mL). The mixture was stirred at 80° C. for 2 h, evaporated, treated with saturated NaHCO$_3$, and extracted with AcOEt. The organic layer was dried over MgSO$_4$ and concentrated in vacuo. The residue was suspended in IPE and the suspension was collected by filtration to give the title compound as white crystals (313 mg).

MS (API+): [M+H]$^+$295.1.

72c) 3-[1-(3H-imidazo[4,5-b]pyridin-2-yl)-2,3-dihydro-1H-indol-5-yl]-1-(1-methylethyl)-1,3-dihydro-2H-imidazo[4,5-b]pyridin-2-one

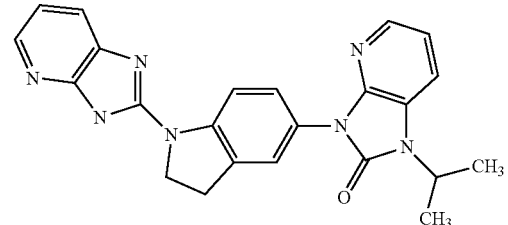

A mixture of 3-(2,3-dihydro-1H-indol-5-yl)-1-(1-methylethyl)-1,3-dihydro-2H-imidazo[4,5-b]pyridin-2-one (200 mg) and 2-chloro-3H-imidazo[4,5-b]pyridine (115 mg) in NMP (4 mL) was stirred at 140° C. for 1.5 h, treated with saturated NaHCO$_3$, and extracted with AcOEt. The organic layer was dried over MgSO$_4$, passed through celite pad covered with activated carbon and concentrated in vacuo. The residue was purified by prep. HPLC. The product was crystallized from EtOH/hexane to give the title compound (15.0 mg).

MS (API+): [M+H]$^+$412.4.

$^1$H NMR (300 MHz, DMSO-d$_6$) δ 1.51 (6H, d, J=7.2 Hz), 3.38-3.45 (2H, m), 4.20-4.35 (2H, m), 4.72 (1H, sep, J=7.2 Hz), 6.97-7.17 (2H, m), 7.36-7.50 (2H, m), 7.60-7.81 (2H, m), 7.96 (1H, d, J=5.3 Hz), 8.01-8.18 (1H, m), 8.34-8.47 (1H, m), 12.20 (1H, brs).

Example 75

1-ethyl-3-[4-(3H-imidazo[4,5-b]pyridin-2-yloxy)phenyl]-1,3-dihydro-2H-imidazo[4,5-b]pyridin-2-one

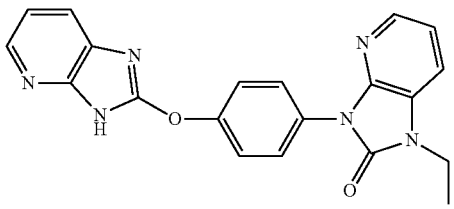 [SMILES: CCn1c(=O)n(-c2ccc(Oc3nc4cccnc4[nH]3)cc2)c2ncccc21]

75a) 3-[4-(benzyloxy)phenyl]-1-ethyl-1,3-dihydro-2H-imidazo[4,5-b]pyridin-2-one

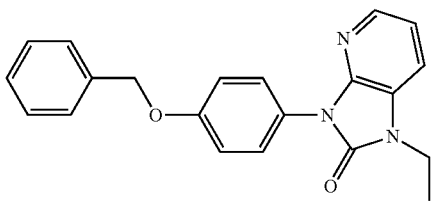 [SMILES: CCn1c(=O)n(-c2ccc(OCc3ccccc3)cc2)c2ncccc21]

The mixture of 3-[4-(benzyloxy)phenyl]-1,3-dihydro-2H-imidazo[4,5-b]pyridin-2-one (2.50 g), sodium hydride (0.378 g) and iodoethane (1.60 mL) in DMF (25 mL) was stirred at 20° C. under a dry atmosphere (CaCl$_2$ tube) for 1 h. The reaction mixture was diluted with MeOH (10 mL) and concentrated under reduced pressure. The residue was purified by column chromatography (NH silica gel, eluted with 0%-30% EtOAc in hexane) to give 3-[4-(benzyloxy)phenyl]-1-ethyl-1,3-dihydro-2H-imidazo[4,5-b]pyridin-2-one (2.70 g) as a colorless solid.

MS (API+): [M+H]$^+$346.4.
$^1$H NMR (300 MHz, CDCl$_3$) δ 1.40 (3H, t, J=7.2 Hz), 4.02 (2H, q, J=7.2 Hz), 5.11 (2H, s), 7.01-7.17 (3H, m), 7.22-7.29 (1H, m), 7.29-7.49 (5H, m), 7.53-7.61 (2H, m), 8.00-8.09 (1H, m).

75b) 1-ethyl-3-(4-hydroxyphenyl)-1,3-dihydro-2H-imidazo[4,5-b]pyridin-2-one

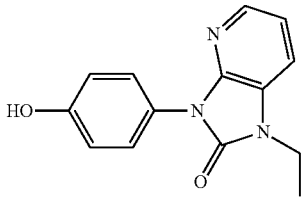 [SMILES: CCn1c(=O)n(-c2ccc(O)cc2)c2ncccc21]

A mixture of 3-[4-(benzyloxy)phenyl]-1-ethyl-1,3-dihydro-2H-imidazo[4,5-b]pyridin-2-one (2.70 g) and 10% palladium-carbon (0.832 g) in EtOH (250 mL) was hydrogenated under balloon pressure at room temperature for 3 h. The catalyst was removed by filtration and the filtrate was concentrated in vacuo to give 1-ethyl-3-(4-hydroxyphenyl)-1,3-dihydro-2H-imidazo[4,5-b]pyridin-2-one (1.42 g) as a white solid.

MS (API+): [M+H]$^+$ 256.1.
$^1$H NMR (300 MHz, DMSO-d$_6$) δ 1.27 (3H, t, J=7.2 Hz), 3.95 (2H, q, J=7.2 Hz), 6.84-6.95 (2H, m), 7.08-7.18 (1H, m), 7.32-7.40 (2H, m), 7.57-7.67 (1H, m), 7.89-7.99 (1H, m), 9.67-9.79 (1H, m).

75c) 1H-imidazo[4,5-b]pyridine-2-thiol

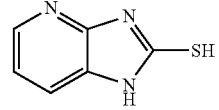

To a solution of pyridine-2,3-diamine (5 g) in EtOH (150 mL) was added carbon disulfide (23 mL) at room temperature. The mixture was stirred at 40° C. under Ar for 10 h. The mixture was cooled to room temperature. The resulting white solid was filtered and washed with ether to give 1H-imidazo[4,5-b]pyridine-2-thiol (5.61 g).

MS (API+): [M+H]$^+$ 152.2.
$^1$H NMR (300 MHz, DMSO-d$_5$) δ 7.13 (1 H, m), 7.47 (1 H, d, J=6.8 Hz), 7.97-8.36 (1 H, m), 12.72 (1 H, br. s.), 13.13 (1 H, br. s.).

75d) 2-(methylsulfanyl)-3H-imidazo[4,5-b]pyridine

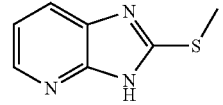

To a solution of 1H-imidazo[4,5-b]pyridine-2-thiol (2 g) in acetone (30 ml) were added MeI (0.910 mL) and K$_2$CO$_3$ (5.48 g) at room temperature. After stirring for 10 h, the mixture was concentrated under reduced pressure. The residue was purified by column chromatography (NH-silica gel, eluted with 10%-100% EtOAc in hexane) to give 2-(methylsulfanyl)-3H-imidazo[4,5-b]pyridine (1.0 g) as a white solid.

MS (API+): [M+H]$^+$166.3.
$^1$H NMR (300 MHz, DMSO-d$_6$) δ ppm 2.71 (3 H, s), 6.83-7.34 (1 H, m), 7.68-8.02 (1 H, m), 8.02-8.32 (1 H, m), 12.68-13.33 (1 H, m).

75e) 2-(methylsulfonyl)-3H-imidazo[4,5-b]pyridine

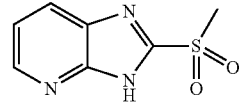

To a solution of 2-(methylsulfanyl)-3H-imidazo[4,5-b]pyridine (500 mg) in EtOAc (10 ml) was added mCPBA (1393 mg) at 0° C. After stirring for 10 h, the mixture was quenched with water, and extracted with ethyl acetate, and the extract was washed with brine, and dried over magnesium sulfate. The crude material was recrystallized from ethyl acetate to give 2-(methylsulfonyl)-3H-imidazo[4,5-b]pyridine (593 mg).

MS (API+): [M+H]+198.2.

¹H NMR (300 MHz, DMSO-d₆) δ 3.52 (3H, s), 7.32-7.41 (1 H, m), 7.50-7.61 (1 H, m), 7.67-7.76 (1 H, m), 8.53-8.63 (1 H, m).

75f) 2-(methylsulfonyl)-1-{[2-(trimethylsilyl)ethoxy]methyl}-1H-imidazo[4,5-b]pyridine

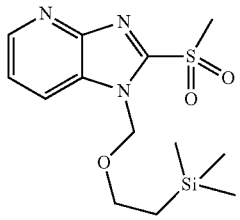 [SMILES: C[Si](C)(C)CCOCn1c(S(C)(=O)=O)nc2ncccc21]

Sodium hydride (146 mg) was added to a solution of 2-(methylsulfonyl)-3H-imidazo[4,5-b]pyridine (600 mg) and [2-(chloromethoxy)ethyl]trimethylsilane (609 mg) in DMF (3 mL) at room temperature. The mixture was stirred at room temperature under a dry atmosphere (CaCl₂ tube) for 1 h. The reaction mixture was diluted with MeOH (2 mL), and concentrated in vacuo. The residue was purified by column chromatography (silica gel, eluted with 0%-30% EtOAc in hexane) to give 2-(methylsulfonyl)-1-[{2-(trimethylsilyl)ethoxy}methyl]-1H-imidazo[4,5-b]pyridine (250 mg) as light brown oil.

MS (API+): [M+H]+328.3.

75g) 1-ethyl-3-[4-(3H-imidazo[4,5-b]pyridin-2-yloxy)phenyl]-1,3-dihydro-2H-imidazo[4,5-b]pyridin-2-one

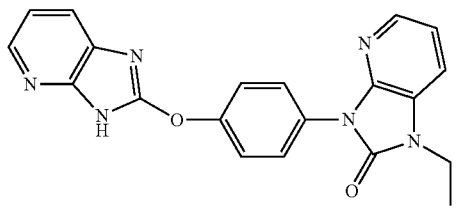 [SMILES: CCn1c(=O)n(-c2ccc(Oc3nc4cccnc4[nH]3)cc2)c2ncccc21]

The mixture of 1-ethyl-3-(4-hydroxyphenyl)-1,3-dihydro-2H-imidazo[4,5-b]pyridin-2-one (281 mg), 2-(methylsulfonyl)-1-{[2-(trimethylsilyl)ethoxy]methyl}-1H-imidazo[4,5-b]pyridine (240 mg) and NaH (35.2 mg) in DMF (dry) (3 ml) was heated at 200° C. for 3 h under microwave irradiation. The reaction mixture was diluted with MeOH, and concentrated in vacuo. The residue was diluted with 6N HCl. The mixture was neutralized with aq. NaHCO₂ at 0° C. and extracted with EtOAc. The organic layer was separated, washed with water and brine, dried over MgSO₄ and concentrated in vacuo. The residue was purified by column chromatography (silica gel, eluted with 0%-100% EtOAc in hexane) to give 1-ethyl-3-[4-(3H-imidazo[4,5-b]pyridin-2-yloxy)phenyl]-1,3-dihydro-2H-imidazo[4,5-b]pyridin-2-one (40 mg) as white crystals.

MS (API+): [M+H]+373.1.

¹H NMR (300 MHz, DMSO-d₆) δ 1.31 (3H, t, J=7.1 Hz), 3.99 (2H, q, J=7.1 Hz), 7.10-7.26 (2H, m), 7.55-7.64 (2H, m), 7.66-7.72 (1H, m), 7.73-7.84 (3H, m), 7.97-8.06 (1H, m), 8.11-8.23 (1H, m).

Example 85

1-ethyl-3-{4-[(1-methyl-1H-imidazo[4,5-b]pyridin-2-yl)oxy]phenyl}-1,3-dihydro-2H-imidazo[4,5-b]pyridin-2-one

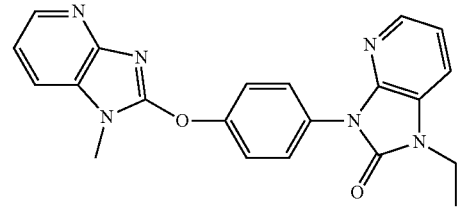 [SMILES: CCn1c(=O)n(-c2ccc(Oc3nc4ncccc4n3C)cc2)c2ncccc21]

85a) N-benzyl-N-methyl-2-nitropyridin-3-amine

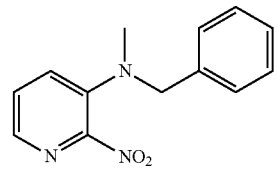 [SMILES: CN(Cc1ccccc1)c1cccnc1[N+](=O)[O-]]

The mixture of N-methylbenzylamine (6.085 mL), TEA (13.19 µL) and 3-chloro-2-nitropyridine (5 g) was stirred at 60° C. under N₂ overnight. The reaction mixture was concentrated in vacuo. The residue was purified by column chromatography (silica gel, eluted with 0%-30% EtOAc in hexane) to give N-benzyl-N-methyl-2-nitropyridin-3-amine (2.6 g) as dark yellow oil.

MS (API+): [M+H]+244.1.

¹H NMR (300 MHz, DMSO-d₆) δ 2.75 (3H, s), 4.44 (2H, s), 7.16-7.47 (5H, m), 7.51-7.62 (1H, m), 7.72-7.82 (1H, m), 7.92-8.02 (1H, m).

85b) N³-methylpyridine-2,3-diamine

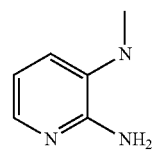

A mixture of N-benzyl-N-methyl-2-nitropyridin-3-amine (2.6 g) and 10% Pd—C (0.569 g) in EtOH (50 mL) was hydrogenated under balloon pressure at room temperature over weekend. The catalyst was removed by filtration and the filtrate was concentrated in vacuo to give N³-methylpyridine-2,3-diamine (1.14 g) as pale yellow oil.

MS (API+): [M+H]+ not detected.

¹H NMR (300 MHz, DMSO-d₆) δ 2.68 (3H, d, J=4.9 Hz), 4.85 (1H, q, J=4.9 Hz), 5.35 (2H, s), 6.41-6.58 (2H, m), 7.21-7.32 (1H, m).

85c) 1-methyl-1,3-dihydro-2H-imidazo[4,5-b]pyridin-2-one

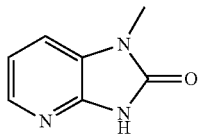

CDI (2.251 g) was added to a solution of $N^3$-methylpyridine-2,3-diamine (1.14 g) in THF (dry) (50 ml) at room temperature. The mixture was stirred at room temperature under a dry atmosphere ($CaCl_2$ tube) over weekend. The reaction mixture was concentrated in vacuo. The residue was purified by column chromatography (silica gel, eluted with 0%-100% EtOAc in hexane) to give 1-methyl-1,3-dihydro-2H-imidazo[4,5-b]pyridin-2-one (1.1 g) as a white solid.

MS (API+): $[M+H]^+$ not detected.

$^1$H NMR (300 MHz, DMSO-$d_6$) δ 3.29 (3H, s), 7.02 (1H, dd, J=7.9, 5.3 Hz), 7.40 (1H, dd, J=7.9, 1.5 Hz), 7.90 (1H, dd, J=5.3, 1.5 Hz), 11.51 (1H, brs).

85d) 2-chloro-1-methyl-1H-imidazo[4,5-b]pyridine

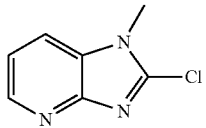

The mixture of 1-methyl-1,3-dihydro-2H-imidazo[4,5-b]pyridin-2-one (1.1 g) and phosphorus oxychloride (6.87 mL) was stirred at 100° C. under a dry atmosphere ($CaCl_2$ tube) for 5 h. The mixture was neutralized with sat.$NaHCO_3$ at 0° C. and extracted with EtOAc. The organic layer was separated, washed with water and brine, dried over $MgSO_4$ and concentrated in vacuo. The residue was purified by column chromatography (NH silica gel, eluted with 0%-50% EtOAc in hexane) to give 2-chloro-1-methyl-1H-imidazo[4,5-b]pyridine (600 mg) as a white solid.

MS (API+): $[M+H]^+$ 168.0.

$^1$H NMR (300 MHz, DMSO-$d_6$) δ 3.83 (3H, s), 7.34 (1H, dd, J=8.1. 4.9 Hz), 8.06 (1H, dd, J=8.1, 1.7 Hz), 8.42 (1H, dd, J=4.9, 1.7 Hz).

85e) 1-ethyl-3-{4-[(1-methyl-1H-imidazo[4,5-b]pyridin-2-yl)oxy]phenyl}-1,3-dihydro-2H-imidazo[4,5-b]pyridin-2-one

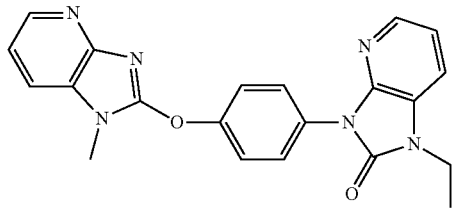 [SMILES: CCn1c(=O)n(-c2ccc(Oc3nc4ncccc4n3C)cc2)c2ncccc21]

The mixture of sodium hydride (14.32 mg), 2-chloro-1-methyl-1H-imidazo[4,5-b]pyridine (100 mg) and 1-ethyl-3-(4-hydroxyphenyl)-1,3-dihydro-2H-imidazo[4,5-b]pyridin-2-one (152 mg) in DMF (3 mL) was stirred at 180° C. under a dry atmosphere ($CaCl_2$ tube) for 20 min. The mixture was neutralized with 1N HCl at 0° C. and extracted with EtOAc. The organic layer was separated, washed with water and brine, dried over $MgSO_4$ and concentrated in vacuo. The residue was purified by column chromatography (silica gel, eluted with 0%-100% EtOAc in hexane) to give 1-ethyl-3-{4-[(1-methyl-1H-imidazo[4,5-b]pyridin-2-yl)oxy]phenyl}-1,3-dihydro-2H-imidazo[4,5-b]pyridin-2-one (150 mg) as white crystals.

MS (API+): $[M+H]^+$ 387.2.

$^1$H NMR (300 MHz, DMSO-$d_6$) δ 1.31 (3H, t, J=7.2 Hz), 3.80 (3H, s), 3.99 (2H, q, J=7.2 Hz), 7.14-7.28 (2H, m), 7.60-7.68 (2H, m), 7.66-7.74 (1H, m), 7.78-7.86 (2H, m), 7.87-7.95 (1H, m), 7.96-8.06 (1H, m), 8.21-8.35 (1H, m).

Example 86

1-ethyl-3-{4-[(3-methyl-3H-imidazo[4,5-b]pyridin-2-yl)oxy]phenyl}-1,3-dihydro-2H-imidazo[4,5-b]pyridin-2-one

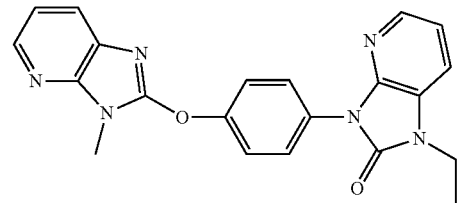 [SMILES: CCn1c(=O)n(-c2ccc(Oc3nc4cccnc4n3C)cc2)c2ncccc21]

86a) N-benzyl-N-methyl-3-nitropyridin-2-amine

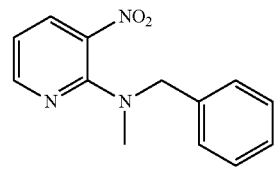 [SMILES: CN(Cc1ccccc1)c1ncccc1[N+](=O)[O-]]

The mixture of 2-chloro-3-nitropyridine (15 g), $Na_2CO_3$ (10.03 g) and N-methylbenzylamine (24.42 mL) in THF (150 mL) was stirred at 80° C. under a dry atmosphere ($CaCl_2$ tube) overnight. The mixture was neutralized with 1N HCl at 0° C. and extracted with EtOAc. The organic layer was separated, washed with water and brine, dried over $MgSO_4$ and concentrated in vacuo. The residue was purified by column chromatography (silica gel, eluted with 0%-30% EtOAc in hexane) to give N-benzyl-N-methyl-3-nitropyridin-2-amine (19 g) as yellow oil.

MS (API+): $[M+H]^+$ not detected.

$^1$H NMR (300 MHz, CDCl$_3$) δ 2.81 (3H, s), 4.94 (2H, s), 6.59-6.82 (1H, m), 7.21-7.44 (5H, m), 8.09-8.18 (1H, m), 8.27-8.43 (1H, m).

86b) N²-methylpyridine-2,3-diamine

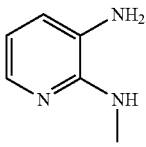

A mixture of N-benzyl-N-methyl-3-nitropyridin-2-amine (15 g) and 10% Pd—C (6.56 g) in EtOH (300 mL) was hydrogenated under balloon pressure at room temperature over weekend. The catalyst was removed by filtration and the filtrate was concentrated in vacuo to give N²-methylpyridine-2,3-diamine (7.00 g) as a tan solid.

MS (API+): [M+H]⁺ not detected.

¹H NMR (300 MHz, DMSO-d₆) δ 2.81 (3H, d, J=4.9 Hz), 4.60 (2H, s), 5.56 (1H, q, J=4.9 Hz), 6.32 (1H, dd, J=7.2, 4.9 Hz), 6.64 (1H, dd, J=7.2, 1.7 Hz), 7.37 (1H, dd, J=4.9, 1.7 Hz).

86c) 3-methyl-1,3-dihydro-2H-imidazo[4,5-b]pyridin-2-one

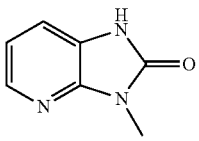

A solution of N²-methylpyridine-2,3-diamine (7 g) and CDI (13.82 g) in THF (100 mL) was refluxed for 5 h. The reaction mixture was concentrated in vacuo. The residue was purified by column chromatography (NH silica gel, eluted with 0%-100% EtOAc in hexane) to give 3-methyl-1,3-dihydro-2H-imidazo[4,5-b]pyridin-2-one (7 g) as a light brown solid.

MS (API+): [M+H]⁺ not detected.

¹H NMR (300 MHz, DMSO-d₆) δ 3.30 (3H, s), 6.96-7.01 (1H, m). 7.24-7.34 (1H, m), 7.90-7.98 (1H, m).

86d) 2-chloro-3-methyl-3H-imidazo[4,5-b]pyridine

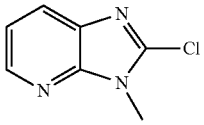

The mixture of 3-methyl-1,3-dihydro-2H-imidazo[4,5-b]pyridin-2-one (1.0 g) in phosphorus oxychloride (10 g) was stirred at 100° C. under a dry atmosphere (CaCl₂ tube) for 5 h. The mixture was neutralized with sat.NaHCO₃ at 0° C. and extracted with EtOAc. The organic layer was separated, washed with water and brine, dried over MgSO₄ and concentrated in vacuo. The residue was purified by column chromatography (NH silica gel, eluted with 0%-50% EtOAc in hexane) to give 2-chloro-3-methyl-3H-imidazo[4,5-b]pyridine (230 mg) as a white solid.

MS (API+): [M+H]⁺168.0.

¹H NMR (300 MHz, DMSO-d₆) δ 3.80 (3H, s), 7.33 (1H, dd, J=8.0, 4.9 Hz), 8.04 (1H, dd, J=8.0, 1.5 Hz), 8.39 (1H, dd, J=1.5 Hz).

86e) 1-ethyl-3-{4-[(3-methyl-3H-imidazo[4,5-b]pyridin-2-yl)oxy]phenyl}-1,3-dihydro-2H-imidazo[4,5-b]pyridin-2-one

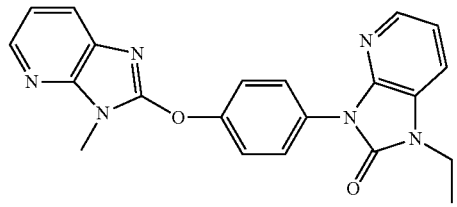 [SMILES: CCn1c(=O)n(-c2ccc(Oc3nc4cccnc4n3C)cc2)c2ncccc21]

2-Chloro-3-methyl-3H-imidazo[4,5-b]pyridine (150 mg) was added to a solution of 1-ethyl-3-(4-hydroxyphenyl)-1,3-dihydro-2H-imidazo[4,5-b]pyridin-2-one (228 mg) and NaH (39.4 mg) in DMF (2 mL) at 100° C. The mixture was stirred at 180° C. under a dry atmosphere (CaCl₂ tube) for 1 h. The mixture was neutralized with 1N HCl at 0° C. and extracted with EtOAc. The organic layer was separated, washed with water and brine, dried over MgSO₄ and concentrated in vacuo. The residue was purified by column chromatography (NH silica gel, eluted with 0%-100% EtOAc in hexane) to give 1-ethyl-3-{4-[(3-methyl-3H-imidazo[4,5-b]pyridin-2-yl)oxy]phenyl}-1,3-dihydro-2H-imidazo[4,5-b]pyridin-2-one (200 mg) as white crystals.

MS (API+): [M+H]⁺387.2.

¹H NMR (300 MHz, DMSO-d₆) δ 1.31 (3H, t, J=7.2 Hz), 3.78 (3H, s), 3.99 (2H, q, J=7.2 Hz), 7.14-7.27 (2H, m), 7.58-7.67 (2H, m), 7.67-7.74 (1H, m), 7.76-7.86 (3H, m), 7.97-8.06 (1H, m), 8.16-8.28 (1H, m).

Example 96

3,3-dimethyl-1-{4-[(3-methyl-3H-imidazo[4,5-b]pyridin-2-yl)oxy]phenyl}-1,3-dihydro-2H-pyrrolo[2,3-b]pyridin-2-one

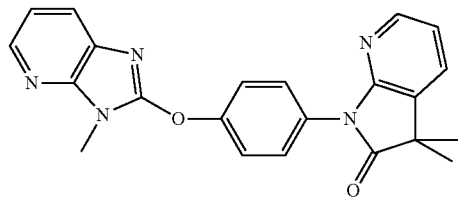 [SMILES: Cn1c(Oc2ccc(N3C(=O)C(C)(C)c4cccnc43)cc2)nc2cccnc21]

96a) 3-methyl-2-(methylsulfonyl)-3H-imidazo[4,5-b]pyridine

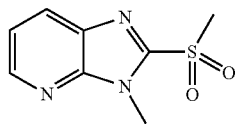

MeI (44.7 ml) was added to a mixture of K₂CO₃ (148 g) and 1H-imidazo[4,5-b]pyridine-2-thiol (54 g) in DMF (500 mL) at room temperature. The mixture was stirred at room temperature under a dry atmosphere (CaCl₂ tube) overnight. The mixture was poured into water at room temperature and the mixture was extracted with EtOAc. The organic layer was separated, washed with water and brine, dried over MgSO₄ and concentrated in vacuo to give 3-methyl-2-(methylsulfanyl)-3H-imidazo[4,5-b]pyridine as a crude product (12 g).

The mixture of 3-methyl-2-(methylsulfanyl)-3H-imidazo[4,5-b]pyridine (12 g) and mCPBA (33.0 g) in EtOAc (200 mL) was stirred at room temperature under a dry atmosphere (CaCl₂ tube) for 3 h. The mixture was neutralized with sat.NaHCO₃ at 0° C. and extracted with EtOAc. The organic layer was separated, washed with water and brine, dried over MgSO₄ and concentrated in vacuo. The residue was purified by column chromatography (NH silica gel, eluted with 0%-30% EtOAc in hexane) to give 3-methyl-2-(methylsulfonyl)-3H-imidazo[4,5-b]pyridine (10 g) as white crystals.

MS (API+): [M+H]⁺212.1.
¹H NMR (300 MHz, DMSO-d₆) δ 3.66 (3H, s), 4.12 (3H, s), 7.43-7.56 (1H, m), 8.25-8.38 (1H, m), 8.56-8.67 (¹H, m).

96b) 3,3-dimethyl-1-{4-[(3-methyl-3H-imidazo[4,5-b]pyridin-2-yl)oxy]phenyl}-1,3-dihydro-2H-pyrrolo[2,3-b]pyridin-2-one

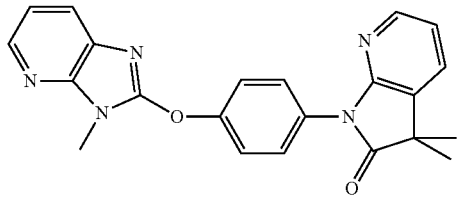 [SMILES: Cn1c(Oc2ccc(N3C(=O)C(C)(C)c4cccnc43)cc2)nc2cccnc21]

3-Methyl-2-(methylsulfonyl)-3H-imidazo[4,5-b]pyridine (90 mg) was added to a solution of 1-(4-hydroxyphenyl)-3,3-dimethyl-1,3-dihydro-2H-pyrrolo[2,3-b]pyridin-2-one (119 mg) and NaH (20.45 mg) in DMF (2 ml) at 100° C. The mixture was heated at 180° C. for 30 min under microwave irradiation. The reaction mixture was diluted with MeOH and concentrated under reduced pressure. The residue was purified by column chromatography (NH silica gel, eluted with 0%-50% EtOAc in hexane) to give 3,3-dimethyl-1-{4-[(3-methyl-3H-imidazo[4,5-b]pyridin-2-yl)oxy]phenyl}-1,3-dihydro-2H-pyrrolo[2,3-b]pyridin-2-one (120 mg) as white crystals.

MS (API+): [M+H]⁺386.2.
¹H NMR (300 MHz, DMSO-d₆) δ 1.46 (6H, s), 3.77 (3H, s), 7.09-7.28 (2H, m), 7.55-7.69 (4H, m), 7.75-7.92 (2H, m), 8.13 (1H, m), 8.17-8.28 (1H, m).

Example 97

3-{4-[(3-methyl-3H-imidazo[4,5-b]pyridin-2-yl)oxy]phenyl}-1-propyl-1,3-dihydro-2H-imidazo[4,5-b]pyridin-2-one

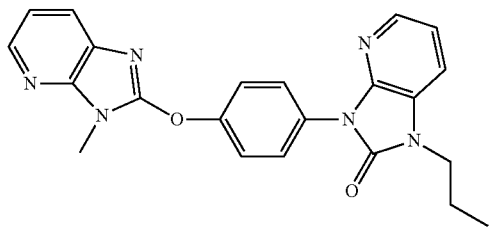 [SMILES: CCCn1c(=O)n(-c2ccc(Oc3nc4cccnc4n3C)cc2)c2ncccc21]

97a) 3-[4-(benzyloxy)phenyl]-1-propyl-1,3-dihydro-2H-imidazo[4,5-b]pyridin-2-one

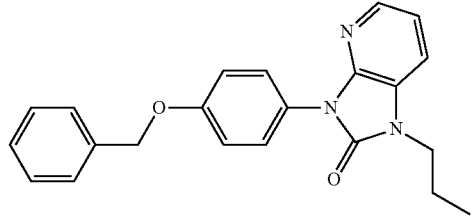 [SMILES: CCCn1c(=O)n(-c2ccc(OCc3ccccc3)cc2)c2ncccc21]

NaH (1.260 g) was added to a solution of 3-[4-(benzyloxy)phenyl]-1,3-dihydro-2H-imidazo[4,5-b]pyridin-2-one (5 g) and 1-iodopropane (3.07 mL) in DMF (50 mL) at room temperature. The mixture was stirred at room temperature under a dry atmosphere (CaCl₂ tube) for 1 h. The reaction mixture was diluted with MeOH and concentrated in vacuo. The residue was purified by column chromatography (NH silica gel, eluted with 0%-50% EtOAc in hexane) to give 3-[4-(benzyloxy)phenyl]-1-propyl-1,3-dihydro-2H-imidazo[4,5-b]pyridin-2-one (1.5 g) as dark yellow oil.

MS (API+): [M+H]⁺360.4.
¹H NMR (300 MHz, DMSO-d₆) δ 0.71-1.12 (3H, m), 1.60-1.88 (2H, m), 3.76-4.02 (2H, m), 5.19 (2H, s), 7.08-7.23 (3H, m), 7.28-7.58 (7H, m), 7.59-7.69 (1H, m), 7.89-8.00 (1H, m).

97b) 3-(4-hydroxyphenyl)-1-propyl-1,3-dihydro-2H-imidazo[4,5-b]pyridin-2-one

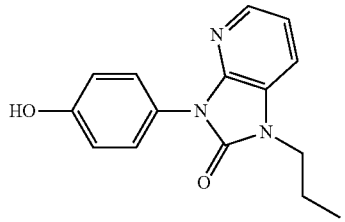 [SMILES: CCCn1c(=O)n(-c2ccc(O)cc2)c2ncccc21]

A mixture of 3-[4-(benzyloxy)phenyl]-1-propyl-1,3-dihydro-2H-imidazo[4,5-b]pyridin-2-one (1.5 g) and 10% Pd—C (0.444 g) in EtOH (40 ml) was hydrogenated under balloon pressure at room temperature for 3 h. The catalyst was removed by filtration and the filtrate was concentrated in vacuo to give 3-(4-hydroxyphenyl)-1-propyl-1,3-dihydro-2H-imidazo[4,5-b]pyridin-2-one (1.05 g) as a light brown solid.

MS (API+): [M+H]⁺ 270.1.
¹H NMR (300 MHz, DMSO-d₆) δ 0.83-0.98 (3H, m), 1.63-1.82 (2H, m), 3.77-3.95 (2H, m), 6.82-6.97 (2H, m), 7.07-7.20 (1H, m), 7.29-7.44 (2H, m), 7.57-7.69 (1H, m), 7.87-8.00 (1H, m), 9.21-10.52 (1H, m).

97c) 3-{4-[(3-methyl-3H-imidazo[4,5-b]pyridin-2-yl)oxy]phenyl}-1-propyl-1,3-dihydro-2H-imidazo[4,5-b]pyridin-2-one

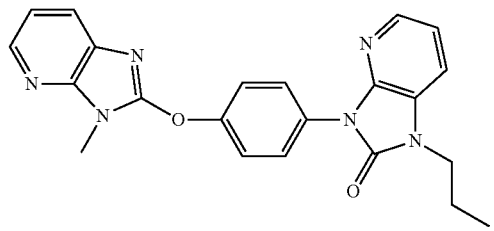 [SMILES: CCCn1c(=O)n(-c2ccc(Oc3nc4cccnc4n3C)cc2)c2ncccc21]

3-Methyl-2-(methylsulfonyl)-3H-imidazo[4,5-b]pyridine (320 mg) was added to a solution of 3-(4-hydroxyphenyl)-1-propyl-1,3-dihydro-2H-imidazo[4,5-b]pyridin-2-one (400 mg) and NaH (65.3 mg) in DMF (5 ml) at 100° C. The mixture was heated at 180° C. for 30 min under microwave irradiation. The reaction mixture was diluted with MeOH and concentrated in vacuo. The residue was purified by column chromatography (NH silica gel, eluted with 0%-50% EtOAc in hexane) to give 3-{4-[(3-methyl-3H-imidazo[4,5-b]pyridin-2-yl)oxy]phenyl}-1-propyl-1,3-dihydro-2H-imidazo[4,5-b]pyridin-2-one (300 mg) as white crystals.

MS (API+): [M+H]⁺401.2.

¹H NMR (300 MHz, DMSO-d₆) δ 0.88-1.00 (3H, m), 1.68-1.86 (2H, m), 3.78 (3H, s), 3.86-3.97 (2H, m), 7.13-7.29 (2H, m), 7.59-7.66 (2H, m), 7.67-7.73 (1H, m), 7.74-7.86 (3H, m), 7.95-8.06 (1H, m), 8.14-8.29 (1H, m).

Example 98

1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

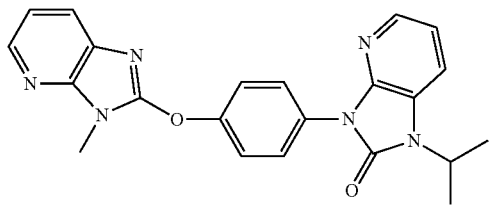 [SMILES: CC(C)n1c(=O)n(-c2ccc(Oc3nc4cccnc4n3C)cc2)c2ncccc21]

98a) 3-[4-(benzyloxy)phenyl]-1-(1-methylethyl)-1,3-dihydro-2H-imidazo[4,5-b]pyridin-2-one

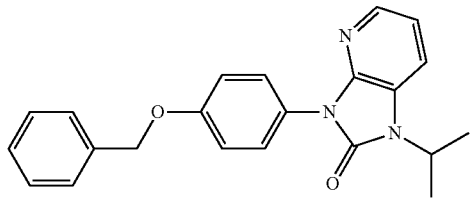 [SMILES: CC(C)n1c(=O)n(-c2ccc(OCc3ccccc3)cc2)c2ncccc21]

NaH (1.260 g) was added to a solution of 3-[4-(benzyloxy)phenyl]-1,3-dihydro-2H-imidazo[4,5-b]pyridin-2-one (5 g) and 2-iodopropane (3.15 ml) in DMF (50 ml) at room temperature. The mixture was stirred at room temperature under a dry atmosphere (CaCl₂ tube) for 1 h. The reaction mixture was diluted with MeOH and concentrated in vacuo. The residue was purified by column chromatography (NH silica gel, eluted with 0%-50% EtOAc in hexane) to give 3-[4-(benzyloxy)phenyl]-1-(1-methylethyl)-1,3-dihydro-2H-imidazo[4,5-b]pyridin-2-one (1.5 g) as dark yellow oil.

MS (API+): [M+H]⁺360.4.

¹H NMR (300 MHz, DMSO-d₆) δ 1.50 (6H, d, J=7.2 Hz), 4.64-4.80 (1H, m), 5.19 (2H, s), 7.05-7.24 (3H, m), 7.28-7.59 (7H, m), 7.70-7.79 (1H, m), 7.87-8.00 (1H, m).

98b) 3-(4-hydroxyphenyl)-1-(1-methylethyl)-1,3-dihydro-2H-imidazo[4,5-b]pyridin-2-one

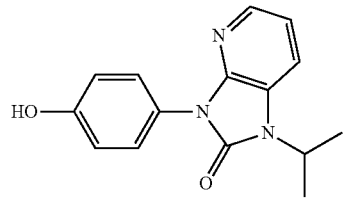 [SMILES: CC(C)n1c(=O)n(-c2ccc(O)cc2)c2ncccc21]

A mixture of 3-[4-(benzyloxy)phenyl]-1-(1-methylethyl)-1,3-dihydro-2H-imidazo[4,5-b]pyridin-2-one (1.5 g) and 10% Pd—C (0.444 g) in EtOH (40 ml) was hydrogenated under balloon pressure at room temperature for 5 h. The catalyst was removed by filtration and the filtrate was concentrated in vacuo to give 3-(4-hydroxyphenyl)-1-(1-methylethyl)-1,3-dihydro-2H-imidazo[4,5-b]pyridin-2-one (670 mg) as a light brown solid.

MS (API+): [M+H]⁺270.1.

¹H NMR (300 MHz, DMSO-d₆) δ 1.40-1.59 (6H, m), 4.62-4.80 (1H, m), 6.81-6.94 (2H, m), 7.04-7.19 (1H, m), 7.29-7.42 (2H, m), 7.63-7.81 (1H, m), 7.87-8.02 (1H, m), 9.52-9.91 (1H, m).

98c) 1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

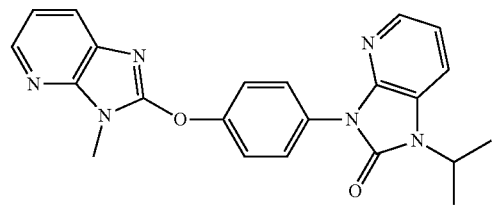 [SMILES: CC(C)n1c(=O)n(-c2ccc(Oc3nc4cccnc4n3C)cc2)c2ncccc21]

3-Methyl-2-(methylsulfonyl)-3H-imidazo[4,5-b]pyridine (270 mg) was added to a solution of 3-(4-hydroxyphenyl)-1-(1-methylethyl)-1,3-dihydro-2H-imidazo[4,5-b]pyridin-2-one (330 mg) and NaH (53.9 mg) in DMF (5 mL) at 100° C. The mixture was heated at 180° C. for 30 min under microwave irradiation. The reaction mixture was diluted with MeOH and concentrated in vacuo. The residue was purified by column chromatography (NH silica gel, eluted with 0%-50% EtOAc in hexane) to give 1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one (150 mg) as white crystals.

MS (API+): [M+H]⁺401.2.

¹H NMR (300 MHz, DMSO-d₆) δ 1.43-1.67 (6H, m), 3.81 (3H, s), 4.64-4.91 (1H, m), 7.08-7.31 (2H, m), 7.54-7.70 (2H, m), 7.70-7.89 (4H, m), 7.93-8.07 (1H, m), 8.18-8.28 (1H, m).

Example 99

1-cyclopropyl-3-{4-[(3-methyl-3H-imidazo[4,5-b]pyridin-2-yl)oxy]phenyl}-1,3-dihydro-2H-imidazo[4,5-b]pyridin-2-one

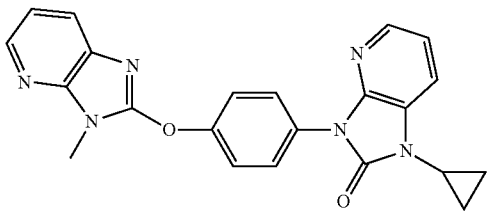 [SMILES: Cn1c(Oc2ccc(-n3c(=O)n(C4CC4)c4cccnc43)cc2)nc2cccnc21]

99a) 3-[4-(benzyloxy)phenyl]-1-cyclopropyl-1,3-dihydro-2H-imidazo[4,5-b]pyridin-2-one

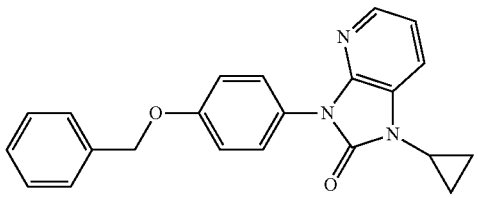 [SMILES: O=c1n(-c2ccc(OCc3ccccc3)cc2)c2ncccc2n1C1CC1]

The mixture of 3-[4-(benzyloxy)phenyl]-1,3-dihydro-2H-imidazo[4,5-b]pyridin-2-one (300 mg), cyclopropylboronic acid (731 mg), TEA (1976 µl), pyridine (1835 µl), copper(II) acetate (1030 mg) and THF (4727 µl) was heated at 140° C. for 30 min under microwave irradiation. The solid was removed by filtration, and the filtrate was concentrated in vacuo. The residue was purified by column chromatography (NH silica gel, eluted with 0%-30% EtOAc in hexane) to give 3-[4-(benzyloxy)phenyl]-1-cyclopropyl-1,3-dihydro-2H-imidazo[4,5-b]pyridin-2-one (120 mg) as white crystals.

MS (API+): [M+H]$^+$358.1.

$^1$H NMR (300 MHz, DMSO-d$_6$) δ 0.91-1.01 (2H, m), 1.01-1.11 (2H, m), 2.92-3.07 (1H, m), 5.18 (2H, s), 7.08-7.21 (3H, m), 7.30-7.46 (3H, m), 7.45-7.53 (4H, m), 7.53-7.62 (1H, m), 7.89-8.00 (1H, m).

99b) 1-cyclopropyl-3-(4-hydroxyphenyl)-1,3-dihydro-2H-imidazo[4,5-b]pyridin-2-one

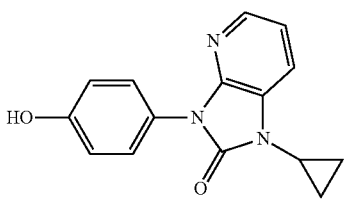 [SMILES: O=c1n(-c2ccc(O)cc2)c2ncccc2n1C1CC1]

A mixture of 3-[4-(benzyloxy)phenyl]-1-cyclopropyl-1,3-dihydro-2H-imidazo[4,5-b]pyridin-2-one (120 mg) and 10% Pd—C (17.87 mg) in EtOH (10 mL) was hydrogenated under balloon pressure at room temperature for 2 h. The catalyst was removed by filtration and the filtrate was concentrated in vacuo to give 1-cyclopropyl-3-(4-hydroxyphenyl)-1,3-dihydro-2H-imidazo[4,5-b]pyridin-2-one (89 mg) as a white solid.

MS (API+): [M+H]$^+$268.1.

$^1$H NMR (300 MHz, DMSO-d$_6$) δ 0.89-1.00 (2H, m), 1.01-1.11 (2H, m), 2.92-3.07 (1H, m), 6.83-6.95 (2H, m), 7.07-7.20 (1H, m), 7.28-7.40 (2H, m), 7.50-7.62 (1H, m), 7.87-8.00 (1H, m), 9.76 (1H, brs).

99c) 1-cyclopropyl-3-{4-[(3-methyl-3H-imidazo[4,5-b]pyridin-2-yl)oxy]phenyl}-1,3-dihydro-2H-imidazo[4,5-b]pyridin-2-one

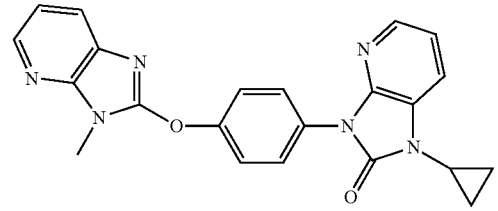 [SMILES: Cn1c(Oc2ccc(-n3c(=O)n(C4CC4)c4cccnc43)cc2)nc2cccnc21]

3-Methyl-2-(methylsulfonyl)-3H-imidazo[4,5-b]pyridine (79 mg) was added to a solution of 1-cyclopropyl-3-(4-hydroxyphenyl)-1,3-dihydro-2H-imidazo[4,5-b]pyridin-2-one (100 mg) and NaH (17.96 mg) in DMF (2 ml) at 100° C. The mixture was heated at 180° C. for 1 h under microwave irradiation. The reaction mixture was diluted with MeOH and concentrated in vacuo. The residue was purified by column chromatography (NH silica gel, eluted with 0%-50% EtOAc in hexane) to give 1-cyclopropyl-3-{4-[(3-methyl-3H-imidazo[4,5-b]pyridin-2-yl)oxy]phenyl}-1,3-dihydro-2H-imidazo[4,5-b]pyridin-2-one (80 mg) as white crystals.

MS (API+): [M+H]$^+$ 399.2.

$^1$H NMR (300 MHz, DMSO-d$_6$). δ 0.94-1.03 (2H, m), 1.03-1.13 (2H, m), 2.93-3.10 (1H, m), 3.78 (3H, s), 7.16-7.27 (2H, m), 7.58-7.67 (3H, m), 7.70-7.87 (3H, m), 7.94-8.06 (1H, m), 8.15-8.27 (1H, m).

Example 100

1-(difluoromethyl)-3-{4-[(1-methyl-1H-benzimidazol-2-yl)oxy]phenyl}-1,3-dihydro-2H-imidazo[4,5-b]pyridin-2-one

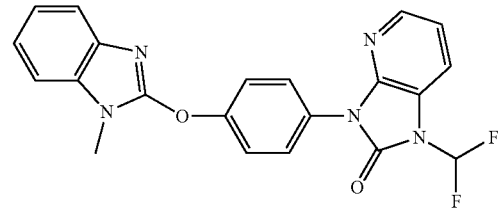 [SMILES: Cn1c(Oc2ccc(-n3c(=O)n(C(F)F)c4cccnc43)cc2)nc2ccccc21]

100a) 3-[4-(benzyloxy)phenyl]-1-(difluoromethyl)-1,3-dihydro-2H-imidazo[4,5-b]pyridin-2-one

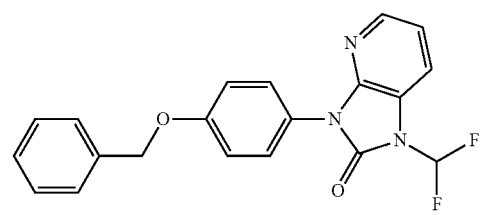 [SMILES: O=c1n(-c2ccc(OCc3ccccc3)cc2)c2ncccc2n1C(F)F]

Difluorochloroacetic acid sodium salt (1.922 g) was added to a solution of 3-[4-(benzyloxy)phenyl]-1,3-dihydro-2H-imidazo[4,5-b]pyridin-2-one (2 g), lithium bromide (1.095 g) and NaH (0.290 g) in DMF (20 ml) at 0° C. The mixture was stirred at 140° C. under a dry atmosphere (CaCl$_2$ tube) for 1 h. The reaction mixture was diluted with MeOH and concentrated in vacuo. The residue was purified by column chromatography (NH silica gel, eluted with 0%-30% EtOAc in hexane) to give 3-[4-(benzyloxy)phenyl]-1-(difluoromethyl)-1,3-dihydro-2H-imidazo[4,5-b]pyridin-2-one (420 mg) as a white solid.

MS (API+): [M+H]$^+$368.1.

$^1$H NMR (300 MHz, DMSO-d$_6$) δ 5.20 (2H, s), 6.99-8.28 (13H, m).

100b) 1-(difluoromethyl)-3-(4-hydroxyphenyl)-1,3-dihydro-2H-imidazo[4,5-b]pyridin-2-one

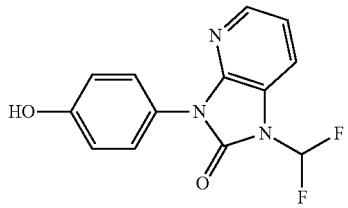 [SMILES: O=c1n(-c2ccc(O)cc2)c2ncccc2n1C(F)F]

A mixture of 3-[4-(benzyloxy)phenyl]-1-(difluoromethyl)-1,3-dihydro-2H-imidazo[4,5-b]pyridin-2-one (420 mg) and 10% Pd—C (60.8 mg) in EtOH (50 ml) was hydrogenated under balloon pressure at room temperature for 3 h. The catalyst was removed by filtration and the filtrate was concentrated in vacuo to give 1-(difluoromethyl)-3-(4-hydroxyphenyl)-1,3-dihydro-2H-imidazo[4,5-b]pyridin-2-one (300 mg) as a white solid.

MS (API+): [M+H]$^+$278.1.

$^1$H NMR (300 MHz, DMSO-d$_6$) δ 6.85-6.98 (2H, m), 7.16-7.29 (1H, m), 7.32-7.45 (2H, m), 7.60-8.04 (2H, m), 8.05-8.16 (1H, m), 9.82 (1H, s).

100c) 1-(difluoromethyl)-3-{4-[(1-methyl-1H-benzimidazol-2-yl)oxy]phenyl}-1,3-dihydro-2H-imidazo[4,5-b]pyridin-2-one

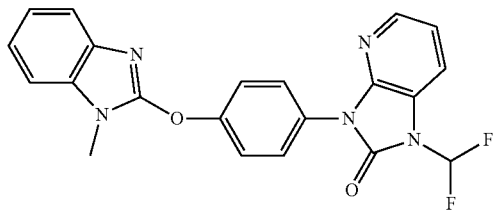 [SMILES: Cn1c(Oc2ccc(-n3c(=O)n(C(F)F)c4cccnc43)cc2)nc2ccccc21]

2-Chloro-1-methyl-1H-benzimidazole (70 mg) was added to a solution of 1-(difluoromethyl)-3-(4-hydroxyphenyl)-1,3-dihydro-2H-imidazo[4,5-b]pyridin-2-one (122 mg) and NaH (25.2 mg) in DMF (3 mL) at 100° C. The mixture was heated at 180° C. for 1 h under microwave irradiation. The reaction mixture was diluted with MeOH and concentrated in vacuo. The residue was purified by column chromatography (NH silica gel, eluted with 0%-50% EtOAc in hexane) to give 1-(difluoromethyl)-3-{4-[(1-methyl-1H-benzimidazol-2-yl)oxy]phenyl}-1,3-dihydro-2H-imidazo[4,5-b]pyridin-2-one (80 mg) as white crystals.

MS (API+): [M+H]$^+$408.1.

$^1$H NMR (300 MHz, DMSO-d$_6$) δ 3.77 (3H, s), 7.08-7.34 (3H, m). 7.37-7.54 (2H, m), 7.57-7.67 (2H, m), 7.66-8.09 (4H, m), 8.12-8.19 (1H, m).

Example 101

1-(difluoromethyl)-3-{4-[(3-methyl-3H-imidazo[4,5-b]pyridin-2-yl)oxy]phenyl}-1,3-dihydro-2H-imidazo[4,5-b]pyridin-2-one

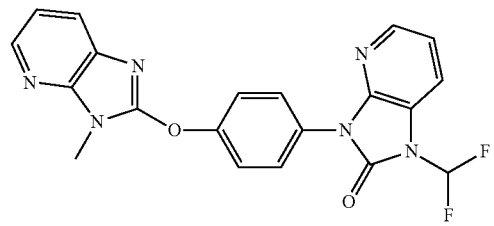 [SMILES: Cn1c(Oc2ccc(-n3c(=O)n(C(F)F)c4cccnc43)cc2)nc2cccnc21]

3-Methyl-2-(methylsulfonyl)-3H-imidazo[4,5-b]pyridine (90 mg) was added to a solution of 1-(difluoromethyl)-3-(4-hydroxyphenyl)-1,3-dihydro-2H-imidazo[4,5-b]pyridin-2-one (124 mg) and NaH (25.6 mg) in DMF (3 mL) at 100° C. The mixture was heated at 180° C. for 1 h under microwave irradiation. The reaction mixture was diluted with MeOH and concentrated in vacuo. The residue was purified by column chromatography (NH silica gel, eluted with 0%-50% EtOAc in hexane) to give 1-(difluoromethyl)-3-{4-[(3-methyl-3H-imidazo[4,5-b]pyridin-2-yl)oxy]phenyl}-1,3-dihydro-2H-imidazo[4,5-b]pyridin-2-one (50 mg) as white crystals.

MS (API+): [M+H]$^+$409.1.

$^1$H NMR (300 MHz, DMSO-d$_6$) δ 3.78 (3H, s), 7.07-7.37 (2H, m), 7.54-8.37 (9H, m).

Example 102

3,3-dimethyl-1-{4-[(1-methyl-1H-benzimidazol-2-yl)oxy]phenyl}-1,3-dihydro-2H-pyrrolo[2,3-b]pyridin-2-one

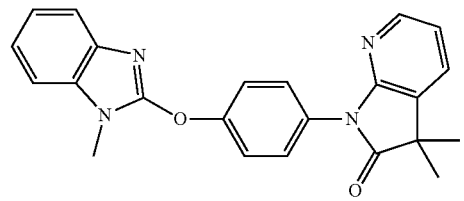 [SMILES: Cn1c(Oc2ccc(N3C(=O)C(C)(C)c4cccnc43)cc2)nc2ccccc21]

NaH (17.28 mg) was added to a solution of 1-[4-(1H-benzimidazol-2-yloxy)phenyl]-3,3-dimethyl-1,3-dihydro-2H-pyrrolo[2,3-b]pyridin-2-one (40 mg) and MeI (10.13 µl) in DMF (1 ml) at room temperature. The mixture was stirred at room temperature under a dry atmosphere (CaCl$_2$ tube) for 1 h. The reaction mixture was diluted with MeOH and concentrated in vacuo. The residue was purified by column chromatography (NH silica gel, eluted with 0%-50% EtOAc in hexane) to give 3,3-dimethyl-1-{4-[(1-methyl-1H-benzimidazol-2-yl)oxy]phenyl}-1,3-dihydro-2H-pyrrolo[2,3-b]pyridin-2-one (35 mg) as white crystals.

MS (API+): [M+H]$^+$385.2.

$^1$H NMR (300 MHz, DMSO-d$_6$) δ 1.45 (6H, s), 3.76 (3H, s), 7.09-7.25 (3H, m), 7.37-7.52 (2H, m), 7.53-7.66 (4H, m), 7.80-7.93 (1H, m), 8.06-8.20 (1H, m).

Example 103

1-cyclopropyl-3-{4-[(1-methyl-1H-benzimidazol-2-yl)oxy]phenyl}-1,3-dihydro-2H-imidazo[4,5-b]pyridin-2-one

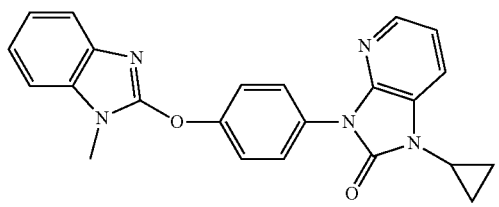 [SMILES: Cn1c(Oc2ccc(-n3c(=O)n(C4CC4)c4cccnc43)cc2)nc2ccccc21]

2-Chloro-1-methyl-1H-benzimidazole (15 mg) was added to a solution of 1-cyclopropyl-3-(4-hydroxyphenyl)-1,3-dihydro-2H-imidazo[4,5-b]pyridin-2-one (24.06 mg) and NaH (5.40 mg) in DMF (1 mL) at 100° C. The mixture was heated at 180° C. for 1 h under microwave irradiation. The reaction mixture was diluted with MeOH and concentrated in vacuo. The residue was purified by column chromatography (NH silica gel, eluted with 0%-50% EtOAc in hexane) to give 1-cyclopropyl-3-{4-[(1-methyl-1H-benzimidazol-2-yl)oxy]phenyl}-1,3-dihydro-2H-imidazo[4,5-b]pyridin-2-one (5.0 mg) as white crystals.

MS (API+): [M+H]$^+$398.2.
$^1$H NMR (300 MHz, DMSO-d$_6$) δ 0.94-1.04 (2H, m), 1.04-1.13 (2H, m), 2.96-3.08 (1H, m), 3.77 (3H, s), 7.10-7.29 (3H, m), 7.38-7.51 (2H, m), 7.54-7.67 (3H, m), 7.67-7.79 (2H, m), 7.95-8.06% (1H, m).

Example 106

6-chloro-1-ethyl-3-{4-[(1-methyl-1H-benzimidazol-2-yl)oxy]phenyl}-1,3-dihydro-2H-imidazo[4,5-b]pyridin-2-one

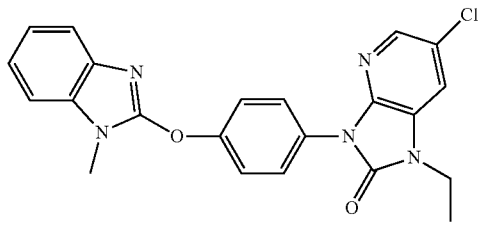 [SMILES: CCn1c(=O)n(-c2ccc(Oc3nc4ccccc4n3C)cc2)c2ncc(Cl)cc21]

106a) tert-butyl (2,5-dichloropyridin-3-yl)carbamate

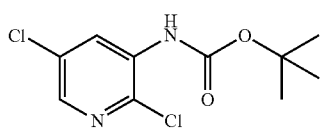 [SMILES: CC(C)(C)OC(=O)Nc1cc(Cl)cnc1Cl]

Boc$_2$O (17.05 mL) was added to a solution of 2,5-dichloropyridin-3-amine (11.4 g) and NaHMDS (1.9M, 81 mL) in THF (200 mL) at 0° C. The mixture was stirred at 0° C. under a dry atmosphere (CaCl$_2$ tube) for 1 h. The mixture was neutralized with 1N HCl at 0° C. and extracted with EtOAc. The organic layer was separated, washed with water and brine, dried over MgSO$_4$ and concentrated in vacuo. The residue was purified by column chromatography (NH silica gel, eluted with 0%-20% EtOAc in hexane) to give tert-butyl (2,5-dichloropyridin-3-yl)carbamate (15.6 g) as colorless oil.

MS (API+): [M+H]$^+$ not detected. $^1$H NMR (300 MHz, DMSO-d$_6$) δ 1.48 (9H, s), 8.20-8.23 (1H, m), 8.23-8.26 (1H, m), 9.07-9.11 (1H, m).

106b) 3-[4-(benzyloxy)phenyl]-6-chloro-1-ethyl-1,3-dihydro-2H-imidazo[4,5-b]pyridin-2-one

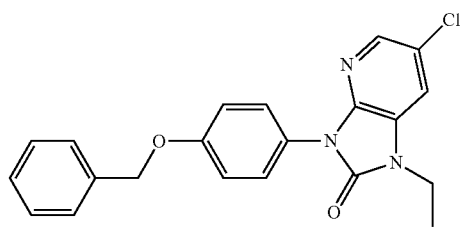 [SMILES: CCn1c(=O)n(-c2ccc(OCc3ccccc3)cc2)c2ncc(Cl)cc21]

The mixture of tert-butyl (2,5-dichloropyridin-3-yl)carbamate (7.0 g), 4-(benzyloxy)aniline (7.95 g), 9,9-dimethyl-4,5-bis(diphenylphosphino)xanthene (1.231 g), Pd$_2$(dba)$_3$ (0.974 g) and sodium tert-butoxide (3.58 g) in toluene (160 mL)-2-propanol (40.0 mL) was stirred at 100° C. under Ar overnight. The reaction mixture was concentrated in vacuo. The residue was purified by column chromatography (silica gel, eluted with 0%-100% EtOAc in hexane) to give intermediate. To the intermediate in DMF (100 mL) were added NaH (3.19 g) and ethyl iodide (20.75 g). The mixture was stirred at room temperature under a dry atmosphere (CaCl$_2$ tube) for 1 h. The reaction mixture was diluted with MeOH and concentrated in vacuo. The residue was purified by column chromatography (NH silica gel, eluted with 0%-50% EtOAc in hexane) to give 3-[4-(benzyloxy)phenyl]-6-chloro-1-ethyl-1,3-dihydro-2H-imidazo[4,5-b]pyridin-2-one (2 g) as a colorless solid.

MS (API+): [M+H]$^+$380.2.
$^1$H NMR (300 MHz, DMSO-d$_6$) δ 1.21-1.36 (3H, m), 3.88-4.02 (2H, m), 5.18 (2H, s), 7.10-7.21 (2H, m), 7.29-7.56 (7H, m), 7.85-7.93 (1H, m), 7.94-8.00 (1H, m).

106c) 6-chloro-1-ethyl-3-(4-hydroxyphenyl)-1,3-dihydro-2H-imidazo[4,5-b]pyridin-2-one

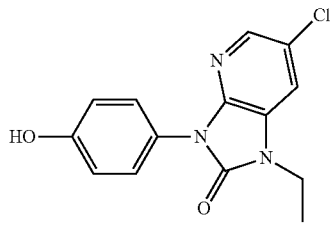 [SMILES: CCn1c(=O)n(-c2ccc(O)cc2)c2ncc(Cl)cc21]

A mixture of 3-[4-(benzyloxy)phenyl]-6-chloro-1-ethyl-1,3-dihydro-2H-imidazo[4,5-b]pyridin-2-one (500 mg) and 10% Pd—C (140 mg) in EtOAc (10 mL) was hydrogenated under balloon pressure at room temperature for 3 h. The catalyst was removed by filtration and the filtrate was concentrated in vacuo. The residue was purified by column chromatography (silica gel, eluted with 0%-50% EtOAc in hexane) to give 6-chloro-1-ethyl-3-(4-hydroxyphenyl)-1,3-dihydro-2H-imidazo[4,5-b]pyridin-2-one (70 mg) as a white solid.

MS (API+): [M+H]⁺290.1.

¹H NMR (300 MHz, DMSO-d₆) δ 1.22-1.32 (3H, m), 3.86-4.01 (2H, m), 6.83-6.96 (2H, m), 7.26-7.46 (2H, m), 7.84-7.94 (1H, m), 7.92-8.04 (1H, m), 9.74 (1H, s).

106d) 6-chloro-1-ethyl-3-{4-[(1-methyl-1H-benzimidazol-2-yl)oxy]phenyl}-1,3-dihydro-2H-imidazo[4,5-b]pyridin-2-one

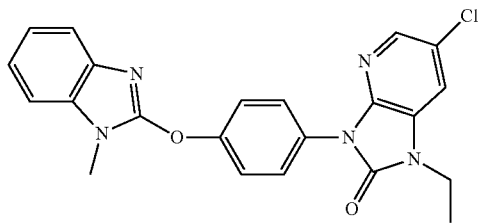 [SMILES: CCn1c(=O)n(-c2ccc(Oc3nc4ccccc4n3C)cc2)c2ncc(Cl)cc21]

2-Chloro-1-methyl-1H-benzimidazole (50 mg) was added to a solution of 6-chloro-1-ethyl-3-(4-hydroxyphenyl)-1,3-dihydro-2H-imidazo[4,5-b]pyridin-2-one (90 mg) and NaH (13.2 mg) in DMF (2 mL) at room temperature. The mixture was heated at 180° C. for 30 min under microwave irradiation. The reaction mixture was diluted with MeOH and concentrated in vacuo. The residue was purified by column chromatography (NH silica gel, eluted with 0%-50% EtOAc in hexane) to give 6-chloro-1-ethyl-3-{4-[(1-methyl-1H-benzimidazol-2-yl)oxy]phenyl}-1,3-dihydro-2H-imidazo[4,5-b]pyridin-2-one (100 mg) as colorless crystals.

MS (API+): [M+H]⁺ 420.1.

¹H NMR (300 MHz, DMSO-d₆) δ 1.25-1.34 (3H, m), 3.76 (3H, s), 3.92-4.04 (2H, m), 7.09-7.29 (2H, m), 7.37-7.52 (2H, m), 7.54-7.65 (2H, m), 7.69-7.81 (2H, m), 7.93-7.99 (1H, m), 7.99-8.07 (1H, m).

Anal. Calcd for

C₂₂H₁₈N₅O₂Cl: C, 62.93; H, 4.32; N, 16.68; Cl, 8.44. Found: C, 62.74; H, 4.38; N, 16.40; Cl.

Mp: 208-210° C.

Example 107

6-chloro-1-ethyl-3-{4-[(3-methyl-3H-imidazo[4,5-b]pyridin-2-yl)oxy]phenyl}-1,3-dihydro-2H-imidazo[4,5-b]pyridin-2-one

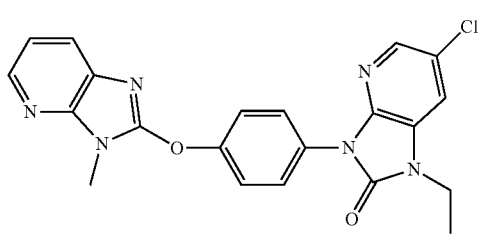 [SMILES: CCn1c(=O)n(-c2ccc(Oc3nc4cccnc4n3C)cc2)c2ncc(Cl)cc21]

3-Methyl-2-(methylsulfonyl)-3H-imidazo[4,5-b]pyridine (90 mg) was added to a solution of 6-chloro-1-ethyl-3-(4-hydroxyphenyl)-1,3-dihydro-2H-imidazo[4,5-b]pyridin-2-one (127 mg) and NaH (18.74 mg) in DMF (2 mL) at room temperature. The mixture was heated at 180° C. for 30 min under microwave irradiation. The reaction mixture was diluted with MeOH and concentrated in vacuo. The residue was purified by column chromatography (NH silica gel, eluted with 0%-50% EtOAc in hexane) to give 6-chloro-1-ethyl-3-{4-[(3-methyl-3H-imidazo[4,5-b]pyridin-2-yl)oxy]phenyl}-1,3-dihydro-2H-imidazo[4,5-b]pyridin-2-one (40 mg) as colorless crystals.

MS (API+): [M+H]⁺421.1.

¹H NMR (300 MHz, DMSO-d₆) δ 1.24-1.41 (3H, m), 3.77 (3H, s), 3.93-4.03 (2H, m), 7.15-7.28 (1H, m), 7.60-7.68 (2H, m), 7.72-7.86 (3H, m), 7.94-7.99 (1H, m), 7.99-8.08 (1H, m), 8.18-8.27 (1H, m).

Example 108

1-ethyl-3-{4-[(3-methyl-3H-imidazo[4,5-b]pyridin-2-yl)oxy]phenyl}-2-oxo-2,3-dihydro-1H-imidazo[4,5-b]pyridine-6-carbonitrile

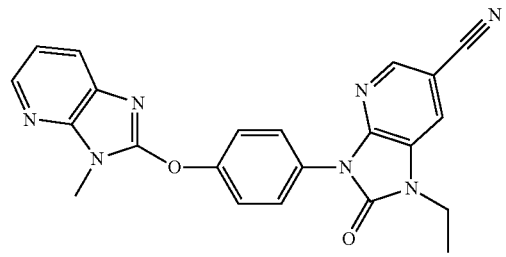 [SMILES: CCn1c(=O)n(-c2ccc(Oc3nc4cccnc4n3C)cc2)c2ncc(C#N)cc21]

108a) 3-[4-(benzyloxy)phenyl]-1-ethyl-2-oxo-2,3-dihydro-1H-imidazo[4,5-b]pyridine-6-carbonitrile

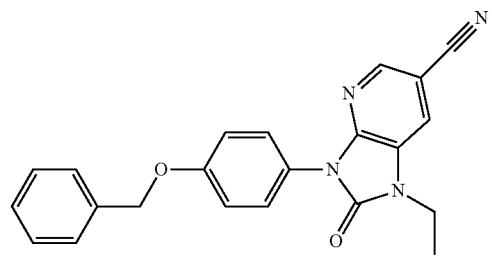 [SMILES: CCn1c(=O)n(-c2ccc(OCc3ccccc3)cc2)c2ncc(C#N)cc21]

The mixture of 3-[4-(benzyloxy)phenyl]-6-chloro-1-ethyl-1,3-dihydro-2H-imidazo[4,5-b]pyridin-2-one (1 g), zinc cyanide (2.474 g), 2-dicyclohexylphosphino-2',6'-dimethoxy-1,1'-biphenyl (0.216 g), Pd₂(dba)₃ (0.241 g) and DMF (20 mL) was heated at 150° C. for 1 h under microwave irradiation. The solid was removed by filtration, and the filtrate was concentrated in vacuo. The residue was purified by column chromatography (silica gel, eluted with 0%-50% EtOAc in hexane) to give 3-[4-(benzyloxy)phenyl]-1-ethyl-2-oxo-2,3-dihydro-1H-imidazo[4,5-b]pyridine-6-carbonitrile (710 mg) as colorless oil.

MS (API+): [M+H]⁺371.2.

¹H NMR (300 MHz, DMSO-d₆) δ 1.25-1.35 (3H, m), 3.85-4.09 (2H, m), 5.19 (2H, s), 7.08-7.24 (2H, m), 7.28-7.57 (7H, m), 8.11-8.22 (1H, m), 8.38-8.50 (1H, m).

108b) 1-ethyl-3-(4-hydroxyphenyl)-2-oxo-2,3-dihydro-1H-imidazo[4,5-b]pyridine-6-carbonitrile

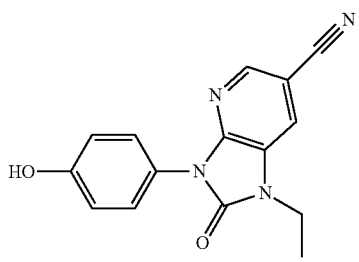 [SMILES: CCn1c(=O)n(-c2ccc(O)cc2)c2ncc(C#N)cc21]

A mixture of 3-[4-(benzyloxy)phenyl]-1-ethyl-2-oxo-2,3-dihydro-1H-imidazo[4,5-b]pyridine-6-carbonitrile (500 mg) and 10% Pd—C (71.8 mg) in EtOAc (50 ml) was hydrogenated under balloon pressure at room temperature for 1 h. The catalyst was removed by filtration and the filtrate was concentrated in vacuo. The residue was purified by column chromatography (silica gel, eluted with 0%-50% EtOAc in hexane) to give 1-ethyl-3-(4-hydroxyphenyl)-2-oxo-2,3-dihydro-1H-imidazo[4,5-b]pyridine-6-carbonitrile (90 mg) as a white solid.

MS (API+): [M+H]⁺281.2.

¹H NMR (300 MHz, DMSO-d₆) δ 1.24-1.34 (3H, m), 3.90-4.01 (2H, m), 6.81-6.99 (2H, m), 7.29-7.39 (2H, m), 8.12-8.19 (1H, m), 8.38-8.48 (1H, m), 9.71-9.84 (1H, m).

108c) 1-ethyl-3-{4-[(3-methyl-3H-imidazo[4,5-b]pyridin-2-yl)oxy]phenyl}-2-oxo-2,3-dihydro-1H-imidazo[4,5-b]pyridine-6-carbonitrile

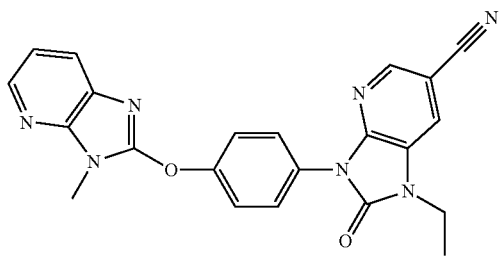 [SMILES: CCn1c(=O)n(-c2ccc(Oc3nc4cccnc4n3C)cc2)c2ncc(C#N)cc21]

3-Methyl-2-(methylsulfonyl)-3H-imidazo[4,5-b]pyridine (45 mg) was added to a solution of 1-ethyl-3-(4-hydroxyphenyl)-2-oxo-2,3-dihydro-1H-imidazo[4,5-b]pyridine-6-carbonitrile (61.5 mg) and NaH (9.0 mg) in DMF (1 mL) at room temperature. The mixture was heated at 180° C. for 30 min under microwave irradiation. The reaction mixture was diluted with MeOH and concentrated under reduced pressure. The residue was purified by column chromatography (NH silica gel, eluted with 0%-50% EtOAc in hexane) to give 1-ethyl-3-{4-[(3-methyl-3H-imidazo[4,5-b]pyridin-2-yl)oxy]phenyl}-2-oxo-2,3-dihydro-1H-imidazo[4,5-b]pyridine-6-carbonitrile (11 mg) as white crystals.

MS (API+): [M+H]⁺412.2.

¹H NMR (300 MHz, DMSO-d₆) δ 1.27-1.40 (3H, m), 3.78 (3H, s), 3.94-4.08 (2H, m), 7.14-7.26 (1H, m), 7.60-7.71 (2H, m), 7.71-7.88 (3H, m), 8.18-8.30 (2H, m), 8.44-8.54 (1H, m).

Example 109

1-ethyl-3-{4-[(1-methyl-1H-benzimidazol-2-yl)oxy]phenyl}-2-oxo-2,3-dihydro-1H-imidazo[4,5-b]pyridine-6-carbonitrile

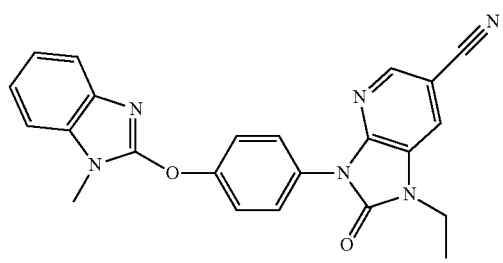 [SMILES: CCn1c(=O)n(-c2ccc(Oc3nc4ccccc4n3C)cc2)c2ncc(C#N)cc21]

2-Chloro-1-methyl-1H-benzimidazole (15 mg) was added to a solution of 1-ethyl-3-(4-hydroxyphenyl)-2-oxo-2,3-dihydro-1H-imidazo[4,5-b]pyridine-6-carbonitrile (25.5 mg) and sodium hydride (4.0 mg) in DMF (1.0 mL) at room temperature. The mixture was heated at 180° C. for 30 min under microwave irradiation. The reaction mixture was diluted with MeOH and concentrated in vacuo. The residue was purified by column chromatography (NH silica gel, eluted with 0%-30% EtOAc in hexane) to give 1-ethyl-3-{4-[(1-methyl-1H-benzimidazol-2-yl)oxy]phenyl}-2-oxo-2,3-dihydro-1H-imidazo[4,5-b]pyridine-6-carbonitrile (5 mg) as white crystals.

MS (API+): [M+H]⁺411.2.

¹H NMR (300 MHz, DMSO-d₆) δ 1.27-1.36 (3H, m), 3.77 (3H, s), 3.92-4.09 (2H, m), 7.08-7.33 (2H, m), 7.38-7.53 (2H, m), 7.55-7.67 (2H, m), 7.68-7.82 (2H, m), 8.12-8.31 (1H, m), 8.41-8.59 (1H, m).

Example 112

1-ethyl-3-{4-[(1-methyl-4,5,6,7-tetrahydro-1H-benzimidazol-2-yl)oxy]phenyl}-1,3-dihydro-2H-imidazo[4,5-b]pyridin-2-one

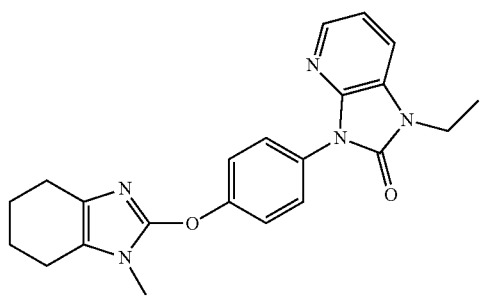 [SMILES: CCn1c(=O)n(-c2ccc(Oc3nc4c(n3C)CCCC4)cc2)c2ncccc21]

112a) 2-(methylsulfanyl)-4,5,6,7-tetrahydro-1H-benzimidazole

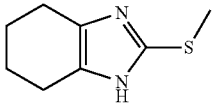

To a solution of 4,5,6,7-tetrahydro-1H-benzimidazole-2-thiol (500 mg) in acetone (5 mL) were added $K_2CO_3$ (1344 mg) and MeI (0.223 mL) at room temperature. After stirring for 1 h, the mixture was quenched with water, and extracted with ethyl acetate, and the extract was washed with brine and dried over magnesium sulfate. The residue was purified by column chromatography (silica gel, eluted with 40%-90% EtOAc in hexane) to give 2-(methylsulfanyl)-4,5,6,7-tetrahydro-1H-benzimidazole (545 mg) as a white solid.

MS (API+): [M+H]$^+$169.0.
$^1$H NMR (300 MHz, DMSO-d$_6$) δ 1.69 (4 H, br. s.), 2.47-2.65 (4 H, m), 3.33 (3 H, s), 11.43-11.98 (1 H, m).

112b) 2-(methylsulfonyl)-4,5,6,7-tetrahydro-1H-benzimidazole

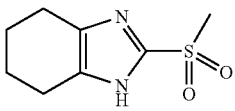

To a solution of 2-(methylsulfanyl)-4,5,6,7-tetrahydro-1H-benzimidazole (280 mg) in EtOAc (5 ml) was added mCPBA (766 mg) at 0° C. After stirring for 10 h, the mixture was quenched with water, and extracted with ethyl acetate, and the extract was washed with brine, and dried over magnesium sulfate. The residue was purified by column chromatography (silica gel, eluted with 20%-80% EtOAc in hexane) to give 2-(methylsulfonyl)-4,5,6,7-tetrahydro-1H-benzimidazole (200 mg) as white crystals.

MS (API+): [M+H]$^+$ 201.0.
$^1$H NMR (300 MHz, DMSO-d$_6$) δ 1.67-1.88 (4 H, m), 2.51-2.65 (4 H, m), 3.23 (3 H, s), 13.17 (1 H, none)

112c) 1-methyl-2-(methylsulfonyl)-4,5,6,7-tetrahydro-1H-benzimidazole

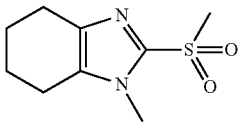

Sodium hydride (55.8 mg) (60% in mineral oil) was added to a solution of 2-(methylsulfonyl)-4,5,6,7-tetrahydro-1H-benzimidazole (233 mg) and MeI (0.080 mL) in DMF (dry) (10 mL) at room temperature. The mixture was stirred at room temperature under a dry atmosphere (CaCl$_2$ tube) for 1 h. The reaction mixture was diluted with MeOH (2 mL), and concentrated in vacuo. The residue was purified by column chromatography (silica gel, eluted with 0%-30% EtOAc in hexane) to give 1-methyl-2-(methylsulfonyl)-4,5,6,7-tetrahydro-1H-benzimidazole (200 mg) as a white solid.

MS (API+): [M+H]$^+$215.0.
$^1$H NMR (300 MHz, DMSO-d$_6$) δ 1.59-1.93 (3 H, m), 2.50 (5 H, br. s.), 3.18-3.43 (6 H, m)

112d) 1-ethyl-3-{4-[(1-methyl-4,5,6,7-tetrahydro-1H-benzimidazol-2-yl)oxy]phenyl}-1,3-dihydro-2H-imidazo[4,5-b]pyridin-2-one

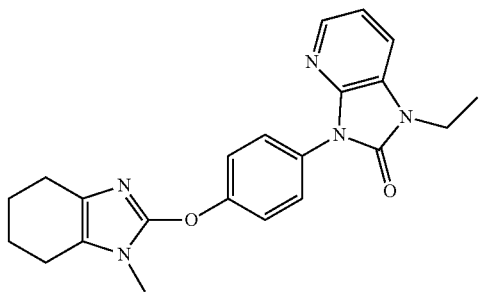 [SMILES: CCn1c(=O)n(-c2ccc(Oc3nc4c(n3C)CCCC4)cc2)c2ncccc21]

1-Methyl-2-(methylsulfonyl)-4,5,6,7-tetrahydro-1H-benzimidazole (84 mg) was added to a solution of 1-ethyl-3-(4-hydroxyphenyl)-1,3-dihydro-2H-imidazo[4,5-b]pyridin-2-one (100 mg) and NaH (18.8 mg) (60% in mineral oil) in DMA (3 mL) in a microwave vessel. The vessel was sealed and subjected to microwave irradiation (at 120° C. set by IR sensor, fixed hold time: on, Absorption level: High) for 1 h in a Biotage Initiator 60EXP. The mixture was poured into water, and the mixture was extracted with ethyl acetate. The extract was washed with brine, dried over magnesium sulfate, and concentrated under reduced pressure. The residue was purified by column chromatography (silica gel, eluted with 20%-100% EtOAc in hexane) to give 1-ethyl-3-{4-[(1-methyl-4,5,6,7-tetrahydro-1H-benzimidazol-2-yl)oxy]phenyl}-1,3-dihydro-2H-imidazo[4,5-b]pyridin-2-one (8.90 mg) as white crystals.

MS (API+): [M+H]$^+$390.1.
$^1$H NMR (300 MHz, DMSO-d$_6$) δ 1.29 (4 H, s), 1.64-1.83 (5 H, m), 2.31-2.40 (3 H, m), 2.42-2.47 (2 H, m), 3.35-3.40 (1 H, m), 3.90-4.03 (2 H, m), 7.11-7.22 (1 H, m), 7.28-7.39 (1 H, m), 7.59-7.72 (3 H, m), 7.93-8.02 (1 H, m).

Example 115

1-ethyl-3-[4-(3H-imidazo[4,5-c]pyridin-2-yloxy)phenyl]-1,3-dihydro-2H-imidazo[4,5-b]pyridin-2-one

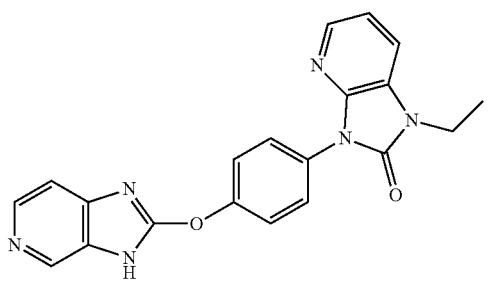 [SMILES: CCn1c(=O)n(-c2ccc(Oc3nc4ccncc4[nH]3)cc2)c2ncccc21]

115a) 1H-imidazo[4,5-c]pyridine-2-thiol

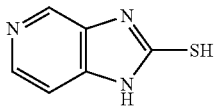

To a solution of pyridine-3,4-diamine (5 g) in EtOH (80 ml) was added carbon disulfide (10 mL) at room temperature. The mixture was stirred at 40° C. under a dry atmosphere (CaCl$_2$ tube) for 10 h. The mixture was cooled to room temperature. The resulting white solid was collected by filtration and washed with ether to give 1H-imidazo[4,5-c]pyridine-2-thiol (6.1 g) as a white solid.

MS (API+): [M+H]$^+$ 152.0

$^1$H NMR (300 MHz, DMSO-d$_6$) δ 7.17 (1 H, d, J=5.29 Hz), 8.25 (1 H, d, J=5.67 Hz), 8.38 (1 H, s), 12.87 (2 H, br. s.).

115b) 2-(methylsulfanyl)-1H-imidazo[4,5-c]pyridine

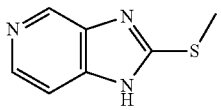

To a solution of 1H-imidazo[4,5-c]pyridine-2-thiol (4 g) in acetone (50 ml) were added potassium carbonate (11 g) and MeI (1.8 ml). After stirring for 3 h, the mixture was filtered. The filtrate was concentrated under reduced pressure. The residue was purified by column chromatography (silica gel, eluted with 10%-70% EtOAc in hexane) to give 2-(methylsulfanyl)-1H-imidazo[4,5-c]pyridine (4.07 g) as a yellow solid.

MS (API+): [M+H]$^+$166.0.

$^1$H NMR (300 MHz, DMSO-d$_6$) δ 2.72 (3 H, s), 7.42-7.52 (1 H, m), 8.09-8.27 (1 H, m), 8.77 (1 H, s)

115c) 2-(methylsulfonyl)-1H-imidazo[4,5-c]pyridine

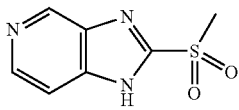

To a solution of 2-(methylsulfanyl)-1H-imidazo[4,5-c]pyridine (4 g) in EtOAc (50 mL) was added mCPBA (11.14 g) at 0° C. After stirring for 10 h, the mixture was quenched with water, and extracted with ethyl acetate, and the extract was washed with brine, and dried over magnesium sulfate. The crude material was recrystallized from ethyl acetate to give 2-(methylsulfonyl)-1H-imidazo[4,5-c]pyridine (1.100 g) as a white solid.

MS (API+): [M+H]$^+$ 198.1.

$^1$H NMR (300 MHz, DMSO-d$_6$) δ 3.39 (3 H, s), 7.76-8.03 (1 H, m), 8.21-8.31 (1 H, m), 9.23 (1 H, s), 13.93-14.52 (1 H, m).

115d) 2-(methylsulfonyl)-1-{[2-(trimethylsilyl)ethoxy]methyl}-1H-imidazo[4,5-c]pyridine

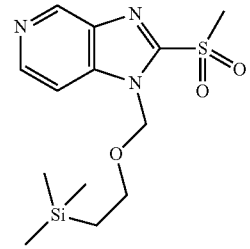 [SMILES: C[Si](C)(C)CCOCn1c(S(C)(=O)=O)nc2cnccc21]

NaH (122 mg) (60% in mineral oil) was added to a solution of 2-(methylsulfonyl)-1H-imidazo[4,5-c]pyridine (500 mg) and 2-(trimethylsilyl)ethoxymethyl chloride (0.538 mL) in DMF (3 ml) at room temperature. The mixture was stirred at room temperature under a dry atmosphere (CaCl$_2$ tube) for 1 h. The reaction mixture was diluted with MeOH (2 mL), and concentrated in vacuo. The residue was purified by column chromatography (silica gel, eluted with 0%-30% EtOAc in hexane) to give 2-(methylsulfonyl)-1-{[2-(trimethylsilyl)ethoxy]methyl}-1H-imidazo[4,5-c]pyridine (330 mg) as a light brown solid.

MS (API+): [M+H]$^+$328.1.

115e) 1-ethyl-3-[4-(3H-imidazo[4,5-c]pyridin-2-yloxy)phenyl]-1,3-dihydro-2H-imidazo[4,5-b]pyridin-2-one

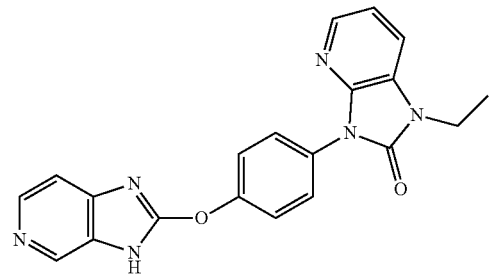 [SMILES: CCn1c(=O)n(-c2ccc(Oc3nc4ccncc4[nH]3)cc2)c2ncccc21]

2-(Methylsulfonyl)-1-{[2-(trimethylsilyl)ethoxy]methyl}-1H-imidazo[4,5-c]pyridine (350 mg) was added to a solution of 1-ethyl-3-(4-hydroxyphenyl)-1,3-dihydro-2H-imidazo[4,5-b]pyridin-2-one (220 mg) and NaH (41.4 mg) (60% in mineral oil) in THF (1 ml) in a microwave vessel. The vessel was sealed and subjected to microwave irradiation (at 120° C. set by IR sensor, fixed hold time: on, Absorption level: High) for 30 min in a Biotage Initiator 60EXP. The mixture was poured into water, and extracted with ethyl acetate, and the extract was washed with brine, dried over magnesium sulfate, and concentrated under reduced pressure. The residue was purified by column chromatography (silica gel, eluted with 0%-20% MeOH in EtOAc) to give intermediate (230 mg) as a white solid. To a solution of the intermediate (120 mg) in THF (2 mL) was added TBAF (0.955 mL) in a microwave vessel. The vessel was sealed and subjected to microwave irradiation (at 100° C. set by IR sensor, fixed hold time: on, Absorption level: Normal) for 1 h in a Biotage Initiator 60EXP. The mixture was poured into water, the mixture was extracted with ethyl acetate, and the extract was washed with brine (20 mL×2), dried over magnesium sulfate, and concentrated under reduced pressure. The residue was purified by column chromatography (NH-silica gel, eluted with 0%-5% Methanol in EtOAc; and then, silica gel, eluted with 0%-5% Methanol in EtOAc) to give 1-ethyl-3-[4-(3H-imidazo[4,5-c]pyridin-2-yloxy)phenyl]-1,3-dihydro-2H-imidazo[4,5-b]pyridin-2-one (32.8 mg) as white crystals.

MS (API+): [M+H]$^+$ 373.2.

$^1$H NMR (300 MHz, DMSO-d$_6$) δ 1.32 (3 H, none), 3.91-4.10 (2 H, m), 7.13-7.26 (1 H, m), 7.43-7.56 (3 H, m), 7.62-7.77 (3 H, m), 7.95-8.03 (1 H, m), 8.03-8.14 (1 H, m), 8.54-8.67 (1 H, m).

Example 118

1-ethyl-6-methyl-3-{4-[(3-methyl-3H-imidazo[4,5-b]pyridin-2-yl)oxy]phenyl}-1,3-dihydro-2H-imidazo[4,5-b]pyridin-2-one

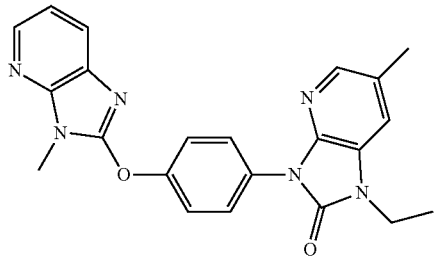 [SMILES: CCn1c(=O)n(-c2ccc(Oc3nc4cccnc4n3C)cc2)c2ncc(C)cc21]

118a) N-[4-(benzyloxy)phenyl]-5-methyl-3-nitropyridin-2-amine

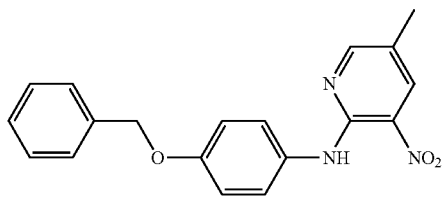

To a mixture of 4-(benzyloxy)aniline hydrochloride (4.10 g) and 2-chloro-5-methyl-3-nitropyridine (3.0 g) in DMF (30 mL) was added TEA (7.27 mL) at room temperature, and the mixture was stirred at room temperature for 2 h. The mixture was heated to 60° C. After stirring at 60° C. overnight, K$_2$CO$_3$ (4.81 g) was added to the mixture. The mixture was heated to 100° C. and stirred at 100° C. overnight. The mixture was poured into water and the mixture was extracted with AcOEt. The combined organic layer was washed with brine, dried over Na$_2$SO$_4$, filtered and concentrated in vacuo. The residue was purified by column chromatography (dry charge, silica gel, eluted with 5%-30% AcOEt in hexane) to give N-[4-(benzyloxy)phenyl]-5-methyl-3-nitropyridin-2-amine (1.33 g) as a red solid.

$^1$H NMR (300 MHz, DMSO-d$_6$) δ 2.26 (3H, s), 5.11 (2H, s), 6.96-7.05 (2H, m), 7.29-7.54 (7H, m), 8.32-8.38 (2H, m), 9.78 (1H, s).

118b) N$^2$-[4-(benzyloxy)phenyl]-5-methylpyridine-2,3-diamine

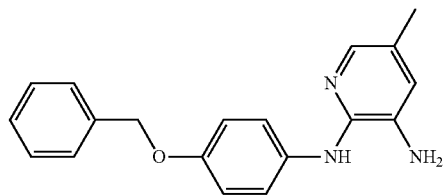 [SMILES: Cc1cnc(Nc2ccc(OCc3ccccc3)cc2)c([N+](=O)[O-])c1]

To a solution of N-[4-(benzyloxy)phenyl]-5-methyl-3-nitropyridin-2-amine (1.33 g) in acetic acid (10 mL) and THF (10 mL) was added zinc (2.59 g) at 0° C., and the mixture was stirred at 0° C. for 2 h. After stirring at room temperature overnight, the mixture was filtered and the filtrate was concentrated in vacuo. The residue was diluted with AcOEt, washed with sat. NaHCO$_3$, dried over Na$_2$SO$_4$, filtered and concentrated in vacuo. The residue was purified by column chromatography (NH silica gel, eluted with 5%-50% AcOEt in hexane) to give N$^2$-[4-(benzyloxy)phenyl]-5-methylpyridine-2,3-diamine (0.63 g) as a blue solid.

MS (API+): [M+H]$^+$306.4.

$^1$H NMR (300 MHz, DMSO-d$_6$) δ 2.08 (3H, s), 4.93 (2H, s), 5.04 (2H, s), 6.70 (1H, d, J=1.9 Hz), 6.89 (2H, d, J=9.1 Hz), 7.23-7.54 (9H, m).

118c) 3-[4-(benzyloxy)phenyl]-6-methyl-1,3-dihydro-2H-imidazo[4,5-b]pyridin-2-one

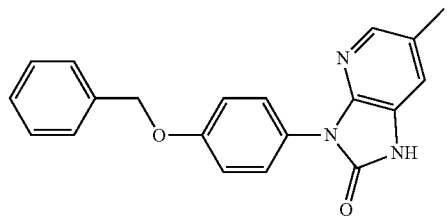 [SMILES: Cc1cnc2c(c1)[nH]c(=O)n2-c1ccc(OCc2ccccc2)cc1]

A solution of N$^2$-[4-(benzyloxy)phenyl]-5-methylpyridine-2,3-diamine (0.63 g) and CDI (0.67 g) in THF (20 mL) was refluxed overnight. The mixture was concentrated in vacuo. The residual solid was washed with AcOEt to give 3-[4-(benzyloxy)phenyl]-6-methyl-1,3-dihydro-2H-imidazo[4,5-b]pyridin-2-one (0.64 g) as an off-white solid.

MS (API+): [M+H]$^+$332.2.

$^1$H NMR (300 MHz, DMSO-d$_6$) δ 2.30 (3H, s), 5.18 (2H, s), 7.09-7.78 (11H, m), 11.23 (1H, brs).

118d) 3-[4-(benzyloxy)phenyl]-1-ethyl-6-methyl-1,3-dihydro-2H-imidazo[4,5-b]pyridin-2-one

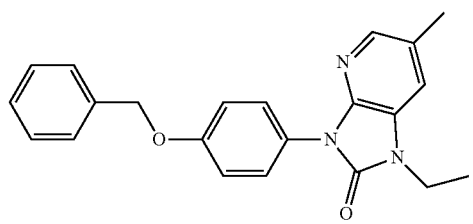 [SMILES: CCn1c(=O)n(-c2ccc(OCc3ccccc3)cc2)c2ncc(C)cc21]

A mixture of 3-[4-(benzyloxy)phenyl]-6-methyl-1,3-dihydro-2H-imidazo[4,5-b]pyridin-2-one (0.64 g), iodoethane (0.20 mL) and cesium carbonate (1.26 g) in DMF (5 mL) was stirred at 50° C. for 4 h. After stirring at room temperature over weekend, the mixture was poured into water, and the mixture was extracted with AcOEt. The organic layer was washed with brine, dried over Na$_2$SO$_4$, filtered and concentrated in vacuo to give 3-[4-(benzyloxy)phenyl]-1-ethyl-6-methyl-1,3-dihydro-2H-imidazo[4,5-b]pyridin-2-one (0.68 g) as a brown oil.

MS (API+): [M+H]$^+$360.2.

118e) 1-ethyl-3-(4-hydroxyphenyl)-6-methyl-1,3-dihydro-2H-imidazo[4,5-b]pyridin-2-one

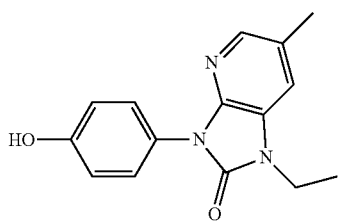 [SMILES: CCn1c(=O)n(-c2ccc(O)cc2)c2ncc(C)cc21]

A mixture of 3-[4-(benzyloxy)phenyl]-1-ethyl-6-methyl-1,3-dihydro-2H-imidazo[4,5-b]pyridin-2-one (0.68 g) and 10% palladium on carbon (0.30 g) in MeOH (15 mL) was hydrogenated under balloon pressure at room temperature for 2 h. The catalyst was removed by filtration and the filtrate was concentrated in vacuo to give 1-ethyl-3-(4-hydroxyphenyl)-6-methyl-1,3-dihydro-2H-imidazo[4,5-b]pyridin-2-one (0.50 g) as a pale yellow solid.

MS (API+): [M+H]$^+$270.2.
$^1$H NMR (300 MHz, DMSO-d$_6$) δ 1.27 (3H, t, J=7.2 Hz), 2.33 (3H, s), 3.92 (2H, q, J=7.2 Hz), 6.83-6.91 (2H, m), 7.31-7.39 (2H, m), 7.48 (1H, d, J=1.5 Hz), 7.74-7.81 (1H, m).

118f) 1-ethyl-6-methyl-3-{4-[(3-methyl-3,1-imidazo[4,5-b]pyridin-2-yl)oxy]phenyl}-1,3-dihydro-2H-imidazo[4,5-b]pyridin-2-one

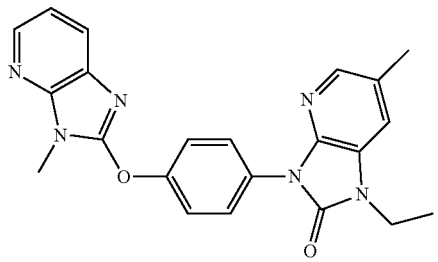 [SMILES: CCn1c(=O)n(-c2ccc(Oc3nc4cccnc4n3C)cc2)c2ncc(C)cc21]

To a solution of 3-methyl-2-(methylsulfonyl)-3H-imidazo[4,5-b]pyridine (156 mg) and 1-ethyl-3-(4-hydroxyphenyl)-6-methyl-1,3-dihydro-2H-imidazo[4,5-b]pyridin-2-one (166 mg) in DMF (3 mL) was added NaH (30 mg) at room temperature, and the mixture was stirred at 150° C. under microwave irradiation for 2 h. The mixture was partitioned between water and AcOEt. The organic layer was washed with brine, dried over Na$_2$SO$_4$, filtered and concentrated in vacuo. The residue was purified by column chromatography (dry charge, NH silica gel, eluted with 50%-100% AcOEt in hexane) and column chromatography (dry charge, silica gel, eluted with 50%-100% AcOEt in hexane), and recrystallized from MeOH to give 1-ethyl-6-methyl-3-{4-[(3-methyl-3H-imidazo[4,5-b]pyridin-2-yl)oxy]phenyl}-1,3-dihydro-2H-imidazo[4,5-b]pyridin-2-one (43 mg) as white crystals.

MS (API+): [M+H]$^+$ 401.3.
$^1$H NMR (300 MHz, DMSO-d$_6$) δ 1.30 (3H, t, J=7.2 Hz), 2.37 (3H, s), 3.77 (3H, s), 3.96 (2H, q, J=7.2 Hz), 7.20 (1H, dd, J=7.7, 5.1 Hz), 7.54-7.66 (3H, m), 7.75-7.87 (4H, m), 8.21 (1H, dd, J=4.9, 1.5 Hz).

mp 217-219° C.
Anal. Calcd for C$_{22}$H$_{20}$N$_6$O$_2$: C, 65.99; H, 5.03; N, 20.99. Found: C, 65.93; H, 5.16; N, 20.89.

Example 119

1-ethyl-6-methoxy-3-{4-[(3-methyl-3H-imidazo[4,5-b]pyridin-2-yl)oxy]phenyl}-1,3-dihydro-2H-imidazo[4,5-b]pyridin-2-one

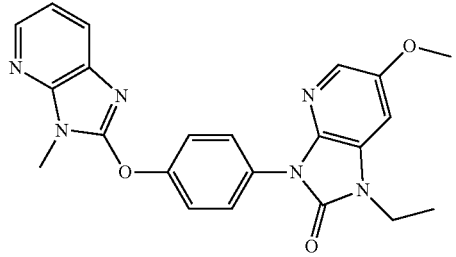 [SMILES: CCn1c(=O)n(-c2ccc(Oc3nc4cccnc4n3C)cc2)c2ncc(OC)cc21]

119a) 3-[4-(benzyloxy)phenyl]-1-ethyl-6-methoxy-1,3-dihydro-2H-imidazo[4,5-b]pyridin-2-one

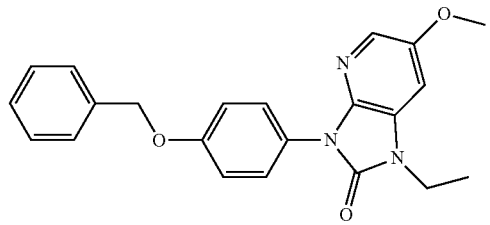 [SMILES: CCn1c(=O)n(-c2ccc(OCc3ccccc3)cc2)c2ncc(OC)cc21]

A mixture of 3-[4-(benzyloxy)phenyl]-6-chloro-1-ethyl-1,3-dihydro-2H-imidazo[4,5-b]pyridin-2-one (190 mg), Pd$_2$dba$_3$ (23 mg), 2-di-tert-butylphosphino-3,4,5,6-tetramethyl-2',4',6'-triisopropyl-1,1'-biphenyl (48 mg) and KOH (145 mg) in dioxane (3 mL) and water (3 mL) was stirred at 100° C. under Ar atmosphere for 6 h. The mixture was cooled to room temperature, and cetyltrimethylammonium bromide (50 mg) and iodomethane (0.034 mL) were added. After stirring at 100° C. for 2 h, the mixture was cooled to room temperature. Iodomethane (0.034 mL) was added to the mixture. After stirring at room temperature, the mixture was poured into water, and the mixture was extracted with AcOEt. The organic layer was dried over Na$_2$SO$_4$, filtered and concentrated in vacuo. The residue was purified by column chromatography (silica gel, eluted with 5%-40% AcOEt in hexane) to give 3-[4-(benzyloxy)phenyl]-1-ethyl-6-methoxy-1,3-dihydro-2H-imidazo[4,5-b]pyridin-2-one (125 mg) as a dark yellow oil.

MS (API+): [M+H]⁺376.3.

¹H NMR (300 MHz, CDCl₃) δ 1.39 (3H, t, J=7.2 Hz), 3.88 (3H, s), 3.98 (2H, q, J=7.4 Hz), 5.11 (2H, s), 6.90 (1H, d, J=2.3 Hz), 7.06-7.15 (2H, m), 7.29-7.49 (5H, m), 7.53-7.62 (2H, m), 7.73 (1H, d, J=2.6 Hz).

119b) 1-ethyl-3-(4-hydroxyphenyl)-6-methoxy-1,3-dihydro-2H-imidazo[4,5-b]pyridin-2-one

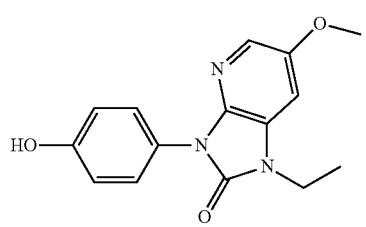 [SMILES: CCn1c(=O)n(-c2ccc(O)cc2)c2ncc(OC)cc21]

A mixture of 3-[4-(benzyloxy)phenyl]-1-ethyl-6-methoxy-1,3-dihydro-2H-imidazo[4,5-b]pyridin-2-one (120 mg) and 10% palladium on carbon (40 mg) in MeOH (10 mL) was hydrogenated under balloon pressure at room temperature for 2 h. The catalyst was removed by filtration and the filtrate was concentrated in vacuo to give 1-ethyl-3-(4-hydroxyphenyl)-6-methoxy-1,3-dihydro-2H-imidazo[4,5-b]pyridin-2-one (75 mg) as white crystals.

MS (API+): [M+H]⁺ 286.1.

¹H NMR (300 MHz, CDCl₃) δ 1.41 (3H, t, J=7.2 Hz), 3.89 (3H, s), 4.00 (2H, q, J=7.2 Hz), 6.76 (2H, d, J=8.7 Hz), 6.94 (1H, d, J=2.3 Hz), 7.16 (1H, brs), 7.29 (2H, d, J=8.7 Hz), 7.73 (1H, d, J=2.3 Hz).

119c) 1-ethyl-6-methoxy-3-{4-[(3-methyl-3H-imidazo[4,5-b]pyridin-2-yl)oxy]phenyl}-1,3-dihydro-2H-imidazo[4,5-b]pyridin-2-one

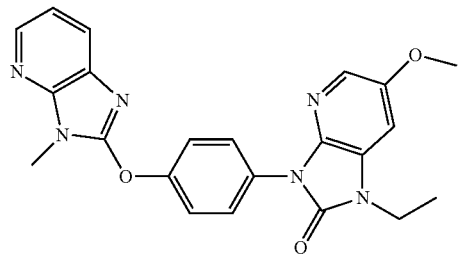 [SMILES: CCn1c(=O)n(-c2ccc(Oc3nc4cccnc4n3C)cc2)c2ncc(OC)cc21]

To a solution of 3-methyl-2-(methylsulfonyl)-3H-imidazo[4,5-b]pyridine (67 mg) and 1-ethyl-3-(4-hydroxyphenyl)-6-methoxy-1,3-dihydro-2H-imidazo[4,5-b]pyridin-2-one (75 mg) in DMF (3 mL) was added NaH (13 mg) at room temperature, and the mixture was stirred at 150° C. under microwave irradiation for 2 h. The mixture was partitioned between water and AcOEt. The organic layer was washed with brine, dried over Na₂SO₄, filtered and concentrated in vacuo. The residue was purified by column chromatography (dry charge, NH silica gel, eluted with 50%-100% AcOEt in hexane) and column chromatography (dry charge, silica gel, eluted with 50%-100% AcOEt in hexane), and recrystallized from MeOH to give 1-ethyl-6-methoxy-3-{4-[(3-methyl-3H-imidazo[4,5-b]pyridin-2-yl)oxy]phenyl}-1,3-dihydro-2H-imidazo[4,5-b]pyridin-2-one (17 mg) as white crystals.

MS (API+): [M+H]⁺417.4.

¹H NMR (300 MHz, DMSO-d₆) δ 1.30 (3H, t, J=7.2 Hz), 3.77 (3H, s), 3.86 (3H, s), 3.98 (2H, q, J=7.2 Hz), 7.20 (1H, dd, J=7.9, 4.9 Hz), 7.50 (1H, d, J=2.3 Hz), 7.58-7.65 (2H, m), 7.73 (1H, d, J=2.3 Hz), 7.76-7.84 (3H, m), 8.21 (1H, dd, J=4.9, 1.3 Hz).

Anal. Calcd for C₂₂H₂₀N₆O₃: C, 63.45; H, 4.84; N, 20.18. Found: C, 63.52; H, 4.86; N, 20.12.

Mp: 197-198° C.

Example 120

1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one

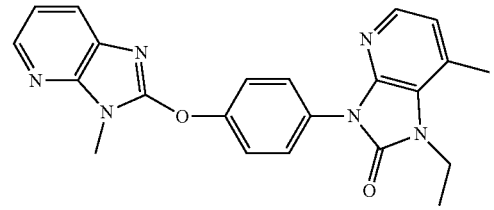 [SMILES: CCn1c(=O)n(-c2ccc(Oc3nc4cccnc4n3C)cc2)c2nccc(C)c21]

Method A 120a) 3-[4-(benzyloxy)phenyl]-7-methyl-1,3-dihydro-2H-imidazo[4,5-b]pyridin-2-one

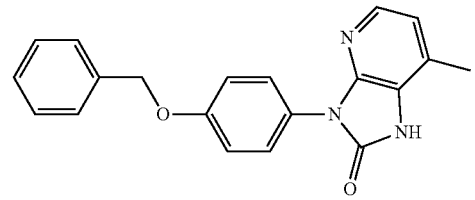 [SMILES: Cc1ccnc2c1[nH]c(=O)n2-c1ccc(OCc2ccccc2)cc1]

A mixture of tert-butyl (2-chloro-4-methylpyridin-3-yl)carbamate (2.00 g), 4-(benzyloxy)aniline hydrochloride (2.91 g), 9,9-dimethyl-4,5-bis(diphenylphosphino)xanthene (381 mg), sodium t-butoxide (1.90 g) and Pd₂(dba)₃ (302 mg) in 2-propanol (6 mL) and toluene (24 mL) was stirred at 100° C. under N₂ atmosphere for 24 h. The reaction mixture was concentrated in vacuo. The residue was dissolved in MeOH, and the precipitate was removed by filtration. The filtrate was concentrated and the residue was purified by column chromatography (NH silica gel, eluted with 15%-50% AcOEt in hexane) to give 3-[4-(benzyloxy)phenyl]-7-methyl-1,3-dihydro-2H-imidazo[4,5-b]pyridin-2-one (988 mg) as a colorless solid.

MS (API+): [M+H]⁺332.3.

¹H NMR (300 MHz, CDCl₃) δ 2.39 (3H, s), 5.12 (2H, s), 6.87 (1H, d, J=5.3 Hz), 7.12 (2H, d, J=9.0 Hz), 7.28-7.50 (5H, m), 7.57 (2H, d, J=8.7 Hz), 7.96 (1H, d, J=5.3 Hz), 9.93 (1H, brs).

120b) 3-[4-(benzyloxy)phenyl]-1-ethyl-7-methyl-1,3-dihydro-2H-imidazo[4,5-b]pyridin-2-one

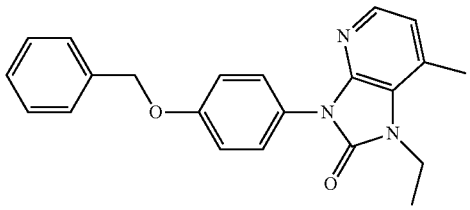 [SMILES: CCn1c(=O)n(-c2ccc(OCc3ccccc3)cc2)c2nccc(C)c21]

Iodoethane (0.289 ml) was added to a mixture of 3-[4-(benzyloxy)phenyl]-7-methyl-1,3-dihydro-2H-imidazo[4,5-b]pyridin-2-one (998 mg) and cesium carbonate (1.96 g) in DMF (10 mL) at room temperature. The mixture was stirred at 50° C. for 4 h. The mixture was diluted with water at room temperature and extracted with AcOEt. The organic layer was separated, washed with water and brine, dried over MgSO$_4$ and concentrated in vacuo. The residue was purified by column chromatography (silica gel, eluted with 15%-30% AcOEt in hexane) to give 3-[4-(benzyloxy)phenyl]-1-ethyl-7-methyl-1,3-dihydro-2H-imidazo[4,5-b]pyridin-2-one (801 mg) as an off-white solid.

MS (API+): [M+H]$^+$360.4

$^1$H NMR (300 MHz, CDCl$_3$) δ 1.41 (3H, t, J=7.2 Hz), 2.61 (3H, s), 4.19 (2H, q, J=7.2 Hz), 5.11 (2H, s), 6.81 (1H, d, J=5.3 Hz), 7.10 (2H, d, J=8.7 Hz), 7.30-7.47 (5H, m), 7.53 (2H, d, J=9.1 Hz), 7.91 (1H, d, J=5.3 Hz).

120c) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one

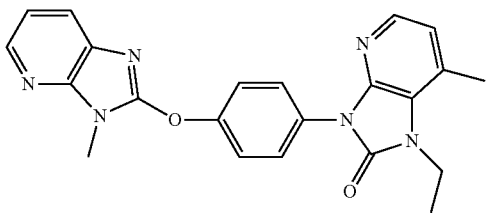 [SMILES: CCn1c(=O)n(-c2ccc(Oc3nc4cccnc4n3C)cc2)c2nccc(C)c21]

A mixture of 3-[4-(benzyloxy)phenyl]-1-ethyl-7-methyl-1,3-dihydro-2H-imidazo[4,5-b]pyridin-2-one (800 mg) and 10% Pd—C (118 mg) in EtOH (20 mL) was hydrogenated under balloon pressure at room temperature overnight. The catalyst was removed by filtration and the filtrate was concentrated in vacuo to give 1-ethyl-3-(4-hydroxyphenyl)-7-methyl-1,3-dihydro-2H-imidazo[4,5-b]pyridin-2-one as a colorless solid. To a mixture of this solid and 3-methyl-2-(methylsulfonyl)-3H-imidazo[4,5-b]pyridine (480 mg) in DMF (10 mL) was added 60% sodium hydride (58.9 mg) at 100° C. The mixture was heated at 180° C. for 30 min under microwave irradiation. The reaction mixture was diluted with MeOH and concentrated under reduced pressure. The residue was purified by column chromatography (NH silica gel, eluted with 30%-50% AcOEt in hexane and silica gel, eluted with 15%-30% AcOEt in hexane). The crude materials were purified by HPLC (C18, eluted with H$_2$O/MeCN containing 0.1% trifluoroacetic acid). To this obtained solution was added sat. NaHCO$_3$ aq, the mixture was extracted with AcOEt, and the extract was dried over MgSO$_4$ and concentrated in vacuo to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (119 mg) as colorless crystals (Form A).

MS (API+): [M+H]$^+$401.3

Alternative methods for 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (method B-F) are described below.

Method B

120d) 1-ethyl-3-(4-hydroxyphenyl)-7-methyl-1,3-dihydro-2H-imidazo[4,5-b]pyridin-2-one

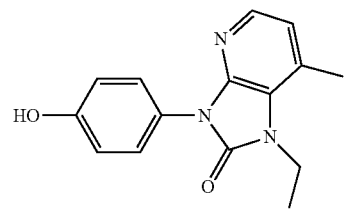 [SMILES: CCn1c(=O)n(-c2ccc(O)cc2)c2nccc(C)c21]

A mixture of 3-[4-(benzyloxy)phenyl]-1-ethyl-7-methyl-1,3-dihydro-2H-imidazo[4,5-b]pyridin-2-one (21.4 g) and 10% Pd—C (3.17 g) in EtOH (400 mL) was hydrogenated under balloon pressure at room temperature for 2 h. The catalyst was removed by filtration and the filtrate was concentrated in vacuo. The solid was washed with THF-hexane to give 1-ethyl-3-(4-hydroxyphenyl)-7-methyl-1,3-dihydro-2H-imidazo[4,5-b]pyridin-2-one (10.90 g) as a solid.

MS (API+): [M+H]$^+$270.4

$^1$H NMR (300 MHz, CDCl$_3$) δ 1.44 (3H, d, J=6.9 Hz), 2.65 (3H, s), 4.21 (2H, q, J=6.9 Hz), 6.74 (2H, d, J=8.7 Hz), 6.90 (1H, d, J=5.3 Hz), 7.22 (2H, d, J=8.7 Hz), 7.94 (1H, d, J=5.3 Hz).

120e) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one

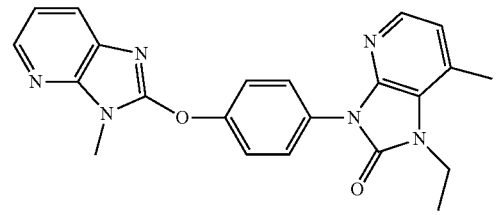 [SMILES: CCn1c(=O)n(-c2ccc(Oc3nc4cccnc4n3C)cc2)c2nccc(C)c21]

To a solution of 3-methyl-2-(methylsulfonyl)-3H-imidazo[4,5-b]pyridine (1.0 g) and 1-ethyl-3-(4-hydroxyphenyl)-7-methyl-1,3-dihydro-2H-imidazo[4,5-b]pyridin-2-one (1.3 g) in DMF (10 mL) was added 60% NaH (0.23 g) at room temperature, and the mixture was stirred at 180° C. under microwave irradiation for 30 min. To the mixture was added EtOH (10 mL). The formed crystals were collected by filtration and washed with EtOH. This microwave reaction was repeated two additional times with the same amount of starting material. The combined crystals were recrystallized from EtOH containing 5% distilled water (270 mL) and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (3.3 g) as white crystals (Form A).

MS (API+): [M+H]$^+$401.3

$^1$H NMR (300 MHz, DMSO-d$_6$) δ 1.32 (3H, t, J=7.2 Hz), 2.61 (3H, s), 3.77 (3H, s), 4.12 (2H, q, J=7.2 Hz), 7.00 (1H, d, J=5.7 Hz), 7.20 (1H, dd, J=7.9, 4.9 Hz), 7.58-7.66 (2H, m), 7.71-7.78 (2H, m), 7.80 (1H, dd, J=7.9, 1.1 Hz), 7.87 (1H, d, J=4.9 Hz), 8.22 (1H, dd, J=4.9, 1.5 Hz).

Anal. Calcd for C$_{22}$H$_{20}$N$_6$O$_2$: C, 65.99; H, 5.03; N, 20.99. Found: C, 65.76; H, 5.07; N, 20.85.

Powder X-ray Diffraction (PXRD) Analysis:

Form A is characterized by PXRD Pattern using CuKα X-ray radiation, having peaks selected from a list consisting of:
- 9.302 angstrom; middle
- 8.1102 angstrom; middle
- 5.6255 angstrom; high
- 5.487 angstrom; middle
- 4.8439 angstrom; high
- 4.371 angstrom; high
- 3.7479 angstrom; low
- 3.6043 angstrom; high
- 3.5092 angstrom; middle
- 3.2178 angstrom; high d-value.

Method D 120l) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form G)

Crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (100 mg, Form A) was dissolved in EtOH (20 mL) at 80° C. and the solution was allowed to cool to room temperature. The mixture was stirred at room temperature for 350 h. The solid was collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (50 mg) as crystals (Form G).

Crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (40.0 g, Form A) was dissolved in DMSO (400 ml) at 95° C. and the solution was allowed to cool to 85° C. To the solution was slowly added EtOH (400 mL) at 85° C., and then the mixture was allowed to cool to 80° C. To the solution was added seed crystals (Form G: 50 mg) at 80° C. The mixture was stirred and maintained at 73° C. for 20 h. The solid was collected by filtration and washed with EtOH (500 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (19.5 g) as white crystals (Form G).

Method E 120m) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form G)

Crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (600 mg, Form A) was stirred in EtOH (60 mL) at room temperature for 168 h. The solid was collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (350 mg) as crystals (Form G).

MS (API+): [M+H]$^+$401.1.

$^1$H NMR (400 MHz, DMSO-d$_6$) δ1.25-1.38 (3H, m), 2.61 (3H, s), 3.78 (3H, s), 4.04-4.18 (2H, m), 6.96-7.04 (1H, m), 7.17-7.25 (1H, m), 7.59-7.66 (2H, m), 7.71-7.77 (2H, m), 7.78-7.83 (1H, m), 7.85-7.91 (1H, m), 8.16-8.28 (1H, m).

Anal. Calcd for C$_{22}$H$_{20}$N$_6$O$_2$: C, 65.99; H, 5.03; N, 20.99. Found: C, 65.73; H, 5.12; N, 20.85.

Method F 120n) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form G)

Crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (3.0 g) obtained in 120s') was dissolved in DMSO (33 mL) at 90° C. To the solution was slowly added EtOH (30 mL) at 80-90° C. To the solution was added crystals (Form G) obtained in 120m) as seed crystals at 80-90° C. The mixture was stirred at 60-65° C. for 6 h and at room temperature for 18 h. The solid was collected by filtration and washed with EtOH (15 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (1.3 g) as white crystals (Form G).

Method G 120p) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form G)

Crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (3.0 g) obtained by 120s') was dissolved in DMSO (33 ml) at 90-95° C. To the solution was slowly added AcOEt (30 ml) at 70-90° C. To the solution was added crystals (Form G) obtained in 120n) as seed crystals at 80-90° C. The mixture was stirred at 45-50° C. for 25 min and at 70-75° C. for 3 h. The mixture was gradually cooled to 0-5° C. and stirred for 1 h. The solid was collected by filtration and washed with AcOEt (15 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (2.6 g) as white crystals (Form G).

Method H 120q) 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form G)

A solution of 3-methyl-2-(methylsulfonyl)-3H-imidazo[4,5-b]pyridine (20.4 g, 96.55 mmol) in DMA (117 mL) was added to a solution of 1-ethyl-3-(4-hydroxyphenyl)-7-methyl-1,3-dihydro-2H-imidazo[4,5-b]pyridin-2-one (26.0 g, 96.55 mmol) and potassium tert-butoxide (11.4 g) in DMA (96 mL) at room temperature. The mixture was stirred at 95-100° C. for 1.5 h. Water (221 ml) was added at 80-100° C. The precipitate was collected at room temperature and dried over under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (35.8 g) as crude product. The obtained crude 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (10.0 g) was dissolved in DMSO (150 ml) at 90-100° C. The solution was filtered through filter paper and washed with DMSO (10 mL). The combined filtrate was slowly added to a mixture of crystals (Form G: 100 mg) obtained in 120p) (as seed crystals) in AcOEt (100 ml) at 5-30° C. After stirring at room temperature for 17 h, the mixture was stirred at 70° C. for 1 h. The mixture was gradually cooled to 25° C. and stirred for 2 h. The mixture was stirred at 0-10° C. for 1 h and at room temperature for 1 h. The solids were collected by filtration and dried at 50° C. under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (8.0 g) as white crystals (Form G).
Method I 120r) 1-ethyl-7-methyl-3-{4-[(3-methyl-3H-imidazo [4,5-b]pyridin-2-yl)oxy]phenyl}-1,3-dihydro-2H-imidazo[4,5-b]pyridin-2-one (crystals of Form G)

A solution of 3-methyl-2-(methylsulfonyl)-3H-imidazo[4,5-b]pyridine (40.8 g, 193.09 mmol) in DMA (234 ml) was added to a solution of 1-ethyl-3-(4-hydroxyphenyl)-7-methyl-1,3-dihydro-2H-imidazo[4,5-b]pyridin-2-one (52.0 g, 193.09 mmol) and potassium tert-butoxide (22.8 g) in DMA (192 mL) at room temperature. The mixture was stirred at 90-100° C. for 1 h. Water (442 mL) was added at 80-100° C. The precipitate was collected at room temperature and dried over under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (72.4 g) as crude product. The crude 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (60.0 g) was dissolved in DMSO (900 mL) at 90-100° C. The solution was filtered through filter paper and washed with DMSO (60 mL). The combined filtrate was slowly added to a mixture of crystals (Form G: 600 mg) obtained in 120q) (as seed crystals) in AcOEt (600 mL) at 0-30° C. The mixture was stirred at 70° C. for 0.5 h and cooled to room temperature. After stirring at room temperature for 1 h, the mixture was stirred at 0-10° C. for 1 h and at room temperature for 1 h. The solids were collected by filtration and dried at 50° C. under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (47.9 g) as white crystals (Form G).
MS (ESI+): [M+H]$^+$401.2
$^1$H NMR (500 MHz, CDCl$_3$) δ 1.42 (3H, t), 2.62 (3H, s), 3.84 (3H, s), 4.15-4.27 (2H, m), 6.81-6.92 (1H, m), 7.10-7.18 (1H, m), 7.52-7.61 (2H, m), 7.73-7.80 (1H, m), 7.82-7.87 (2H, m), 7.91-7.95 (1H, m), 8.20-8.29 (1H, m).
Method J 120s) 1-ethyl-7-methyl-3-{4-[(3-methyl-3H-imidazo [4,5-b]pyridin-2-yl)oxy]phenyl}-1,3-dihydro-2H-imidazo[4,5-b]pyridin-2-one (crystals of Form G)

120s') A solution of 3-methyl-2-(methylsulfonyl)-3H-imidazo[4,5-b]pyridine (78.4 g, 371.33 mmol) in DMA (420 mL) was added to a solution of 1-ethyl-3-(4-hydroxyphenyl)-7-methyl-1,3-dihydro-2H-imidazo[4,5-b]pyridin-2-one (100.0 g, 371.33 mmol) and potassium tert-butoxide (51.5 g) in DMA (370 mL) at room temperature. The mixture was stirred at 90-100° C. for 1 h. Water (780 mL) was added at 90-100° C. The precipitate was collected at room temperature and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (127.7 g) as crystals. The obtained crystals (125.0 g) were dissolved in DMSO (1375 mL) at 90-95° C. To the solution was slowly added EtOH (1250 mL) at 80-95° C., and then the mixture was allowed to cool to room temperature. The solid was collected by filtration and washed with EtOH (625 mL) to give 1-ethyl-7-methyl-3-{4-[(3-methyl-3H-imidazo[4,5-b] pyridin-2-yl)oxy]phenyl}-1,3-dihydro-2H-imidazo[4,5-b] pyridin-2-one (103.9 g) as crystals.

120s") The mixture of the obtained crystals (55.0 g) in a solution of DMSO (275 mL) and EtOH (275 mL) was stirred at 70-75° C. for 0.5 h and then the mixture was allowed to cool to room temperature. The solid was collected by filtration and washed with EtOH (165 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (52.2 g) as crystals (Form A). The obtained crystals (5.0 g) were dissolved in DMSO (50 mL) at 95° C. The solution was filtered through filter paper and washed with DMSO (5 mL). To the combined filtrate was added EtOH (50 mL) slowly at 73-95° C. To the solution was added crystals (Form G: 5 mg) obtained in 120p) (as seed crystals) at 73° C. The mixture was allowed to cool to room temperature. After stirring at 70-75° C. for 7 h, the mixture was cooled to room temperature. After stirring at 70-75° C. for 8 h, the mixture was cooled to room temperature. After stirring at 70-75° C. for 2 h, the mixture was stirred at room temperature for 1 h, and at 0-10° C. for 1 h. The solids were collected by filtration and dried at 50° C. under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (4.5 g) as white crystals (Form G).
Powder X-ray Diffraction (PXRD) Analysis:

Form G is characterized by PXRD Pattern using CuKα X-ray radiation, having peaks selected from a list consisting of:

9.2245 angstrom; middle
7.8796 angstrom; high
6.763 angstrom; middle
6.2059 angstrom; middle
6.1289 angstrom; middle
5.7268 angstrom; high
5.1275 angstrom; middle
4.638 angstrom; middle
4.267 angstrom; middle
3.9939 angstrom; middle
3.9345 angstrom; middle
3.7921 angstrom; high
3.7479 angstrom; high
3.0579 angstrom; middle d-value.

Example 121

7-methyl-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

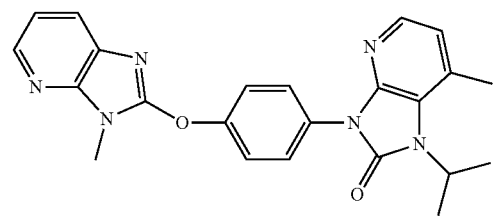 [SMILES: Cc1ccnc2c1n(C(C)C)c(=O)n2-c1ccc(Oc2nc3cccnc3n2C)cc1]

121a) 3-[4-(benzyloxy)phenyl]-7-methyl-1-(1-methylethyl)-1,3-dihydro-2H-imidazo[4,5-b]pyridin-2-one

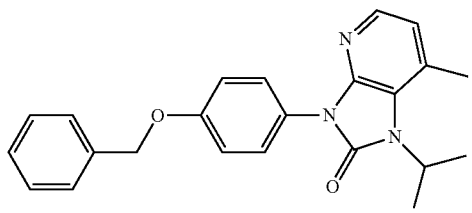 [SMILES: Cc1ccnc2c1n(C(C)C)c(=O)n2-c1ccc(OCc2ccccc2)cc1]

A suspension of 3-[4-(benzyloxy)phenyl]-7-methyl-1,3-dihydro-2H-imidazo[4,5-b]pyridin-2-one (360 mg), 2-iodopropane (0.217 mL) and potassium carbonate (180 mg) in DMF (10 mL) was stirred overnight at room temperature. The reaction mixture was poured into water, and the mixture was extracted with AcOEt. The extract was washed with water and brine, dried over MgSO$_4$, and concentrated under reduced pressure. The residue was purified by column chromatography (silica gel, eluted with 15%-20% AcOEt in hexane) to give the title compound (218 mg) as colorless oil.

MS (API+): [M+H]$^+$374.3

$^1$H NMR (300 MHz, CDCl$_3$) δ 1.68 (6H, d, J=6.8 Hz), 2.60 (3H, s), 4.72-4.88 (1H, m), 5.11 (2H, s), 6.78 (1H, d, J=5.3 Hz), 7.06-7.13 (2H, m), 7.28-7.47 (5H, m), 7.47-7.55 (2H, m), 7.88 (1H, d, J=5.3 Hz).

121b) 7-methyl-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

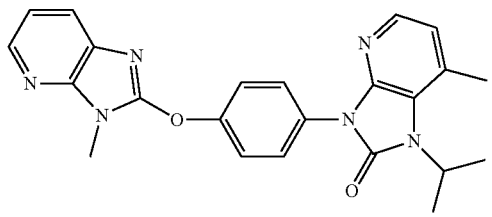 [SMILES: Cc1ccnc2c1n(C(C)C)c(=O)n2-c1ccc(Oc2nc3cccnc3n2C)cc1]

A mixture of 3-[4-(benzyloxy)phenyl]-7-methyl-1-(1-methylethyl)-1,3-dihydro-2H-imidazo[4,5-b]pyridin-2-one (215 mg) and 10% Pd—C (30.6 mg) in EtOH (10 mL) was hydrogenated under balloon pressure at room temperature for 1 h. The catalyst was removed by filtration and the filtrate was concentrated in vacuo to give 3-(4-hydroxyphenyl)-7-methyl-1-(1-methylethyl)-1,3-dihydro-2H-imidazo[4,5-b]pyridin-2-one as a colorless solid. To a solution of this solid in DMF (10 mL) were added sodium hydride (27.8 mg) and 3-methyl-2-(methylsulfonyl)-3H-imidazo[4,5-b]pyridine (164 mg) at 100° C. The mixture was heated at 180° C. for 30 min under microwave irradiation. The precipitate was collected by filtration and washed with AcOEt and MeOH to give the title compound (175 mg) as colorless crystals.

MS (API+): [M+H]$^+$415.4

$^1$H NMR (300 MHz, DMSO-d$_6$) δ 1.60 (6H, d, J=6.8 Hz), 2.62 (3H, s), 3.78 (3H, s), 4.83 (1H, quin, J=6.8 Hz), 6.98 (1H, d, J=5.3 Hz), 7.20 (1H, dd, J=7.9, 4.9 Hz), 7.57-7.64 (2H, m), 7.68-7.75 (2H, m), 7.80 (1H, dd, J=7.9, 1.5 Hz), 7.84 (1H, d, J=5.3 Hz), 8.22 (1H, dd, J=4.9, 1.5 Hz).

mp 270-271° C.

Example 122

6-methyl-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

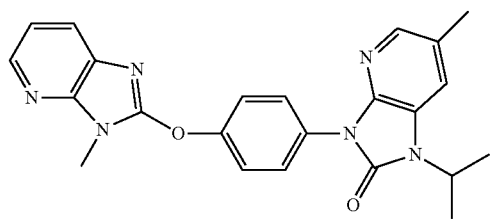 [SMILES: Cc1cnc2c(c1)n(C(C)C)c(=O)n2-c1ccc(Oc2nc3cccnc3n2C)cc1]

122a) 3-[4-(benzyloxy)phenyl]-6-methyl-1-(1-methylethyl)-1,3-dihydro-2H-imidazo[4,5-b]pyridin-2-one

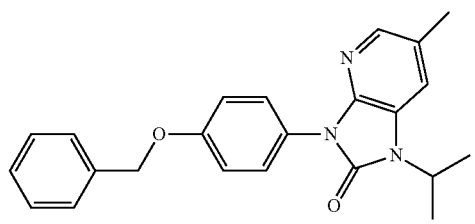 [SMILES: Cc1cnc2c(c1)n(C(C)C)c(=O)n2-c1ccc(OCc2ccccc2)cc1]

NaH (84 mg) was added to a solution of 3-[4-(benzyloxy)phenyl]-6-methyl-1,3-dihydro-2H-imidazo[4,5-b]pyridin-2-one (346 mg) and 2-iodopropane (0.208 mL) in DMF (dry) (4 mL) at room temperature. The mixture was stirred at room temperature under a dry atmosphere (CaCl$_2$ tube) for 1 h. The mixture was poured into water, and the mixture was extracted with EtOAc. The organic layer was separated, washed with brine, dried over MgSO$_4$ and concentrated in vacuo. The residue was purified by column chromatography (NH silica gel, EtOAc/hexane) to give the title compound (283 mg) as a yellow oil.

MS (API+): [M+H]+374.2.

122b) 3-(4-hydroxyphenyl)-6-methyl-1-(1-methylethyl)-1,3-dihydro-2H-imidazo[4,5-b]pyridin-2-one

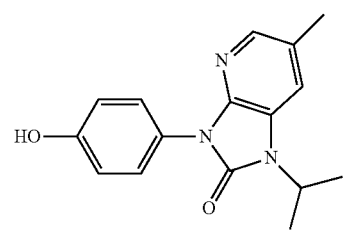 [SMILES: Cc1cnc2c(c1)n(C(C)C)c(=O)n2-c1ccc(O)cc1]

A mixture of 3-[4-(benzyloxy)phenyl]-6-methyl-1-(1-methylethyl)-1,3-dihydro-2H-imidazo[4,5-b]pyridin-2-one (283 mg) and 10% palladium on carbon (50% wet) (87 mg) in MeOH (4.2 mL) and EtOAc (4.2 mL) was hydrogenated under balloon pressure at room temperature overnight. The solid was filtrated and washed with MeOH (10 ml) to remove the catalyst. The filtrate was concentrated in vacuo to give the title compound (210 mg) as a gray solid.

$^1$H NMR (300 MHz, CDCl$_3$) δ 1.59 (5H, d, J=7.2 Hz), 2.40 (3H, s), 4.82 (1H, t, J=7.0 Hz), 6.60-6.90 (2H, m), 7.25 (2H, s), 7.27-7.32 (2H, m), 7.87 (1H, s).

122c) 6-methyl-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

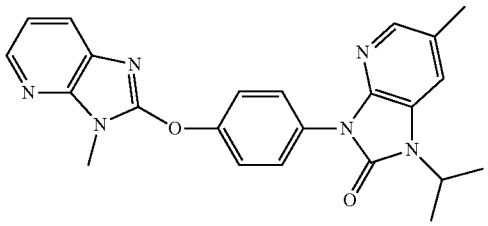 [SMILES: Cc1cnc2c(c1)n(C(C)C)c(=O)n2-c1ccc(Oc2nc3cccnc3n2C)cc1]

To a mixture of 3-methyl-2-(methylsulfonyl)-3H-imidazo[4,5-b]pyridine (198 mg) and 3-(4-hydroxyphenyl)-6-methyl-1-(1-methylethyl)-1,3-dihydro-2H-imidazo[4,5-b]pyridin-2-one (177 mg) in DMF (1.5 mL) was added NaH (40.0 mg), and the mixture was stirred at 100° C. for 1 h. The mixture was heated at 180° C. for 30 min under microwave irradiation. The mixture was poured into water, and the mixture was extracted with EtOAc. The organic layer was separated, washed with brine, dried over Na$_2$SO$_4$ and concentrated in vacuo. The residue was purified by column chromatography (silica gel, EtOAc/hexane) to give the title compound (125 mg) as white crystals.

MS (API+): [M+H]+ 415.1.

$^1$H NMR (300 MHz, DMSO-d$_6$) δ 1.52 (6H, d, J=7.2 Hz), 2.36 (3H, s), 3.77 (3H, s), 4.71 (1H, quin, J=6.9 Hz), 7.20 (1H, dd, J=7.9, 4.9 Hz), 7.53-7.71 (3H, m), 7.71-7.86 (4H, m), 8.22 (1H, dd, J=4.9, 1.5 Hz).

Anal. Calcd for C$_{23}$H$_{22}$N$_6$O$_2$: C, 66.65; H, 5.35; N, 20.28. Found: C, 66.55; H, 5.44; N, 20.23.

mp 252° C.

Example 123

1-[4-(imidazo[1,2-a]pyridin-2-yloxy)phenyl]-3,3-dimethyl-1,3-dihydro-2H-pyrrolo[2,3-b]pyridin-2-one

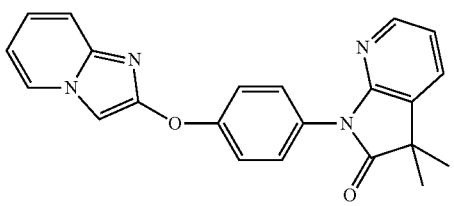 [SMILES: CC1(C)C(=O)N(c2ccc(Oc3cn4ccccc4n3)cc2)c2ncccc21]

123a) 1-[4-(imidazo[1,2-a]pyridin-2-yloxy)phenyl]-1,3-dihydro-2H-pyrrolo[2,3-b]pyridin-2-one

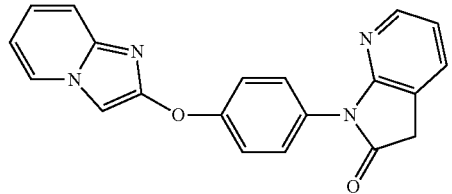 [SMILES: O=C1Cc2cccnc2N1c1ccc(Oc2cn3ccccc3n2)cc1]

Ethyl 2-chloroimidazo[1,2-a]pyridine-3-carboxylate (2.00 g) was added to a solution of p-bromophenol (1.617 g) and NaH (0.427 g) in DMF (dry) (10 ml) at 100° C. The mixture was stirred at 100° C. under a dry atmosphere overnight. The reaction mixture was diluted with MeOH, and concentrated in vacuo. The residue was purified by column chromatography (silica gel, eluted with 0%-30% EtOAc in hexane) to give ethyl 2-(4-bromophenoxy)imidazo[1,2-a]pyridine-3-carboxylate (1.5 g) as a colorless solid and 2-(4-bromophenoxy)imidazo[1,2-a]pyridine (530 mg) as a colorless solid. The mixture of 2-(4-bromophenoxy)imidazo[1,2-a]pyridine (410 mg), 1,3-dihydro-2H-pyrrolo[2,3-b]pyridine-2-one (164 mg), trans-N,N'-dimethylcyclohexane-1,2-diamine (174 mg), copper(I) iodide (116 mg), K$_2$CO$_3$ (338 mg) and THF (dry) (5 mL) was heated at 180° C. for 3 h under microwave irradiation. The solid was removed by filtration, and the filtrate was concentrated in vacuo. The residue was purified by column chromatography (silica gel, EtOAc/hexane) to give the title compound (72 mg) as an orange solid (mixture with 1,3-dihydro-2H-pyrrolo[2,3-b]pyridine-2-one, ca. 20% purity).

This product was subjected to the next reaction without further purification.

MS (API+): [M+H]+ 343.1.

123b) 1-[4-(imidazo[1,2-a]pyridin-2-yloxy)phenyl]-3,3-dimethyl-1,3-dihydro-2H-pyrrolo[2,3-b]pyridin-2-one

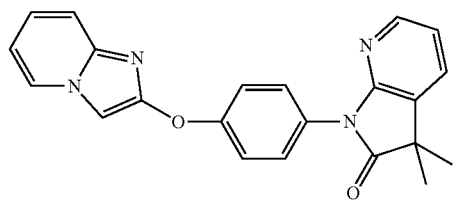 [SMILES: CC1(C)C(=O)N(c2ccc(Oc3cn4ccccc4n3)cc2)c2ncccc21]

A mixture of 1-[4-(imidazo[1,2-a]pyridin-2-yloxy)phenyl]-1,3-dihydro-2H-pyrrolo[2,3-b]pyridin-2-one (72 mg, mixture with 1,3-dihydro-2H-pyrrolo[2,3-b]pyridine-2-one, ca. 20% purity), iodomethane (0.110 ml), and sodium hydride (70.8 mg) in DMF (1 mL) was stirred at 0° C. to room temperature overnight. The mixture was quenched with water at room temperature and extracted with EtOAc. The organic layer was separated, washed with brine, dried over MgSO$_4$ and concentrated in vacuo. The residue was purified by column chromatography (silica gel, EtOAc/hexane) and column chromatography (NH silica gel, EtOAc/hexane) to give the title compound (7.40 mg) as a colorless oil.

MS (API+): [M+H]+371.3.

$^1$H NMR (300 MHz, CDCl$_3$) δ 1.46-1.55 (6H, m), 6.81 (1H, t, J=6.2 Hz), 7.02 (1H, dd, J=7.6, 5.3 Hz), 7.12 (1H, s), 7.14-7.22 (1H, m), 7.29-7.41 (2H, m), 7.48-7.59 (4H, m), 8.03 (1H, d, J=6.8 Hz), 8.17 (1H, dd, J=5.3, 1.5 Hz).

Example 124

1-ethyl-3-[4-(imidazo[1,2-a]pyridin-2-yloxy)phenyl]-6-methyl-1,3-dihydro-2H-imidazo[4,5-b]pyridin-2-one

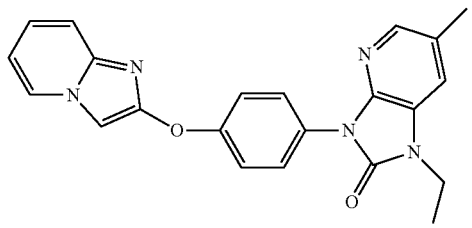 [SMILES: CCn1c(=O)n(-c2ccc(Oc3cn4ccccc4n3)cc2)c2ncc(C)cc21]

124a) ethyl 2-[4-(1-ethyl-6-methyl-2-oxo-1,2-dihydro-3H-imidazo[4,5-b]pyridin-3-yl)phenoxy]imidazo[1,2-a]pyridine-3-carboxylate

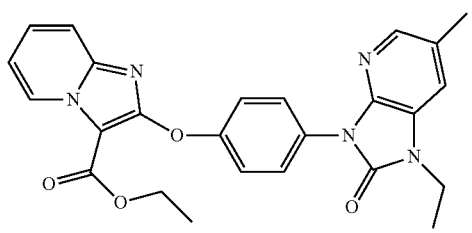 [SMILES: CCOC(=O)c1c(Oc2ccc(-n3c(=O)n(CC)c4cc(C)cnc43)cc2)nc2ccccn12]

The mixture of ethyl 2-chloroimidazo[1,2-a]pyridine-3-carboxylate (504 mg), 1-ethyl-3-(4-hydroxyphenyl)-6-methyl-1,3-dihydro-2H-imidazo[4,5-b]pyridin-2-one (302 mg) and NaH (67.3 mg) in DME (4 mL) was heated at 50° C. for 1 h. The mixture was heated at 200° C. for 3 h under microwave irradiation. The mixture was poured into sat. NaHCO$_2$, and the mixture was extracted with EtOAc. The organic layer was separated, washed with brine, dried over Na$_2$SO$_4$ and concentrated in vacuo. The residue was purified by column chromatography (silica gel, EtOAc/hexane) to give the title compound (62.0 mg) as a white solid.

MS (API+): [M+H]+458.2.

124b) 1-ethyl-3-[4-(imidazo[1,2-a]pyridin-2-yloxy)phenyl]-6-methyl-1,3-dihydro-2H-imidazo[4,5-b]pyridin-2-one

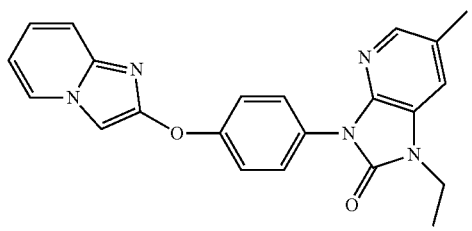

To a solution of ethyl 2-[4-(1-ethyl-6-methyl-2-oxo-1,2-dihydro-3H-imidazo[4,5-b]pyridin-3-yl)phenoxy]imidazo[1,2-a]pyridine-3-carboxylate (62 mg) in EtOH (4 mL) was added sodium hydroxide (1.084 ml). The mixture was stirred at 50° C. for 2 h. Hydrochloric acid (2.168 mL) was added to the mixture, and the mixture was stirred at 60° C. for 10 h. The mixture was concentrated under reduced pressure. The residue was purified by column chromatography (silica gel, EtOAc/hexane) to give the title compound (42.0 mg) as a colorless oil.

MS (API+): [M+H]+386.2.
$^1$H NMR (300 MHz, CDCl$_3$) δ 1.41 (3H, t, J=7.2 Hz), 2.40 (3H, s), 4.00 (2H, q, J=7.2 Hz), 6.76-6.86 (1H, m), 7.10 (2H, s), 7.13-7.22 (1H, m), 7.30-7.40 (2H, m), 7.51 (1H, d, J=9.1 Hz), 7.68-7.75 (2H, m), 7.88 (1H, s), 8.02 (1H, d, J=6.4 Hz).

Anal. Calcd for C$_{22}$H$_{19}$N$_5$O$_2$-0.5 H$_2$O: C, 67.06; H, 5.11; N, 17.77. Found: C, 67.25; H, 5.16; N, 17.71.

Example 125

7-ethyl-9-{4-[(1-methyl-1H-benzimidazol-2-yl)oxy]phenyl}-7,9-dihydro-8H-purin-8-one

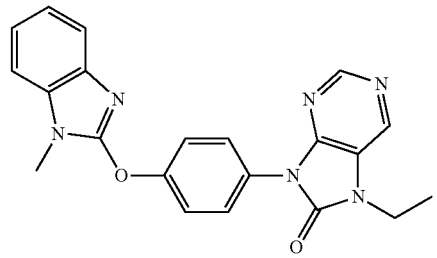 [SMILES: CCn1c(=O)n(-c2ccc(Oc3nc4ccccc4n3C)cc2)c2ncncc21]

125a) 2-(4-bromophenoxy)-1-methyl-1H-benzimidazole

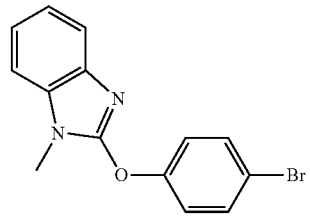 [SMILES: Cn1c(Oc2ccc(Br)cc2)nc2ccccc21]

Triethylamine (18 ml) was added to a mixture of 2-chloro-1-methyl-1H-benzimidazole (7.2 g) and p-bromophenol (22.5 g) at room temperature. The mixture was stirred at 120° C. for 6 h. The mixture was quenched with water at room temperature and extracted with EtOAc. The organic layer was separated, washed with 1 N NaOH aq. and brine, dried over MgSO$_4$ and concentrated in vacuo. The residue was purified by column chromatography (NH silica gel, eluted with 10%-15% EtOAc in hexane) to give 2-(4-bromophenoxy)-1-methyl-1H-benzimidazole (3.2 g) as colorless crystals.

MS (API+): [M+H]$^+$304.92.
$^1$H NMR (300 MHz, CDCl$_3$) δ 3.73 (3H, s), 7.13-7.35 (5H, m), 7.50-7.61 (3H, m).

125b) N-(diphenylmethylidene)-4-[(1-methyl-1H-benzimidazol-2-yl)oxy]aniline

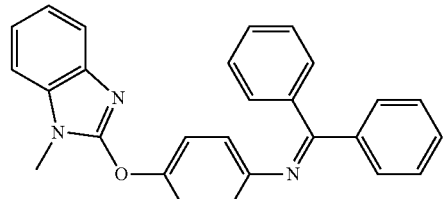

To a suspension of 2-(4-bromophenoxy)-1-methyl-1H-benzimidazole (1.0 g), Pd$_2$(dba)$_3$ (0.076 g), sodium tert-butoxide (0.48 g) and xantphos (0.19 g) in dioxane (10 mL) was added benzophenone imine (0.83 ml), and the mixture was stirred at 100° C. under Ar atmosphere for 6 h. After stirring at room temperature overnight, the mixture was poured into water, and the mixture was extracted with AcOEt. The organic layer was dried over Na$_2$SO$_4$, filtered and concentrated in vacuo. The residual crystals were washed with AcOEt to obtain N-(diphenylmethylidene)-4-[(1-methyl-1H-benzimidazol-2-yl)oxy]aniline (0.81 g) as pale yellow crystals.

MS (API+): [M+H]$^+$404.2.

$^1$H NMR (300 MHz, DMSO-d$_6$) δ 3.67 (3H, s), 6.74-6.82 (2H, m), 7.07-7.26 (6H, m), 7.33-7.59 (8H, m), 7.64-7.71 (2H, m).

125c)
4-[(1-methyl-1H-benzimidazol-2-yl)oxy]aniline

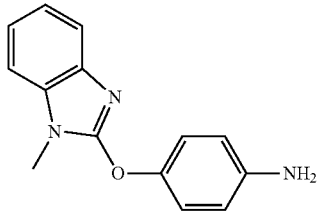 [SMILES: Cn1c(Oc2ccc(N)cc2)nc2ccccc21]

To a suspension of N-(diphenylmethylidene)-4-[(1-methyl-1H-benzimidazol-2-yl)oxy]aniline (810 mg) in THF (10 ml) was added 1 N HCl aq (10 mL) at room temperature, and the mixture was stirred at room temperature for 1 h. The mixture was neutralized with sat. NaHCO$_3$ aq. and extracted with AcOEt. The organic layer was dried over Na$_2$SO$_4$, filtered and concentrated in vacuo. The residue was purified by column chromatography (silica gel, eluted with 5%-100% AcOEt in hexane) to give 4-[(1-methyl-1H-benzimidazol-2-yl)oxy]aniline (440 mg) as colorless crystals.

MS (API+): [M+H]$^+$ 240.2.

$^1$H NMR (300 MHz, DMSO-d$_6$) δ 3.68 (3H, s), 5.06 (2H, s), 6.55-6.64 (2H, m), 6.99-7.18 (4H, m), 7.30-7.43 (2H, m).

125d) 6-chloro-N-{4-[(1-methyl-1H-benzimidazol-2-yl)oxy]phenyl}-5-nitropyrimidin-4-amine

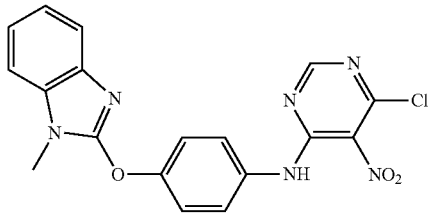 [SMILES: Cn1c(Oc2ccc(Nc3ncnc(Cl)c3[N+](=O)[O-])cc2)nc2ccccc21]

To a solution of 4-[(1-methyl-1H-benzimidazol-2-yl)oxy]aniline (0.30 g) and TEA (0.26 ml) in THF (15 mL) was added 4,6-dichloro-5-nitropyrimidine (0.24 g) at room temperature, and the mixture was stirred at room temperature for 2 h. The mixture was poured into water, and the mixture was extracted with AcOEt. The organic layer was washed with brine, dried over Na$_2$SO$_4$, filtered and concentrated in vacuo. The residue was purified by column chromatography (dry charge, silica gel, eluted with 5%-50% AcOEt in hexane) to give 6-chloro-N-{4-[(1-methyl-1H-benzimidazol-2-yl)oxy]phenyl}-5-nitropyrimidin-4-amine (0.24 g) as a yellow solid.

MS (API+): [M+H]$^+$ 397.3.

$^1$H NMR (300 MHz, CDCl$_3$) δ 3.75 (3H, s), 7.17-7.26 (3H, m), 7.43-7.51 (2H, m), 7.54-7.65 (3H, m), 8.48 (1H, s), 9.22 (1H, s).

125e) N$^4$-{4-[(1-methyl-1H-benzimidazol-2-yl)oxy]phenyl}pyrimidine-4,5-diamine

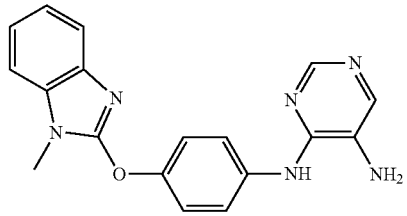 [SMILES: Cn1c(Oc2ccc(Nc3ncncc3N)cc2)nc2ccccc21]

A mixture of 6-chloro-N-{4-[(1-methyl-1H-benzimidazol-2-yl)oxy]phenyl}-5-nitropyrimidin-4-amine (240 mg) and 10% palladium on carbon (160 mg) in MeOH (10 mL) and THF (10 mL) was hydrogenated under balloon pressure at room temperature overnight. To the mixture was added TEA (0.50 mL). The catalyst was removed by filtration and the filtrate was concentrated in vacuo. The residue was purified by column chromatography (silica gel, eluted with 0%-5% MeOH in AcOEt) to give N$^4$-{4-[(1-methyl-1H-benzimidazol-2-yl)oxy]phenyl}pyrimidine-4,5-diamine (80 mg) as a colorless solid.

MS (API+): [M+H]$^+$333.4.

125f) 9-{4-[(1-methyl-1H-benzimidazol-2-yl)oxy]phenyl}-7,9-dihydro-8H-purin-8-one

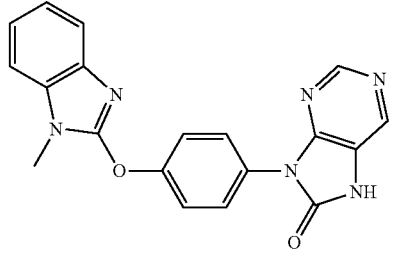 [SMILES: Cn1c(Oc2ccc(-n3c(=O)[nH]c4cncnc43)cc2)nc2ccccc21]

A solution of N$^4$-{4-[(1-methyl-1H-benzimidazol-2-yl)oxy]phenyl}pyrimidine-4,5-diamine (80 mg) and CDI (39 mg) in THF (20 mL) was refluxed for 3 h. CDI (39 mg) was added to the mixture. After refluxing overnight, the mixture was concentrated in vacuo. The residual solid was washed with AcOEt to give 9-{4-[(1-methyl-1H-benzimidazol-2-yl)oxy]phenyl}-7,9-dihydro-8H-purin-8-one (56 mg) as white crystals.

MS (API+): [M+H]$^+$359.3.

125g) 7-ethyl-9-{4-[(1-methyl-1H-benzimidazol-2-yl)oxy]phenyl}-7,9-dihydro-8H-purin-8-one

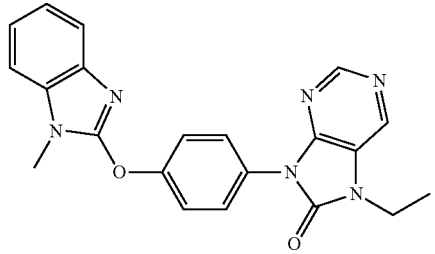 [SMILES: CCn1c(=O)n(-c2ccc(Oc3nc4ccccc4n3C)cc2)c2ncncc21]

A mixture of 9-{4-[(1-methyl-1H-benzimidazol-2-yl)oxy]phenyl}-7,9-dihydro-8H-purin-8-one (56 mg), iodoethane (20 μL) and cesium carbonate (120 mg) in DMF (3 ml) was stirred at 50° C. for 4 h. The mixture was poured into water, and the mixture was extracted with AcOEt. The organic layer was washed with brine, dried over $Na_2SO_4$, filtered and concentrated in vacuo. The residual crystals were recrystallized from AcOEt to give 7-ethyl-9-{4-[(1-methyl-1H-benzimidazol-2-yl)oxy]phenyl}-7,9-dihydro-8H-purin-8-one (40 mg) as white crystals.

MS (API+): [M+H]+ 387.4.

$^1$H NMR (300 MHz, DMSO-$d_6$) δ 1.34 (3H, t, J=7.2 Hz), 3.77 (3H, s), 4.01 (2H, q, J=7.2 Hz), 7.11-7.24 (2H, m), 7.40-7.51 (2H, m), 7.58-7.66 (2H, m), 7.72-7.79 (2H, m), 8.64 (1H, s), 8.65 (1H, s).

mp 242-243° C.

Anal. Calcd for $C_{21}H_{18}N_6O_2$: C, 65.27; H, 4.70; N, 21.75. Found: C, 64.99; H, 4.77; N, 21.70.

Example 126

6-chloro-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

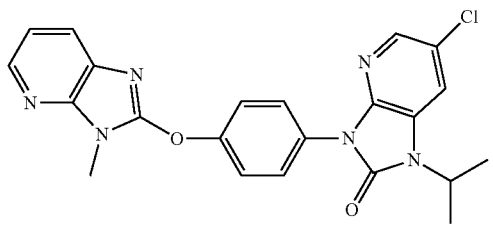 [SMILES: CC(C)n1c(=O)n(-c2ccc(Oc3nc4cccnc4n3C)cc2)c2ncc(Cl)cc21]

126a) 3-[4-(benzyloxy)phenyl]-6-chloro-1-(1-methylethyl)-1,3-dihydro-2H-imidazo[4,5-b]pyridin-2-one

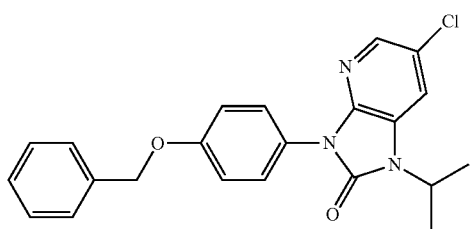 [SMILES: CC(C)n1c(=O)n(-c2ccc(OCc3ccccc3)cc2)c2ncc(Cl)cc21]

Di-tert-butyl dicarbonate (17.05 mL) was added to a solution of 2,5-dichloropyridin-3-amine (11.4 g) and NaHMDS (81 mL) in THF (dry) (200 mL) at 0° C. The mixture was stirred at 0° C. under a dry atmosphere for 1 h. The mixture was neutralized with 1N HCl at 0° C. and extracted with EtOAc. The organic layer was separated, washed with water and brine, dried over $MgSO_4$ and concentrated in vacuo. The residue was purified by column chromatography (NH silica gel, eluted with 0%-20% EtOAc in hexane) to give tert-butyl 2,5-dichloropyridin-3-ylcarbamate (15.6 g) as colorless oil. The mixture of tert-butyl 2,5-dichloropyridin-3-ylcarbamate (7.5 g), 4-benzyloxyaniline hydrochloride (10.08 g), 9,9-dimethyl-4,5-bis(diphenylphosphino)xanthene (1.319 g), $Pd_2(dba)_3$ (1.044 g) and sodium tert-butoxide (6.57 g) in toluene (160 mL)-2-propanol (40.0 mL) was stirred at 100° C. under Ar overnight. The reaction mixture was concentrated in vacuo. The residue was purified by column chromatography (silica gel, eluted with 0%-100% EtOAc in hexane) to give intermediate. To the intermediate in DMF (100 mL) were added 2-iodopropane (5.69 mL) and NaH (2.280 g), and the mixture was stirred at room temperature under a dry atmosphere ($CaCl_2$ tube) for 1 h. The reaction mixture was diluted with MeOH and concentrated in vacuo. The residue was purified by column chromatography (NH silica gel, eluted with 0%-50% EtOAc in hexane) to give 3-[4-(benzyloxy)phenyl]-6-chloro-1-(1-methylethyl)-1,3-dihydro-2H-imidazo[4,5-b]pyridin-2-one (560 mg) as a colorless solid.

MS (API+): [M+H]+394.2.

$^1$H NMR (300 MHz, DMSO-$d_6$) δ 1.41-1.57 (6H, m), 4.57-4.78 (1H, m), 5.18 (2H, s), 7.09-7.21 (2H, m), 7.26-7.60 (7H, m), 7.81-8.08 (2H, m).

126b) 6-chloro-3-(4-hydroxyphenyl)-1-(1-methylethyl)-1,3-dihydro-2H-imidazo[4,5-b]pyridin-2-one

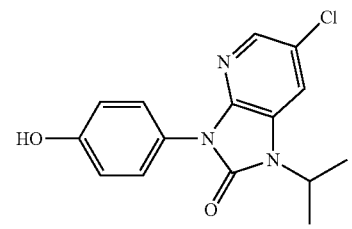 [SMILES: CC(C)n1c(=O)n(-c2ccc(O)cc2)c2ncc(Cl)cc21]

A mixture of 3-[4-(benzyloxy)phenyl]-6-chloro-1-(1-methylethyl)-1,3-dihydro-2H-imidazo[4,5-b]pyridin-2-one (600 mg) and 10% Pd—C (162 mg) in EtOAc (50 mL) was hydrogenated under balloon pressure at room temperature for 1 h. The catalyst was removed by filtration and the filtrate was concentrated in vacuo. The residue was purified by column chromatography (silica gel, eluted with 0%-50% EtOAc in hexane) to give 6-chloro-3-(4-hydroxyphenyl)-1-(1-methylethyl)-1,3-dihydro-2H-imidazo[4,5-b]pyridin-2-one (200 mg) as a white solid.

MS (API+): [M+H]+304.1.

$^1$H NMR (300 MHz, DMSO-$d_6$) δ 1.38-1.65 (6H, m), 4.54-4.82 (1H, m), 6.84-6.96 (2H, m), 7.30-7.41 (2H, m), 7.89-7.94 (1H, m), 7.93-7.98 (1H, m), 9.74 (1H, s).

126c) 6-chloro-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one

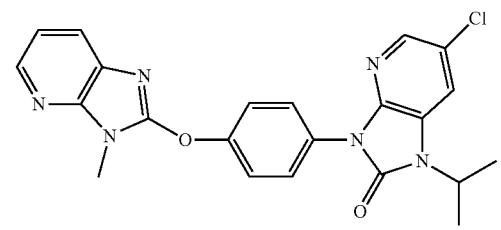

3-Methyl-2-(methylsulfonyl)-3H-imidazo[4,5-b]pyridine (100 mg) was added to a solution of 6-chloro-3-(4-hydroxyphenyl)-1-(1-methylethyl)-1,3-dihydro-2H-imidazo[4,5-b]pyridin-2-one (148 mg) and NaH (20.83 mg) in DMF (3 mL) at room temperature. The mixture was heated at 180° C. for 30 min under microwave irradiation. The reaction mixture was diluted with MeOH and concentrated in vacuo. The residue was purified by column chromatography (silica gel, eluted with 0%-50% EtOAc in hexane) to give 6-chloro-1-(1-methylethyl)-3-{4-[(3-methyl-3H-imidazo[4,5-b]pyridin-2-yl)oxy]phenyl}-1,3-dihydro-2H-imidazo[4,5-b]pyridin-2-one (120 mg) as white crystals:

MS (API+): [M+H]+435.2.

$^1$H NMR (300 MHz, DMSO-$d_6$) δ 1.38-1.64 (6H, m), 3.77 (3H, s), 4.71 (1H, s), 7.15-7.28 (1H, m), 7.57-7.67 (2H, m), 7.69-7.86 (3H, m), 7.90-8.10 (2H, m), 8.16-8.27 (1H, m).

Example 127

6-(difluoromethoxy)-1-ethyl-3-{4-[(3-methyl-3H-imidazo[4,5-b]pyridin-2-yl)oxy]phenyl}-1,3-dihydro-2H-imidazo[4,5-b]pyridin-2-one

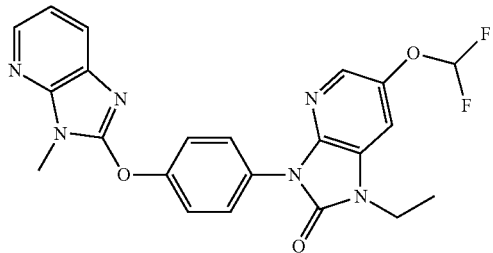 [SMILES: CCn1c(=O)n(-c2ccc(Oc3nc4cccnc4n3C)cc2)c2ncc(OC(F)F)cc21]

127a) 3-[4-(benzyloxy)phenyl]-1-ethyl-6-hydroxy-1,3-dihydro-2H-imidazo[4,5-b]pyridin-2-one

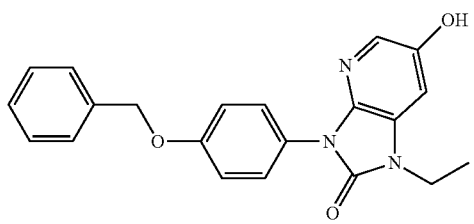 [SMILES: CCn1c(=O)n(-c2ccc(OCc3ccccc3)cc2)c2ncc(O)cc21]

A mixture of 3-[4-(benzyloxy)phenyl]-6-chloro-1-ethyl-1,3-dihydro-2H-imidazo[4,5-b]pyridin-2-one (1.72 g), Pd$_2$dba$_3$ (0.21 g), 2-di-tert-butylphosphino-3,4,5,6-tetramethyl-2',4',6'-triisopropyl-1,1'-biphenyl (0.44 g) and KOH (1.10 g) in dioxane (15 mL) and water (15 mL) was stirred at 100° C. under Ar atmosphere for 3 h. After stirring at room temperature overnight, the mixture was acidified with 1 N HCl aq (11 mL) and diluted with water. The mixture was extracted with AcOEt. The organic layer was dried over MgSO$_4$, filtered and concentrated in vacuo. The residue was purified by column chromatography (silica gel, eluted with 10%-70% AcOEt in hexane) to give 3-[4-(benzyloxy)phenyl]-1-ethyl-6-hydroxy-1,3-dihydro-2H-imidazo[4,5-b]pyridin-2-one (1.31 g) as a pale yellow solid.

MS (API+): [M+H]$^+$362.3.

$^1$H NMR (300 MHz, DMSO-$d_6$) δ 1.25 (3H, t, J=7.2 Hz), 3.90 (2H, q, J=7.2 Hz), 5.17 (2H, s), 7.08-7.17 (3H, m), 7.30-7.56 (8H, m), 9.58 (1H, brs).

127b) 3-[4-(benzyloxy)phenyl]-6-(difluoromethoxy)-1-ethyl-1,3-dihydro-2H-imidazo[4,5-b]pyridin-2-one

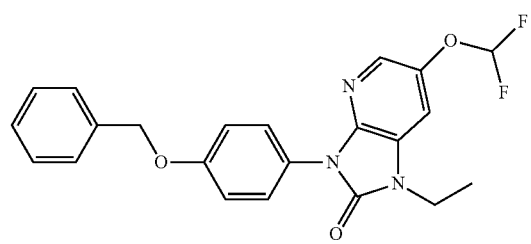 [SMILES: CCn1c(=O)n(-c2ccc(OCc3ccccc3)cc2)c2ncc(OC(F)F)cc21]

A mixture of 3-[4-(benzyloxy)phenyl]-1-ethyl-6-hydroxy-1,3-dihydro-2H-imidazo[4,5-b]pyridin-2-one (300 mg), sodium chlorodifluoroacetate (253 mg), K$_2$CO$_3$ (172 mg), DMF (3 ml), and water (0.60 mL) was refluxed overnight. The reaction mixture was poured into water, and the mixture was extracted with AcOEt. The extract was washed with brine, dried over MgSO$_4$, and concentrated under reduced pressure. The residue was purified by column chromatography (silica gel, eluted with 10%-40% AcOEt in hexane) to give 3-[4-(benzyloxy)phenyl]-6-(difluoromethoxy)-1-ethyl-1,3-dihydro-2H-imidazo[4,5-b]pyridin-2-one (110 mg) as a pale yellow oil.

MS (API+): [M+H]$^+$412.1.

$^1$H NMR (300 MHz, CDCl$_3$) δ 1.39 (3H, t, J=7.2 Hz), 3.98 (2H, q, J=7.2 Hz), 5.10 (2H, s), 6.50 (1H, t, J=73.3 Hz), 7.04-7.17 (3H, m), 7.27-7.49 (5H, m), 7.50-7.61 (2H, m), 7.92 (1H, d, J=2.3 Hz).

127c) 6-(difluoromethoxy)-1-ethyl-3-(4-hydroxyphenyl)-1,3-dihydro-2H-imidazo[4,5-b]pyridin-2-one

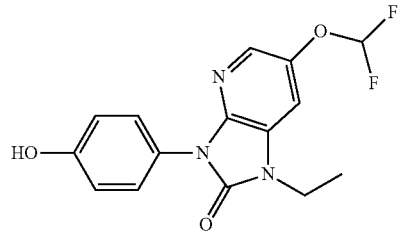 [SMILES: CCn1c(=O)n(-c2ccc(O)cc2)c2ncc(OC(F)F)cc21]

A mixture of 3-[4-(benzyloxy)phenyl]-6-(difluoromethoxy)-1-ethyl-1,3-dihydro-2H-imidazo[4,5-b]pyridin-2-one (110 mg) and 10% palladium on carbon (40 mg) in MeOH (10 mL) was hydrogenated under balloon pressure at room temperature for 2 h. The catalyst was removed by filtration and the filtrate was concentrated in vacuo to give 6-(difluoromethoxy)-1-ethyl-3-(4-hydroxyphenyl)-1,3-dihydro-2H-imidazo[4,5-b]pyridin-2-one (86 mg) as a pale yellow oil.

MS (API+): [M+H]$^+$322.3.

127d) 6-(difluoromethoxy)-1-ethyl-3-{4-[(3-methyl-3H-imidazo[4,5-b]pyridin-2-yl)oxy]phenyl}-1,3-dihydro-2H-imidazo[4,5-b]pyridin-2-one

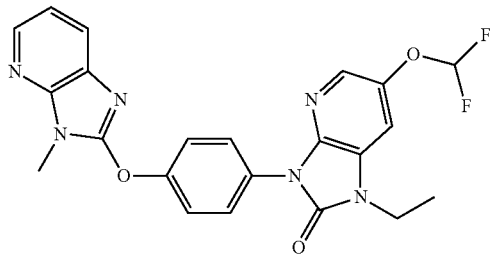 [SMILES: CCn1c(=O)n(-c2ccc(Oc3nc4cccnc4n3C)cc2)c2ncc(OC(F)F)cc21]

To a solution of 3-methyl-2-(methylsulfonyl)-3H-imidazo[4,5-b]pyridine (62 mg) and 6-(difluoromethoxy)-1-ethyl-3-(4-hydroxyphenyl)-1,3-dihydro-2H-imidazo[4,5-b]pyridin-2-one (86 mg) in DMF (3 ml) was added NaH (13 mg) at room temperature, and the mixture was stirred at 180° C. under microwave irradiation for 30 min. The mixture was partitioned between water and AcOEt. The organic layer was washed with brine, dried over $Na_2SO_4$, filtered and concentrated in vacuo. The residue was purified by column chromatography (dry charge, NH silica gel, eluted with 50%-100% AcOEt in hexane) and recrystallized from AcOEt/hexane to give 6-(difluoromethoxy)-1-ethyl-3-{4-[(3-methyl-3H-imidazo[4,5-b]pyridin-2-yl)oxy]phenyl}-1,3-dihydro-2H-imidazo[4,5-b]pyridin-2-one (56 mg) as white crystals.

MS (API+): [M+H]$^+$453.4.

$^1$H NMR (300 MHz, DMSO-$d_6$) δ 1.30 (3H, t, J=7.2 Hz), 3.77 (3H, s), 4.00 (2H, q, J=7.2 Hz), 7.21 (1H, dd, J=7.9, 4.9 Hz), 7.24 (1H, t, J=74.0 Hz), 7.59-7.67 (2H, m), 7.73-7.84 (4H, m), 7.92 (1H, d, J=2.3 Hz), 8.22 (1H, dd, J=4.9, 1.5 Hz).

Anal. Calcd for $C_{22}H_{18}N_6O_3F_2$: C, 58.41; H, 4.01; N, 18.58. Found: C, 58.30; H, 4.15; N, 18.43.

Mp: 195-197° C.

Example 128

6-(2,2-difluoroethoxy)-1-ethyl-3-{4-[(3-methyl-3H-imidazo[4,5-b]pyridin-2-yl)oxy]phenyl}-1,3-dihydro-2H-imidazo[4,5-b]pyridin-2-one

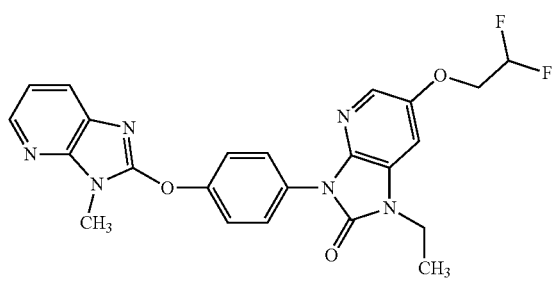 [SMILES: CCn1c(=O)n(-c2ccc(Oc3nc4cccnc4n3C)cc2)c2ncc(OCC(F)F)cc21]

128a) 3-[4-(benzyloxy)phenyl]-6-(2,2-difluoroethoxy)-1-ethyl-1,3-dihydro-2H-imidazo[4,5-b]pyridin-2-one

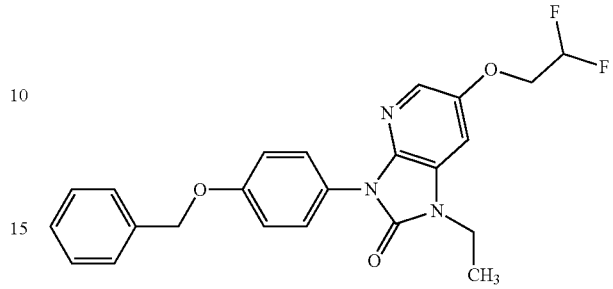

2,2-Difluoroethyl trifluoromethanesulfonate (213 mg) was added to a solution of 3-[4-(benzyloxy)phenyl]-1-ethyl-6-hydroxy-1,3-dihydro-2H-imidazo[4,5-b]pyridin-2-one (300 mg) and potassium carbonate (229 mg) in DMF (5 mL) at room temperature. The mixture was stirred at ambient temperature under a dry atmosphere ($CaCl_2$ tube) for 3 h. The mixture was quenched with water at room temperature and extracted with AcOEt. The organic layer was separated, washed with water and brine, dried over $MgSO_4$ and concentrated in vacuo. The residue was purified by column chromatography (silica gel, eluted with 15%-50% AcOEt in hexane) to give 3-[4-(benzyloxy)phenyl]-6-(2,2-difluoroethoxy)-1-ethyl-1,3-dihydro-2H-imidazo[4,5-b]pyridin-2-one (301 mg) as colorless oil.

MS (API+): [M+H]$^+$426.4

$^1$H NMR (300 MHz, CDCl$_3$) δ 1.39 (3H, d, J=7.3 Hz), 3.98 (2H, q, J=7.3 Hz), 4.24 (2H, td, J=13.0, 4.0 Hz), 5.11 (2H, s), 6.10 (1H, tt, J=55.0, 4.0 Hz), 6.96 (1H, d, J=2.6 Hz), 7.11 (2H, d, J=8.7 Hz), 7.28-7.48 (5H, m), 7.56 (2H, d, J=8.7 Hz), 7.73 (1H, d, J=2.6 Hz).

128b) 6-(2,2-difluoroethoxy)-1-ethyl-3-{4-[(3-methyl-3H-imidazo[4,5-b]pyridin-2-yl)oxy]phenyl}-1,3-dihydro-2H-imidazo[4,5-b]pyridin-2-one

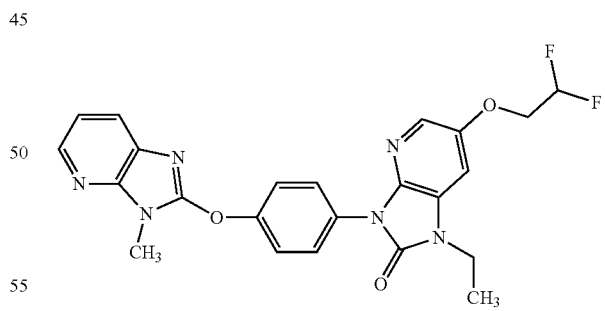

A mixture of 3-[4-(benzyloxy)phenyl]-6-(2,2-difluoroethoxy)-1-ethyl-1,3-dihydro-2H-imidazo[4,5-b]pyridin-2-one (300 mg) and 10% Pd—C (37.5 mg) in EtOH (10 mL) was hydrogenated under balloon pressure at room temperature overnight. The catalyst was removed by filtration and the filtrate was concentrated in vacuo to give 6-(2,2-difluoroethoxy)-1-ethyl-3-(4-hydroxyphenyl)-1,3-dihydro-2H-imidazo[4,5-b]pyridin-2-one as a colorless solid. To a solution of this product and 3-methyl-2-(methylsulfonyl)-3H-imidazo[4,5-b]pyridine (153 mg) in DMF (5 ml) was added sodium hydride (34.1 mg) at 100° C., and the mixture was heated at 180° C. for 30 min under microwave irradiation. The mixture was quenched with water at room temperature and extracted with AcOEt. The organic layer was separated, washed with sat. NaHCO₃ aq. and brine, dried over MgSO₄ and concentrated in vacuo. The residue was purified by column chromatography (NH silica gel, eluted with 15%-50% AcOEt in hexane) to give 6-(2,2-difluoroethoxy)-1-ethyl-3-{4-[(3-methyl-3H-imidazo[4,5-b]pyridin-2-yl)oxy]phenyl}-1,3-dihydro-2H-imidazo[4,5-b]pyridin-2-one (264 mg) as a colorless solid. The solid was crystallized from AcOEt-hexane.

MS (API+): [M+H]⁺467.3

¹H NMR (300 MHz, CDCl₃) δ 1.42 (3H, t, J=7.2 Hz), 3.84 (3H, s), 4.01 (2H, q, J=7.2 Hz), 4.26 (2H, td, J=13.0, 4.1 Hz), 6.12 (1H, tt, J=55.0, 4.0 Hz), 6.98 (1H, d, J=2.6 Hz), 7.15 (1H, dd, J=7.9, 4.9 Hz), 7.56 (2H, d, J=8.7 Hz), 7.72-7.82 (2H, m), 7.88 (2H, d, J=9.0 Hz), 8.25 (1H, dd, J=4.9, 1.5 Hz).

Anal. Calcd for C₂₃H₂₀N₆O₃F₂-0.5H₂O: C, 58.10; H, 4.45; N, 17.68; F, 8.15. Found: C, 58.20; H, 4.39; N, 17.65.

mp 171-172° C.

Example 129

1-ethyl-3-{4-[(3-methyl-3H-imidazo[4,5-b]pyridin-2-yl)oxy]phenyl}-6-(2,2,2-trifluoroethoxy)-1,3-dihydro-2H-imidazo[4,5-b]pyridin-2-one

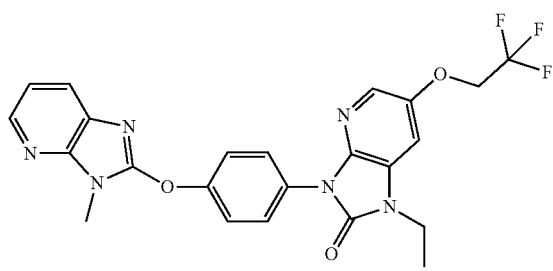 [SMILES: CCn1c(=O)n(-c2ccc(Oc3nc4cccnc4n3C)cc2)c2ncc(OCC(F)(F)F)cc21]

129a) 3-[4-(benzyloxy)phenyl]-1-ethyl-6-(2,2,2-trifluoroethoxy)-1,3-dihydro-2H-imidazo[4,5-b]pyridin-2-one

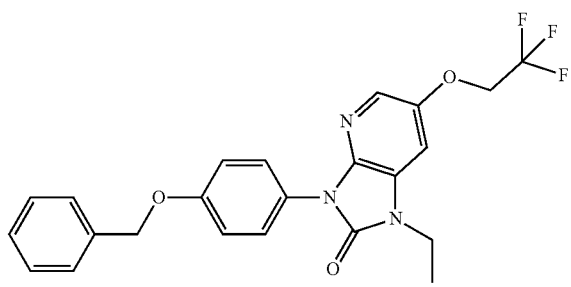 [SMILES: CCn1c(=O)n(-c2ccc(OCc3ccccc3)cc2)c2ncc(OCC(F)(F)F)cc21]

2,2,2-Trifluoroethyl trifluoromethanesulfonate (0.144 mL) was added to a solution of 3-[4-(benzyloxy)phenyl]-1-ethyl-6-hydroxy-1,3-dihydro-2H-imidazo[4,5-b]pyridin-2-one (300 mg) and potassium carbonate (229 mg) in DMF (5 ml) at room temperature. The mixture was stirred at ambient temperature under a dry atmosphere (CaCl₂ tube) for 3 h. The mixture was quenched with water at room temperature and extracted with AcOEt. The organic layer was separated, washed with water and brine, dried over MgSO₄ and concentrated in vacuo. The residue was purified by column chromatography (silica gel, eluted with 15%-50% AcOEt in hexane) to give 3-[4-(benzyloxy)phenyl]-1-ethyl-6-(2,2,2-trifluoroethoxy)-1,3-dihydro-2H-imidazo[4,5-b]pyridin-2-one (308 mg) as colorless oil.

MS (API+): [M+H]⁺444.4

¹H NMR (300 MHz, CDCl₃) δ 1.40 (3H, d, J=7.2 Hz), 3.99 (2H, q, J=7.2 Hz), 4.40 (2H, q, J=7.9 Hz), 5.11 (2H, s), 6.99 (1H, d, J=2.3 Hz), 7.11 (2H, d, J=8.7 Hz), 7.28-7.49 (5H, m), 7.55 (2H, d, J=9.1 Hz), 7.74 (1H, d, J=2.6 Hz).

129b) 1-Ethyl-3-{4-[(3-methyl-3H-imidazo[4,5-b]pyridin-2-yl)oxy]phenyl}-6-(2,2,2-trifluoroethoxy)-1,3-dihydro-2H-imidazo[4,5-b]pyridin-2-one

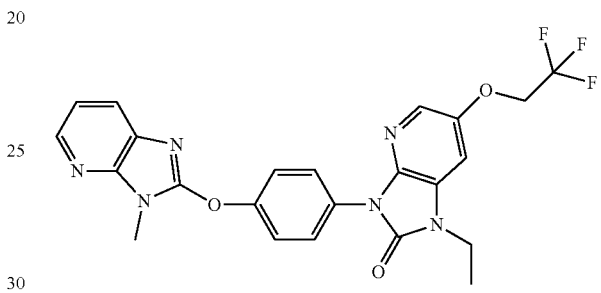

A mixture of 3-[4-(benzyloxy)phenyl]-1-ethyl-6-(2,2,2-trifluoroethoxy)-1,3-dihydro-2H-imidazo[4,5-b]pyridin-2-one (305 mg) and 10% Pd—C (36.6 mg) in EtOH (10 mL) was hydrogenated under balloon pressure at room temperature overnight. The catalyst was removed by filtration and the filtrate was concentrated in vacuo to give 1-ethyl-3-(4-hydroxyphenyl)-6-(2,2,2-trifluoroethoxy)-1H-imidazo[4,5-b]pyridin-2(3H)-one as colorless solid. To a solution of this product and 3-methyl-2-(methylsulfonyl)-3H-imidazo[4,5-b]pyridine (149 mg) in DMF (5 mL), sodium hydride (33.1 mg) was added at 100° C. and the mixture was heated at 180° C. for 30 min under microwave irradiation. The mixture was quenched with water at room temperature and extracted with AcOEt. The organic layer was separated, washed with sat. NaHCO₃ aq. and brine, dried over MgSO₄ and concentrated in vacuo. The residue was purified by column chromatography (NH silica gel, eluted with 15%-50% AcOEt in hexane) to give 1-ethyl-3-{4-[(3-methyl-3H-imidazo[4,5-b]pyridin-2-yl)oxy]phenyl}-6-(2,2,2-trifluoroethoxy)-1,3-dihydro-2H-imidazo[4,5-b]pyridin-2-one (262 mg) as colorless solid. The solid was crystallized from AcOEt-hexane.

MS (API+): [M+H]⁺485.3

¹H NMR (300 MHz, CDCl₃) δ 1.42 (3H, t, J=7.3 Hz), 3.85 (3H, s), 4.01 (2H, q, J=7.3 Hz), 4.43 (2H, q, J=8.0 Hz), 7.02 (1H, d, J=2.3 Hz), 7.15 (1H, dd, J=7.9, 4.9 Hz), 7.56 (2H, d, J=9.0 Hz), 7.75-7.82 (2H, m), 7.87 (2H, d, J=9.4 Hz), 8.25 (1H, dd, J=4.9, 1.5 Hz).

Anal. Calcd for C₂₃H₉N₆O₃F₃-0.5H₂O: C, 55.98; H, 4.09; N, 17.03. Found: C, 55.88; H, 4.19; N, 16.94.

mp 178-179° C.

Example 130

1-ethyl-3-{4-[(3-methyl-3H-imidazo[4,5-b]pyridin-2-yl)oxy]phenyl}-7-(trifluoromethyl)-1,3-dihydro-2H-imidazo[4,5-b]pyridin-2-one

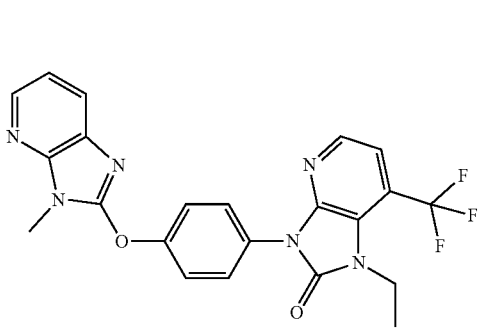 [SMILES: CCn1c(=O)n(-c2ccc(Oc3nc4cccnc4n3C)cc2)c2nccc(C(F)(F)F)c21]

130a) methyl 2-fluoro-4-(trifluoromethyl)pyridine-3-carboxylate

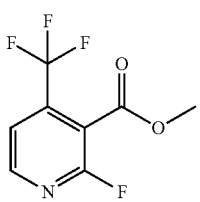

To a mixture of 2-fluoro-4-(trifluoromethyl)pyridine-3-carboxylic acid (1.06 g) and K₂CO₃ (0.701 g) in DMF (dry) (10 mL) was added MeI (0.317 mL). The mixture was stirred at room temperature for 3 h. The mixture was directly purified by column chromatography (silica gel, EtOAc/hexane) to give the title compound (1.13 g, containing EtOAc and hexane, ca. 75% purity).

MS (API+): [M+H]⁺224.0

130b) methyl 2-{[4-(benzyloxy)phenyl]amino}-4-(trifluoromethyl)pyridine-3-carboxylate

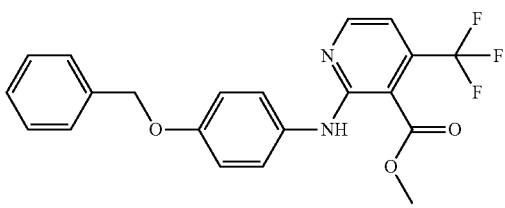 [SMILES: COC(=O)c1c(C(F)(F)F)ccnc1Nc1ccc(OCc2ccccc2)cc1]

A mixture of 4-(benzyloxy)aniline (1010 mg), DIEA (1.771 mL) and methyl 2-fluoro-4-(trifluoromethyl)pyridine-3-carboxylate (1130 mg) in NMP (10 mL) was stirred at 150° C. for 2 h and at 200° C. for 1 h under microwave irradiation. The mixture was poured into water, and the mixture was extracted with EtOAc. The organic layer was separated, washed with water and brine, dried over Na₂SO₄ and concentrated in vacuo. The residue was purified by column chromatography (silica gel, EtOAc/hexane) to give the title compound (225 mg).

MS (API+): [M+H]⁺403.3

130c) 2-{[4-(benzyloxy)phenyl]amino}-4-(trifluoromethyl)pyridine-3-carboxylic acid

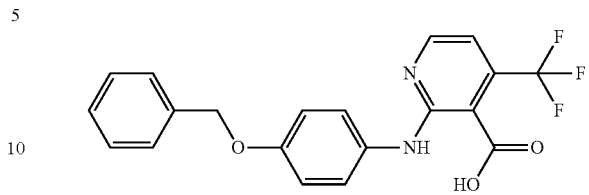

To a mixture of methyl 2-{[4-(benzyloxy)phenyl]amino}-4-(trifluoromethyl)pyridine-3-carboxylate (255 mg) in MeOH (5 mL) was added 1N NaOH (2.54 mL), and the mixture was stirred at 60° C. for 3 h. After MeOH was evaporated, to the water phase was added 1N HCl (pH=ca. 2). The precipitate was collected by filtration to give the title compound (221 mg).

MS (API+): [M+H]⁺389.3

130d) 3-[4-(benzyloxy)phenyl]-7-(trifluoromethyl)-1,3-dihydro-2H-imidazo[4,5-b]pyridin-2-one

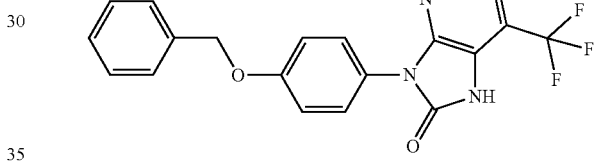

To a solution of 2-{[4-(benzyloxy)phenyl]amino}-4-(trifluoromethyl)pyridine-3-carboxylic acid (221 mg) and Et₃N (0.238 mL) in toluene (15 mL) was added diphenylphosphoryl azide (0.245 mL) at room temperature. The mixture was stirred at 110° C. for 4 h. After cooling, the solvent was evaporated, and the precipitate was collected by filtration to give the title compound (197 mg).

MS (API+): [M+H]⁺386.2

130e) 3-[4-(benzyloxy)phenyl]-1-ethyl-7-(trifluoromethyl)-1,3-dihydro-2H-imidazo[4,5-b]pyridin-2-one

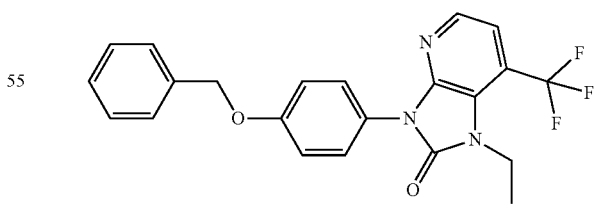

To a mixture of NaH (40.9 mg), 3-[4-(benzyloxy)phenyl]-7-(trifluoromethyl)-1,3-dihydro-2H-imidazo[4,5-b]pyridin-2-one (197 mg) in DMF (dry) (3 mL) was added iodoethane (0.082 mL), and the mixture was stirred at room temperature for 3 h. To the mixture was added sat. NaHCO₃ aq. and the mixture was extracted with EtOAc. The organic layer was separated, washed with brine, dried over Na$_2$SO$_4$ and concentrated in vacuo to give the title compound (197 mg).
MS (API+): [M+H]$^+$414.1

130f) 1-ethyl-3-(4-hydroxyphenyl)-7-(trifluoromethyl)-1,3-dihydro-2H-imidazo[4,5-b]pyridin-2-one

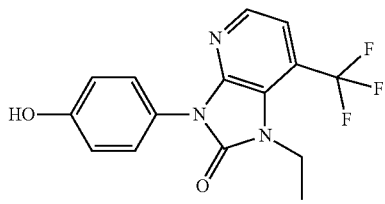 [SMILES: CCn1c(=O)n(-c2ccc(O)cc2)c2nccc(C(F)(F)F)c21]

A mixture of 3-[4-(benzyloxy)phenyl]-1-ethyl-7-(trifluoromethyl)-1,3-dihydro-2H-imidazo[4,5-b]pyridin-2-one (197 mg) and 10% palladium on carbon (50% wet, 68 mg) in MeOH (6.5 ml) and EtOAc (6.5 mL) was hydrogenated under balloon pressure at room temperature for 4 h. The solid was filtered and washed with MeOH (10 ml) to remove the catalyst. The filtrate was concentrated in vacuo to give the title compound (103 mg).
MS (API+): [M+H]$^+$324.2

130g) 1-ethyl-3-{4-[(3-methyl-3H-imidazo[4,5-b]pyridin-2-yl)oxy]phenyl}-7-(trifluoromethyl)-1,3-dihydro-2H-imidazo[4,5-b]pyridin-2-one

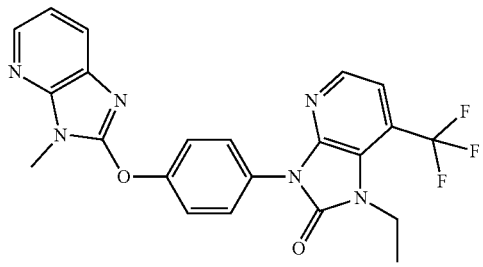 [SMILES: CCn1c(=O)n(-c2ccc(Oc3nc4cccnc4n3C)cc2)c2nccc(C(F)(F)F)c21]

To a mixture of 3-methyl-2-(methylsulfonyl)-3H-imidazo[4,5-b]pyridine (81 mg) and 1-ethyl-3-(4-hydroxyphenyl)-7-(trifluoromethyl)-1,3-dihydro-2H-imidazo[4,5-b]pyridin-2-one (103 mg) in DMF (dry) (1.5 ml) was added NaH (19.12 mg), and the mixture was stirred at 100° C. for 1 h. The mixture was heated at 180° C. for 30 min under microwave irradiation. The mixture was poured into water, and the mixture was extracted with EtOAc. The organic layer was separated, washed with brine, dried over Na$_2$SO$_4$ and concentrated in vacuo. The residue was purified by column chromatography (silica gel, EtOAc/hexane) to give the title compound as white crystals (62.2 mg).
MS (API+): [M+H]$^+$455.3.
$^1$H NMR (300 MHz, DMSO-d$_6$) δ 1.30 (3H, t, J=7.0 Hz), 3.78 (3H, s), 4.00-4.10 (2H, m), 7.21 (1H, dd, J=7.7, 5.1 Hz), 7.48 (1H, d, J=5.3 Hz), 7.60-7.69 (2H, m), 7.72-7.78 (2H, m), 7.81 (1H, dd, J=7.9, 1.5 Hz), 8.17 (1H, d, J=5.7 Hz), 8.22 (1H, dd, J=4.9, 1.5 Hz).
Anal. Calcd for C$_{22}$H$_{17}$N$_6$O$_2$F$_3$: C, 58.15; H, 3.77; N, 18.49. Found: C, 58.05; H, 3.84; N, 18.33.
m.p. 244-246° C.

Example 132

1-ethyl-6-fluoro-3-{4-[(1-methyl-1H-benzimidazol-2-yl)oxy]phenyl}-1,3-dihydro-2H-imidazo[4,5-b]pyridin-2-one

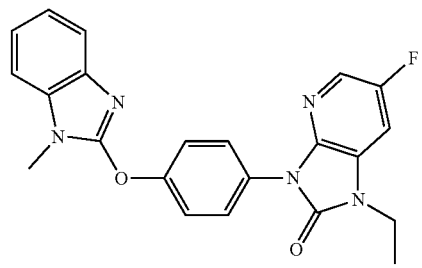 [SMILES: CCn1c(=O)n(-c2ccc(Oc3nc4ccccc4n3C)cc2)c2ncc(F)cc21]

132a) N$^2$-[4-(benzyloxy)phenyl]-5-fluoropyridine-2,3-diamine

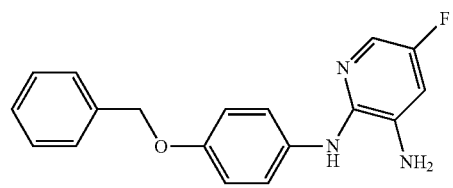 [SMILES: Nc1cc(F)cnc1Nc1ccc(OCc2ccccc2)cc1]

A mixture of 4-(benzyloxy)aniline (2.26 g), 2-chloro-5-fluoro-3-nitropyridine (2 g) and K$_2$CO$_3$ (3.13 g) in DMF (20 mL) was stirred at 120° C. for 5 h, treated with water, and extracted with AcOEt. The organic layer was dried over MgSO$_4$ and concentrated in vacuo. The residue was suspended in IPE and collected by filtration. The solid obtained above was dissolved in EtOH (20 ml), and Pt/C (2 g) was added. Under H$_2$ atmosphere, the mixture was stirred for 1 h, filtered and evaporated. The residue was chromatographed on silica gel eluting with Hexane/AcOEt to give the title compound (0.85 g).
$^1$H NMR (300 MHz, DMSO-d$_6$) δ 5.04 (2H, s), 5.39 (2H, s), 6.69-6.80 (1H, m), 6.86-6.94 (2H, m), 7.29-7.50 (8H, m), 7.54 (1H, s).

132b) 1-ethyl-6-fluoro-3-(4-hydroxyphenyl)-1,3-dihydro-2H-imidazo[4,5-b]pyridin-2-one

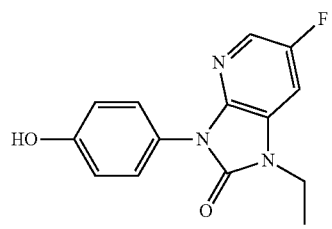 [SMILES: CCn1c(=O)n(-c2ccc(O)cc2)c2ncc(F)cc21]

A mixture of N$^2$-[4-(benzyloxy)phenyl]-5-fluoropyridine-2,3-diamine (0.85 g) and 1,1'-carbonylbis(1H-imidazole) (0.45 g) in DME (10 mL) was stirred at 100° C. for 4 h, and then Cs$_2$CO$_3$ (0.90 g) and 1,1'-carbonylbis(1H-imidazole) (0.892 g) were added successively. The mixture was stirred at 100° C. for 10 min, treated with water, and extracted with AcOEt. The organic layer was dried over MgSO$_4$ and concentrated in vacuo. The residue was dissolved in DMF (10 ml), and then Cs₂CO₃ (3.58 g) and iodoethane (1.29 g) were added successively. The mixture was stirred at 100° C. for 2 h, treated with water, and extracted with AcOEt. The organic layer was dried over MgSO₄ and concentrated in vacuo. The residue was dissolved in EtOH (30 mL), and Pd/C (1.5 g) was added. Under H₂ atmosphere, the mixture was stirred at room temperature for 30 min, filtered and evaporated. The residue was chromatographed on silica gel eluting with AcOEt/Hexane to give the title compound (0.52 g).

MS (API+): [M+H]⁺274.3.

132c) 1-ethyl-6-fluoro-3-{4-[(1-methyl-1H-benzimidazol-2-yl)oxy]phenyl}-1,3-dihydro-2H-imidazo[4,5-b]pyridin-2-one

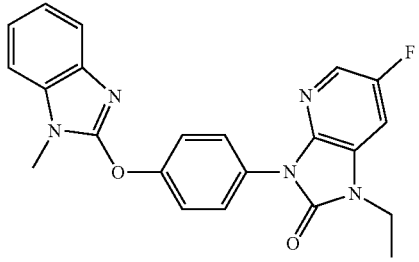 [SMILES: CCn1c(=O)n(-c2ccc(Oc3nc4ccccc4n3C)cc2)c2ncc(F)cc21]

To a stirred solution of 1-ethyl-6-fluoro-3-(4-hydroxyphenyl)-1,3-dihydro-2H-imidazo[4,5-b]pyridin-2-one (100 mg) in DMF (4 mL) was added 60% sodium hydride (13.2 mg) at room temperature. The mixture was stirred at room temperature for 30 min, and then 2-chloro-1-methyl-1H-benzimidazole (67.1 mg) was added. The mixture was exposed to microwave irradiation at 180° C. for 30 min, treated with water, and extracted with AcOEt. The organic layer was dried over MgSO₄ and concentrated in vacuo. The residue was chromatographed on NH-silica gel eluting with AcOEt/Hexane. Crystallization from AcOEt/Hexane gave the title compound (104 mg).

MS (API+): [M+H]⁺404.2.
¹H NMR (300 MHz, DMSO-d₆) δ 1.30 (3H, t, J=7.2 Hz), 3.76 (3H, s), 3.98 (2H, q, J=7.2 Hz), 7.09-7.25 (2H, m), 7.39-7.52 (2H, m), 7.56-7.64 (2H, m), 7.73-7.79 (2H, m), 7.83-7.91 (1H, m), 7.96-8.01 (1H, m).

Example 133

1-ethyl-6-fluoro-3-{4-[(3-methyl-3H-imidazo[4,5-b]pyridin-2-yl)oxy]phenyl}-1,3-dihydro-2H-imidazo[4,5-b]pyridin-2-one

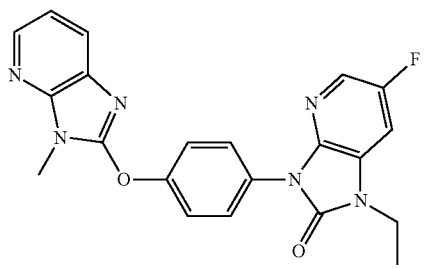 [SMILES: CCn1c(=O)n(-c2ccc(Oc3nc4cccnc4n3C)cc2)c2ncc(F)cc21]

133a) N²-[4-(benzyloxy)phenyl]-5-fluoropyridine-2,3-diamine

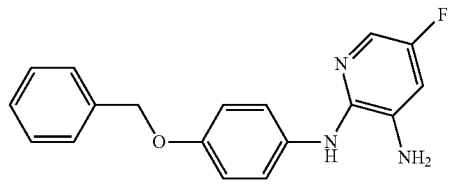 [SMILES: Nc1cc(F)cnc1Nc1ccc(OCc2ccccc2)cc1]

A mixture of 4-(benzyloxy)aniline (2.26 g), 2-chloro-5-fluoro-3-nitropyridine (2 g) and K₂CO₃ (3.13 g) in DMF (20 ml) was stirred at 120° C. for 5 h, treated with water, and extracted with AcOEt. The organic layer was dried over MgSO₄ and concentrated in vacuo. The residue was suspended in IPE and collected by filtration. The obtained solid was dissolved in EtOH (20 ml), and Pt/C (2 g) was added. Under H₂ atmosphere, the mixture was stirred for 1 h, filtered and evaporated. The residue was chromatographed on silica gel eluting with Hexane/AcOEt to give the title compound (0.85 g).

¹H NMR (300 MHz, DMSO-d₆) δ 5.04 (2H, s), 5.39 (2H, s), 6.69-6.80 (1H, m), 6.86-6.94 (2H, m), 7.29-7.50 (8H, m), 7.54 (1H, s).

133b) 1-ethyl-6-fluoro-3-(4-hydroxyphenyl)-1,3-dihydro-2H-imidazo[4,5-b]pyridin-2-one

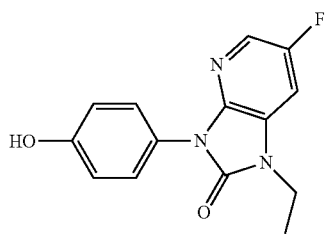 [SMILES: CCn1c(=O)n(-c2ccc(O)cc2)c2ncc(F)cc21]

A mixture of N²-[4-(benzyloxy)phenyl]-5-fluoropyridine-2,3-diamine (0.85 g) and 1,1'-carbonylbis(1H-imidazole) (0.45 g) in DME (10 mL) was stirred at 100° C. for 4 h, and then Cs₂CO₃ (0.90 g) and 1,1'-carbonylbis(1H-imidazole) (0.892 g) were added successively. The mixture was stirred at 100° C. for 10 min, treated with water, and extracted with AcOEt. The organic layer was dried over MgSO₄ and concentrated in vacuo. The residue was dissolved in DMF (10 mL), and then Cs₂CO₃ (3.58 g) and iodoethane (1.29 g) were added successively. The mixture was stirred at 100° C. for 2 h, treated with water, and extracted with AcOEt. The organic layer was dried over MgSO₄ and concentrated in vacuo. The residue was dissolved in EtOH (30 ml), and Pd/C (1.5 g) was added. Under H₂ atmosphere, the mixture was stirred at room temperature for 30 min, filtered and evaporated. The residue was chromatographed on silica gel eluting with AcOEt/Hexane to give the title compound (0.52 g).

MS (API+): [M+H]⁺274.3.

133c) 1-ethyl-6-fluoro-3-{4-[(3-methyl-3H-imidazo[4,5-b]pyridin-2-yl)oxy]phenyl}-1,3-dihydro-2H-imidazo[4,5-b]pyridin-2-one To a stirred solution of 1-ethyl-6-fluoro-3-(4-hydroxyphenyl)-1,3-dihydro-2H-imidazo[4,5-b]pyridin-2-one (100 mg)

in DMF (4 mL) was added 60% sodium hydride (13.2 mg) at room temperature. The mixture was stirred at room temperature for 30 min, and then 3-methyl-2-(methylsulfonyl)-3H-imidazo[4,5-b]pyridine (85 mg) was added. The mixture was exposed to microwave irradiation at 180° C. for 30 min, treated with water, and extracted with AcOEt. The organic layer was dried over $MgSO_4$ and concentrated in vacuo. The residue was chromatographed on NH-silica gel eluting with AcOEt/Hexane. Crystallization from AcOEt/Hexane gave the title compound (96 mg).

MS (API+): [M+H]⁺405.2.

$^1$H NMR (300 MHz, DMSO-$d_6$) δ 1.31 (3H, t, J=7.2 Hz), 3.77 (3H, s), 3.98 (2H, q, J=7.2 Hz), 7.21 (1H, dd, J=7.9, 4.9 Hz), 7.57-7.66 (2H, m), 7.72-7.91 (4H, m), 7.95-8.05 (1H, m), 8.18-8.24 (1H, m).

Example 134

3-[4-(2,3-dihydro-1H-imidazo[2',1':2,3]imidazo[4,5-b]pyridin-1-yl)phenyl]-1-ethyl-1,3-dihydro-2H-imidazo[4,5-b]pyridin-2-one

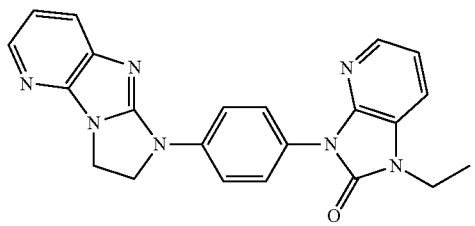 [SMILES: CCn1c(=O)n(-c2ccc(N3CCn4c3nc3cccnc34)cc2)c2ncccc21]

134a) ethyl N-(3-nitropyridin-2-yl)glycinate

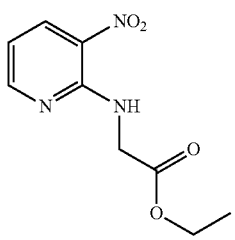 [SMILES: CCOC(=O)CNc1ncccc1[N+](=O)[O-]]

To a solution of 2-chloro-3-nitropyridine (25.3 g) in EtOH (300 mL) were added ethyl 2-aminoacetate hydrochloride (28.7 g) and triethylamine (28.9 ml) at room temperature, and the mixture was refluxed for 1 day. The mixture was concentrated under reduced pressure. The residual crystals were removed by filtration and washed with AcOEt. The filtrate was concentrated under reduced pressure. The residue was purified by column chromatography (silica gel, eluted with 20%-70% AcOEt in hexane). The residual crystals were removed by filtration and washed with IPE. The filtrate was concentrated under reduced pressure to give the title compound (26.9 g).

$^1$H NMR (300 MHz, $CDCl_3$) δ 1.30 (3H, t, J=7.2 Hz), 4.26 (2H, q, J=7.2 Hz), 4.38 (2H, d, J=5.3 Hz), 6.72 (1H, dd, J=8.3, 4.5 Hz), 8.40 (1H, dd, J=4.5, 1.9 Hz), 8.44 (1H, dd, J=8.3, 1.9 Hz), 8.50 (1H, brs).

134b) ethyl N-(3-aminopyridin-2-yl)glycinate

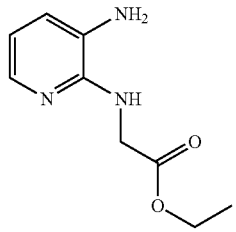

A mixture of ethyl N-(3-nitropyridin-2-yl)glycinate (26 g) and 10% palladium on carbon (50% wet, 7.3 g) in AcOEt (250 mL) was hydrogenated under balloon pressure at room temperature for 8 h. The catalyst was removed by filtration. To the filtrate were added triethylamine (5.0 ml) and 10% palladium on carbon (50% wet, 7.3 g). The mixture was hydrogenated under balloon pressure at room temperature overnight. The mixture was concentrated under reduced pressure. The residue was purified by column chromatography (silica gel, eluted with 10%-50% AcOEt in hexane) to give the title compound (18 g).

$^1$H NMR (300 MHz, DMSO-$d_6$) δ 1.17 (3H, t, J=7.2 Hz), 3.98-4.13 (4H, m), 4.72 (2H, s), 6.07 (1H, t, J=6.0 Hz), 6.38 (1H, dd, J=7.3, 5.1 Hz), 6.70 (1H, dd, J=7.5, 1.5 Hz), 7.31 (1H, dd, J=4.9, 1.5 Hz).

134c) ethyl (2-oxo-1,2-dihydro-3H-imidazo[4,5-b]pyridin-3-yl)acetate

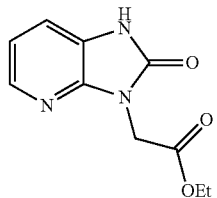 [SMILES: CCOC(=O)Cn1c(=O)[nH]c2cccnc21]

To a solution of ethyl N-(3-aminopyridin-2-yl)glycinate (18 g) in THF (200 mL) was added CDI (15 g) at room temperature, and the mixture was stirred at room temperature overnight. The mixture was concentrated under reduced pressure. The residual crystals were washed with AcOEt to give the title compound (5.5 g).

$^1$H NMR (300 MHz, $CDCl_3$) δ 1.30 (3H, t, J=7.2 Hz), 4.26 (2H, q, J=7.2 Hz), 4.77 (2H, s), 7.02 (1H, dd, J=7.6, 5.3 Hz), 7.31 (1H, dd, J=7.6, 1.1 Hz), 8.05 (1H, dd, J=5.3, 1.1 Hz), 9.70 (1H, brs).

134d) ethyl (2-chloro-3H-imidazo[4,5-b]pyridin-3-yl)acetate

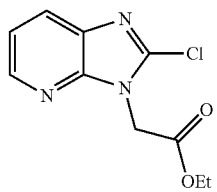 [SMILES: CCOC(=O)Cn1c(Cl)nc2cccnc21]

A mixture of ethyl (2-oxo-1,2-dihydro-3H-imidazo[4,5-b]pyridin-3-yl)acetate (14.5 g) and phosphoryl chloride (100 mL) was stirred at 100° C. overnight. The mixture was poured into ice, neutralized with saturated sodium bicarbonate solution and extracted with AcOEt. The organic layer was dried over Na₂SO₄, filtered and concentrated under reduced pressure. The residue was diluted with AcOEt and insoluble crystals were removed by filtration. The filtrate was concentrated under reduced pressure. The residue was purified by column chromatography (silica gel, eluted with 10%-40% AcOEt in hexane) to give the title compound (5.46 g).

¹H NMR (300 MHz, CDCl₃) δ 1.29 (3H, t, J=7.2 Hz), 4.26 (2H, q, J=7.2 Hz), 5.07 (2H, s), 7.23-7.32 (1H, m), 7.99 (1H, dd, J=8.1, 1.5 Hz), 8.36 (1H, dd, J=4.9, 1.5 Hz).

134e) ethyl {2-[(4-nitrophenyl)amino]-3H-imidazo[4,5-b]pyridin-3-yl}acetate

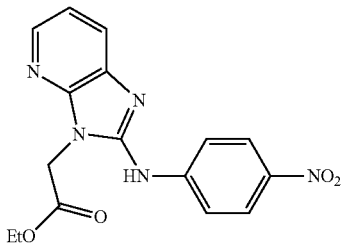 [SMILES: CCOC(=O)Cn1c(Nc2ccc([N+](=O)[O-])cc2)nc2cccnc21]

A mixture of ethyl (2-chloro-3H-imidazo[4,5-b]pyridin-3-yl)acetate (2.8 g) and 4-nitroaniline (1.6 g) was stirred at 150° C. for 1 h to give the title compound (4.0 g).

¹H NMR (300 MHz, DMSO-d₆) δ 1.22 (3H, t, J=7.2 Hz), 4.18 (2H, q, J=7.2 Hz), 5.21 (2H, s), 7.20 (1H, dd, J=7.6, 4.9 Hz), 7.85 (1H, d, J=7.6 Hz), 8.06-8.20 (3H, m), 8.23-8.34 (2H, m), 9.98 (1H, brs).

134f) 2-{2-[(4-nitrophenyl)amino]-3H-imidazo[4,5-b]pyridin-3-yl}ethanol

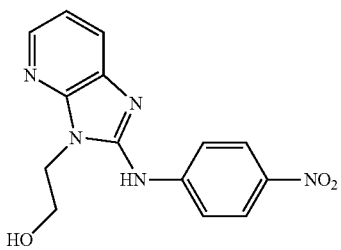 [SMILES: O=[N+]([O-])c1ccc(Nc2nc3cccnc3n2CCO)cc1]

To a suspension of ethyl {2-[(4-nitrophenyl)amino]-3H-imidazo[4,5-b]pyridin-3-yl}acetate (3.6 g) in THF (120 mL) was added lithium borohydride (0.77 g) at room temperature, and the mixture was refluxed for 2 h. The mixture was cooled to room temperature, quenched with water and extracted with AcOEt. The organic layer was dried over Na₂SO₄, filtered and concentrated under reduced pressure. The residue was purified by column chromatography (silica gel, eluted with 50%-100% AcOEt in hexane) to give the title compound (2.2 g).

¹H NMR (300 MHz, DMSO-d₆) δ 3.80 (2H, t, J=5.5 Hz), 4.45 (2H, t, J=5.5 Hz), 7.17 (1H, dd, J=7.6, 4.9 Hz), 7.82 (1H, dd, J=7.6, 1.1 Hz), 8.06-8.19 (3H, m), 8.23-8.33 (2H, m).

134g) 1-(4-nitrophenyl)-2,3-dihydro-1H-imidazo[2',1':2,3]imidazo[4,5-b]pyridine

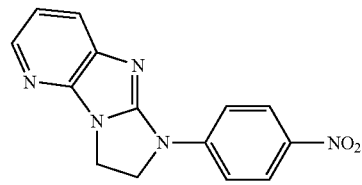 [SMILES: O=[N+]([O-])c1ccc(N2CCn3c2nc2cccnc23)cc1]

To a solution of 2-{2-[(4-nitrophenyl)amino]-3H-imidazo[4,5-b]pyridin-3-yl}ethanol (2.2 g) and triethylamine (10 mL) in THF (100 mL) was added methanesulfonyl chloride (1.1 mL) at 0° C., and the mixture was stirred at 0° C. for 2 h. The mixture was poured into water and extracted with AcOEt. The organic layer was washed with brine, dried over Na₂SO₄, filtered and concentrated under reduced pressure. A mixture of the residue and potassium carbonate (3.1 g) in NMP (30 mL) was stirred at 100° C. overnight. After cooling to room temperature, the mixture was diluted with water. The formed crystals were collected by filtration to give the title compound (1.7 g).

¹H NMR (300 MHz, DMSO-d₆) δ 4.40-4.51 (2H, m), 4.64-4.75 (2H, m), 7.16 (1H, dd, J=8.0, 4.9 Hz), 7.83 (1H, d, J=8.0 Hz), 8.03 (2H, d, J=9.1 Hz), 8.09 (1H, d, J=4.9 Hz), 8.35 (2H, d, J=9.1 Hz).

134h) 4-(2,3-dihydro-1H-imidazo[2',1':2,3]imidazo[4,5-b]pyridin-1-yl)aniline

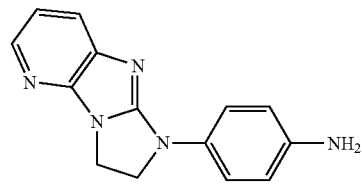 [SMILES: Nc1ccc(N2CCn3c2nc2cccnc23)cc1]

A mixture of 1-(4-nitrophenyl)-2,3-dihydro-1H-imidazo[2',1':2,3]imidazo[4,5-b]pyridine (1.7 g) and 10% palladium on carbon (50% wet, 1.0 g) in MeOH (150 ml) was hydrogenated under balloon pressure at room temperature for 1 day. The catalyst was removed by filtration and the filtrate was concentrated under reduced pressure to give the title compound (1.2 g).

MS (API+): [M+H]⁺ 252.4.

134i) 3-[4-(2,3-dihydro-1H-imidazo[2',1':2,3]imidazo[4,5-b]pyridin-1-yl)phenyl]-1,3-dihydro-2H-imidazo[4,5-b]pyridin-2-one

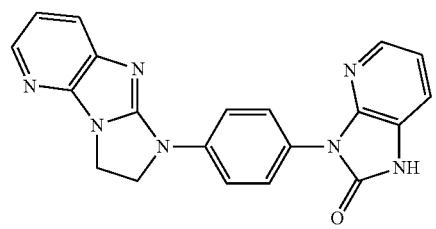 [SMILES: O=c1[nH]c2cccnc2n1-c1ccc(N2CCn3c2nc2cccnc23)cc1]

The mixture of 2-chloro-3-nitropyridine (189 mg), 4-(2,3-dihydro-1H-imidazo[2',1':2,3]imidazo[4,5-b]pyridin-1-yl)aniline (300 mg) and DIPEA (1.0 ml) in DMSO (5 mL) was stirred at 120° C. for 4 h. The mixture was diluted with AcOEt and THF, and washed with water. The organic layer was dried over Na₂SO₄, filtered and concentrated under reduced pressure. A mixture of the residue and 10% palladium on carbon (50% wet, 0.20 g) in MeOH (30 ml) was hydrogenated under balloon pressure at room temperature for 1 day. The catalyst was removed by filtration and the filtrate was concentrated under reduced pressure.

A solution of the residue and CDI (193 mg) in THF (15 mL) was refluxed for overnight. To the mixture was added CDI (193 mg), and the mixture was refluxed for 5 h. After cooling to room temperature, the formed precipitate was collected by filtration to give the title compound (165 mg).

$^1$H NMR (300 MHz, DMSO-$d_6$) δ 4.38-4.49 (2H, m), 4.58-4.70 (2H, m), 7.05-7.14 (2H, m), 7.40 (1H, dd, J=7.9, 1.5 Hz), 7.67 (2H, d, J=9.1 Hz), 7.74 (1H, dd, J=7.7, 1.3 Hz), 7.91-7.99 (3H, m), 8.02 (1H, dd, J=4.9, 1.5 Hz), 11.36 (1H, s).

134j) 3-[4-(2,3-dihydro-1H-imidazo[2',1':2,3]imidazo[4,5-b]pyridin-1-yl)phenyl]-1-ethyl-1,3-dihydro-2H-imidazo[4,5-b]pyridin-2-one

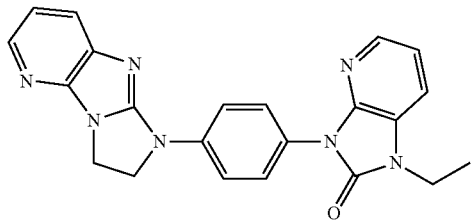 [SMILES: CCn1c(=O)n(-c2ccc(N3CCn4c3nc3cccnc34)cc2)c2ncccc21]

A mixture of 3-[4-(2,3-dihydro-1H-imidazo[2',1':2,3]imidazo[4,5-b]pyridin-1-yl)phenyl]-1,3-dihydro-2H-imidazo[4,5-b]pyridin-2-one (165 mg), iodoethane (0.054 mL) and cesium carbonate (291 mg) in DMF (3 mL) was stirred at 50° C. for 6 h. The mixture was poured into water and extracted with AcOEt. The organic layer was washed with brine, dried over Na₂SO₄, filtered and concentrated under reduced pressure. The residual crystals were dissolved in THF, and the solution was filtered through NH-silica gel. The filtrate was concentrated under reduced pressure. The residual crystals were recrystallized from EtOH to give the title compound (94 mg).

$^1$H NMR (300 MHz, DMSO-$d_6$) δ 1.30 (3H, t, J=7.2 Hz), 3.98 (2H, q, J=7.2 Hz), 4.37-4.49 (2H, m), 4.57-4.71 (2H, m), 7.10 (1H, dd, J=7.9, 4.9 Hz), 7.17 (1H, dd, J=7.7, 5.1 Hz), 7.62-7.71 (3H, m), 7.74 (1H, dd, J=7.7, 1.3 Hz), 7.91-8.06 (4H, m).

MS (ESI+): [M+H]⁺ 398.1.

mp 255-256° C.

Anal. Calcd for C₂₂H₁₉N₇O: C, 66.49; H, 4.82; N, 24.67. Found: C, 66.24; H, 4.85; N, 24.41.

Example 135

1,7-dimethyl-3-{4-[(3-methyl-3H-imidazo[4,5-b]pyridin-2-yl)oxy]phenyl}-1,3-dihydro-2H-imidazo[4,5-b]pyridin-2-one

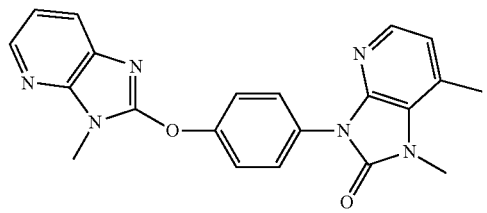 [SMILES: Cc1ccnc2c1n(C)c(=O)n2-c1ccc(Oc2nc3cccnc3n2C)cc1]

135a) 3-[4-(benzyloxy)phenyl]-1,7-dimethyl-1,3-dihydro-2H-imidazo[4,5-b]pyridin-2-one

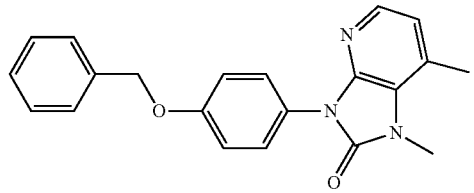 [SMILES: Cc1ccnc2c1n(C)c(=O)n2-c1ccc(OCc2ccccc2)cc1]

MeI (0.377 mL) was added to a solution of 3-[4-(benzyloxy)phenyl]-7-methyl-1,3-dihydro-2H-imidazo[4,5-b]pyridin-2-one (2.0 g) and NaH (0.362 g) in DMF (20 mL) at 20° C. The mixture was stirred at 20° C. under a dry atmosphere for 1 h. The mixture was diluted with sat. NaHCO₃ at 20° C. and extracted with EtOAc. The organic layer was separated, washed with water and brine, dried over MgSO₄ and concentrated in vacuo to give 3-[4-(benzyloxy)phenyl]-1,7-dimethyl-1,3-dihydro-2H-imidazo[4,5-b]pyridin-2-one (2.0 g). This product was subjected to the next reaction without further purification.

135b) 3-(4-hydroxyphenyl)-1,7-dimethyl-1,3-dihydro-2H-imidazo[4,5-b]pyridin-2-one

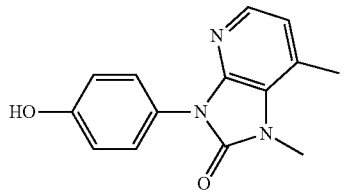 [SMILES: Cc1ccnc2c1n(C)c(=O)n2-c1ccc(O)cc1]

A mixture of 3-[4-(benzyloxy)phenyl]-1,7-dimethyl-1,3-dihydro-2H-imidazo[4,5-b]pyridin-2-one (2.0 g) and 10% Pd—C (0.308 g) in DMF (10 mL)-EtOAc (100 mL) was hydrogenated under balloon pressure at 20° C. for 1 h. The catalyst was removed by filtration and the filtrate was concentrated in vacuo. The residue was purified by column chromatography (NH silica gel, eluted with 50%-100% EtOAc in hexane) to give 3-(4-hydroxyphenyl)-1,7-dimethyl-1,3-dihydro-2H-imidazo[4,5-b]pyridin-2-one (1.30 g) as a light brown solid. This product was subjected to the next reaction without further purification.

135c) 1,7-dimethyl-3-{4-[(3-methyl-3H-imidazo[4,5-b]pyridin-2-yl)oxy]phenyl}-1,3-dihydro-2H-imidazo[4,5-b]pyridin-2-one

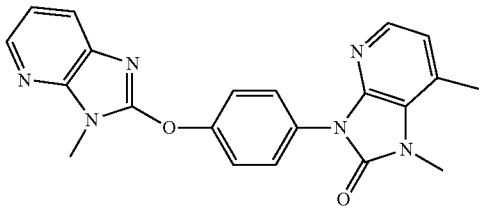 [SMILES: Cc1ccnc2c1n(C)c(=O)n2-c1ccc(Oc2nc3cccnc3n2C)cc1]

3-Methyl-2-(methylsulfonyl)-3H-imidazo[4,5-b]pyridine (600 mg) was added to a solution of 3-(4-hydroxyphenyl)-1,7-dimethyl-1,3-dihydro-2H-imidazo[4,5-b]pyridin-2-one (725 mg) and potassium tert-butoxide (351 mg) in DMA (4 ml) at 20° C. The mixture was stirred at 150° C. under a dry atmosphere for 30 min. The reaction mixture was diluted with MeOH and concentrated in vacuo. The residue was purified by column chromatography (NH silica gel, eluted with 0%-50% EtOAc in hexane) to give 1,7-dimethyl-3-{4-[(3-methyl-3H-imidazo[4,5-b]pyridin-2-yl)oxy]phenyl}-1,3-dihydro-2H-imidazo[4,5-b]pyridin-2-one (150 mg) as colorless crystals.

MS (API+): [M+H]$^+$ 387.1.

$^1$H NMR (300 MHz, DMSO-d$_6$) δ 2.59-2.69 (3H, s), 3.66 (3H, s), 3.78 (3H, s), 6.91-7.06 (1H, m), 7.13-7.28 (1H, m), 7.56-7.66 (2H, m), 7.70-7.76 (2H, m), 7.77-7.83 (1H, m), 7.83-7.89 (1H, m), 8.15-8.28 (1H, m).

Example 136

1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one 4-oxide

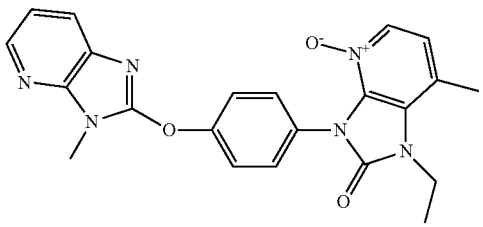 [SMILES: CCn1c(=O)n(-c2ccc(Oc3nc4cccnc4n3C)cc2)c2c1c(C)cc[n+]2[O-]]

Triisopropylsilyl chloride (2.384 mL) was added to a solution of 1-ethyl-3-(4-hydroxyphenyl)-7-methyl-1,3-dihydro-2H-imidazo[4,5-b]pyridin-2-one (2 g) and NaH (0.594 g) in DMF (20 mL) at 20° C. The mixture was stirred at 20° C. under a dry atmosphere (CaCl$_2$ tube) for 1 h. The mixture was poured into sat. NaHCO$_3$ at 0° C. and extracted with EtOAc. The organic layer was separated, washed with water and brine, dried over MgSO$_4$ and concentrated in vacuo. The residue was purified by column chromatography (NH silica gel, eluted with 0%-25% EtOAc in hexane) to give 1-ethyl-7-methyl-3-(4-{[tris(1-methylethyl)silyl]oxy}phenyl)-1,3-dihydro-2H-imidazo[4,5-b]pyridin-2-one (4.0 g) as light brown crystals.

Trifluoroacetic anhydride (3.92 mL) was added to a suspension of 1-ethyl-7-methyl-3-(4-{[tris(1-methylethyl)silyl]oxy}phenyl)-1,3-dihydro-2H-imidazo[4,5-b]pyridin-2-one (4 g) and urea hydrogen peroxide (2.74 g) in EtOAc (20 mL) at 0° C. The mixture was stirred at room temperature under a dry atmosphere (CaCl$_2$ tube) overnight. The mixture was neutralized with sat. NaHCO$_3$ at 0° C. and extracted with EtOAc. The organic layer was separated, washed with water and brine, dried over MgSO$_4$ and concentrated in vacuo. The residue was purified by column chromatography (NH silica gel, eluted with 0%-100% EtOAc in hexane) to give 1-ethyl-7-methyl-3-(4-{[tris(1-methylethyl)silyl]oxy}phenyl)-1,3-dihydro-2H-imidazo[4,5-b]pyridin-2-one 4-oxide (250 mg) as colorless crystals.

Tetrabutylammonium fluoride (0.566 mL) was added to a solution of 1-ethyl-7-methyl-3-(4-{[tris(1-methylethyl)silyl]oxy}phenyl)-1,3-dihydro-2H-imidazo[4,5-b]pyridin-2-one 4-oxide (250 mg) in THF (5 mL) at room temperature. The mixture was stirred at room temperature under a dry atmosphere (CaCl$_2$ tube) for 30 min. The reaction mixture was concentrated in vacuo. The residue was purified by column chromatography (silica gel, eluted with 0%-100% EtOAc in hexane) to give 1-ethyl-3-(4-hydroxyphenyl)-7-methyl-1,3-dihydro-2H-imidazo[4,5-b]pyridin-2-one 4-oxide (170 mg) as a colorless solid. 3-Methyl-2-(methylsulfonyl)-3H-imidazo[4,5-b]pyridine (126 mg) was added to a solution of 1-ethyl-3-(4-hydroxyphenyl)-7-methyl-1,3-dihydro-2H-imidazo[4,5-b]pyridin-2-one 4-oxide (170 mg) and NaH (23.83 mg) in DMA (1 mL) at room temperature. The mixture was stirred at 150° C. under a dry atmosphere (CaCl$_2$ tube) for 30 min. The reaction mixture was concentrated in vacuo. The residue was purified by column chromatography (NH silica gel, eluted with 50%-100% EtOAc in hexane) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one 4-oxide as colorless crystals.

MS (API+): [M+H]$^+$417.2.

$^1$H NMR (300 MHz, DMSO-d$_6$) δ 1.23-1.40 (3H, m), 2.58 (3H, s), 3.77 (3H, s), 4.01-4.19 (2H, m), 6.96-7.05 (1H, m), 7.15-7.29 (1H, m), 7.40-7.57 (4H, m), 7.75-7.90 (2H, m), 8.15-8.29 (1H, m).

Example 137

(1-ethyl-3-{4-[(3-methyl-3H-imidazo[4,5-b]pyridin-2-yl)oxy]phenyl}-2-oxo-2,3-dihydro-1H-imidazo[4,5-b]pyridin-7-yl)methyl acetate

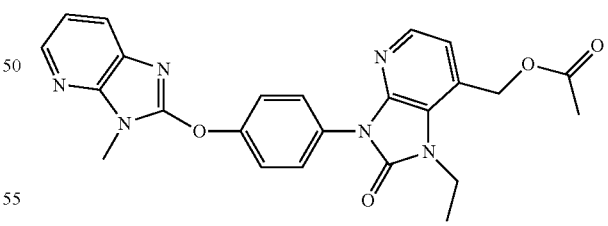

The mixture of 1-ethyl-7-methyl-3-(4-{[tris(1-methylethyl)silyl]oxy}phenyl)-1,3-dihydro-2H-imidazo[4,5-b]pyridin-2-one 4-oxide (500 mg) in acetic anhydride (10 mL) was stirred at 80° C. under a dry atmosphere (CaCl$_2$ tube) for 2 h. The reaction mixture was concentrated in vacuo. The residue was purified by column chromatography (silica gel, eluted with 0%-30% EtOAc in hexane) to give [1-ethyl-2-oxo-3-(4-{[tris(1-methylethyl)silyl]oxy}phenyl)-2,3-dihydro-1H-imidazo[4,5-b]pyridin-7-yl]methyl acetate (300 mg) as colorless oil.

Tetrabutylammonium fluoride (1.241 mL) was added to a solution of [1-ethyl-2-oxo-3-(4-{[tris(1-methylethyl)silyl]oxy}phenyl)-2,3-dihydro-1H-imidazo[4,5-b]pyridin-7-yl]methyl acetate (300 mg) in THF (dry) (1 ml) at room temperature. The mixture was stirred at room temperature under a dry atmosphere (CaCl$_2$ tube) for 30 min. The reaction mixture was concentrated in vacuo. The residue was purified by column chromatography (silica gel, eluted with 20%-100% 50 EtOAc in hexane) to give [1-ethyl-3-(4-hydroxyphenyl)-2-oxo-2,3-dihydro-1H-imidazo[4,5-b]pyridin-7-yl]methyl acetate (170 mg) as a white solid.

3-Methyl-2-(methylsulfonyl)-3H-imidazo[4,5-b]pyridine (110 mg) was added to a solution of [1-ethyl-3-(4-hydroxyphenyl)-2-oxo-2,3-dihydro-1H-imidazo[4,5-b]pyridin-7-yl]methyl acetate (170 mg) and potassium tert-butoxide (69.9 mg) in DMA (1 mL) at room temperature. The mixture was stirred at 100° C. under a dry atmosphere (CaCl$_2$ tube) for 30 min. The reaction mixture was concentrated in vacuo. The residue was purified by column chromatography (NH silica gel, eluted with 0%-100% EtOAc in hexane) to give (1-ethyl-3-{4-[(3-methyl-3H-imidazo[4,5-b]pyridin-2-yl)oxy]phenyl}-2-oxo-2,3-dihydro-1H-imidazo[4,5-b]pyridin-7-yl)methyl acetate (10 mg) as colorless crystals.

MS (API+): [M+H]$^+$459.2.
$^1$H NMR (300 MHz, DMSO-d$_6$) δ1.28-1.41 (3H, m), 2.14 (3H, s), 3.78 (3H, s), 4.00-4.18 (2H, m), 5.40 (2H, s), 7.15-7.26 (2H, m), 7.56-7.87 (5H, m), 7.95-8.04 (1H, m), 8.12-8.28 (1H, m).

Example 138

1-ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one

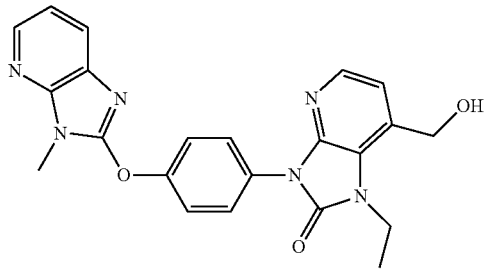 [SMILES: CCn1c(=O)n(-c2ccc(Oc3nc4cccnc4n3C)cc2)c2nccc(CO)c21]

To a stirred mixture of [1-ethyl-3-(4-hydroxyphenyl)-2-oxo-2,3-dihydro-1H-imidazo[4,5-b]pyridin-7-yl]methyl acetate (150 mg) and EtOH (3 mL) was added 1 N NaOH (2 mL) at 0° C. The mixture was stirred at 0° C. for 30 min, treated with saturated NH$_4$Cl solution, and extracted with AcOEt. The organic layer was dried over MgSO$_4$ and concentrated in vacuo. The residue was dissolved in DMA (4 ml) and KOtBu (52 mg) was added at room temperature. The mixture was stirred for 2 min, and then 3-methyl-2-(methylsulfonyl)-3H-imidazo[4,5-b]pyridine (97 mg) was added. The mixture was stirred at 150° C. for 30 min, treated with water, and extracted with AcOEt. The organic layer was dried over MgSO$_4$ and concentrated in vacuo. The residue was chromatographed on NH-silica gel eluting with AcOEt/MeOH=20/1. The product was crystallized from AcOEt/Hexane to give 1-ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one (46 mg).

MS (API+): [M+H]$^+$ 417.2.
$^1$H NMR (300 MHz, DMSO-d$_6$) δ 1.32 (3H, t, J=7.2 Hz), 3.78 (3H, s), 4.13 (2H, q, J=7.2 Hz), 4.80 (2H, d, J=5.5 Hz), 5.67 (1H, t, J=5.5 Hz), 7.14-7.26 (2H, m), 7.59-7.68 (2H, m), 7.71-7.87 (3H, m), 7.97 (1H, d, J=5.3 Hz), 8.17-8.28 (1H, m).

Alternative route for 1-ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one is described below.

138a) 1-ethyl-7-methyl-3-(4-{[tris(1-methylethyl)silyl]oxy}phenyl)-1,3-dihydro-2H-imidazo[4,5-b]pyridin-2-one

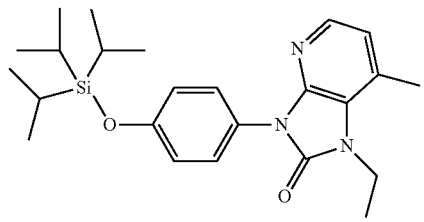 [SMILES: CCn1c(=O)n(-c2ccc(O[Si](C(C)C)(C(C)C)C(C)C)cc2)c2nccc(C)c21]

To a stirred mixture of 1-ethyl-3-(4-hydroxyphenyl)-7-methyl-1,3-dihydro-2H-imidazo[4,5-b]pyridin-2-one (10 g) and 1H-imidazole (3.79 g) in DMF (100 mL) was added triisopropylsilyl chloride (9.54 mL) at 0° C. The mixture was stirred at room temperature for 3 days, treated with water, and extracted with AcOEt. The organic layer was dried over MgSO$_4$ and concentrated in vacuo. The residue was purified by silica gel column chromatography (AcOEt/Hexane=1/10) to give the title compound (11.5 g).

MS (API+): [M+H]$^+$ 426.2.
$^1$H NMR (300 MHz, DMSO-d$_6$) δ1.05-1.19 (18H, m), 1.23-1.37 (6H, m), 2.59 (3H, s), 4.08 (2H, d, J=7.2 Hz), 6.89-7.05 (3H, m), 7.46 (2H, d, J=8.7 Hz), 7.80-7.86 (1H, m).

138b) 1-ethyl-7-methyl-3-(4-{[tris(1-methylethyl)silyl]oxy}phenyl)-1,3-dihydro-2H-imidazo[4,5-b]pyridin-2-one 4-oxide

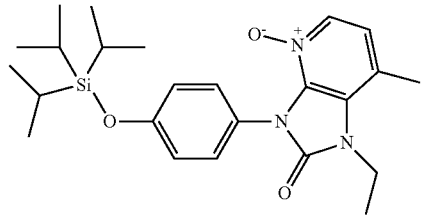

To a stirred mixture of 1-ethyl-7-methyl-3-(4-{[tris(1-methylethyl)silyl]oxy}phenyl)-1,3-dihydro-2H-imidazo[4,5-b]pyridin-2-one (5 g) and urea hydrogen peroxide (2.32 g) in CH$_2$Cl$_2$ (50 mL) was added trifluoroacetic anhydride (3.32 ml) at 0° C. The mixture was stirred at room temperature for 12 h, and treated with saturated NaHCO$_3$ solution. The organic layer was separated and the aqueous layer was extracted with AcOEt. The organic layer was combined, dried over MgSO$_4$ and concentrated in vacuo. The residue was purified by silica gel column chromatography (NH, AcOEt) to give the title compound (1.0 g).

MS (API+): [M+H]$^+$442.3.

¹H NMR (300 MHz, DMSO-d₆) δ0.99-1.17 (18H, m), 1.22-1.36 (6H, m), 2.56 (3H, s), 4.06 (2H, q, J=7.2 Hz), 6.82-6.91 (2H, m), 6.92-7.00 (1H, m), 7.14-7.24 (2H, m), 7.73 (1H, d, J=6.8 Hz).

138c) [1-ethyl-2-oxo-3-(4-{[tris(1-methylethyl)silyl]oxy}phenyl)-2,3-dihydro-1H-imidazo[4,5-b]pyridin-7-yl]methyl acetate

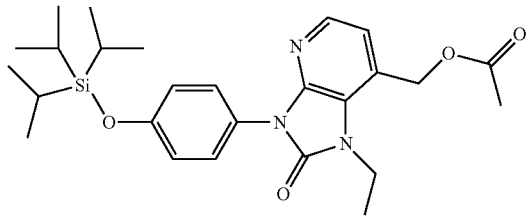 [SMILES: CCn1c(=O)n(-c2ccc(O[Si](C(C)C)(C(C)C)C(C)C)cc2)c2nccc(COC(C)=O)c21]

A mixture of 1-ethyl-7-methyl-3-(4-{[tris(1-methylethyl)silyl]oxy}phenyl)-1,3-dihydro-2H-imidazo[4,5-b]pyridin-2-one 4-oxide (1 g) and Ac₂O (20 mL) was stirred at 80° C. for 2 h, and concentrated in vacuo. The residue was purified by silica gel column chromatography (AcOEt/hexane) to give the title compound (0.49 g).

MS (API+): [M+H]⁺484.3.

¹H NMR (300 MHz, DMSO-d₆) δ1.03-1.15 (18H, m), 1.24-1.39 (6H, m), 2.13 (3H, s), 4.03 (2H, q, J=7.2 Hz), 5.37 (2H, s), 6.91-7.09 (2H, m), 7.07-7.29 (1H, m), 7.45-7.50 (2H, m), 7.95 (1H, d, J=5.3 Hz).

138d) [1-ethyl-3-(4-hydroxyphenyl)-2-oxo-2,3-dihydro-1H-imidazo[4,5-b]pyridin-7-yl]methyl acetate

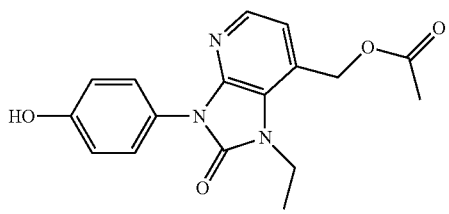 [SMILES: CCn1c(=O)n(-c2ccc(O)cc2)c2nccc(COC(C)=O)c21]

To a stirred solution of [1-ethyl-2-oxo-3-(4-{[tris(1-methylethyl)silyl]oxy}phenyl)-2,3-dihydro-1H-imidazo[4,5-b]pyridin-7-yl]methyl acetate (480 mg) in THF (5 mL) was added a solution of tetrabutylammonium fluoride (778 mg) in THF (2 mL) at 0° C. The mixture was stirred at 0° C. for 30 min, treated with water, and extracted with AcOEt. The organic layer was dried over MgSO₄ and concentrated in vacuo. The residue was purified by silica gel column chromatography (AcOEt/Hexane=1/1) to give the title compound (276 mg).

MS (API+): [M+H]⁺328.1.

¹H NMR (300 MHz, DMSO-d₆) δ1.30 (3H, t, J=7.2 Hz), 2.12 (3H, s), 4.03 (2H, q, J=7.2 Hz), 5.36 (2H, s), 6.80-6.95 (2H, m), 7.12 (1H, d, J=5.3 Hz), 7.28-7.41 (2H, m), 7.93 (1H, d, J=5.3 Hz), 9.71 (1H, s).

138e) 1-ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one

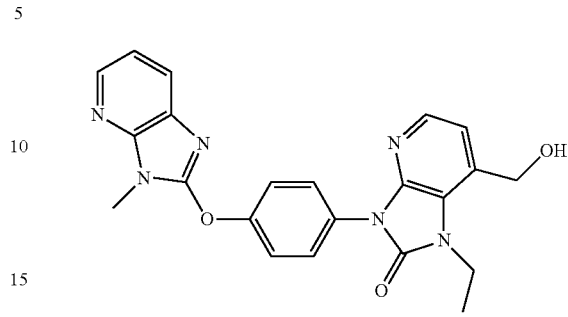

To a stirred mixture of [1-ethyl-3-(4-hydroxyphenyl)-2-oxo-2,3-dihydro-1H-imidazo[4,5-b]pyridin-7-yl]methyl acetate (150 mg) and EtOH (3 mL) was added 1N NaOH (2 mL) at 0° C. The mixture was stirred at 0° C. for 30 min, treated with saturated NH₄Cl solution, and extracted with AcOEt. The organic layer was dried over MgSO₄ and concentrated in vacuo. The residue was dissolved in DMA (4 mL) and KOtBu (52 mg) was added at room temperature. The mixture was stirred for 2 min, and then 3-methyl-2-(methylsulfonyl)-3H-imidazo[4,5-b]pyridine (97 mg) was added. The mixture was stirred at 150° C. for 30 min, treated with water, and extracted with AcOEt. The organic layer was dried over MgSO₄ and concentrated in vacuo. The residue was purified by silica gel column chromatography (NH, AcOEt/MeOH=20/1) and crystallized from AcOEt/hexane to give the title compound (46 mg).

MS (API+): [M+H]⁺ 417.2.

¹H NMR (300 MHz, DMSO-d₆) δ 1.32 (3H, t, J=7.2 Hz), 3.78 (3H, s), 4.13 (2H, q, J=7.2 Hz), 4.80 (2H, d, J=5.5 Hz), 5.67 (1H, t, J=5.5 Hz), 7.14-7.26 (2H, m), 7.59-7.68 (2H, m), 7.71-7.87 (3H, m), 7.97 (1H, d, J=5.3 Hz), 8.17-8.28 (1H, m).

Example 139

1-ethyl-3-[2-(5-methylpyridin-2-yl)-2H-indazol-5-yl]-1,3-dihydro-2H-imidazo[4,5-b]pyridin-2-one

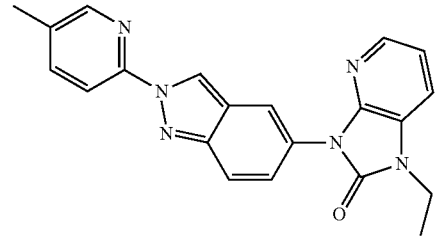 [SMILES: CCn1c(=O)n(-c2ccc3nn(-c4ccc(C)cn4)cc3c2)c2ncccc21]

139a) 1-(5-methylpyridin-2-yl)-2H-indazol-5-amine

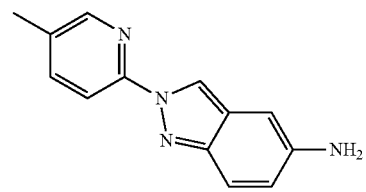 [SMILES: Cc1ccc(-n2cc3cc(N)ccc3n2)nc1]

To a stirred solution of 5-nitro-1H-indazole (500 mg) in DMF (10 mL) was added 60% sodium hydride (12.9 mg) at room temperature. The mixture was stirred for 30 min, and 5-bromo-2-chloropyridine (649 mg) was added. The mixture was exposed to microwave irradiation at 230° C. for 1 h, treated with sat. ammonium chloride solution, and extracted with AcOEt. The organic layer was dried over MgSO₄ and concentrated in vacuo. The residue was chromatographed on silica gel eluting with AcOEt/Hexane to give a mixture of 1-(5-bromopyridin-2-yl)-5-nitro-1H-indazole and 2-(5-bromopyridin-2-yl)-5-nitro-2H-indazole.

To the mixture of 1-(5-bromopyridin-2-yl)-5-nitro-1H-indazole and 2-(5-bromopyridin-2-yl)-5-nitro-2H-indazole were added methylboronic acid (141 mg), Pd(Ph₃P)₄ (91 mg), DME (3 mL) and a solution of Cs₂CO₃ (766 mg) in H₂O (1 ml), successively. The mixture was exposed to microwave irradiation 140° C. for 1 h, treated with water, and extracted with AcOEt. The organic layer was dried over MgSO₄ and concentrated in vacuo to give a mixture of 1-(5-methylpyridin-2-yl)-5-nitro-1H-indazole and 2-(5-methylpyridin-2-yl)-5-nitro-2H-indazole.

The mixture of 1-(5-methylpyridin-2-yl)-5-nitro-1H-indazole and 2-(5-methylpyridin-2-yl)-5-nitro-2H-indazole was dissolved in EtOH (20 mL), and 10% Pd/C (250 mg) was added. Under H₂ atmosphere, the mixture was stirred at room temperature for 12 h, filtered and concentrated in vacuo. The residue was chromatographed on silica gel eluting with AcOEt/Hexane to give the title compound (61 mg).

¹H NMR (300 MHz, DMSO-d₆) δ 2.36 (3H, s), 5.04 (2H, s), 6.58 (1H, d, J=1.9 Hz), 6.86 (1H, dd, J=9.1, 1.9 Hz), 7.44 (1H, d, J=9.1 Hz), 7.75-7.90 (1H, m), 7.95-8.06 (1H, m), 8.35 (1H, d, J=2.3 Hz), 8.72 (1H, d, J=0.8 Hz).

139b) 3-[2-(5-methylpyridin-2-yl)-2H-indazol-5-yl]-1,3-dihydro-2H-imidazo[4,5-b]pyridin-2-one

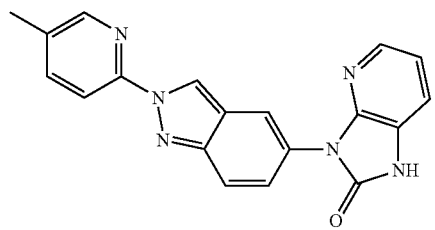 [SMILES: Cc1ccc(-n2cc3cc(-n4c(=O)[nH]c5cccnc54)ccc3n2)nc1]

Under argon atmosphere, a mixture of 1-(5-methylpyridin-2-yl)-2H-indazol-5-amine (60 mg), tert-butyl 2-chloropyridin-3-ylcarbamate (67.3 mg), Pd₂(dba)₃ (24.5 mg), Xantphos (31.0 mg) and sodium tert-butoxide (28.3 mg) in 2-propanol (2 ml) and toluene (0.5 mL) was stirred at 90° C. for 24 h, treated with water and extracted with EtOAc. The organic layer was separated, dried over MgSO₄ and concentrated in vacuo. The residue was chromatographed on silica gel eluting with AcOEt/Hexane to give the title compound as white crystals (31 mg).

MS (API+): [M+H]⁺343.3.

139c) 1-ethyl-3-[2-(5-methylpyridin-2-yl)-2H-indazol-5-yl]-1,3-dihydro-2H-imidazo[4,5-b]pyridin-2-one

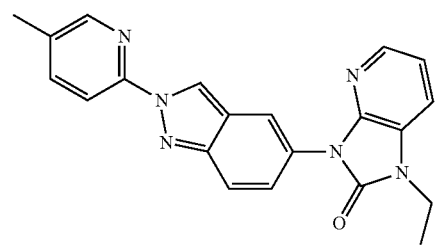 [SMILES: CCn1c(=O)n(-c2ccc3nn(-c4ccc(C)cn4)cc3c2)c2ncccc21]

A mixture of 3-[2-(5-methylpyridin-2-yl)-2H-indazol-5-yl]-1,3-dihydro-2H-imidazo[4,5-b]pyridin-2-one (31 mg) and iodoethane (15.5 mg) in DMF (2 mL) was stirred at 50° C. for 3 h, treated with water, and extracted with AcOEt. The organic layer was dried over MgSO₄ and concentrated in vacuo. The residue was chromatographed on silica gel eluting with AcOEt/Hexane. The product was crystallized from AcOEt/Hexane to give the title compound as white crystals (5.4 mg).

MS (API+): [M+H]⁺371.0.

Example compounds shown in the following Tables 1-12 (including compounds shown in the above-mentioned Examples) were obtained by a method known per se, or a method similar to those in the above-mentioned Examples, or a method analogous thereto.

Particularly, the Example compounds described in the column under "Referred Example No." in Tables 1-12 were produced according to the synthetic method described in the Referred Example.

In addition, the compound of each Example in Tables 1-12 was synthesized using the compound described in the column under "Raw material".

TABLE 1

| Example No. | MS | STRUCTURE | SALT | Name | Reffered Example No. | Raw Material, Conditions |
|---|---|---|---|---|---|---|
| 14 | 345 | 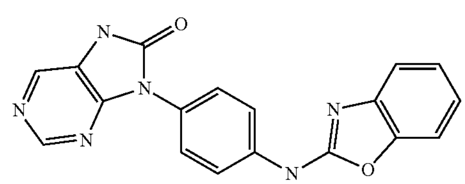 [SMILES: O=c1[nH]c2cncnc2n1-c1ccc(Nc2nc3ccccc3o2)cc1] | | 9-[4-(1,3-benzoxazol-2-ylamino)phenyl]-7,9-dihydro-8H-purin-8-one | 1 | 4-chloro-5-nitropyrimidine |

TABLE 1-continued

| Example No. | MS | STRUCTURE | SALT | Name | Reffered Example No. | Raw Material, Conditions |
|---|---|---|---|---|---|---|
| 15 | 383 | 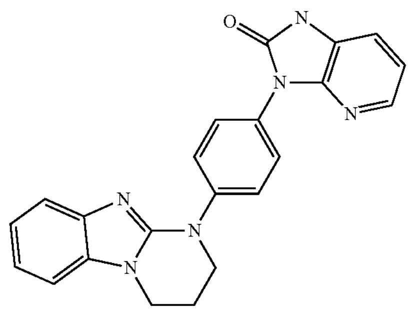 [SMILES: O=c1[nH]c2cccnc2n1-c1ccc(N2CCCn3c2nc2ccccc23)cc1] | | 3-[4-(3,4-dihydropyrimido[1,2-a]benzimidazol-1(2H)-yl)phenyl]-1,3-dihydro-2H-imidazo[4,5-b]pyridin-2-one | 2 | 1,3-dibromopropane |
| 16 | 397 | 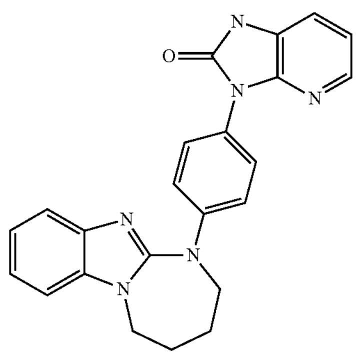 [SMILES: O=c1[nH]c2cccnc2n1-c1ccc(N2CCCCn3c2nc2ccccc23)cc1] | | 3-[4-(2,3,4,5-tetrahydro-1H-[1,3]diazepino[1,2-a]benzimidazol-1-yl)phenyl]-1,3-dihydro-2H-imidazo[4,5-b]pyridin-2-one | 2 | 1,4-diiodobutane |
| 17 | 358 | 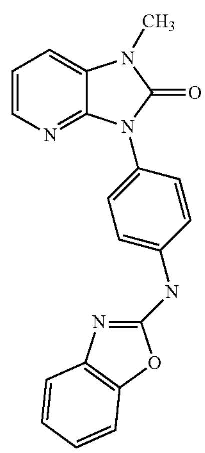 [SMILES: Cn1c(=O)n(-c2ccc(Nc3nc4ccccc4o3)cc2)c2ncccc21] | | 3-[4-(1,3-benzoxazol-2-ylamino)phenyl]-1-methyl-1,3-dihydro-2H-imidazo[4,5-b]pyridin-2-one | 12c, 3, 1c, 1a | 12c) tert-butyl 2-chloropyridin-3-ylcarbamate, 4-nitroaniline |
| 18 | 502.1 | 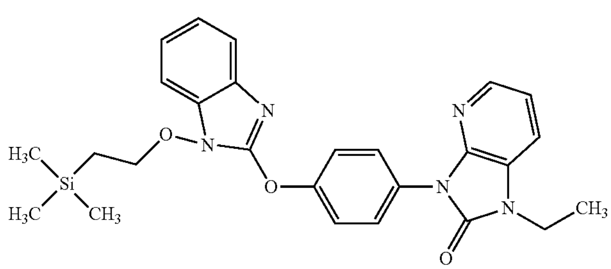 [SMILES: CCn1c(=O)n(-c2ccc(Oc3nc4ccccc4n3OCC[Si](C)(C)C)cc2)c2ncccc21] | | 1-ethyl-3-{4-[(1-{[2-(trimethylsilyl)ethoxy]methyl}-1H-benzimidazol-2-yl)oxy]phenyl)-1,3-dihydro-2H-imidazo[4,5-b]pyridin-2-one | 12d | 3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one |

TABLE 1-continued

| Example No. | MS | STRUCTURE | SALT | Name | Reffered Example No. | Raw Material, Conditions |
|---|---|---|---|---|---|---|
| 19 | 386.2 | 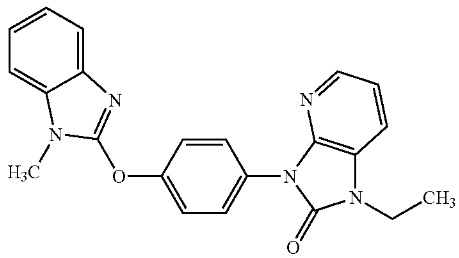 [SMILES: CCn1c(=O)n(-c2ccc(Oc3nc4ccccc4n3C)cc2)c2ncccc21] | | 1-ethyl-3-{4-[(1-methyl-1H-benzimidazol-2-yl)oxy]phenyl}-1,3-dihydro-2H-imidazo[4,5-b]pyridin-2-one | 3 | 3-[4-(1H-benzimidazol-2-yloxy)phenyl]-1-ethyl-1,3-dihydro-2H-imidazo[4,5-b]pyridin-2-one hydrochloride |
| 20 | 371.3 | 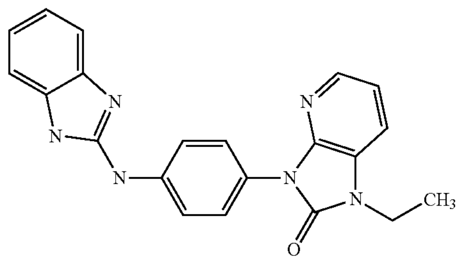 [SMILES: CCn1c(=O)n(-c2ccc(Nc3nc4ccccc4[nH]3)cc2)c2ncccc21] | | 3-[4-(1H-benzimidazol-2-ylamino)phenyl]-1-ethyl-1,3-dihydro-2H-imidazo[4,5-b]pyridin-2-one | — | 3-(4-aminophenyl)-1-ethyl-1,3-dihydro-2H-imidazo[4,5-b]pyridin-2-one, phenylenediamine, 1,1'-thiocarbonyldiimidazole, N,N'-dicyclohexylcarbodiimide |

TABLE 2

| Example No. | MS | STRUCTURE | SALT | Name | Reffered Example No. | Raw Material |
|---|---|---|---|---|---|---|
| 21 | 400.1 | 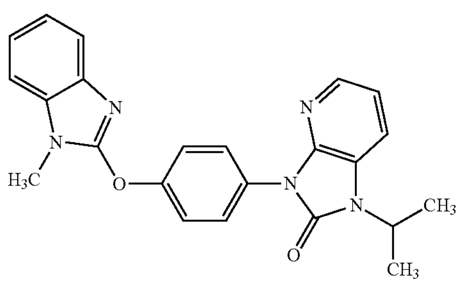 [SMILES: CC(C)n1c(=O)n(-c2ccc(Oc3nc4ccccc4n3C)cc2)c2ncccc21] | | 3-{4-[(1-methyl-1H-benzimidazol-2-yl)oxy]phenyl}-1-(1-methylethyl)-1,3-dihydro-2H-imidazo[4,5-b]pyridin-2-one | 3 | 3-[4-(1H-benzimidazol-2-yloxy)phenyl]-1-(1-methylethyl)-1,3-dihydro-2H-imidazo[4,5-b]pyridin-2-one |
| 22 | 386.0 | 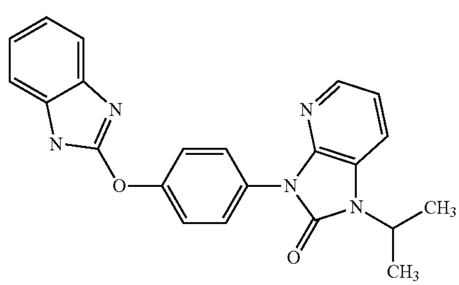 [SMILES: CC(C)n1c(=O)n(-c2ccc(Oc3nc4ccccc4[nH]3)cc2)c2ncccc21] | HCl | 3-[4-(1H-benzimidazol-2-yloxy)phenyl]-1-(1-methylethyl)-1,3-dihydro-2H-imidazo[4,5-b]pyridin-2-one hydrochloride | 3, 1c, 7e, 8 | 3) 3-[4-(benzyloxy)phenyl]-1,3-dihydro-2H-imidazo[4,5-b]pyridin-2-one, 2-iodopropane |

TABLE 2-continued

| Example No. | MS | STRUCTURE | SALT | Name | Reffered Example No. | Raw Material |
|---|---|---|---|---|---|---|
| 23 | 426.1 | 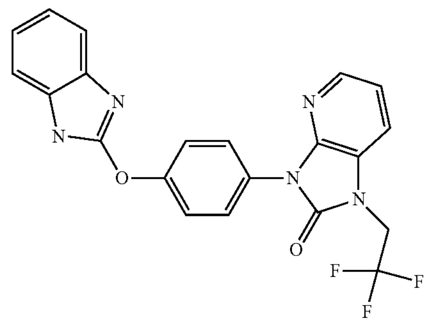 [SMILES: O=c1n(CC(F)(F)F)c2cccnc2n1-c1ccc(Oc2nc3ccccc3[nH]2)cc1] | HCl | 3-[4-(1H-benzimidazol-2-yloxy)phenyl]-1-(2,2,2-trifluoroethyl)-1,3-dihydro-2H-imidazo[4,5-b]pyridin-2-one hydrochloride | 22 | 2-iodo-1,1,1-trifluoroethane |
| 24 | 397.1 | 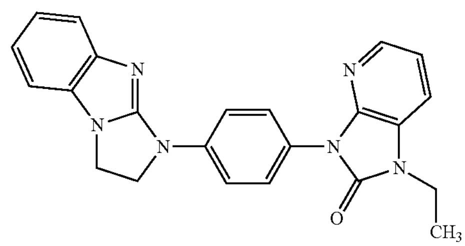 [SMILES: CCn1c(=O)n(-c2ccc(N3CCn4c3nc3ccccc34)cc2)c2ncccc21] | | 3-[4-(2,3-dihydro-1H-imidazo[1,2-a]benzimidazol-1-yl)phenyl]-1-ethyl-1,3-dihydro-2H-imidazo[4,5-b]pyridin-2-one | 12d | 3-[4-(2,3-dihydro-1H-imidazo[1,2-a]benzimidazol-1-yl)phenyl]-1,3-dihydro-2H-imidazo[4,5-b]pyridin-2-one |
| 25 | 455.3 | 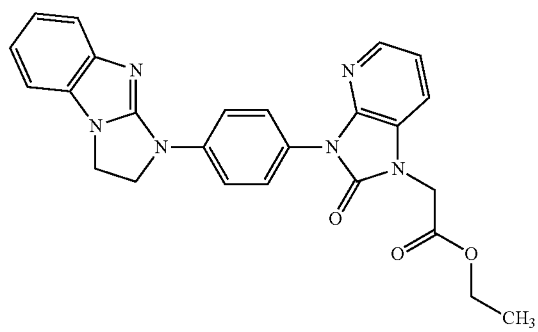 [SMILES: CCOC(=O)Cn1c(=O)n(-c2ccc(N3CCn4c3nc3ccccc34)cc2)c2ncccc21] | | ethyl {3-[4-(2,3-dihydro-1H-imidazo[1,2-a]benzimidazol-1-yl)phenyl]-2-oxo-2,3-dihydro-1H-imidazo[4,5-b]pyridin-1-yl}acetate | 3 | ethyl bromoacetate |
| 26 | 413 | 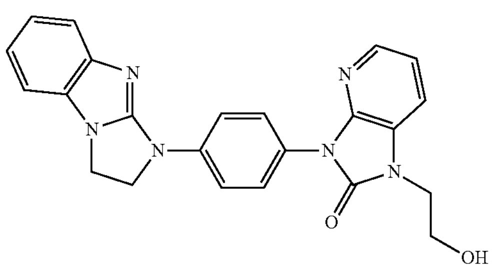 [SMILES: O=c1n(CCO)c2cccnc2n1-c1ccc(N2CCn3c2nc2ccccc23)cc1] | | 3-[4-(2,3-dihydro-1H-imidazo[1,2-a]benzimidazol-1-yl)phenyl]-1-(2-hydroxyethyl)-1,3-dihydro-2H-imidazo[4,5-b]pyridin-2-one | — | ethyl {3-[4-(2,3-dihydro-1H-imidazo[1,2-a]benzimidazol-1-yl)phenyl]-2-oxo-2,3-dihydro-1H-imidazo[4,5-b]pyridin-1-yl}acetate, LAH |
| 27 | 390.4 | 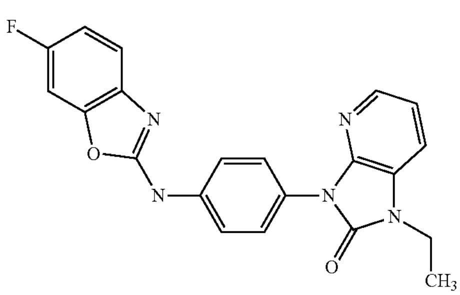 [SMILES: CCn1c(=O)n(-c2ccc(Nc3nc4ccc(F)cc4o3)cc2)c2ncccc21] | | 1-ethyl-3-{4-[(6-fluoro-1,3-benzoxazol-2-yl)amino]phenyl}-1,3-dihydro-2H-imidazo[4,5-b]pyridin-2-one | 17 | 2-chloro-5-fluoro-benzoxazol |

TABLE 3

| Example No. | MS | STRUCTURE | SALT | Name | Reffered Example No. | Raw Material |
|---|---|---|---|---|---|---|
| 28 | 404.3 | 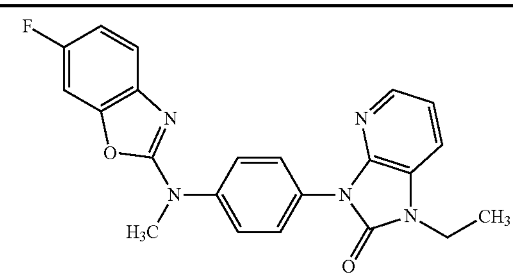 | | 1-ethyl-3-{4-[(6-fluoro-1,3-benzoxazol-2-yl)(methyl)amino]phenyl}-1,3-dihydro-2H-imidazo[4,5-b]pyridin-2-one | 3 | 1-ethyl-3-{4-[(6-fluoro-1,3-benzoxazol-2-yl)amino]phenyl}-1,3-dihydro-2H-imidazo[4,5-b]pyridin-2-one |
| 29 | 422.3 | 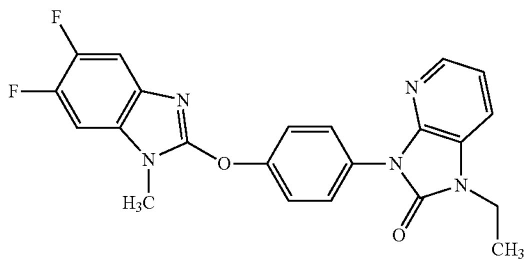 [SMILES: CCn1c(=O)n(-c2ccc(Oc3nc4cc(F)c(F)cc4n3C)cc2)c2ncccc21] | | 3-{4-[(5,6-difluoro-1-methyl-1H-benzimidazol-2-yl)oxy]phenyl}-1-ethyl-1,3-dihydro-2H-imidazo[4,5-b]pyridin-2-one | 7e | 2-chloro-5,6-difluoro-1-methyl-1H-benzimidazole, 1-ethyl-3-(4-hydroxyphenyl)-1,3-dihydro-2H-imidazo[4,5-b]pyridin-2-one, NaH, DMF, microwave, 200° C. |
| 30 | 444.4 | 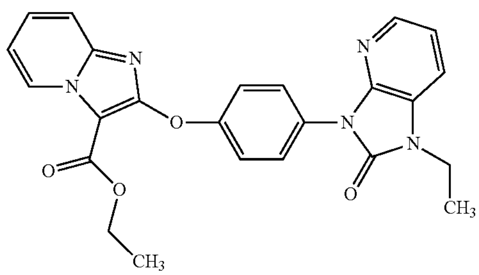 [SMILES: CCOC(=O)c1c(Oc2ccc(-n3c(=O)n(CC)c4cccnc43)cc2)nc2ccccn12] | | ethyl 2-[4-(1-ethyl-2-oxo-1,2-dihydro-3H-imidazo[4,5-b]pyridin-3-yl)phenoxy]imidazo[1,2-a]pyridine-3-carboxylate | 7e | ethyl 2-chloroimidazo[1,2-a]pyridine-3-carboxylate |
| 31 | 372.4 | 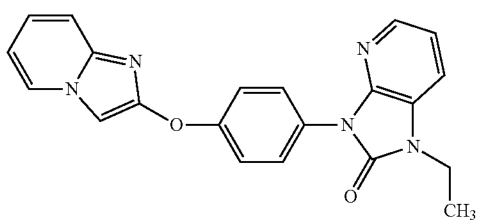 [SMILES: CCn1c(=O)n(-c2ccc(Oc3cn4ccccc4n3)cc2)c2ncccc21] | | 1-ethyl-3-[4-(imidazo[1,2-a]pyridin-2-yloxy)phenyl]-1,3-dihydro-2H-imidazo[4,5-b]pyridin-2-one | — | ethyl 2-[4-(1-ethyl-2-oxo-1,2-dihydro-3H-imidazo[4,5-b]pyridin-3-yl)phenoxy]imidazo[1,2-a]pyridine-3-carboxylate, DMF, 200° C. |
| 32 | 404 | 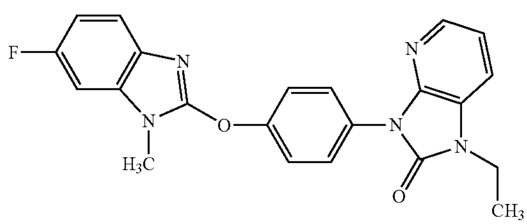 [SMILES: CCn1c(=O)n(-c2ccc(Oc3nc4ccc(F)cc4n3C)cc2)c2ncccc21] | | 1-ethyl-3-{4-[(6-fluoro-1-methyl-1H-benzimidazol-2-yl)oxy]phenyl}-1,3-dihydro-2H-imidazo[4,5-b]pyridin-2-one | 29 | 2-chloro-6-fluoro-1-methyl-1H-benzimidazole (US2003/166637), 1-ethyl-3-(4-hydroxyphenyl)-1,3-dihydro-2H-imidazo[4,5-b]pyridin-2-one |
| 33 | 404 | 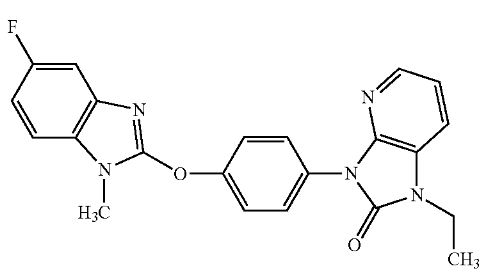 [SMILES: CCn1c(=O)n(-c2ccc(Oc3nc4cc(F)ccc4n3C)cc2)c2ncccc21] | | 1-ethyl-3-{4-[(5-fluoro-1-methyl-1H-benzimidazol-2-yl)oxy]phenyl}-1,3-dihydro-2H-imidazo[4,5-b]pyridin-2-one | 29 | 2-chloro-5-fluoro-1-methyl-1H-benzimidazole, 1-ethyl-3-(4-hydroxyphenyl)-1,3-dihydro-2H-imidazo[4,5-b]pyridin-2-one |

TABLE 3-continued

| Example No. | MS | STRUCTURE | SALT | Name | Reffered Example No. | Raw Material |
|---|---|---|---|---|---|---|
| 34 | 430.1 | 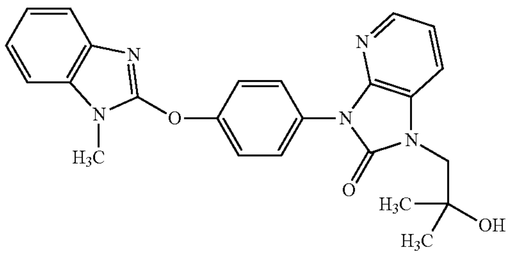 [SMILES: Cn1c(Oc2ccc(-n3c(=O)n(CC(C)(C)O)c4cccnc43)cc2)nc2ccccc21] | | 1-(2-hydroxy-2-methylpropyl)-3-{4-[(1-methyl-1H-benzimidazol-2-yl)oxy]phenyl}-1,3-dihydro-2H-imidazo[4,5-b]pyridin-2-one | 25, 1c, 29 | 25) 3-[4-(benzyloxy)phenyl]-1,3-dihydro-2H-imidazo[4,5-b]pyridin-2-one 29) 2-chloro-1-methyl-1H-benzimidazole, MeMgBr |

TABLE 4

| Example No. | MS | STRUCTURE | SALT | Name | Reffered Example No. | Raw Material |
|---|---|---|---|---|---|---|
| 35 | 402.1 | 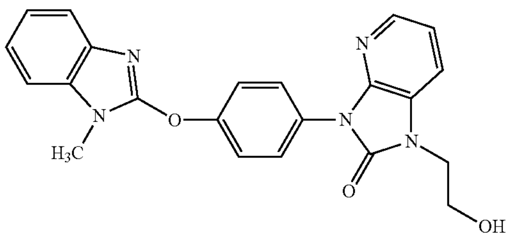 [SMILES: Cn1c(Oc2ccc(-n3c(=O)n(CCO)c4cccnc43)cc2)nc2ccccc21] | | 1-(2-hydroxyethyl)-3-{4-[(1-methyl-1H-benzimidazol-2-yl)oxy]phenyl}-1,3-dihydro-2H-imidazo[4,5-b]pyridin-2-one | 25, 1c, 29, 26 | 25) 3-[4-(benzyloxy)phenyl]-1,3-dihydro-2H-imidazo[4,5-b]pyridin-2-one 29) 2-chloro-1-methyl-1H-benzimidazole |
| 36 | 384.2 | 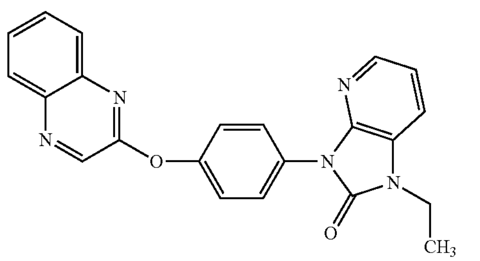 [SMILES: CCn1c(=O)n(-c2ccc(Oc3cnc4ccccc4n3)cc2)c2ncccc21] | | 1-ethyl-3-[4-(quinoxalin-2-yloxy)phenyl]-1,3-dihydro-2H-imidazo[4,5-b]pyridin-2-one | 7e | 2-chloro-quinoxaline, 1-ethyl-3-(4-hydroxyphenyl)-1,3-dihydro-2H-imidazo[4,5-b]pyridin-2-one |
| 37 | 428.5 | 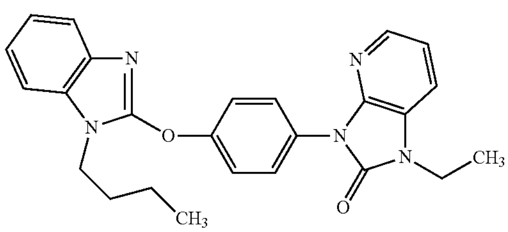 [SMILES: CCCCn1c(Oc2ccc(-n3c(=O)n(CC)c4cccnc43)cc2)nc2ccccc21] | | 3-{4-[(1-butyl-1H-benzimidazol-2-yl)oxy]phenyl}-1-ethyl-1,3-dihydro-2H-imidazo[4,5-b]pyridin-2-one | 7f | 1-ethyl-3-{4-[(1-{[2-(trimethylsilyl)ethoxy]methyl}-1H-benzimidazol-2-yl)oxy]phenyl}-1,3-dihydro-2H-imidazo[4,5-b]pyridin-2-one |
| 38 | 414.4 | 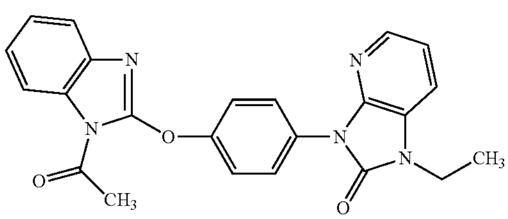 [SMILES: CCn1c(=O)n(-c2ccc(Oc3nc4ccccc4n3C(C)=O)cc2)c2ncccc21] | | 3-{4-[(1-acetyl-1H-benzimidazol-2-yl)oxy]phenyl}-1-ethyl-1,3-dihydro-2H-imidazo[4,5-b]pyridin-2-one | — | 3-[4-(1H-benzimidazol-2-yloxy)phenyl]-1-ethyl-1,3-dihydro-2H-imidazo[4,5-b]pyridin-2-one, acetyl chloride, triethyl amine, THF |
| 39 | 416.5 | 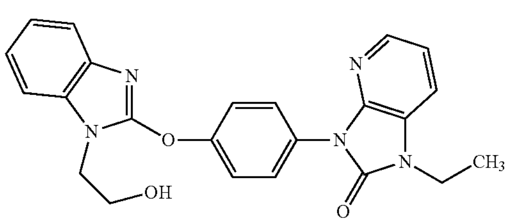 [SMILES: CCn1c(=O)n(-c2ccc(Oc3nc4ccccc4n3CCO)cc2)c2ncccc21] | | 1-ethyl-3-(4-{(1-(2-hydroxyethyl)-1H-benzimidazol-2-yl)oxy}phenyl)-1,3-dihydro-2H-imidazo[4,5-b]pyridin-2-one | 25, 26 | 3-[4-(1H-benzimidazol-2-yloxy)phenyl]-1-ethyl-1,3-dihydro-2H-imidazo[4,5-b]pyridin-2-one |

TABLE 4-continued

| Example No. | MS | STRUCTURE | SALT | Name | Reffered Example No. | Raw Material |
|---|---|---|---|---|---|---|
| 40 | 444.4 | 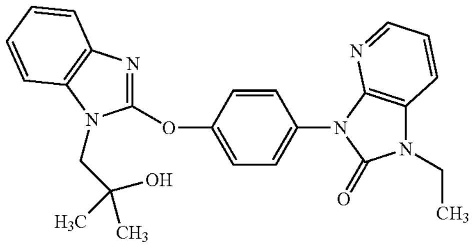 [SMILES: CCn1c(=O)n(-c2ccc(Oc3nc4ccccc4n3CC(C)(C)O)cc2)c2ncccc21] | | 1-ethyl-3-(4-{[1-(2-hydroxy-2-methylpropyl)-1H-benzimidazol-2-yl]oxy}phenyl)-1,3-dihydro-2H-imidazo[4,5-b]pyridin-2-one | 39 | ethyl {2-[4-(1-ethyl-2-oxo-1,2-dihydro-3H-imidazo[4,5-b]pyridin-3-yl)phenoxyl-1H-benzimidazol-1-yl}acetate, MeMgBr, THF |
| 41 | 386.3 | 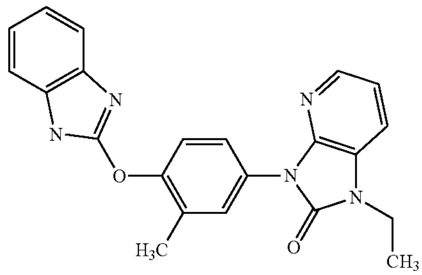 [SMILES: CCn1c(=O)n(-c2ccc(Oc3nc4ccccc4[nH]3)c(C)c2)c2ncccc21] | HCl | 3-[4-(1H-benzimidazol-2-yloxy)-3-methylphenyl]-1-ethyl-1,3-dihydro-2H-imidazo[4,5-b]pyridin-2-one hydrochloride | 7a, 7b, 7c, 22 | 4-(benzyloxy)-3-methylaniline |

TABLE 5

| Example No. | MS | MOLSTRUCTURE | SALT | NAME | Reffered Example No. | Raw Material |
|---|---|---|---|---|---|---|
| 42 | 400.1 | | | 1-ethyl-3-{3-methyl-4-[(1-methyl-1H-benzimidazol-2-yl)oxy]phenyl}-1,3-dihydro-2H-imidazo[4,5-b]pyridin-2-one | 3 | 3-[4-(1H-benzimidazol-2-yloxy)-3-methylphenyl]-1-ethyl-1,3-dihydro-2H-imidazo[4,5-b]pyridin-2-one |
| 43 | 404.3 | | | 1-ethyl-3-{3-fluoro-4-[(1-methyl-1H-benzimidazol-2-yl)oxy]phenyl}-1,3-dihydro-2H-imidazo[4,5-b]pyridin-2-one | 7a, 7b, 7c, 3, 1c, 7e | 7a) 4-(benzyloxy)-3-fluoroaniline 7e) 1-methyl-2-(methylsulfonyl)-1H-benzimidazole |
| 44 | 371.4 | | | 1-[4-(2-oxo-3-phenylimidazolidin-1-yl)phenyl]-1,3-dihydro-2H-pyrrolo[2,3-b]pyridin-2-one | 5a then 5a | 5a) 1,4-diiodobenzene, 1-phenylimidazolidin-2-one, then 5a) 1,3-dihydro-2H-pyrrolo[2,3-b]pyridin-2-one |

TABLE 5-continued

| Example No. | MS | MOLSTRUCTURE | SALT | NAME | Reffered Example No. | Raw Material |
|---|---|---|---|---|---|---|
| 45 | 329.4 | | | 1-[4-(2,3-dihydro-1H-pyrrolo[2,3-b]pyridin-1-yl)phenyl]-1,3-dihydro-2H-pyrrolo[2,3-b]pyridin-2-one | 44 | 1,4-diiodobenzene, 2,3-dihydro-1H-pyrrolo[2,3-b]pyridine |
| 46 | 373.3 | | | 1-ethyl-3-[4-([1,2,4]triazolo[1,5-a]pyridin-2-yloxy)phenyl]-1,3-dihydro-2H-imidazo[4,5-b]pyridin-2-one | 29 | 1-ethyl-3-(4-hydroxyphenyl)-1,3-dihydro-2H-imidazo[4,5-b]pyridin-2-one, 2-chloro-[1,2,4]triazolo[1,5-a]pyridine |
| 47 | 390.4 | | | 1-ethyl-3-{4-[(7-fluoro-1H-benzimidazol-2-yl)oxy]phenyl}-1,3-dihydro-2H-imidazo[4,5-b]pyridin-2-one | 29, 8 | 1-ethyl-3-(4-hydroxyphenyl)-1,3-dihydro-2H-imidazo[4,5-b]pyridin-2-one, 4-fluoro-2-(methylsulfonyl)-1-((2-(trimethylsilyl)ethoxy)methyl)-1H-benzo[d]midazole |
| 48 | 411.4 | | | 1-ethyl-3-[1-(1-methyl-1H-benzimidazol-2-yl)-2,3-dihydro-1H-indol-5-yl]-1,3-dihydro-2H-imidazo[4,5-b]pyridin-2-one | 3 | 3-[1-(1H-benzimidazol-2-yl)-2,3-dihydro-1H-indol-5-yl]-1-ethyl-1,3-dihydro-2H-imidazo[4,5-b]pyridin-2-one |

TABLE 6

| Example No. | MS | MOLSTRUCTURE | SALT | NAME | Reffered Example No. | Raw Material |
|---|---|---|---|---|---|---|
| 49 | 386.3 | | | 3-[4-(1H-benzimidazol-2-yloxy)-2-methylphenyl]-1-ethyl-1,3-dihydro-2H-imidazo[4,5-b]pyridin-2-one | 7a, 7b, 7c, 22 | 4-(benzyloxy)-2-methylaniline |

TABLE 6-continued

| Example No. | MS | MOLSTRUCTURE | SALT | NAME | Reffered Example No. | Raw Material |
|---|---|---|---|---|---|---|
| 50 | 412.3 | | | 3-[4-(1H-benzimidazol-2-yloxy)-2-methylphenyl]-1-(cyclopropylmethyl)-1,3-dihydro-2H-imidazo[4,5-b]pyridin-2-one | 49 | (bromomethyl)cyclopropane |
| 51 | 400.4 | | | 1-ethyl-3-{2-methyl-4-[(1-methyl-1H-benzimidazol-2-yl)oxy]phenyl}-1,3-dihydro-2H-imidazo[4,5-b]pyridin-2-one | 3 | 3-[4-(1H-benzimidazol-2-yloxy)-2-methylphenyl]-1-ethyl-1,3-dihydro-2H-imidazo[4,5-b]pyridin-2-one |
| 52 | 432.1 | | | 3-[4-(1-benzyl-2-methyl-1H-benzimidazol-4-yl)phenyl]-1,3-dihydro-2H-imidazo[4,5-b]pyridin-2-one | 8 | 3-[4-(1-benzyl-2-methyl-1H-benzimidazol-4-yl)phenyl]-1-{[2-(trimethylsilyl)ethoxy]methyl}-1,3-dihydro-2H-imidazo[4,5-b]pyridin-2-one |
| 53 | 460.1 | | | 3-[4-(1-benzyl-2-methyl-1H-benzimidazol-4-yl)phenyl]-1-ethyl-1,3-dihydro-2H-imidazo[4,5-b]pyridin-2-one | 12d | 3-[4-(1-benzyl-2-methyl-1H-benzimidazol-4-yl)phenyl]-1,3-dihydro-2H-imidazo[4,5-b]pyridin-2-one |
| 54 | 370.1 | | | 1-ethyl-3-[4-(2-methyl-1H-benzimidazol-4-yl)phenyl]-1,3-dihydro-2H-imidazo[4,5-b]pyridin-2-one | 1c | 3-[4-(1-benzyl-2-methyl-1H-benzimidazol-4-yl)phenyl]-1-ethyl-1,3-dihydro-2H-imidazo[4,5-b]pyridin-2-one |
| 55 | 339.4 | | | 3-(4-quinolin-8-ylphenyl)-1,3-dihydro-2H-imidazo[4,5-b]pyridin-2-one | 8 | 3-(4-quinolin-8-ylphenyl)-1-{[2-(trimethylsilyl)ethoxy]methyl}-1,3-dihydro-2H-imidazo[4,5-b]pyridin-2-one |

TABLE 7

| Example No. | MS | MOLSTRUCTURE | SALT | NAME | Reffered Example No. | Raw Material |
|---|---|---|---|---|---|---|
| 56 | 367.3 | | | 1-ethyl-3-(4-quinolin-8-ylphenyl)-1,3-dihydro-2H-imidazo[4,5-b]pyridin-2-one | 8 | 3-(4-quinolin-8-ylphenyl)-1-{[2-(trimethylsilyl)ethoxy]methyl}-1,3-dihydro-2H-imidazo[4,5-b]pyridin-2-one |
| 57 | 399.2 | | | 1-{4-[(1-ethyl-1H-benzimidazol-2-yl)oxy]phenyl}-3,3-dimethyl-1,3-dihydro-2H-pyrrolo[2,3-b]pyridin-2-one | 9 | iodoethane |
| 58 | 374.1 | | | 4-(3,3-dimethyl-2-oxo-2,3-dihydro-1H-pyrrolo[2,3-b]pyridin-1-yl)phenyl phenylcarbamate | 9 | PHENYL ISOCYANATE |
| 59 | 388.2 | | | 4-(3,3-dimethyl-2-oxo-2,3-dihydro-1H-pyrrolo[2,3-b]pyridin-1-yl)phenyl methyl(phenyl)carbamate | 9 | PHENYL ISOCYANATE |
| 60 | 402.2 | | 2HCl | 3-[4-(1H-benzimidazol-2-yloxy)phenyl]-1-ethyl-5-methoxy-1,3-dihydro-2H-imidazo[4,5-b]pyridin-2-one | 7a, 7b, 7c, 22 | 4-(benzyloxy)laniline |
| 61 | 374.1 | | 2HCl | 3-[4-(1H-benzimidazol-2-yloxy)phenyl]-7-methoxy-1,3-dihydro-2H-imidazo[4,5-b]pyridin-2-one | 7a, 7b, 7c, 22 | 4-(benzyloxy)laniline |

TABLE 7-continued

| Example No. | MS | MOLSTRUCTURE | SALT | NAME | Reffered Example No. | Raw Material |
|---|---|---|---|---|---|---|
| 63 | 402.1 | 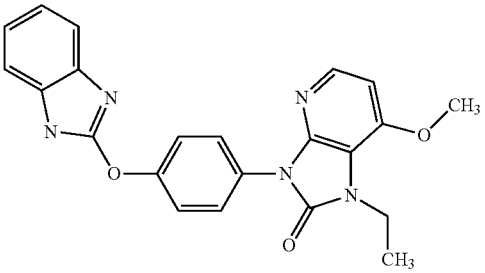 [SMILES: CCn1c(=O)n(-c2ccc(Oc3nc4ccccc4[nH]3)cc2)c2nccc(OC)c21] | 2HCl | 3-[4-(1H-benzimidazol-2-yloxy)phenyl]-1-ethyl-7-methoxy-1,3-dihydro-2H-imidazo[4,5-b]pyridin-2-one | 7a, 7b, 7c, 22 | 4-(benzyloxy)laniline |

TABLE 8

| Example No. | MS | MOLSTRUCTURE | SALT | NAME | Reffered Example No. | Raw Material |
|---|---|---|---|---|---|---|
| 66 | 362 | 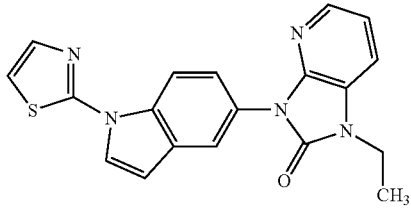 [SMILES: CCn1c(=O)n(-c2ccc3c(ccn3-c3nccs3)c2)c2ncccc21] | | 1-ethyl-3-[1-(1,3-thiazol-2-yl)-1H-indol-5-yl]-1,3-dihydro-2H-imidazo[4,5-b]pyridin-2-one | 13f | 2-CHLOROTHIAZOLE |
| 67 | 404.3 | 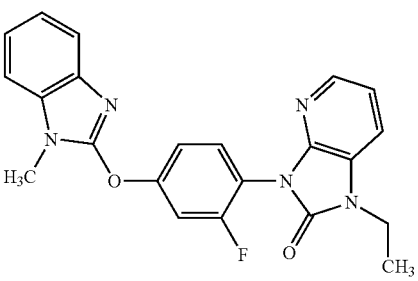 [SMILES: CCn1c(=O)n(-c2ccc(Oc3nc4ccccc4n3C)cc2F)c2ncccc21] | | 1-ethyl-3-{2-fluoro-4-[(1-methyl-1H-benzimidazol-2-yl)oxy]phenyl}-1,3-dihydro-2H-imidazo[4,5-b]pyridin-2-one | 7a, 7b, 7c, 22 | 4-(benzyloxy)-2-fluorolaniline |
| 68 | 412.3 | 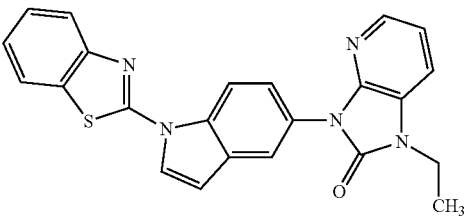 [SMILES: CCn1c(=O)n(-c2ccc3c(ccn3-c3nc4ccccc4s3)c2)c2ncccc21] | | 3-[1-(1,3-benzothiazol-2-yl)-1H-indol-5-yl]-1-ethyl-1,3-dihydro-2H-imidazo[4,5-b]pyridin-2-one | 13f | 2-Chlorobenzothiazole |
| 73 | 367.3 | 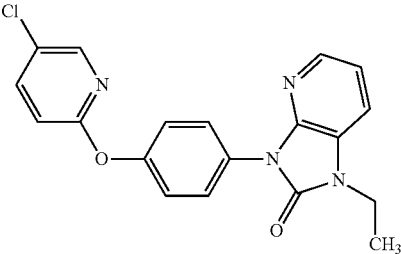 [SMILES: CCn1c(=O)n(-c2ccc(Oc3ccc(Cl)cn3)cc2)c2ncccc21] | | 3-{4-[(5-chloropyridin-2-yl)oxy]phenyl}-1-ethyl-1,3-dihydro-2H-imidazo[4,5-b]pyridin-2-one | 75 | 2,5-DICHLORO-PYRIDINE |

TABLE 8-continued

| Example No. | MS | MOLSTRUCTURE | SALT | NAME | Reffered Example No. | Raw Material |
|---|---|---|---|---|---|---|
| 74 | 401.3 | | | 1-ethyl-3-(4-{[5-(trifluoromethyl)pyridin-2-yl]oxy}phenyl)-1,3-dihydro-2H-imidazo[4,5-b]pyridin-2-one | 75 | 2-CHLORO-5-TRIFLUORO-METHYLPYRIDINE |
| 76 | 412 | | | 1-ethyl-3-{4-[(1-methyl-4-phenyl-1H-imidazol-2-yl)oxy]phenyl}-1,3-dihydro-2H-imidazo[4,5-b]pyridin-2-one | 75 | 4-phenyl-1H-imidazole-2-thiol |

TABLE 9

| Example No. | MS | MOLSTRUCTURE | SALT | NAME | Reffered Example No. | Raw Material |
|---|---|---|---|---|---|---|
| 77 | 486.1 | | | 3-{4-[(1-{[2-(trimethylsilyl)ethoxy]methyl}-1H-benzimidazol-2-yl)carbonyl]phenyl}-1,3-dihydro-2H-imidazo[4,5-b]pyridin-2-one | 7a, 7b, 7c, 22 | tert-butyl 4-aminobenzoate |
| 78 | 472.1 | | | 3-[4-(1-methyl-1H-benzimidazol-4-yl)phenyl]-1-{[2-(trimethylsilyl)ethoxy]methyl}-1,3-dihydro-2H-imidazo[4,5-b]pyridin-2-one | 12d | 4-bromo-1-methyl-1H-benzimidazole |

TABLE 9-continued

| Example No. | MS | MOLSTRUCTURE | SALT | NAME | Reffered Example No. | Raw Material |
|---|---|---|---|---|---|---|
| 79 | 514.3 | | | 1-ethyl-3-{4-[(1-{[2-(trimethylsilyl)ethoxy]methyl}-1H-benzimidazol-2-yl)carbonyl]phenyl}-1,3-dihydro-2H-imidazo[4,5-b]pyridin-2-one | 7a, 7b, 7c, 22 | tert-butyl 4-aminobenzoate |
| 80 | 384.1 | | | 3-[4-(1H-benzimidazol-2-ylcarbonyl)phenyl]-1-ethyl-1,3-dihydro-2H-imidazo[4,5-b]pyridin-2-one | 7a, 7b, 7c, 22 | tert-butyl 4-aminobenzoate |
| 81 | 370.2 | | | 1-ethyl-3-[4-(1-methyl-1H-benzimidazol-7-yl)phenyl]-1,3-dihydro-2H-imidazo[4,5-b]pyridin-2-one | 12d | 7-bromo-1-methyl-1H-benzimidazole |
| 82 | 370.2 | | | 1-ethyl-3-[4-(1-methyl-1H-benzimidazol-4-yl)phenyl]-1,3-dihydro-2H-imidazo[4,5-b]pyridin-2-one | 12d | 4-bromo-1-methyl-1H-benzimidazole |
| 83 | 398.2 | | | 1-ethyl-3-{4-[(1-methyl-1H-benzimidazol-2-yl)carbonyl]phenyl}-1,3-dihydro-2H-imidazo[4,5-b]pyridin-2-one | 7a, 7b, 7c, 22 | tert-butyl 4-aminobenzoate |

TABLE 10

| Example No. | MS | MOLSTRUCTURE | SALT | NAME | Reffered Example No. | Raw Material |
|---|---|---|---|---|---|---|
| 84 | 429.2 | | | ethyl 3-[4-(1-ethyl-2-oxo-1,2-dihydro-3H-imidazo[4,5-b]pyridin-3-yl)phenyl]furo[3,2-b]pyridine-6-carboxylate | 12d | ethyl 3-bromofuro[3,2-b]pyridine-6-carboxylate |
| 87 | 443.2 | | | ethyl 2-[4-(3,3-dimethyl-2-oxo-2,3-dihydro-1H-pyrrolo[2,3-b]pyridin-1-yl)phenoxy]imidazo[1,2-a]pyridine-3-carboxylate | 75 | ethyl 2-chloroimidazo[1,2-a]pyridine-3-carboxylate |
| 88 | 405.1 | | | 3-{4-[(4,5-dichloro-1-methyl-1H-imidazol-2-yl)oxy]phenyl}-1-ethyl-1,3-dihydro-2H-imidazo[4,5-b]pyridin-2-one | 75 | 2,4,5-trichloro-1-methyl-1H-imidazole |
| 89 | 386 | | HCl | 1-ethyl-3-{4-[(7-methyl-1H-benzimidazol-2-yl)oxy]phenyl}-1,3-dihydro-2H-imidazo[4,5-b]pyridin-2-one | 75 | 7-methyl-2-(methylsulfonyl)-1H-benzimidazole |
| 90 | 386.2 | | HCl | 1-ethyl-3-{4-[(6-methyl-1H-benzimidazol-2-yl)oxy]phenyl}-1,3-dihydro-2H-imidazo[4,5-b]pyridin-2-one | 75 | 6-methyl-2-(methylsulfonyl)-1H-benzimidazole |
| 91 | 404.2 | | | 1-ethyl-3-(4-{[1-methyl-4-(trifluoromethyl)-1H-imidazol-2-yl]oxy}phenyl)-1,3-dihydro-2H-imidazo[4,5-b]pyridin-2-one | 75 | 4-(trifluoromethyl)-1H-imidazole-2-thiol |

TABLE 10-continued

| Example No. | MS | MOLSTRUCTURE | SALT | NAME | Reffered Example No. | Raw Material |
|---|---|---|---|---|---|---|
| 92 | 494.1 | | | 3-{4-[(4,5-dibromo-1-methyl-1H-imidazol-2-yl)oxy]phenyl}-1-ethyl-1,3-dihydro-2H-imidazo[4,5-b]pyridin-2-one | 75 | 2,4,5-tribromo-1-methyl-1H-imidazole |

TABLE 11

| Example No. | MS | MOLSTRUCTURE | SALT | NAME | Reffered Example No. | Raw Material |
|---|---|---|---|---|---|---|
| 93 | 336.1 | | | 1-ethyl-3-{4-[(1-methyl-1H-imidazol-2-yl)oxy]phenyl}-1,3-dihydro-2H-imidazo[4,5-b]pyridin-2-one | 75 | 2-bromo-1-methyl-1H-imidazole |
| 94 | 358.1 | | | 1-{4-[(3-methyl-3H-imidazo[4,5-b]pyridin-2-yl)oxy]phenyl}-1,3-dihydro-2H-pyrrolo[2,3-b]pyridin-2-one | 5, 75 | 4-bromophenol |
| 95 | 398.2 | | | 1'-{4-[(3-methyl-3H-imidazo[4,5-b]pyridin-2-yl)oxy]phenyl}spiro[cyclobutane-1,3'-pyrrolo[2,3-b]pyridin]-2'(1'H)-one | 5, 75 | 4-bromophenol |
| 96 | 386.2 | | | 3,3-dimethyl-1-{4-[(3-methyl-3H-imidazo[4,5-b]pyridin-2-yl)oxy]phenyl}-1,3-dihydro-2H-pyrrolo[2,3-b]pyridin-2-one | 5, 75 | 4-bromophenol |
| 104 | 400.3 | | | 1-ethyl-5-methyl-3-{4-[(1-methyl-1H-benzimidazol-2-yl)oxy]phenyl}-1,3-dihydro-2H-imidazo[4,5-b]pyridin-2-one | 7a, 7b, 7c, 22 | 4-(benzyloxy)laniline |

TABLE 11-continued

| Example No. | MS | MOLSTRUCTURE | SALT | NAME | Reffered Example No. | Raw Material |
|---|---|---|---|---|---|---|
| 105 | 401.3 | | | 1-ethyl-5-methyl-3-{4-[(3-methyl-3H-imidazo[4,5-b]pyridin-2-yl)oxy]phenyl}-1,3-dihydro-2H-imidazo[4,5-b]pyridin-2-one | 7a, 7b, 7c, 22 | 4-(benzyl-oxy)laniline |
| 110 | 420 | | | 3-{4-[(3-bromo-1,2,4-thiadiazol-5-yl)oxy]phenyl)-1-ethyl-1,3-dihydro-2H-imidazo[4,5-b]pyridin-2-one | 7a, 7b, 7c, 22 | 4-(benzyl-oxy)laniline |

TABLE 12

| Example No. | MS | MOLSTRUCTURE | SALT | NAME | Reffered Example No. | Raw Material |
|---|---|---|---|---|---|---|
| 111 | 508.2 | | | 1-ethyl-3-{4-[(1-{[2-(trimethylsilyl)ethoxy]methyl}-1H-thieno[3,4-d]imidazol-2-yl)oxy]phenyl}-1,3-dihydro-2H-imidazo[4,5-b]pyridin-2-one | 7a, 7b, 7b, 22 | 4-(benzyl-oxy)laniline |
| 113 | 378.1 | | | 1-ethyl-3-[4-(1H-thieno[3,4-d]imidazol-2-yloxy)phenyl]-1,3-dihydro-2H-imidazo[4,5-b]pyridin-2-one | 7a, 7b, 7c, 22 | 4-(benzyl-oxy)laniline |

TABLE 12-continued

| Example No. | MS | MOLSTRUCTURE | SALT | NAME | Reffered Example No. | Raw Material |
|---|---|---|---|---|---|---|
| 114 | 503.2 | | | 1-ethyl-3-{4-[(3-{[2-(trimethylsilyl)ethoxy]methyl}-3H-imidazo[4,5-c]pyridin-2-yl)oxy]phenyl}-1,3-dihydro-2H-imidazo[4,5-b]pyridin-2-one | 7a, 7b, 7c, 22 | 4-(benzyloxy)laniline |
| 116 | 458.1 | | | ethyl 2-{4-[1-(1-methylethyl)-2-oxo-1,2-dihydro-3H-imidazo[4,5-b]pyridin-3-yl]phenoxy}imidazo[1,2-a]pyridine-3-carboxylate | 7a, 7b, 7c, 22 | 4-(benzyloxy)laniline |
| 117 | 386 | | | 3-[4-(imidazo[1,2-a]pyridin-2-yloxy)phenyl]-1-(1-methylethyl)-1,3-dihydro-2H-imidazo[4,5-b]pyridin-2-one | 7a, 7b, 7c, 22 | 4-(benzyloxy)laniline |
| 131 | 357 | | | 1-ethyl-3-(1-pyrimidin-2-yl-1H-indol-5-yl)-1,3-dihydro-2H-imidazo[4,5-b]pyridin-2-one | 69 | 2-chloropyrimidine |

Reference Example

Examples of the compound having a PDE10A inhibitory activity include the compounds described as Reference Examples 1-223 in the following Tables 13-39. The compounds of Reference Examples 1-223 can be produced according to the synthetic methods described in the Examples of the present invention or a method analogous thereto. Furthermore, the compounds of Reference Examples can be produced according to the synthetic methods of the compounds described in WO2008/004117, WO2010/0057121, WO2010/57126, WO2006/072828, WO2008/001182 or WO2010/090737, or a method analogous thereto.

The compounds of Reference Examples 1-223 are useful as PDE10A inhibitors or drugs for the prophylaxis or treatment of mental diseases such as schizophrenia and the like, and the administration subject, target disease, administration route, dosage form and the like are the same as those explained for medicaments containing compound (I) or a prodrug thereof.

TABLE 13
| Ref. Ex. No. | compound | compound name |
| --- | --- | --- |
| 1 | 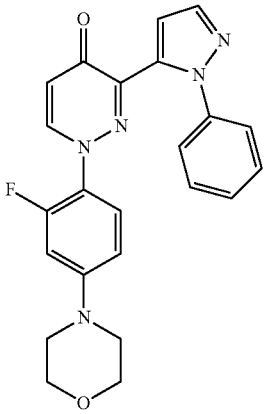 [SMILES: O=c1ccn(-c2ccc(N3CCOCC3)cc2F)nc1-c1ccnn1-c1ccccc1] | 1-[2-fluoro-4-(morpholin-4-yl)phenyl]-3-(1-phenyl-1H-pyrazol-5-yl)pyridazin-4(1H)-one |
| 2 | 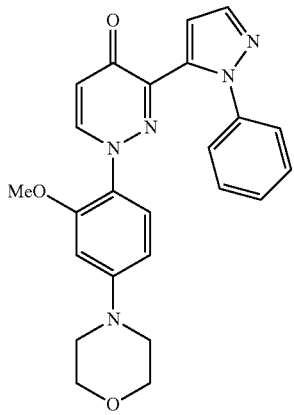 [SMILES: COc1cc(N2CCOCC2)ccc1-n1ccc(=O)c(-c2ccnn2-c2ccccc2)n1] | 1-[2-methoxy-4-(morpholin-4-yl)phenyl]-3-(1-phenyl-1H-pyrazol-5-yl)pyridazin-4(1H)-one |
| 3 | 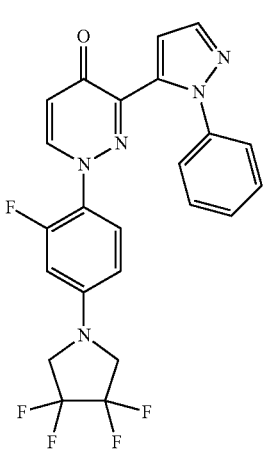 | 1-[2-fluoro-4-(3,3,4,4-tetrafluoropyrrolidin-1-yl)phenyl]-3-(1-phenyl-1H-pyrazol-5-yl)pyridazin-4(1H)-one |

TABLE 13-continued

| Ref. Ex. No. | compound | compound name |
| --- | --- | --- |
| 4 | | 1-[2-methoxy-4-(3,3,4,4-tetrafluoropyrrolidin-1-yl)phenyl]-3-(1-phenyl-1H-pyrazol-5-yl)pyridazin-4(1H)-one |
| 5 | | 1-[4-(4,4-difluoropiperidin-1-yl)-2-fluorophenyl]-3-(1-phenyl-1H-pyrazol-5-yl)pyridazin-4(1H)-one |
| 6 | | 1-[4-(4,4-difluoropiperidin-1-yl)-2-methoxyphenyl]-3-(1-phenyl-1H-pyrazol-5-yl)pyridazin-4(1H)-one |

TABLE 13-continued

| Ref. Ex. No. | compound | compound name |
| --- | --- | --- |
| 7 | | 1-[4-(3,6-dihydro-2H-pyran-4-yl)-2-fluorophenyl]-3-(1-phenyl-1H-pyrazol-5-yl)pyridazin-4(1H)-one |
| 8 | | 1-[4-(3,6-dihydro-2H-pyran-4-yl)-2-methoxyphenyl]-3-(1-phenyl-1H-pyrazol-5-yl)pyridazin-4(1H)-one |

TABLE 14

| | | |
| --- | --- | --- |
| 9 | | 1-[2-fluoro-4-(tetrahydro-2H-pyran-4-yl)phenyl]-3-(1-phenyl-1H-pyrazol-5-yl)pyridazin-4(1H)-one |
| 10 | | 1-[2-methoxy-4-(tetrahydro-2H-pyran-4-yl)phenyl]-3-(1-phenyl-1H-pyrazol-5-yl)pyridazin-4(1H)-one |

TABLE 14-continued

| | | |
|---|---|---|
| 11 | | 1-[4-(3,3-difluoropyrrolidin-1-yl)-2-fluorophenyl]-3-(1-phenyl-1H-pyrazol-5-yl)pyridazin-4(1H)-one |
| 12 | | 1-[4-(3,3-difluoropyrrolidin-1-yl)-2-methoxyphenyl]-3-(1-phenyl-1H-pyrazol-5-yl)pyridazin-4(1H)-one |
| 13 | | 1-[2-fluoro-4-{1H pyrazol-1-yl}phenyl]-3-(1-phenyl-1H-pyrazol-5-yl)pyridazin-4(1H)-one |
| 14 | | 1-[2-methoxy-4-(1H-pyrazol-1-yl)phenyl]-3-(1-phenyl-1H-pyrazol-5-yl)pyridazin-4(1H)-one |

TABLE 14-continued

| | | |
|---|---|---|
| 15 | | 1-{4-[1-(difluoromethyl)-1H-pyrazol-4-yl]-2-fluorophenyl}-3-(1-phenyl-1H-pyrazol-5-yl)pyridazin-4(1H)-one |
| 16 | | 1-{4-[1-(difluoromethyl)-1H-pyrazol-4-yl]-2-methoxyphenyl}-3-(1-phenyl-1H-pyrazol-5-yl)pyridazin-4(1H)-one |

TABLE 15

| | | |
|---|---|---|
| 17 | | 1-[4-(3,5-dimethylisoxazol-4-yl)-2-fluorophenyl]-3-(1-phenyl-1H-pyrazol-5-yl)pyridazin-4(1H)-one |

TABLE 15-continued

| # | Name |
|---|---|
| 18 | 1-[4-(3,5-dimethylisoxazol-4-yl)-2-methoxyphenyl]-3-(1-phenyl-1H-pyrazol-5-yl)pyridazin-4(1H)-one |
| 19 | 1-[2-fluoro-4-(1-methyl-1H-pyrazol-4-yl)phenyl]-3-(1-phenyl-1H-pyrazol-5-yl)pyridazin-4(1H)-one |
| 20 | 1-[2-methoxy-4-(1-methyl-1H-pyrazol-4-yl)phenyl]-3-(1-phenyl-1H-pyrazol-5-yl)pyridazin-4(1H)-one |
| 21 | 1-[2-fluoro-4-(2-oxo-1,3-oxazolidin-3-yl)phenyl]-3-(1-phenyl-1H-pyrazol-5-yl)pyridazin-4(1H)-one |
| 22 | 1-[2-methoxy-4-(2-oxo-1,3-oxazolidin-3-yl)phenyl]-3-(1-phenyl-1H-pyrazol-5-yl)pyridazin-4(1H)-one |
| 23 | 1-[4-(5,5-dimethyl-2-oxo-1,3-oxazolidin-3-yl)-2-fluorophenyl]-3-(1-phenyl-1H-pyrazol-5-yl)pyridazin-4(1H)-one |
| 24 | 1-[4-(5,5-dimethyl-2-oxo-1,3-oxazolidin-3-yl)-2-methoxyphenyl]-3-(1-phenyl-1H-pyrazol-5-yl)pyridazin-4(1H)-one |
| 25 | 1-[4-(4,4-dimethyl-2-oxo-1,3-oxazolidin-3-yl)-2-fluorophenyl]-3-(1-phenyl-1H-pyrazol-5-yl)pyridazin-4(1H)-one |

TABLE 16

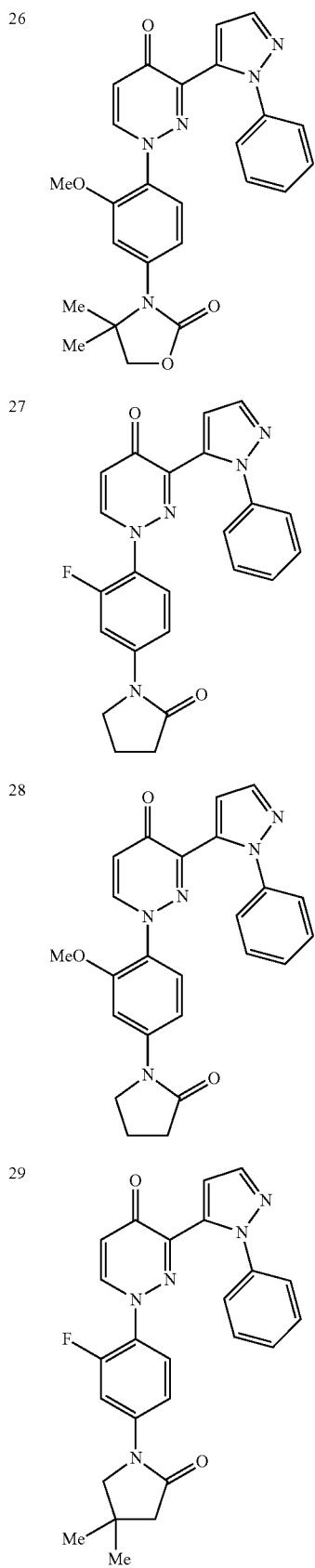

26 — 1-[4-(4,4-dimethyl-2-oxo-1,3-oxazolidin-3-yl)-2-methoxyphenyl]-3-(1-phenyl-1H-pyrazol-5-yl)pyridazin-4(1H)-one 27 — 1-[2-fluoro-4-(2-oxopyrrolidin-1-yl)phenyl]-3-(1-phenyl-1H-pyrazol-5-yl)pyridazin-4(1H)-one 28 — 1-[2-methoxy-4-(2-oxopyrrolidin-1-yl)phenyl]-3-(1-phenyl-1H-pyrazol-5-yl)pyridazin-4(1H)-one 29 — 1-[4-(4,4-dimethyl-2-oxopyrrolidin-1-yl)-2-fluorophenyl]-3-(1-phenyl-1H-pyrazol-5-yl)pyridazin-4(1H)-one TABLE 16-continued

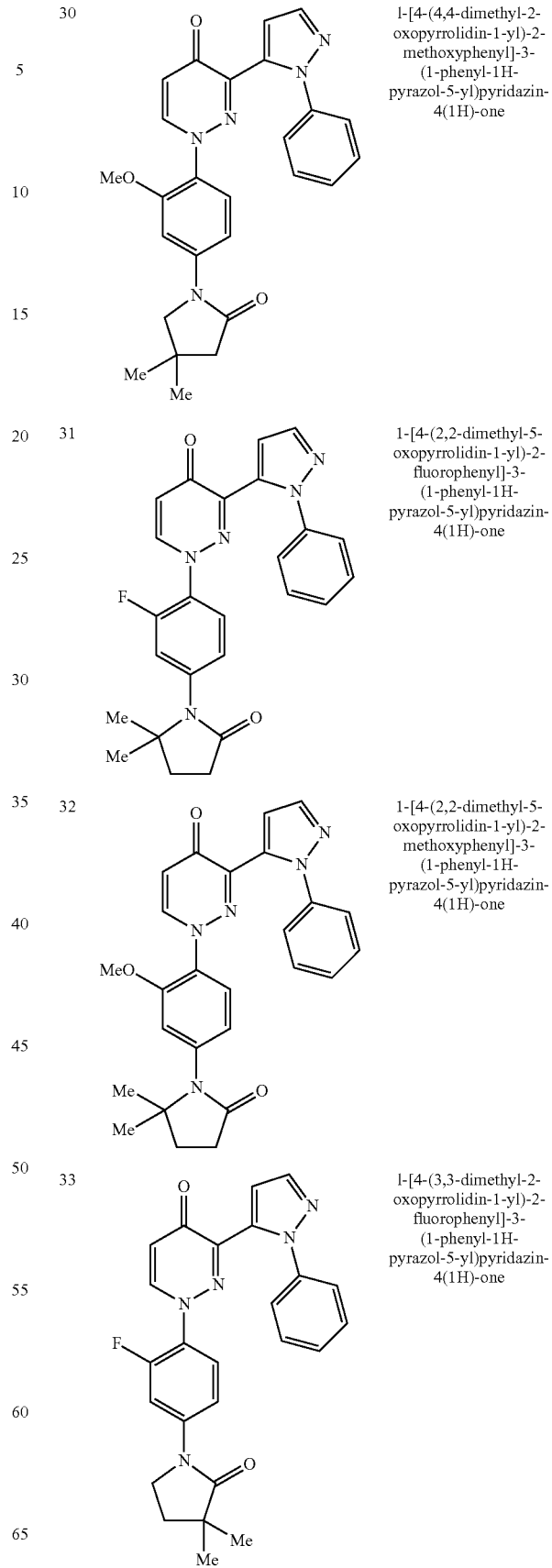

30 — 1-[4-(4,4-dimethyl-2-oxopyrrolidin-1-yl)-2-methoxyphenyl]-3-(1-phenyl-1H-pyrazol-5-yl)pyridazin-4(1H)-one 31 — 1-[4-(2,2-dimethyl-5-oxopyrrolidin-1-yl)-2-fluorophenyl]-3-(1-phenyl-1H-pyrazol-5-yl)pyridazin-4(1H)-one 32 — 1-[4-(2,2-dimethyl-5-oxopyrrolidin-1-yl)-2-methoxyphenyl]-3-(1-phenyl-1H-pyrazol-5-yl)pyridazin-4(1H)-one 33 — 1-[4-(3,3-dimethyl-2-oxopyrrolidin-1-yl)-2-fluorophenyl]-3-(1-phenyl-1H-pyrazol-5-yl)pyridazin-4(1H)-one TABLE 16-continued

| 34 | | 1-[4-(3,3-dimethyl-2-oxopyrrolidin-1-yl)-2-methoxyphenyl]-3-(1-phenyl-1H-pyrazol-5-yl)pyridazin-4(1H)-one |

TABLE 17

| 35 | | 1-[2-fluoro-4-(3-methyl-2-oxopyrrolidin-1-yl)phenyl]-3-(1-phenyl-1H-pyrazol-5-yl)pyridazin-4(1H)-one |
| 36 | | 1-[2-methoxy-4-(3-methyl-2-oxopyrrolidin-1-yl)phenyl]-3-(1-phenyl-1H-pyrazol-5-yl)pyridazin-4(1H)-one |

TABLE 17-continued

| 37 | | 1-[2-fluoro-4-(2-methyl-5-oxopyrrolidin-1-yl)phenyl]-3-(1-phenyl-1H-pyrazol-5-yl)pyridazin-4(1H)-one |
| 38 | | 1-[2-methoxy-4-(2-methyl-5-oxopyrrolidin-1-yl)phenyl]-3-(1-phenyl-1H-pyrazol-5-yl)pyridazin-4(1H)-one |
| 39 | | 6-{3-fluoro-4-[4-oxo-3-(1-phenyl-1H-pyrazol-5-yl)pyridazin-1(4H)-yl]phenyl}-4-oxa-6-azaspiro[2.4]heptan-5-one |
| 40 | | 6-{3-methoxy-4-[4-oxo-3-(1-phenyl-1H-pyrazol-5-yl)pyridazin-1(4H)-yl]phenyl}-4-oxa-6-azaspiro[2.4]heptan-5-one |

TABLE 17-continued

| 41 | 1-[4-(3-tert-butyl-2-oxoimidazolidin-1-yl)-2-fluorophenyl]-3-(1-phenyl-1H-pyrazol-5-yl)pyridazin-4(1H)-one |
| 42 | 1-[4-(3-tert-butyl-2-oxoimidazolidin-1-yl)-2-methoxyphenyl]-3-(1-phenyl-1H-pyrazol-5-yl)pyridazin-4(1H)-one |

TABLE 18

| 43 | 1-[2-fluoro-4-(2-oxoimidazolidin-1-yl)phenyl]-3-(1-phenyl-1H-pyrazol-5-yl)pyridazin-4(1H)-one |
| 44 | 1-[2-methoxy-4-(2-oxoimidazolidin-1-yl)phenyl]-3-(1-phenyl-1H-pyrazol-5-yl)pyridazin-4(1H)-one |
| 45 | 1-[2-fluoro-4-(3-methyl-2-oxoimidazolidin-1-yl)phenyl]-3-(1-phenyl-1H-pyrazol-5-yl)pyridazin-4(1H)-one |
| 46 | 1-[2-methoxy-4-(3-methyl-2-oxoimidazolidin-1-yl)phenyl]-3-(1-phenyl-1H-pyrazol-5-yl)pyridazin-4(1H)-one |

TABLE 18-continued

| 47 | 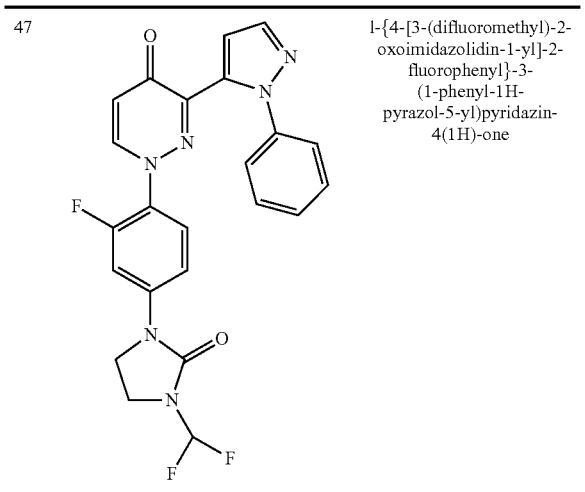 | 1-{4-[3-(difluoromethyl)-2-oxoimidazolidin-1-yl]-2-fluorophenyl}-3-(1-phenyl-1H-pyrazol-5-yl)pyridazin-4(1H)-one |

TABLE 18-continued

| 50 | 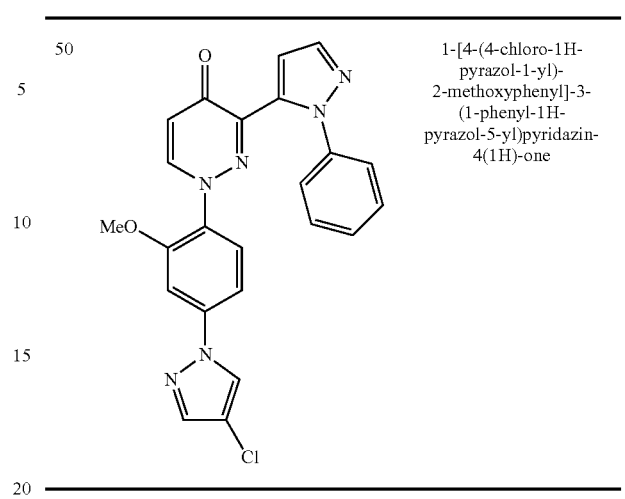 | 1-[4-(4-chloro-1H-pyrazol-1-yl)-2-methoxyphenyl]-3-(1-phenyl-1H-pyrazol-5-yl)pyridazin-4(1H)-one |

TABLE 19

| 48 | 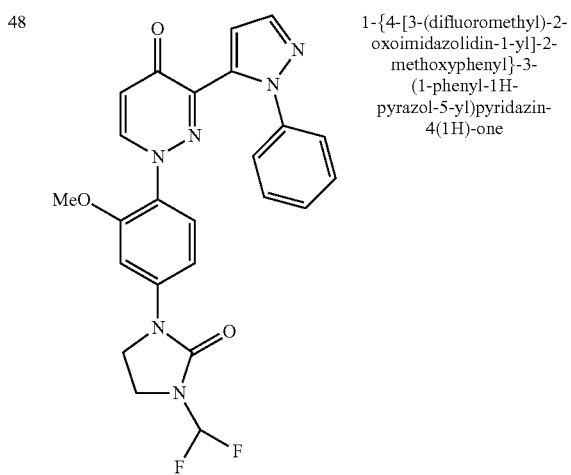 | 1-{4-[3-(difluoromethyl)-2-oxoimidazolidin-1-yl]-2-methoxyphenyl}-3-(1-phenyl-1H-pyrazol-5-yl)pyridazin-4(1H)-one |

| 51 | 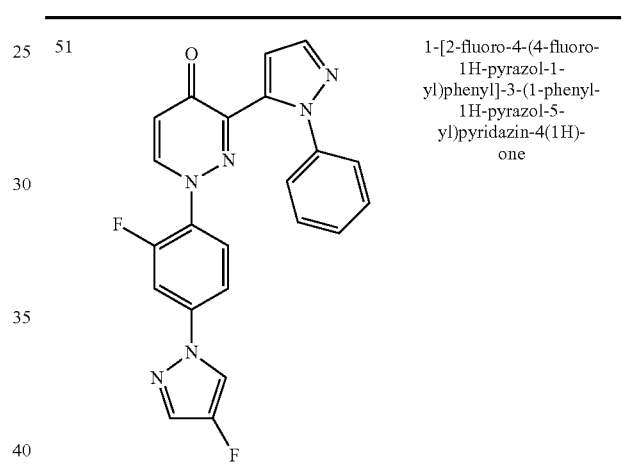 | 1-[2-fluoro-4-(4-fluoro-1H-pyrazol-1-yl)phenyl]-3-(1-phenyl-1H-pyrazol-5-yl)pyridazin-4(1H)-one |

| 49 | 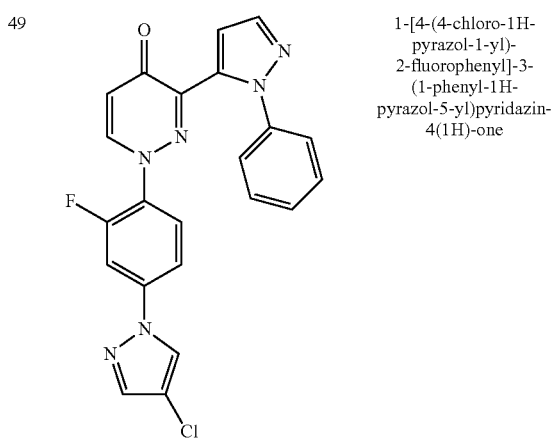 | 1-[4-(4-chloro-1H-pyrazol-1-yl)-2-fluorophenyl]-3-(1-phenyl-1H-pyrazol-5-yl)pyridazin-4(1H)-one |

| 52 | 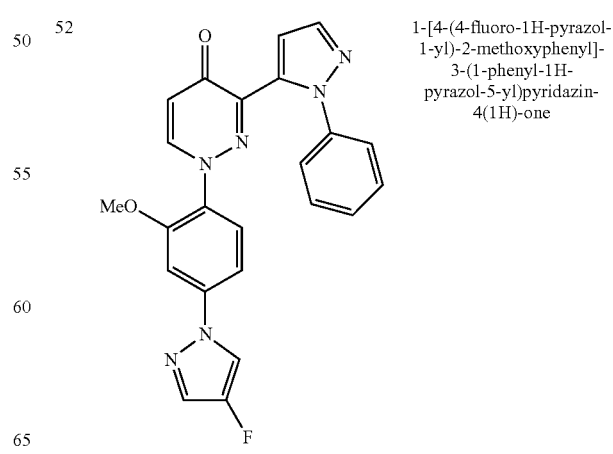 | 1-[4-(4-fluoro-1H-pyrazol-1-yl)-2-methoxyphenyl]-3-(1-phenyl-1H-pyrazol-5-yl)pyridazin-4(1H)-one |

TABLE 19-continued

| No. | Structure | Name |
|---|---|---|
| 53 | 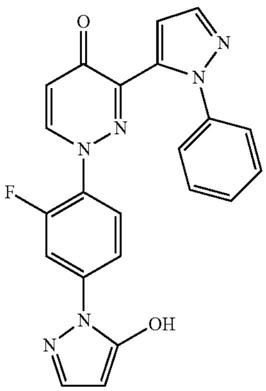 [SMILES: O=c1ccn(-c2ccc(-n3nccc3O)cc2F)nc1-c1ccnn1-c1ccccc1] | 1-[2-fluoro-4-(5-hydroxy-1H-pyrazol-1-yl)phenyl]-3-(1-phenyl-1H-pyrazol-5-yl)pyridazin-4(1H)-one |
| 54 | 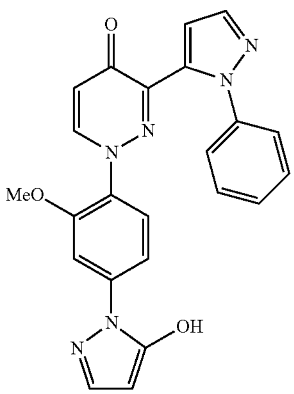 [SMILES: COc1cc(-n2nccc2O)ccc1-n1ccc(=O)c(-c2ccnn2-c2ccccc2)n1] | 1-[4-(5-hydroxy-1H-pyrazol-1-yl)-2-methoxyphenyl]-3-(1-phenyl-1H-pyrazol-5-yl)pyridazin-4(1H)-one |
| 55 | 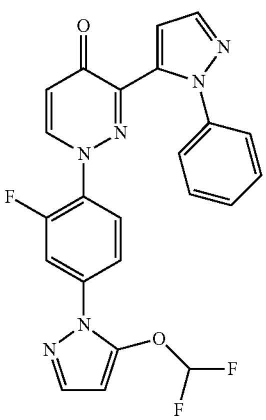 [SMILES: O=c1ccn(-c2ccc(-n3nccc3OC(F)F)cc2F)nc1-c1ccnn1-c1ccccc1] | 1-{4-[5-(difluoromethoxy)-1H-pyrazol-1-yl]-2-fluorophenyl}-3-(1-phenyl-1H-pyrazol-5-yl)pyridazin-4(1H)-one |
| 56 | 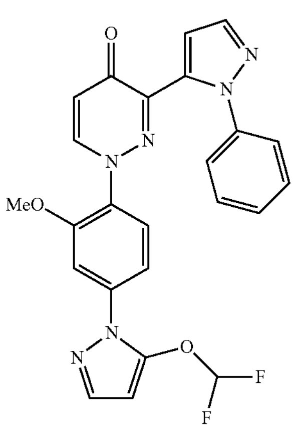 [SMILES: COc1cc(-n2nccc2OC(F)F)ccc1-n1ccc(=O)c(-c2ccnn2-c2ccccc2)n1] | 1-{4-[5-(difluoromethoxy)-1H-pyrazol-1-yl]-2-methoxyphenyl}-3-(1-phenyl-1H-pyrazol-5-yl)pyridazin-4(1H)-one |
| 57 | | 1-{4-[2-(difluoromethyl)-5-oxo-2,5-dihydro-1H-pyrazol-1-yl]-2-fluorophenyl}-3-(1-phenyl-1H-pyrazol-5-yl)pyridazin-4(1H)-one |
| 58 | | 1-{4-[2-(difluoromethyl)-5-oxo-2,5-dihydro-1H-pyrazol-1-yl]-2-methoxyphenyl}-3-(1-phenyl-1H-pyrazol-5-yl)pyridazin-4(1H)-one |

TABLE 20

| No. | Structure | Name |
|---|---|---|
| 59 | 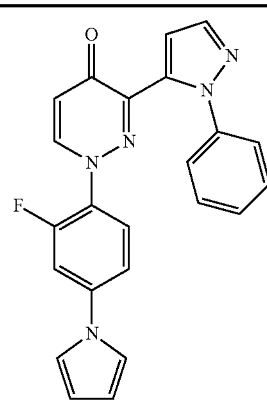 | 1-[2-fluoro-4-(1H-pyrrol-1-yl)phenyl]-3-(1-phenyl-1H-pyrazol-5-yl)pyridazin-4(1H)-one |
| 60 | 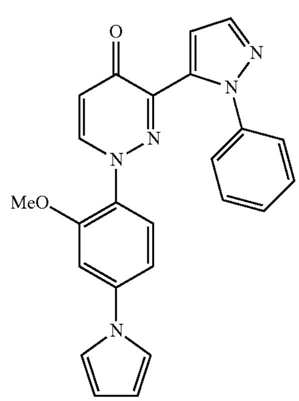 | 1-[2-methoxy-4-(1H-pyrrol-1-yl)phenyl]-3-(1-phenyl-1H-pyrazol-5-yl)pyridazin-4(1H)-one |

TABLE 20-continued

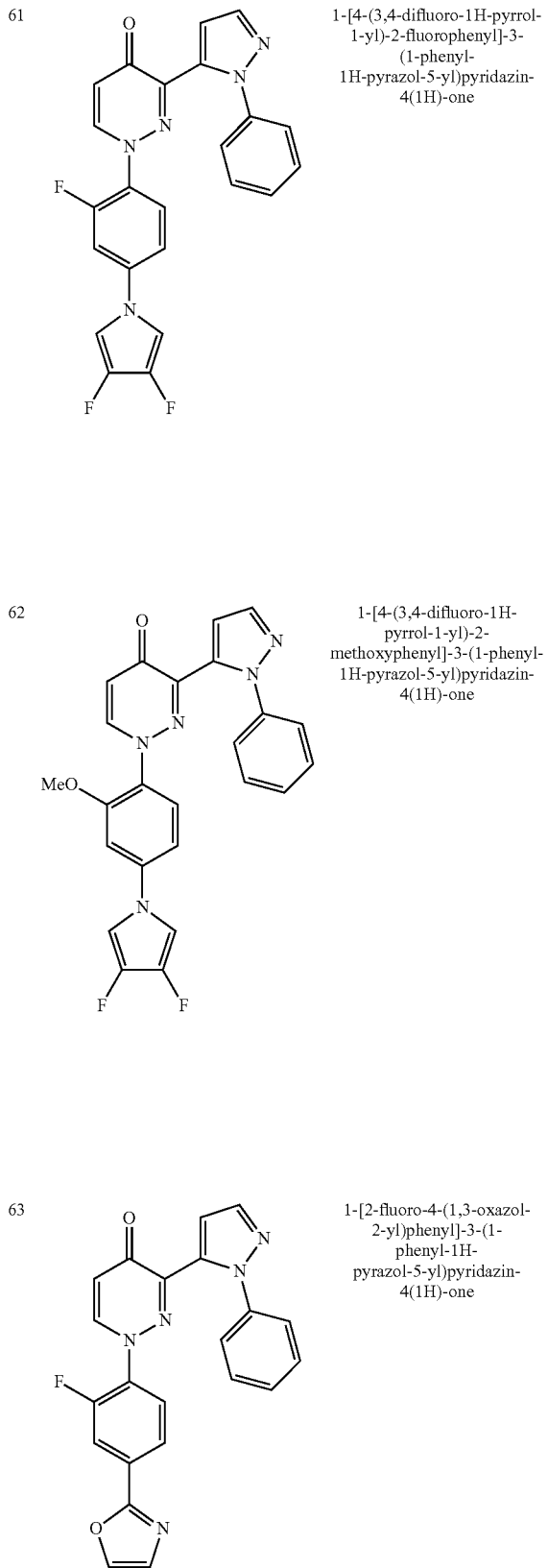

61    1-[4-(3,4-difluoro-1H-pyrrol-1-yl)-2-fluorophenyl]-3-(1-phenyl-1H-pyrazol-5-yl)pyridazin-4(1H)-one 62    1-[4-(3,4-difluoro-1H-pyrrol-1-yl)-2-methoxyphenyl]-3-(1-phenyl-1H-pyrazol-5-yl)pyridazin-4(1H)-one 63    1-[2-fluoro-4-(1,3-oxazol-2-yl)phenyl]-3-(1-phenyl-1H-pyrazol-5-yl)pyridazin-4(1H)-one

TABLE 20-continued

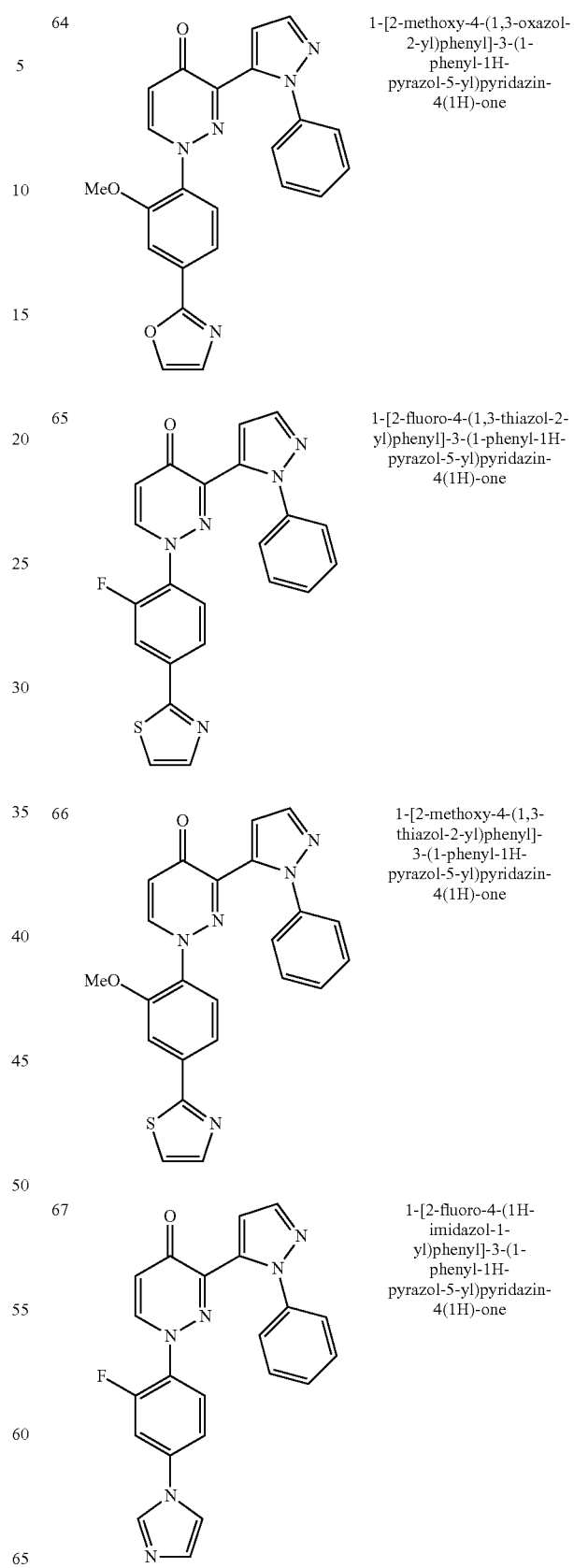

64    1-[2-methoxy-4-(1,3-oxazol-2-yl)phenyl]-3-(1-phenyl-1H-pyrazol-5-yl)pyridazin-4(1H)-one 65    1-[2-fluoro-4-(1,3-thiazol-2-yl)phenyl]-3-(1-phenyl-1H-pyrazol-5-yl)pyridazin-4(1H)-one 66    1-[2-methoxy-4-(1,3-thiazol-2-yl)phenyl]-3-(1-phenyl-1H-pyrazol-5-yl)pyridazin-4(1H)-one 67    1-[2-fluoro-4-(1H-imidazol-1-yl)phenyl]-3-(1-phenyl-1H-pyrazol-5-yl)pyridazin-4(1H)-one

TABLE 21

| 68 | | 1-[4-(1H-imidazol-1-yl)-2-methoxyphenyl]-3-(1-phenyl-1H-pyrazol-5-yl)pyridazin-4(1H)-one |
|---|---|---|
| 69 | | 1-{2-fluoro-4-[3-(trifluoromethyl)pyrrolidin-1-yl]phenyl}-3-(1-phenyl-1H-pyrazol-5-yl)pyridazin-4(1H)-one |
| 70 | | 1-{2-methoxy-4-[3-(trifluoromethyl)pyrrolidin-1-yl]phenyl}-3-(1-phenyl-1H-pyrazol-5-yl)pyridazin-4(1H)-one |

TABLE 21-continued

| 71 | | 1-[4-(2,5-dihydro-1H-pyrrol-1-yl)-2-fluorophenyl]-3-(1-phenyl-1H-pyrazol-5-yl)pyridazin-4(1H)-one |
|---|---|---|
| 72 | | 1-[4-(2,5-dihydro-1H-pyrrol-1-yl)-2-methoxyphenyl]-3-(1-phenyl-1H-pyrazol-5-yl)pyridazin-4(1H)-one |
| 73 | | 1-[4-(3,3-difluoro-piperidin-1-yl)-2-fluorophenyl]-3-(1-phenyl-1H-pyrazol-5-yl)pyridazin-4(1H)-one |
| 74 | | 1-[4-(3,3-difluoro-piperidin-1-yl)-2-methoxyphenyl]-3-(1-phenyl-1H-pyrazol-5-yl)pyridazin-4(1H)-one |

TABLE 21-continued

| | | |
|---|---|---|
| 75 | | 4-{3-fluoro-4-[4-oxo-3-(1-phenyl-1H-pyrazol-5-yl)pyridazin-1(4H)-yl]phenyl}morpholin-3-one |
| 76 | | 4-{3-methoxy-4-[4-oxo-3-(1-phenyl-1H-pyrazol-5-yl)pyridazin-1(4H)-yl]phenyl}morpholin-3-one |

TABLE 22

| | | |
|---|---|---|
| 77 | | 1-[4-(3,3-difluoroazetidin-1-yl)-2-fluorophenyl]-3-(1-phenyl-1H-pyrazol-5-yl)pyridazin-4(1H)-one |

TABLE 22-continued

| | | |
|---|---|---|
| 78 | | 1-[4-(3,3-difluoroazetidin-1-yl)-2-methoxyphenyl]-3-(1-phenyl-1H-pyrazol-5-yl)pyridazin-4(1H)-one |
| 79 | | 1-[2-fluoro-4-(3-fluoroazetidin-1-yl)phenyl]-3-(1-phenyl-1H-pyrazol-5-yl)pyridazin-4(1H)-one |
| 80 | | 1-[4-(3-fluoroazetidin-1-yl)-2-methoxyphenyl]-3-(1-phenyl-1H-pyrazol-5-yl)pyridazin-4(1H)-one |

TABLE 22-continued

| | | |
|---|---|---|
| 81 | 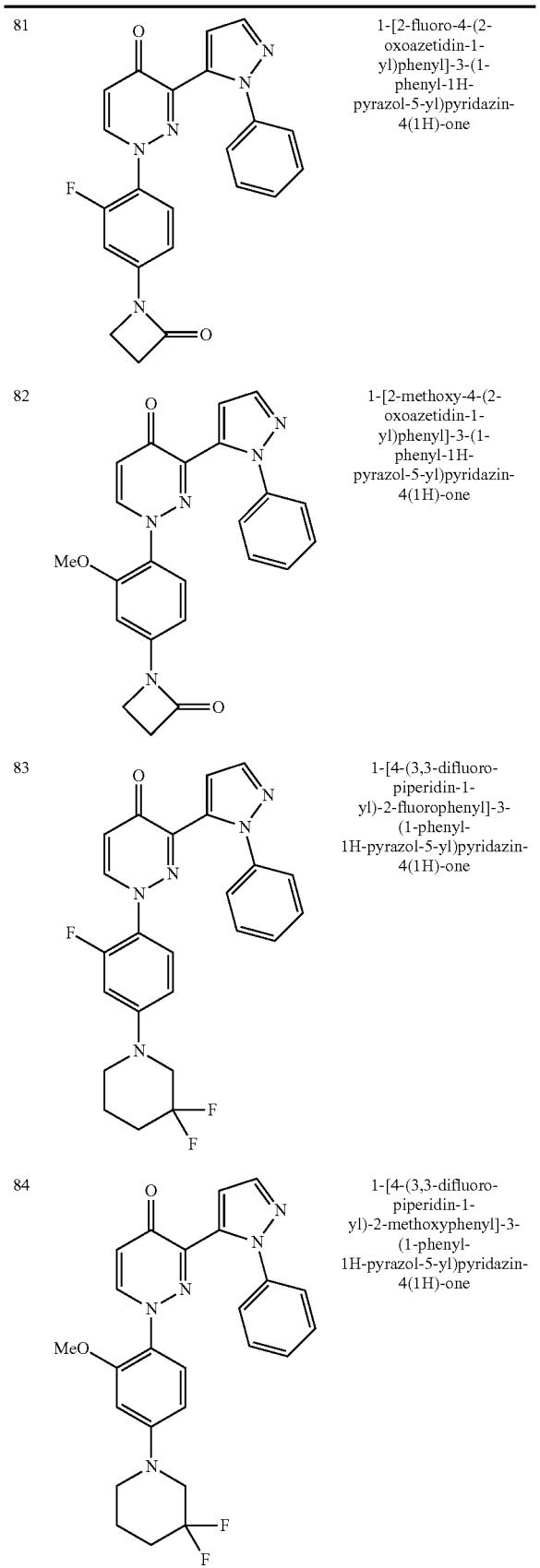 | 1-[2-fluoro-4-(2-oxoazetidin-1-yl)phenyl]-3-(1-phenyl-1H-pyrazol-5-yl)pyridazin-4(1H)-one |
| 82 | | 1-[2-methoxy-4-(2-oxoazetidin-1-yl)phenyl]-3-(1-phenyl-1H-pyrazol-5-yl)pyridazin-4(1H)-one |
| 83 | | 1-[4-(3,3-difluoro-piperidin-1-yl)-2-fluorophenyl]-3-(1-phenyl-1H-pyrazol-5-yl)pyridazin-4(1H)-one |
| 84 | | 1-[4-(3,3-difluoro-piperidin-1-yl)-2-methoxyphenyl]-3-(1-phenyl-1H-pyrazol-5-yl)pyridazin-4(1H)-one |

TABLE 22-continued

| | | |
|---|---|---|
| 85 | 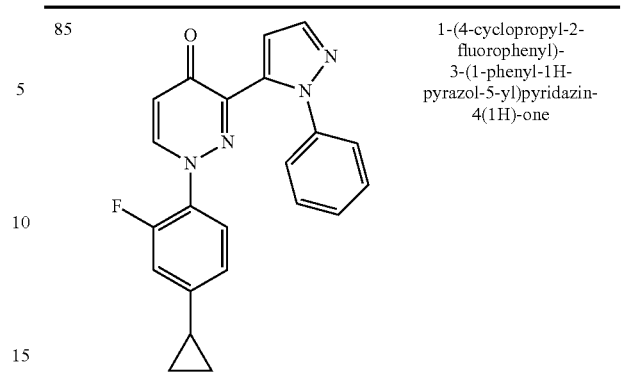 | 1-(4-cyclopropyl-2-fluorophenyl)-3-(1-phenyl-1H-pyrazol-5-yl)pyridazin-4(1H)-one |

TABLE 23

| | | |
|---|---|---|
| 86 | 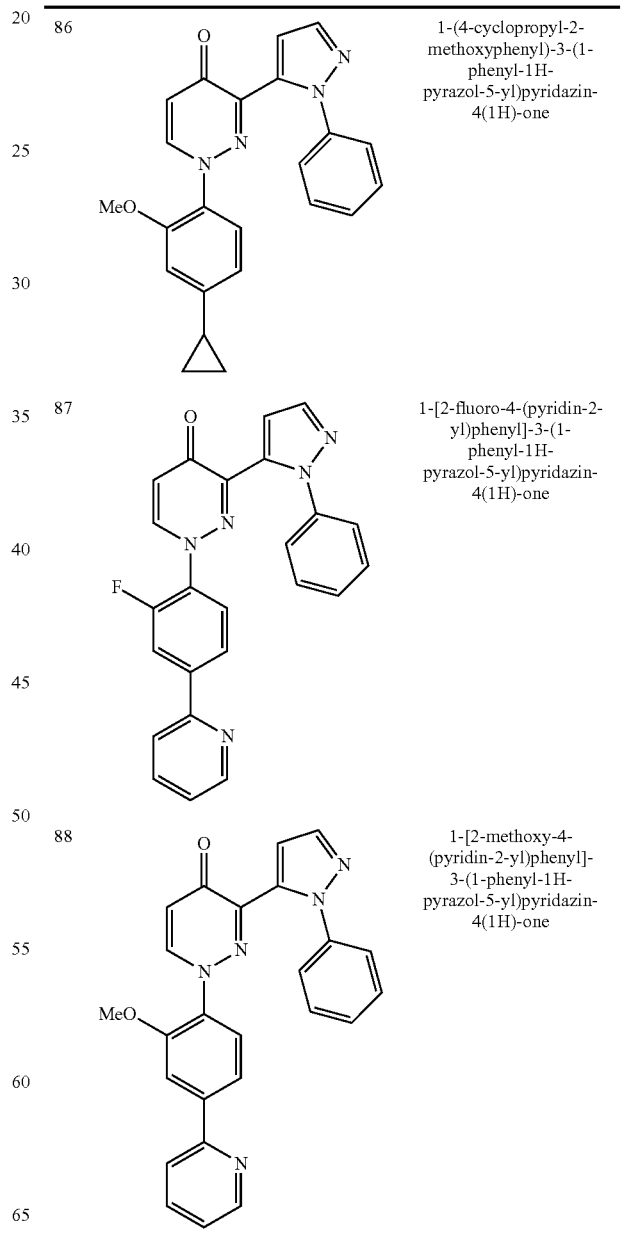 | 1-(4-cyclopropyl-2-methoxyphenyl)-3-(1-phenyl-1H-pyrazol-5-yl)pyridazin-4(1H)-one |
| 87 | | 1-[2-fluoro-4-(pyridin-2-yl)phenyl]-3-(1-phenyl-1H-pyrazol-5-yl)pyridazin-4(1H)-one |
| 88 | | 1-[2-methoxy-4-(pyridin-2-yl)phenyl]-3-(1-phenyl-1H-pyrazol-5-yl)pyridazin-4(1H)-one |

TABLE 23-continued

| | | |
|---|---|---|
| 89 | | 1-[2-fluoro-4-(pyridin-3-yl)phenyl]-3-(1-phenyl-1H-pyrazol-5-yl)pyridazin-4(1H)-one |
| 90 | | 1-[2-methoxy-4-(pyridin-3-yl)phenyl]-3-(1-phenyl-1H-pyrazol-5-yl)pyridazin-4(1H)-one |
| 91 | | 1-[2-fluoro-4-(pyridin-4-yl)phenyl]-3-(1-phenyl-1H-pyrazol-5-yl)pyridazin-4(1H)-one |
| 92 | | 1-[2-methoxy-4-(pyridin-4-yl)phenyl]-3-(1-phenyl-1H-pyrazol-5-yl)pyridazin-4(1H)-one |
| 93 | | 1-{4-[(2R,6S)-2,6-dimethylmorpholin-4-yl]-2-fluorophenyl}-3-(1-phenyl-1H-pyrazol-5-yl)pyridazin-4(1H)-one |
| 94 | | 1-{4-[(2R,6S)-2,6-dimethylmorpholin-4-yl]-2-methoxyphenyl}-3-(1-phenyl-1H-pyrazol-5-yl)pyridazin-4(1H)-one |

TABLE 24

| | | |
|---|---|---|
| 95 | | 1-[2-fluoro-4-(8-oxa-3-azabicyclo[3.2.1]octa-3-yl)phenyl]-3-(1-phenyl-1H-pyrazol-5-yl)pyridazin-4(1H)-one |

TABLE 24-continued

| | | |
|---|---|---|
| 96 | | 1-[2-methoxy-4-(8-oxa-3-azabicyclo[3.2.1]octa-3-yl)phenyl]-3-(1-phenyl-1H-pyrazol-5-yl)pyridazin-4(1H)-one |
| 97 | | 1-[2-fluoro-4-(1,4-oxazepan-4-yl)phenyl]-3-(1-phenyl-1H-pyrazol-5-yl)pyridazin-4(1H)-one |
| 98 | | 1-[2-methoxy-4-(1,4-oxazepan-4-yl)phenyl]-3-(1-phenyl-1H-pyrazol-5-yl)pyridazin-4(1H)-one |
| 99 | | 1-{4-[5-(cyclopropyl-methoxy)-1H-pyrazol-1-yl]-2-fluorophenyl}-3-(1-phenyl-1H-pyrazol-5-yl)pyridazin-4(1H)-one |
| 100 | | 1-{4-[5-(cyclopropyl-methoxy)-1H-pyrazol-1-yl]-2-methoxyphenyl}-3-(1-phenyl-1H-pyrazol-5-yl)pyridazin-4(1H)-one |
| 101 | | 1-{2-fluoro-4-[5-(2,2,2-trifluoroethoxy)-1H-pyrazol-1-yl]phenyl}-3-(1-phenyl-1H-pyrazol-5-yl)pyridazin-4(1H)-one |
| 102 | | 1-{2-methoxy-4-[5-(2,2,2-trifluoroethoxy)-1H-pyrazol-1-yl]phenyl}-3-(1-phenyl-1H-pyrazol-5-yl)pyridazin-4(1H)-one |

TABLE 24-continued

| | | |
|---|---|---|
| 103 | 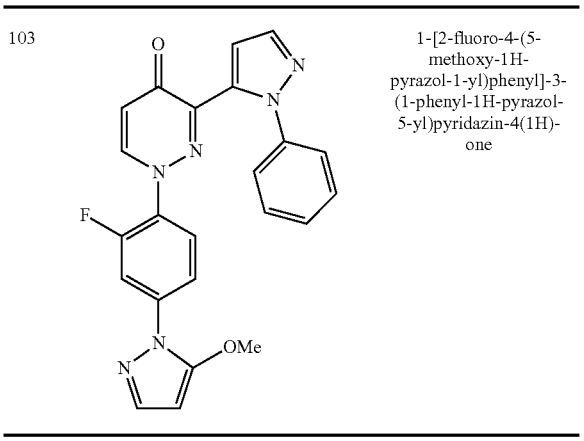 | 1-[2-fluoro-4-(5-methoxy-1H-pyrazol-1-yl)phenyl]-3-(1-phenyl-1H-pyrazol-5-yl)pyridazin-4(1H)-one |

TABLE 25

| | | |
|---|---|---|
| 104 | 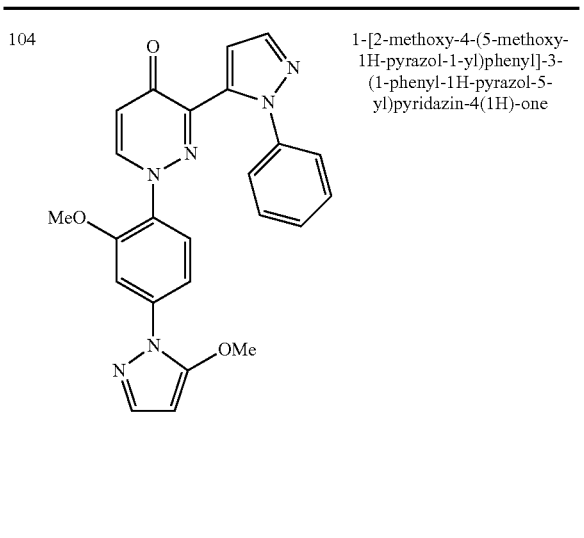 | 1-[2-methoxy-4-(5-methoxy-1H-pyrazol-1-yl)phenyl]-3-(1-phenyl-1H-pyrazol-5-yl)pyridazin-4(1H)-one |
| 105 | 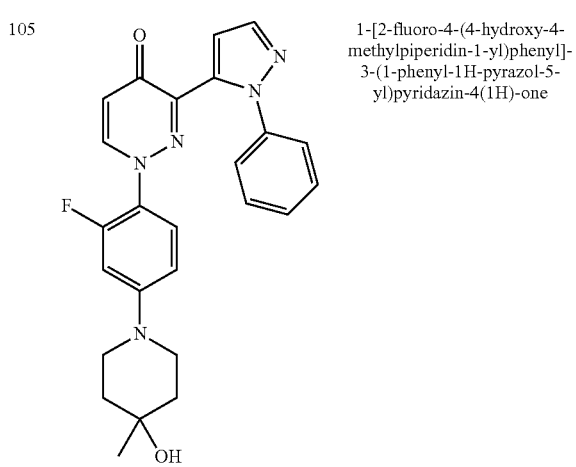 | 1-[2-fluoro-4-(4-hydroxy-4-methylpiperidin-1-yl)phenyl]-3-(1-phenyl-1H-pyrazol-5-yl)pyridazin-4(1H)-one |

TABLE 25-continued

| | | |
|---|---|---|
| 106 | 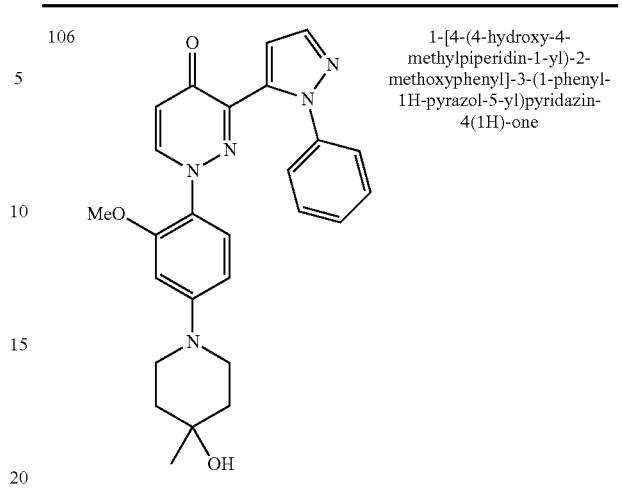 | 1-[4-(4-hydroxy-4-methylpiperidin-1-yl)-2-methoxyphenyl]-3-(1-phenyl-1H-pyrazol-5-yl)pyridazin-4(1H)-one |
| 107 | 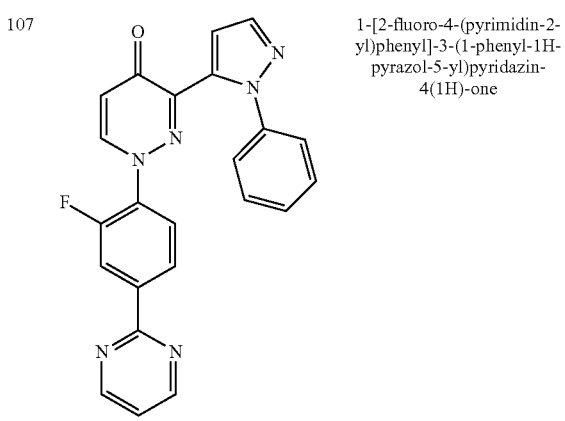 | 1-[2-fluoro-4-(pyrimidin-2-yl)phenyl]-3-(1-phenyl-1H-pyrazol-5-yl)pyridazin-4(1H)-one |
| 108 | 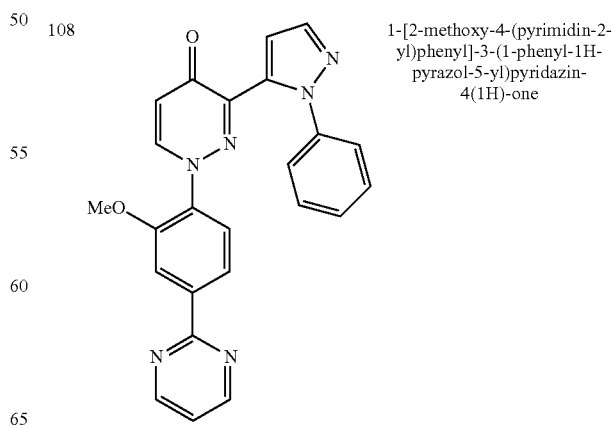 | 1-[2-methoxy-4-(pyrimidin-2-yl)phenyl]-3-(1-phenyl-1H-pyrazol-5-yl)pyridazin-4(1H)-one |

TABLE 25-continued

| 109 | 1-[2-fluoro-4-(pyrazin-2-yl)phenyl]-3-(1-phenyl-1H-pyrazol-5-yl)pyridazin-4(1H)-one |
| 110 | 1-[2-methoxy-4-(pyrazin-2-yl)phenyl]-3-(1-phenyl-1H-pyrazol-5-yl)pyridazin-4(1H)-one |
| 111 | 1-[2-fluoro-4-(pyrimidin-5-yl)phenyl]-3-(1-phenyl-1H-pyrazol-5-yl)pyridazin-4(1H)-one |

TABLE 26

| 112 | 1-[2-methoxy-4-(pyrimidin-5-yl)phenyl]-3-(1-phenyl-1H-pyrazol-5-yl)pyridazin-4(1H)-one |
| 113 | 1-[2-fluoro-4-(pyrimidin-4-yl)phenyl]-3-(1-phenyl-1H-pyrazol-5-yl)pyridazin-4(1H)-one |
| 114 | 1-[2-methoxy-4-(pyrimidin-4-yl)phenyl]-3-(1-phenyl-1H-pyrazol-5-yl)pyridazin-4(1H)-one |
| 115 | 1-[2-fluoro-4-(pyridazin-3-yl)phenyl]-3-(1-phenyl-1H-pyrazol-5-yl)pyridazin-4(1H)-one |

TABLE 26-continued

| 116 | 1-[2-methoxy-4-(pyridazin-3-yl)phenyl]-3-(1-phenyl-1H-pyrazol-5-yl)pyridazin-4(1H)-one |
| 117 | 1-[2-fluoro-3-(1H-pyrazol-1-yl)phenyl]-3-(1-phenyl-1H-pyrazol-5-yl)pyridazin-4(1H)-one |
| 118 | 1-[2-methoxy-3-(1H-pyrazol-1-yl)phenyl]-3-(1-phenyl-1H-pyrazol-5-yl)pyridazin-4(1H)-one |
| 119 | 1-[2-fluoro-5-(1H-pyrazol-1-yl)phenyl]-3-(1-phenyl-1H-pyrazol-5-yl)pyridazin-4(1H)-one |
| 120 | 1-[2-methoxy-5-(1H-pyrazol-1-yl)phenyl]-3-(1-phenyl-1H-pyrazol-5-yl)pyridazin-4(1H)-one |

TABLE 27

| 121 | 3-[1-(3-chlorophenyl)-1H-pyrazol-5-yl]-1-[2-fluoro-4-(1H-pyrazol-1-yl)phenyl]pyridazin-4(1H)-one |
| 122 | 3-[1-(3-chlorophenyl)-1H-pyrazol-5-yl]-1-[2-methoxy-4-(1H-pyrazol-1-yl)phenyl]pyridazin-4(1H)-one |
| 123 | 1-[2-fluoro-4-(1H-pyrazol-1-yl)phenyl]-3-{1-[3-(trifluoromethyl)phenyl]-1H-pyrazol-5-yl}pyridazin-4(1H)-one |

TABLE 27-continued

| | | |
|---|---|---|
| 124 | | 1-[2-methoxy-4-(1H-pyrazol-1-yl)phenyl]-3-{1-[3-(trifluoromethyl)phenyl]-1H-pyrazol-5-yl}pyridazin-4(1H)-one |
| 125 | | 1-[2-fluoro-4-(1H-pyrazol-1-yl)phenyl]-3-{1-[3-(trifluoromethoxy)phenyl]-1H-pyrazol-5-yl}pyridazin-4(1H)-one |
| 126 | | 1-[2-methoxy-4-(1H-pyrazol-1-yl)phenyl]-3-{1-[3-(trifluoromethoxy)phenyl]-1H-pyrazol-5-yl}pyridazin-4(1H)-one |
| 127 | | 1-[2-fluoro-4-(1H-pyrazol-1-yl)phenyl]-3-(3-methyl-1-phenyl-1H-pyrazol-5-yl)pyridazin-4(1H)-one |
| 128 | | 1-[2-methoxy-4-(1H-pyrazol-1-yl)phenyl]-3-(3-methyl-1-phenyl-1H-pyrazol-5-yl)pyridazin-4(1H)-one |
| 129 | | 3-[1-(3-chlorophenyl)-3-methyl-1H-pyrazol-5-yl]-1-[2-fluoro-4-(1H-pyrazol-1-yl)phenyl]pyridazin-4(1H)-one |

TABLE 28

| | | |
|---|---|---|
| 130 | | 3-[1-(3-chlorophenyl)-3-methyl-1H-pyrazol-5-yl]-1-[2-methoxy-4-(1H-pyrazol-1-yl)phenyl]pyridazin-4(1H)-one |

TABLE 28-continued

| 131 | (structure) | 1-[2-fluoro-4-(1H-pyrazol-1-yl)phenyl]-3-{3-methyl-1-[3-(trifluoromethyl)phenyl]-1H-pyrazol-5-yl}pyridazin-4(1H)-one |
| 132 | (structure) | 1-[2-methoxy-4-(1H-pyrazol-1-yl)phenyl]-3-{3-methyl-1-[3-(trifluoromethyl)phenyl]-1H-pyrazol-5-yl}pyridazin-4(1H)-one |
| 133 | (structure) | 1-[2-fluoro-4-(1H-pyrazol-1-yl)phenyl]-3-{3-methyl-1-[3-(trifluoromethoxy)phenyl]-1H-pyrazol-5-yl}pyridazin-4(1H)-one |
| 134 | (structure) | 1-[2-methoxy-4-(1H-pyrazol-1-yl)phenyl]-3-{3-methyl-1-[3-(trifluoromethoxy)phenyl]-1H-pyrazol-5-yl}pyridazin-4(1H)-one |
| 135 | (structure) | 1-[2-fluoro-4-(1H-pyrazol-1-yl)phenyl]-3-(4-methyl-1-phenyl-1H-pyrazol-5-yl)pyridazin-4(1H)-one |
| 136 | (structure) | 1-[2-methoxy-4-(1H-pyrazol-1-yl)phenyl]-3-(4-methyl-1-phenyl-1H-pyrazol-5-yl)pyridazin-4(1H)-one |
| 137 | (structure) | 3-[1-(3-chlorophenyl)-4-methyl-1H-pyrazol-5-yl]-1-[2-fluoro-4-(1H-pyrazol-1-yl)phenyl]pyridazin-4(1H)-one |

TABLE 28-continued

TABLE 29

| 138 | 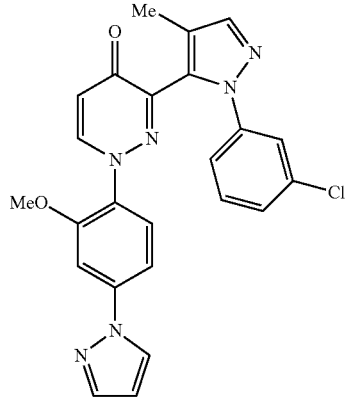 [SMILES: COc1cc(-n2cccn2)ccc1-n1ccc(=O)c(-c2c(C)cnn2-c2cccc(Cl)c2)n1] | 3-[1-(3-chlorophenyl)-4-methyl-1H-pyrazol-5-yl]-1-[2-methoxy-4-(1H-pyrazol-1-yl)phenyl]pyridazin-4(1H)-one |
| --- | --- | --- |
| 139 | 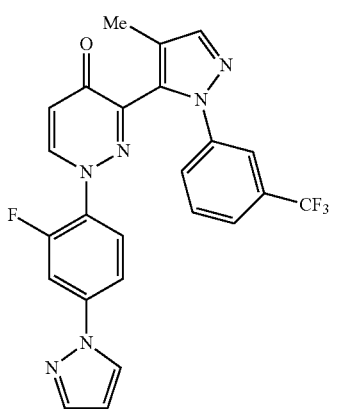 [SMILES: Cc1cnn(-c2cccc(C(F)(F)F)c2)c1-c1nn(-c2ccc(-n3cccn3)cc2F)ccc1=O] | 1-[2-fluoro-4-(1H-pyrazol-1-yl)phenyl]-3-{4-methyl-1-[3-(trifluoromethyl)phenyl]-1H-pyrazol-5-yl}pyridazin-4(1H)-one |
| 140 | 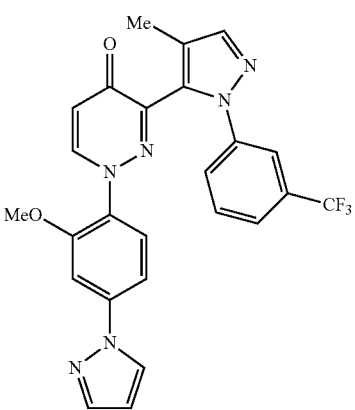 [SMILES: COc1cc(-n2cccn2)ccc1-n1ccc(=O)c(-c2c(C)cnn2-c2cccc(C(F)(F)F)c2)n1] | 1-[2-methoxy-4-(1H-pyrazol-1-yl)phenyl]-3-{4-methyl-1-[3-(trifluoromethyl)phenyl]-1H-pyrazol-5-yl}pyridazin-4(1H)-one |

TABLE 29-continued

| 141 | 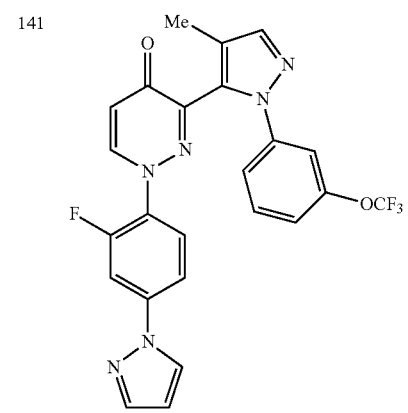 | 1-[2-fluoro-4-(1H-pyrazol-1-yl)phenyl]-3-{4-methyl-1-[3-(trifluoromethoxy)phenyl]-1H-pyrazol-5-yl}pyridazin-4(1H)-one |
| --- | --- | --- |
| 142 | 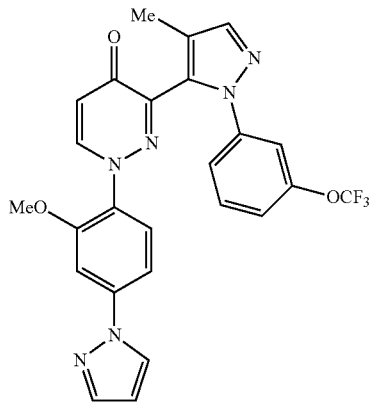 [SMILES: COc1cc(-n2cccn2)ccc1-n1ccc(=O)c(-c2c(C)cnn2-c2cccc(OC(F)(F)F)c2)n1] | 1-[2-methoxy-4-(1H-pyrazol-1-yl)phenyl]-3-{4-methyl-1-[3-(trifluoromethoxy)phenyl]-1H-pyrazol-5-yl}pyridazin-4(1H)-one |
| 143 | 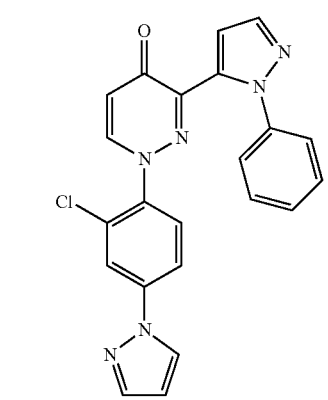 [SMILES: O=c1ccn(-c2ccc(-n3cccn3)cc2Cl)nc1-c1ccnn1-c1ccccc1] | 1-[2-chloro-4-(1H-pyrazol-1-yl)phenyl]-3-(1-phenyl-1H-pyrazol-5-yl)pyridazin-4(1H)-one |
| 144 | 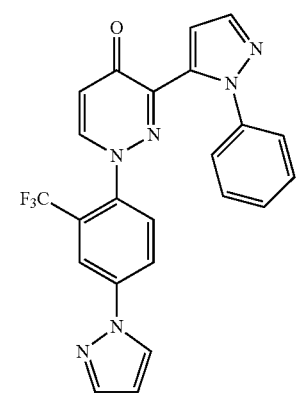 [SMILES: O=c1ccn(-c2ccc(-n3cccn3)cc2C(F)(F)F)nc1-c1ccnn1-c1ccccc1] | 3-(1-phenyl-1H-pyrazol-5-yl)-1-[4-(1H-pyrazol-1-yl)-2-(trifluoromethyl)phenyl]pyridazin-4(1H)-one |

TABLE 29-continued

| | | |
|---|---|---|
| 145 | 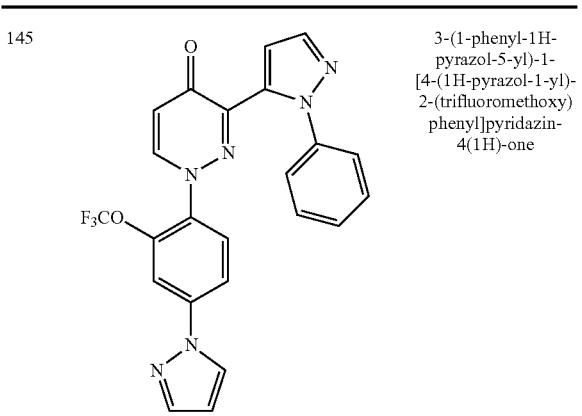 | 3-(1-phenyl-1H-pyrazol-5-yl)-1-[4-(1H-pyrazol-1-yl)-2-(trifluoromethoxy)phenyl]pyridazin-4(1H)-one |
| 146 | 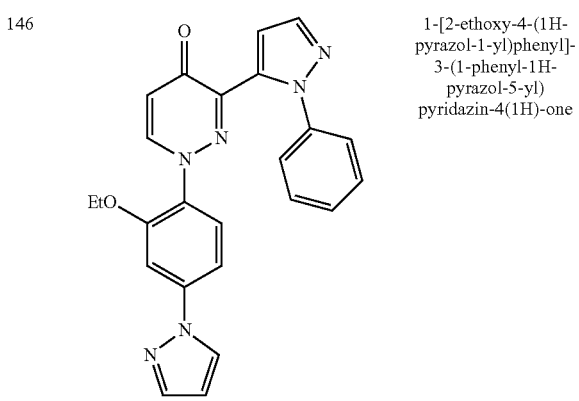 | 1-[2-ethoxy-4-(1H-pyrazol-1-yl)phenyl]-3-(1-phenyl-1H-pyrazol-5-yl)pyridazin-4(1H)-one |

TABLE 30

| | | |
|---|---|---|
| 147 | 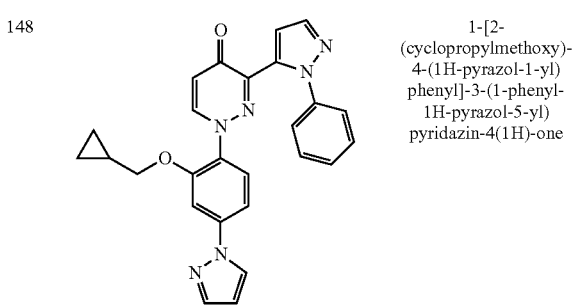 | 1-[2-(difluoromethoxy)-4-(1H-pyrazol-1-yl)phenyl]-3-(1-phenyl-1H-pyrazol-5-yl)pyridazin-4(1H)-one |
| 148 | 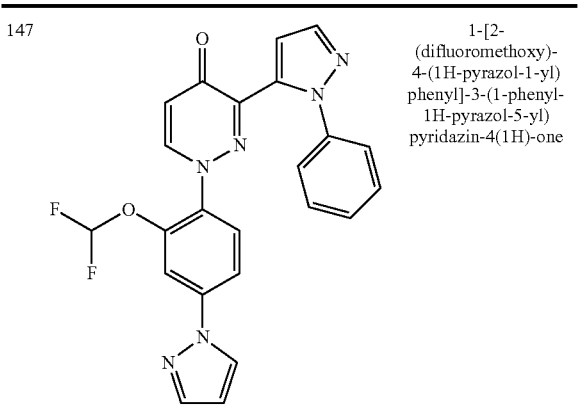 | 1-[2-(cyclopropylmethoxy)-4-(1H-pyrazol-1-yl)phenyl]-3-(1-phenyl-1H-pyrazol-5-yl)pyridazin-4(1H)-one |

TABLE 30-continued

| | | |
|---|---|---|
| 149 | 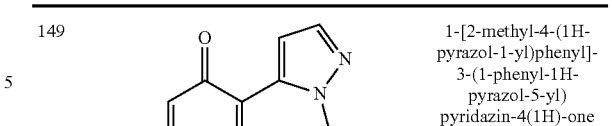 | 1-[2-methyl-4-(1H-pyrazol-1-yl)phenyl]-3-(1-phenyl-1H-pyrazol-5-yl)pyridazin-4(1H)-one |
| 150 | 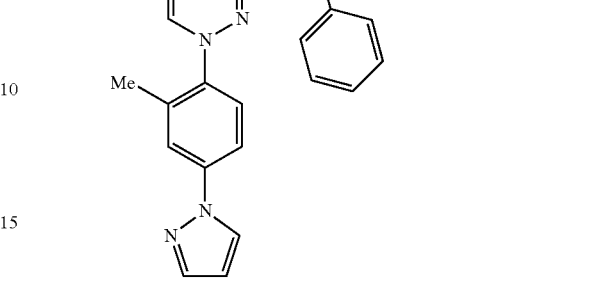 | 1-[2-ethyl-4-(1H-pyrazol-1-yl)phenyl]-3-(1-phenyl-1H-pyrazol-5-yl)pyridazin-4(1H)-one |
| 151 | 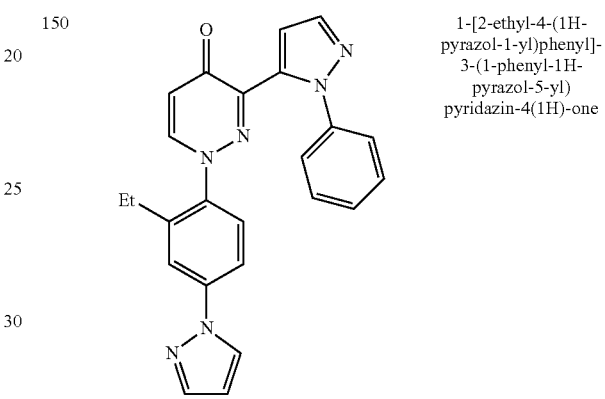 | 1-[2-(1-methylethyl)-4-(1H-pyrazol-1-yl)phenyl]-3-(1-phenyl-1H-pyrazol-5-yl)pyridazin-4(1H)-one |
| 152 | 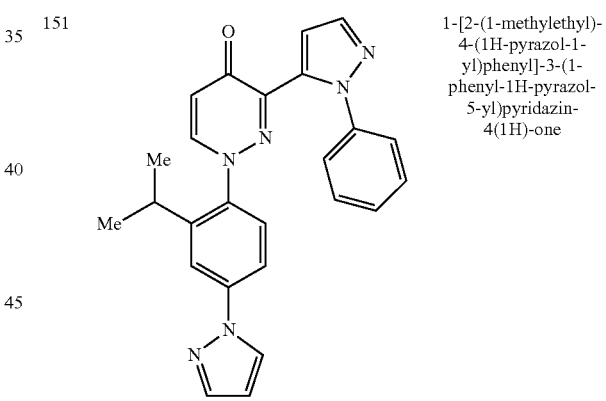 | 1-[2-fluoro-4-(3-oxa-8-azabicyclo[3.2.1]oct-8-yl)phenyl]-3-(1-phenyl-1H-pyrazol-5-yl)pyridazin-4(1H)-one |

TABLE 30-continued

| 153 | 1-[2-methoxy-4-(3-oxa-8-azabicyclo[3.2.1]oct-8-yl)phenyl]-3-(1-phenyl-1H-pyrazol-5-yl)pyridazin-4(1H)-one |
| 154 | 3-[1-(3-chlorophenyl)-1H-pyrazol-5-yl]-1-[2-fluoro-4-(2-oxo-1,3-oxazolidin-3-yl)phenyl]pyridazin-4(1H)-one |
| 155 | 3-[1-(3-chlorophenyl)-1H-pyrazol-5-yl]-1-[2-methoxy-4-(2-oxo-1,3-oxazolidin-3-yl)phenyl]pyridazin-4(1H)-one |

TABLE 31

| 156 | 1-[2-fluoro-4-(2-oxo-1,3-oxazolidin-3-yl)phenyl]-3-{1-[3-(trifluoromethyl)phenyl]-1H-pyrazol-5-yl}pyridazin-4(1H)-one |
| 157 | 1-[2-methexy-4-(2-oxo-1,3-oxazolidin-3-yl)phenyl]-3-{1-[3-(trifluoromethyl)phenyl]-1H-pyrazol-5-yl}pyritiazin-4(1H)-one |
| 158 | 1-[2-fluoro-4-(2-oxo-1,3-oxazolidin-3-yl)phenyl]-3-{1-[3-(trifluoromethoxy)phenyl]-1H-pyrazol-5-yl}pyridazin-4(1H)-one |
| 159 | 1-[2-methoxy-4-(2-oxo-1,3-oxazolidin-3-yl)phenyl]-3-{1-[3-(trifluoromethoxy)phenyl]-1H-pyrazol-5-yl}pyridazin-4(1H)-one |

TABLE 31-continued

| | | |
|---|---|---|
| 160 | 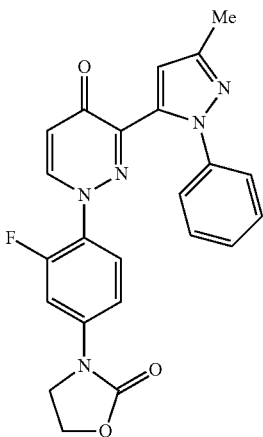 [SMILES: Cc1cc(-c2nn(-c3ccc(N4CCOC4=O)cc3F)ccc2=O)n(-c2ccccc2)n1] | 1-[2-fluoro-4-(2-oxo-1,3-oxazolidin-3-yl)phenyl]-3-(3-methyl-1-phenyl-1H-pyrazol-5-yl)pyridazin-4(1H)-one |
| 161 | 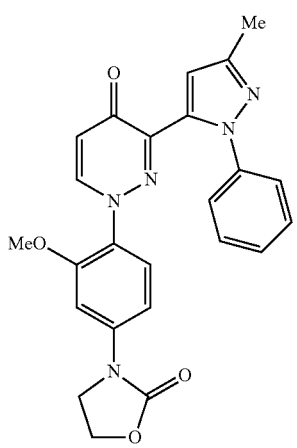 [SMILES: COc1cc(N2CCOC2=O)ccc1-n1ccc(=O)c(-c2cc(C)nn2-c2ccccc2)n1] | 1-[2-methoxy-4-(2-oxo-1,3-oxazolidin-3-yl)phenyl]-3-(3-methyl-1-phenyl-1H-pyrazol-5-yl)pyridazin-4(1H)-one |
| 162 | 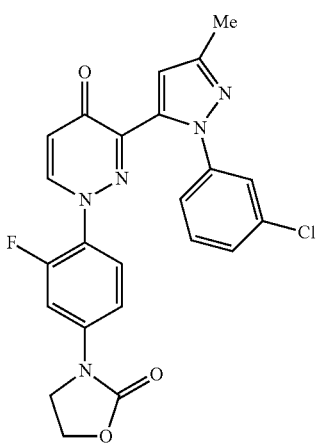 [SMILES: Cc1cc(-c2nn(-c3ccc(N4CCOC4=O)cc3F)ccc2=O)n(-c2cccc(Cl)c2)n1] | 3-[1-(3-chlorophenyl)-3-methyl-1H-pyrazol-5-yl]-1-[2-fluoro-4-(2-oxo-1,3-oxazolidin-3-yl)phenyl]pyridazin-4(1H)-one |

TABLE 31-continued

| | | |
|---|---|---|
| 163 | 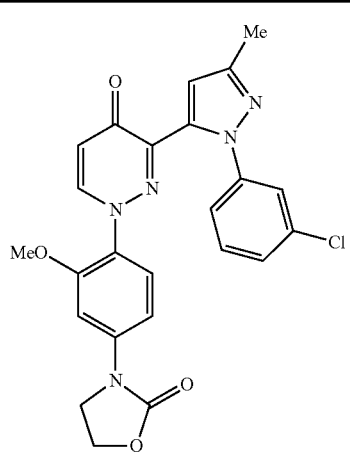 | 3-[1-(3-chlorophenyl)-3-methyl-1H-pyrazol-5-yl]-1-[2-methoxy-4-(2-oxo-1,3-oxazolidin-3-yl)phenyl]pyridazin-4(1H)-one |

TABLE 32

| | | |
|---|---|---|
| 164 | 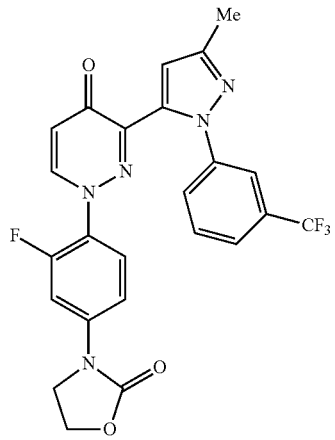 [SMILES: Cc1cc(-c2nn(-c3ccc(N4CCOC4=O)cc3F)ccc2=O)n(-c2cccc(C(F)(F)F)c2)n1] | 1-[2-fluoro-4-(2-oxo-1,3-oxazolidin-3-yl)phenyl]-3-{3-methyl-1-[3-(trifluoromethyl)phenyl]-1H-pyrazol-5-yl}pyridazin-4(1H)-one |
| 165 | 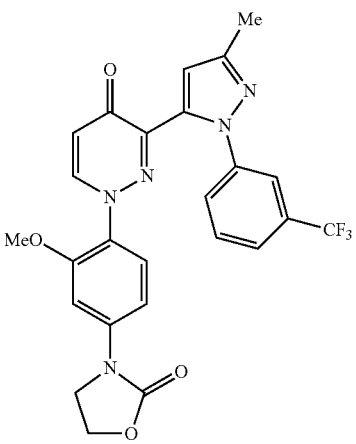 [SMILES: COc1cc(N2CCOC2=O)ccc1-n1ccc(=O)c(-c2cc(C)nn2-c2cccc(C(F)(F)F)c2)n1] | 1-[2-methoxy-4-(2-oxo-1,3-oxazolidin-3-yl)phenyl]-3-{3-methyl-1-[3-(trifluoromethyl)phenyl]-1H-pyrazol-5-yl}pyridazin-4(1H)-one |

TABLE 32-continued

| | | |
|---|---|---|
| 166 | 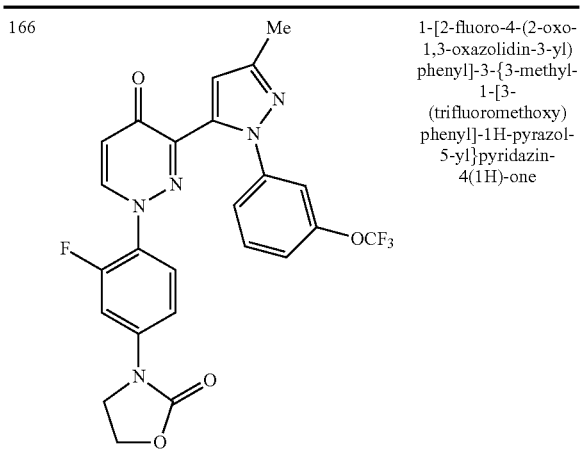 | 1-[2-fluoro-4-(2-oxo-1,3-oxazolidin-3-yl)phenyl]-3-{3-methyl-1-[3-(trifluoromethoxy)phenyl]-1H-pyrazol-5-yl}pyridazin-4(1H)-one |
| 167 | 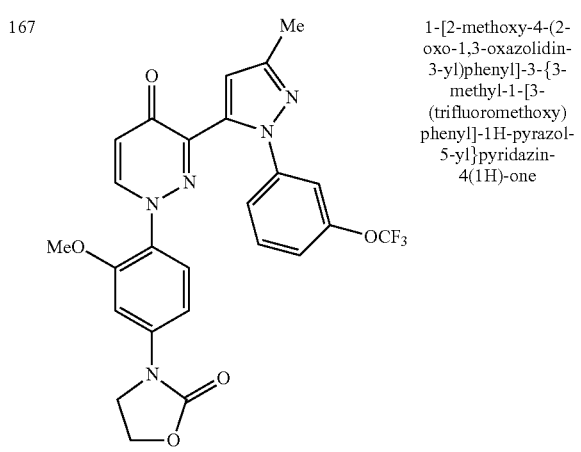 | 1-[2-methoxy-4-(2-oxo-1,3-oxazolidin-3-yl)phenyl]-3-{3-methyl-1-[3-(trifluoromethoxy)phenyl]-1H-pyrazol-5-yl}pyridazin-4(1H)-one |
| 168 | 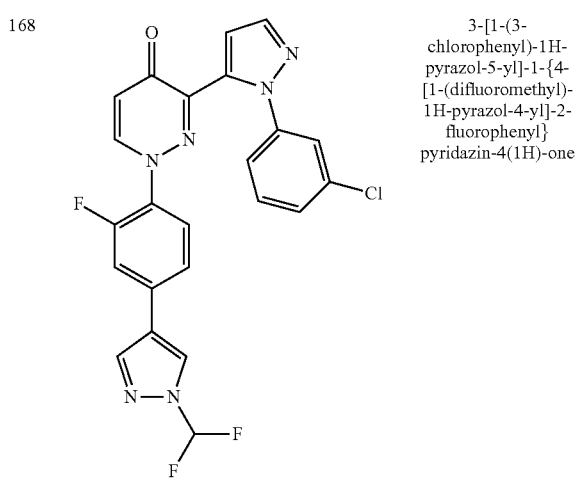 | 3-[1-(3-chlorophenyl)-1H-pyrazol-5-yl]-1-{4-[1-(difluoromethyl)-1H-pyrazol-4-yl]-2-fluorophenyl}pyridazin-4(1H)-one |
| 169 | 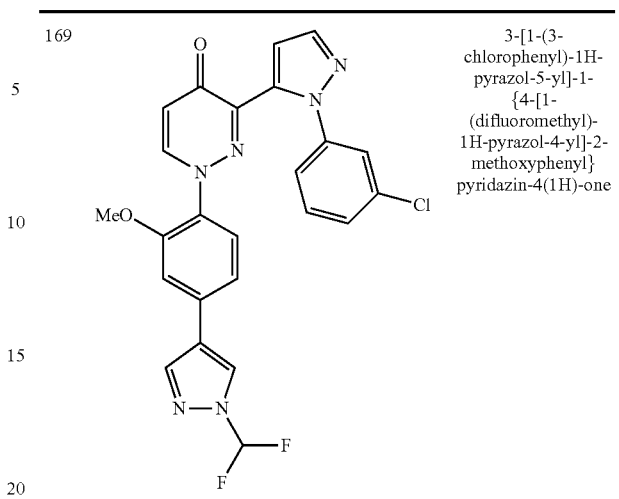 | 3-[1-(3-chlorophenyl)-1H-pyrazol-5-yl]-1-{4-[1-(difluoromethyl)-1H-pyrazol-4-yl]-2-methoxyphenyl}pyridazin-4(1H)-one |
| 170 | 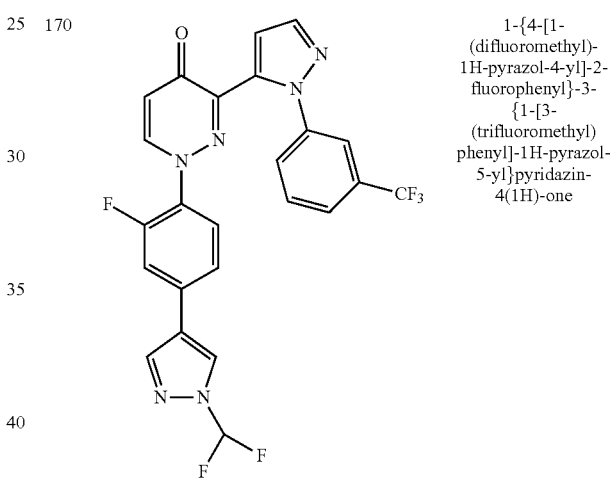 | 1-{4-[1-(difluoromethyl)-1H-pyrazol-4-yl]-2-fluorophenyl}-3-{1-[3-(trifluoromethyl)phenyl]-1H-pyrazol-5-yl}pyridazin-4(1H)-one |
| 171 | 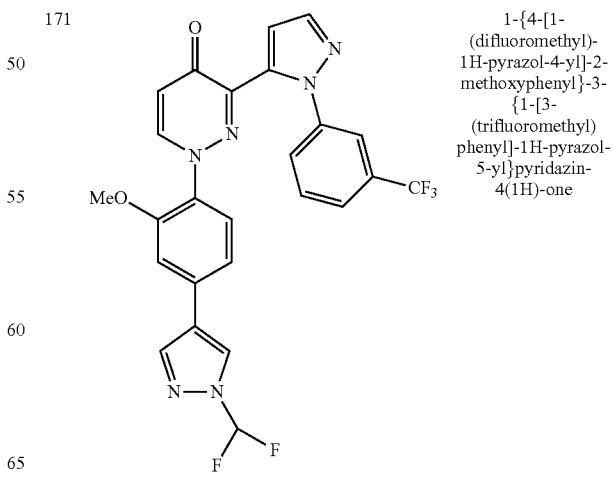 | 1-{4-[1-(difluoromethyl)-1H-pyrazol-4-yl]-2-methoxyphenyl}-3-{1-[3-(trifluoromethyl)phenyl]-1H-pyrazol-5-yl}pyridazin-4(1H)-one |

TABLE 33

| | | |
|---|---|---|
| 172 | 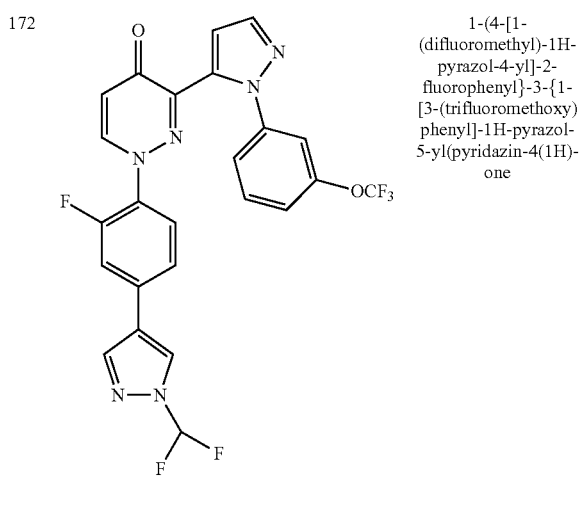 | 1-(4-[1-(difluoromethyl)-1H-pyrazol-4-yl]-2-fluorophenyl}-3-{1-[3-(trifluoromethoxy)phenyl]-1H-pyrazol-5-yl(pyridazin-4(1H)-one |
| 173 | 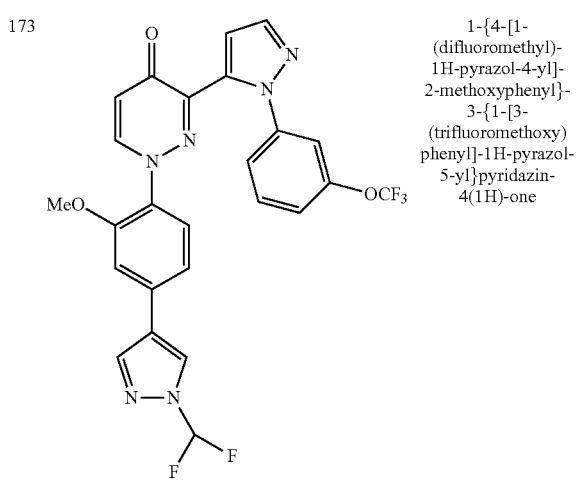 | 1-{4-[1-(difluoromethyl)-1H-pyrazol-4-yl]-2-methoxyphenyl}-3-{1-[3-(trifluoromethoxy)phenyl]-1H-pyrazol-5-yl}pyridazin-4(1H)-one |
| 174 | 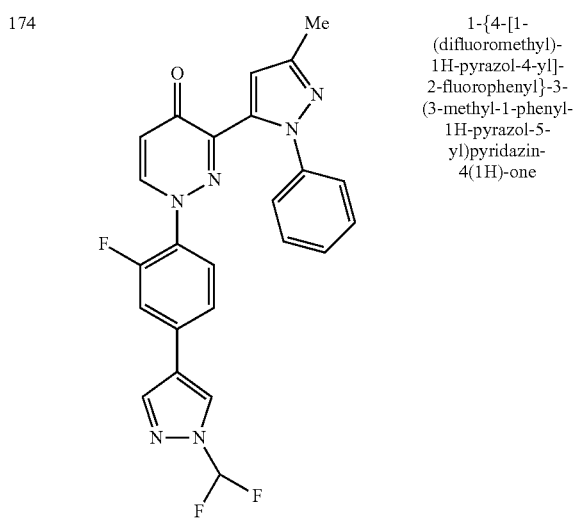 | 1-{4-[1-(difluoromethyl)-1H-pyrazol-4-yl]-2-fluorophenyl}-3-(3-methyl-1-phenyl-1H-pyrazol-5-yl)pyridazin-4(1H)-one |

TABLE 33-continued

| | | |
|---|---|---|
| 175 | 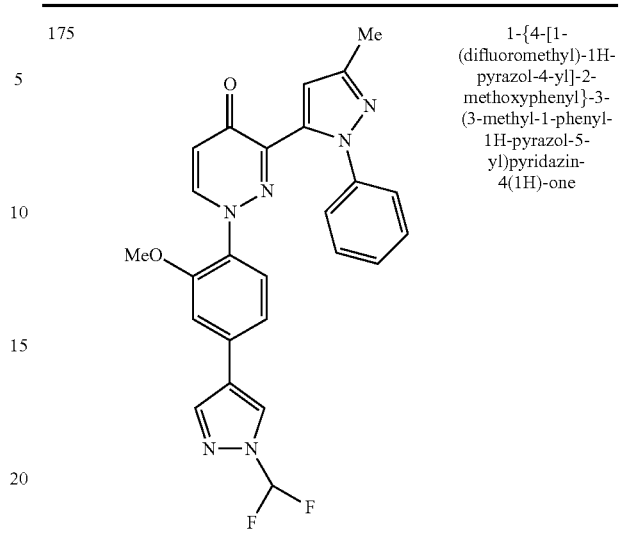 | 1-{4-[1-(difluoromethyl)-1H-pyrazol-4-yl]-2-methoxyphenyl}-3-(3-methyl-1-phenyl-1H-pyrazol-5-yl)pyridazin-4(1H)-one |
| 176 | 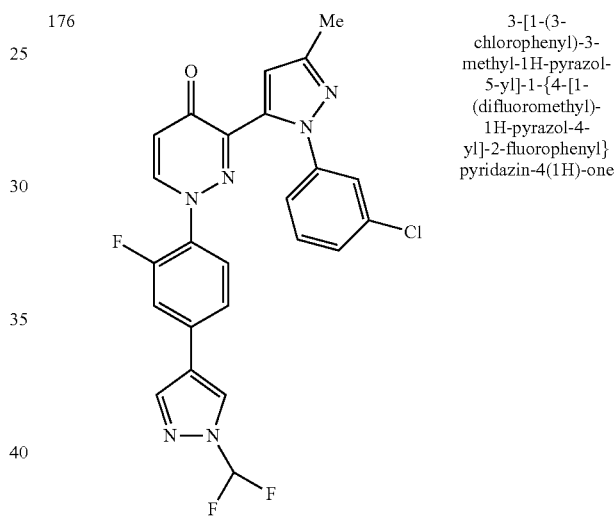 | 3-[1-(3-chlorophenyl)-3-methyl-1H-pyrazol-5-yl]-1-{4-[1-(difluoromethyl)-1H-pyrazol-4-yl]-2-fluorophenyl}pyridazin-4(1H)-one |
| 177 | 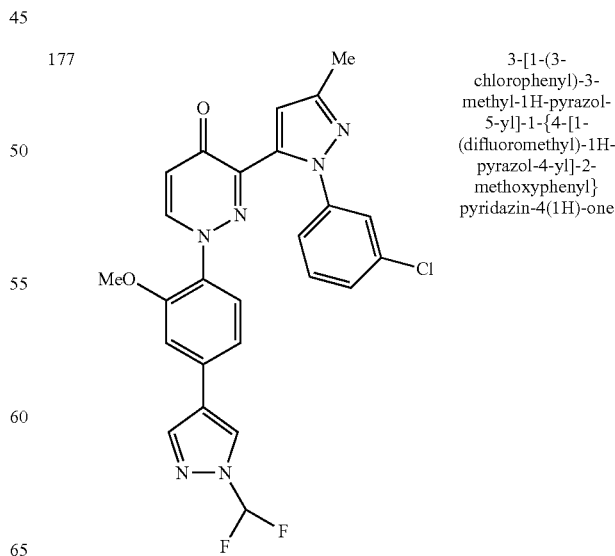 | 3-[1-(3-chlorophenyl)-3-methyl-1H-pyrazol-5-yl]-1-{4-[1-(difluoromethyl)-1H-pyrazol-4-yl]-2-methoxyphenyl}pyridazin-4(1H)-one |

TABLE 33-continued

| 178 | 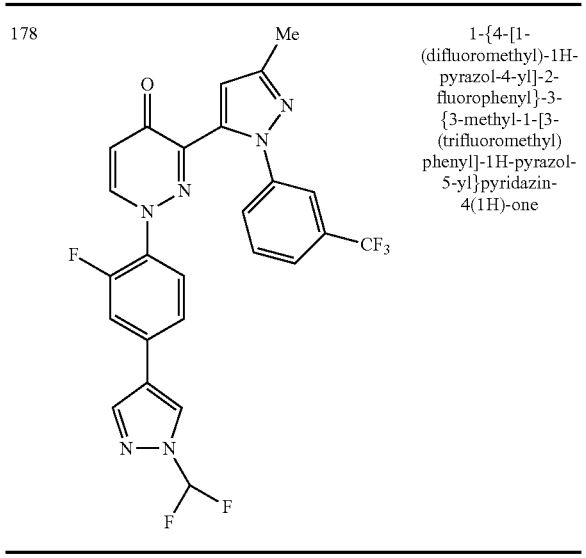 | 1-{4-[1-(difluoromethyl)-1H-pyrazol-4-yl]-2-fluorophenyl}-3-{3-methyl-1-[3-(trifluoromethyl)phenyl]-1H-pyrazol-5-yl}pyridazin-4(1H)-one |

TABLE 34

| 179 | 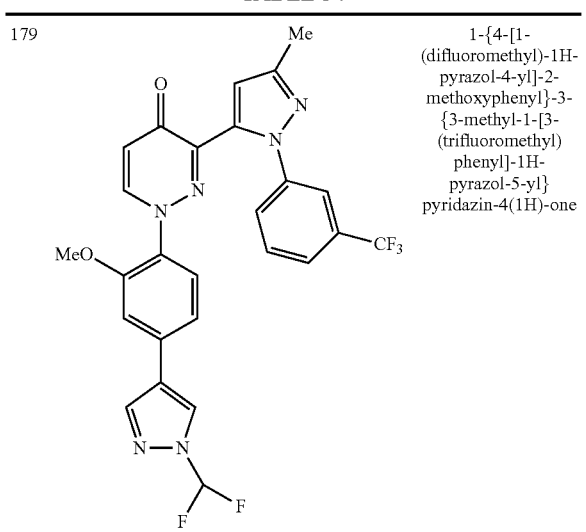 | 1-{4-[1-(difluoromethyl)-1H-pyrazol-4-yl]-2-methoxyphenyl}-3-{3-methyl-1-[3-(trifluoromethyl)phenyl]-1H-pyrazol-5-yl}pyridazin-4(1H)-one |
| 180 | | 1-{4-[1-(difluoromethyl)-1H-pyrazol-4-yl]-2-fluorophenyl}-3-{3-methyl-1-[3-(trifluoromethoxy)phenyl]-1H-pyrazol-5-yl}pyridazin-4(1H)-one |

TABLE 34-continued

| 181 | 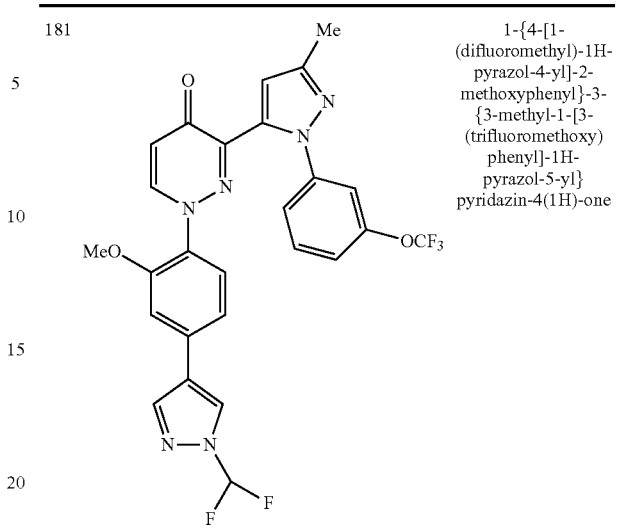 | 1-{4-[1-(difluoromethyl)-1H-pyrazol-4-yl]-2-methoxyphenyl}-3-{3-methyl-1-[3-(trifluoromethoxy)phenyl]-1H-pyrazol-5-yl}pyridazin-4(1H)-one |
| 182 | 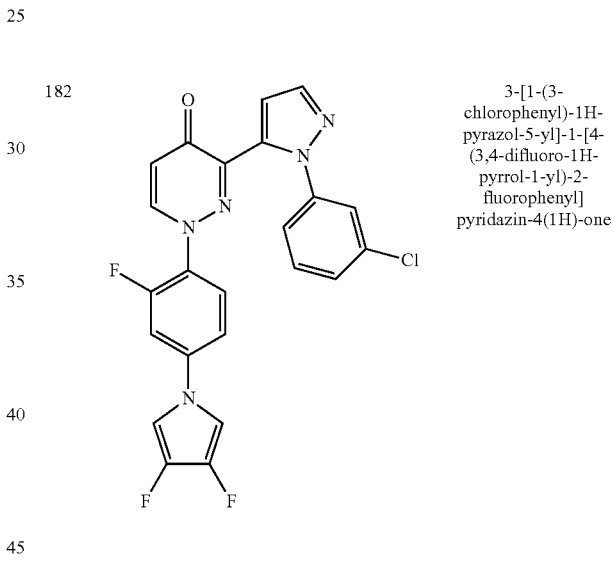 | 3-[1-(3-chlorophenyl)-1H-pyrazol-5-yl]-1-[4-(3,4-difluoro-1H-pyrrol-1-yl)-2-fluorophenyl]pyridazin-4(1H)-one |
| 183 | 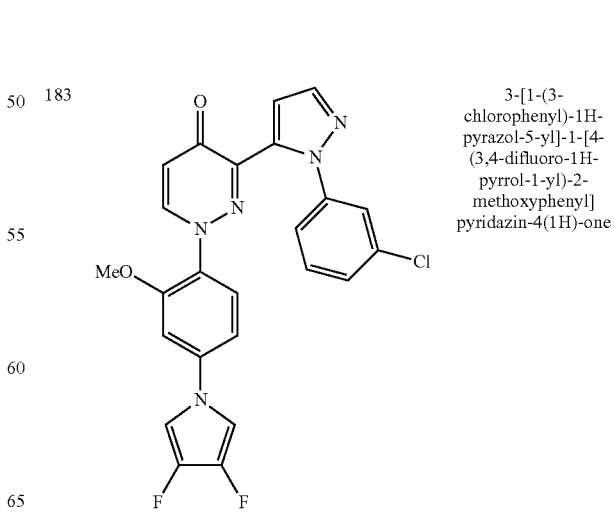 | 3-[1-(3-chlorophenyl)-1H-pyrazol-5-yl]-1-[4-(3,4-difluoro-1H-pyrrol-1-yl)-2-methoxyphenyl]pyridazin-4(1H)-one |

TABLE 34-continued

184 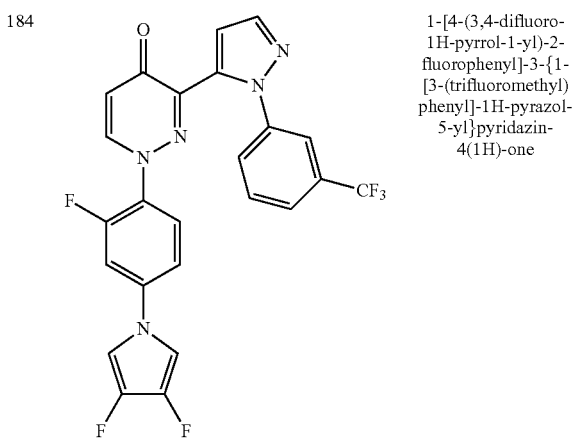 1-[4-(3,4-difluoro-1H-pyrrol-1-yl)-2-fluorophenyl]-3-{1-[3-(trifluoromethyl)phenyl]-1H-pyrazol-5-yl}pyridazin-4(1H)-one 185 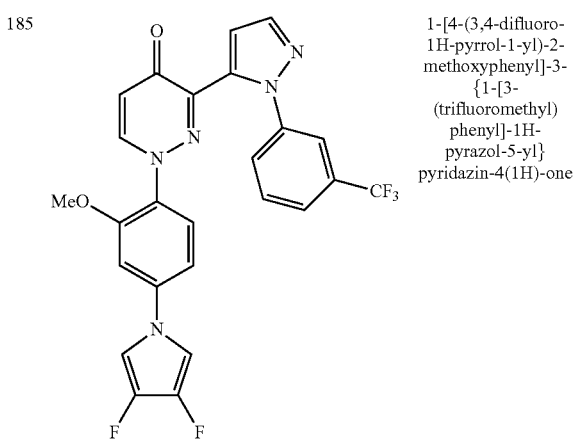 1-[4-(3,4-difluoro-1H-pyrrol-1-yl)-2-methoxyphenyl]-3-{1-[3-(trifluoromethyl)phenyl]-1H-pyrazol-5-yl}pyridazin-4(1H)-one 186 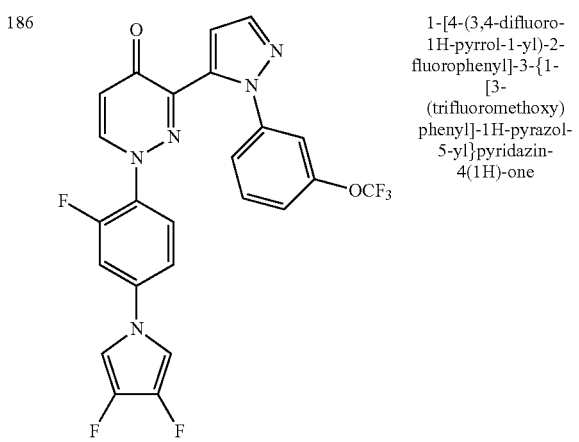 1-[4-(3,4-difluoro-1H-pyrrol-1-yl)-2-fluorophenyl]-3-{1-[3-(trifluoromethoxy)phenyl]-1H-pyrazol-5-yl}pyridazin-4(1H)-one

TABLE 35

187 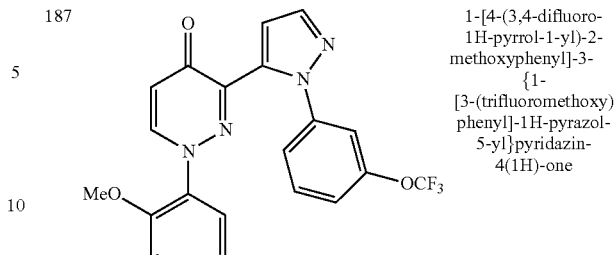 1-[4-(3,4-difluoro-1H-pyrrol-1-yl)-2-methoxyphenyl]-3-{1-[3-(trifluoromethoxy)phenyl]-1H-pyrazol-5-yl}pyridazin-4(1H)-one 188 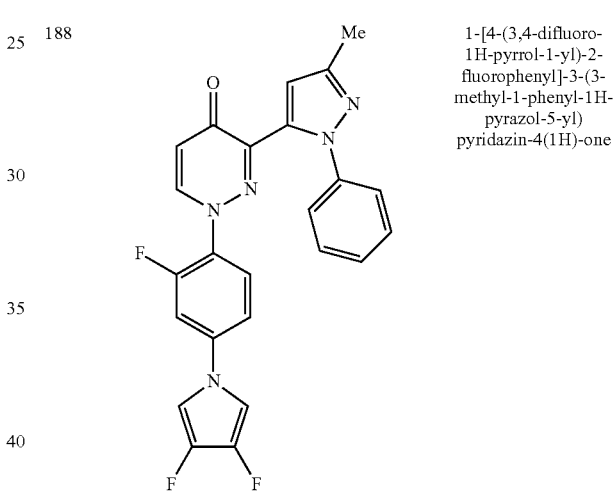 1-[4-(3,4-difluoro-1H-pyrrol-1-yl)-2-fluorophenyl]-3-(3-methyl-1-phenyl-1H-pyrazol-5-yl)pyridazin-4(1H)-one 189 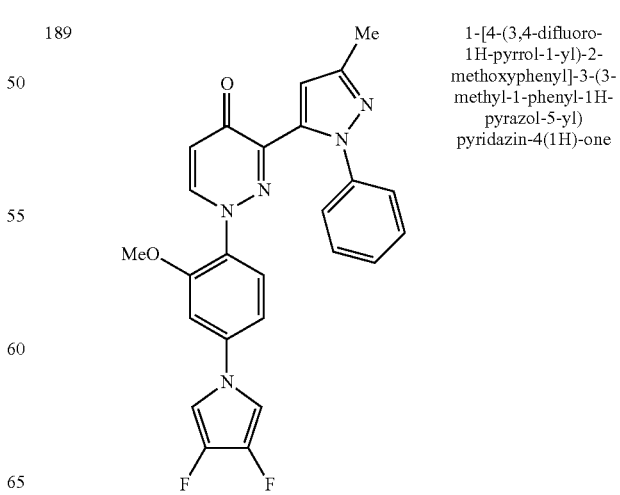 1-[4-(3,4-difluoro-1H-pyrrol-1-yl)-2-methoxyphenyl]-3-(3-methyl-1-phenyl-1H-pyrazol-5-yl)pyridazin-4(1H)-one

TABLE 35-continued

| | | | |
|---|---|---|---|
| 190 | 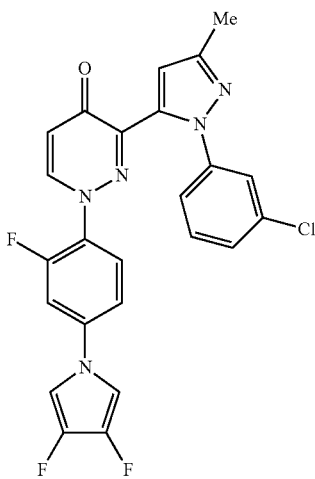 [SMILES: Cc1cc(-c2nn(-c3ccc(-n4cc(F)c(F)c4)cc3F)ccc2=O)n(-c2cccc(Cl)c2)n1] | 3-[1-(3-chlorophenyl)-3-methyl-1H-pyrazol-5-yl]-1-[4-(3,4-difluoro-1H-pyrrol-1-yl)-2-fluorophenyl]pyridazin-4(1H)-one | |
| 191 | 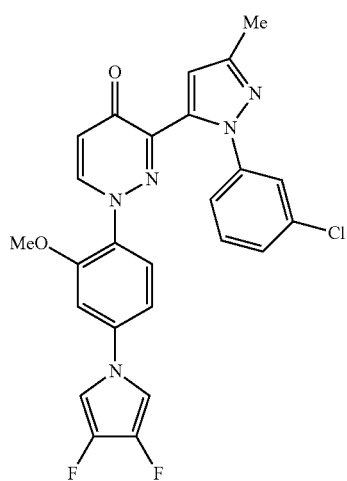 [SMILES: COc1cc(-n2cc(F)c(F)c2)ccc1-n1ccc(=O)c(-c2cc(C)nn2-c2cccc(Cl)c2)n1] | 3-[1-(3-chlorophenyl)-3-methyl-1H-pyrazol-5-yl]-1-[4-(3,4-difluoro-1H-pyrrol-1-yl)-2-methoxyphenyl]pyridazin-4(1H)-one | |
| 192 | 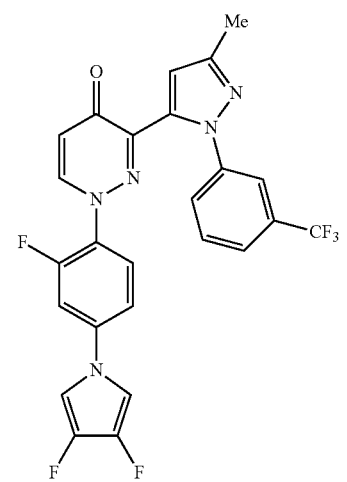 [SMILES: Cc1cc(-c2nn(-c3ccc(-n4cc(F)c(F)c4)cc3F)ccc2=O)n(-c2cccc(C(F)(F)F)c2)n1] | 1-[4-(3,4-difluoro-1H-pyrrol-1-yl)-2-fluorophenyl]-3-{3-methyl-1-[3-(trifluoromethyl)phenyl]-1H-pyrazol-5-yl}pyridazin-4(1H)-one | |

TABLE 35-continued

| 193 | 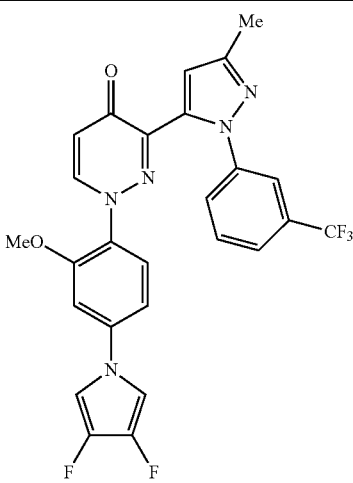 | 1-[4-(3,4-difluoro-1H-pyrrol-1-yl)-2-methoxyphenyl]-3-{3-methyl-1-[3-(trifluoromethyl)phenyl]-1H-pyrazol-5-yl}pyridazin-4(1H)-one |
|---|---|---|
| 194 | 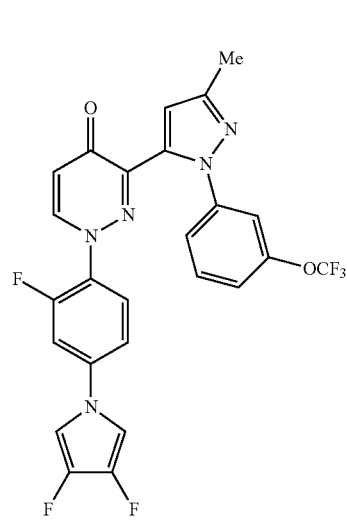 [SMILES: Cc1cc(-c2nn(-c3ccc(-n4cc(F)c(F)c4)cc3F)ccc2=O)n(-c2cccc(OC(F)(F)F)c2)n1] | 1-[4-(3,4-difluoro-1H-pyrrol-1-yl)-2-fluorophenyl]-3-{3-methy-1-[3-(trifluoromethoxy)phenyl]-1H-pyrazol-5-yl}pyridazin-4(1H)-one |

TABLE 36

| 195 | 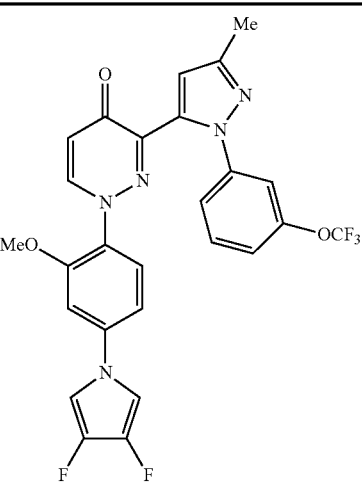 | 1-[4-(3,4-difluoro-1H-pyrrol-1-yl)-2-methoxyphenyl]-3-{3-methyl-1-[3-(trifluoromethoxy)phenyl]-1H-pyrazol-5-yl}pyridazin-4(1H)-one |
|---|---|---|

TABLE 36-continued

| | | |
|---|---|---|
| 196 | [structure] | 3-[1-(3-chlorophenyl)-1H-pyrazol-5-yl]-1-{4-[5-(difluoromethoxy)-1H-pyrazol-1-yl]-2-fluorophenyl}pyridazin-4(1H)-one |
| 197 | [structure] | 3-[1-(3-chlorophenyl)-1H-pyrazol-5-yl]-1-{4-[5-(difluoromethoxy)-1H-pyrazol-1-yl]-2-methoxyphenyl}pyridazin-4(1H)-one |
| 198 | [structure] | 1-{4-[5-(difluoromethoxy)-1H-pyrazol-1-yl]-2-fluorophenyl}-3-{1-[3-(trifluoromethyl)phenyl]-1H-pyrazol-5-yl}pyridazin-4(1H)-one |
| 199 | [structure] | 1-{4-[5-(difluoromethoxy)-1H-pyrazol-1-yl]-2-methoxypheyl}-3-{1-[3-(trifluoromethyl)phenyl]-1H-pyrazol-5-yl}pyridazin-4(1H)-one |
| 200 | [structure] | 1-{4-[5-(difluoromethoxy)-1H-pyrazol-1-yl]-2-fluorophenyl}-3-{1-[3-(trifluoromethoxy)phenyl]-1H-pyrazol-5-yl}pyridazin-4(1H)-one |
| 201 | [structure] | 1-{4-[5-(difluoromethoxy)-1H-pyrazol-1-yl]-2-methoxyphenyl}-3-{1-[3-(trifluoromethoxy)phenyl]-1H-pyrazol-5-yl}pyridazin-4(1H)-one |
| 202 | [structure] | 1-{4-[5-(difluoromethoxy)-1H-pyrazol-1-yl]-2-fluorophenyl}-3-(3-methyl-1-phenyl-1H-pyrazol-5-yl)pyridazin-4(1H)-one |

TABLE 36-continued

| 203 | 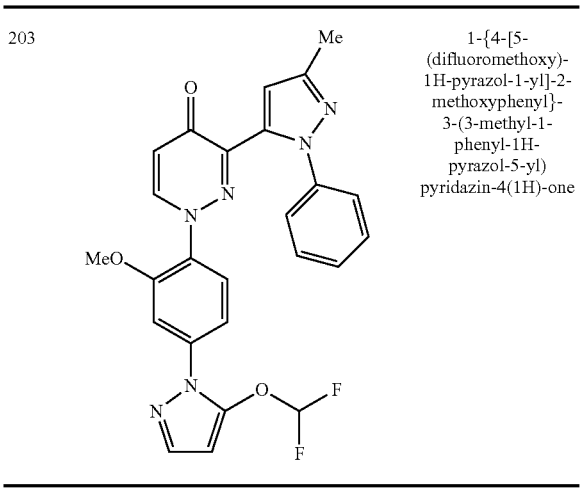 | 1-{4-[5-(difluoromethoxy)-1H-pyrazol-1-yl]-2-methoxyphenyl}-3-(3-methyl-1-phenyl-1H-pyrazol-5-yl)pyridazin-4(1H)-one |

TABLE 37

| 204 | 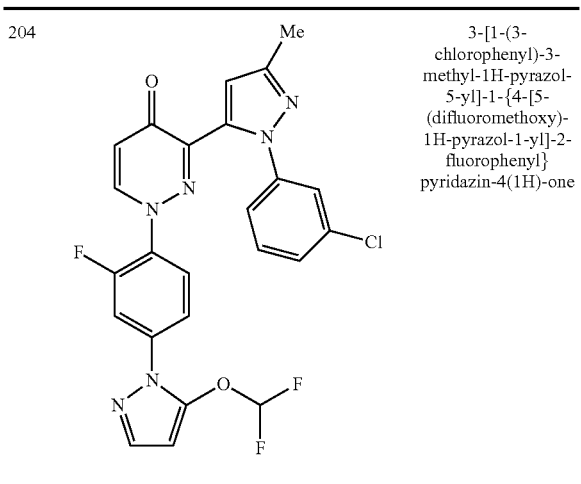 | 3-[1-(3-chlorophenyl)-3-methyl-1H-pyrazol-5-yl]-1-{4-[5-(difluoromethoxy)-1H-pyrazol-1-yl]-2-fluorophenyl}pyridazin-4(1H)-one |

| 205 | 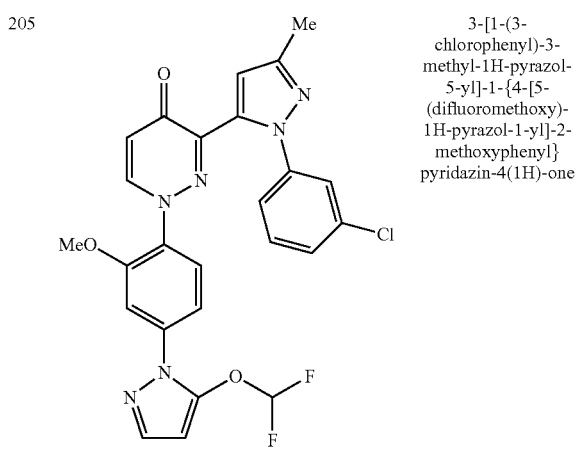 | 3-[1-(3-chlorophenyl)-3-methyl-1H-pyrazol-5-yl]-1-{4-[5-(difluoromethoxy)-1H-pyrazol-1-yl]-2-methoxyphenyl}pyridazin-4(1H)-one |

TABLE 37-continued

| 206 | 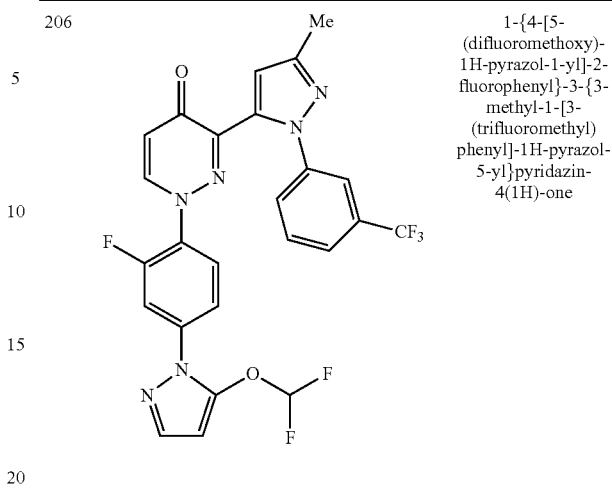 | 1-{4-[5-(difluoromethoxy)-1H-pyrazol-1-yl]-2-fluorophenyl}-3-{3-methyl-1-[3-(trifluoromethyl)phenyl]-1H-pyrazol-5-yl}pyridazin-4(1H)-one |

| 207 | 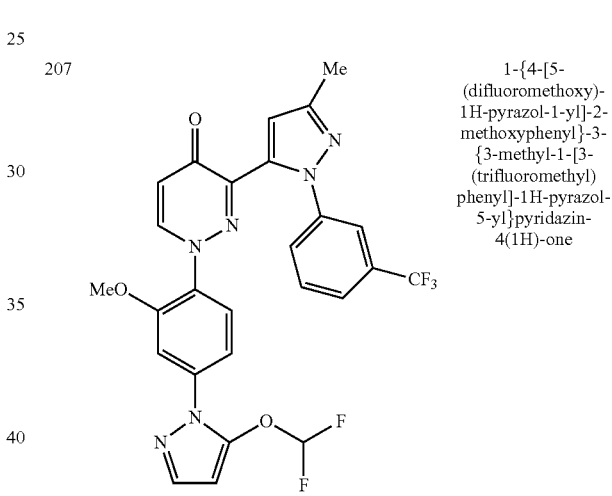 | 1-{4-[5-(difluoromethoxy)-1H-pyrazol-1-yl]-2-methoxyphenyl}-3-{3-methyl-1-[3-(trifluoromethyl)phenyl]-1H-pyrazol-5-yl}pyridazin-4(1H)-one |

| 208 | 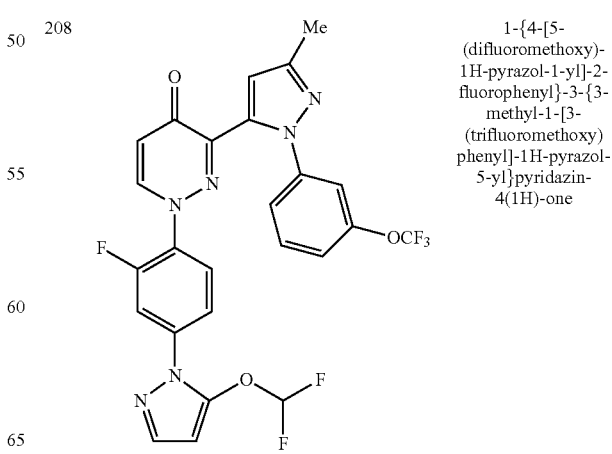 | 1-{4-[5-(difluoromethoxy)-1H-pyrazol-1-yl]-2-fluorophenyl}-3-{3-methyl-1-[3-(trifluoromethoxy)phenyl]-1H-pyrazol-5-yl}pyridazin-4(1H)-one |

TABLE 37-continued

| # | Structure | Name |
|---|---|---|
| 209 | 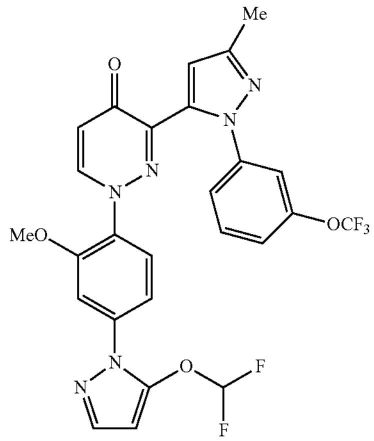 [SMILES: COc1cc(-n2nccc2OC(F)F)ccc1-n1ccc(=O)c(-c2cc(C)nn2-c2cccc(OC(F)(F)F)c2)n1] | 1-{4-[5-(difluoromethoxy)-1H-pyrazol-1-yl]-2-methoxyphenyl}-3-{3-methyl-1-[3-(trifluoromethoxy)phenyl]-1H-pyrazol-5-yl}pyridazin-4(1H)-one |
| 210 | 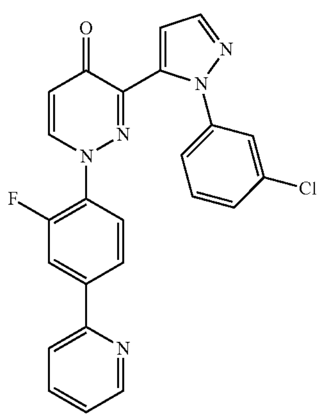 [SMILES: O=c1ccn(-c2ccc(-c3ccccn3)cc2F)nc1-c1ccnn1-c1cccc(Cl)c1] | 3-[1-(3-chlorophenyl)-1H-pyrazol-5-yl]-1-[2-fluoro-4-(pyridin-2-yl)phenyl]pyridazin-4(1H)-one |
| 211 | 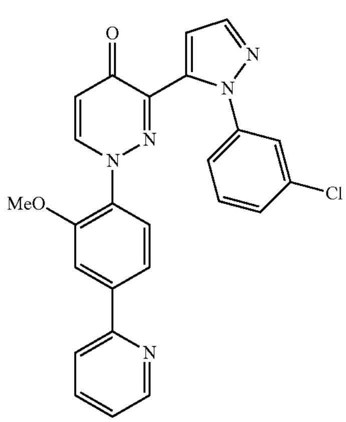 [SMILES: COc1cc(-c2ccccn2)ccc1-n1ccc(=O)c(-c2ccnn2-c2cccc(Cl)c2)n1] | 3-[1-(3-chlorophenyl)-1H-pyrazol-5-yl]-1-[2-methoxy-4-(pyridin-2-yl)phenyl]pyridazin-4(1H)-one |

TABLE 38

| # | Structure | Name |
|---|---|---|
| 212 | 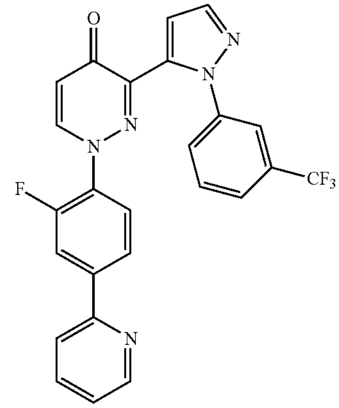 [SMILES: O=c1ccn(-c2ccc(-c3ccccn3)cc2F)nc1-c1ccnn1-c1cccc(C(F)(F)F)c1] | 1-[2-fluoro-4-(pyridin-2-yl)phenyl]-3-{1-[3-(trifluoromethyl)phenyl]-1H-pyrazol-5-yl}pyridazin-4(1H)-one |
| 213 | 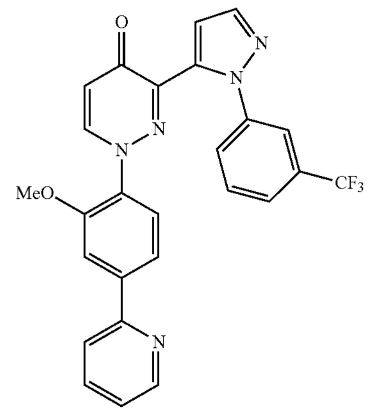 [SMILES: COc1cc(-c2ccccn2)ccc1-n1ccc(=O)c(-c2ccnn2-c2cccc(C(F)(F)F)c2)n1] | 1-[2-methoxy-4-(pyridin-2-yl)phenyl]-3-{1-[3-(trifluoromethyl)phenyl]-1H-pyrazol-5-yl}pyridazin-4(1H)-one |
| 214 | 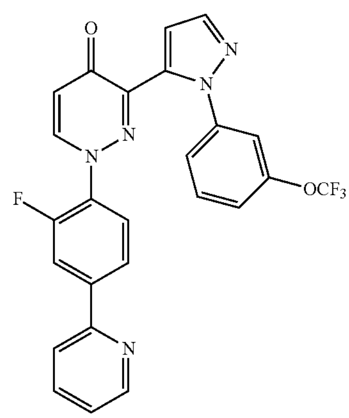 [SMILES: O=c1ccn(-c2ccc(-c3ccccn3)cc2F)nc1-c1ccnn1-c1cccc(OC(F)(F)F)c1] | 1-[2-fluoro-4-(pyridin-2-yl)phenyl]-3-{1-[3-(trifluoromethoxy)phenyl]-1H-pyrazol-5-yl}pyridazin-4(1H)-one |
| 215 | 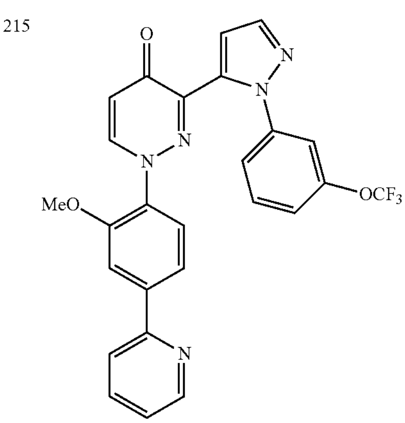 | 1-[2-methoxy-4-(pyridin-2-yl)phenyl]-3-{1-[3-(trifluoromethoxy)phenyl]-1H-pyrazol-5-yl}pyridazin-4(1H)-one |

TABLE 38-continued

| 216 | 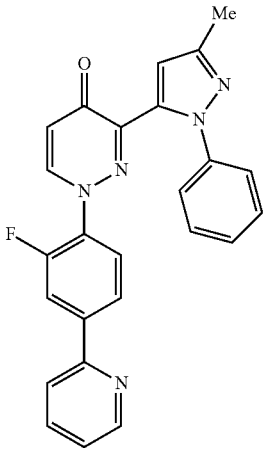 [SMILES: Cc1cc(-c2nn(-c3ccc(-c4ccccn4)cc3F)ccc2=O)n(-c2ccccc2)n1] | 1-[2-fluoro-4-(pyridin-2-yl)phenyl]-3-(3-methyl-1-phenyl-1H-pyrazol-5-yl)pyridazin-4(1H)-one |
|---|---|---|
| 217 | 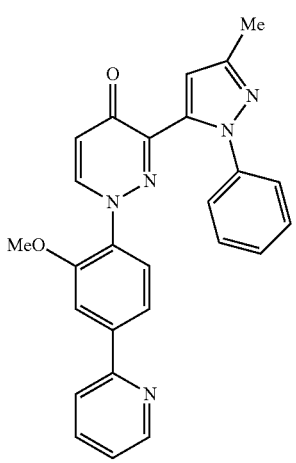 [SMILES: COc1cc(-c2ccccn2)ccc1-n1ccc(=O)c(-c2cc(C)nn2-c2ccccc2)n1] | 1-[2-methoxy-4-(pyridin-2-yl)phenyl]-3-(3-methyl-1-phenyl-1H-pyrazol-5-yl)pyridazin-4(1H)-one |
| 218 | 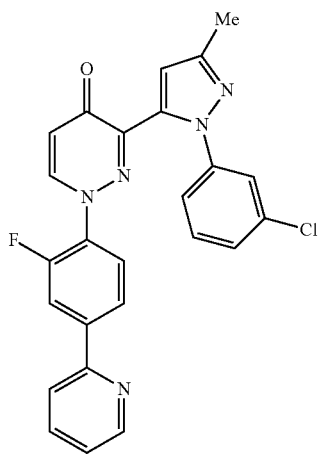 [SMILES: Cc1cc(-c2nn(-c3ccc(-c4ccccn4)cc3F)ccc2=O)n(-c2cccc(Cl)c2)n1] | 3-[1-(3-chlorophenyl)-3-methyl-1H-pyrazol-5-yl]-1-[2-fluoro-4-(pyridin-2-yl)phenyl]pyridazin-4(1H)-one |

TABLE 38-continued

| 219 | 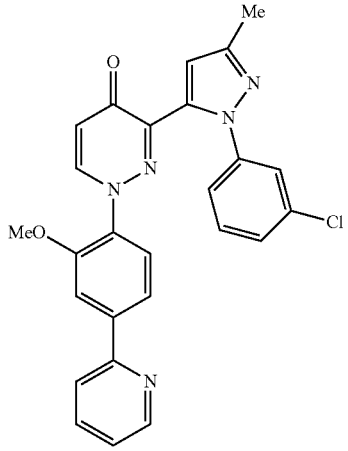 [SMILES: COc1cc(-c2ccccn2)ccc1-n1ccc(=O)c(-c2cc(C)nn2-c2cccc(Cl)c2)n1] | 3-[1-(3-chlorophenyl)-3-methyl-1H-pyrazol-5-yl]-1-[2-methoxy-4-(pyridin-2-yl)phenyl]pyridazin-4(1H)-one |
| --- | --- | --- |
| 220 | 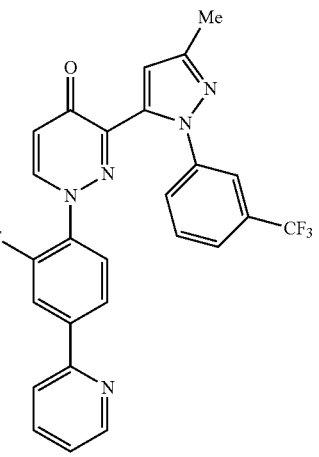 | 1-[2-fluoro-4-(pyridin-2-yl)phenyl]-3-{3-methyl-1-[3-(trifluoromethyl)phenyl]-1H-pyrazol-5-yl}pyridazin-4(1H)-one |

TABLE 39

| 221 | 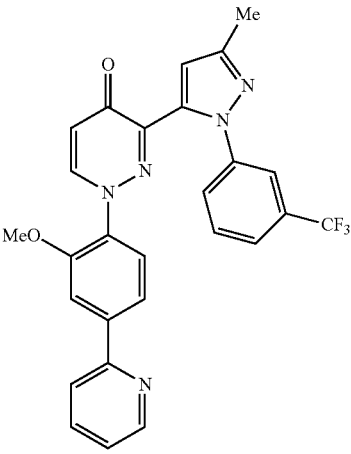 [SMILES: COc1cc(-c2ccccn2)ccc1-n1ccc(=O)c(-c2cc(C)nn2-c2cccc(C(F)(F)F)c2)n1] | 1-[2-methoxy-4-(pyridin-2-yl)phenyl]-3-{3-methyl-1-[3-(trifluoromethyl)phenyl]-1H-pyrazol-5-yl}pyridazin-4(1H)-one |

TABLE 39-continued

| 222 | [structure: 1-(2-fluoro-4-(pyridin-2-yl)phenyl)-pyridazin-4(1H)-one with pyrazole bearing Me and OCF3-phenyl substituents] | 1-[2-fluoro-4-{pyridin-2-yl}phenyl]-3-{3-methyl-1-[3-(trifluoromethoxy)phenyl]-1H-pyrazol-5-yl}pyridazin-4(1H)-one |
| --- | --- | --- |
| 223 | [structure: 1-(2-methoxy-4-(pyridin-2-yl)phenyl)-pyridazin-4(1H)-one with pyrazole bearing Me and OCF3-phenyl substituents] | 1-[2-methoxy-4-(pyridin-2-yl)phenyl]-3-{3-methyl-1-[3-(trifluoromethoxy)phenyl]-1H-pyrazol-5-yl}pyridazin-4(1H)-one |

Test Example 1

PDE Enzyme Inhibition

Human PDE10A enzyme was generated from Sf9 or COS-7 cells transfected with the full-length gene. Cloned enzyme was extracted from homogenized cell pellets. The extracted enzyme from sf9 cells was partially purified using His-tag affinity column. The enzyme was stored at −70° C. until use. PDE activity was measured using a SPA (Scintillation Proximity Assay) (GE Healthcare). To evaluate the inhibitory activity, 10 μL of serial diluted compounds were incubated with 20 μL of PDE enzyme in assay buffer (50 mM HEPES-NaOH, 8.3 mM $MgCl_2$, 1.7 mM EGTA, 0.1% BSA (pH 7.4)) for 30 min. at room temperature. Final concentration of DMSO in the assay was 1 percent as compounds were tested in duplicate in 96-well half-area plates (Corning). To start the reaction, 10 μL of substrate [$^3$H] cGMP (25 or 50 nM; enclosed in SPA kits from GE Healthcare or purchased from PerkinElmer, respectively) was added for a final assay volume of 40 μL. After 60 min incubation at room temperature, yttrium SPA beads containing Zinc sulphate were added (20 μL at 6 mg/mL) to terminate the PDE reaction. After being settled for 60 min, assay plates were counted in a scintillation counter (PerkinElmer) to allow calculation of inhibition rate. Inhibition rate was calculated on the basis of 0% control wells with DMSO and 100% control wells without enzyme. The results are shown in Table 40.

TABLE 40

| Ex. No. | Percent inhibition (10 μM) | Percent inhibition (1 μM) | Percent inhibition (0.1 μM) |
| --- | --- | --- | --- |
| 1 | 100 | 98 | |
| 2 | 103 | 104 | |
| 3 | | | 99 |
| 8 | | | 98 |
| 9 | 99 | 99 | |
| 12 | 99 | 93 | |
| 13 | 101 | 100 | |
| 24 | | | 98 |
| 27 | | | 102 |
| 31 | 98 | 99 | |
| 39 | 101 | 100 | |
| 40 | 101 | 99 | |
| 48 | 100 | 96 | |
| 64 | 101 | 100 | |
| 65 | 101 | 100 | |
| 71 | 97 | 99 | |
| 72 | 110 | 104 | |
| 75 | 101 | 98 | |
| 85 | 99 | 95 | |
| 86 | 98 | 97 | |
| 97 | 98 | 97 | |
| 98 | 101 | 99 | |
| 99 | 105 | 100 | |
| 100 | 100 | 99 | |
| 101 | 99 | 101 | |
| 102 | 106 | 99 | |
| 103 | 103 | 101 | |
| 106 | 102 | 103 | |
| 107 | 102 | 103 | |
| 108 | 102 | 100 | |
| 109 | 102 | 99 | |
| 112 | 98 | 99 | |
| 115 | 97 | 100 | |
| 118 | 104 | 102 | |
| 119 | 103 | 99 | |
| 120 | 106 | 109 | |
| 121 | 99 | 103 | |
| 122 | 107 | 109 | |
| 123 | 101 | 96 | |
| 124 | 99 | 99 | |
| 125 | 101 | 99 | |
| 126 | 100 | 98 | |
| 127 | 101 | 101 | |
| 128 | 91 | 94 | |
| 129 | 96 | 89 | |
| 130 | 98 | 95 | |
| 132 | 107 | 104 | |
| 133 | 101 | 104 | |
| 134 | 104 | 101 | |
| 135 | 99 | 94 | |
| 136 | 98 | 81 | |
| 137 | 98 | 88 | |
| 138 | 105 | 93 | |

Test Example 2

(1) Animals

Male ICR mice were supplied by CLEA Japan, Inc (Japan). After arrival to the vivarium, animals were allowed more than 1 week for acclimation. They were housed under a 12 h-12 h light/dark cycle in a temperature- and humidity-controlled laboratory and allowed food and water ad libitum. The care and use of the animals and the experimental protocols used in this research were approved by the Experimental Animal Care and Use Committee of Takeda Pharmaceutical Company, Ltd (Osaka, Japan).

(2) Drug Administration

The compounds were suspended in 0.5% (w/v) methylcellulose in distilled water, and the suspension was administered by orally. MK-801 hydrogen maleate ((5R,10S)-(+)-5-Methyl-10,11-dihydro-5H-dibenzo[a,d]cyclohepten-5,10-imine maleate, Sigma-Aldrich, St Louis, Mo.) was dissolved in saline, and administered subcutaneously (s.c.). All drugs were dosed in a volume of 20 mL/kg body weight for mice.

(3) Measurement of Striatal Tissue Cyclic Nucleotides

Male ICR mice (28-42 g) were sacrificed by focused microwave irradiation of the brain at 60 min after administration of the compounds. Striatum were isolated and homogenized in 0.5 N HCl followed by centrifugation. Supernatant concentrations of cyclic nucleotides were measured using enzyme immunoassay kits (Cayman Chemical, Ann Arbor, Mich.). Values were expressed as the percentage of the average of the vehicle-treated samples. All data were represented as means plus the standard errors of the means (n=8). The variance of data was judged by Bartlett's test. The statistical significance was determined by the Dunnett's t-test (for homogenous data) or the Steel's test (for non-homogenous data) with significance set at #P<0.05.

(4) Inhibition of MK-801-Induced Hyperlocomotion

The widely used animal models of psychosis have been the measurement of the extent of hyperlocomotion induced by psychostimulants (e.g., amphetamine, cocaine, methamphetamine, MK-801 and phencyclidine) in rodents (Schizophrenia Bulletin 2010, vol. 36: 1066-1072; Psychopharmacology 1999, vol. 145: 237-250). The compounds were tested for its ability to antagonize MK-801-induced hyperlocomotion in mice. Male ICR mice (28-42 g) were habituated to the locomotor chambers with infrared sensors (Brain Science Idea Co., Ltd. Japan) for more than 60 min. Animals were removed from each chamber and treated with either vehicle or test compounds (p.o.) and immediately returned to the chamber. After 60 min, animals were again removed from the chambers and treated with either saline or MK-801 (0.3 mg/kg, s.c.), and then immediately returned to the test chamber. Activity count was recorded every 1 min bins. Total amounts of activity were measured during 120 min after MK-801 treatment. Data were represented as means plus the standard errors of the means (n=8-9). Statistical analysis was performed with the Welch's t-test for comparison between control group and MK-801+vehicle treated group with significance set at ***P<0.001 and the Dunnett's test for comparisons with vehicle-treated group with significance set at #P<0.05.

Figure 1B:
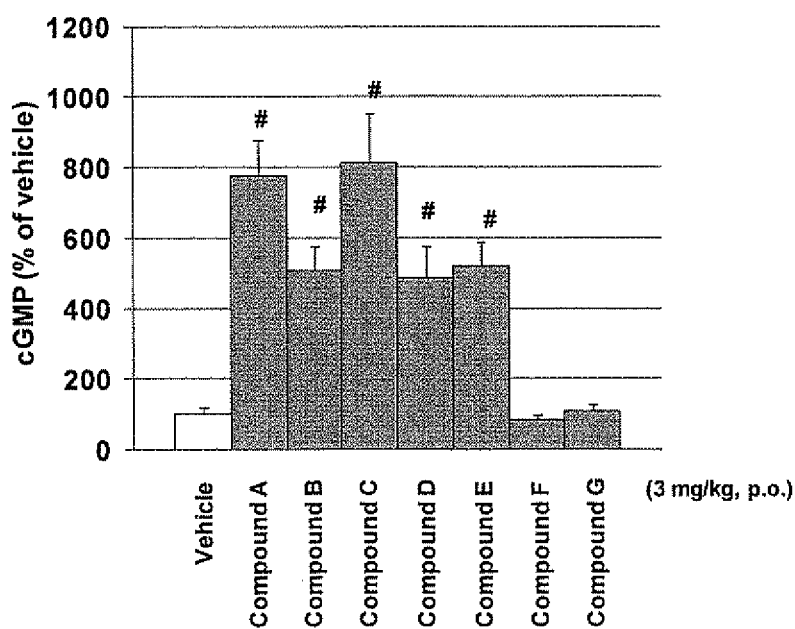
Figure 2:
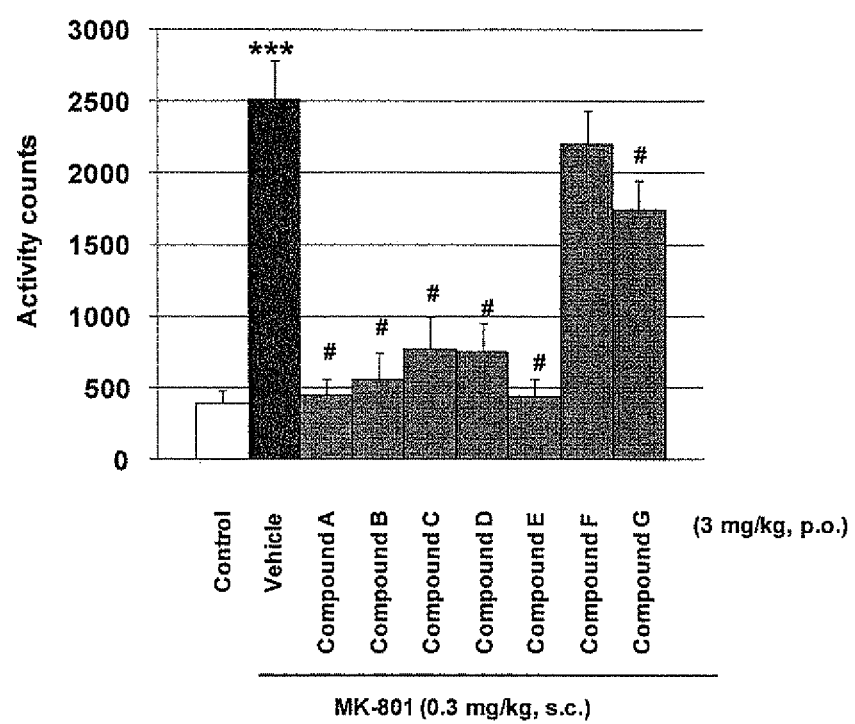
FIG. 2 shows inhibition of MK-801-induced hyperlocomotion by compounds in mice. By orally administered 60 min before MK-801 (0.3 mg/kg, s.c.) treatment, compounds produced the inhibition of MK-801-induced hyperlocomotion.

Compounds in Figures (FIG. 1 and FIG. 2) correspond to the compounds of the following Examples.

Compound A: Example 118
Compound B: Example 119
Compound C: Example 120
Compound D: Example 122
Compound E: Example 133
Compound F: Example 135
Compound G: Example 138

Formulation Example 1

| | | |
|---|---|---|
| (1) Compound of Example 1 | | 10.0 g |
| (2) Lactose | | 70.0 g |
| (3) Cornstarch | | 50.0 g |
| (4) Soluble starch | | 7.0 g |
| (5) Magnesium stearate | | 3.0 g |

After 10.0 g of the compound of Example 1 and 3.0 g of magnesium stearate are granulated in 70 mL aqueous solution of soluble starch (7.0 g as soluble starch) and then dried, the resulting mixture is mixed with 70.0 g of lactose and 50.0 g of cornstarch (lactose, cornstarch, soluble starch and magnesium stearate are all products in compliance with Japanese Pharmacopoeia 14$^{th}$ Edition). The mixture is compressed to obtain a tablet.

The invention claimed is:

1. A method for treating schizophrenia, autism, Alzheimer's disease, bipolar disorders, Parkinson's disease or Huntington's disease in a mammal, which comprises administering an effective amount of a compound represented by the formula (I) to the mammal:

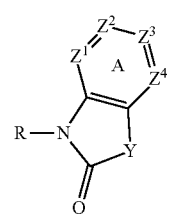

(I)

wherein
ring A represents an optionally substituted 6-membered ring,
any one of $Z^1$ to $Z^4$ represent —N═, and the others represent —CH═;
Y represents an oxygen atom, a sulfur atom, an optionally substituted methylene group or —NR$^c$—;
R$^c$ represents a hydrogen atom, or a substituent; and
R represents
(1) a group represented by the formula:

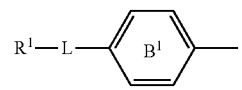

wherein
R$^1$ represents a 5- to 10-membered heterocyclic group, which is optionally substituted;
L represents a sulfur atom, an oxygen atom, an optionally substituted methylene group, —CO—, —NR$^a$—, —CH$_2$O—, —OCH$_2$—, —NR$^a$COO—, —OCONR$^a$—, —NR$^a$CONR$^b$—, —NR$^a$COCH$_2$—, —CH$_2$CONR$^a$—, —NR$^a$CO—, —CONR$^a$—,

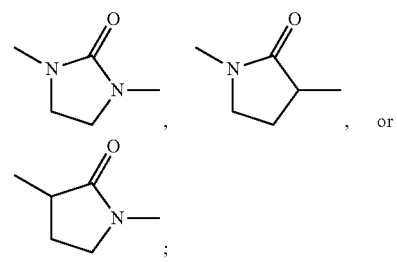

R$^a$ and R$^b$ are the same or different and each represents a hydrogen atom, or an optionally substituted C$_{1-6}$ alkyl group, or
L and R$^1$ in combination optionally form an optionally substituted bi- or tri-cyclic fused heterocyclic group; and ring B¹ represents a benzene ring, a pyridine ring, a pyrimidine ring, a pyrazine ring or a pyridazine ring, each of which is optionally substituted; or
(2) a group represented by the formula:

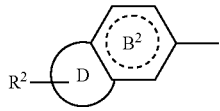

wherein
R² represents a phenyl group or 5- to 10-membered heterocyclic group, each of which is optionally substituted;
the partial structure of the formula:

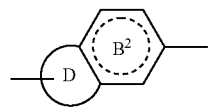

is

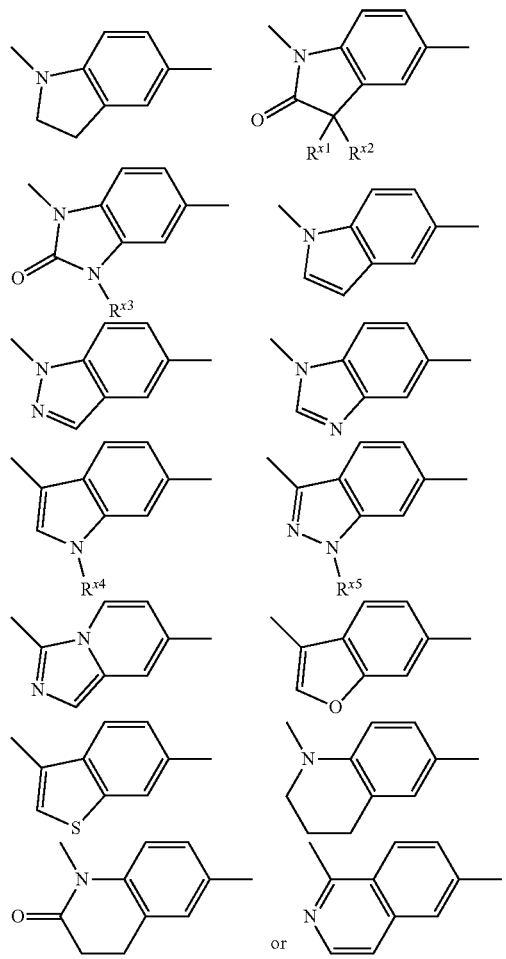

wherein
R$^{x1}$ and R$^{x2}$ are the same or different and each is a hydrogen atom or an optionally substituted C$_{1-6}$ alkyl group,
R$^{x3}$, R$^{x4}$ and R$^{x5}$ are each a hydrogen atom or an optionally substituted C$_{1-6}$ alkyl group, and the ring-constituting atom(s) optionally further have substituent(s),
or a salt thereof.

2. The method according to claim 1, wherein the partial structure of formula (I):

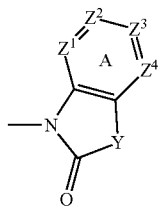

is a group represented by the formula:

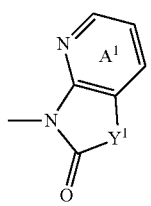

wherein
Y¹ represents an optionally substituted methylene group or —NR$^c$—,
R$^c$ represents a hydrogen atom, or a substituent, and
ring A¹ represents an optionally substituted pyridine ring,
or
a group represented by the formula:

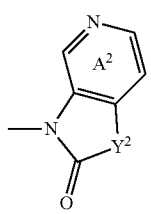

wherein
Y² represents —NR$^d$—,
R$^d$ represents a substituent, and
ring A² represents an optionally substituted pyridine ring.

3. The method according to claim 1, wherein L is an oxygen atom, or —NR$^a$— wherein R$^a$ represents a hydrogen atom or an optionally substituted C$_{1-6}$ alkyl group, or L and R¹ in combination optionally form an optionally substituted bi- or tri-cyclic fused heterocyclic group.

4. The method according to claim 2, wherein the partial structure of formula (I):

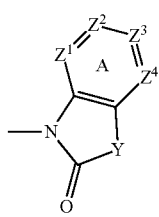

is a group represented by the formula:

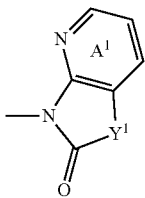

wherein each symbol is as defined in claim 2.

5. The method according to claim 2, wherein the partial structure of formula (I):

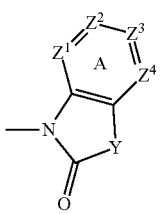

is a group represented by the formula:

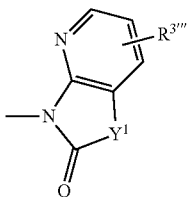

wherein
R$^{3'''}$ represents a hydrogen atom, a halogen atom, an optionally substituted C$_{1-4}$ alkyl group, or an optionally substituted C$_{1-4}$ alkoxy group, and
Y$^1$ is as defined in claim 2.

6. The method according to claim 2, wherein the partial structure of formula (I):

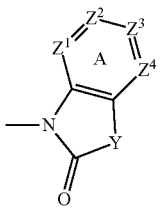

is a group represented by the formula:

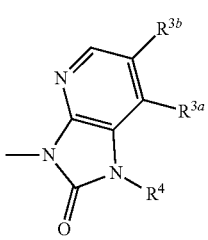

wherein
R$^{3a}$ and R$^{3b}$ represent the same or different a hydrogen atom, a halogen atom, cyano, an optionally substituted C$_{1-4}$ alkyl group or an optionally substituted C$_{1-4}$ alkoxy group, and R$^4$ represents an optionally substituted C$_{1-4}$ alkyl group,
provided that when one of R$^{3a}$ and R$^{3b}$ is a hydrogen atom, the other is not a hydrogen atom.

7. The method according to claim 1, wherein ring B$^1$ is an optionally substituted benzene ring.

8. The method according to claim 1, wherein the 5- to 10-membered heterocyclic group which may be substituted representing R$^1$ is a group represented by the formula:

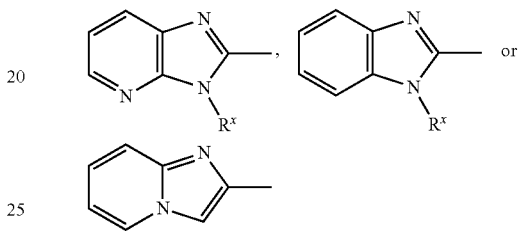

wherein R$^x$ represents a hydrogen atom or an optionally substituted C$_{1-6}$ alkyl group.

9. The method according to claim 1, wherein the compound represented by formula (I) is 1-Ethyl-6-methyl-3-{4-[(3-methyl-3H-imidazo[4,5-b]pyridin-2-yl)oxy]phenyl}-1,3-dihydro-2H-imidazo[4,5-b]pyridin-2-one.

10. The method according to claim 1, wherein the compound represented by formula (I) is 1-Ethyl-6-methoxy-3-{4-[(3-methyl-3H-imidazo[4,5-b]pyridin-2-yl)oxy]phenyl}-1,3-dihydro-2H-imidazo[4,5-b]pyridin-2-one.

11. The method according to claim 1, wherein the compound represented by formula (I) is 1-Ethyl-7-methyl-3-{4-[(3-methyl-3H-imidazo[4,5-b]pyridin-2-yl)oxy]phenyl}-1,3-dihydro-2H-imidazo[4,5-b]pyridin-2-one.

12. The method according to claim 1, wherein the compound represented by formula (I) is 6-Methyl-1-(1-methylethyl)-3-{4-[(3-methyl-3H-imidazo[4,5-b]pyridin-2-yl)oxy]phenyl}-1,3-dihydro-2H-imidazo [4,5-b]pyridin-2-one.

13. The method according to claim 1, wherein the compound represented by formula (I) is 1-Ethyl-6-fluoro-3-{4-[(3-methyl-3H-imidazo[4,5-b]pyridin-2-yl)oxy]phenyl}-1,3-dihydro-2H-imidazo[4,5-b]pyridin-2-one.

14. The method according to claim 1, wherein the compound represented by formula (I) is 1,7-Dimethyl-3-{4-[(3-methyl-3H-imidazo[4,5-b]pyridin-2-yl)oxy]phenyl}-1,3-dihydro-2H-imidazo[4,5-b]pyridin-2-one.

15. The method according to claim 1, wherein the compound represented by formula (I) is 1-Ethyl-7-(hydroxymethyl)-3-{4-[(3-methyl-3H-imidazo[4,5-b]pyridin-2-yl)oxy]phenyl}-1,3-dihydro-2H-imidazo[4,5-b]pyridin-2-one.

* * * * *